US012433950B2

(12) United States Patent
Zhao et al.

(10) Patent No.: US 12,433,950 B2
(45) Date of Patent: Oct. 7, 2025

(54) CONJUGATION LINKERS, CELL BINDING MOLECULE-DRUG CONJUGATES CONTAINING THE LINKERS, METHODS OF MAKING AND USES SUCH CONJUGATES WITH THE LINKERS

(71) Applicant: Hangzhou DAC Biotech Co., Ltd., Hangzhou (CN)

(72) Inventors: Yongxin Robert Zhao, Hangzhou (CN); Qingliang Yang, Hangzhou (CN); Yuanyuan Huang, Hangzhou (CN); Hangbo Ye, Hangzhou (CN); Huihui Guo, Hangzhou (CN)

(73) Assignee: HANGZHOU DAC BIOTECH CO., LTD., Hangzhou (CN)

( * ) Notice: Subject to any disclaimer, the term of this patent is extended or adjusted under 35 U.S.C. 154(b) by 2 days.

(21) Appl. No.: 17/835,395

(22) Filed: Jun. 8, 2022

(65) Prior Publication Data

US 2022/0313838 A1 Oct. 6, 2022

Related U.S. Application Data

(62) Division of application No. 16/348,749, filed as application No. PCT/CN2016/105799 on Nov. 14, 2016.

(51) Int. Cl.
*A61K 47/68* (2017.01)

(52) U.S. Cl.
CPC .... *A61K 47/6803* (2017.08); *A61K 47/68031* (2023.08); *A61K 47/68035* (2023.08); *A61K 47/6829* (2017.08); *A61K 47/6831* (2017.08); *A61K 47/6855* (2017.08); *A61K 47/6863* (2017.08); *A61K 47/6883* (2017.08); *A61K 47/6889* (2017.08)

(58) Field of Classification Search
None
See application file for complete search history.

(56) References Cited

U.S. PATENT DOCUMENTS

| | | | |
|---|---|---|---|
| 6,087,328 | A | 7/2000 | Lees |
| 2007/0213278 | A1 | 9/2007 | Wong et al. |
| 2010/0009902 | A1 | 1/2010 | Defrees |

(Continued)

FOREIGN PATENT DOCUMENTS

| | | | |
|---|---|---|---|
| CN | 101616691 | A | 12/2009 |
| CN | 105641707 | A | 6/2016 |

(Continued)

OTHER PUBLICATIONS

Database Caplus Chemical Abstracts Service, Columbus, Ohio, US; Registry No. 1001321-52-3, N-[3,5-bis[[[(11aS)-2,3,5,11a-tetrahydro-7-methoxy-2methylene-5-oxo-1H-pyrrolo[2,1-c][1,4]benzodiazepin-8-yl]oxy]methyl]phenyl]-4-mercapto-4-methyl- pentanamide, 2008 (Year: 2008).*

(Continued)

*Primary Examiner* — Karl J Puttlitz
(74) *Attorney, Agent, or Firm* — Panitch Scwharze Belsiario & Nadel LLP

(57) ABSTRACT

The present invention relates to linkers having a group of propiolyl, substituted acryl (acryloyl), or disubstituted propanoyl, and using such linkers for the conjugation of compounds, in particular, cytotoxic agents to a cell-binding molecule.

9 Claims, 47 Drawing Sheets

(56) References Cited

U.S. PATENT DOCUMENTS

| | | | | |
|---|---|---|---|---|
| 2010/0047257 | A1 * | 2/2010 | Blanc | A61P 35/04 536/23.53 |
| 2010/0143387 | A1 | 6/2010 | Kraehmer et al. | |
| 2012/0035115 | A1 | 2/2012 | Manoharan et al. | |
| 2012/0225089 | A1 | 9/2012 | Bouchard et al. | |
| 2014/0249319 | A1 | 9/2014 | Nguyen | |
| 2015/0152190 | A1 | 6/2015 | Barnett et al. | |
| 2015/0250896 | A1 | 9/2015 | Zhao | |
| 2015/0314017 | A1 * | 11/2015 | Zhao | C07D 519/00 546/261 |
| 2016/0272669 | A1 | 9/2016 | Wang et al. | |
| 2019/0117790 | A1 | 4/2019 | Song et al. | |
| 2020/0079820 | A1 | 3/2020 | Zhao et al. | |
| 2020/0079850 | A1 | 3/2020 | Stafford et al. | |
| 2021/0308277 | A1 | 10/2021 | Zhao et al. | |
| 2022/0313836 | A1 | 10/2022 | Zhao et al. | |
| 2022/0313837 | A1 | 10/2022 | Zhao et al. | |
| 2022/0323602 | A1 | 10/2022 | Zhao et al. | |
| 2023/0071112 | A1 | 3/2023 | Zhao et al. | |

FOREIGN PATENT DOCUMENTS

| | | | | |
|---|---|---|---|---|
| CN | 105849086 | A | 8/2016 | |
| CN | 109689107 | A | 4/2019 | |
| EP | 1838332 | A1 | 10/2007 | |
| EP | 3445401 | A1 | 2/2019 | |
| JP | 2002504096 | A | 2/2002 | |
| JP | 2008526864 | A | 7/2008 | |
| JP | 2010519182 | A | 6/2010 | |
| JP | 2011-058001 | A | 3/2011 | |
| JP | 2012531459 | A | 12/2012 | |
| JP | 2015521590 | A | 7/2015 | |
| JP | 2015-533832 | A | 11/2015 | |
| JP | 2016501859 | A | 1/2016 | |
| JP | 2019515907 | A | 6/2019 | |
| JP | 7138350 | B2 | 9/2022 | |
| JP | 7295640 | B2 | 6/2023 | |
| KR | 20150023563 | A | 3/2015 | |
| WO | 9847530 | A2 | 10/1998 | |
| WO | 2010037179 | A1 | 4/2010 | |
| WO | 2014197854 | A1 | 12/2014 | |
| WO | 2015/151080 | A2 | 10/2015 | |
| WO | WO-2015151081 | A2 * | 10/2015 | A61K 47/6803 |
| WO | WO-2015155753 | A2 * | 10/2015 | A61K 47/6817 |
| WO | 2016/057936 | A1 | 4/2016 | |
| WO | 2016059622 | A2 | 4/2016 | |
| WO | 2016164580 | A1 | 10/2016 | |
| WO | 2017046658 | A1 | 3/2017 | |

OTHER PUBLICATIONS

Brandley et al., "Phosphorylation of Extracellular Carbohydrates by Intact Cells: Chicken Hepatocytes Specifically Adhere to and Phosphorylate Immobilized N-Acetylglucosamine," The Journal of Biological Chemistry, Oct. 15, 1985, vol. 260, No. 23, pp. 12474-12483. (10 pages).
Examination Report No. 1 issued on Feb. 4, 2020, by the Australian Patent Office in corresponding Australian Patent Application No. 2016429272. (21 pages).
Examination Report No. 2 issued on Nov. 20, 2020, by the Australian Patent Office in Australian Patent Application No. 2016429272. (9 pages).
Extended European Search Report issued on Sep. 7, 2021, by the European Patent Office in corresponding European Patent Application No. 21171676.6. (10 pages).
Grant of Patent issued on Oct. 25, 2021, by the Korean Patent Office in corresponding Korean Patent Application No. 10-2019-7017166 and an English translation of the Grant. (6 pages).
Griebenow et al., "Site-specific conjugation of peptides and proteins via rebridging of disulfide bonds using the thiol-yne coupling reaction," Bioconjugate Chemistry, Mar. 31, 2016, vol. 27, No. 4, pp. 911-917. (Abstract and Experimental part, 22 pages).
International Search Report (PCT/ISA/210) issued on Apr. 18, 2017, by the Chinese Patent Office as the International Searching Authority for International Application No. PCT/CN2016/105799. (2 pages).
Japanese Search Report issued on Oct. 6, 2020, by the Japanese Patent Office in corresponding Japanese Patent Application No. 2019-524954 with an English translation of the Report. (21 pages).
Nakamura, Taku, "Crosslinking of gelatin by reactivepolymer: Effect of Polymer Structure on Gelation Time," Contemporary Topics in Polymer Science, 1984, vol. 4, pp. 141-147. (8 pages).
Notice of Final Rejection issued on Jul. 13, 2021, by the Korean Intellectual Property Office in corresponding Korean Patent Application No. 10-2019-7017166 and an English translation of the Notice. (37 pages).
Notice of Reasons for Refusal issued on Jul. 28, 2021, by the Japanese Patent Office in corresponding Japanese Patent Application No. 2019-524954 and an English translation of the Notice. (4 pages).
Notice of Reasons for Refusal issued on Oct. 6, 2020, by the Japanese Patent Office in corresponding Japanese Patent Application No. 2019-524954 and an English translation of the Notice. (9 pages).
Notification of Reason for Refusal issued on Dec. 4, 2020, by the Korean Intellectual Property Office in corresponding Korean Patent Application No. 10-2019-7017166 and an English translation of the Notification. (44 pages).
Notification of Reasons for Refusal issued on Jan. 14, 2022, by the Korean Patent Office in corresponding Korean Patent Application No. 10-2021-7032859 and an English translation of the Notification. (15 pages).
Notification of Reasons for Refusal issued on Jan. 14, 2022, by the Korean Patent Office in corresponding Korean Patent Application No. 10-2021-7032860 and an English translation of the Notification. (15 pages).
Office Action issued on Feb. 23, 2021, by the Canadian Patent Office in corresponding Canadian Patent Application No. 3,042,442. (6 pages).
Office Action issued on Jul. 23, 2020, by the Canadian Patent Office in corresponding Canadian Patent Application No. 3,042,442. (6 pages).
Office Action issued on Nov. 4, 2021, by the Canadian Patent Office in corresponding Canadian Patent Application No. 3,042,442. (4 pages).
Patent Examination Report 3 issued on Jul. 2, 2021, by the New Zealand Patent Office in corresponding New Zealand Patent Application No. 752394. (1 page).
Pilkington-Miksa et al., "Design, synthesis, and biological evaluation of novel cRGD-paclitaxel conjugates for integrin-assisted drug delivery," Bioconjugate chemistry (2012), vol. 23, No. 8, pp. 1610-1622. (13 pages).
The Extended European Search Report issued on Jun. 8, 2020, by the European Patent Office in corresponding European Patent Application No. 16921340.2. (7 pages).
The First Office Action issued on Aug. 3, 2021, by the State Intellectual Property Office of the People's Republic of China in corresponding Chinese Patent Application No. 201680090956.2, and an English translation of the Action. (15 pages).
Vilà et al., "Solid-Phase Synthesis of Peptide Conjugates Derived from the Antimicrobial Cyclic Decapeptide BPC194," European Journal of Organic Chemistry, (2015), vol. 5, pp. 1117-1129. (1 page).
Written Opinion issued on Apr. 18, 2017, by the State Intellectual Property Office of People's Republic of China in corresponding International Application No. PCT/CN2016/105799. (3 pages).
Yao et al., "Methods to Design and Synthesize Antibody-Drug Conjugates (ADCs)," International Journal of Molecular Sciences, Feb. 2, 2016, vol. 17, No. 2, p. 194. (1 page).
Yao et al., "Methods to Design and Synthesize Antibody-Drug Conjugates (ADCs)," International Journal of Molecular Sciences, 2016, vol. 17, pp. 1-16. (16 pages).
Zlatopolskiy et al., "Synthesis of 18F-Labelled β-Lactams Using the Kinugasa Reaction," Chemistry: A European Journal, 2014, vol. 20, pp. 4697-4703. (7 pages).

(56) References Cited

OTHER PUBLICATIONS

Notification Concerning Transmittal of International Preliminary Report on Patentability (Chapter I of the Patent Cooperation Treaty) and International Preliminary Report on Patentability issued on May 14, 2019, by the State Intellectual Property Office of People's Republic of China in corresponding International Application No. PCT/CN2016/105799. (5 pages).
Notice of Reasons for Refusal issued on Apr. 5, 2022, by the Japanese Patent Office in corresponding Japanese Patent Application No. 2019-524954 and an English translation of the Notice. (4 pages).
Examination Report No. 1 for standard patent application issued on Apr. 29, 2022, by the Australian Patent Office in corresponding Australian Patent Application No. 2021200562. (4 pages).
Notice of acceptance for application issued on Apr. 13, 2023, by the Australian Government, IP Australia in corresponding Australian Patent Application No. 2021200562 (3 pages).
Notice of Final Rejection issued on Sep. 7, 2023, by the Korean Intellectual Property Office in corresponding Korean Patent Application No. 10-2022-7036870, with English translation of the Notice (12 pages).
Notice of Final Rejection issued on Sep. 7, 2023, by the Korean Intellectual Property Office in corresponding Korean Patent Application No. 10-2022-7036869, with English translation of the Request (12 pages).
Request for Submission of an Opinion issued on Oct. 13, 2023, by the Korean Intellectual Property Office in corresponding Korean Patent Application No. 10-2022-7036868, with English translation of the Request (9 pages).
Request for Submission of an Opinion issued on Oct. 13, 2023, by the Korean Intellectual Property Office in corresponding Korean Patent Application No. 10-2022-7036871, with English translation of the Request (9 pages).
Search Report by Registered Search Organization issued on Sep. 14, 2023, by Japanese Registered Search Organization in corresponding Japanese Patent Application No. 2022-136679, with English translation of the Search Report (95 pages).
Notice of Reasons for Refusal issued on Oct. 3, 2023, by the Japanese Patent Office in corresponding Japanese Patent Application No. 2022-136679, with English translation of the Notice (17 pages).
Su, et al., "Azide-alkyne cycloaddition for universal post-synthetic modifications of nucleic acids and effective synthesis of bioactive nucleic acid conjugates," Organic & Biomolecular Chemistry, 2014, 12 (34), 6624-6633.
Li, et.al., "Poly(ethylene glycol) Conjugated Poly(lactide)-Based Polyelectrolytes: Synthesis and Formation of Stable Self-Assemblies Induced by Stereocomplexation," Langmuir, 2015, 31 (8), 2321-2333.
Office Action issued on Oct. 17, 2023, by the U.S. Patent and Trademark Office in related U.S. Appl. No. 16/348,749, U.S. Patent and Trademark Office, Alexandria, VA (17 pages).
Office Action issued on Jan. 31, 2023, by the U.S. Patent and Trademark Office in U.S. Appl. No. 16/348,749, U.S. Patent and Trademark Office, Alexandria, VA. (33 pages).
Carey, F. A. Organic Chemistry, 6th Ed. McGraw Hill, 2006, chapter 1, 9 pages.
Chen, et al., "Determination of Drug-to-Antibody Ratio for Antibody-Drug Conjugates Purified from Serum", Agilent Technologies, 2016, 10 pages.
Notice of Grant for Patent issued on Aug. 10, 2023, by the Australian Patent Office in corresponding AU Patent No. 2021200562 (1 page).
Notification to Grant Patent Right for Invention issued on Feb. 9, 2023, by the State Intellectual Property Office of People's Republic of China in corresponding CN Application No. 201680090956.2, and English translation of the Notification (3 pages).
Office Action (Examination Report) issued on Aug. 12, 2024, by the Australian Patent Office in corresponding AU Application No. 2023203116 (4 pages).
Office Action issued on Aug. 17, 2022, by the State Intellectual Property Office of People's Republic of China in corresponding CN Application No. 201680090956.2, and English translation of the Office Action (9 pages).
Office Action issued on Aug. 6, 2021, by the State Intellectual Property Office of People's Republic of China in corresponding CN Application No. 201680090956.2, and English translation of the Office Action and Search Report (14 pages).
Office Action issued on Feb. 25, 2022, by the State Intellectual Property Office of People's Republic of China in corresponding CN Application No. 201680090956.2, and English translation of the Office Action (11 pages).
Office Action issued on Jul. 9, 2024, by the Japanese Patent Office in corresponding JP Application No. 2022-136679, and English translation of the Office Action (7 pages).
Final Office Action issued on Jun. 12, 2024, by the U.S. Patent and Trademark Office in U.S. Appl. No. 16/348,749 (16 pages).
Office Action (Request for the Submission of an Opinion) issued on Jan. 5, 2023, by the Intellectual Property Office in corresponding Korean Patent Application No. 10-2022-7036870, and an English Translation of the Office Action. (15 pages).
Office Action (Request for the Submission of an Opinion) issued on Jan. 5, 2023, by the Intellectual Property Office in corresponding Korean Patent Application No. 10-2022-7036871, and an English Translation of the Office Action. (11 pages).
Office Action (Request for the Submission of an Opinion) issued on Jan. 5, 2023, by the Intellectual Property Office in corresponding Korean Patent Application No. 10-2022-7036869, and an English Translation of the Office Action. (16 pages).
Database Caplus Chemical Abstracts Service, Columbus, Ohio, US; Registry No. 1001321-52-3, N-[3,5-bis[[[(11aS)-2,3,5,11a-tetrahydro-7-methoxy-2methylene-5-oxo-1H-pyrrolo[2,1-c][1,4]benzodiazepin-8-yl]oxy]methyl]phenyl]-4-mercapto-4-methyl-pentanamide, 2008.
Office Action issued on Oct. 24, 2024, by the U.S. Patent and Trademark Office in related U.S. Appl. No. 17/835,419 (32 pages).
Office Action issued on Oct. 25, 2024, by the U.S. Patent and Trademark Office in related U.S. Appl. No. 17/835,311 (24 pages).
Office Action issued on Oct. 29, 2024, by the U.S. Patent and Trademark Office in related U.S. Appl. No. 17/835,041 (35 pages).
Office Action issued on Sep. 26, 2024, by the U.S. Patent and Trademark Office in related U.S. Appl. No. 17/835,081 (26 pages).
Office Action issued on Oct. 31, 2024, by the U.S. Patent and Trademark Office in related U.S. Appl. No. 16/348,749 (18 pages).
Office Action issued on May 13, 2022, by the Canadian Patent Office in corresponding Canadian Patent Application No. 3,042,442. (4 pages).
Decision to Grant a Patent issued on Aug. 2, 2022, by the Japanese Patent Office in corresponding Japanese Patent Application No. 2019-524954 and an English translation of the Decision. (6 pages).
Written Decision on Registration issued on Jul. 22, 2022, by the Korean Patent Office in corresponding Korean Patent Application No. 10-2021-7032859 and an English translation of the Decision. (6 pages).
Written Decision on Registration issued on Jul. 22, 2022, by the Korean Patent Office in corresponding Korean Patent Application No. 10-2021-7032860 and an English translation of the Decision. (6 pages).
Notice of Final Rejection issued on Nov. 17, 2023, by the Korean Intellectual Property Office in corresponding Korean Patent Application No. 10-2022-7036868 (2 pages).
Notice of Final Rejection issued on Nov. 17, 2023, by the Korean Intellectual Property Office in corresponding Korean Patent Application No. 10-2022-7036871 (2 pages).
Office Action issued on Jan. 24, 2024, by the U.S. Patent and Trademark Office in U.S. Appl. No. 16/348,749 (17 pages).
Office Action issued on May 3, 2023, by the Korean Intellectual Property Office in corresponding Korean Patent Application No. 10-2022-7036868, and an English Translation of the Office Action. (15 pages).
Office Action (Examination Search Report) issued on Feb. 24, 2023, by the Canadian Intellectual Property Office in Canadian Patent Application No. 3,042,442 (6 pages).

(56) References Cited

OTHER PUBLICATIONS

Office Action issued on Aug. 4, 2023, by the U.S. Patent and Trademark Office in U.S. Appl. No. 16/348,749, U.S. Patent and Trademark Office, Alexandria, VA. (16 pages).
Office Action issued on Jan. 3, 2025, by the U.S. Patent and Trademark Office in related U.S. Appl. No. 17/835,081 (7 pages).
Office Action issued on Jan. 29, 2025, by the U.S. Patent and Trademark Office in related U.S. Appl. No. 16/348,749 (9 pages).
Decision to Grant a Patent issued on Jan. 21, 2025, by the Japanese Patent Office in corresponding JP Application No. 2022-136679, and English translation of the Decision (6 pages).

* cited by examiner p=0-100, n=1-20, L is a linker 7 8 10 11 13 14 42 16 82 83 84 85 86 9 87 55 p = 0-100, $m_1$, n = 1-20, Aa is amino acid, L is a linker 143, 144, 40, 145, 146, 147, 148, 149, 150, 151, 152, 153, 154, 155

Boc-MMAF 221

MMAF 222

Z-L-Alaine-MMAF 223

L-Alaine-MMAF 224

225 226 227

228 229

230

231 MMAF029

232

231
233
234
235
231
236
237
238
239

260

261

262, MMAF(OMe)

263

264

265

266

267

268

280
281
282
274
283
284
285
286
288
289

12
290
291
201
292
293
294
271
295
296

312

313

311

294

314

318

334

340

341

342

343

344

345

346 347 348 349 350 351 352 353 354 355

221

356

334

357

358

359

360

361

396 397 398 399 400 401 402 403 404 62 405 406 407 408 409 410 411

467

468

469

470

471

472

473

496

36 + 352 (2.2eq) EDC/DMA

497

498

36 + 259 (2.2eq) EDC/DMA

499

500

ST1,

ST2

ST3

,

ST4

ST5,

ST6,

ST7,

,

ST8,

, $X_1$, $X_1'$, $X_2$, $X_2'$, $X_3$, $X_3'$, $X_4$, $X_4'$, $L_1$, $L_1'$, $L_2$, $L_2'$, $L_3$, $L_3'$, $L_4$, $L_4'$ and T are defined the same as $X_1$ in Formula (I); In addition, $X_1$, $X_1'$, $X_2$, $X_2'$, $X_3$, $X_3'$, $X_4$, and $X_4'$ can be absent.

,

ST9,

,

ST10,

,

ST11,

ST12,

,

ST13,

ST14

$X_1$, $X_1'$, $X_2$, $X_2'$, $X_3$, $X_3'$, $X_4$, $X_4'$, $L_1$, $L_1'$, $L_2$, $L_2'$, $L_3$, $L_3'$, $L_4$, $L_4'$ and T are defined the same as $X_1$ in Formula (I); In addition, $X_1$, $X_1'$, $X_2$, $X_2'$, $X_3$, $X_3'$, $X_4$, and $X_4'$ can be absent.

CONJUGATION LINKERS, CELL BINDING MOLECULE-DRUG CONJUGATES CONTAINING THE LINKERS, METHODS OF MAKING AND USES SUCH CONJUGATES WITH THE LINKERS

CROSS REFERENCE OF RELATED APPLICATIONS

This application is a division of U.S. patent application Ser. No. 16/348,749, filed on May 9, 2019, now U.S. Pat. No. 12,364,767, entitled "CONJUGATION LINKERS, CELL BINDING MOLECULE-DRUG CONJUGATES CONTAINING THE LINKERS, METHODS OF MAKING AND USES SUCH CONJUGATES WITH THE LINKERS," which in turn is a national stage application of PCT/CN2016/105799, filed on Nov. 14, 2016. The entire content of each of the prior applications is hereby incorporated by reference.

FIELD OF THE INVENTION

The present invention relates to linkers having a group of propiolyl, substituted acryl (acryloyl), or disubstituted propanoyl, used for the conjugation of compounds, in particular, cytotoxic agents to a cell-binding molecule. The present invention also relates to methods of making cell-binding agent-drug (cytotoxic agent) conjugates in a specific manner comprising either modification of drugs with these linkers first, followed by reaction with prepared cell-binding agents; or modification of cell-binding agents with these linkers first, followed by reaction with drugs, or directly conjugate a synthetic linker-drug assembly to a cell-binding molecule.

BACKGROUND OF THE INVENTION

The major challenge of chemotherapeutic drugs is their narrow therapeutic windows due to they normally cannot discriminate between normal and malignant cells, thus causes side effects which limit the tolerated doses below the clinically effective ones. In contrast, immunotherapy, typically in the form of monoclonal antibodies (mAb) can specifically bind to certain proteins or molecules of malignant cells, leaving normal cells unharmed, and thus has less side effects and much wider therapeutic windows than the chemotherapy. Antibody-drug conjugates (ADC) are a kind of immunotherapies that combines a tumor specific binding monoclonal antibody conjugated with payloads of a highly potent cytotoxic agent for targeted treatment of cancers. This approach has shown promising activity in the treatment of Hodgkin's lymphoma with US FDA approval drug, Adcetris (brentuximab vedotin) and in the treatment of HER-2 positive breast cancer with US FDA approval drug, Kadcyla (ado-trastuzumab emtansine). During the past two decades, both the academic community and the pharmaceutical industry have been making increasing investments of time and money in ADCs. With over 50 ADCs are in the clinical trials, drugmakers industry expectations are that another 8-10 ADC drugs could be market-approved within next a couple of years (Lambert, J. M. Ther. Deliv. 2016, 7, 279-82; Jerjian, T. V. et al. Pharmacotherapy 2016, 36, 99-116; Donaghy, H. MAbs 2016, 8, 659-71; de Goeij, B. E. and Lambert, J. M. Curr Opin Immunol 2016, 40, 14-23; Mehrling, T. Future Oncol, 2015, 11, 549).

Many critical parameters that govern successful antibody-drug conjugate development for clinical use include the selection of the tumor target antigen that has restricted expression on normal cells, the antibody being highly selective against the target, the cytotoxic molecule needed highly potent to induce target cell death when internalized the cell and released, the linker bridging the cytotoxic molecule and the antibody that is stable in circulation, but releases the cytotoxic agent in target cells, and the adequate conjugation chemistry used for the attachment of cytotoxic molecules to the antibody. Although there are lots of progresses in development of ADCs, the mechanism behind the off-target toxicity of ADCs is still poorly understood and a quite number of ADCs that have been terminated during clinical trial phases due to their therapeutic windows in the clinics are much narrower than the preclinical models and dosing regimens are hampered by dose limiting toxicities (DLTs) that could not always be predicted based on preclinical data (de Goeij, B. E. and Lambert, J. M. Curr Opin Immunol 2016, 40, 14-23). Thus research and development into ADC chemistry and design are now expanding the scopes of the linker-payload compartments and conjugate chemistry beyond the sole potent payloads, and especially to address activity of the linker-payload of ADCs toward targets/target diseases (Lambert, J. M. Ther Deliv 2016, 7, 279-82; Zhao, R. Y. et al, 2011, J. Med. Chem. 54, 3606-23). Nowadays many drug developers and academic institutions are highly focusing on establishing novel reliable methods for site-specific ADC conjugation, which seem to have longer circulation half-life, higher efficacy, potentially decreased off-target toxicity, and a narrow range of in vivo pharmacokinetic (PK) properties of ADCs as well as better batch-to-batch consistency in ADC production (Hamblett, K. J. et al, Clin. Cancer Res. 2004, 10, 7063-70; Adem, Y. T. et al, Bioconjugate Chem. 2014, 25, 656-664; Boylan, N. J. Bioconjugate Chem. 2013, 24, 1008-1016; Strop, P., et al 2013 Chem. Biol. 20, 161-67; Wakankar, A. mAbs, 2011, 3, 161-172).

There are several approaches developed in recent years for the site selective ADC preparation (Panofsky, S, 2014, mAbs 6, 34). They include incorporation of unpaired cysteines, e.g. engineered reactive cysteine residues, called THIOMAB from Genentech (Junutula, J. R., et al 2010 Clin. Cancer Res. 16, 4769; Junutula, J. R., et al 2008 Nat Biotechnol. 26, 925-32; U.S. Pat. Nos. 8,309,300; 7,855, 275; 7,521,541; 7,723,485, WO2008/141044), genetically introduced glutamine tag with *Streptoverticillium mobaraense* transglutaminase (mTG) (Strop, P., Bioconjugate Chem., 2014, 25, 855-862; Strop, P., et al., 2013, Chem. Biol. 20, 161-167; U.S. Pat. No. 8,871,908 for Rinat-Pfizer) or with Microbial transglutaminase (MTGase) (Dennler, P., et al, 2014, Bioconjug. Chem. 25, 569-578. US pat appl 20130189287 for Innate Pharma; U.S. Pat. No. 7,893,019 for Bio-Ker S.r.l. (IT)), incorporation of thiolfucose (Okeley, N. M., et al 2013 Bioconjugate Chem. 24, 1650), incorporation of unnatural amino acids through mutagenesis (Axup, J. Y., et al., 2012, Proc. Natl. Acad. Sci. 109, 16101-16106; Zimmerman, E. S., et al., 2014, Bioconjug. Chem. 25, 351-361; Wu, P., et al, 2009 Proc. Natl. Acad. Sci. 106, 3000-5; Rabuka, D., et al, 2012 Nat. Protoc. 7, 1052-67; U.S. Pat. No. 8,778,631 and US Pat Appl. 20100184135, WO2010/081110 for Sutro Biopharma; WO2006/069246, 2007/059312, U.S. Pat. Nos. 7,332,571, 7,696,312, and 7,638,299 for Ambrx; WO2007/130453, U.S. Pat. Nos. 7,632,492 and 7,829,659 for Allozyne), incorporation of selenocysteine into antibodies (Hofer, T., et al 2009, Biochemistry 48, 12047-12057; U.S. Pat. No. 8,916,159 for US National Cancer Institute), Conversion of cysteines located in the CXPXR consensus sequence to formylglycine (FGly) with formylglycine generating enzyme (FGE) (Drake, P. M., et al., 2014, Bioconjug. Chem. 25, 1331-1341. Carrico, I. S. et al U.S. Pat. Nos. 7,985,783; 8,097,701; 8,349,910, and US Pat Appl 20140141025, 20100210543 for Redwood Bioscience), via glycoengineeringly introduction of sialic acid with the use of galactosyl- and sialytransferases (Zhou, Q., et al 2014, Bioconjug. Chem., 25, 510-520, US Pat Appl 20140294867 for Sanofi-Genzyme). However the above methods are required antibody-engineering processes and reoptimization of cell culture conditions. Therefore a simple homogeneous conjugation method was practically used through rebridging the reduced inter chain disulfide bonds of a native antibody, such as, using bromo or dibromo-maleimides, called next generation maleimides (NGMs) (Schumacher, F. F., et al 2014, Org. Biomol. Chem. 12, 7261-69; UCL Cancer Institute), or applying bis-alkylating reagents via a three-carbon bridge (Badescu, G., et al., 2014, Bioconjug. Chem. 25, 1124-36; WO2013/190272, WO2014/064424 for PolyTherics Ltd). We have disclosed several conjugation methods of rebridging a pair of thiols of the reduced inter chain disulfide bonds of a native antibody, such as using bromo maleimide and dibromomaleimide linkers (WO2014/009774), 2,3-disubstituted succinic/2-monosubstituted/2,3-disubstituted fumaric or maleic linkers (WO2015/155753, WO20160596228), acetylenedicarboxylic linkers (WO2015/151080, WO20160596228) or hydrazine linkers (WO2015/151081). In this patent application, we extend the scopes of our earlier patent application. More importantly, the disulfur bridge linkers of the present patent application are able to conjugate two or more drugs per linker for achieving higher DARs (≥4) or to conjugate to two more sites of thiols on a cell-binding molecule, or on two or more cell-binding molecules. Thus the major advantages of this patent for immunoconjugates include: prolonged the half-lives of the conjugates during the targeted delivery; conjugated in steps of two or more different function molecules/drugs that act in different phases of the cell cycle to increase the number of target cells exposed to the particular pharmaceutical drugs or effectors; possibly conjugates of two or more cell-binding molecules for dual, tri- or multiple targeting strategies on proliferate cells; minimized exposure to non-target cells, tissues or organs through conjugation of the function molecules; precisely controlled over drug payloads and drug ratios at the specific sites leading to homogenous final products.

SUMMARY OF THE INVENTION

The present invention provides linkers containing a thiol reactive group of substituted acrylic group, or propiolic group, with optionally having a group of phosphoric amide, amine, hydrazine, triazole, heteroaromatic, acetylamide, glycoside and their analogs among the linker to conjugate a drug and/or a function molecule, and/or a cell-binding agent (e.g., an antibody).

In one aspect of the present invention, the linker is represented by Formula (I) and (II)

(I)

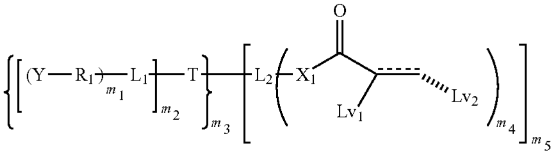

-continued (II)

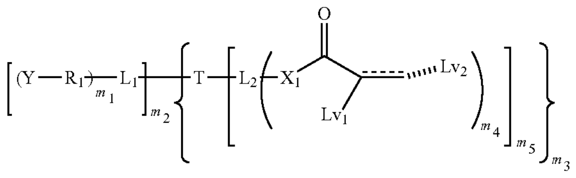

Wherein

"——" and "ııııı" represent a single bond, and "ııııı" can be an enantiomer or stereoisomer bond when linked to a single or a double bond.

---- represents either a single bond, or a double bond, or a triple bond.

It provided that when ---- represents a single bond, both $L_{V1}$ and $L_{V2}$ are not H; when ---- represents a double bond, either $L_{V1}$ or $L_{V2}$ can be H, but they are not H at the same time; when ---- represents a triple bond, $L_{V1}$ is absent and $L_{V2}$ can optionally be H.

$L_{V1}$ and $L_{V2}$ represent the same or different leaving group that can be substituted by a thiol. Such leaving groups are, but are not limited to, a halide (e.g., fluoride, chloride, bromide, and iodide), methanesulfonyl (mesyl), toluenesulfonyl (tosyl), trifluoromethyl-sulfonyl (triflate), trifluoromethylsulfonate, nitrophenoxyl, N-succinimidyloxyl (NHS), phenoxyl; dinitrophenoxyl; pentafluorophenoxyl, tetrafluorophenoxyl, trifluorophenoxyl, difluorophenoxyl, monofluorophenoxyl, pentachlorophenoxyl, 1H-imidazole-1-yl, chlorophenoxyl, dichlorophenoxyl, trichlorophenoxyl, tetrachlorophenoxyl, N-(benzotriazol-yl)oxyl, 2-ethyl-5-phenylisoxazolium-3'-sulfonyl, phenyloxadiazole-sulfonyl (-sulfone-ODA), 2-ethyl-5-phenylisoxazolium-yl, phenyloxadiazol-yl (ODA), oxadiazol-yl, or an intermediate molecule generated with a condensation reagent for Mitsunobu reactions.

Y is a function group that enables to react with a cytotoxic drug, to form a disulfide, ether, ester, thioether, thioester, peptide, hydrazone, carbamate, carbonate, amine (secondary, tertiary, or quarter), imine, cycloheteroalkyane, heteroaromatic, alkyloxime or amide bond; Preferably Y has the following structures:

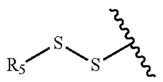

disulfide;

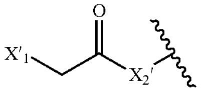

haloacetyl;

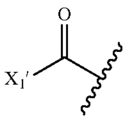

halide (acid halide);
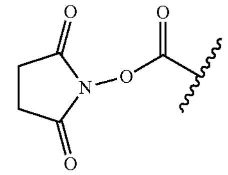 [SMILES: *C(=O)ON1C(=O)CCC1=O]
N-hydroxysuccinimide ester;
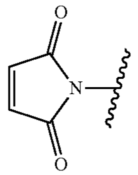 [SMILES: *N1C(=O)C=CC1=O]
maleimide;
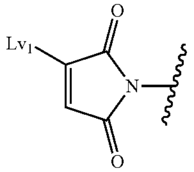
monosubstituted maleimide;
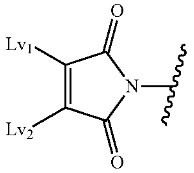
disubstituted maleimide;
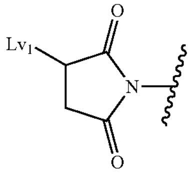
monosubstituted succinimide;
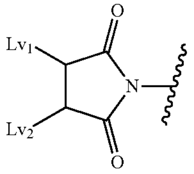
disubstituted succinimide; —CHO aldehyde;
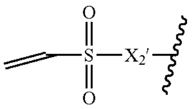
ethenesulfonyl;
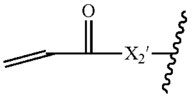
acryl (acryloyl);
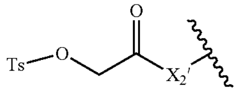
2-(tosyloxy)acetyl;
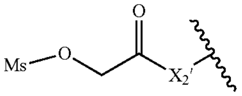
2-(mesyloxy)acetyl;
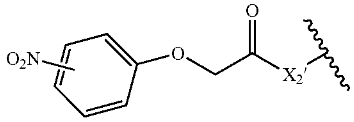
2-(nitrophenoxy)acetyl;
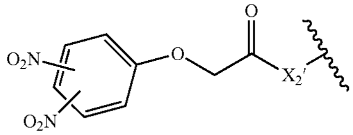
2-(dinitrophenoxy)acetyl;
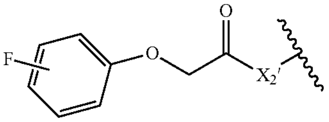

2-(fluorophenoxy)-acetyl;

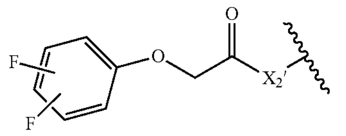

2-(difluorophenoxy)-acetyl;

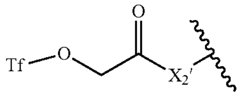

2-(((trifluoromethyl)-sulfonyl)oxy)acetyl;

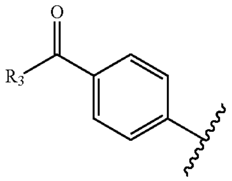

ketone, or aldehyde,

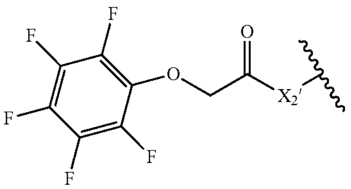

(pentafluorophenoxy)acetyl;

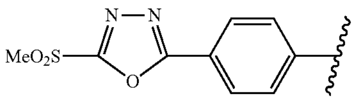, methylsulfonephenyloxadiazole (ODA);

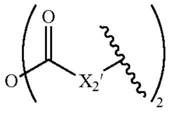, 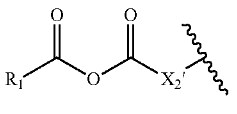

acid anhydride,

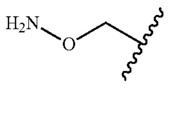

alkyloxyamino;

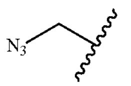 [SMILES: *CN=[N+]=[N-]]

azido,

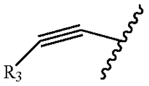

alkynyl, or

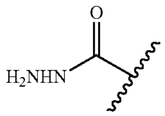

hydrazide. Wherein $X_1$' is F, Cl, Br, I or $L_{V3}$; $X_2$' is O, NH, $N(R_1)$, or $CH_2$; $R_3$ and $R_5$ are independently H, $R_1$, aromatic, heteroaromatic, or aromatic group wherein one or several H atoms are replaced independently by $—R_1$, -halogen, $—OR_1$, $—SR_1$, $—NR_1R_2$, $—NO_2$, $—S(O)R_1$, $—S(O)_2R_1$, or $—COOR_1$; $L_{V3}$ is a leaving group selected from nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, anhydrides formed its self, or formed with the other anhydride, e.g. acetyl anhydride, formyl anhydride; or an intermediate molecule generated with a condensation reagent for peptide coupling reactions or for Mitsunobu reactions.

$R_1$ can be absent, or can be selected from $C_1$-$C_8$ (1-8 carbon atoms) of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 2-8 carbon atoms of esters, ether, or amide; or peptides containing 1-8 amino acids; or polyethyleneoxy unit of formula $(OCH_2CH_2)_p$ or $(OCH_2CH(CH_3))_p$, wherein p is an integer from 0 to about 1000, or combination of above groups thereof.

Additionally $R_1$ is a chain of atoms selected from C, N, O, S, Si, and P, preferably having 0~500 atoms, which covalently connects to Y and $L_1$. The atoms used in forming the $R_1$ may be combined in all chemically relevant ways, such as forming alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, peptides, acyloxylamines, hydroxamic acids, or combination above thereof.

T is $CH_2$, NH, NHNH, $N(R_3)$, $N(R_3)N(R_{3'})$, O, S, $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; a peptide containing 1~4 units of aminoacids, preferably selected from aspartic acid, glutamic acid, arginine, histidine, lysine, serine, threonine, asparagine, glutamine, cysteine, selenocysteine, tyrosine, phenylalanine, glycine, proline, tryptophan, alanine; or one of the following structures:

-continued
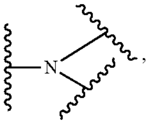,
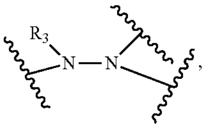,
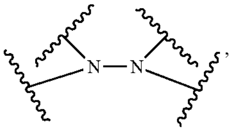,
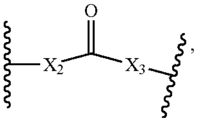,
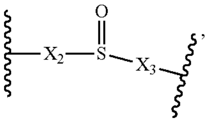,
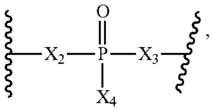,
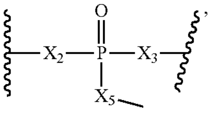,
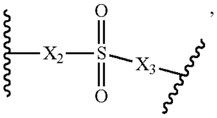,
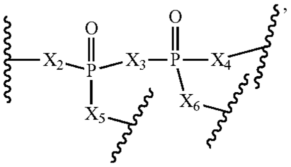,
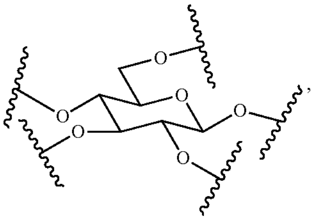,
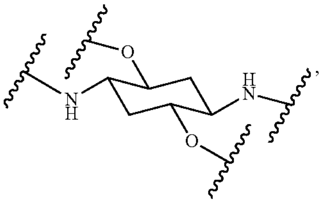,
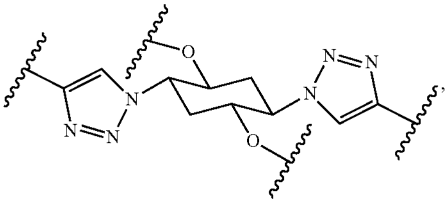,
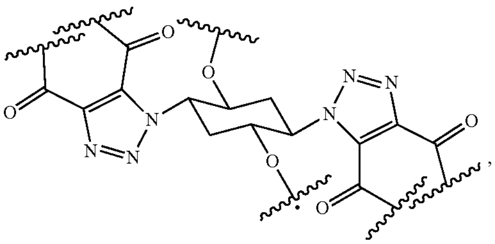,
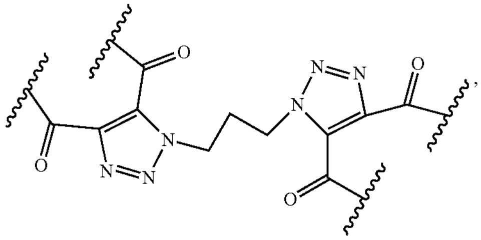,
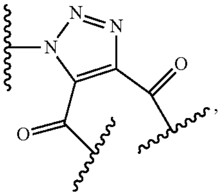,
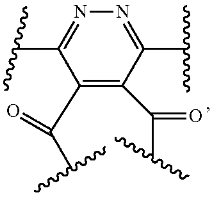
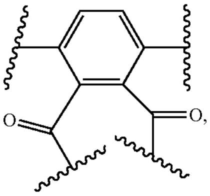
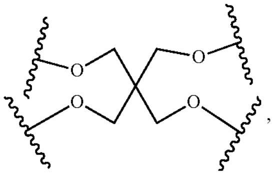,
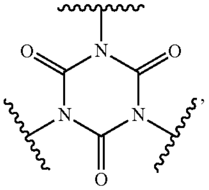,
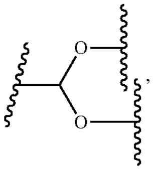,
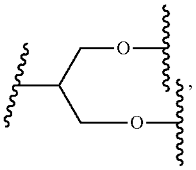,
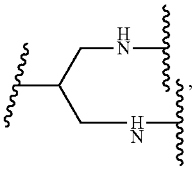,
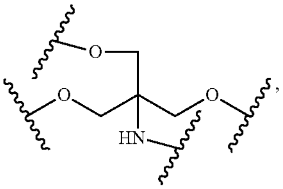,
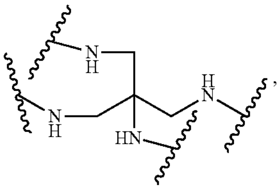,
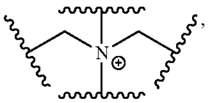,
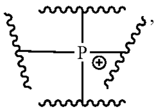,
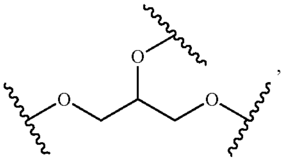, -continued

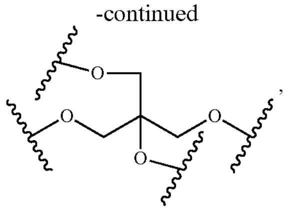

,

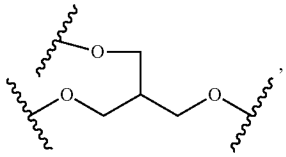

,

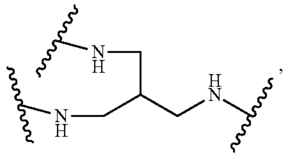

,

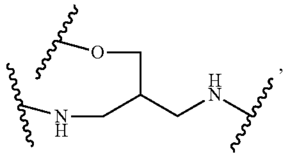

,

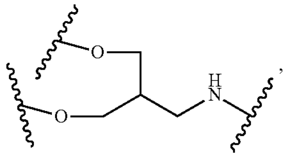

, wherein ⸙ is the site of linkage.

$X_1$, $X_2$, $X_3$, $X_4$, $X_5$, $X_6$, $X_{1'}$, $X_{2'}$ and $X_{3'}$ are independently selected from NH; NHNH; $N(R_3)$; $N(R_3)N(R_{3'})$; O; S; $C_1$-$C_6$ of alkyl; $C_2$-$C_6$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 amino acids; Wherein $R_3$ and $R_{3'}$ are independently H; $C_1$-$C_8$ of alkyl; $C_2$-$C_8$ of hetero-alkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 carbon atoms of esters, ether, or amide; or polyethyleneoxy unit of formula $(OCH_2CH_2)_p$ or $(OCH_2CH(CH_3))_p$, wherein p is an integer from 0 to about 1000, or combination above thereof.

$L_1$ and $L_2$ are, the same or different, independently selected from O, NH, S, NHNH, $N(R_3)$, $N(R_3)N(R_{3'})$, polyethyleneoxy unit of formula $(OCH_2CH_2)_pOR_3$, or $(OCH_2CH(CH_3))_pOR_3$, or $NH(CH_2CH_2O)_pR_3$, or $NH(CH_2CH(CH_3)O)_pR_3$, or $N[(CH_2CH_2O)_pR_3][(CH_2CH_2O)_{p'}R_{3'}]$, or $(OCH_2CH_2)_pCOOR_3$, or $CH_2CH_2(OCH_2CH_2)_pCOOR_3$, wherein p and p' are independently an integer selected from 0 to about 1000, or combination thereof; $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; Wherein $R_3$ and $R_{3'}$ are independently H; $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 carbon atoms of esters, ether, or amide; or 1-8 amino acids; or polyethyleneoxy unit of formula $(OCH_2CH_2)_p$ or $(OCH_2CH(CH_3))_p$, wherein p is an integer from 0 to about 1000, or combination above thereof.

$L_1$ or $L_2$ may be composed of one or more linker components of 6-maleimidocaproyl ("MC"), maleimidopropanoyl ("MP"), valine-citrulline ("val-cit" or "vc"), alanine-phenylalanine ("ala-phe" or "af"), p-aminobenzyloxycarbonyl ("PAB"), 4-thiopentanoate ("SPP"), 4-(N-maleimidomethyl)cyclohexane-1 carboxylate ("MCC"), (4-acetyl)amino-benzoate ("SIAB"), 4-thio-butyrate (SPDB), 4-thio-2-hydroxysulfonyl-butyrate (2-Sulfo-SPDB), or natural or unnatural peptides having 1~8 natural or unnatural amino acid unites.

$m_1$, $m_2$, $m_3$, $m_4$ and $m_5$ are independently an integer from 1 to 10, preferably from 1 to 4.

In addition, $L_1$, $L_2$, $X_1$, $X_2$, $X_3$, $X_{1'}$, $X_{2'}$ and $X_{3'}$ can be independently absent.

In another aspect, this invention provides a cell-binding agent-drug conjugate of Formula (III), (IV), (V), (VI), (VII), (VIII), or (IX) in which the cell-binding agent, Cb, and the drug, "Drug", has respectively reacted at the ends of the bridge linker:

(III)

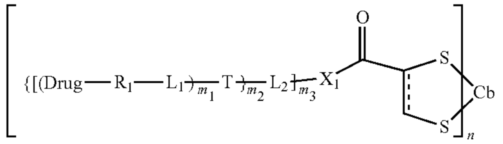

(IV)

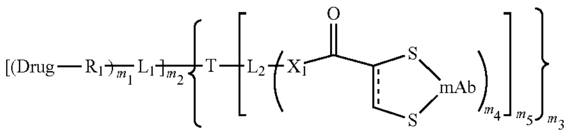

(VI)

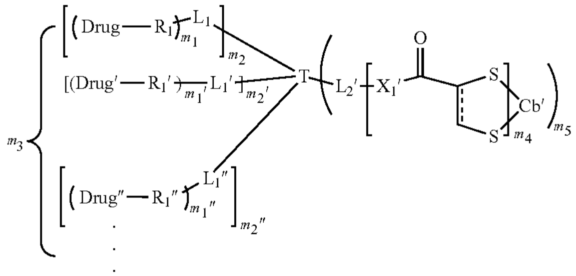

(VII)

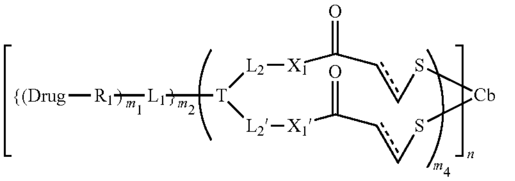

(VIII)

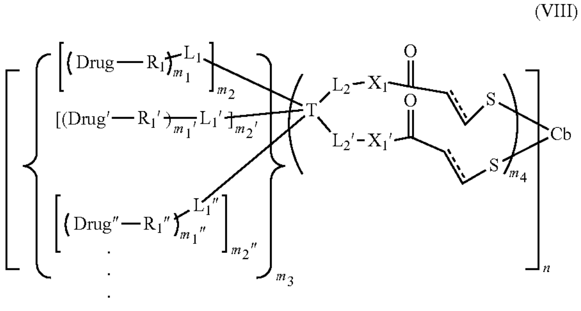

-continued (IX)

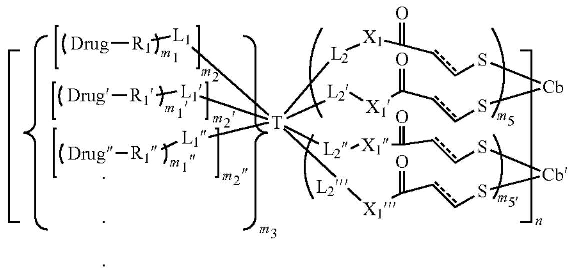

Wherein:

Cb, Cb', Cb", Cb"' represent the same or different, a cell-binding agent, or an immunotherapeutical protein, preferably an antibody or an antibody fragment.

Inside the right bracket (square parentheses) of formula (III), (VII), (VIII) and (IX) are the linker-drug components that are conjugated to pairs of thiols of the cell-binding agent/molecule. The thiols are preferred pairs of sulfur atoms reduced from the inter chain disulfide bonds of the cell-binding agent by a reduction agent selected from dithiothreitol (DTT), dithioerythritol (DTE), L-glutathione (GSH), tris (2-carboxyethyl) phosphine (TCEP), 2-mercaptoethylamine (β-MEA), or/and beta mercaptoethanol (β-ME, 2-ME).

Drug, Drug', and Drug" represent the same or different of, a cytotoxic agent, or a therapeutic drug, or an immunotherapeutical protein, or a function molecule for enhancement of binding or stabilization of the cell-binding agent, or a cell-surface receptor binding ligand, which is linked to the cell-binding agent via the bridge linker of the patent through $R_1$ that can be containing an $C_1$-$C_8$ of alkane; $C_2$-$C_8$ of alkylene, alkenylene, alkynylene, aromatic, ether, polyoxyalkylene, ester, amine, imine, polyamine, hydrazine, hydrazone, amide, urea, semicarbazide, carbazide, alkoxyamine, urethanes, amino acid, peptide, acyloxylamine, hydroxamic acid, disulfide, thioether, thioester, carbamate, carbonate, heterocyclic ring, heteroalkyl, heteroaromatic, or alkoxime; or combination above thereof. "Drug" can also be a cytotoxic molecule, an immunotherapeutic compound, a chemotherapeutic compound, an antibody or an antibody fragment, siRNA or DNA molecule, or a cell surface binding ligand.

"$\overline{\underline{----}}$" represents either single bond or double bond.

Inside the square bracket are agents that are conjugated to a cell-binding molecule through a pair of sulfur atoms on the cell-binding molecule.

$m_1$, $m_{1'}$, $m_{1''}$, $m_2$, $m_{2'}$, $m_{2''}$, $m_3$, $m_4$, $m_5$, $m_{4'}$, $m_{5'}$, $m_{4''}$, $m_{5''}$, $m_{4'''}$, $m_{5'''}$, $m_{4''''}$ and $m_{5''''}$ are independently an integer from 1 to 10, preferably from 1 to 4.

$X_1$, $X_{1'}$, $X_1$", $X_1$"' and $X_2$"" are independently selected from NH; NHNH; $N(R_3)$; $N(R_3)N(R_{3'})$; O; S; $C_1$-$C_6$ of alkyl; $C_2$-$C_6$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 amino acids; Wherein $R_3$ and $R_{3'}$ are independently H; $C_1$-$C_8$ of alkyl; $C_2$-$C_8$ of hetero-alkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 carbon atoms of esters, ether, or amide; or polyethyleneoxy unit of formula $(OCH_2CH_2)_p$ or $(OCH_2CH(CH_3))_p$, wherein p is an integer from 0 to about 1000, or combination above thereof. In addition, $X_1$, $X_1$', $X_1$", $X_1$"' and $X_2$"" can be independently absent.

$R_1$, $R_{1'}$, and $R_{1''}$, are the same or different, selected from $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 2-8 carbon atoms of esters, ether, or amide; or polyethyleneoxy unit of formula $(OCH_2CH_2)_p$ or $(OCH_2CH(CH_3))_p$, wherein p is an integer from 0 to about 1000, or combination of above groups thereof.

$L_1$, $L_{1'}$, $L_{1''}$, $L_{1'''}$, $L_2$, $L_{2'}$, $L_{2''}$ and $L_{2'''}$ are defined the same as $L_1$ and $L_2$ in formula (I) and (II) and they may not be the same at the same time.

n is 1~20; and T are described the same previously in Formula (I).

In a further aspect, the present invention provides a modified cell-binding agent of Formula (III), in which the cell-binding agent, Cb, through its pair of thiols generated with reduction of disulfide bonds, has reacted with the bridge linker, which has Y, the function groups capable of reacting with a drug:

(X)

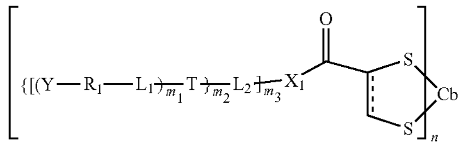

(XI)

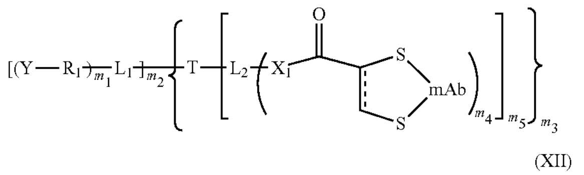

(XII)

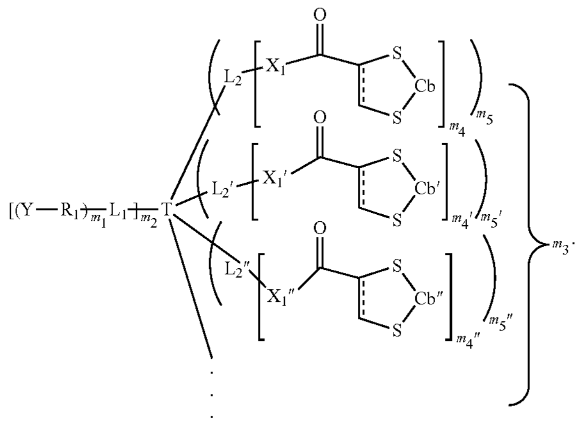

(XIII)

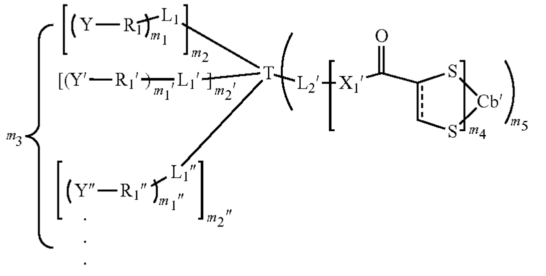

-continued (XIV)

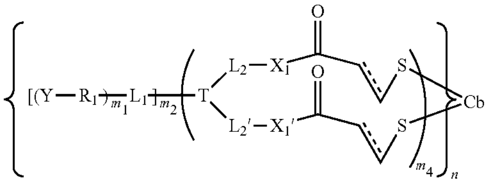

(XV)

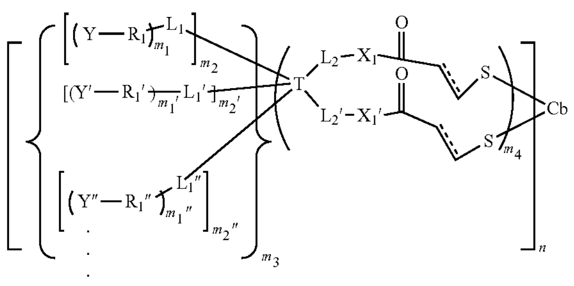

(XVI)

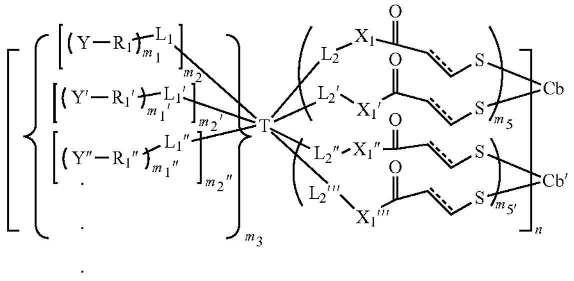

Wherein "——", $Z_1$, $Z_2$, n, $R_1$, $R_2$, $m_1$, $m_2$, $X_1$, and $X_2$ are defined the same as in Formula (I) and (II); "⎓" and Cb are defined the same as in Formula (III)-(IX).

In an even further aspect, the present invention provides a modified drug of Formula (XVII) and (XVIII), in which the drug, "Drug", has reacted with the linker of Formula (I) and (II), which still have a thiol reactive group of substituted acrylic group, or propiolic group, capable of reacting with a pair of thiols of the cell-binding agent:

(XVII)

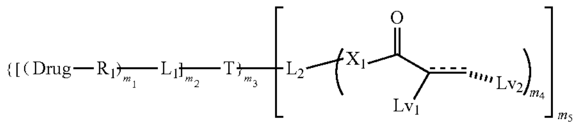

(XVIII)

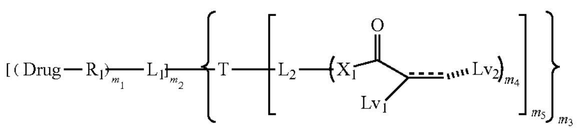

Wherein "ııııııı", "⎓", $L_1$, $L_2$, $R_1$, T, $m_1$, $m_2$, $m_3$, $m_4$, $m_5$, $X_1$, $L_{V1}$ and $L_{V2}$ are defined the same as in Formula (I). $Drug_1$ is defined the same as in Formula (II).

The present invention further relates to a method of making a cell-binding molecule-drug conjugate of Formula (III)-(IX), wherein the drugs, "Drug" is linked to a cell-binding agent via the bridge linker.

The present invention also relates to a method of making a modified cell-binding molecule of Formula (X)—(XVI), wherein the cell-binding molecule is reacted with the linker of Formula (I) and (II).

The present invention also relates to a method of making a modified drug of formula (XVII) and (XVIII), wherein a Drug is reacted with the bridge linker of Formula (I) and (II).

DETAILED DESCRIPTION OF THE INVENTION

Definitions

Figure 1:
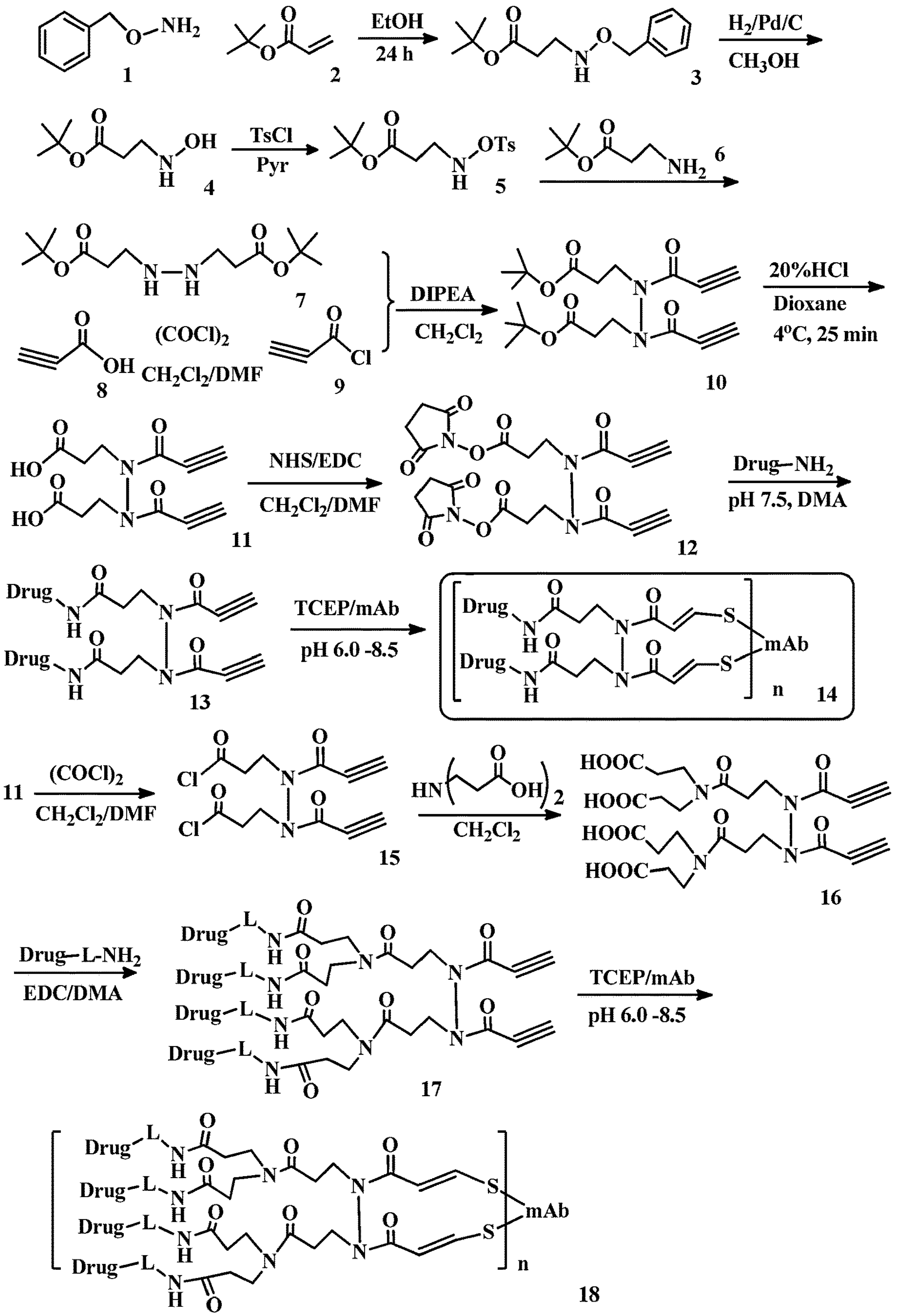
FIG. 1 shows the synthesis of the linkers of the patent application containing two or four drugs, and the application of the linkers in the conjugation to an antibody via a pair of thiols.
Figure 2:
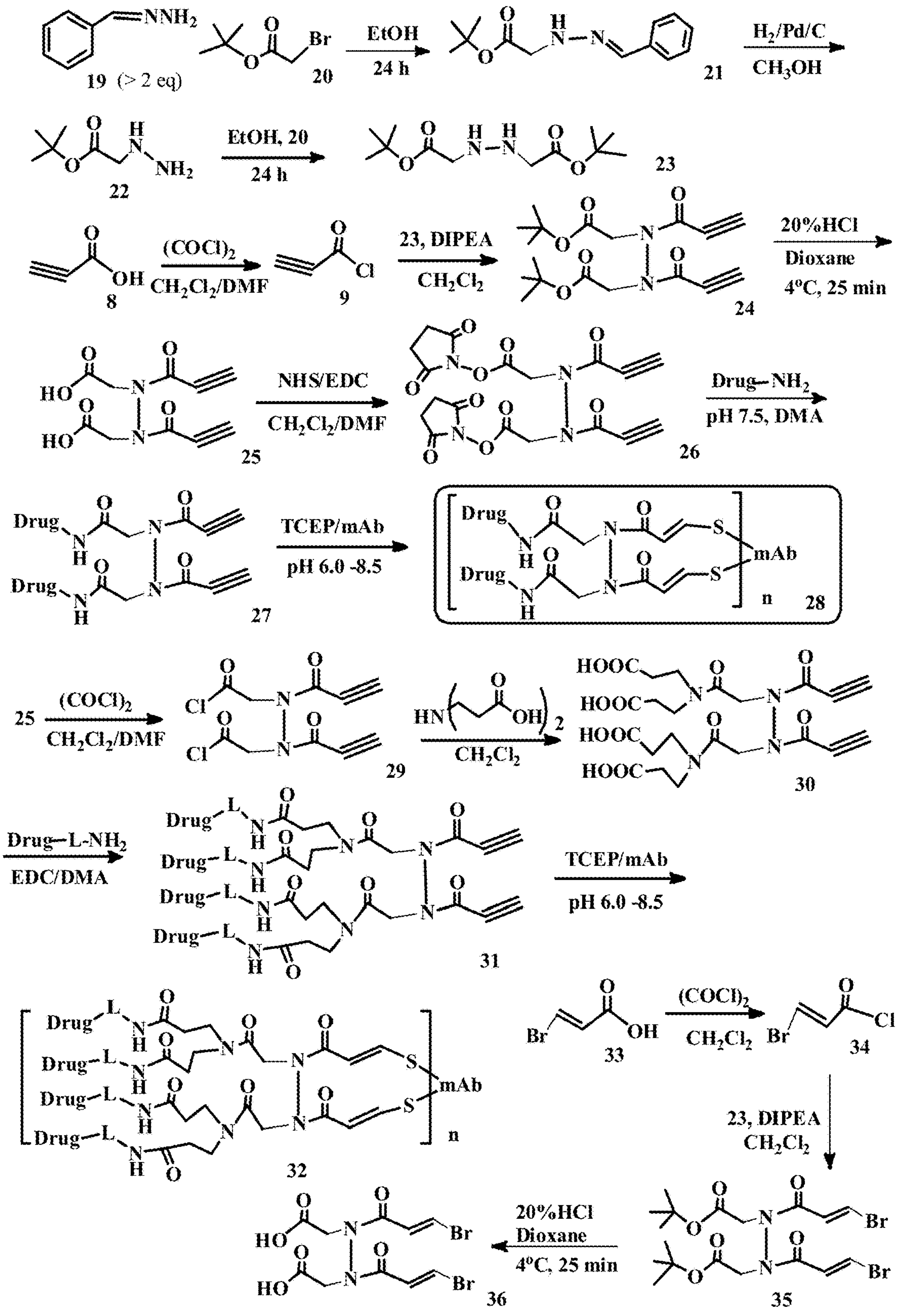
FIG. 2 shows the synthesis of the linkers of the patent application containing two or four drugs, and the application of the linkers in the conjugation to an antibody via a pair of thiols.
Figure 3:
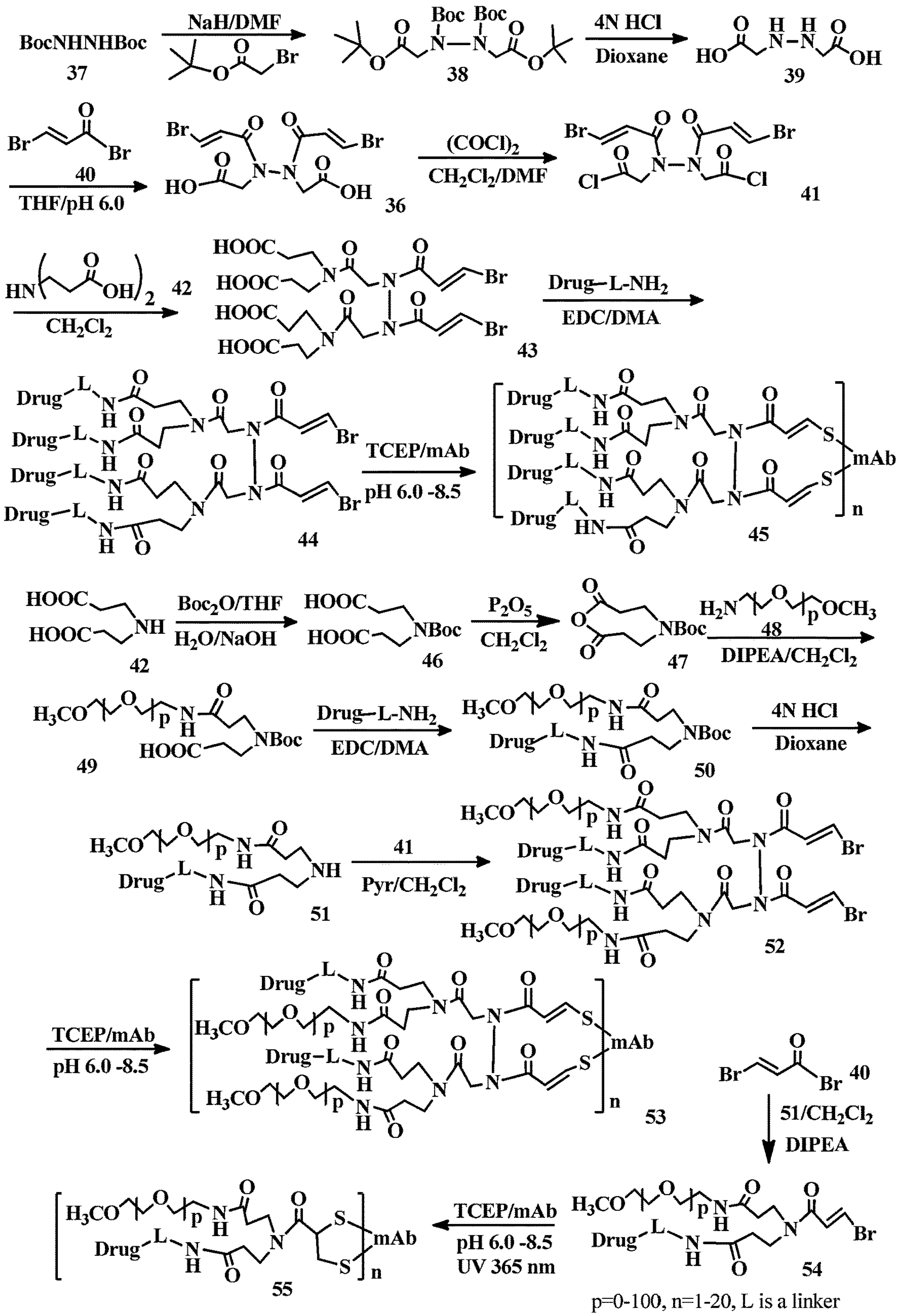
FIG. 3 shows the synthesis of the linkers of the patent application containing a drug and a polyethylene glycol, and the application of the linkers in the conjugation to an antibody via a pair of thiols.
Figure 4:
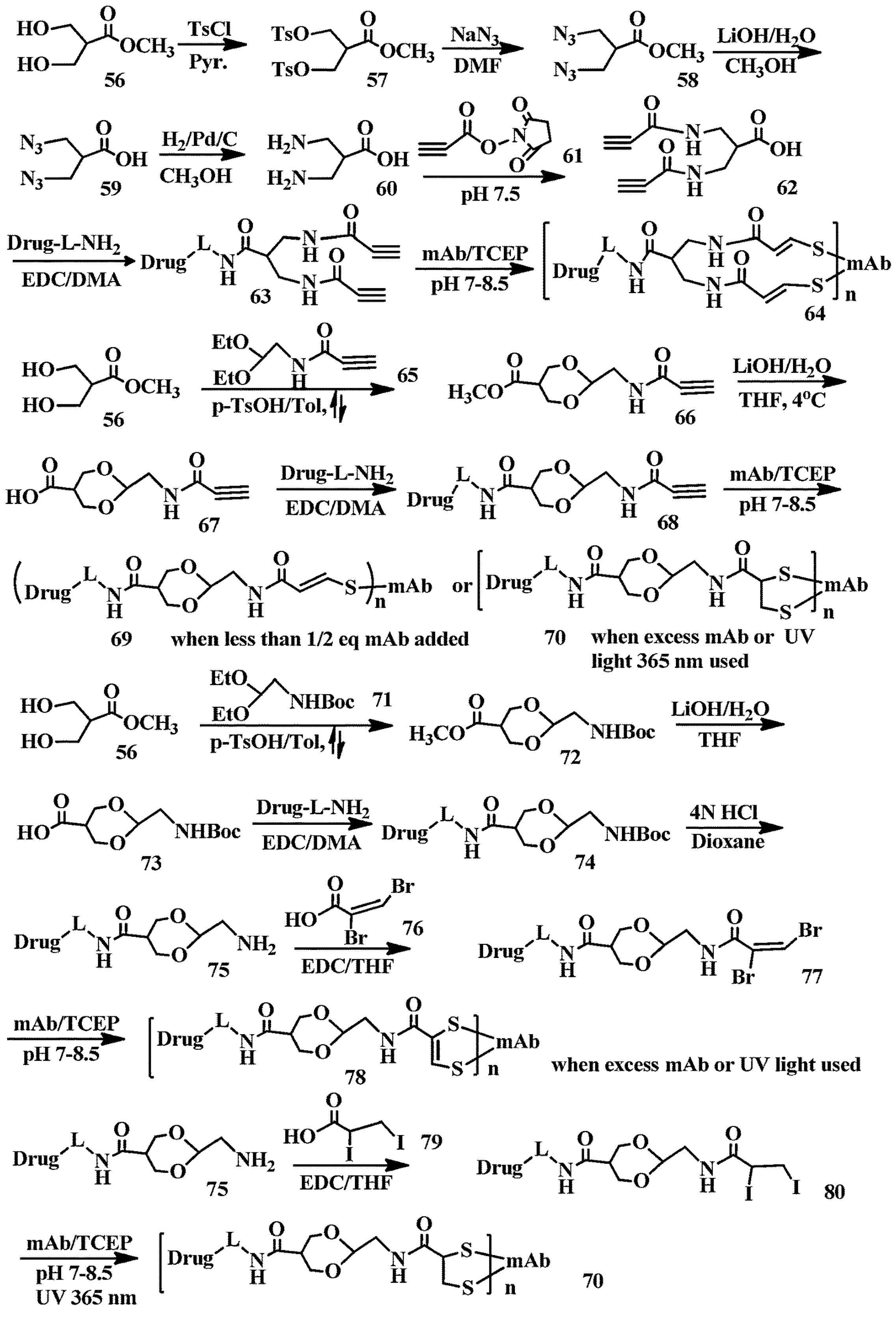
FIG. 4 shows the synthesis of the linkers of the patent application containing a drug, and the application of the linkers in the conjugation to an antibody via a pair of thiols.
Figure 5:
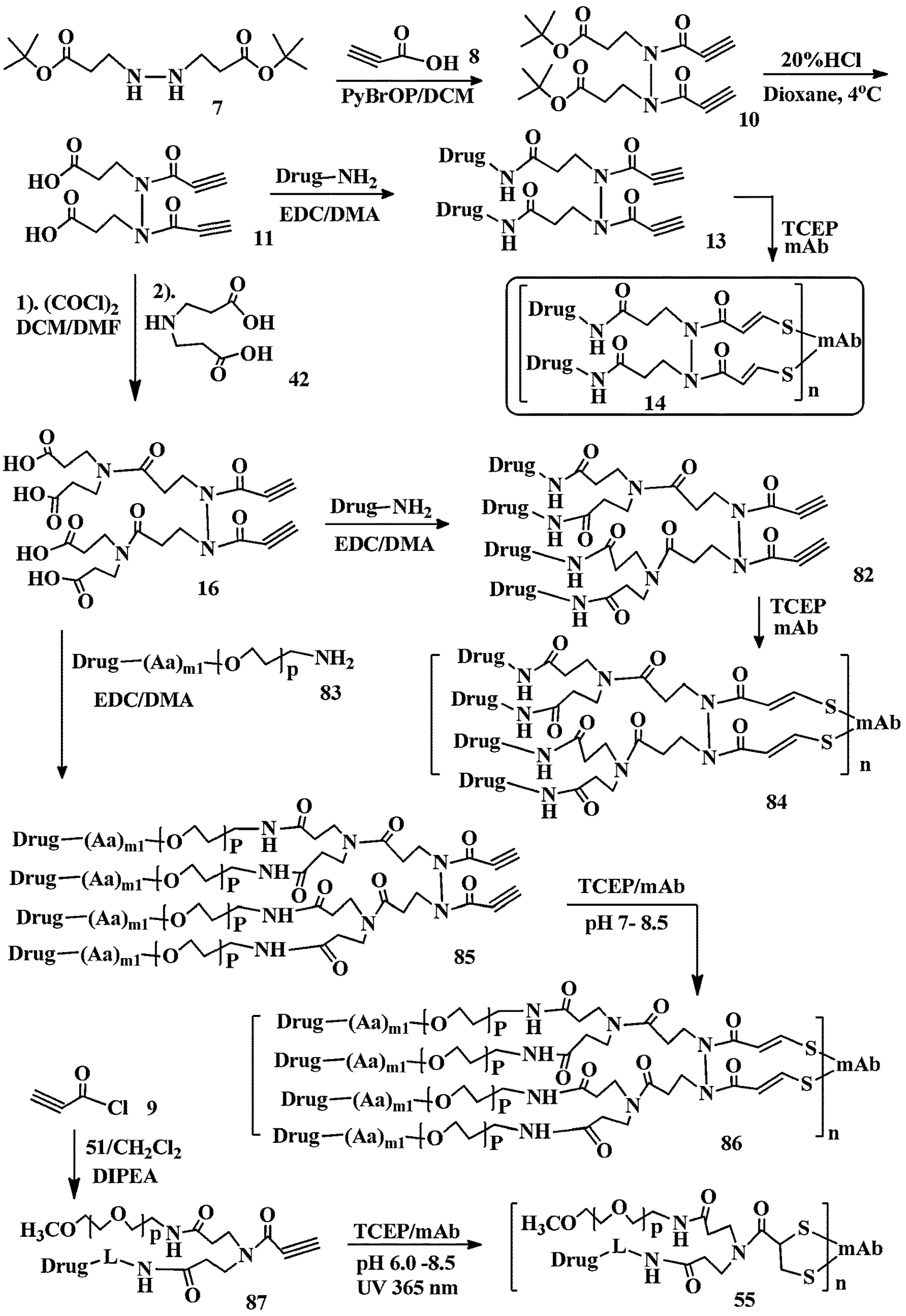
FIG. 5 shows the synthesis of the linkers of the patent application containing a drug, an amino acid, and a polyethylene glycol, and the application of the linkers in the conjugation to an antibody via a pair of thiols.
Figure 6:
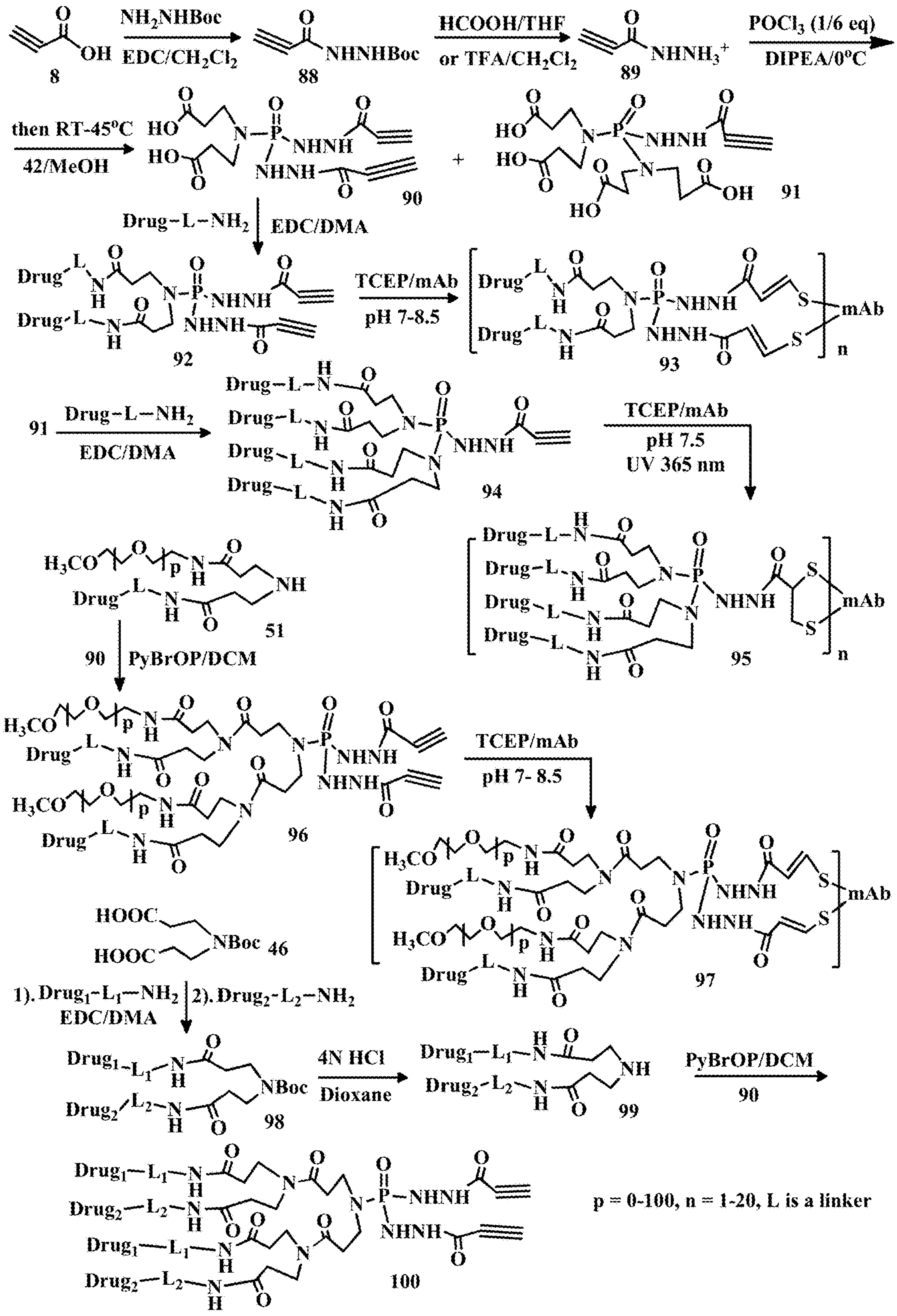
FIG. 6 shows the synthesis of the linkers containing a drug, a phosphamide and a polyethylene glycol, and the application of the linkers in the conjugation to an antibody via a pair of thiols.
Figure 7:
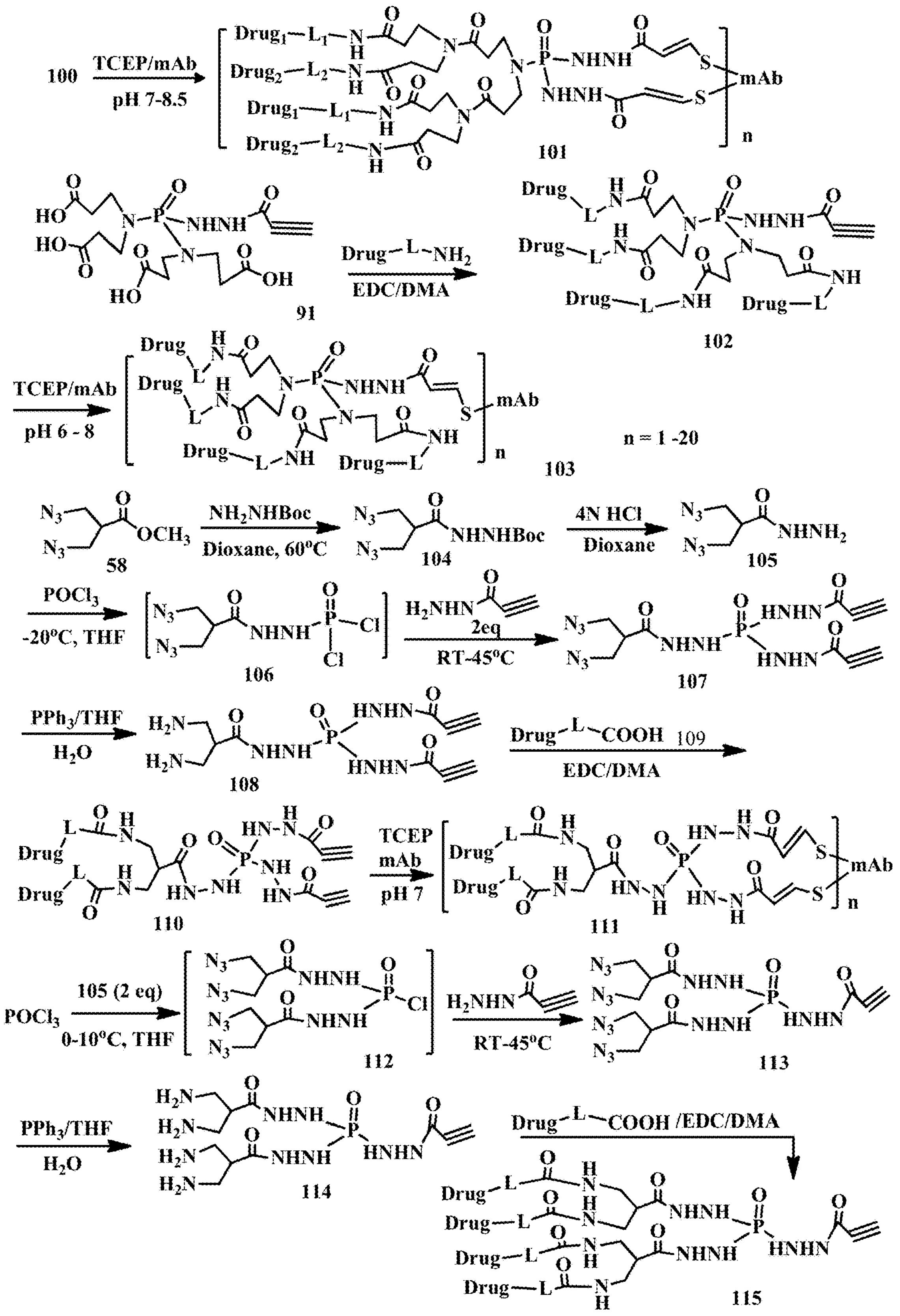
FIG. 7 shows the synthesis of the linkers containing a drug and a phosphamide, and the application of the linkers in the conjugation to an antibody via a pair of thiols.
Figure 8:
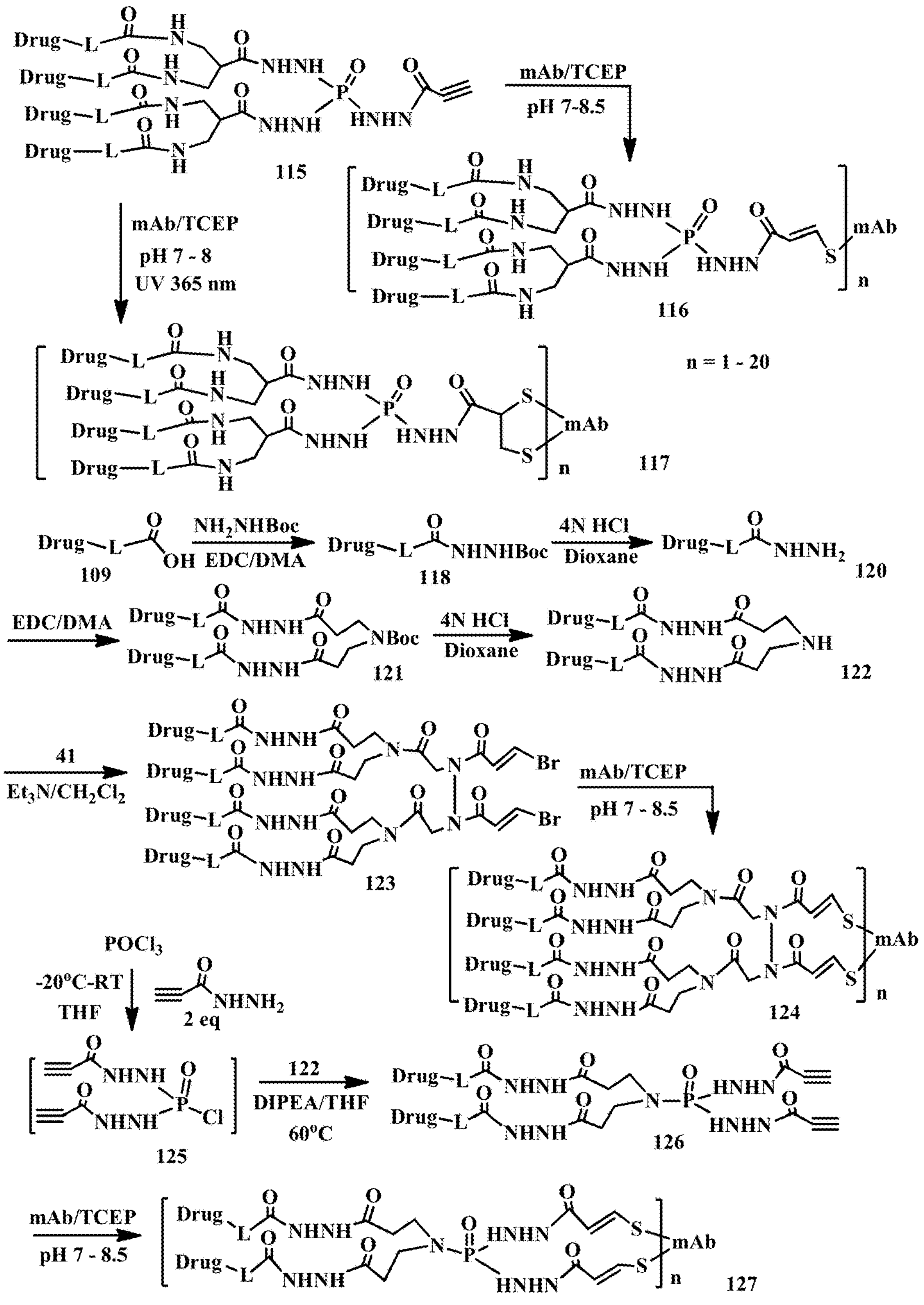
FIG. 8 shows the synthesis of the linkers containing drugs and a phosphamide, and the application of the linkers in the conjugation to an antibody via a pair of thiols.
Figure 9:
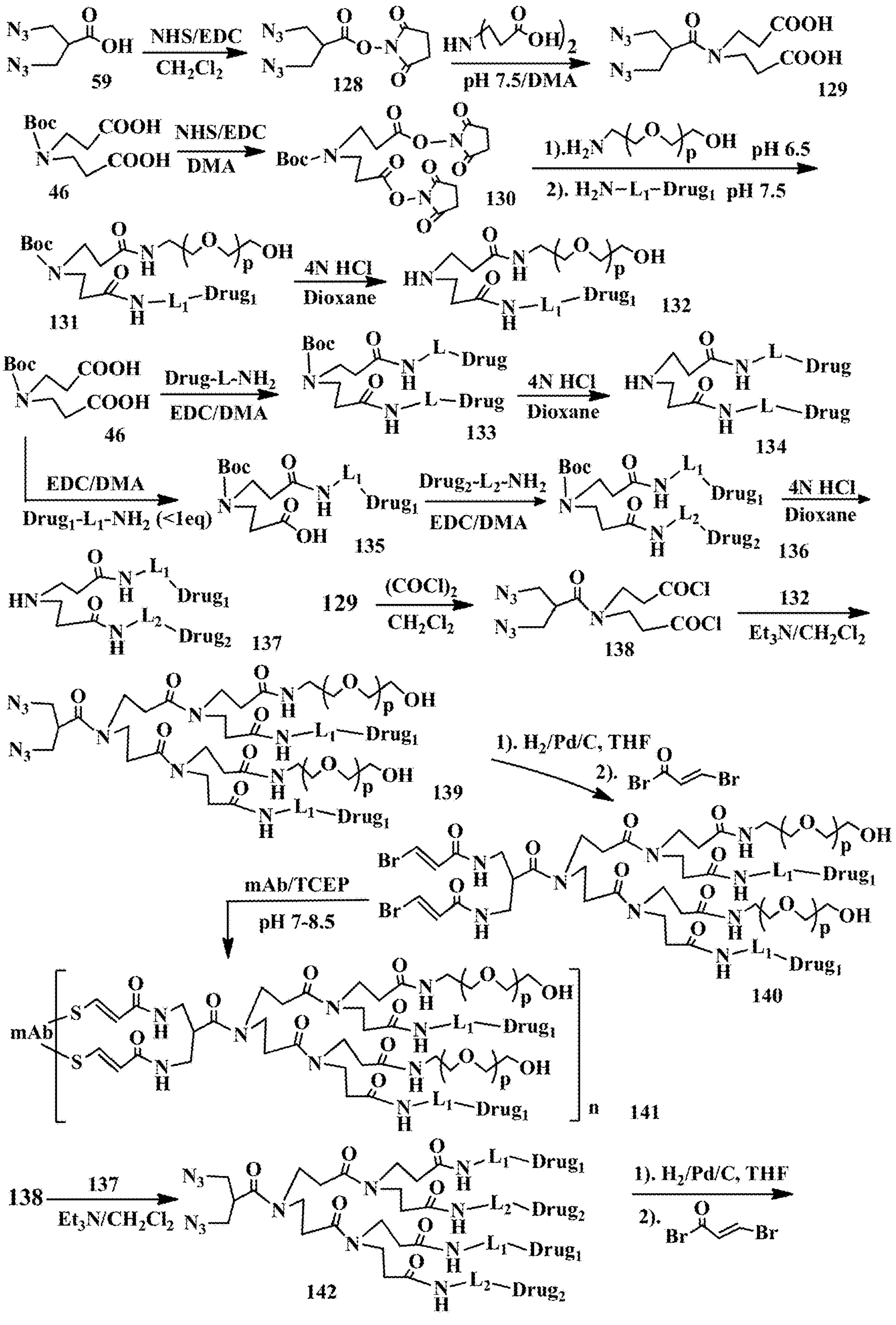
FIG. 9 shows the synthesis of the linkers of the patent application containing a drug and a polyethylene glycol, and the application of the linkers in the conjugation to an antibody via a pair of thiols.
Figure 10:
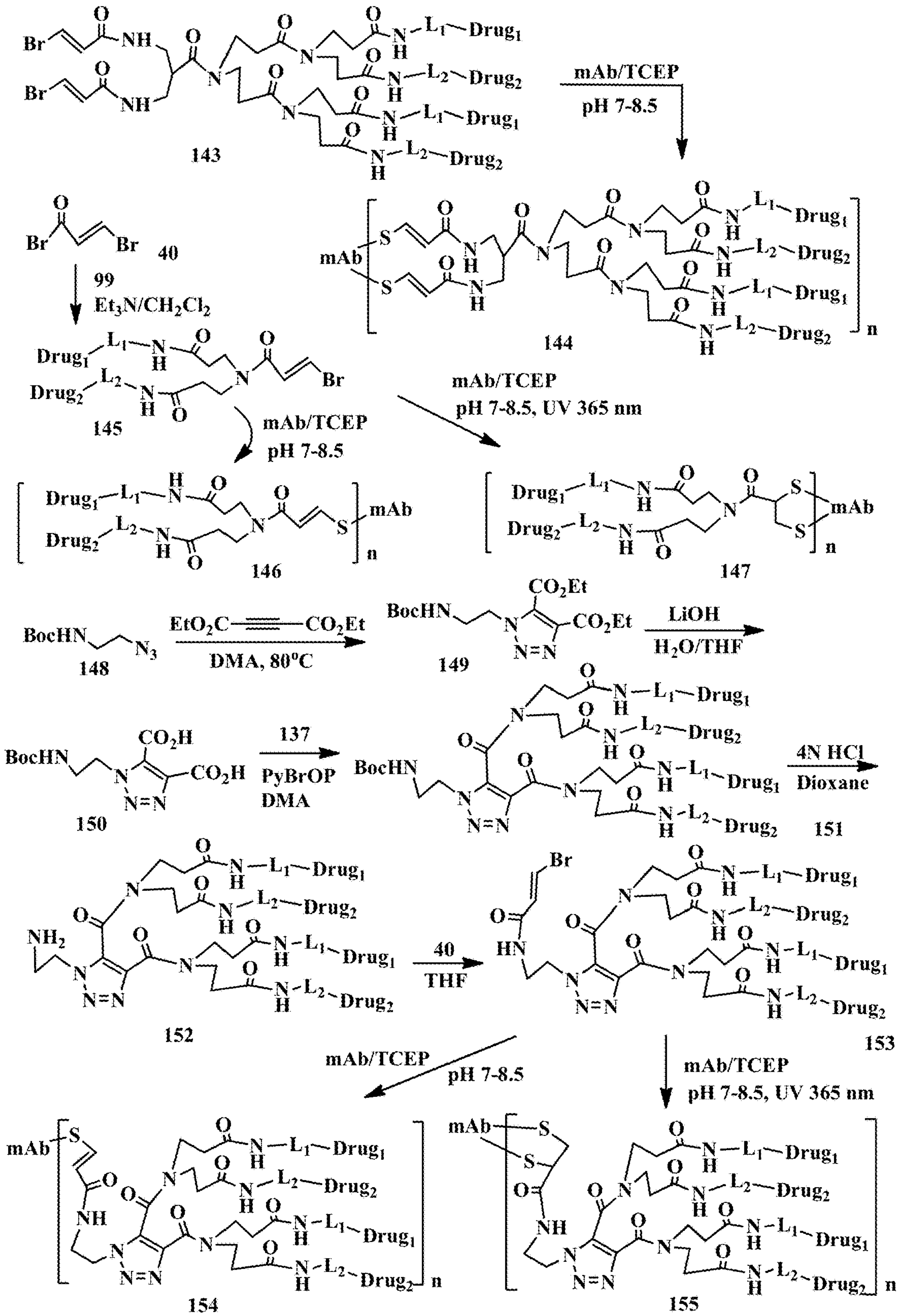
FIG. 10 shows the synthesis of the linkers of the patent application containing drugs and a linker component $L_1$ and $L_2$, and the application of the linkers in the conjugation to an antibody via a pair of thiols.
Figure 11:
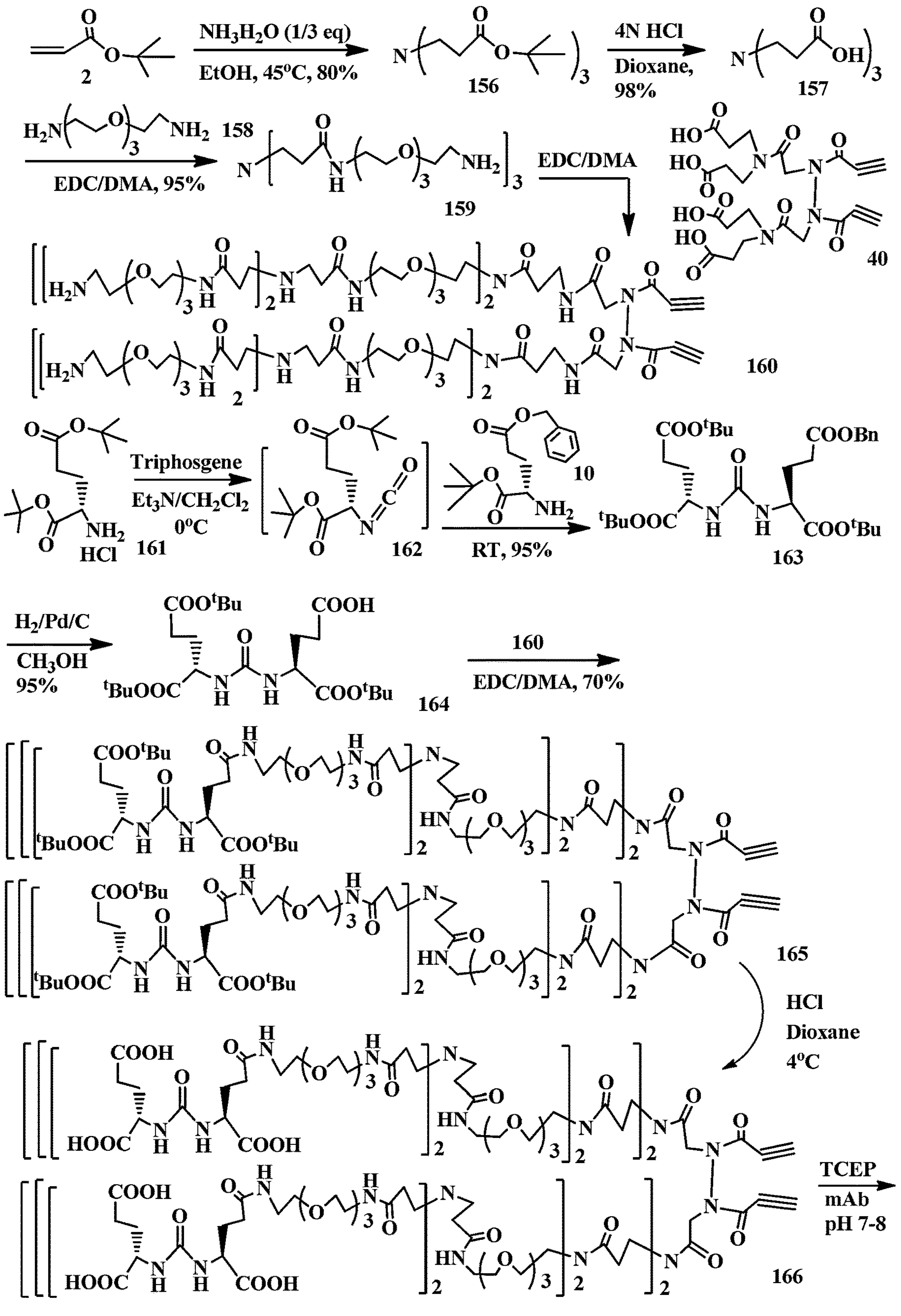
FIG. 11 shows the synthesis of the linkers of the patent application containing a prostate surface antigen (PSA) binding ligand.
Figure 12:
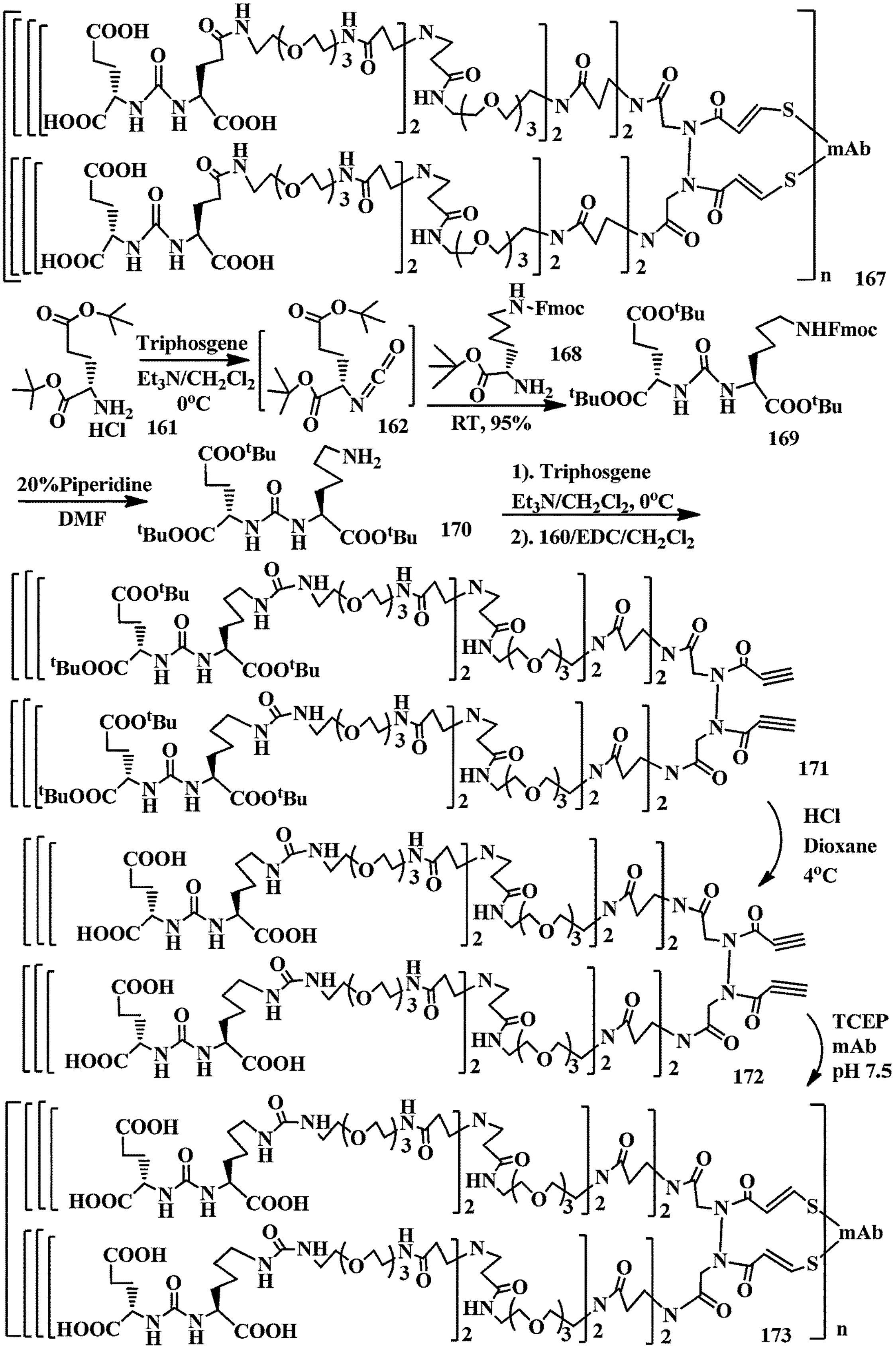
FIG. 12 shows the synthesis of the linkers containing a prostate surface antigen (PSA) binding ligand, and the application of the linkers in the conjugation to an antibody via a pair of thiols.
Figure 13:
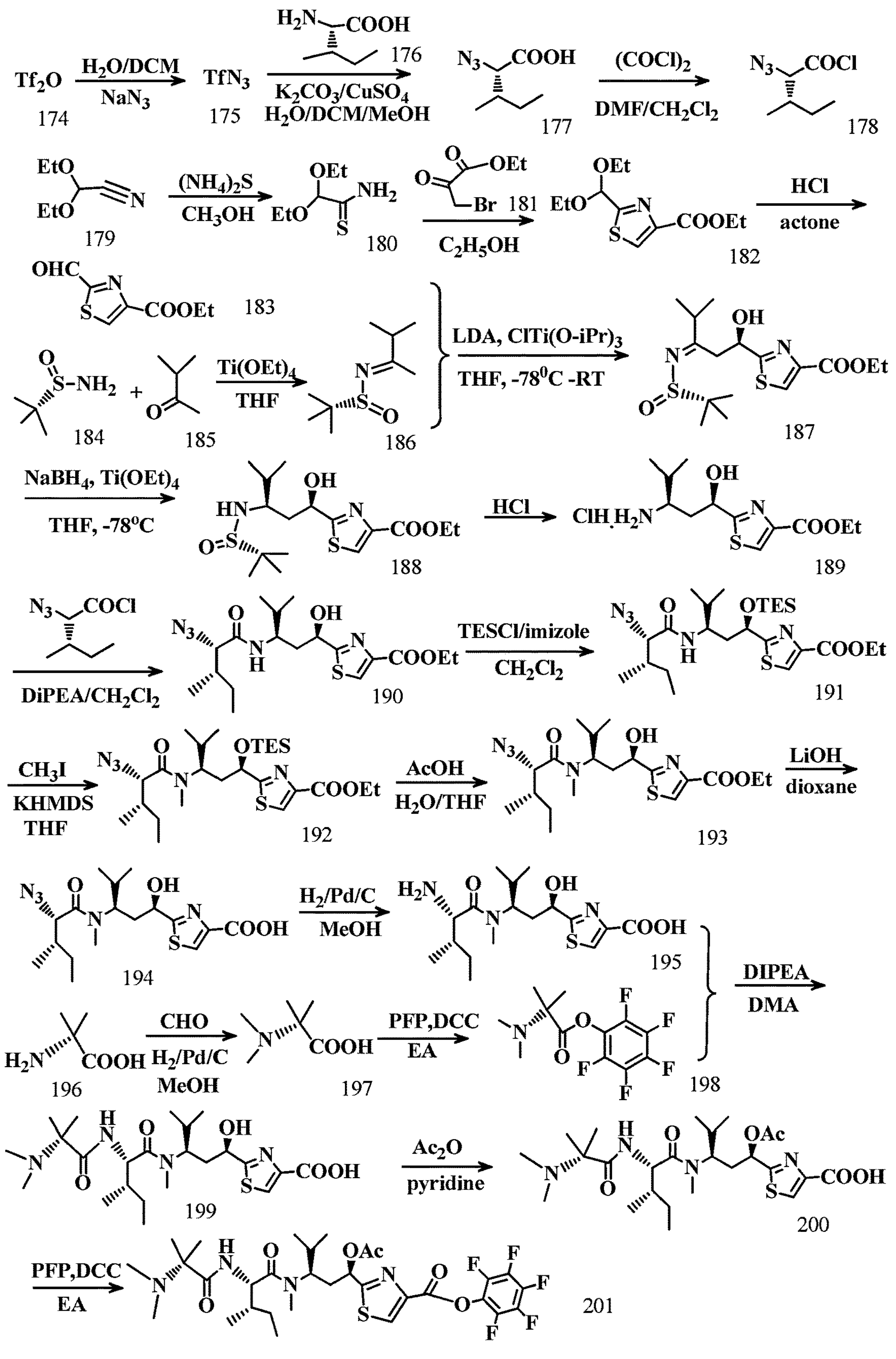
FIG. 13 shows the synthesis of intermediates of Tubulysin analogs.
Figure 14:
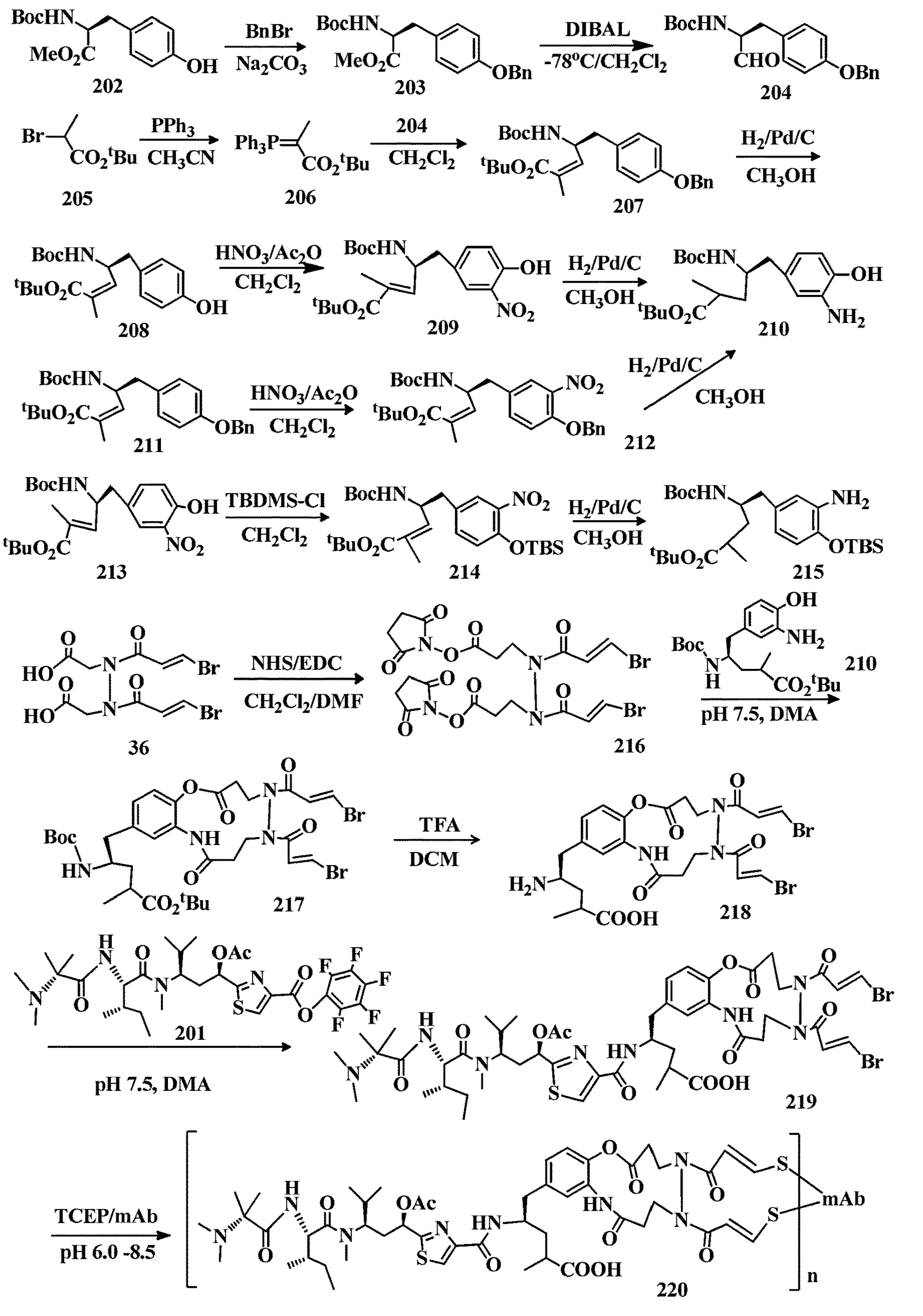
FIG. 14 shows the synthesis of a conjugatable Tubulysin analog, and the conjugate of antibody-tubulysin analog via a linker of this patent application.
Figure 15:
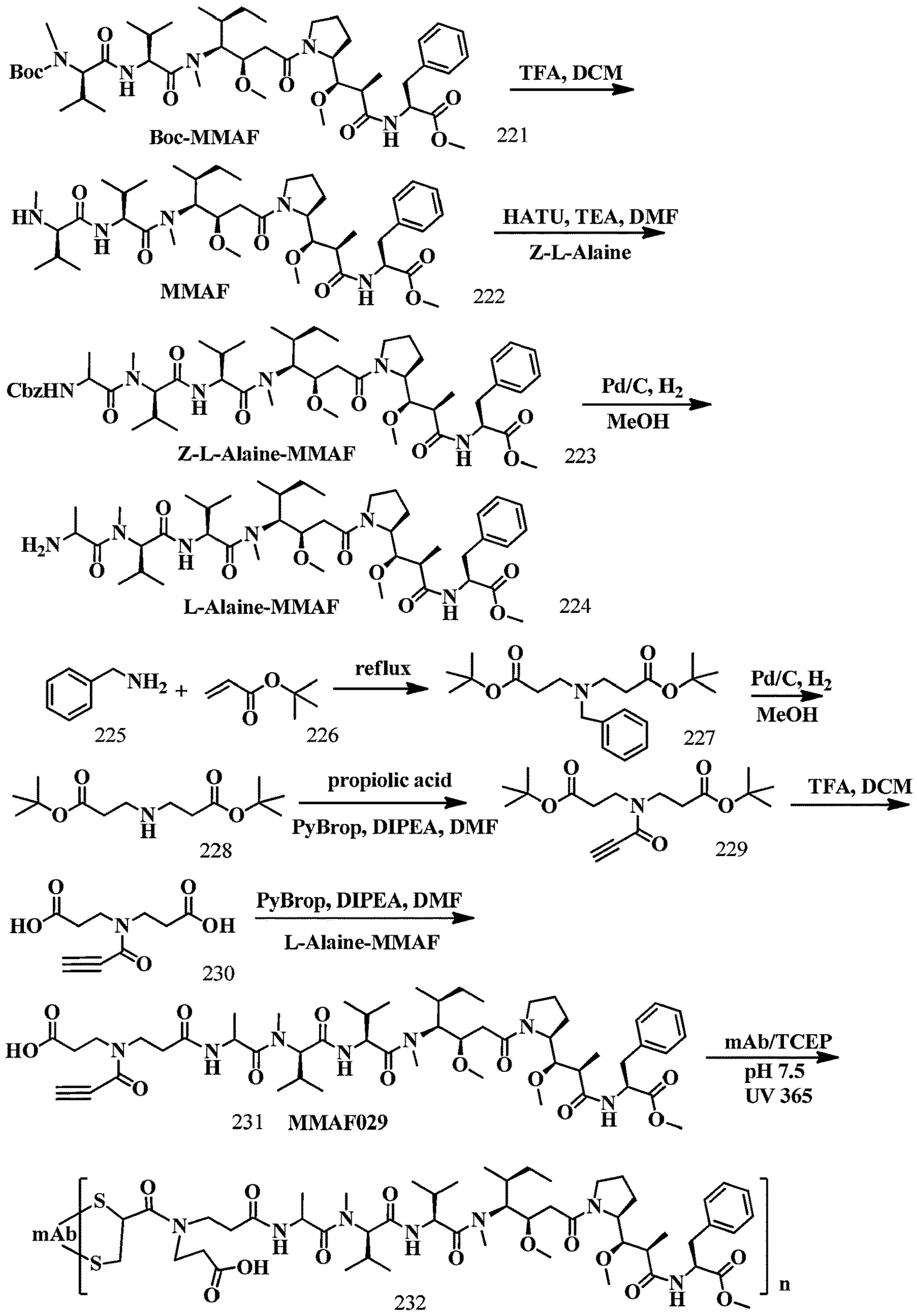
FIG. 15 shows the synthesis of a conjugate of antibody-MMAF analog via a linker of this patent application.
Figure 16:
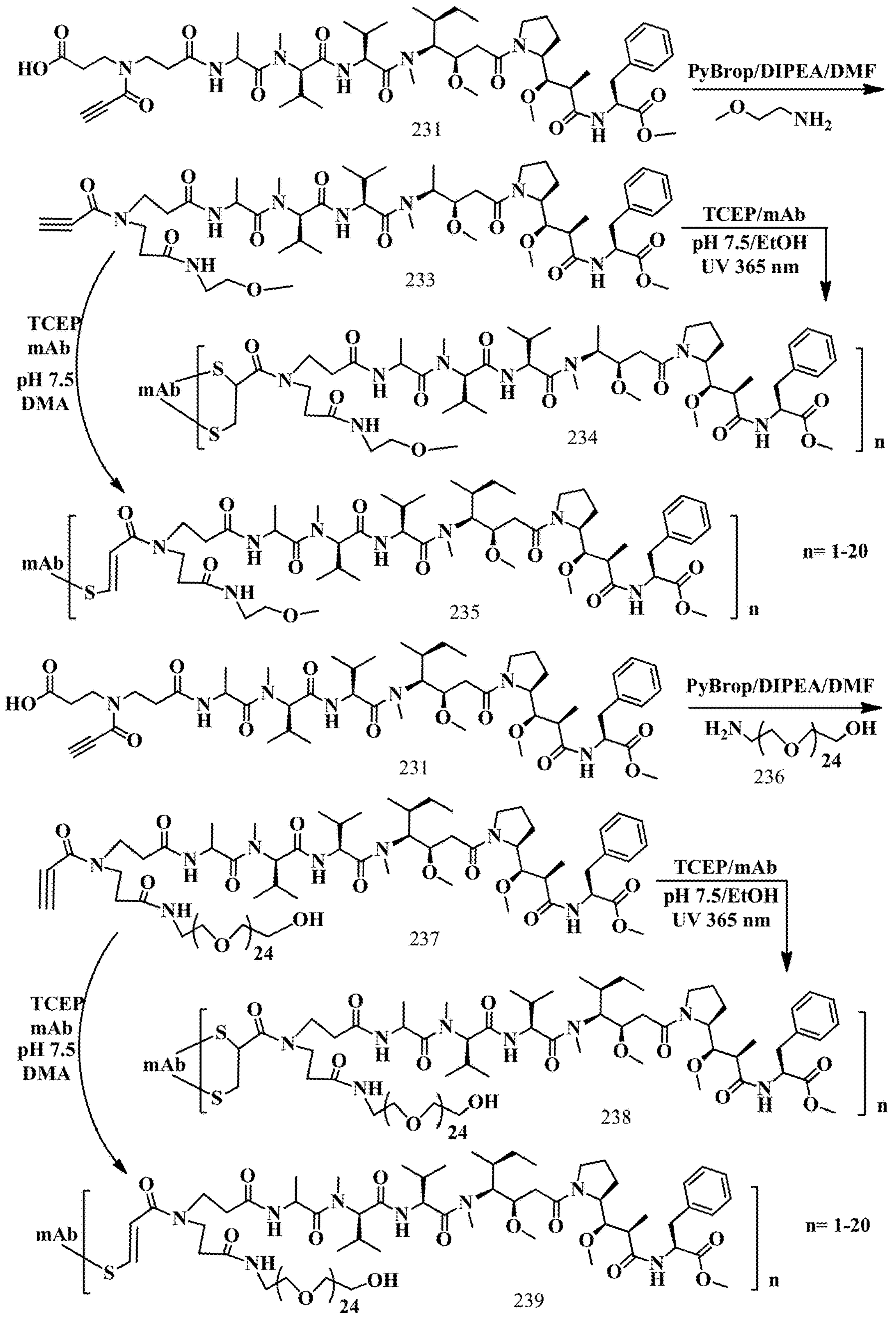
FIG. 16 shows the synthesis of a conjugate of antibody-MMAF analog via a linker of this patent application.
Figure 17:
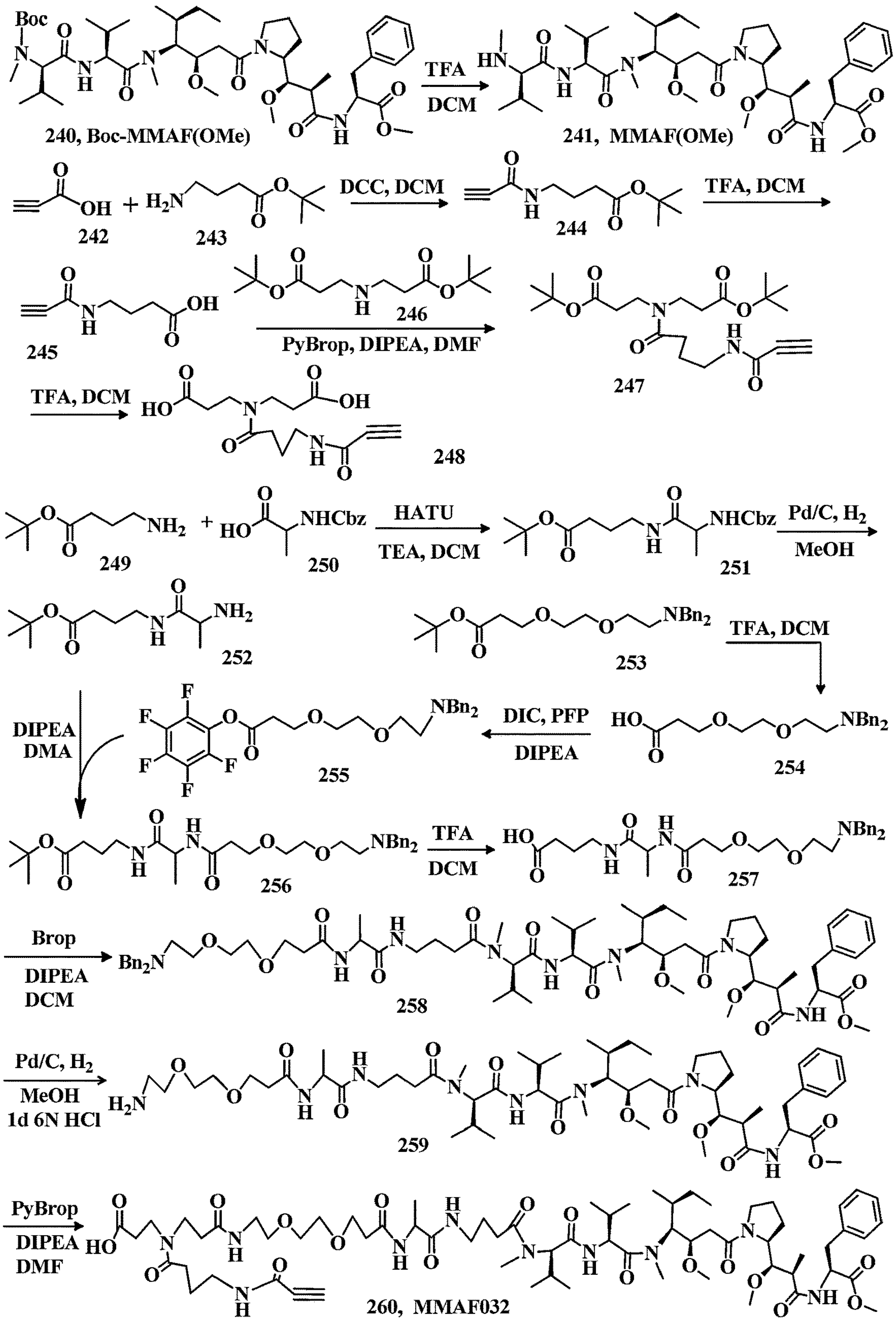
FIG. 17 shows the synthesis of a conjugate of antibody-MMAF analog via a linker of this patent application.
Figure 18:
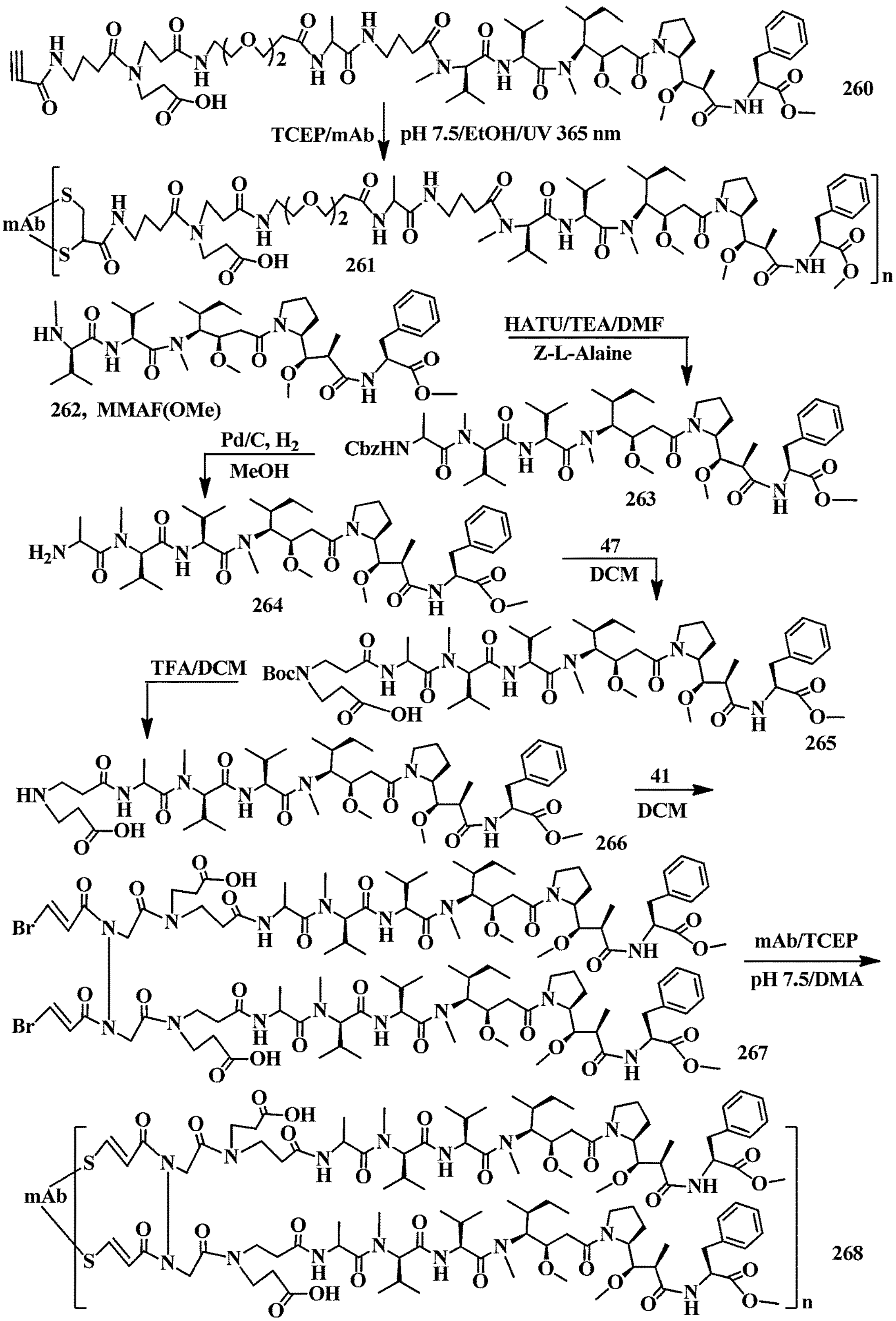
FIG. 18 shows the synthesis of a conjugate of antibody-MMAF analogs via a linker of this patent application.
Figure 19:
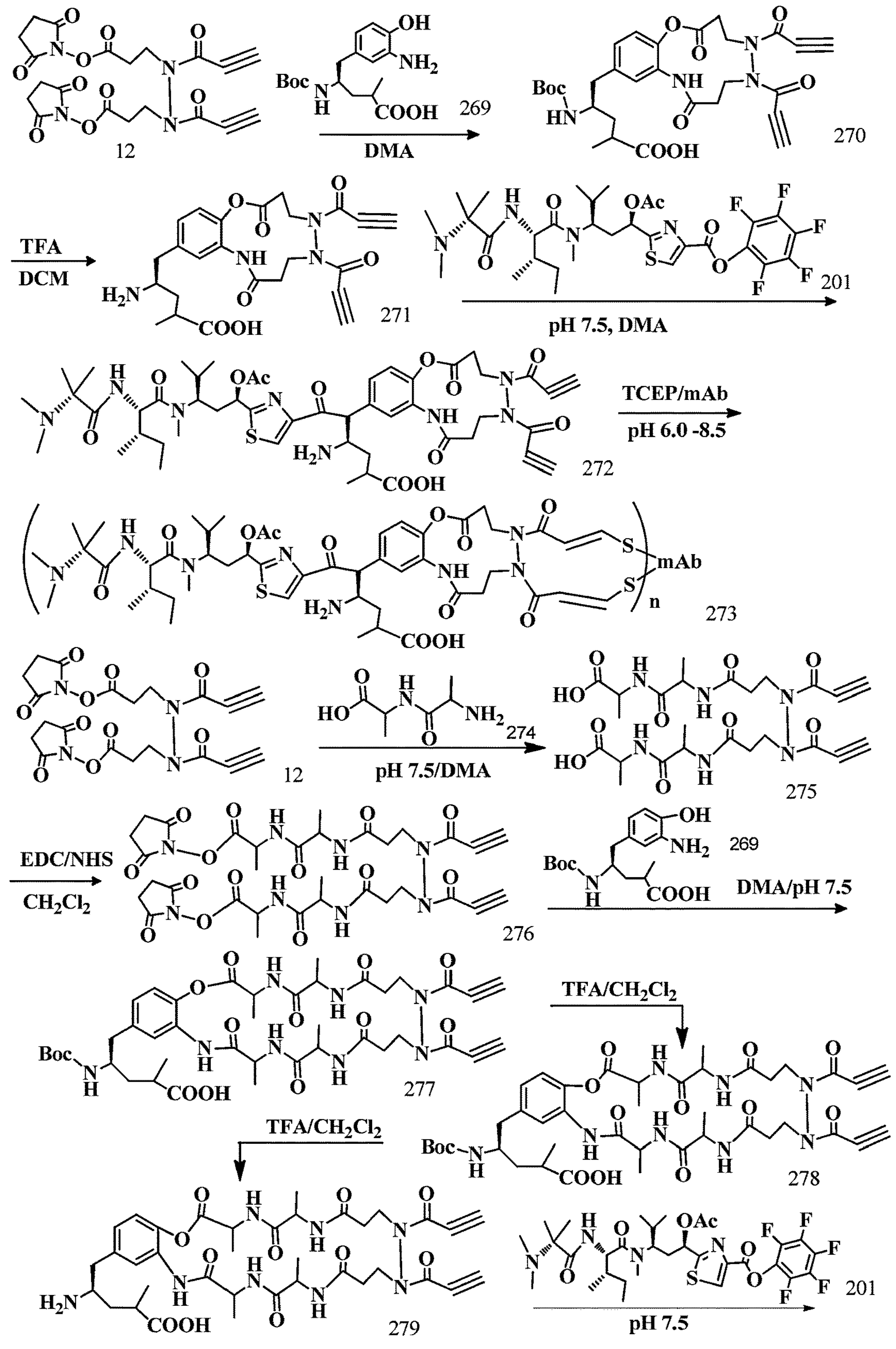
FIG. 19 shows the synthesis of components of Tubulysin analogs, and a conjugate of antibody-Tubulysin analog via a linker of this patent application.
Figure 20:
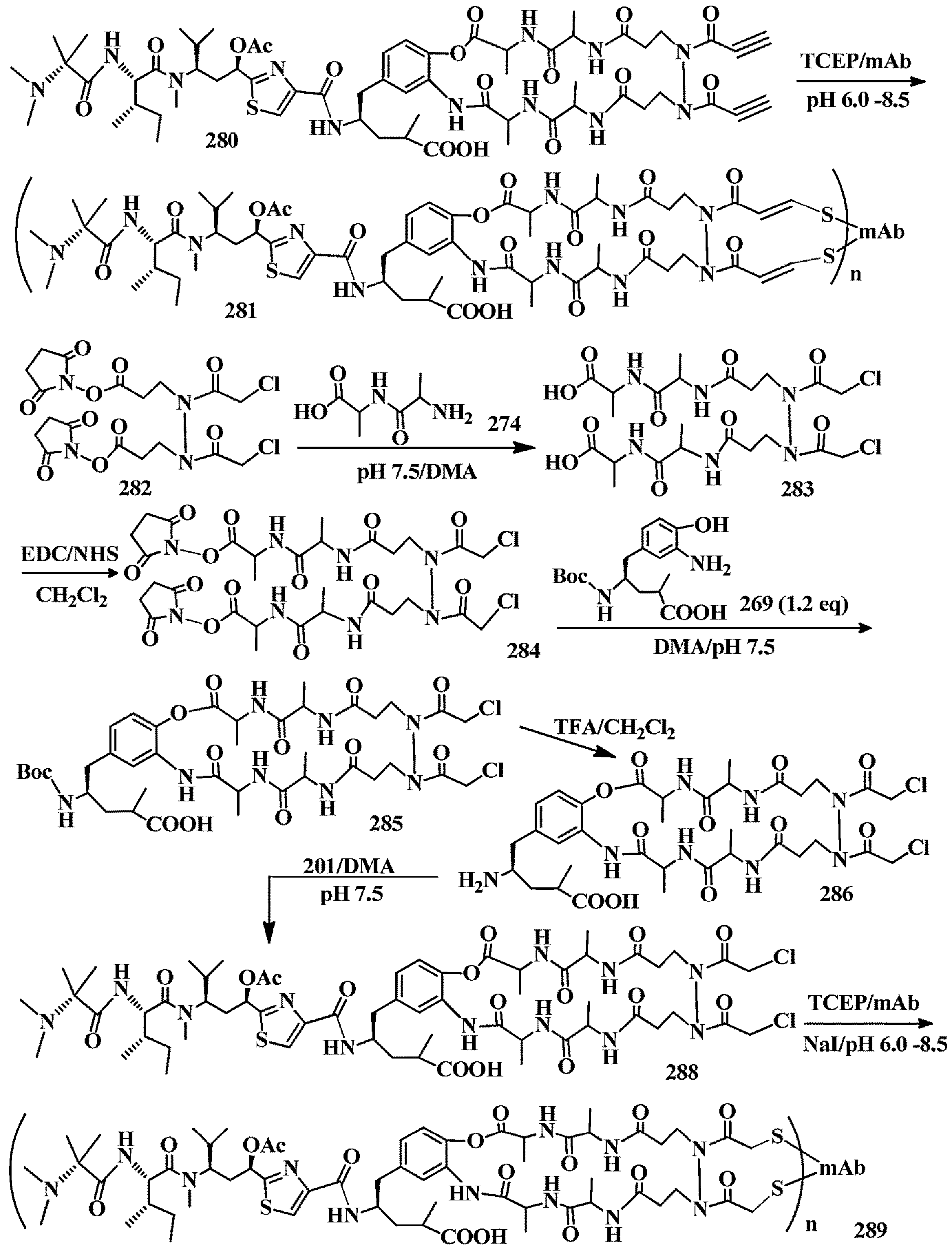
FIG. 20 shows the synthesis of conjugates of antibody-tubulysin analogs via the linkers of this patent application.
Figure 21:
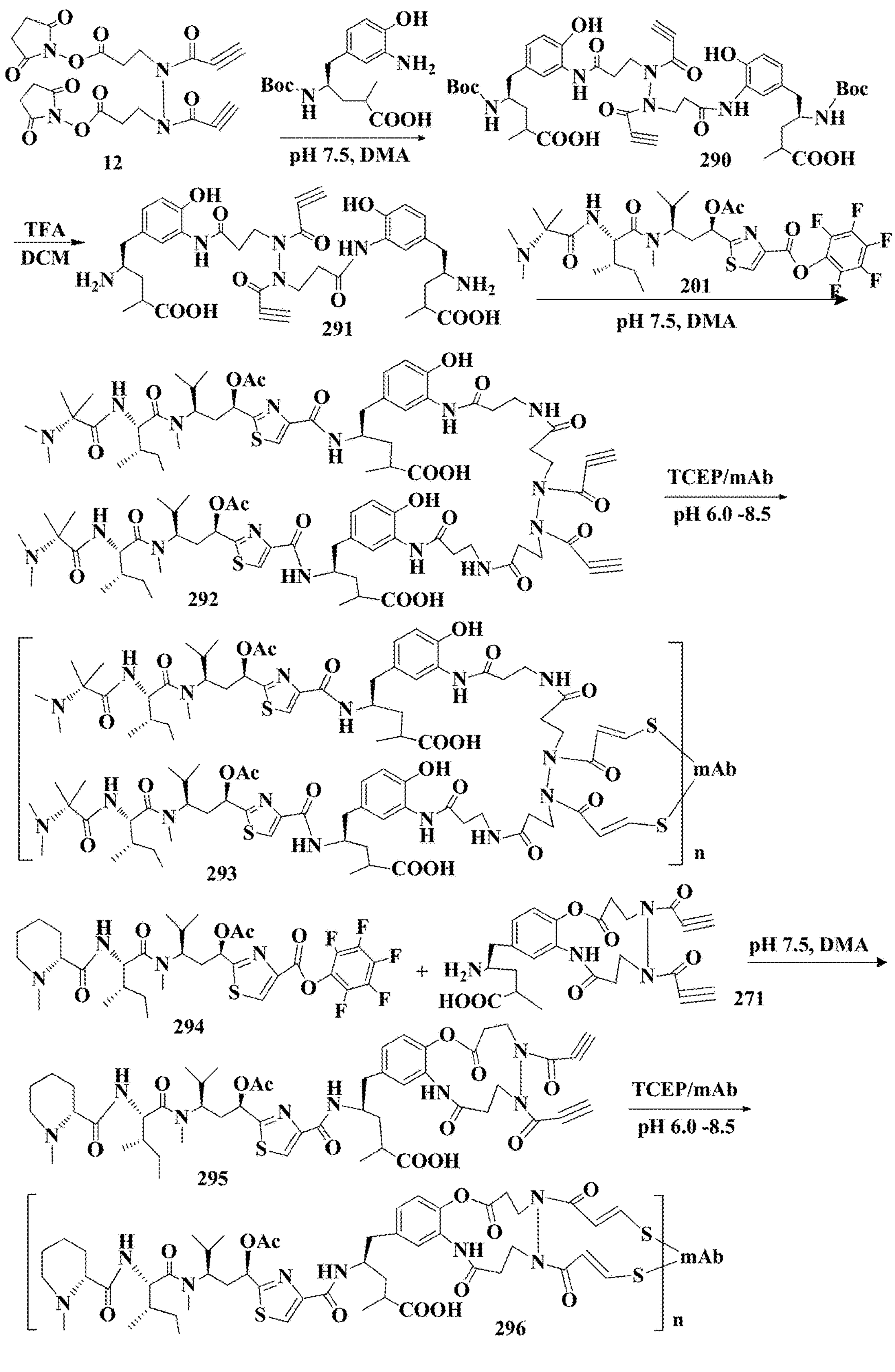
FIG. 21 shows the synthesis of conjugates of antibody-tubulysin analogs via the linkers of this patent application.
Figure 22:
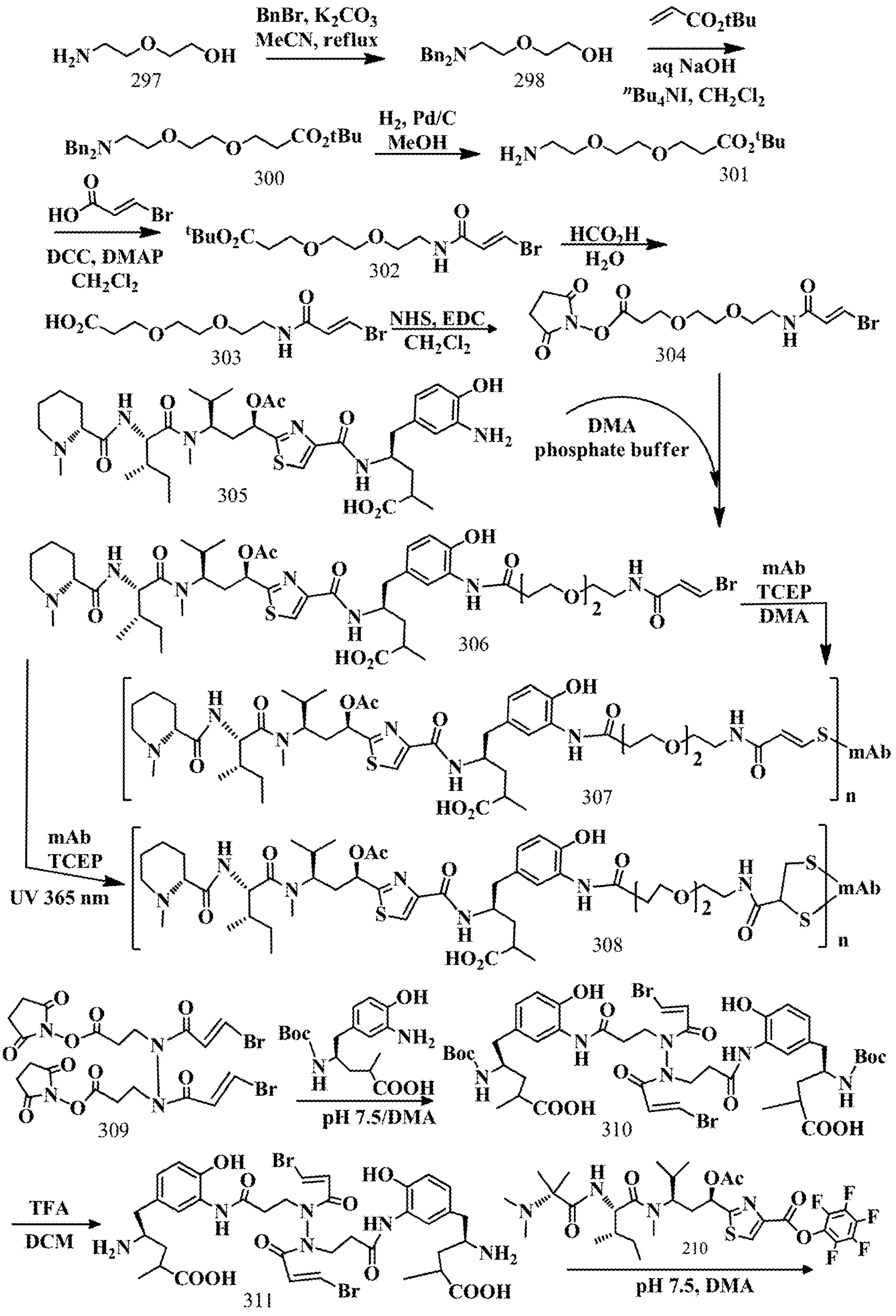
FIG. 22 shows the synthesis of a conjugate of antibody-tubulysin analog via a linker of this patent application.
Figure 23:
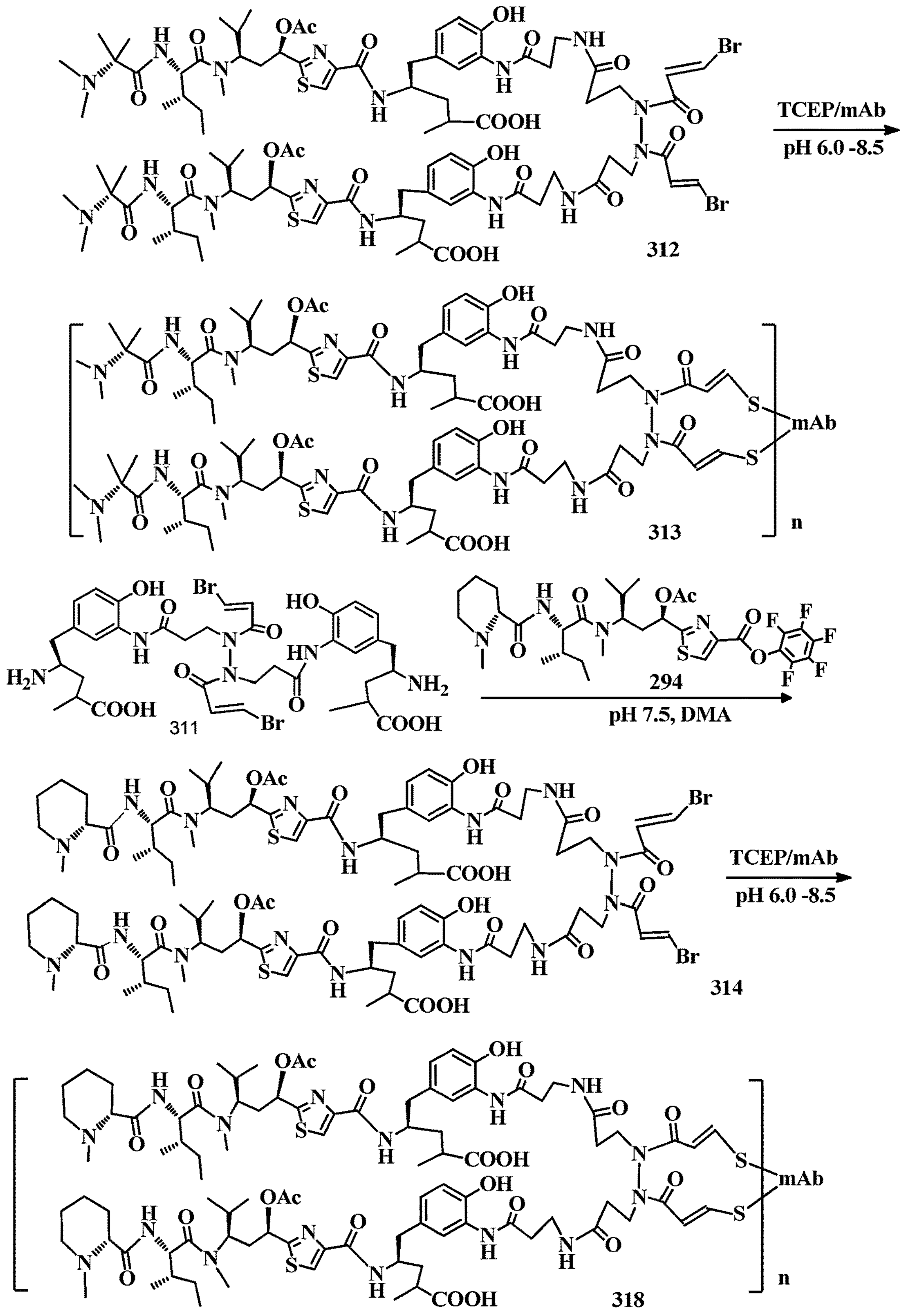
FIG. 23 shows the synthesis of conjugates of antibody-tubulysin analogs via the linkers of this patent application.
Figure 24:
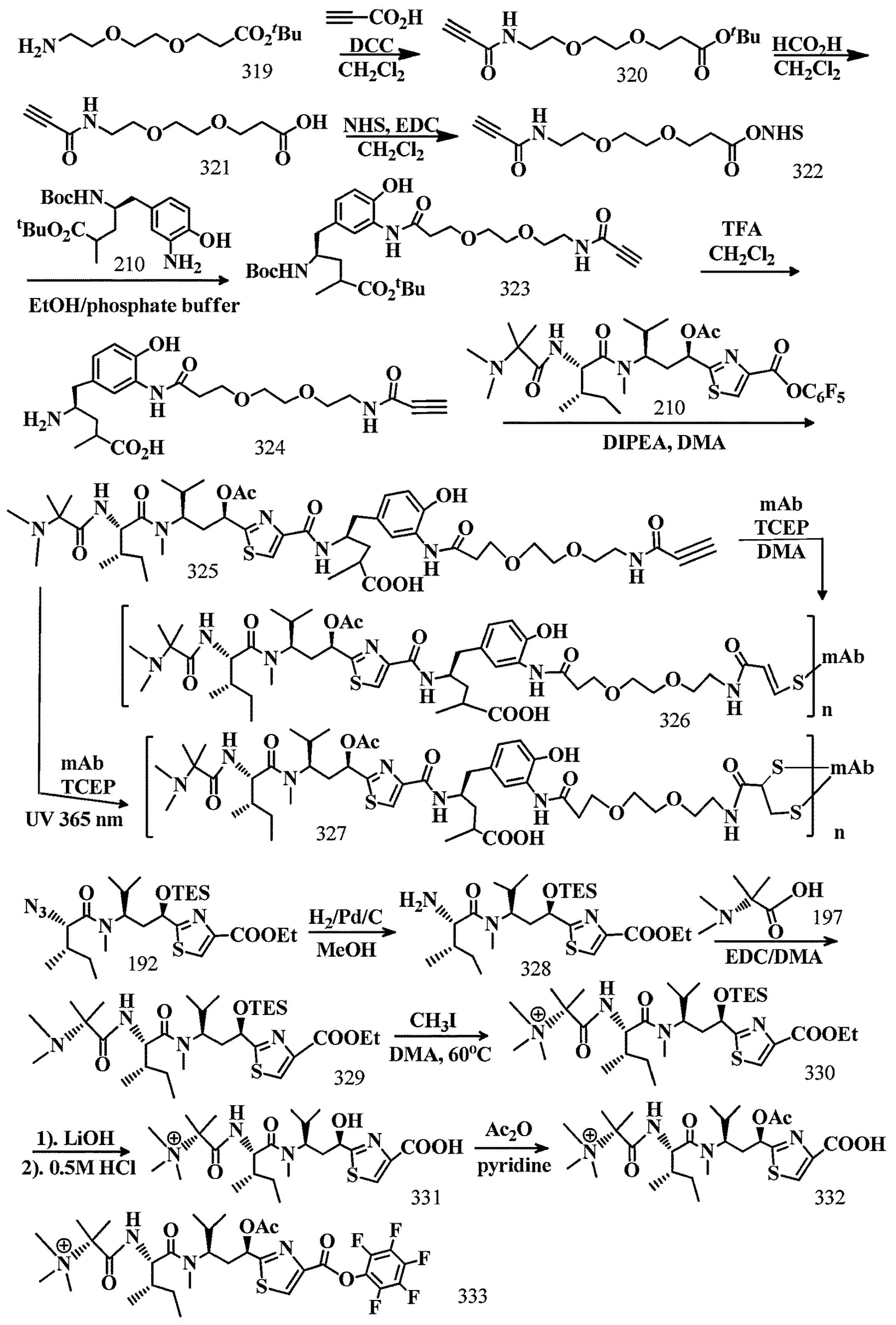
FIG. 24 shows the synthesis of conjugates of antibody-tubulysin analogs via the linkers of this patent application.
Figure 25:
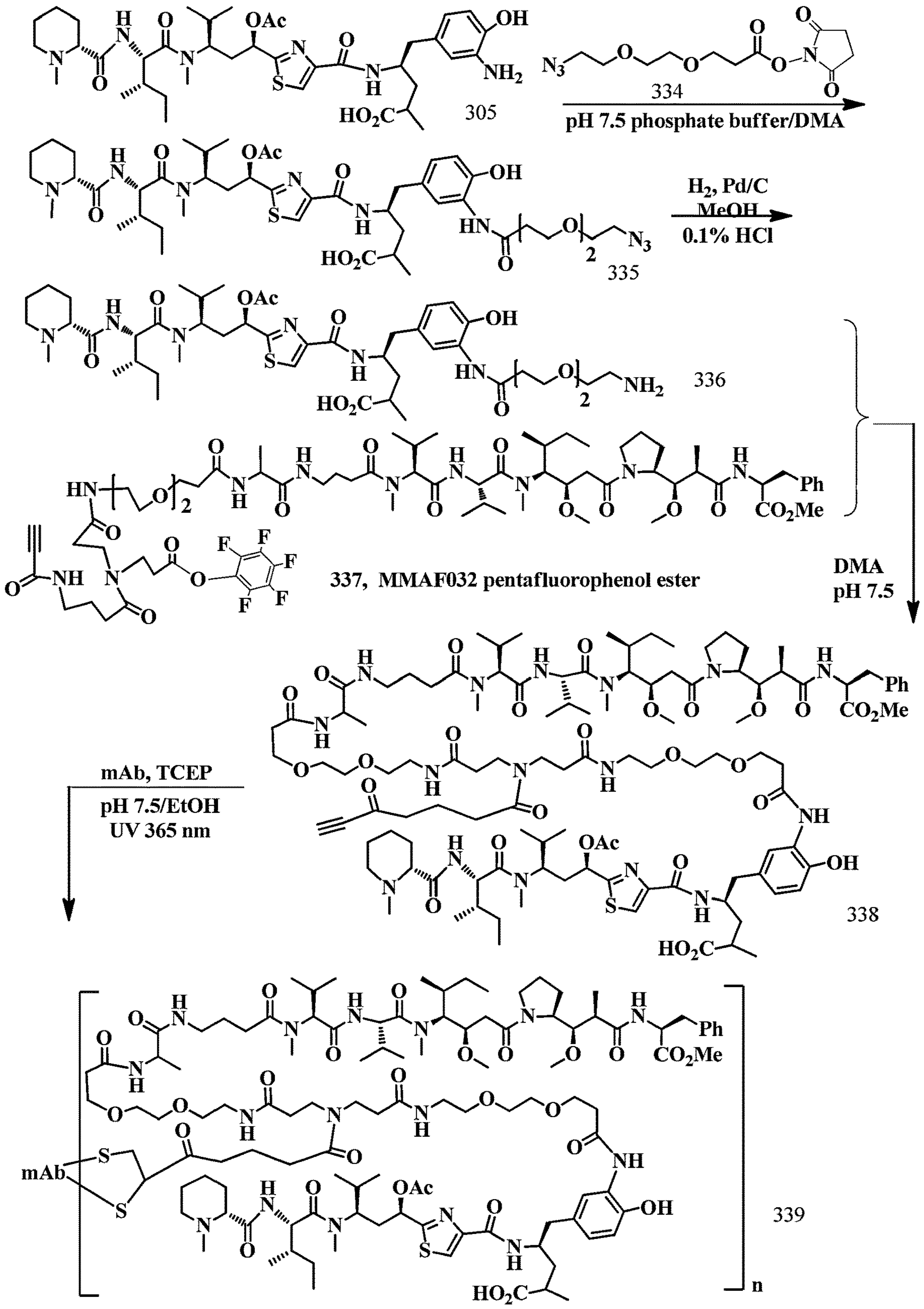
FIG. 25 shows the synthesis of a conjugate containing both MMAF analog and tubulysin analog via a linker of this patent application.
Figure 26:
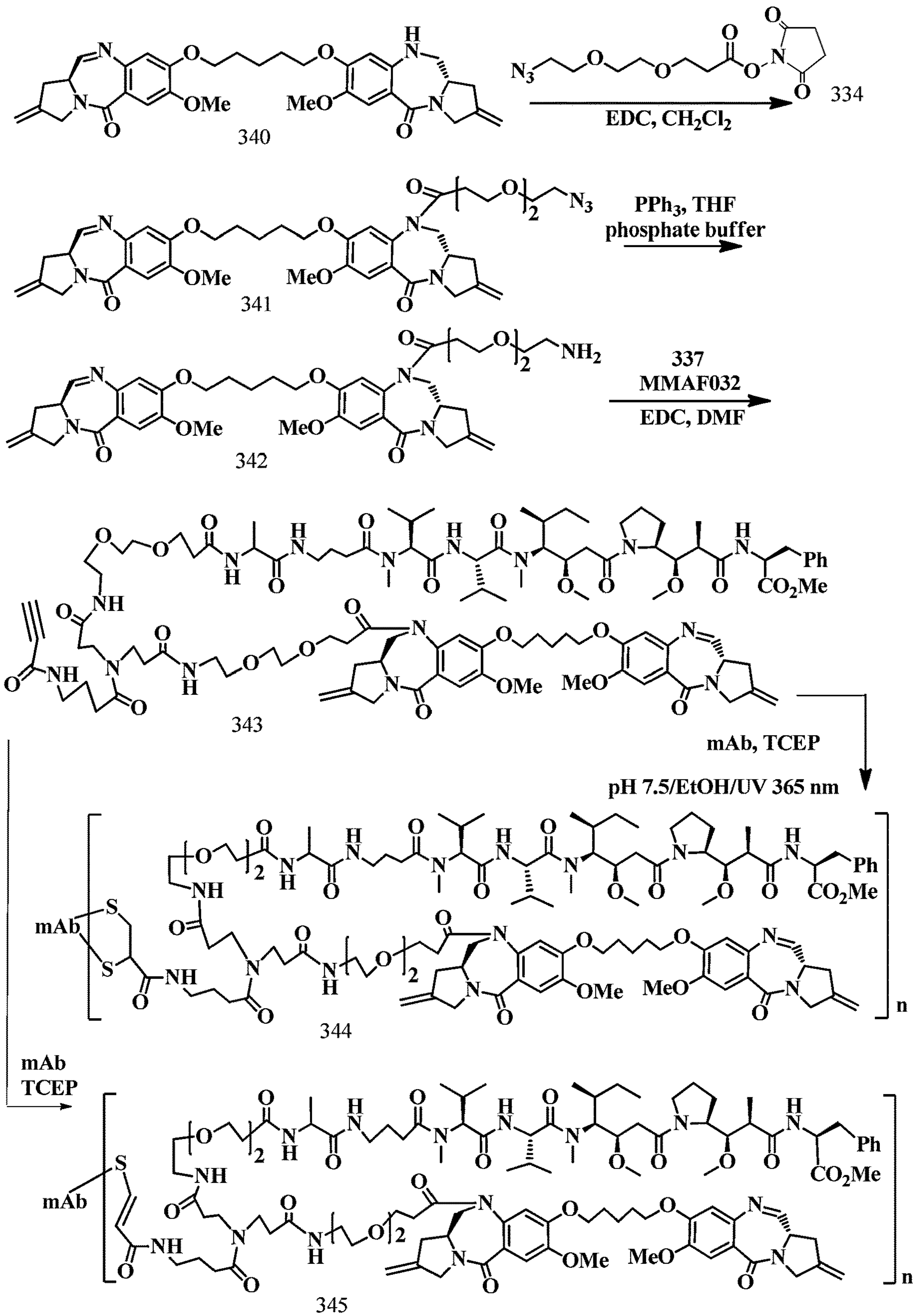
FIG. 26 shows the synthesis of a conjugate containing both MMAF analog and PBD dimer analog via a linker of this patent application.
Figure 27:
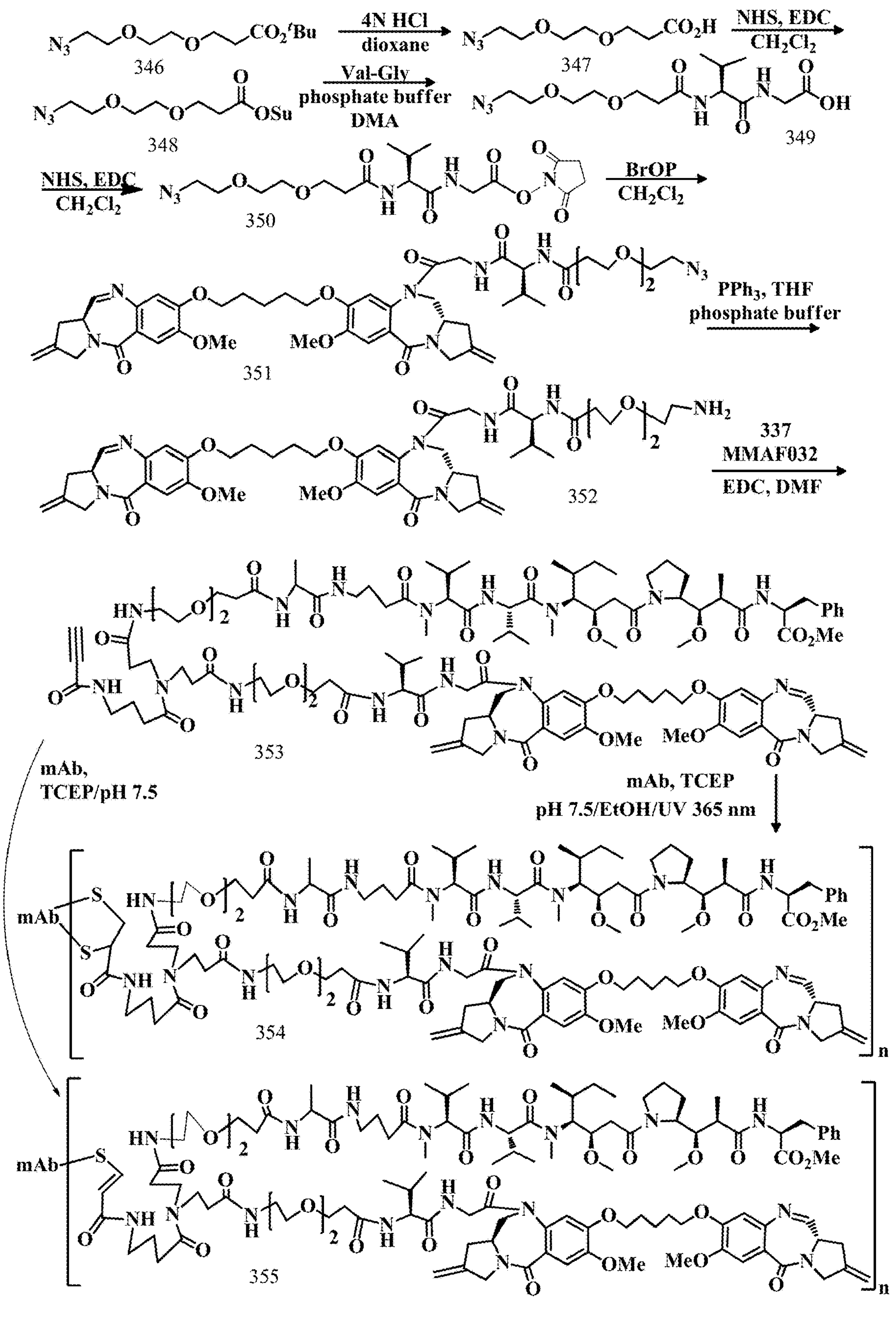
FIG. 27 shows the synthesis of a conjugate containing both MMAF analog and PBD dimer analog via a linker of this patent application.
Figure 28:
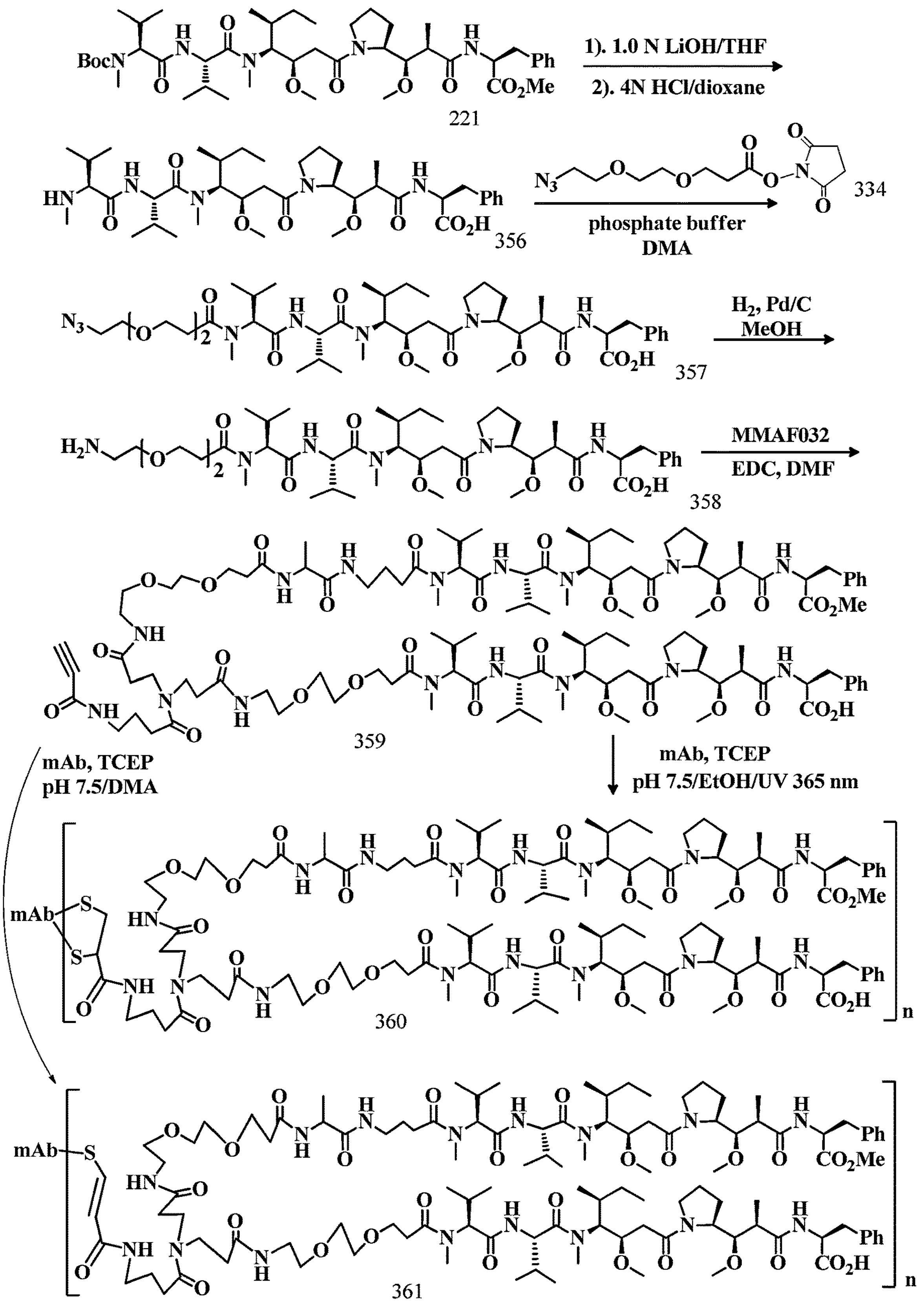
FIG. 28 shows the synthesis of a conjugate containing two MMAF analogs via a linker of this patent application.
Figure 29:
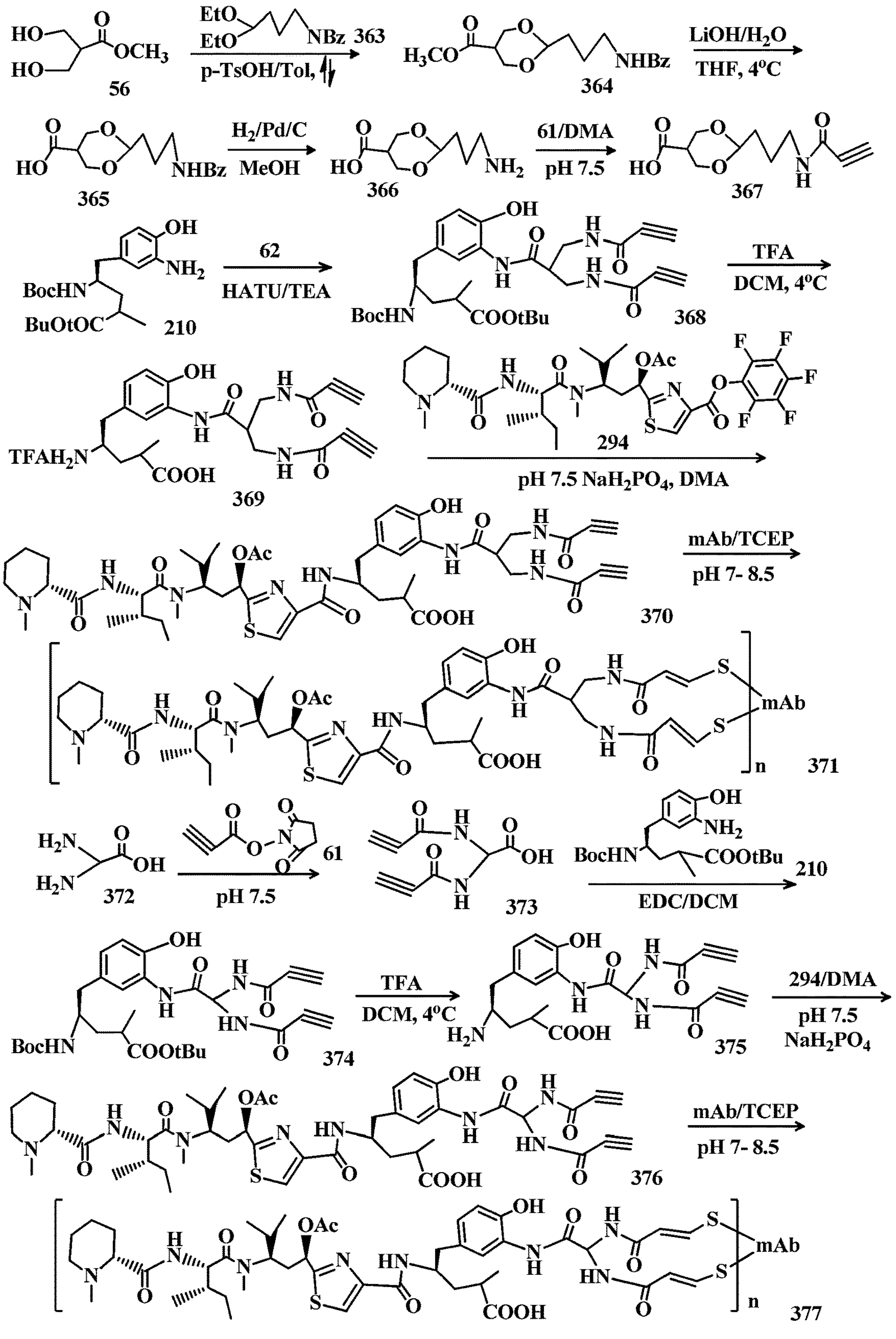
FIG. 29 shows the synthesis of conjugates of antibody-tubulysin analogs via the linkers of this patent application.
Figure 30:
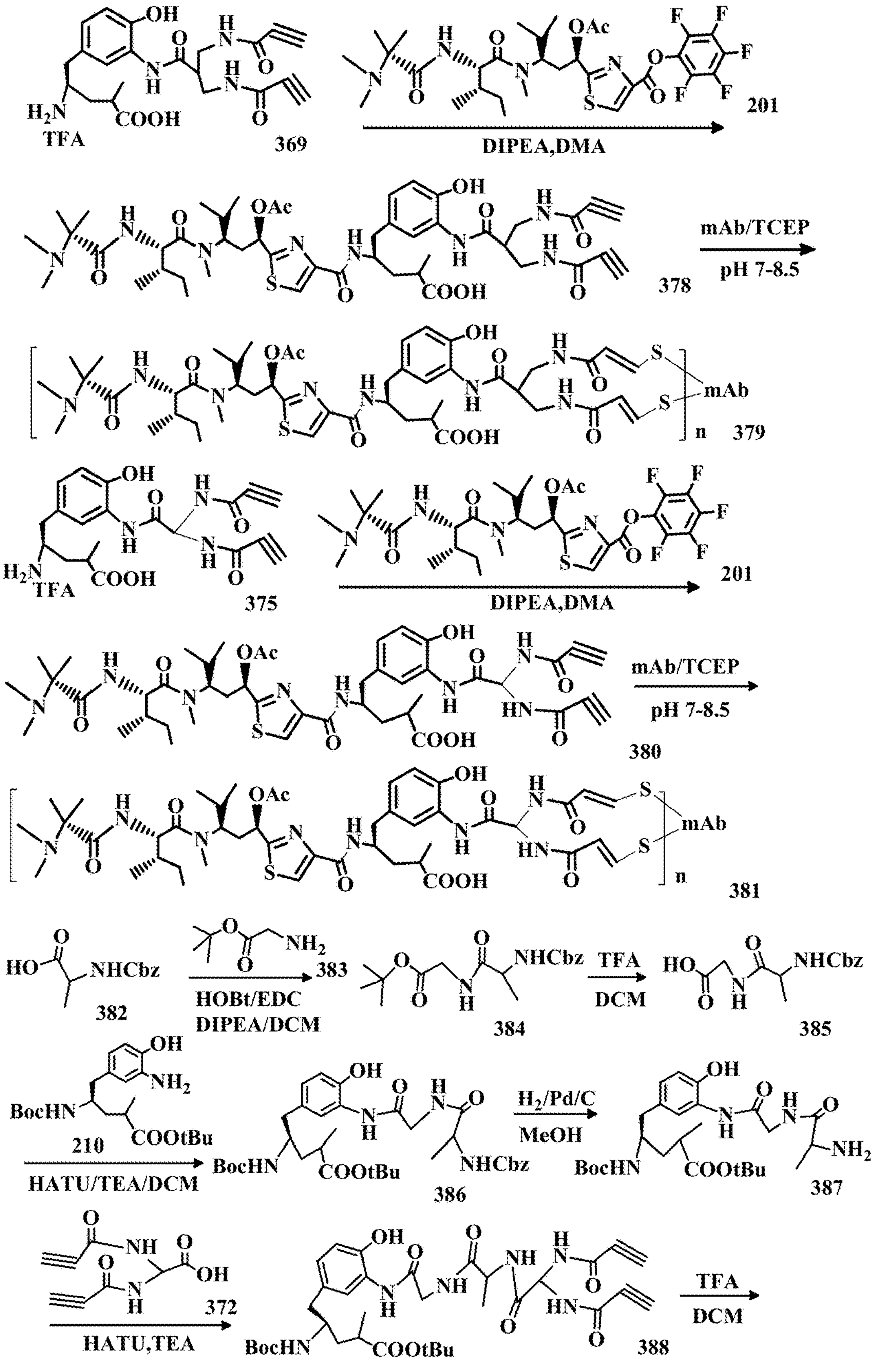
FIG. 30 shows the synthesis of conjugates of antibody-tubulysin analogs via the linkers of this patent application.
Figure 31:
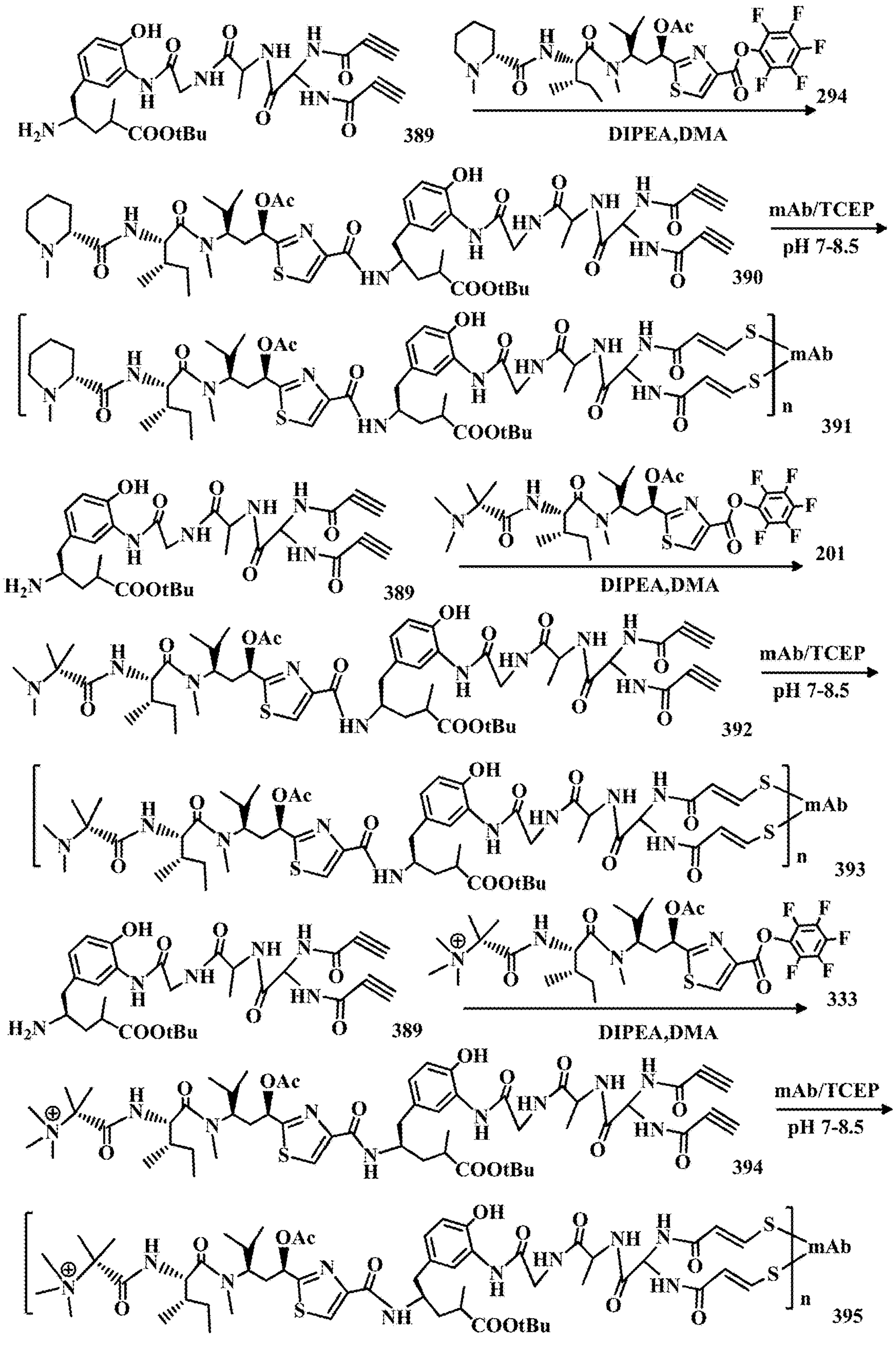
FIG. 31 shows the synthesis of conjugates of antibody-tubulysin analogs via the linkers of this patent application.
Figure 32:
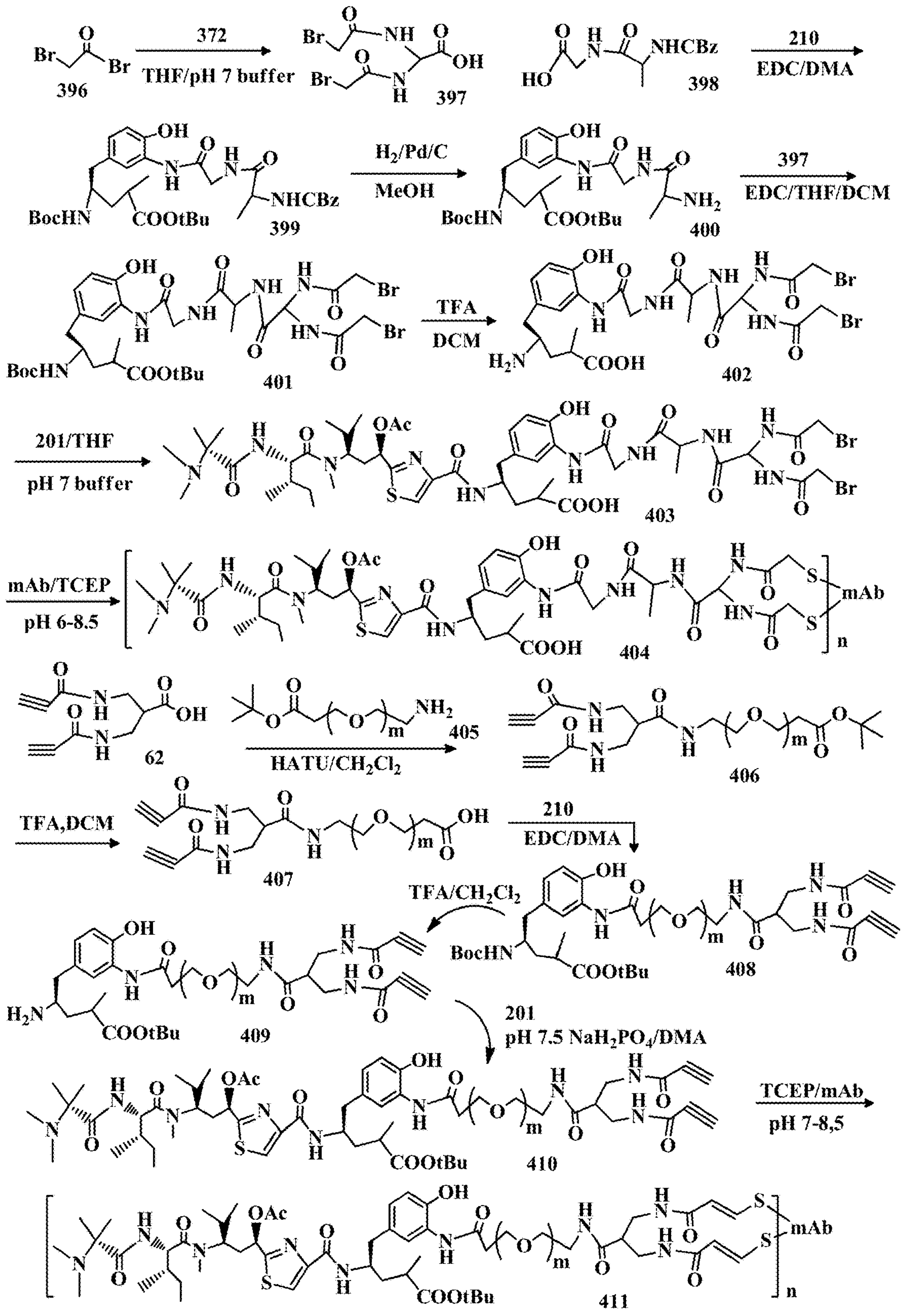
FIG. 32 shows the synthesis of conjugates of antibody-tubulysin analogs via the linkers of this patent application.
Figure 33:
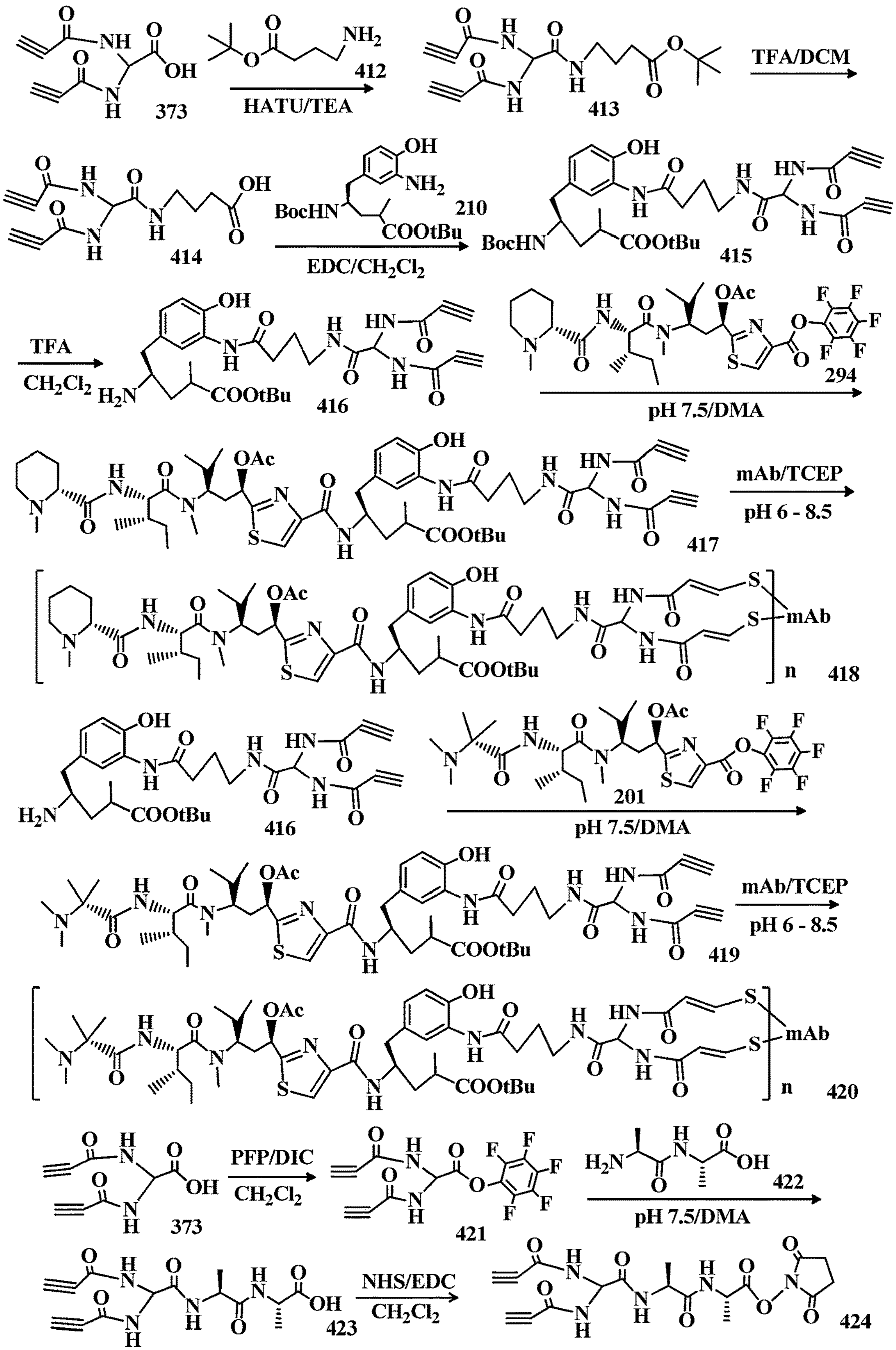
FIG. 33 shows the synthesis of conjugates of antibody-tubulysin analogs via the linkers of this patent application.
Figure 34:
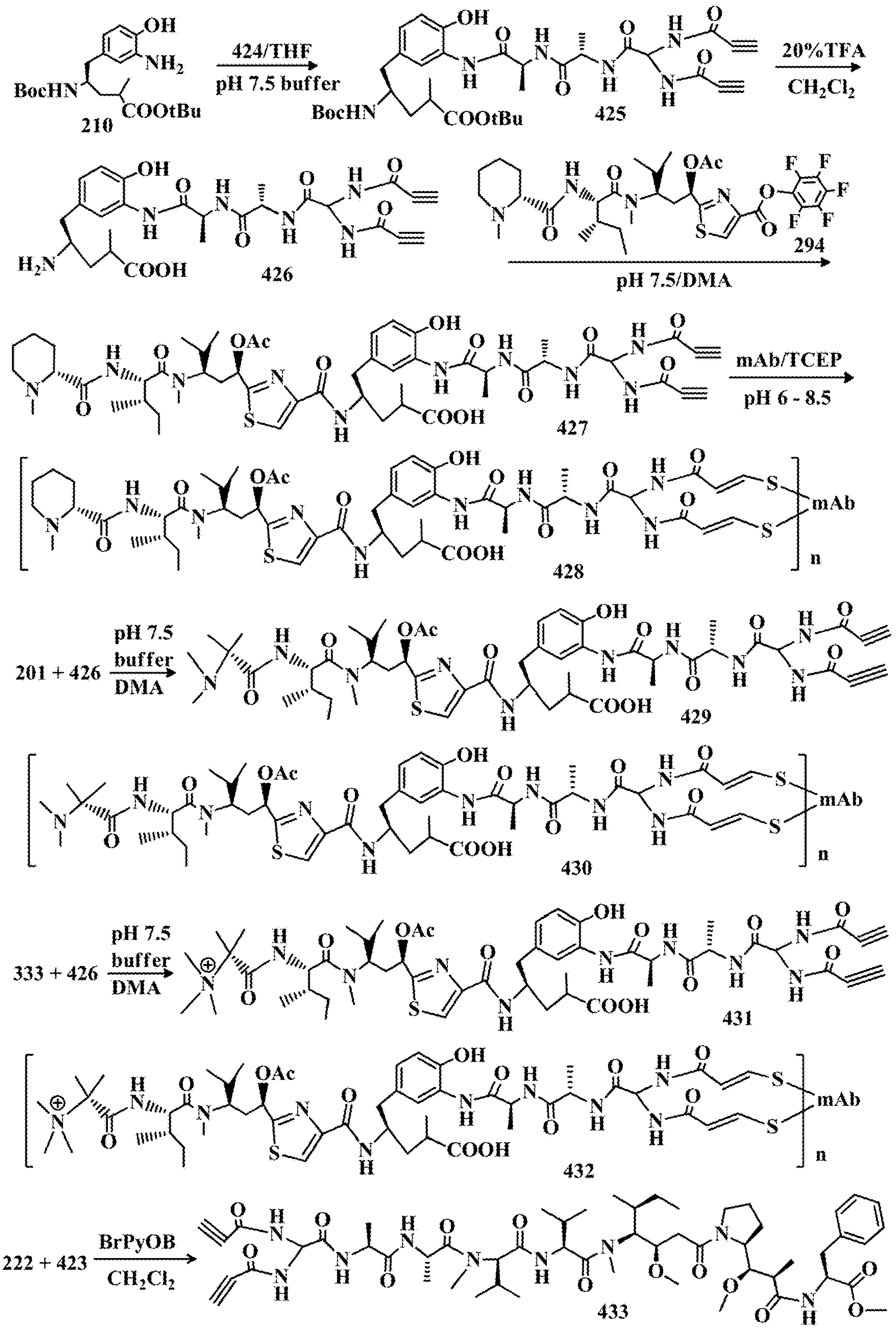
FIG. 34 shows the synthesis of conjugates of antibody-tubulysin analogs and a conjugatable MMAF analog via the linkers of this patent application.
Figure 35:
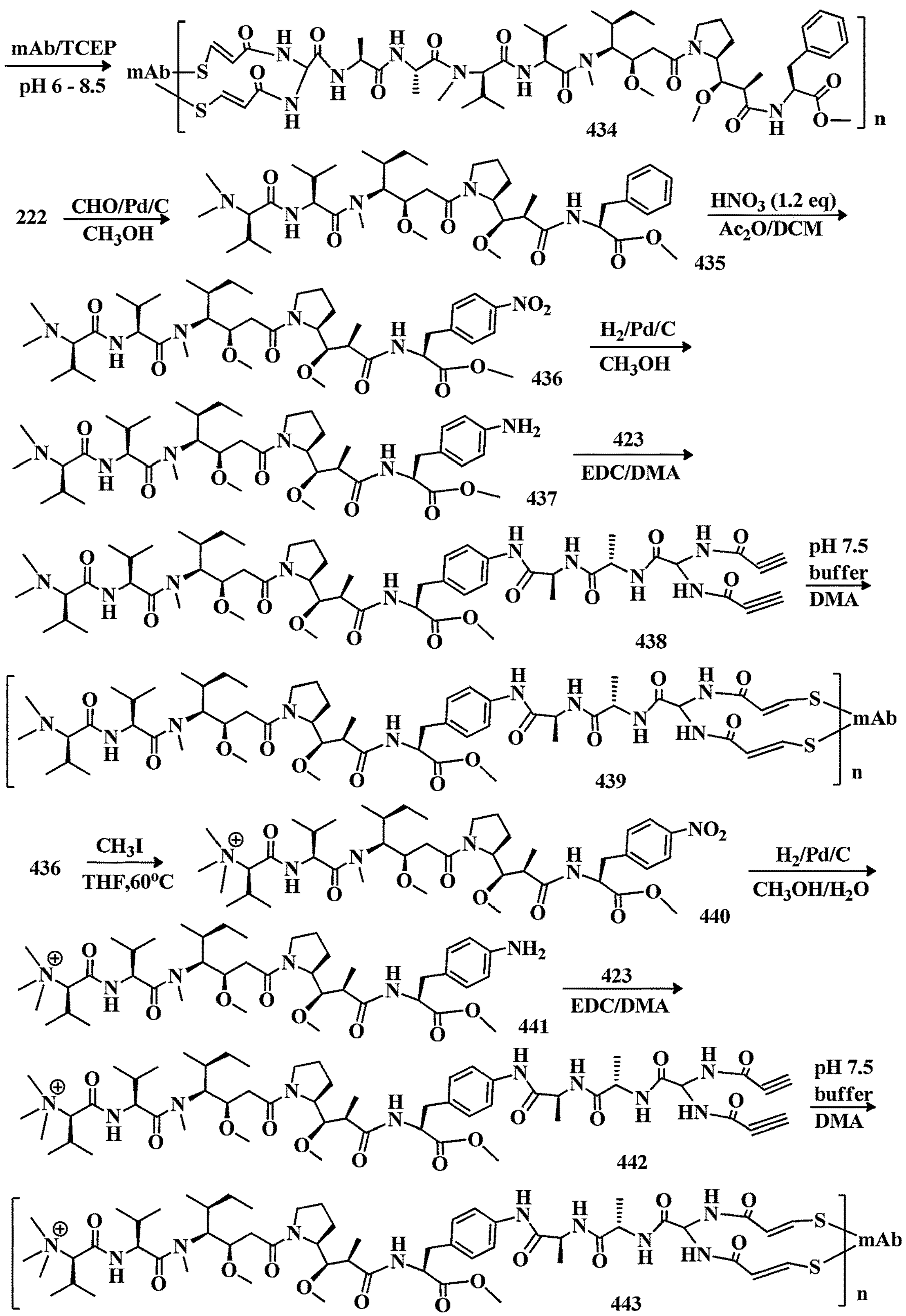
FIG. 35 shows the synthesis of conjugates of antibody-MMAF analogs via the linkers of this patent application.
Figure 36:
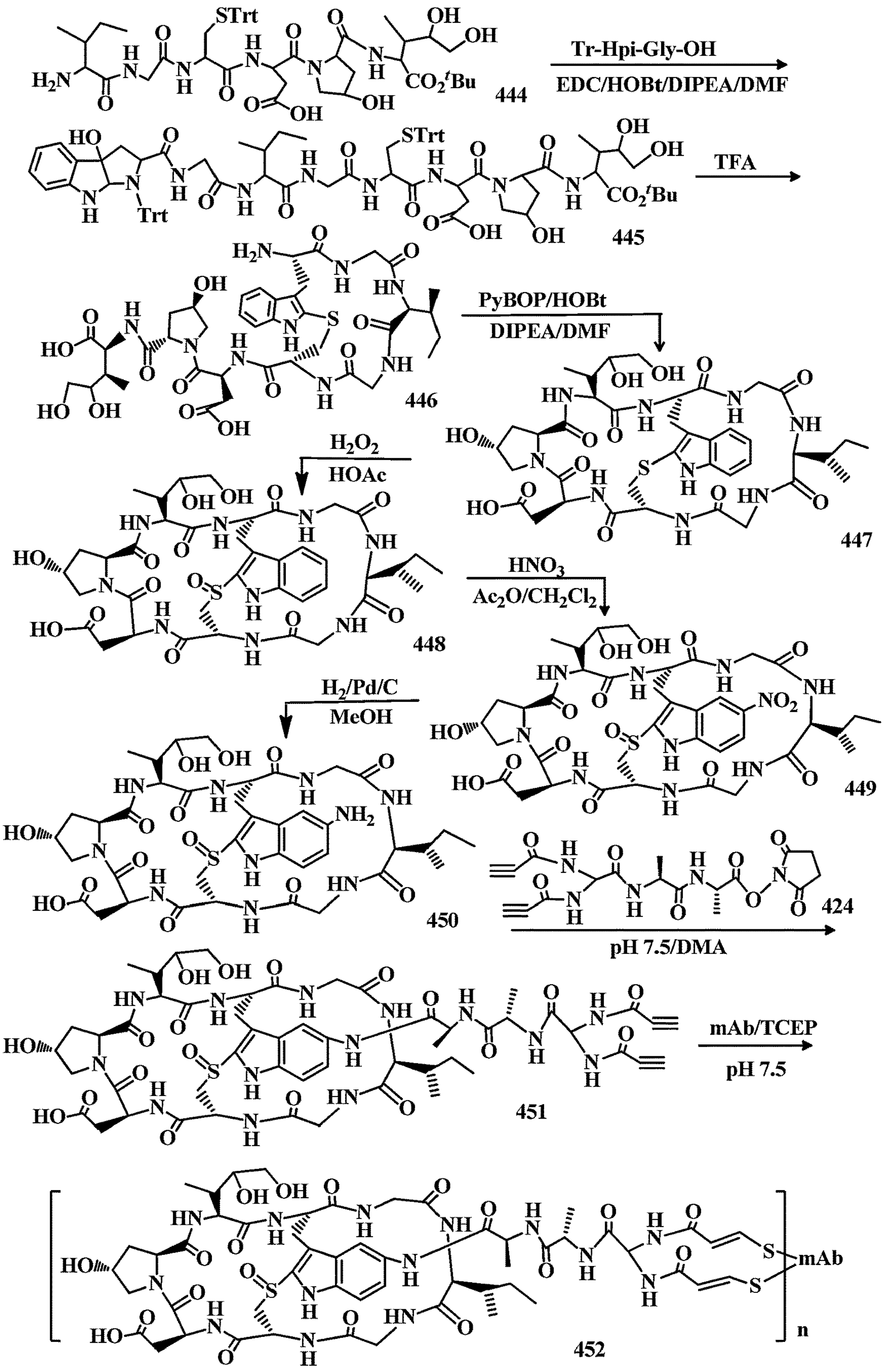
FIG. 36 shows the synthesis of conjugates of antibody-amatoxin analogs via the linkers of this patent application.
Figure 37:
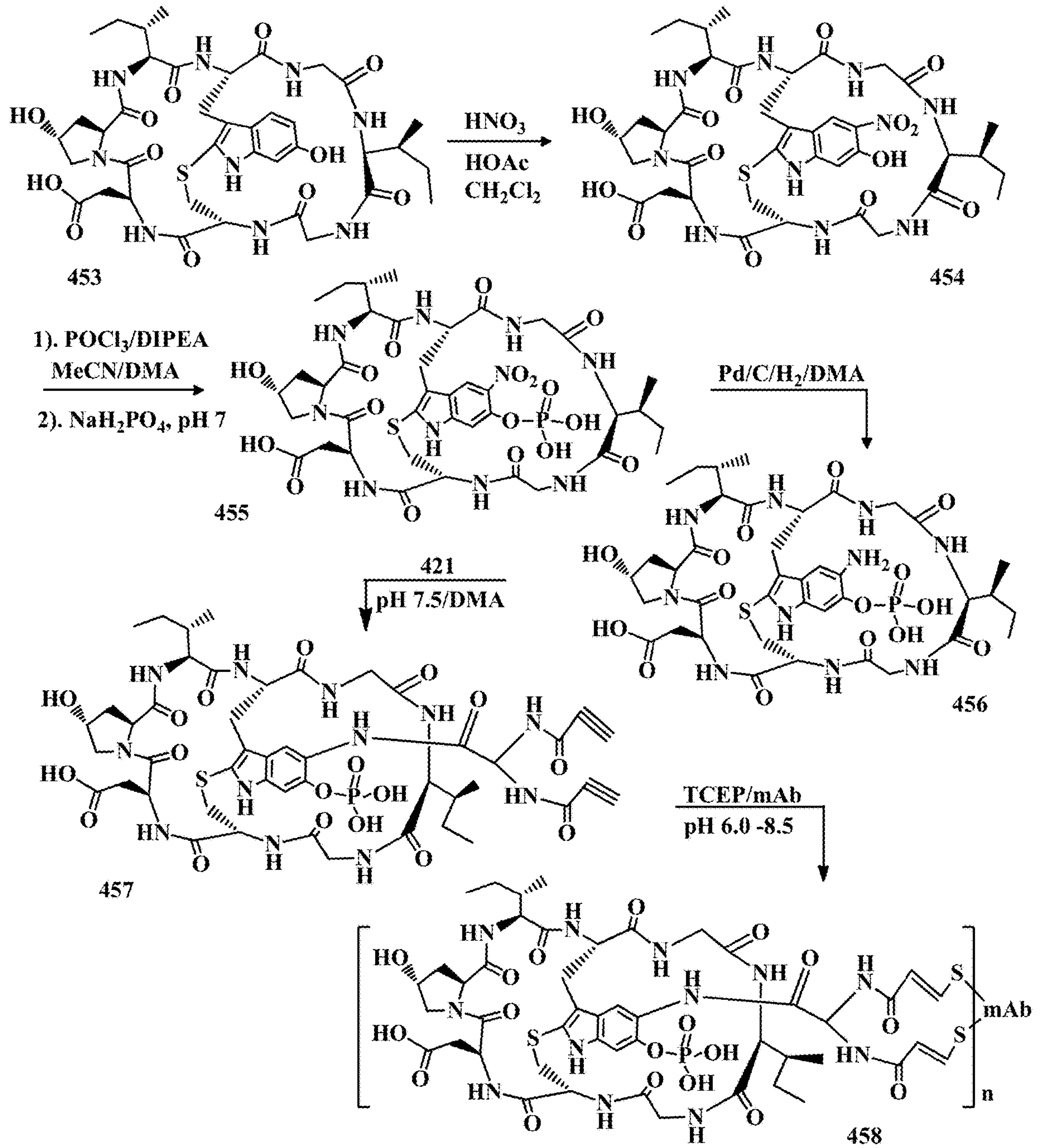
FIG. 37 shows the synthesis of conjugates of antibody-amatoxin analogs via the linkers of this patent application.
Figure 37:
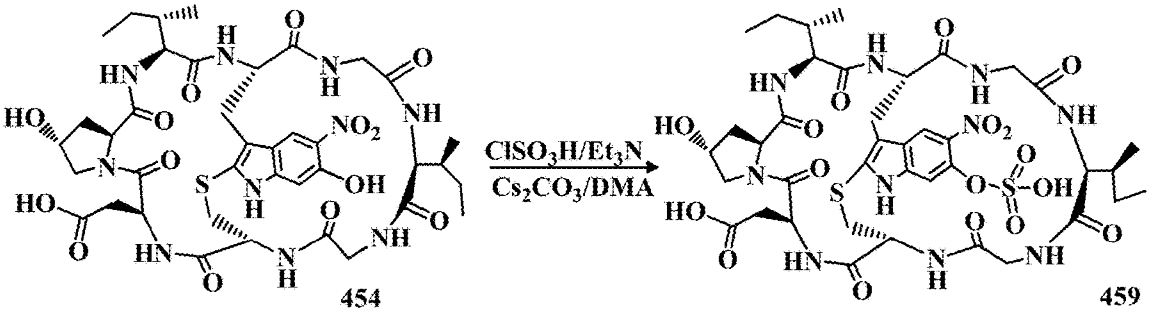
Figure 38:
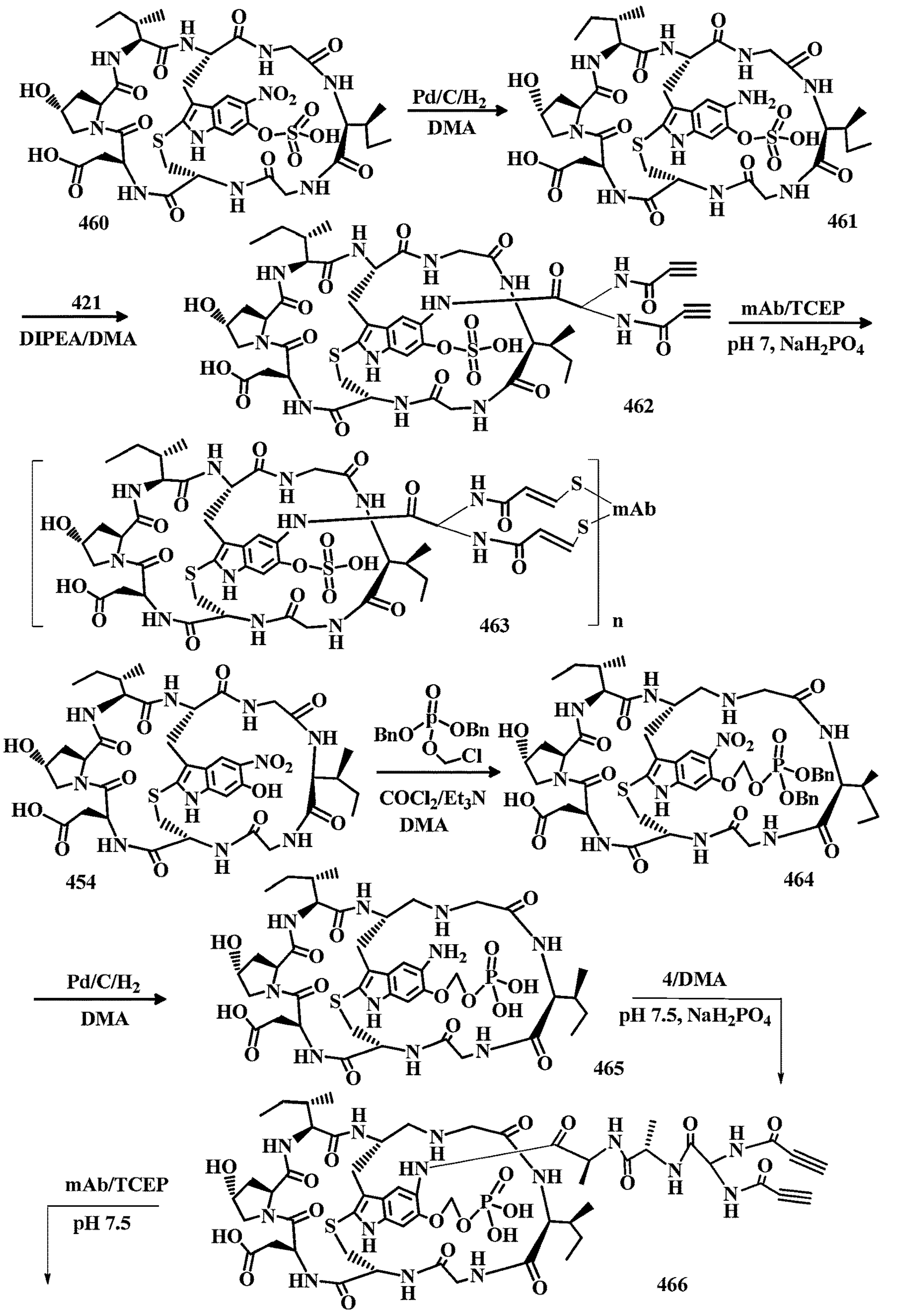
FIG. 38 shows the synthesis of conjugates of antibody-amatoxin analogs via the linkers of this patent application.
Figure 39:
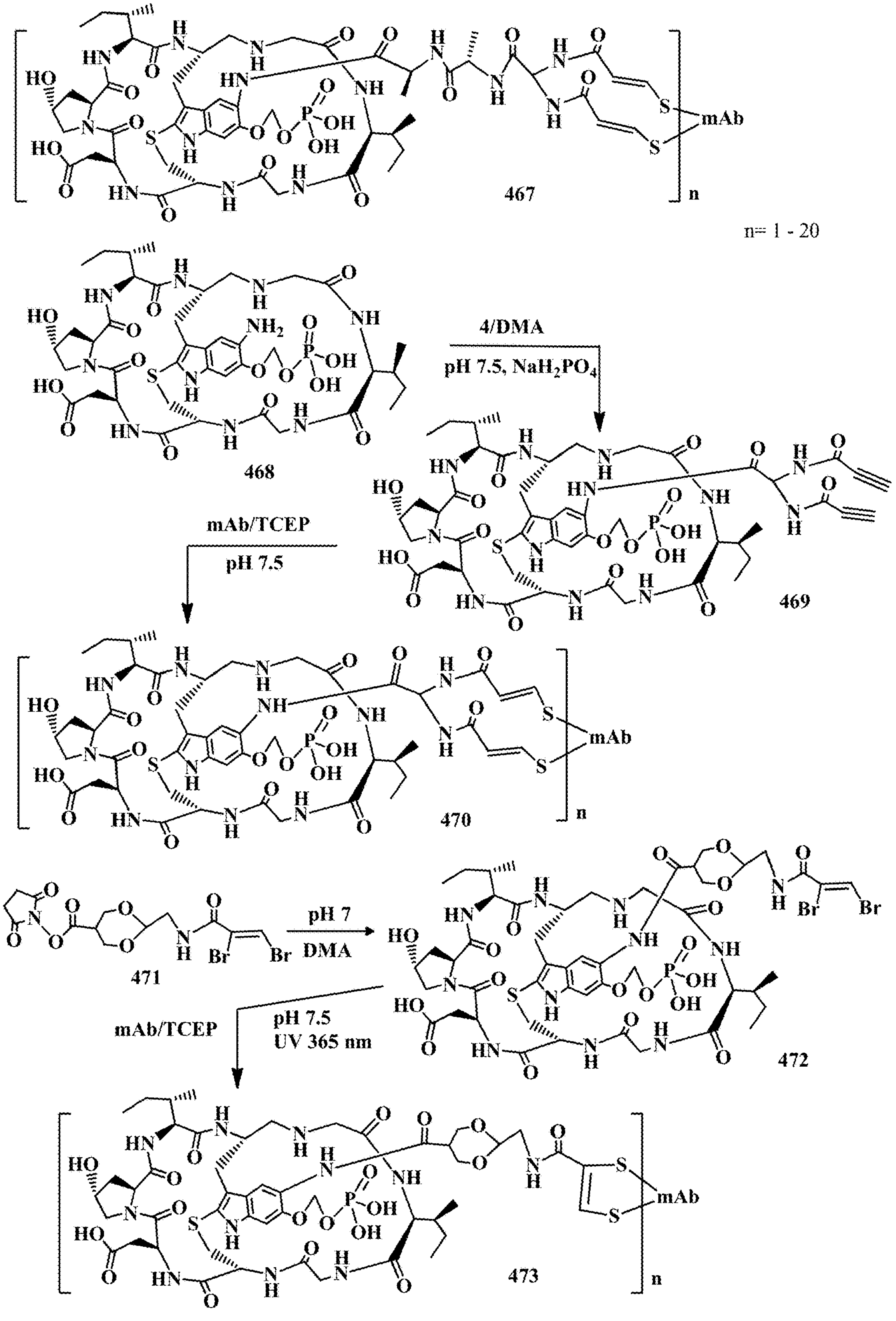
FIG. 39 shows the synthesis of conjugates of antibody-amatoxin analogs via the linkers of this patent application.
Figure 40:
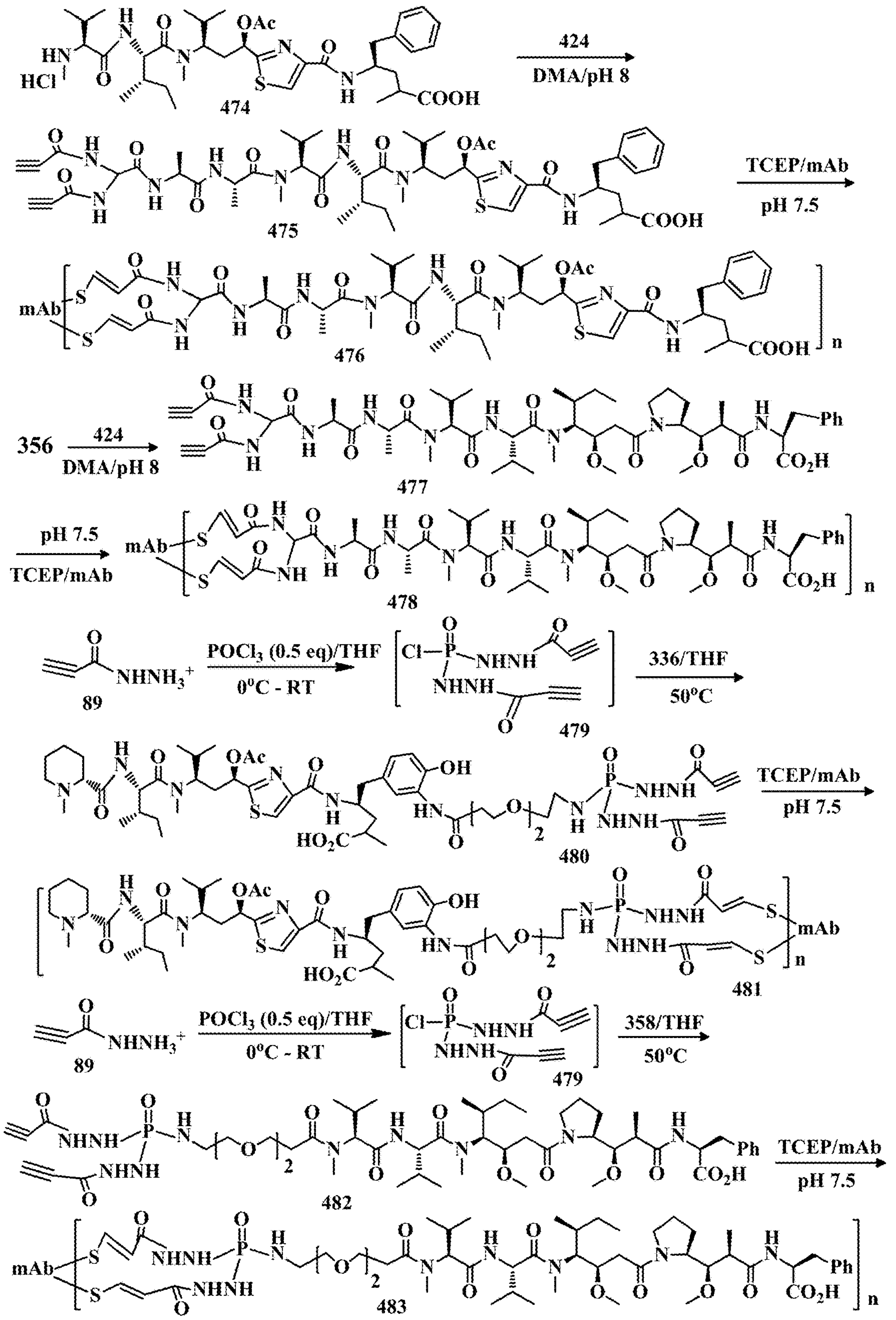
FIG. 40 shows the synthesis of conjugates of antibody-Tubulysin analog, and antibody-MMAF analog via the linkers of this patent application.
Figure 41:
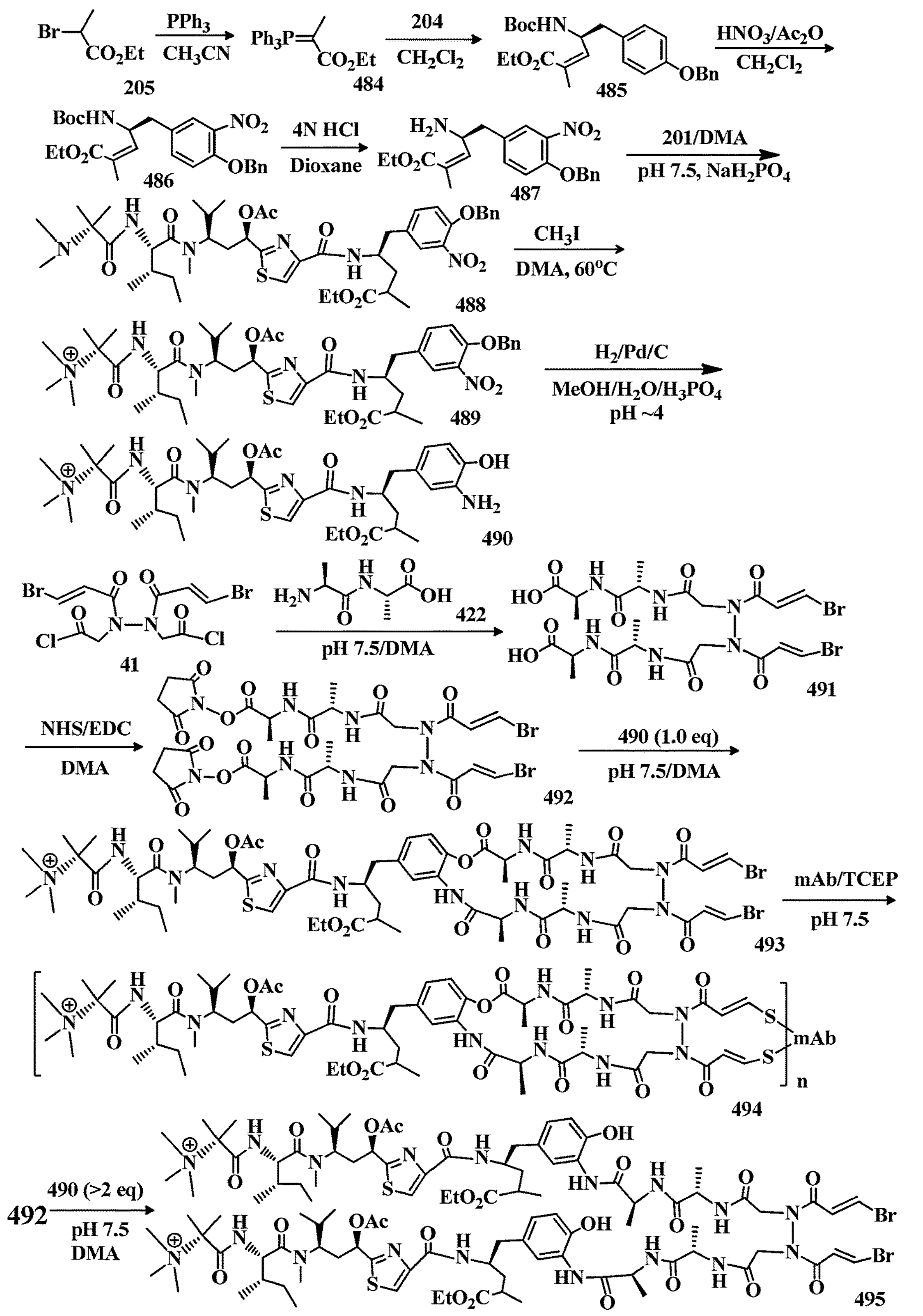
FIG. 41 shows the synthesis of conjugates of antibody-Tubulysin analog via the linkers of this patent application.
Figure 42:
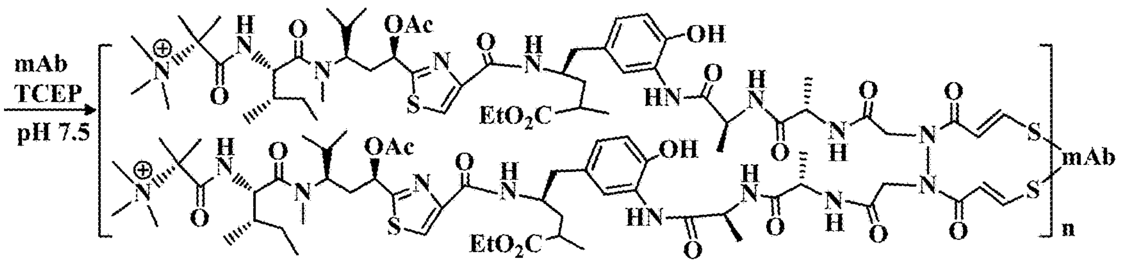
FIG. 42 shows the synthesis of conjugates of antibody-Tubulysin analog, antibody-PBD dimer analog and antibody-MMAF analog via the linkers of this patent application.
Figure 42:
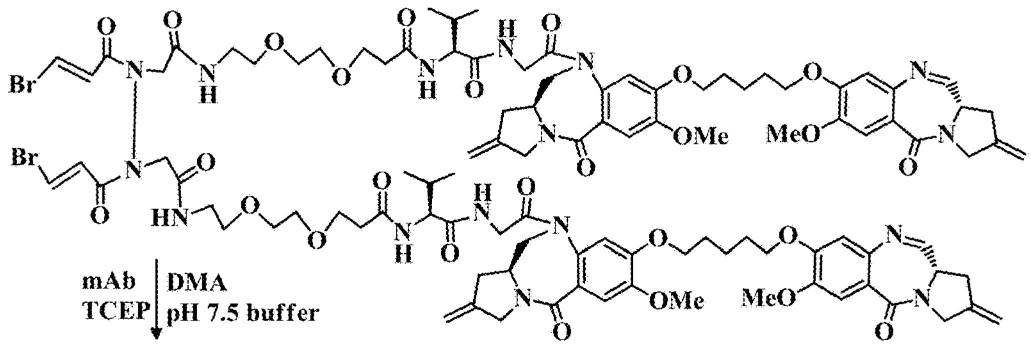
Figure 42:
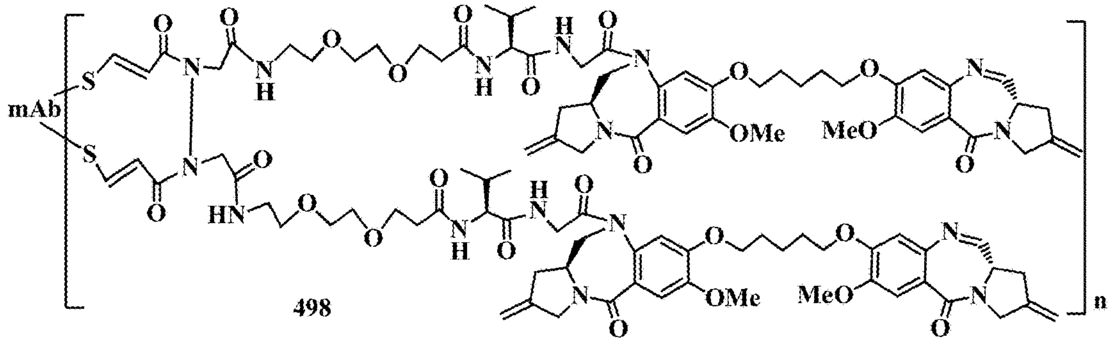
Figure 42:
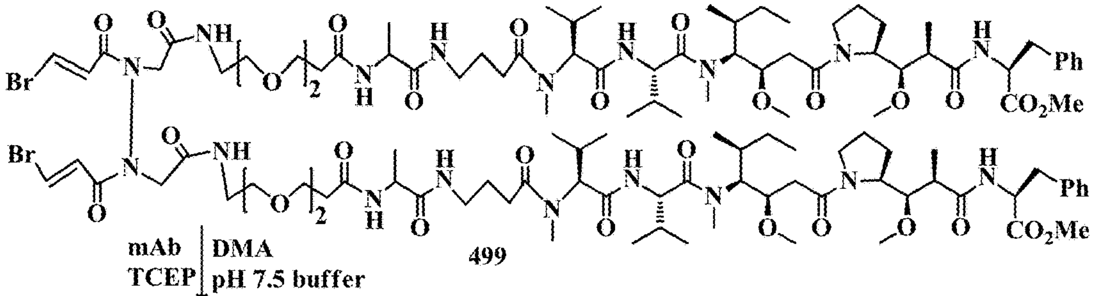
Figure 42:
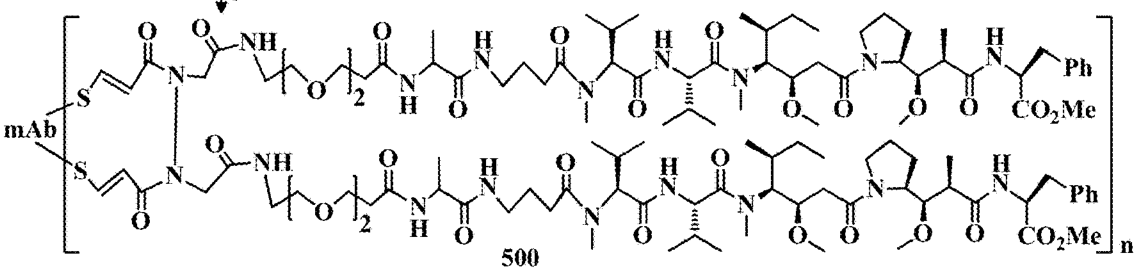
Figure 43:
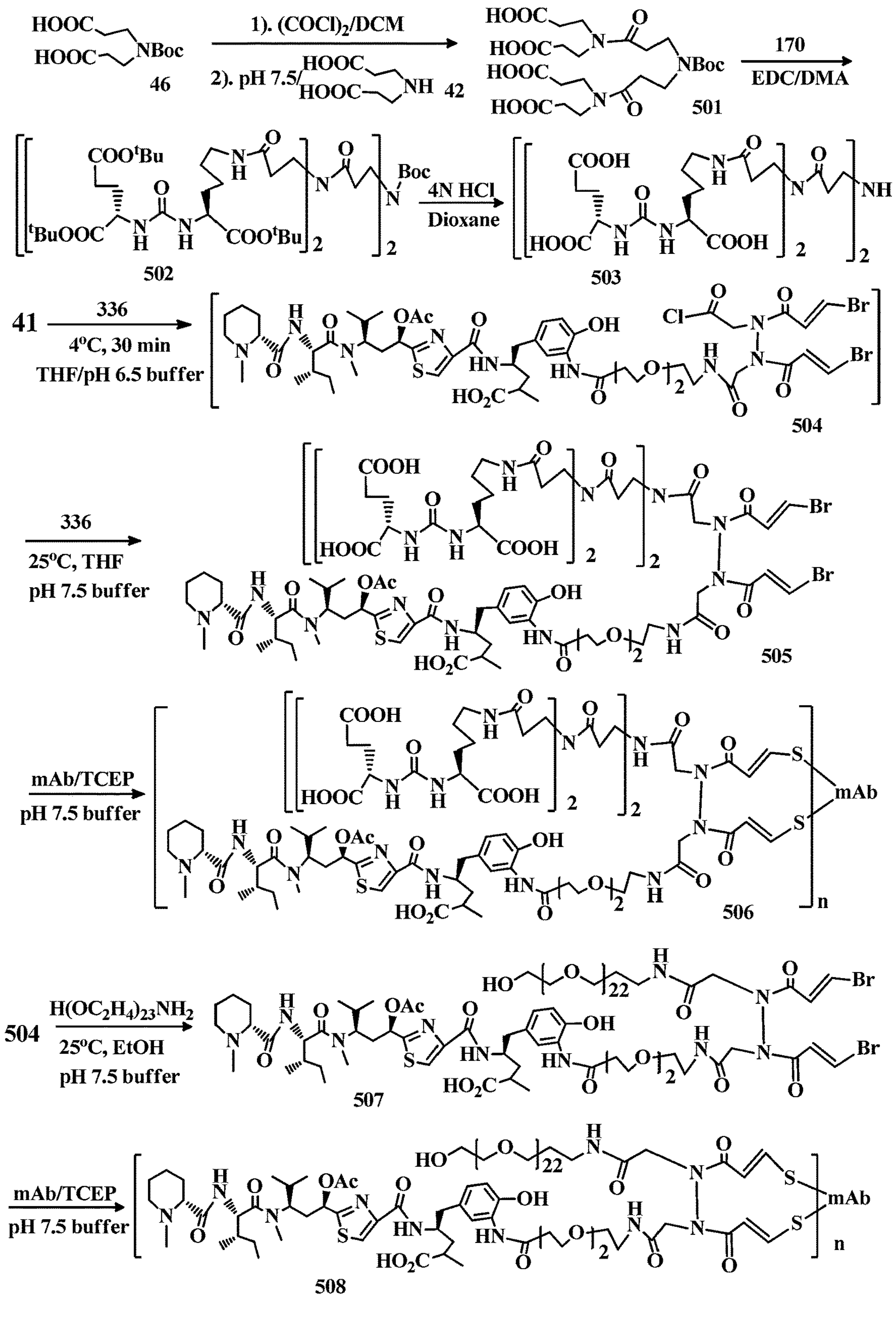
FIG. 43 shows the synthesis of conjugates of antibody-Tubulysin analog containing PMSA binding ligands, and antibody-Tubulysin analog containing a PEG chain via the linkers of this patent application.
Figure 44:
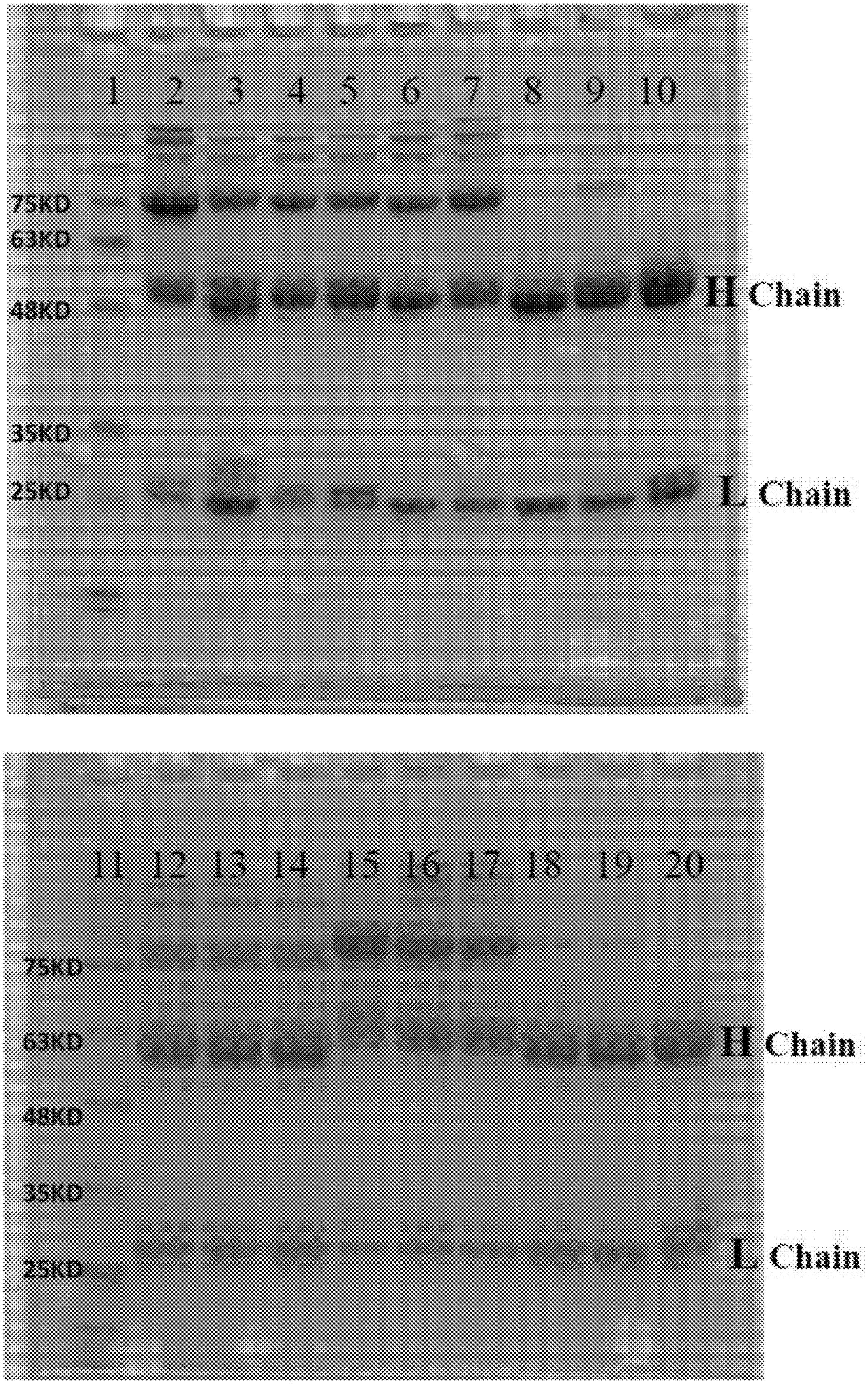
FIG. 44 shows the SDS-PAGE gels containing reduce agent DTT in the development. Lane 1 and 11 are biomarker, Lane 2 and Lane 16 are conjugate 232, Lane 3 and Lane 15 are conjugate 339, Lane 4 is conjugate 234, Lane 5 is conjugate 238, Lane 6 is conjugate 261, Lane 7 and Lane 17 are conjugate 308, Lane 8 is conjugate 239, Lane 9 is conjugate 476, Lane 10 is conjugate 478, Lane 12 is conjugate 360, Lane 14 is conjugate 238, Lane 18 is conjugate 481, Lane 19 is conjugate 483, and Lane 20 is T-DM1. The conjugates 232, 234, 238, 261, 308, 339, 354 and 360 via the bridge linkers of this patent application had the major bands of 75 KD which indicates that the heavy chain and the light chain of the mAb were crossly linked with the linkers. But the linkage between the two heavy chains of these conjugates could be replaced by the reduced agent of DTT, resulted in faint 150 KD bands. Also the cross linkages of the conjugates 476, 478, 481 and 483 were replaced by DTT inside the SDS-PAGE (reversible conjugation), and the 75 KD and 150 KD bands were very faint too. In comparison, none cross-linked T-DM1 had no 75 KD band and conjugate 239 which was prepared without using UV light had a faint 75 KD band indicated it might not be cross linked at the conjugation condition.

"Alkyl" refers to an aliphatic hydrocarbon group or univalent groups derived from alkane by removal of one or two hydrogen atoms from carbon atoms. It may be straight or branched having $C_1$-$C_8$ (1 to 8 carbon atoms) in the chain. "Branched" means that one or more lower C numbers of alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl, cyclohexyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$-$C_8$ alkyl, —O—($C_1$-$C_8$alkyl), -aryl, —C(O)R', —OC(O)R', —C(O)OR', —$C(O)NH_2$, —C(O)NHR', —$C(O)N(R')_2$, —NHC(O)R', —SR', —$S(O)_2R'$, —S(O)R', —OH, -halogen, —$N_3$, —$NH_2$, —NH(R'), —N(R') 2 and —CN; where each R' is independently selected from —$C_1$-$C_8$ alkyl and aryl.

"Halogen" refers to fluorine, chlorine, bromine or iodine atom; preferably fluorine and chlorine atom.

"Heteroalkyl" refers to $C_2$-$C_8$ alkyl in which one to four carbon atoms are independently replaced with a heteroatom from the group consisting of O, S and N.

"Carbocycle" refers to a saturated or unsaturated ring having 3 to 8 carbon atoms as a monocycle or 7 to 13 carbon atoms as a bicycle. Monocyclic carbocycles have 3 to 6 ring atoms, more typically 5 or 6 ring atoms. Bicyclic carbocycles have 7 to 12 ring atoms, arranged as a bicycle [4,5], [5,5], [5,6] or [6,6] system, or 9 or 10 ring atoms arranged as a bicycle [5,6] or [6,6] system. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl.

A "$C_3$-$C_8$ carbocycle" refers to a 3-, 4-, 5-, 6-, 7- or 8-membered saturated or unsaturated nonaromatic carbocyclic ring. A $C_3$-$C_8$ carbocycle group can be unsubstituted or substituted with one or more groups including, but not limited to, —$C_1$-$C_8$ alkyl, —O—($C_1$-$C_8$alkyl), -aryl, —C(O)R', —OC(O)R', —C(O)OR', —C(O)$NH_2$, —C(O)NHR', —C(O)N$(R')_2$, —NHC(O)R', —SR', —S(O)R', —S$(O)_2$R', —OH, -halogen, —$N_3$, —$NH_2$, —NH(R'), —N(R') 2 and —CN; where each R' is independently selected from —$C_1$-$C_8$ alkyl and aryl.

"Alkenyl" refers to an aliphatic hydrocarbon group containing a carbon-carbon double bond which may be straight or branched having 2 to 8 carbon atoms in the chain. Exemplary alkenyl groups include ethenyl, propenyl, n-butenyl, i-butenyl, 3-methylbut-2-enyl, n-pentenyl, hexylenyl, heptenyl, octenyl.

"Alkynyl" refers to an aliphatic hydrocarbon group containing a carbon-carbon triple bond which may be straight or branched having 2 to 8 carbon atoms in the chain. Exemplary alkynyl groups include ethynyl, propynyl, n-butynyl, 2-butynyl, 3-methylbutynyl, 5-pentynyl, n-pentynyl, hexylynyl, heptynyl, and octynyl.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethyl (—$CH_2CH_2$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene, propargyl and 4-pentynyl.

"Aryl" or Ar refers to an aromatic or hetero aromatic group, composed of one or several rings, comprising three to fourteen carbon atoms, preferentially six to ten carbon atoms. The term of "hetero aromatic group" refers one or several carbon on aromatic group, preferentially one, two, three or four carbon atoms are replaced by 0, N, Si, Se, P or S, preferentially by 0, S, and N. The term aryl or Ar also refers to an aromatic group, wherein one or several H atoms are replaced independently by —R', -halogen, —OR', or —SR', —NR'R", —N═NR', —N═R', —NR'R", —$NO_2$, —S(O)R', —S$(O)_2$R', —S$(O)_2$OR', —OS$(O)_2$OR', —PR'R", —P(O)R'R", —P(OR')(OR"), —P(O)(OR')(OR")

or —OP(O)(OR')(OR") wherein R', R" are independently H, alkyl, alkenyl, alkynyl, heteroalkyl, aryl, arylalkyl, carbonyl, or pharmaceutical salts.

"Heterocycle" refers to a ring system in which one to four of the ring carbon atoms are independently replaced with a heteroatom from the group of O, N, S, Se, B, Si and P. Preferable heteroatoms are O, N and S. Heterocycles are also described in The Handbook of Chemistry and Physics, 78th Edition, CRC Press, Inc., 1997-1998, p. 225 to 226, the disclosure of which is hereby incorporated by reference. Preferred nonaromatic heterocyclic include epoxy, aziridinyl, thiiranyl, pyrrolidinyl, pyrazolidinyl, imidazolidinyl, oxiranyl, tetrahydrofuranyl, dioxolanyl, tetrahydropyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydropyridyl, dihydropyridyl, tetrahydropyrimidinyl, dihydrothiopyranyl, azepanyl, as well as the fused systems resulting from the condensation with a phenyl group.

The term "heteroaryl" or aromatic heterocycles refers to a 3 to 14, preferably 5 to 10 membered aromatic hetero, mono-, bi-, or multi-cyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazolyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "cycloalkyl", "alkenyl", "alkynyl", "aryl", "heteroaryl", "heterocyclic" and the like refer also to the corresponding "alkylene", "cycloalkylene", "alkenylene", "alkynylene", "arylene", "heteroarylene", "heterocyclene" and the likes which are formed by the removal of two hydrogen atoms.

"Arylalkyl" refers to an acyclic alkyl radical in which one of the hydrogen atoms bonded to a carbon atom, typically a terminal or $sp^3$ carbon atom, is replaced with an aryl radical.

Typical arylalkyl groups include, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

"Heteroarylalkyl" refers to an acyclic alkyl radical in which one of the hydrogen atoms bonded to a carbon atom, typically a terminal or $sp^3$ carbon atom, is replaced with a heteroaryl radical. Examples of heteroarylalkyl groups are 2-benzimidazolylmethyl, 2-furylethyl.

Examples of a "hydroxyl protecting group" include, methoxymethyl ether, 2-methoxyethoxymethyl ether, tetrahydropyranyl ether, benzyl ether, p-methoxybenzyl ether, trimethylsilyl ether, triethylsilyl ether, triisopropylsilyl ether, t-butyldimethylsilyl ether, triphenylmethylsilyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, a halide (e.g., chloride, bromide, and iodide), methanesulfonyl (mesyl), p-toluenesulfonyl (tosyl), trifluoromethylsulfonyl (triflate), and trifluoromethylsulfonate. A preferred leaving group is selected from nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, anhydrides formed its self, or formed with the other anhydride, e.g. acetyl anhydride, formyl anhydride; or an intermediate molecule generated with a condensation reagent for peptide coupling reactions or for Mitsunobu reactions.

The following abbreviations may be used herein and have the indicated definitions: Boc, tert-butoxy carbonyl; BroP, bromotrispyrrolidinophosphonium hexafluorophosphate; CDI, 1,1'-carbonyldiimidazole; DCC, dicyclohexylcarbodiimide; DCE, dichloroethane; DCM, dichloromethane; DIAD, diisopropylazodicarboxylate; DIBAL-H, diisobutylaluminium hydride; DIPEA, diisopropylethylamine; DEPC, diethyl phosphorocyanidate; DMA, N,N-dimethyl acetamide; DMAP, 4-(N, N-dimethylamino)pyridine; DMF, N,N-dimethylformamide; DMSO, dimethylsulfoxide; DTT, dithiothreitol; EDC, 1-(3-dimethylaminopropyl)-3-ethylcarbodiimide hydrochloride; ESI-MS, electrospray mass spectrometry; HATU, 0-(7-azabenzotriazol-1-yl)-N, N, N', N'-tetramethyluronium hexafluorophosphate; HOBt, 1-hydroxybenzotriazole; HPLC, high pressure liquid chromatography; NHS, N-Hydroxysuccinimide; MMP, 4-methylmorpholine; PAB, p-aminobenzyl; PBS, phosphate-buffered saline (pH 7.0-7.5); PEG, polyethylene glycol; SEC, size-exclusion chromatography; TCEP, tris(2-carboxyethyl) phosphine; TFA, trifluoroacetic acid; THF, tetrahydrofuran; Val, valine.

The "amino acid(s)" can be natural and/or unnatural amino acids, preferably alpha-amino acids. Natural amino acids are those encoded by the genetic code, which are alanine, arginine, asparagine, aspartic acid, cysteine, glutamic acid, glutamine, glycine, histidine, isoleucine, leucine, lysine, methionine, phenylalanine, proline, serine, threonine, tyrosine. tryptophan and valine. The unnatural amino acids are derived forms of proteinogenic amino acids. Examples include hydroxyproline, lanthionine, 2-aminoisobutyric acid, dehydroalanine, gamma-aminobutyric acid (the neurotransmitter), ornithine, citrulline, beta alanine (3-aminopropanoic acid), gamma-carboxyglutamate, selenocysteine (present in many noneukaryotes as well as most eukaryotes, but not coded directly by DNA), pyrrolysine (found only in some archaea and one bacterium), N-formylmethionine (which is often the initial amino acid of proteins in bacteria, mitochondria, and chloroplasts), 5-hydroxytryptophan, L-dihydroxyphenylalanine, triiodothyronine, L-3,4-dihydroxyphenylalanine (DOPA), and O-phosphoserine. The term amino acid also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. Preferably, an amino acid mimetic is a compound that has a structure different from the general chemical structure of an alpha-amino acid but functions in a manner similar to one. The term "unnatural amino acid" is intended to represent the "D" stereochemical form, the natural amino acids being of the "L" form. When 1~8 amino acids are used in this patent application, amino acid sequence is then preferably a cleavage recognition sequence for a protease. Many cleavage recognition sequences are known in the art. See, e.g., Matayoshi et al. Science 247: 954 (1990); Dunn et al. Meth. Enzymol. 241: 254 (1994); Seidah et al. Meth. Enzymol. 244: 175 (1994); Thornberry, Meth. Enzymol. 244: 615 (1994); Weber et al. Meth. Enzymol. 244: 595 (1994); Smith et al. Meth. Enzymol. 244: 412 (1994); and Bouvier et al. Meth. Enzymol. 248: 614 (1995); the disclosures of which are incorporated herein by reference. In particular, the sequence is selected from the group consisting of Val-Cit, Ala-Val, Ala-Ala, Val-Val, Val-Ala-Val, Lys-Lys, Ala-Asn-Val, Val-Leu-Lys, Cit-Cit, Val-Lys, Ala-Ala-Asn, Lys, Cit, Ser, and Glu.

The "glycoside" is a molecule in which a sugar group is bonded through its anomeric carbon to another group via a glycosidic bond. Glycosides can be linked by an O— (an O-glycoside), N— (a glycosylamine), S— (a thioglycoside), or C— (a C-glycoside) glycosidic bond. Its core the empirical formula is $C_m(H_2O)_n$ (where m could be different from n, and m and n are <36), Glycoside herein includes glucose (dextrose), fructose (levulose) allose, altrose, mannose, gulose, iodose, galactose, talose, galactosamine, glucosamine, sialic acid, N-acetylglucosamine, sulfoquinovose (6-deoxy-6-sulfo-D-glucopyranose), ribose, arabinose, xylose, lyxose, sorbitol, mannitol, sucrose, lactose, maltose, trehalose, maltodextrins, raffinose, Glucuronic acid (glucuronide), and stachyose. It can be in D form or L form, 5 atoms cyclic furanose forms, 6 atoms cyclic pyranose forms, or acyclic form, α-isomer (the —OH of the anomeric carbon below the plane of the carbon atoms of Haworth projection), or a β-isomer (the —OH of the anomeric carbon above the plane of Haworth projection). It is used herein as a monosaccharide, disaccharide, polyols, or oligosaccharides containing 3-6 sugar units.

"Pharmaceutically" or "pharmaceutically acceptable" refer to molecular entities and compositions that do not produce an adverse, allergic or other untoward reaction when administered to an animal, or a human, as appropriate.

"Pharmaceutically acceptable solvate" or "solvate" refer to an association of one or more solvent molecules and a disclosed compound. Examples of solvents that form pharmaceutically acceptable solvates include, but are not limited to, water, isopropanol, ethanol, methanol, DMSO, ethyl acetate, acetic acid and ethanolamine.

"Pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

As used herein, "pharmaceutical salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucuronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutical salts of the present invention can be synthesized from the parent compound which contains a basic or acidic moiety by conventional chemical methods.

Generally, such salts can be prepared via reaction the free acidic or basic forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in Remington's Pharmaceutical Sciences, $17^{th}$ ed., Mack Publishing Company, Easton, PA, 1985, p. 1418, the disclosure of which is hereby incorporated by reference.

"Administering" or "administration" refers to any mode of transferring, delivering, introducing or transporting a pharmaceutical drug or other agent to a subject. Such modes include oral administration, topical contact, intravenous, intraperitoneal, intramuscular, intralesional, intranasal, subcutaneous or intrathecal administration. Also contemplated by the present invention is utilization of a device or instrument in administering an agent. Such device may utilize active or passive transport and may be slow-release or fast-release delivery device.

The novel conjugates disclosed herein use the bridge linkers. Examples of some suitable linkers and their synthesis are shown in FIGS. 1 to 34.

The Bridge Linkers

The synthetic routes to produce bridge linkers as well as the preparation of the conjugates of drugs to a cell binding molecules of the present invention are shown in FIGS. 1-20. The bridge linkers possess two elements: a) A Substituent that is one or two more thiol reactive groups of substituted acrylic groups, or propiolic groups, which can react to a pair of thiols to form covalent thioether bonds, and b) A group, such as but not limited to, a disulfide, maleimide, haloacetyl, aldehyde, ketone, azide, amine, alkoxyamine, hydrazide, ethenesulfonyl, acyl halide (acid halide), acryl (acryloyl), and/or acid anhydride group, capable of reaction with a drug. The bridge substituents of substituted acrylic group, or propiolic groups with an amine, an alcohol, or a thiol group to form amide, ester or thioester bonds. The synthesis of these bridge linkers and their application for antibody conjugation are exampled in FIGS. 1-20.

Preferably, the bridge linkers are compounds of the Formula (I) and (II) below:

(I)

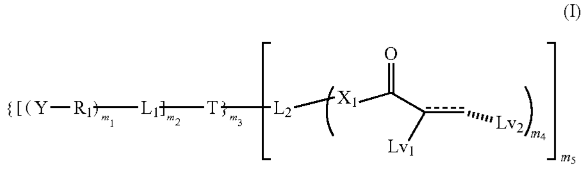

(II)

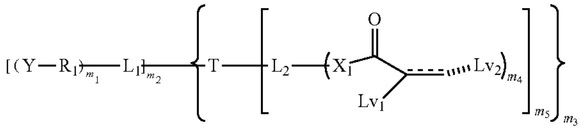

Wherein

"——" and "ıııııı" represent a single bond, and "ıııııı" can be an enantiomer or stereoisomer bond when linked to a single or a double bond.

⩶ represents either a single bond, or a double bond, or a triple bond.

It provided that when ⩶ represents a single bond, both $L_{V1}$ and $L_{V2}$ are not H; when ⩶ represents a double bond, either $L_{V1}$ or $L_{V2}$ can be H, but they are not H at the same time; when ⩶ represents a triple bond, $L_{V1}$ is absent and $L_{V2}$ can optionally be H.

$L_{V1}$ and $L_{V2}$ represent the same or different leaving group that can be substituted by a thiol. Such leaving groups are, but are not limited to, a halide (e.g., fluoride, chloride, bromide, and iodide), methanesulfonyl (mesyl), toluenesulfonyl (tosyl), trifluoromethyl-sulfonyl (triflate), trifluoromethylsulfonate, nitrophenoxyl, N-succinimidyloxyl (NHS), phenoxyl; dinitrophenoxyl; pentafluorophenoxyl, tetrafluorophenoxyl, trifluorophenoxyl, difluorophenoxyl, monofluorophenoxyl, pentachlorophenoxyl, 1H-imidazole-1-yl, chlorophenoxyl, dichlorophenoxyl, trichlorophenoxyl, tetrachlorophenoxyl, N-(benzotriazol-yl)oxyl, 2-ethyl-5-phenylisoxazolium-3'-sulfonyl, phenyloxadiazole-sulfonyl (-sulfone-ODA), 2-ethyl-5-phenylisoxazolium-yl, phenyloxadiazol-yl (ODA), oxadiazol-yl, or an intermediate molecule generated with a condensation reagent for Mitsunobu reactions.

Y is a function group that enables to react with a drug or a cytotoxic agent, to form a disulfide, ether, ester, thioether, thioester, peptide, hydrazone, carbamate, carbonate, amine (secondary, tertiary, or quarter), imine, cycloheteroalkyane, heteroaromatic, alkyloxime or amide bond; Preferably Y has the following structures:

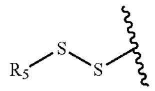

disulfide;

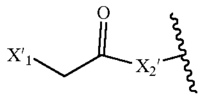

haloacetyl;

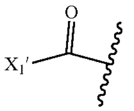

acyl halide (acid halide);

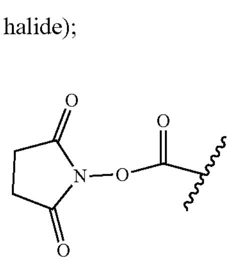

N-hydroxysuccinimide ester;

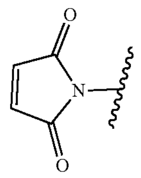 [SMILES: *N1C(=O)C=CC1=O]
maleimide;
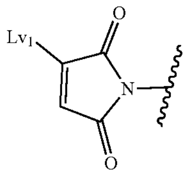
monosubstituted maleimide;
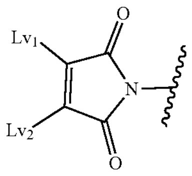
disubstituted maleimide;
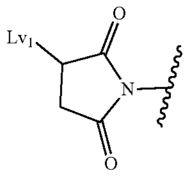
monosubstituted succinimide;
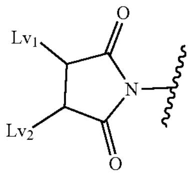
disubstituted succinimide; —CHO aldehyde;
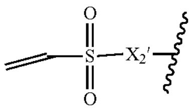
ethenesulfonyl;
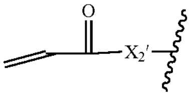
acryl (acryloyl);
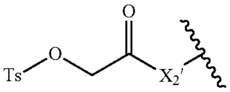
2-(tosyloxy)acetyl;
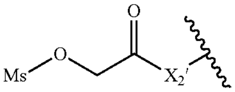
2-(mesyloxy)acetyl;
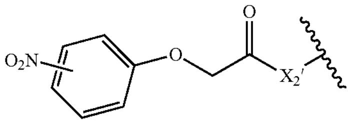
2-(nitrophenoxy)acetyl;
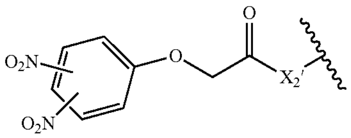
2-(dinitrophenoxy)acetyl;
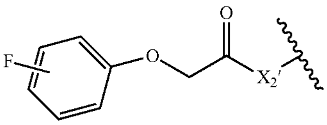
2-(fluorophenoxy)-acetyl;
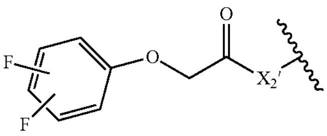
2-(difluorophenoxy)-acetyl;
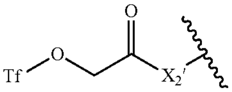

2-(((trifluoromethyl)-sulfonyl)oxy)acetyl;

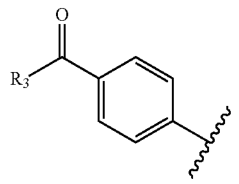

ketone, or aldehyde,

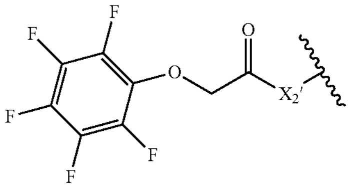

2-(pentafluorophenoxy)acetyl;

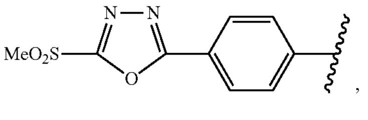 [SMILES: *c1ccc(-c2nnc(S(C)(=O)=O)o2)cc1]

methylsulfonephenyloxadiazole (ODA);

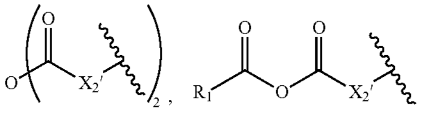

acid anhydride,

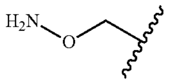

alkyloxyamino;

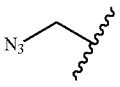

azido,

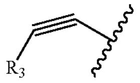

alkynyl, or

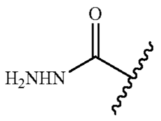

hydrazide. Wherein $X_{1'}$ is F, Cl, Br, I or $L_{V3}$; $X_2'$ is O, NH, $N(R_1)$, or $CH_2$; $R_3$ and $R_5$ are independently H, $R_1$, aromatic, heteroaromatic, or aromatic group wherein one or several H atoms are replaced independently by —$R_1$, -halogen, —$OR_1$, —$SR_1$, —$NR_1R_2$, —$NO_2$, —$S(O)R_1$, —$S(O)_2R_1$, or —$COOR_1$; $L_{V3}$ is a leaving group selected from nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, anhydrides formed its self, or formed with the other anhydride, e.g. acetyl anhydride, formyl anhydride; or an intermediate molecule generated with a condensation reagent for peptide coupling reactions or for Mitsunobu reactions.

$R_1$ can be absent, or can be selected from $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or $C_2$-$C_8$ (2-8 carbon atoms) of esters, ether, or amide; or peptides containing 1-8 amino acids, or polyethyleneoxy unit of formula $(OCH_2CH_2)_p$ or $(OCH_2CH(CH_3))_p$, wherein p is an integer from 0 to about 1000, or combination of above groups thereof.

Additionally $R_1$ is a chain of atoms selected from C, N, O, S, Si, and P, preferably having 0-500 atoms, which covalently connects to Y and $L_1$. The atoms used in forming the $R_1$ may be combined in all chemically relevant ways, such as forming alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, peptides, acyloxylamines, hydroxamic acids, or combination above thereof.

T is $CH_2$, NH, NHNH, $N(R_3)$, $N(R_3)N(R_{3'})$, O, S, $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; a peptide containing 1~4 units of amino acids, preferably selected from aspartic acid, glutamic acid, arginine, histidine, lysine, serine, threonine, asparagine, glutamine, cysteine, selenocysteine, tyrosine, phenylalanine, glycine, proline, tryptophan, alanine; or one of the following structures:

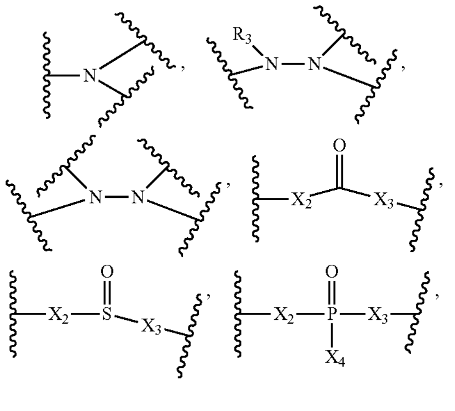

-continued
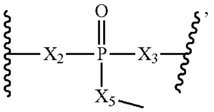,
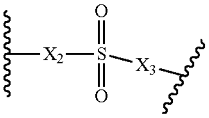,
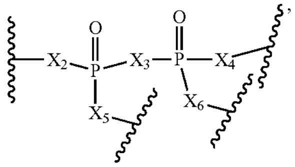,
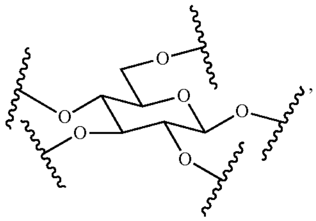,
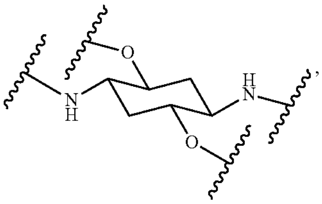,
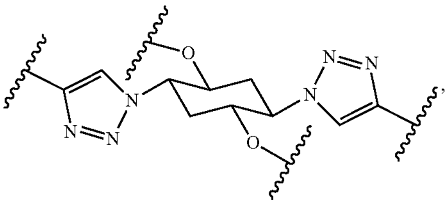,
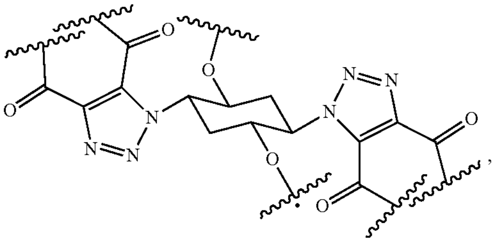,
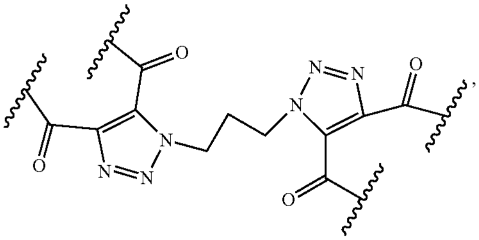,
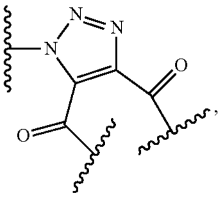,
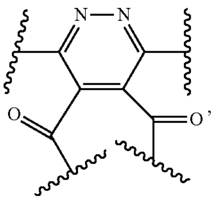,
-continued
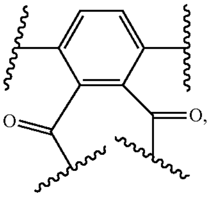,
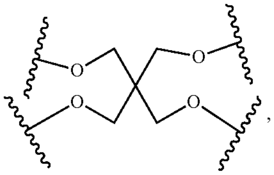,
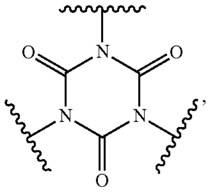,
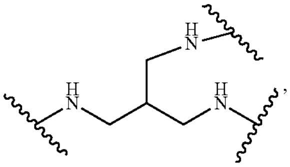,
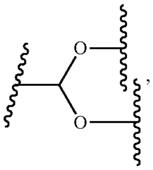,
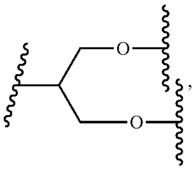,
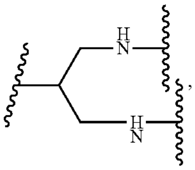,
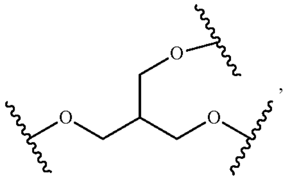,
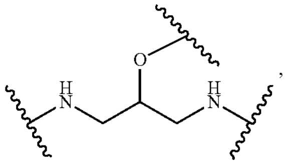,
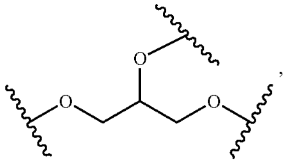,
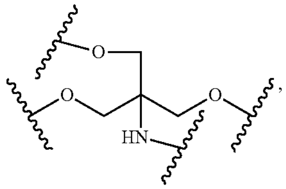, -continued

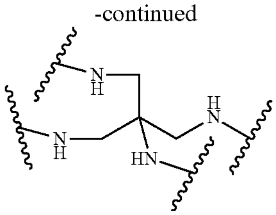
,

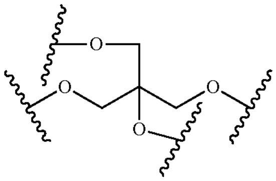
,

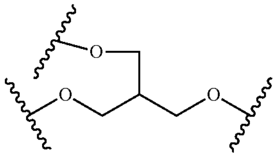
,

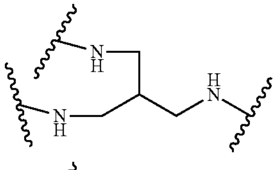
,

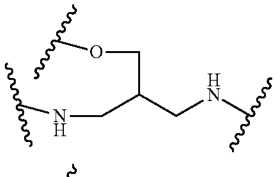
,

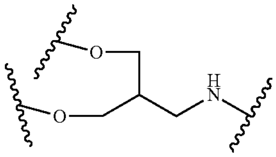
, wherein ⌇ is the site of linkage.

$X_1$, $X_2$, $X_3$, $X_4$, $X_5$, $X_6$, $X_{1'}$, $X_{2'}$ and $X_{3'}$ are independently selected from NH; NHNH; $N(R_3)$; $N(R_3)N(R_{3'})$; O; S; $C_1$-$C_6$ of alkyl; $C_2$-$C_6$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 amino acids; Wherein $R_3$ and $R_{3'}$ are independently H; $C_1$-$C_8$ of alkyl; $C_2$-$C_8$ of hetero-alkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 carbon atoms of esters, ether, or amide; or polyethyleneoxy unit of formula $(OCH_2CH_2)_p$ or $(OCH_2CH(CH_3))_p$, wherein p is an integer from 0 to about 1000, or combination above thereof.

m, $m_1$, $m_2$, $m_3$, $m_4$ and $m_5$ are independently an integer from 1 to 10, preferably from 1 to 4.

$L_1$ and $L_2$ are, the same or different, independently selected from O, NH, S, NHNH, $N(R_3)$, $N(R_3)N(R_{3'})$, polyethyleneoxy unit of formula $(OCH_2CH_2)_pOR_3$, or $(OCH_2CH(CH_3))_pOR_3$, or $NH(CH_2CH_2O)_pR_3$, or $NH(CH_2CH(CH_3)O)_pR_3$, or $N[(CH_2CH_2O)_pR_3][(CH_2CH_2O)_{p'}R_{3'}]$, or $(OCH_2CH_2)_pCOOR_3$, or $CH_2CH_2(OCH_2CH_2)_pCOOR_3$, wherein p and p' are independently an integer selected from 0 to about 1000, or combination thereof; $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; Wherein $R_3$ and $R_{3'}$ are independently H; $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 carbon atoms of esters, ether, or amide; or 1-8 amino acids; or polyethyleneoxy unit of formula $(OCH_2CH_2)_p$ or $(OCH_2CH(CH_3))_p$, wherein p is an integer from 0 to about 1000, or combination above thereof.

$L_1$ or $L_2$ may contain a self-immolative or a non-self-immolative component, peptidic units, a hydrazone bond, a disulfide, an ester, an oxime, an amide, or a thioether bond. The self-immolative unit includes, but is not limited to, aromatic compounds that are electronically similar to the para-aminobenzylcarbamoyl (PAB) groups such as 2-aminoimidazol-5-methanol derivatives, heterocyclic PAB analogs, beta-glucuronide, and ortho or para-aminobenzylacetals.

Preferably, the self-immolative linker component has one of the following structures:

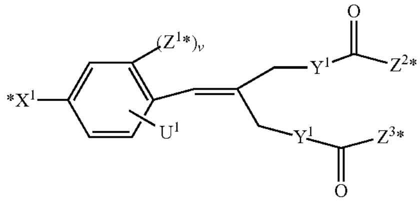

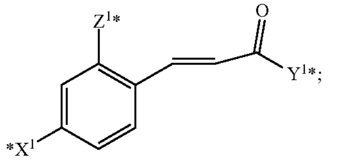

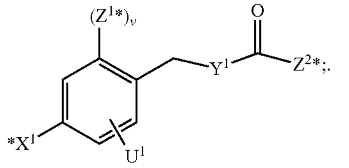

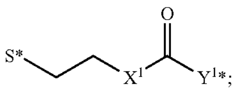
or
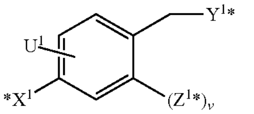

wherein the (*) atom is the point of attachment of additional spacer or releasable linker units, or the cytotoxic agent, and/or the binding molecule (CBA); $X^1$, $Y^1$, $Z^2$ and $Z^3$ are independently NH, O, or S; $Z^1$ is independently H, $NHR_1$, $OR_1$, $SR_1$, $COX_1R_1$, where $X_1$ and $R_1$ are defined above; v is 0 or 1; $U^1$ is independently H, OH, $C_1$-$C_6$ alkyl, $(OCH_2CH_2)_n$, F, Cl, Br, I, $OR_5$, $SR_5$, $NR_5R_5'$, $N{=}NR_5$, $N{=}R_5$, $NR_5R_5'$, $NO_2$, $SOR_5R_5'$, $SO_2R_5$, $SO_3R_5$, $OSO_3R_5$, $PR_5R_5'$, $POR_5R_5'$, $PO_2R_5R_5'$, $OPO(OR_5)(OR_5')$, or $OCH_2PO(OR_5(OR_5')$ wherein $R_5$ and $R_5'$ are independently selected from H, $C_1$~$C_8$ of alkyl; $C_2$~$C_8$ of alkenyl, alkynyl, heteroalkyl, or amino acid; $C_3$~$C_8$ of aryl, heterocyclic, carbocyclic, cycloalkyl, heterocycloalkyl, heteroaralkyl, alkylcarbonyl, or glycoside; or pharmaceutical cation salts.

The non-self-immolative linker component is one of the following structures:

$*(CH_2CH_2O)_r*$;
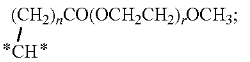
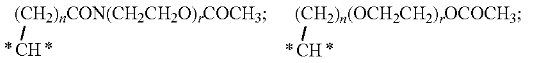
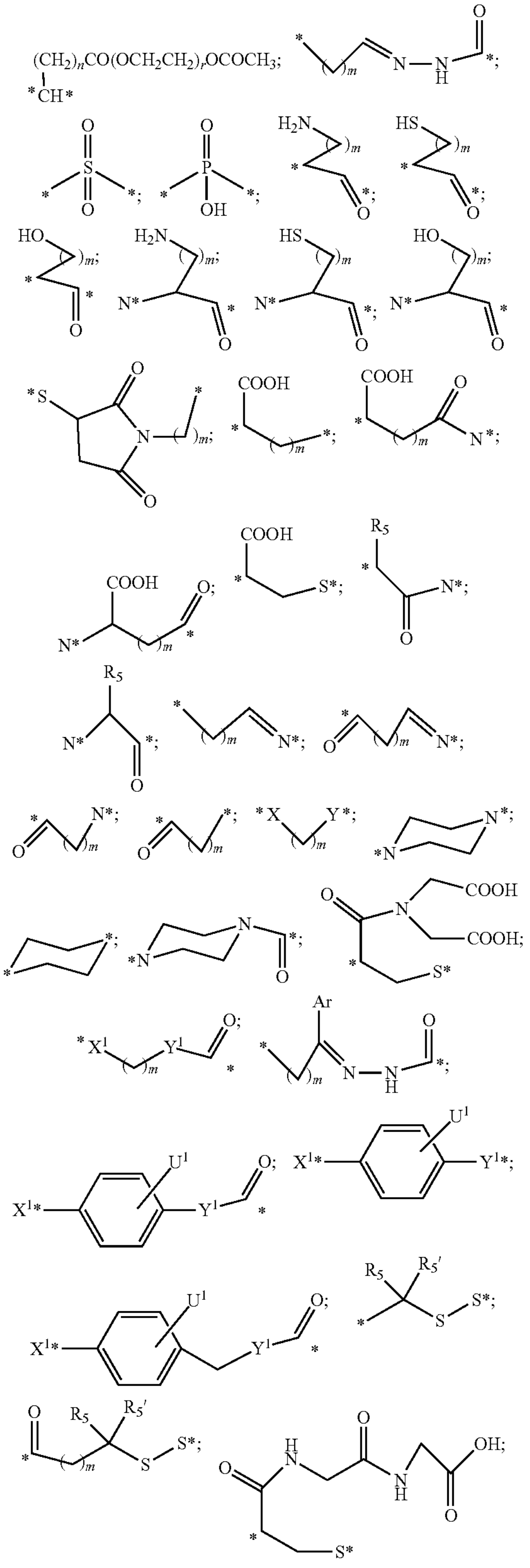
-continued
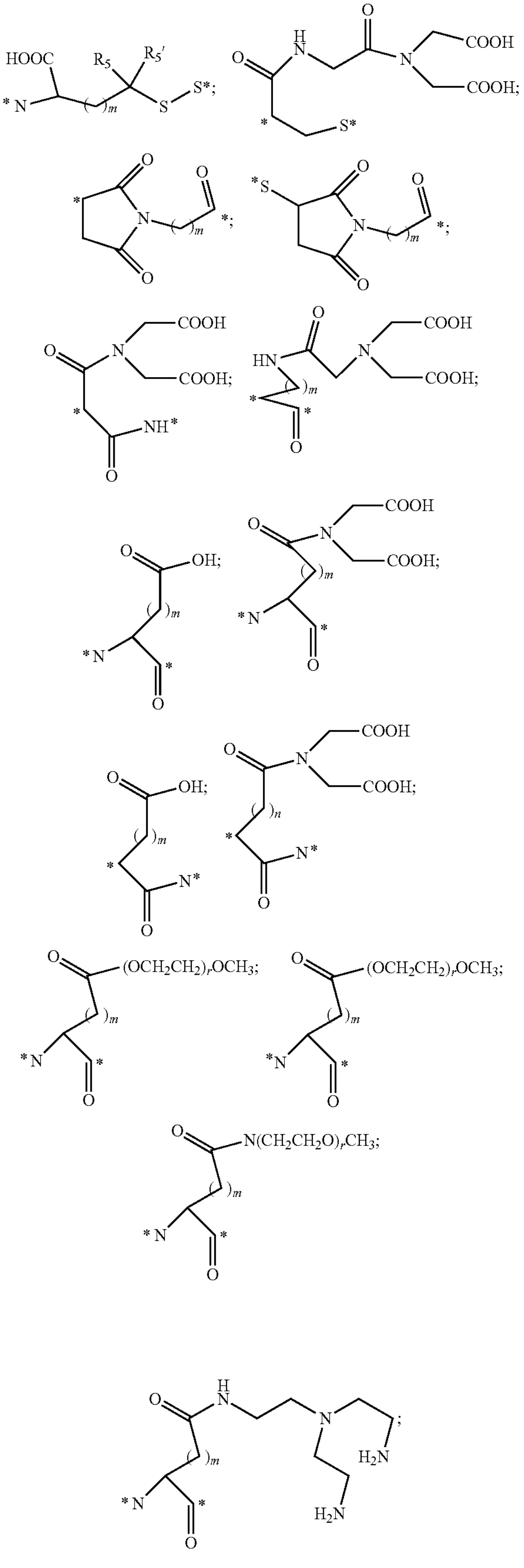

-continued

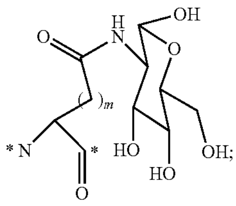

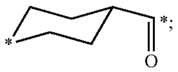

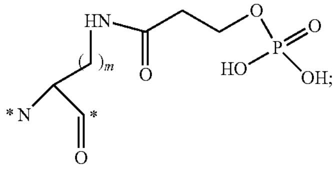

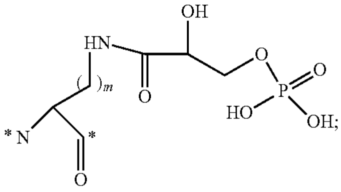

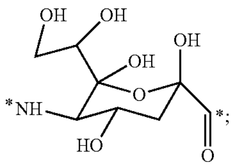

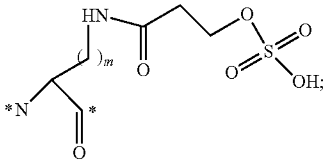

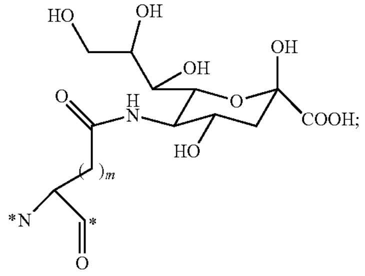

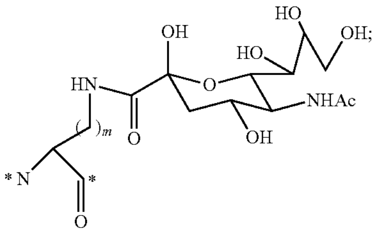

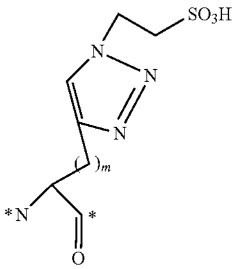

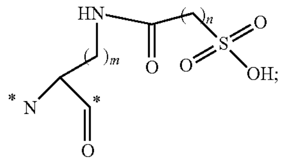

-continued

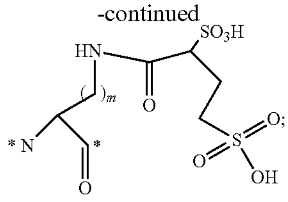

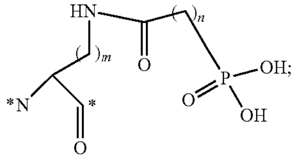

Wherein the (*) atom is the point of attachment of additional spacer or releasable linkers, the cytotoxic agents, and/or the binding molecules; $X^1$, $Y^1$, $U^1$, $R_5$, $R_5$' are defined as above; r is 0~100; m and n are 0~6 independently.

More preferably, $L_1$ or $L_2$ may be composed of one or more linker components as shown below:

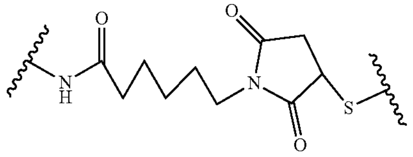 [SMILES: *NC(=O)CCCCCN1C(=O)CC(S*)C1=O]

6-maleimidocaproyl (MC),

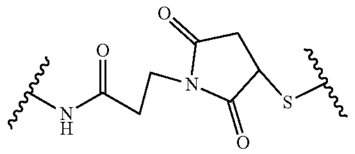 [SMILES: *NC(=O)CCN1C(=O)CC(S*)C1=O]

maleimido propanoyl (MP),

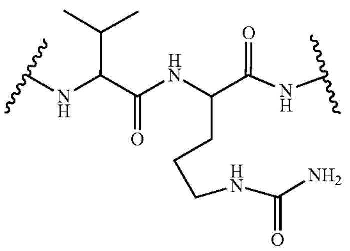 [SMILES: *NC(=O)C(CCCNC(N)=O)NC(=O)C(N*)C(C)C]

valine-citrulline (val-cit),

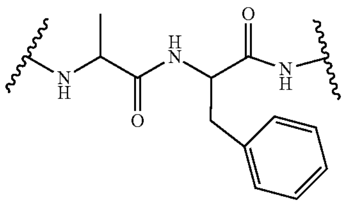 [SMILES: *NC(=O)C(Cc1ccccc1)NC(=O)C(C)N*]

alanine-phenylalanine (ala-phe),

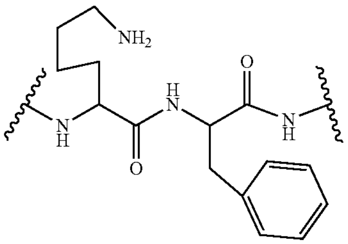 [SMILES: *NC(=O)C(Cc1ccccc1)NC(=O)C(CCCCN)N*]
lysine-phenylalanine (lys-phe),
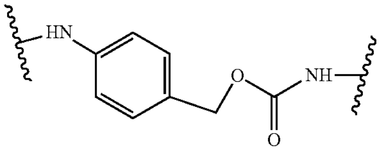 [SMILES: *NC(=O)OCc1ccc(N*)cc1]
p-aminobenzyloxycarbonyl (PAB),
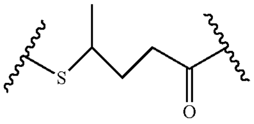 [SMILES: *SC(C)CCC(*)=O]
4-thio-pentanoate (SPP),
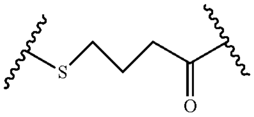 [SMILES: *SCCCC(*)=O]
4-thio-butyrate (SPDB),
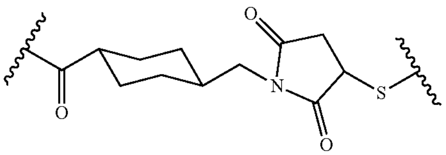 [SMILES: *SC1CC(=O)N(CC2CCC(C(*)=O)CC2)C1=O]
4-(N-maleimidomethyl)cyclo-hexane-1-carboxylate (MCC),
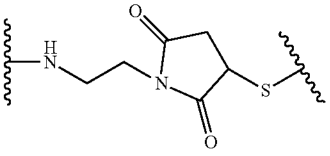 [SMILES: *NCCN1C(=O)CC(S*)C1=O]
maleimidoethyl (ME),
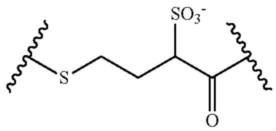
4-thio-2-hydroxysulfonyl-butyrate (2-Sulfo-SPDB),
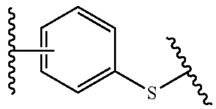
aryl-thiol (PySS),
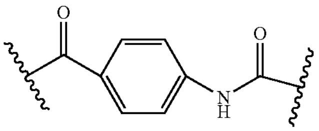 [SMILES: *C(=O)Nc1ccc(C(*)=O)cc1]
(4-acetyl)aminobenzoate (SIAB),
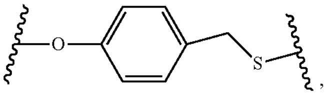 [SMILES: *Oc1ccc(CS*)cc1]
oxylbenzylthio,
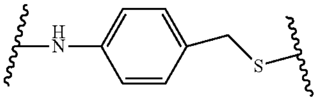 [SMILES: *Nc1ccc(CS*)cc1]
aminobenzylthio,
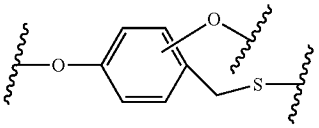
dioxylbenzylthio,
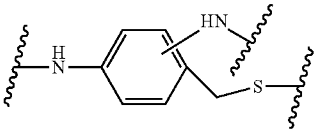
diaminobenzylthio,

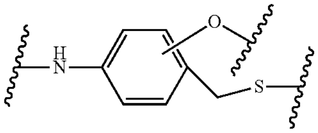
amino-oxylbenzylthio,
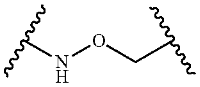 [SMILES: *CON*]
alkoxy amino (AOA),
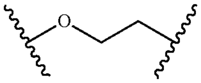 [SMILES: *CCO*]
ethyleneoxy (EO),
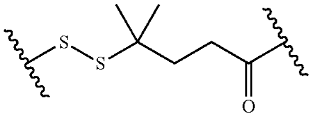 [SMILES: *SSC(C)(C)CCC(*)=O]
4-methyl-4-dithio-pentanoic (MPDP),
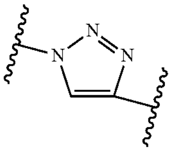 [SMILES: *c1cn(*)nn1]
triazole,
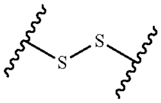 [SMILES: *SS*]
dithio,
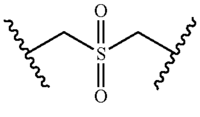 [SMILES: *CS(=O)(=O)C*]
alkylsulfonyl,
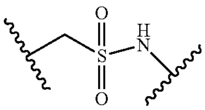 [SMILES: *CS(=O)(=O)N*]
alkylsulfonamide,
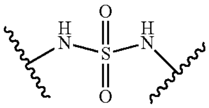 [SMILES: *NS(=O)(=O)N*]
sulfon-bisamide,
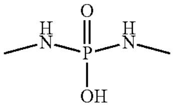
Phosphondiamide,
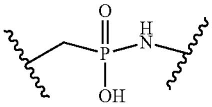 [SMILES: *CP(=O)(O)N*]
alkylphosphonamide,
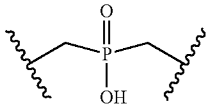 [SMILES: *CP(=O)(O)C*]
phosphinic acid,
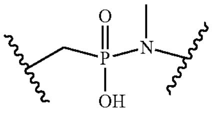 [SMILES: *CP(=O)(O)N(*)C]
N-methylphosphonamidic acid,
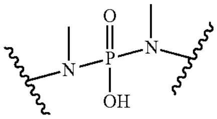 [SMILES: *N(C)P(=O)(O)N(*)C]
N,N'-dimethyphosphon-amidic acid,
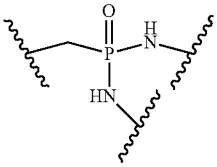 [SMILES: *CP(=O)(N*)N*]
—N,N'-dimethylphosphondiamide,

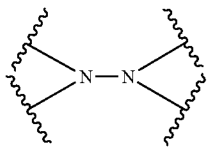 [SMILES: *N(*)N(*)*]

hydrazine,

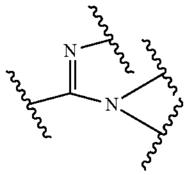 [SMILES: */N=C(/*)N(*)*]

acetimidamide;

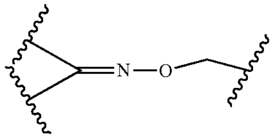 [SMILES: *CON=C(*)*]

oxime,

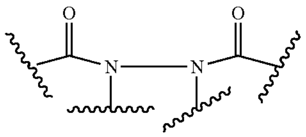

acetylacetohydrazide,

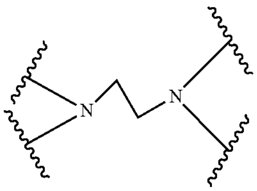 [SMILES: *N(*)CCN(*)*]

aminoethyl-amine,

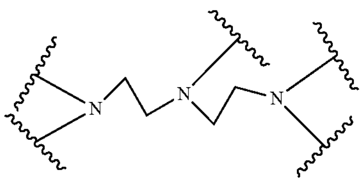 [SMILES: *N(*)CCN(*)CCN(*)*]

aminoethyl-aminoethyl-amine, and L- or D-, natural or unnatural peptides containing 1-20 amino acids.

Further preferably, $L_1$ or $L_2$ may be a releasable linker. The term releasable linker refers to a linker that includes at least one bond that can be broken under physiological conditions, such as a pH-labile, acid-labile, base-labile, oxidatively labile, metabolically labile, biochemically labile or enzyme-labile bond. It is appreciated that such physiological conditions resulting in bond breaking do not necessarily include a biological or metabolic process, and instead may include a standard chemical reaction, such as a hydrolysis or substitution reaction, for example, an endosome having a lower pH than cytosolic pH, and/or disulfide bond exchange reaction with a intracellular thiol, such as a millimolar range of abundant of glutathione inside the malignant cells.

Examples of the releasable linkers (L, $L_1$ or $L_2$) include, but not limited: —$(CR_5R_6)_m(Aa)r(CR_7R_8)_n(OCH_2CH_2)_t$—, —$(CR_5R_6)_m(CR_7R_8)_n(Aa)_r(OCH_2CH_2)_t$—, -$(Aa)_r$-$(CR_5R_6)_m(CR_7R_8)_n(OCH_2CH_2)_t$—, —$(CR_5R_6)_m(CR_7R_8)_n(OCH_2CH_2)_r(Aa)_t$-, —$(CR_5R_6)_m$—$(CR_7{=}CR_8)(CR_9R_{10})_n(Aa)_t(OCH_2CH_2)_r$—, —$(CR_5R_6)_m(NR_{11}CO)(Aa)_t(CR_9R_{10})_n$—$(OCH_2CH_2)_r$—, —$(CR_5R_6)_m(Aa)_t(NR_{11}CO)(CR_9R_{10})_n(OCH_2CH_2)_r$—, —$(CR_5R_6)_m(OCO)(Aa)_t(CR_9R_{10})_n(OCH_2CH_2)_r$—, —$(CR_5R_6)_m(OCNR_7)(Aa)_t(CR_9R_{10})_n(OCH_2CH_2)_r$—, —$(CR_5R_6)_m(CO)(Aa)_t(CR_9R_{10})_n(OCH_2CH_2)_r$—, —$(CR_5R_6)_m(NR_{11}CO)(Aa)_t(CR_9R_{10})_n(OCH_2CH_2)_r$—, —$(CR_5R_6)_m$—$(OCO)(Aa)_t(CR_9R_{10})_n$—$(OCH_2CH_2)_r$—, —$(CR_5R_6)_m(OCNR_7)(Aa)_t(CR_9R_{10})_n(OCH_2CH_2)_r$—, —$(CR_5R_6)_m(CO)(Aa)_t(CR_9R_{10})_n$—$(OCH_2CH_2)_r$—, —$(CR_5R_6)_m$-phenyl-$CO(Aa)_t(CR_7R_8)_n$—, —$(CR_5R_6)_m$-furyl-$CO(Aa)_t(CR_7R_8)_n$—, —$(CR_5R_6)_m$-oxazolyl-$CO(Aa)_t(CR_7R_8)_n$—, —$(CR_5R_6)_m$-thiazolyl-$CO(Aa)_t(CCR7R_8)_n$—, —$(CR_5R_6)_t$-thienyl-$CO(CR_7R_8)_n$—, —$(CR_5R_6)_t$-imidazolyl-CO—$(CR_7R_8)_n$—, —$(CR_5R_6)_t$-morpholino-$CO(Aa)_r$-$(CR_7R_8)_n$—, —$(CR_5R_6)_t$piperazino-$CO(Aa)_r$-$(CR_7R_8)_n$—, —$(CR_5R_6)_t$—N-methylpiperazin-$CO(Aa)_r$-$(CR_7R_8)_n$—, —$(CR_5R_6)_m$-$(Aa)_t$phenyl-, —$(CR_5R_6)_m$-$(Aa)_t$furyl-, —$(CR_5R_6)_m$-oxazolyl$(Aa)_t$-, —$(CR_5R_6)_m$-thiazolyl$(Aa)_t$-, —$(CR_5R_6)_m$-thienyl-$(Aa)_t$-, —$(CR_5R_6)_m$-imidazolyl$(Aa)_t$-, —$(CR_5R_6)_m$-morpholino-$(Aa)_t$-, —$(CR_5R_6)_m$-piperazino-$(Aa)_t$-, —$(CR_5R_6)_m$—N-methylpiperazino-$(Aa)_t$-, —$K(CR_5R_6)_m(Aa)_r(CR_7R_8)_n(OCH_2CH_2)_t$—, —$K(CR_5R_6)_m(CR_7R_8)_n(Aa)_r(OCH_2CH_2)_t$—, —$K(Aa)_r$-$(CR_5R_6)_m(CR_7R_8)_n(OCH_2CH_2)_t$—, —$K(CR_5R_6)_m(CR_7R_8)_n(OCH_2CH_2)_r(Aa)_t$-, —$K(CR_5R_6)_m$—$(CR_7{=}CR_8)(CR_9R_{10})_n(Aa)_t(OCH_2CH_2)_r$—, —$K(CR_5R_6)_m(NR_{11}CO)(Aa)_t(CR_9R_{10})_n(OCH_2CH_2)_r$—, —$K(CR_5R_6)_m(Aa)_t(NR_{11}CO)(CR_9R_{10})_n(OCH_2CH_2)_r$—, —$K(CR_5R_6)_m(OCO)(Aa)_t(CR_9R_{10})_n$—$(OCH_2CH_2)_r$—, —$K(CR_5R_6)_m(OCNR_7)(Aa)_t(CR_9R_{10})_n(OCH_2CH_2)_r$—, —$K(CR_5R_6)_m(CO)(Aa)_r$-$(CR_9R_{10})_n(OCH_2CH_2)_r$—, —$K(CR_5R_6)_m(NR_{11}CO)(Aa)_t(CR_9R_{10})_n(OCH_2CH_2)_r$—, —$K(CR_5R_6)_m$—$(OCO)(Aa)_t(CR_9R_{10})_n(OCH_2CH_2)_r$—, —$K(CR_5R_6)_m(OCNR_7)(Aa)_t(CR_9R_{10})_n(OCH_2CH_2)_r$—, —K—$(CR_5R_6)_m(CO)(Aa)_t(CR_9R_{10})_n(OCH_2CH_2)_r$—, —$K(CR_5R_6)_m$-phenyl-$CO(Aa)_t(CR_7R_8)_n$—, —K—$(CR_5R_6)_m$-furyl-$CO(Aa)_r$-$(CR_7R_8)_n$—, —$K(CR_5R_6)_m$-oxazolyl-$CO(Aa)_t(CR_7R_8)_n$—, —$K(CR_5R_6)_m$-thiazolyl-$CO(Aa)_r$-$(CR_7R_8)_n$—, —$K(CR_5R_6)_t$-thienyl-$CO(CR_7R_8)_n$—, —$K(CR_5R_6)_t$imidazolyl-CO—$(CR_7R_8)_n$—, —$K(CR_5R_6)_t$morpholino-$CO(Aa)_t(CR_7R_8)_n$—, —$K(CR_5R_6)_t$piperazino-$CO(Aa)_r$-$(CR_7R_8)_n$—, —$K(CR_5R_6)_t$—N-methylpiperazin$CO(Aa)_t(CR_7R_8)_n$—, —$K(CR_5R_6)_m(Aa)_t$phenyl, —K—$(CR_5R_6)_m$-$(Aa)_t$furyl-, —$K(CR_5R_6)_m$-oxazolyl$(Aa)_t$-, —$K(CR_5R_6)_m$-thiazolyl$(Aa)_t$-, —$K(CR_5R_6)_m$-thienyl-$(Aa)_t$-, —$K(CR_5R_6)_m$-imidazolyl$(Aa)_t$-, —$K(CR_5R_6)_m$-morpholino$(Aa)_t$-, —$K(CR_5R_6)_m$-piperazino-$(Aa)_t$G, —$K(CR_5R_6)_m$N-methylpiperazino$(Aa)_t$-; wherein m, Aa, m, n, $R_3$, $R_4$, and $R_5$ are described above; t and r are 0-100 independently; $R_6$, $R_7$, and $R_8$ are independently chosen from H; halide; $C_1$~$C_8$ of alkyl, aryl, alkenyl, alkynyl, ether, ester, amine or amide, which optionally substituted by one or more halide, CN, $NR_1R_2$, $CF_3$, $OR_1$, Aryl, heterocycle, $S(O)R_1$, $SO_2R_1$, —$CO_2H$, —$SO_3H$, —$OR_1$, —$CO_2R_1$, —$CONR_1$, —$PO_2R_1R_2$, —$PO_3H$ or $P(O)R_1R_2R_3$; K is $NR_1$, —SS—, —C(=O)—, —C(=O)NH—, —C(=O)O—, —C=NH—O—, —C=N—NH—, —C(=O)NH—NH—, O, S, Se, B, Het (heterocyclic or heteroaromatic ring having $C_3$-$C_8$), or peptides containing 1-20 amino acids.

In addition, $L_1$, $L_2$, $X_1$, $X_2$, $X_3$, $X_{1'}$, $X_{2'}$ and $X_{3'}$ can be independently absent.

In the Formula (I) or (II), wherein substituted acrylic groups, or propiolic groups are capable of reacting with a thiol, preferably a pair of thiols of the cell-binding agent; The pair of thiols are preferred pairs of sulfur atoms reduced from the inter chain disulfide bonds of the cell-binding agent by a reducing agent, such as dithiothreitol (DTT), dithioerythritol (DTE), L-glutathione (GSH), tris (2-carboxyethyl) phosphine (TCEP), 2-mercaptoethylamine (β-MEA), or/and beta mercaptoethanol (β-ME, 2-ME).

Examples of the functional group, Y, which enables linkage of a drug or a cytotoxic agent, include groups that enable linkage via a disulfide, thioether, thioester, peptide, hydrazone, ester, carbamate, carbonate, alkoxime or an amide bond. Such functional groups include, but are not limited to, thiol, disulfide, amino, carboxyl, aldehydes, ketone, maleimido, haloacetyl, hydrazines, alkoxyamino, and/or hydroxy.

Examples of the functional group, Y, that enables reaction with the terminal of amine of a drug/cytotoxic agent, can be, but not limited to, N-hydroxysuccinimide esters, p-nitrophenyl esters, dinitrophenyl esters, pentafluorophenyl esters, carboxylic acid chlorides or carboxylic acid anhydride; With the terminal of thiol, can be, as but not limited to, pyridyldisulfides, nitropyridyldisulfides, maleimides, haloacetates, methylsulfonephenyloxadiazole (ODA), carboxylic acid chlorides and carboxylic acid anhydride; With the terminal of ketone or aldehyde, can be, as but not limited to, amines, alkoxyamines, hydrazines, acyloxylamine, or hydrazide; With the terminal of azide, can be, as but not limited to, alkyne.

In preferred embodiments, $R_1$, $L_1$, or $L_2$, are independently linear alkyl having from 1-6 carbon atoms, or polyethyleneoxy unit of formula $(OCH_2CH_2)_p$, p=1~100, or a peptide containing 1~4 units of amino acids (L or D), or combination above.

In preferred embodiments, $L_{V1}$ and $L_{V2}$ are the same or independently OH; F; Cl; Br; I; nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, anhydrides formed its self, or formed with the other anhydride, e.g. acetyl anhydride, formyl anhydride; or an intermediate molecule generated with a condensation reagent for peptide coupling reactions, or for Mitsunobu reactions, e.g. condensation reagents are: EDC (N-(3-Dimethylaminopropyl)-N'-ethylcarbodiimide), DCC (Dicyclohexyl-carbodiimide), N,N'-Diisopropylcarbodiimide (DIC), N-Cyclohexyl-N'-(2-morpholino-ethyl)carbodiimide metho-p-toluenesulfonate (CMC, or CME-CDI), 1,1'-Carbonyldiimidazole (CDI), TBTU (O-(Benzotriazol-1-yl)-N,N,N',N'-tetramethyluronium tetrafluoroborate), N,N,N',N'-Tetramethyl-O-(1H-benzotriazol-1-yl)uronium hexafluorophosphate (HBTU), (Benzotriazol-1-yloxy)tris(dimethylamino)phosphonium hexafluorophosphate (BOP), (Benzotriazol-1-yloxy)tripyrrolidinophosphonium hexafluorophosphate (PyBOP), Diethyl cyanophosphonate (DEPC), Chloro-N,N,N',N'-tetramethylformamidiniumhexafluorophosphate, 1-[Bis(dimethylamino)methylene]-1H-1,2,3-triazolo[4,5-b]pyridinium 3-oxid hexafluorophosphate (HATU), 1-[(Dimethylamino)(morpholino)methylene]-1H-[1,2,3]triazolo[4,5-b]pyridine-1-ium 3-oxide hexafluorophosphate (HDMA), 2-Chloro-1,3-dimethyl-imidazolidinium hexafluorophosphate (CIP), Chlorotripyrrolidinophosphonium hexafluorophosphate (PyCloP), Fluoro-N,N,N',N'-bis(tetramethylene)formamidinium hexafluorophosphate (BTFFH), N,N,N',N'-Tetramethyl-S-(1-oxido-2-pyridyl)thiuronium hexafluorophosphate, O-(2-Oxo-1(2H)pyridyl)-N,N,N',N'-tetramethyluronium tetrafluoroborate (TPTU), S-(1-Oxido-2-pyridyl)-N,N,N',N'-tetramethylthiuronium tetrafluoroborate, O-[(Ethoxycarbonyl)-cyanomethylenamino]-N,N,N',N'-tetramethyluronium hexafluorophosphate (HOTU), (1-Cyano-2-ethoxy-2-oxoethylidenaminooxy) dimethylamino-morpholino-carbenium hexafluorophosphate (COMU), O-(Benzotriazol-1-yl)-N,N,N',N'-bis(tetramethylene)uronium hexafluorophosphate (HBPyU), N-Benzyl-N'-cyclohexyl-carbodiimide (with, or without polymer-bound), Dipyrrolidino(N-succinimidyloxy)carbenium hexafluoro-phosphate (HSPyU), Chlorodipyrrolidinocarbenium hexafluorophosphate (PyClU), 2-Chloro-1,3-dimethylimidazolidinium tetrafluoroborate (CIB), (Benzotriazol-1-yloxy)dipiperidino-carbenium hexafluorophosphate (HBPipU), 0-(6-Chlorobenzotriazol-1-yl)-N,N,N',N'-tetramethyluronium tetrafluoroborate (TCTU), Bromotris(dimethylamino)-phosphonium hexafluorophosphate (BroP), Propylphosphonic anhydride (PPACA, T3P®), 2-Morpholinoethyl isocyanide (MEI), N,N,N',N'-Tetramethyl-O—(N-succinimidyl)uronium hexafluorophosphate (HSTU), 2-Bromo-1-ethyl-pyridinium tetrafluoroborate (BEP), 0-[(Ethoxycarbonyl)cyano-methylenamino]-N,N,N',N'-tetramethyluronium tetrafluoroborate (TOTU), 4-(4,6-Dimethoxy-1,3,5-triazin-2-yl)-4-methylmorpholiniumchloride (MMTM, DMTMM), N,N,N',N'-Tetramethyl-O—(N-succinimidyl)uronium tetrafluoroborate (TSTU), 0-(3,4-Dihydro-4-oxo-1,2,3-benzotriazin-3-yl)-N,N,N',N'-tetramethyluronium tetrafluoro-borate (TDBTU), 1,1'-(Azodicarbonyl)-dipiperidine (ADD), Di-(4-chlorobenzyl)azodicarboxylate (DCAD), Di-tert-butyl azodicarboxylate (DBAD), Diisopropyl azodicarboxylate (DIAD), Diethyl azodicarboxylate (DEAD). In addition, $L_{V1}$ and $L_{V2}$ can be an anhydride, formed by acid themselves or formed with other $C_1$-$C_8$ acid anhydrides.

In preferred embodiments, Formula (I) or (II) having the following structures:

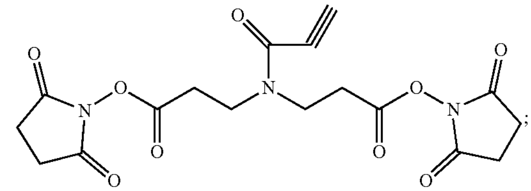
;
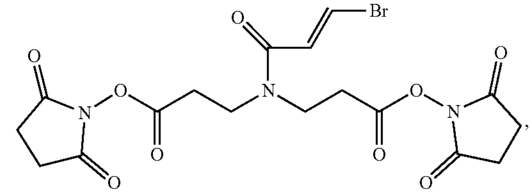
,
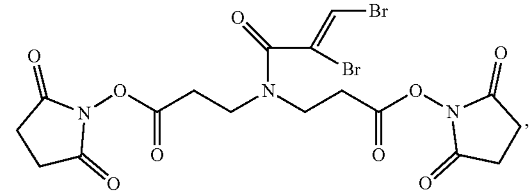
,
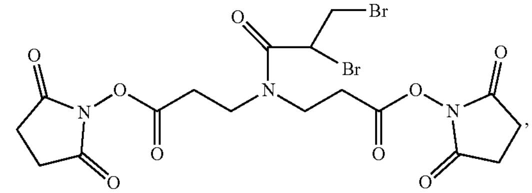
,
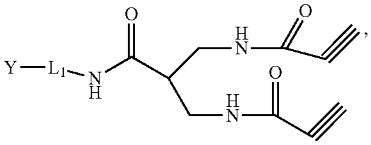
,
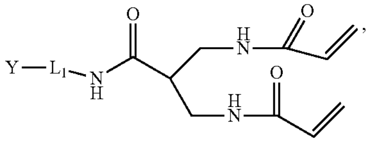
,
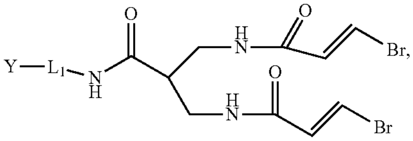
,
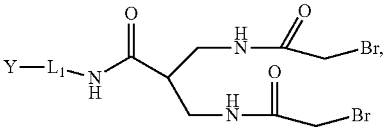
,
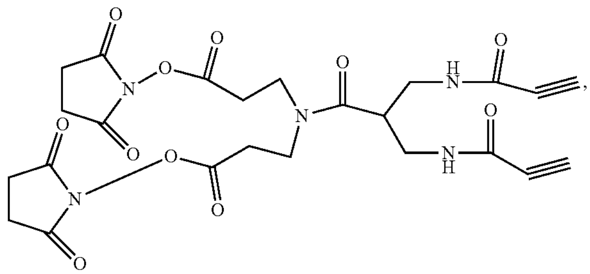
, -continued
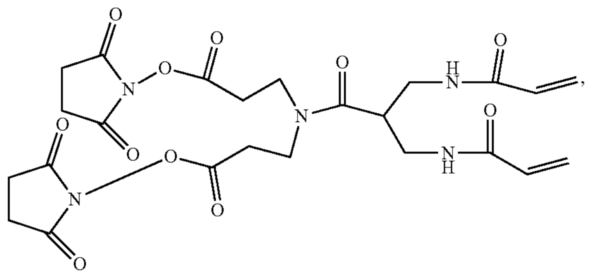
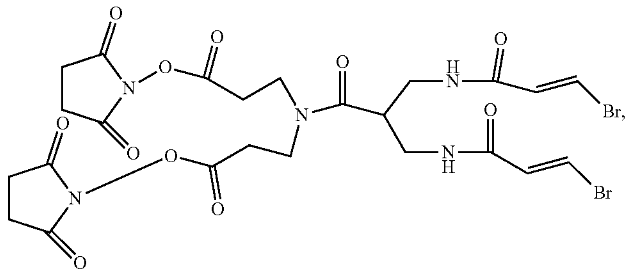
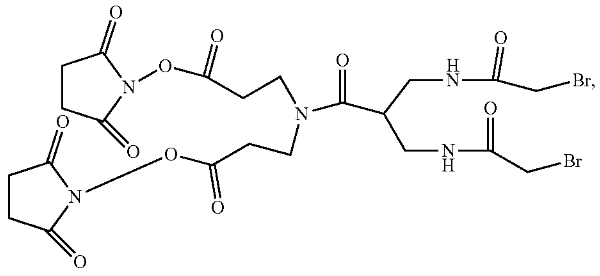
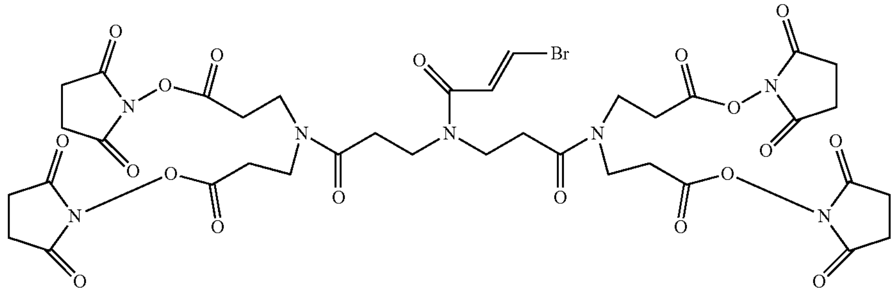
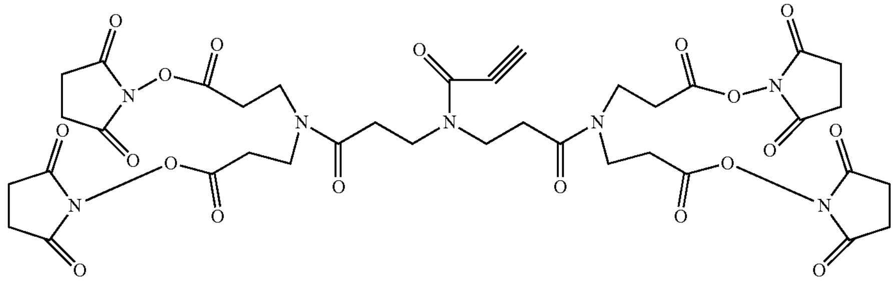

-continued
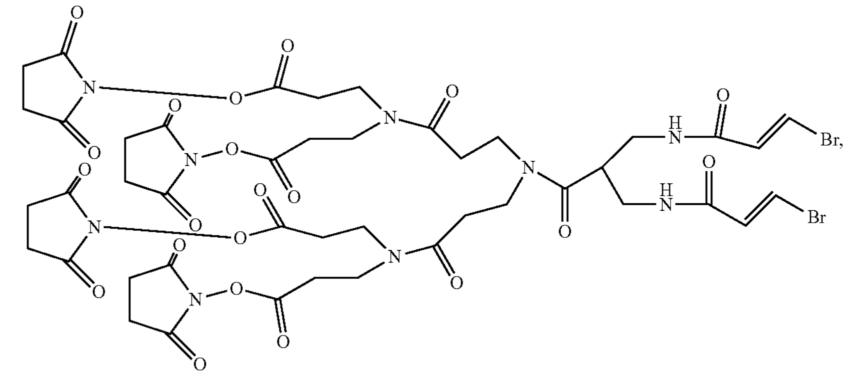
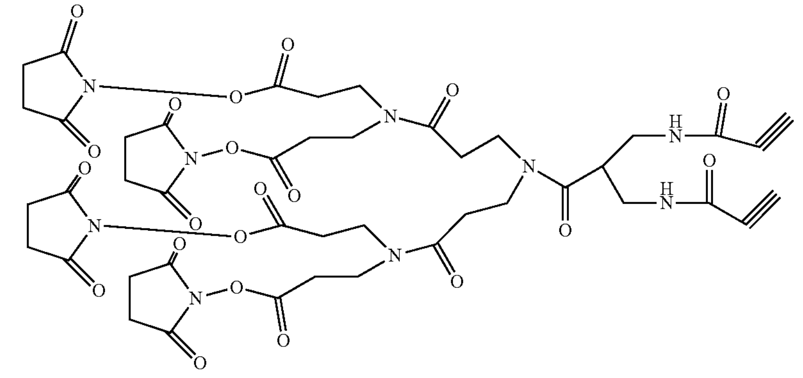
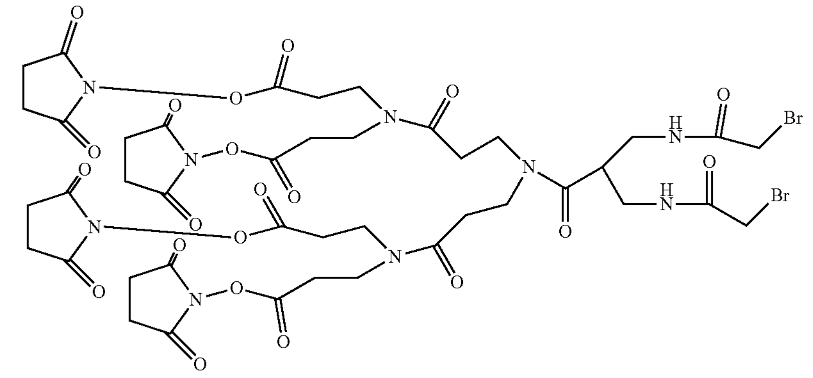
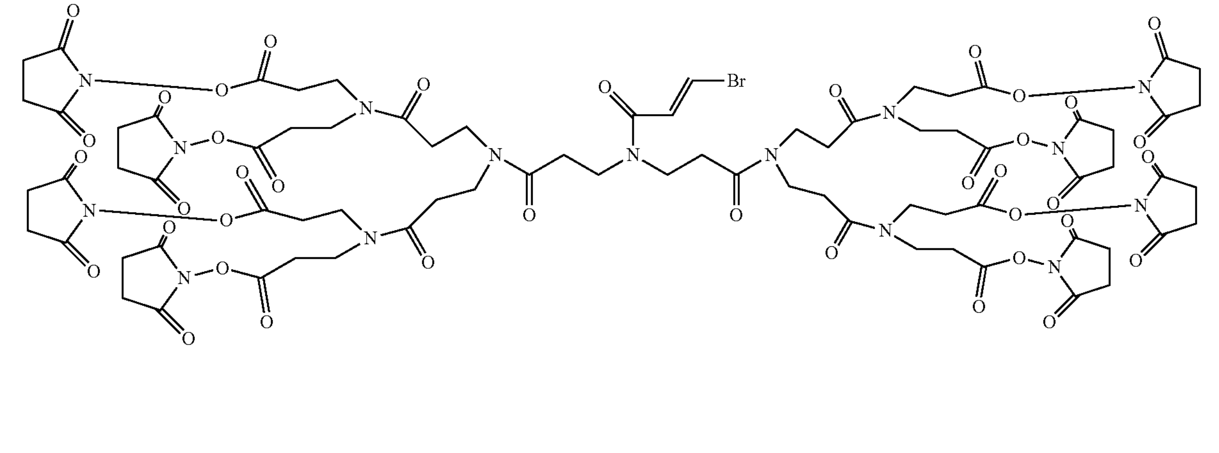

-continued
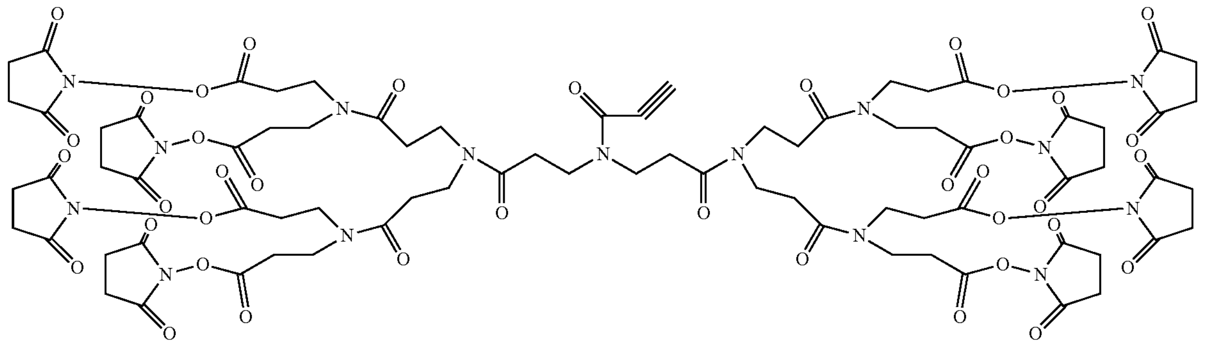
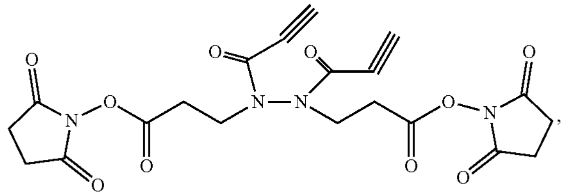
,
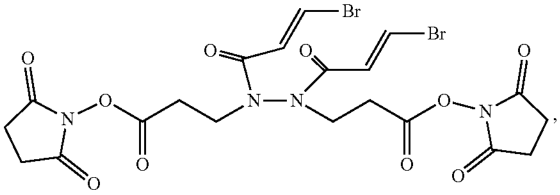
,
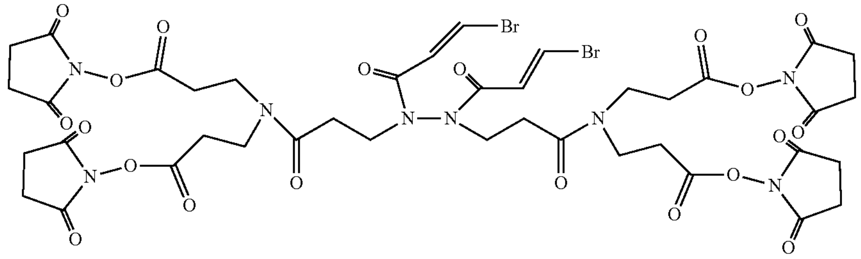
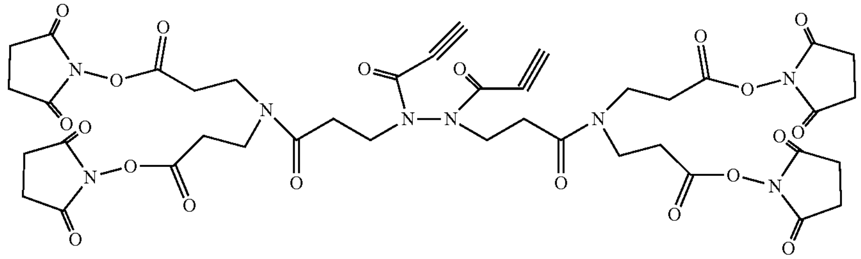
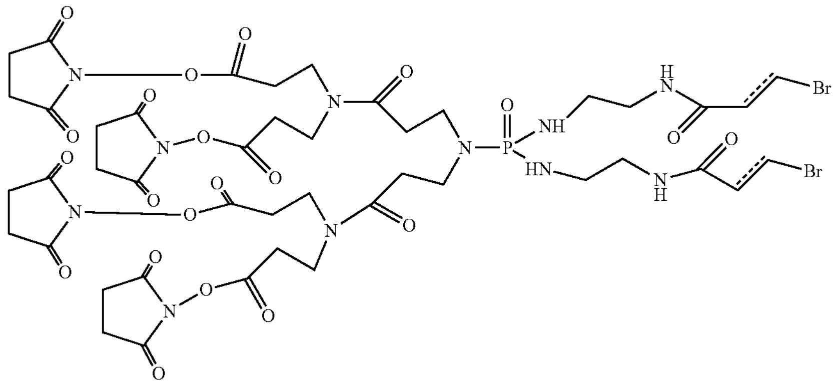

-continued

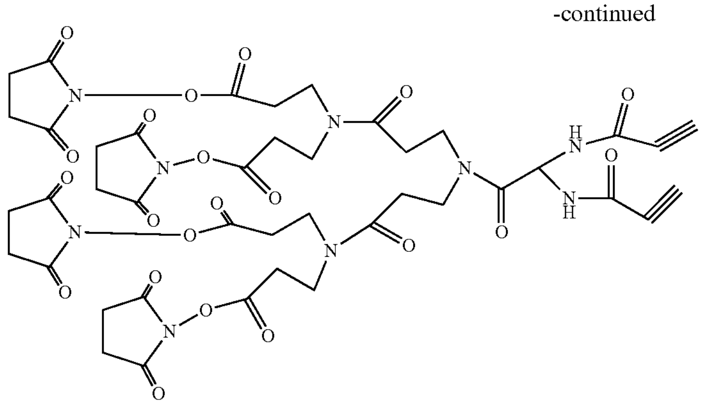

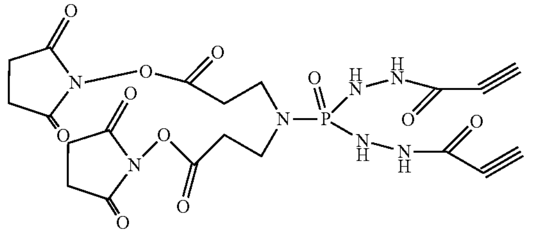

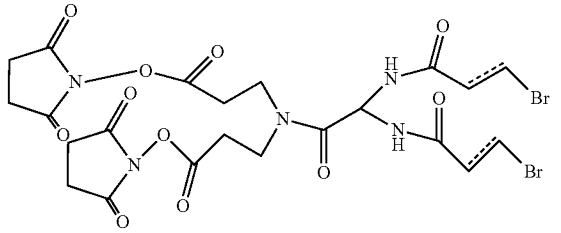

The detail examples of the synthesis of the bridge linkers are shown in FIGS. 1-33. Normally the bridge substituents of propiolyl, or substituted acryl (acryloyl) group, or disubstituted propanoyl group, can be condensated with linker components containing function groups capable to react to drugs of desired conjugation.

Cell-Binding Agent-Drug Conjugates

The conjugates of the present invention can be represented by the following formula (III), (IV), (V), (VI), (VII), (VIII), or (IX):

(III)

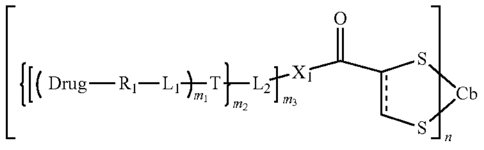

(IV)

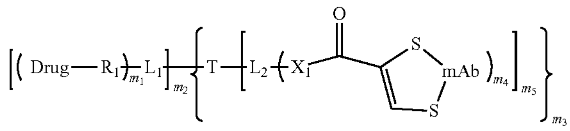

-continued (V)

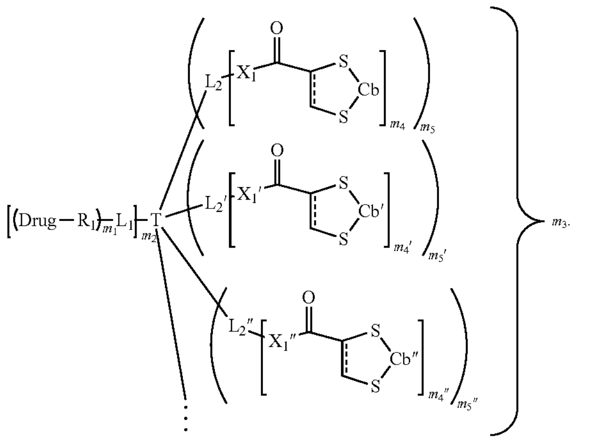

(VI)

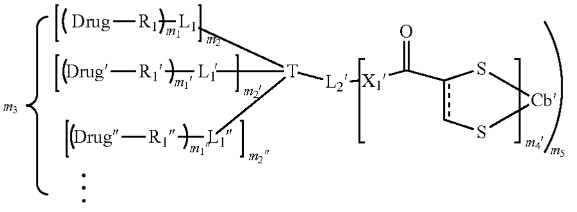

-continued (VII)

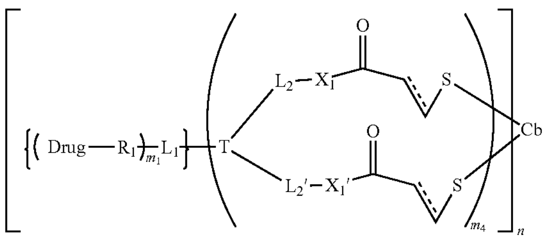

(VIII)

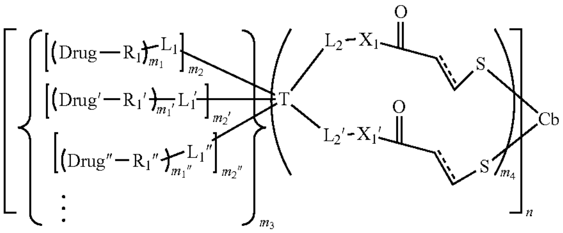

(IX)

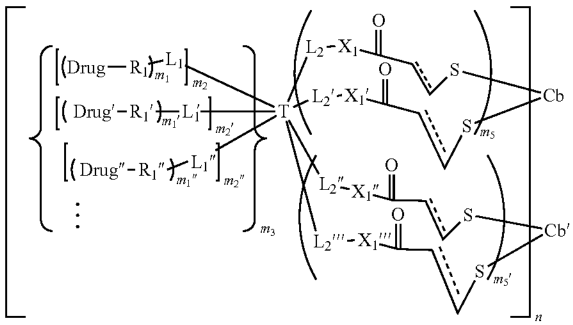

Wherein:

n is 1~20; and T is described the same previously in Formula (I).

Cb, Cb', Cb'', Cb''' represent the same or different, a cell-binding agent, or an immunotherapeutical protein, preferably an antibody or an antibody fragment.

Inside the right bracket (square parentheses) of formula (III), (VII), (VIII) and (IX) are the linker-drug components that are conjugated to pairs of thiols of the cell-binding agent/molecule. The thiols are preferred pairs of sulfur atoms reduced from the inter chain disulfide bonds of the cell-binding agent by a reduction agent selected from dithiothreitol (DTT), dithioerythritol (DTE), dithiolbutylamine (DTBA), L-glutathione (GSH), tris (2-carboxyethyl) phosphine (TCEP), 2-mercaptoethylamine (0-MEA), or/and beta mercaptoethanol (β-ME, 2-ME).

Drug, Drug', and Drug'' represent the same or different of, a cytotoxic agent, or a therapeutic drug, or an immunotherapeutical protein, or a function molecule for enhancement of binding or stabilization of the cell-binding agent, or a cell-surface receptor binding ligand, which is linked to the cell-binding agent via the bridge linker of the patent through $R_1$ containing an $C_1$-$C_8$ of alkane; $C_2$-$C_8$ of alkylene, alkenylene, alkynylene, aromatic, ether, polyoxyalkylene, ester, amine, imine, polyamine, hydrazine, hydrazone, amide, urea, semicarbazide, carbazide, alkoxyamine, urethanes, amino acid, peptide, acyloxylamine, hydroxamic acid, disulfide, thioether, thioester, carbamate, carbonate, heterocyclic ring, heteroalkyl, heteroaromatic, or alkoxime; or combination above thereof. "Drug'' Drug', and Drug" can also be an immunotherapeutic compound, a chemotherapeutic compound, an antibody or an antibody fragment, siRNA or DNA molecule, or a cell surface binding ligand.

"⎓" represents either single bond or double bond.

Inside the square bracket are agents that are conjugated to a cell-binding molecule through a pair of sulfur atoms on the cell-binding molecule.

$m_1$, $m_{1'}$, $m_{1''}$, $m_2$, $m_{2'}$, $m_{2''}$, $m_3$, $m_4$, $m_5$, $m_{4'}$, $m_{5'}$, $m_{4''}$, $m_{5''}$, $m_{4'''}$, $m_{5'''}$, $m_{4''''}$ and $m_{5''''}$ are independently an integer from 1 to 10, preferably from 1 to 4.

$X_1$, $X_{1'}$, $X_{1''}$, $X_{1'''}$ and $X_{2''''}$ are independently selected from NH; NHNH; $N(R_3)$; $N(R_3)N(R_{3'})$; O; S; $C_1$-$C_6$ of alkyl; $C_2$-$C_6$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 amino acids; Wherein $R_3$ and $R_{3'}$ are independently H; $C_1$-$C_8$ of alkyl; $C_2$-$C_8$ of hetero-alkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 carbon atoms of esters, ether, or amide; or polyethyleneoxy unit of formula $(OCH_2CH_2)_p$ or $(OCH_2CH(CH_3))_p$, wherein p is an integer from 0 to about 1000, or combination above thereof. In addition, $X_1$, $X_{1'}$, $X_{1''}$, $X_{1'''}$ and $X_{2''''}$ can be independently absent.

$R_1$, $R_2$, $R_{1'}$, and $R_{1''}$, are the same or different, selected from $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or $C_2$-$C_8$ of esters, ether, or amide; or polyethyleneoxy unit of formula $(OCH_2CH_2)_p$ or $(OCH_2CH(CH_3))_p$, wherein p is an integer from 0 to about 1000, or combination of above groups thereof.

$L_1$, $L_{1'}$, $L_{1''}$, $L_{1'''}$, $L_2$, $L_{2'}$, $L_{2''}$ and $L_{2'''}$ are defined the same as $L_1$ and $L_2$ in formula (I) and (II) and they can be the same or different.

$L_1$, $L_{1'}$, $L_{1''}$, $L_{1'''}$, $L_2$, $L_{2'}$, $L_{2''}$ and $L_{2'''}$ may be composed of one or more linker components. Exemplary the linker components include 6-maleimidocaproyl ("MC"), maleimidopropanoyl ("MP"), valine-citrulline ("val-cit" or "vc"), alanine-phenylalanine ("ala-phe" or "af"), p-aminobenzyloxycarbonyl ("PAB"), 4-thiopentanoate ("SPP"), 4-(N-maleimidomethyl)-cyclohexane-1 carboxylate ("MCC"), (4-acetyl)aminobenzoate ("SIAB"), 4-thio-butyrate (SPDB), 4-thio-2-hydroxysulfonyl-butyrate (2-Sulfo-SPDB), ethyleneoxy-$CH_2CH_2O$— as one or more repeating units ("EO" or "PEO"). Additional linker components are known in the art and some are described herein.

Example structures of the components of the linker containing are:

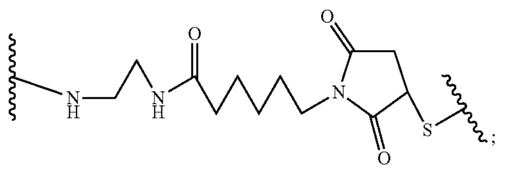 [SMILES: *NCCNC(=O)CCCCCN1C(=O)CC(S*)C1=O];

(MC, 6-maleimidocaproyl containing)

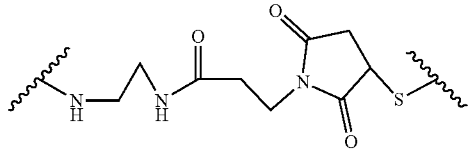 [SMILES: *NCCNC(=O)CCN1C(=O)CC(S*)C1=O]

(MP, maleimidopropanoyl containing)
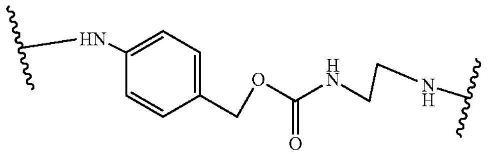 [SMILES: *NCCNC(=O)OCc1ccc(N*)cc1]
(PAB, p-aminobenzyloxycarbonyl containing)
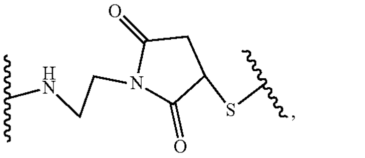
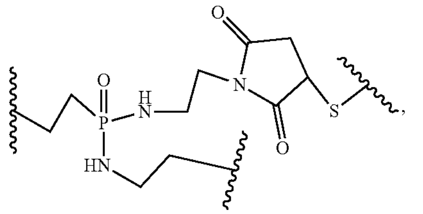
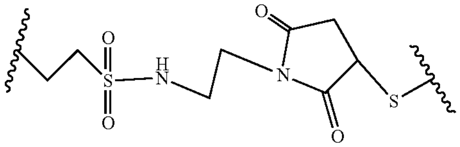
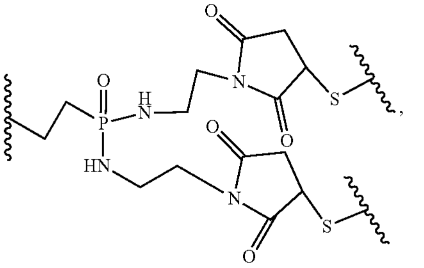
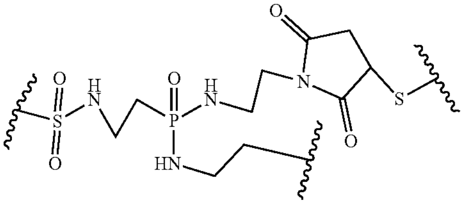
(ME, maleimidoethyl containing).
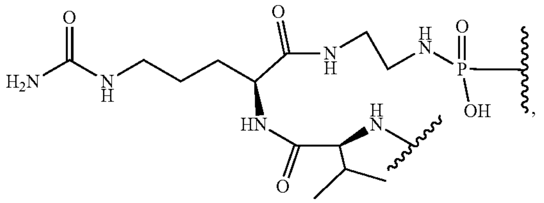
-continued
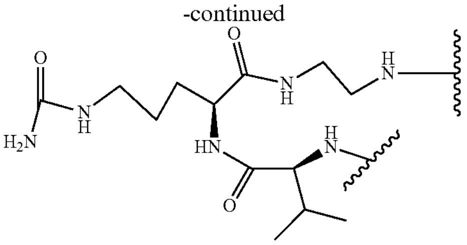
(valine-citrulline containing)
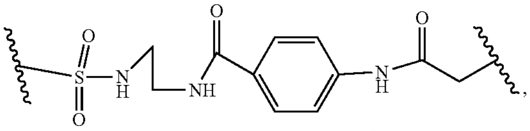
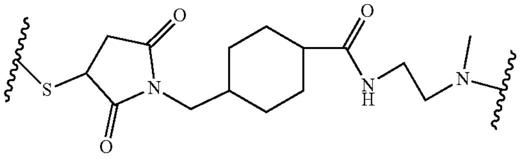
(MCC, 4-(N-maleimidomethyl)cyclohexane-1 carboxylate containing)
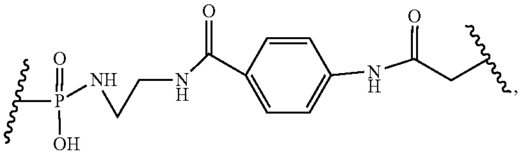
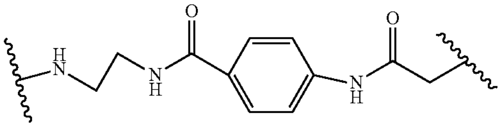
((4-acetyl)aminobenzoate containing)
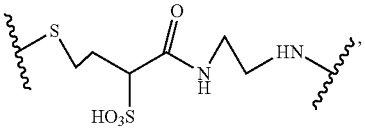
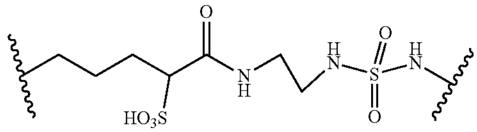
(4-thio-2-hydroxysulfonyl-butyrate, 2-sulfo-SPDB), (PAB),
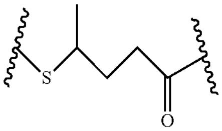 [SMILES: *SC(C)CCC(*)=O]
4-thio-pentanoate (SPP),

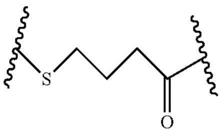 [SMILES: *SCCCC(*)=O]
4-thio-butyrate (SPDB),
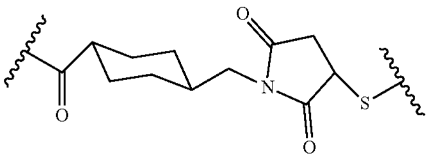 [SMILES: *SC1CC(=O)N(CC2CCC(C(*)=O)CC2)C1=O]
4-(N-maleimidomethyl)cyclo-hexane-1-carboxylate (MCC),
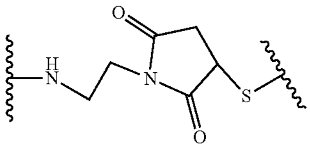 [SMILES: *NCCN1C(=O)CC(S*)C1=O]
maleimidoethyl (ME),
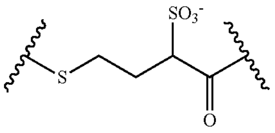
4-thio-2-hydroxysulfonyl-butyrate (2-Sulfo-SPDB),
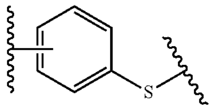
aryl-thiol (PySS),
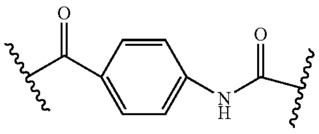 [SMILES: *C(=O)Nc1ccc(C(*)=O)cc1]
(4-acetyl)amino-benzoate (SIAB),
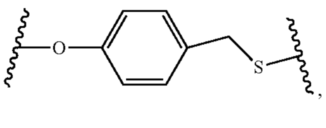 [SMILES: *Oc1ccc(CS*)cc1]
oxylbenzylthio,
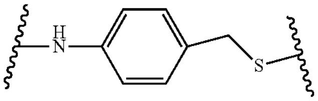 [SMILES: *Nc1ccc(CS*)cc1]
aminobenzylthio,
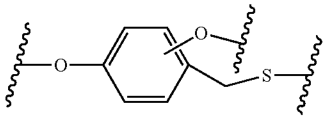
dioxylbenzylthio,
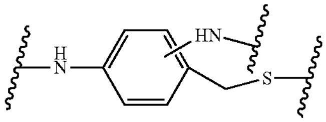
diaminobenzylthio,
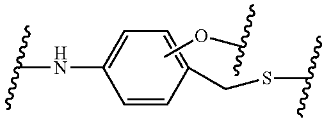
amino-oxylbenzylthio,
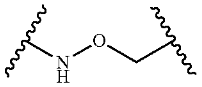 [SMILES: *CON*]
alkoxy amino (AOA),
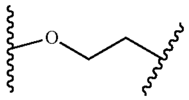 [SMILES: *CCO*]
ethyleneoxy(EO),
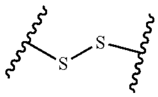 [SMILES: *SS*]
dithio,
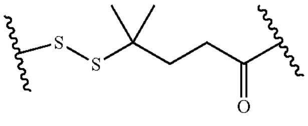 [SMILES: *SSC(C)(C)CCC(*)=O]
4-methyl-4-dithio-pentanoic (MPDP),

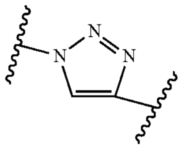 [SMILES: *c1cn(*)nn1]
triazole,
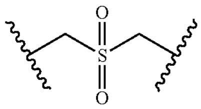 [SMILES: *CS(=O)(=O)C*]
alkylsulfonyl,
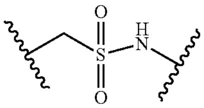 [SMILES: *CS(=O)(=O)N*]
alkylsulfonamide,
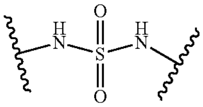 [SMILES: *NS(=O)(=O)N*]
sulfon-bisamide,
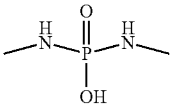
Phosphondiamide,
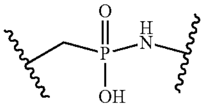 [SMILES: *CP(=O)(O)N*]
alkylphosphonamide,
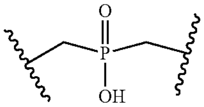 [SMILES: *CP(=O)(O)C*]
phosphinic acid,
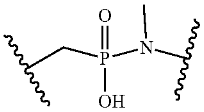 [SMILES: *CP(=O)(O)N(*)C]
N-methylphosphonamidic acid,
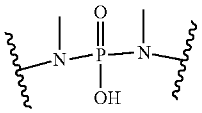 [SMILES: *N(C)P(=O)(O)N(*)C]
N,N'-dimethylphosphonamidic acid,
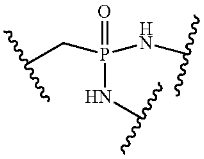 [SMILES: *CP(=O)(N*)N*]
N,N'-dimethylphosphondiamide,
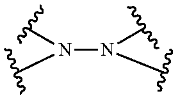 [SMILES: *N(*)N(*)*]
hydrazine,
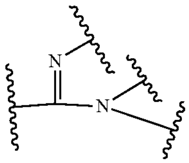 [SMILES: */N=C(/*)N(*)*]
acetimidamide,
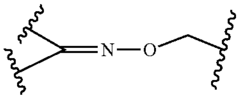 [SMILES: *CON=C(*)*]
oxime,
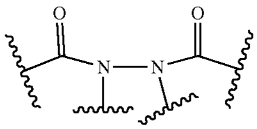 [SMILES: *C(=O)N(*)N(*)C(*)=O]
acetylacetohydrazide,
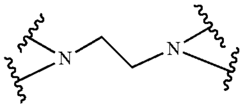 [SMILES: *N(*)CCN(*)*]
aminoethyl-amine,

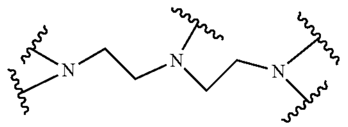 [SMILES: *N(*)CCN(*)CCN(*)*]

aminoethyl-aminoethyl-amine.

As described in more detail below, Drug, Drug', and Drug" can be any of many small molecule drugs, including, but not limited to, tubulysins, calicheamicins, auristatins, maytansinoids, CC-1065 analogs, morpholinos doxorubicins, taxanes, cryptophycins, amatoxins (amanitins), epothilones, geldanamycins, duocarmycins, daunomycins, methotrexates, vindesines, vincristines, and benzodiazepine dimers (e.g., dimmers of pyrrolobenzodiazepine (PBD), tomaymycin, indolinobenzodiazepines, imidazobenzothiadiazepines, or oxazolidinobenzodiazepines).

In general, the Formula (III), (IV), (V) (VI), (VII), (VIII) and (IX) are generated from Formula (I) and (II), wherein "Drug" and "Cb" react to formula (I) and (II) respectively or simultaneously. When two more thiols react a substituted acrylic group, or a propiolic group through addition reaction to form Formula (III), (IV), (V) or (VI), a UV light at wavelength of range 190-390 nm, preferably at 340-380 nm, more preferably at 365 nm is preferred to be used in assisting the reaction. The photochemistry reaction is thus conducted in a quartz or Pyrex flask, or an immersion well reactor containing a UV lamp in temperature control environment, preferred to be conducted in a continuous flow quartz tube or in a Pyrex tube where the UV illumination is maximizing, and at the same time allowing for efficient cooling, which decreases the thermal disability of a cell-binding molecule. In the formation of Formula (VII) (VIII) or (IX) wherein two more thiols are reacted to two or more substituted acrylic groups, or propiolic groups of Formula (I) and (II), a UV light is optionally not needed.

To synthesize the conjugate, a drug or a cell toxicity molecule is first react to the linkers of Formula (I) or (II) in a chemical solvent or in an aqueous media to form Formula (XVII) or (XVIII). The Formula (XVII) or (XVIII) can then be optionally isolated, or can immediately or simultaneously or sequentially react to a pair of free thiols generated through reduction of disulfide bonds of the cell-binding molecule at 25-38° C., pH 5-9 aqueous media with or without addition of 0-30% of water mixable (miscible) organic solvents, such as DMA, DMF, ethanol, methanol, acetone, acetonitrile, THF, isopropanol, dioxane, propylene glycol, or ethylene diol to form Formula (III), (IV), (V) or (VI), wherein assistance of UV beam light at 365 nm is preferably needed, or to form Formula (VII), (VIII) or (IX), wherein a UV light is optionally not needed.

Alternatively, the conjugates of the Formula (III), (IV), (V) (VI), (VII), (VIII) and (IX) can also be obtained through the first reaction of the linkers of the Formula (I) or (II) to a pair of thiols on the cell-binding agent at 0-38° C., pH 5~9 aqueous media with or without addition of 0~30% of water mixable (miscible) organic solvents, to form the modified cell-binding molecule of Formula (X), (XI), (XII) or (XIII), with assistance of a UV beam light at 365 nm, or to form the modified cell-binding molecule of Formula (XIV), (XV) or (XVI) without optionally assistance of UV lights. The pairs of thiols are preferred pairs of disulfide bonds reduced from the inter chain disulfide bonds of the cell-binding agent by a reduction agent which can selected from dithiothreitol (DTT), dithioerythritol (DTE), L-glutathione (GSH), tris (2-carboxyethyl) phosphine (TCEP), 2-mercaptoethylamine (β-MEA), or/and beta mercaptoethanol (β-ME, 2-ME) at pH4~9 aqueous media with or without addition of 0~30% of water mixable (miscible) organic solvents. The reactive group of Y on Formula (X), (XI), (XII), (XIII), (XIV), (XV) or (XVI) which can be containing disulfide, maleimido, haloacetyl, azide, 1-yne, ketone, aldehyde, alkoxyamino, triflate, carbonylimidazole, tosylate, mesylate, 2-ethyl-5-phenylisoxazolium-3'-sulfonate, or carboxyl acid esters of nitrophenol, N-hydroxysuccinimide (NHS), phenol; dinitrophenol, pentafluorophenol, tetrafluorophenol, difluorophenol, monofluorophenol, pentachlorophenol, dichlorophenol, tetrachlorophenol, 1-hydroxybenzotriazole, anhydrides, or hydrazide groups, or other acid ester derivatives, can then react to a drug/cytotoxic agent, Drug, Drug' or Drug" simultaneously or sequentially at 15-38° C., pH 4~9.5 aqueous media with or without addition of 0~30% of water mixable (miscible) organic solvents, to yield the Formula (III), (IV), (V) (VI), (VII), (VIII) and (IX) after purification. The reactive group of a drug/cytotoxic agent reacts to the modified cell-binding molecule in different way accordingly. For example, synthesis of the cell-binding agent-drug conjugates linked via disulfide bonds is achieved by a disulfide exchange between the disulfide bond in the modified cell-binding agent and a drug containing a free thiol group. Synthesis of the cell-binding agent-drug conjugates linked via thioether is achieved by reaction of the maleimido or haloacetyl or ethylsulfonyl modified cell-binding agent and a drug containing a free thiol group. Synthesis of conjugates bearing an acid labile hydrazone can be achieved by reaction of a carbonyl group with the hydrazide moiety in the linker, by methods known in the art (see, for example, P. Hamann et al., Cancer Res. 53, 3336-34, 1993; B. Laguzza et al., J. Med. Chem., 32; 548-55, 1959; P. Trail et al., Cancer Res., 57; 100-5, 1997). Synthesis of conjugates bearing triazole linkage can be achieved by reaction of a 1-yne group of the drug with the azido moiety in the linker, through the click chemistry (Huisgen cycloaddition) (Lutz, J-F. et al, 2008, Adv. Drug Del. Rev. 60, 958-70; Sletten, E. M. et al., 2011, AccChem. Research 44, 666-76). Synthesis of the cell-binding agent-drug conjugates linked via oxime is achieved by reaction of a modified cell-binding agent containing a ketone or aldehyde and a drug containing oxyamine group. A thiol-containing drug can react with the modified cell-binding molecule linker of Formula (X), (XI), (XII), (XIII), (XIV), (XV), or (XVI) bearing a maleimido, or a haloacetyl, or an ethylsulfonyl substituent at pH 5.5~9.0 in aqueous buffer to give a cell-binding molecule-drug conjugate via a thioether linkage. A thiol-containing drug can undergo disulfide exchange with a modified linker of Formula (X), (XI), (XII), (XIII), (XIV), (XV), or (XVI) bearing a pyridyldithio moiety to give a conjugate a disulfide bond linkage. A drug bearing a hydroxyl group or a thiol group can be reacted with a modified bridge linker of Formula (X), (XI), (XII), (XIII), (XIV), (XV), or (XVI) bearing a halogen, particularly the alpha halide of carboxylates, in the presence of a mild base, e.g. pH 8.0~9.5, to give a modified drug bearing an ether or thiol ether link. A hydroxyl group containing drug can be condensed with a cross linker of Formula (I) or (II) bearing a carboxyl group, in the presence of a dehydrating agent, such as EDC or DCC, to give ester linkage, then the subject drug modified bridge linker undergoes the conjugation with a cell-binding molecule. A drug containing an amino group can condensate with a carboxyl ester of NHS, imidazole, nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate on the cell-binding molecule-linker of Formula (X), (XI), (XII), (XIII), (XIV), (XV), or (XVI) to give a conjugate via amide bond linkage.

The conjugate may be purified by standard biochemical means, such as gel filtration on a Sephadex G25 or Sephacryl S300 column, adsorption chromatography, and ion exchange or by dialysis. In some cases, a small molecule as a cell-binding agent (e.g. folic acid, melanocyte stimulating hormone, EGF etc) conjugated with a small molecular drug can be purified by chromatography such as by HPLC, medium pressure column chromatography or ion exchange chromatography.

In preferred embodiments, Formula (III), (IV), (V), (VI), (VII), (VIII), or (IX) having the following structures:

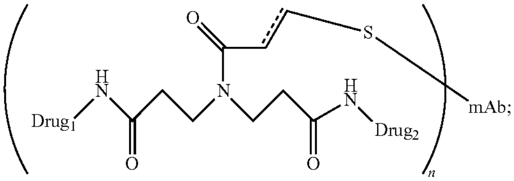

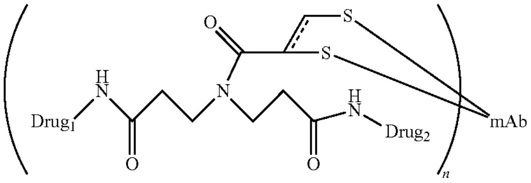

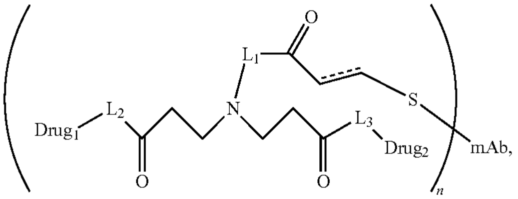

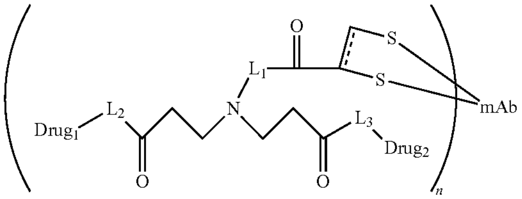

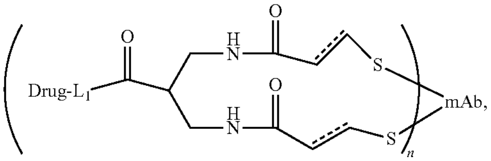

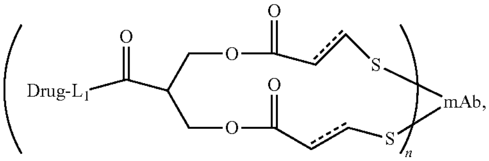

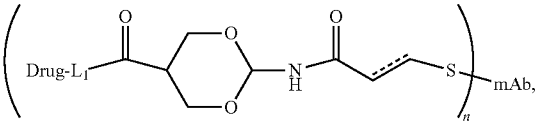

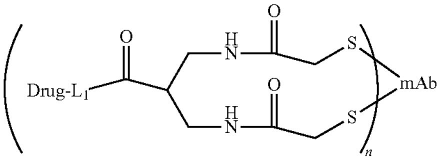
,

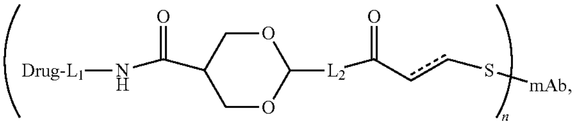

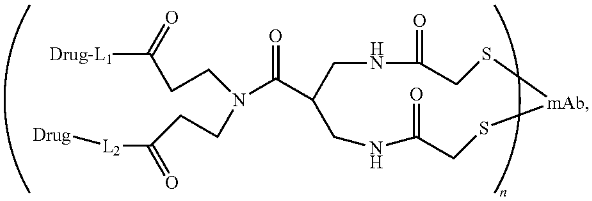

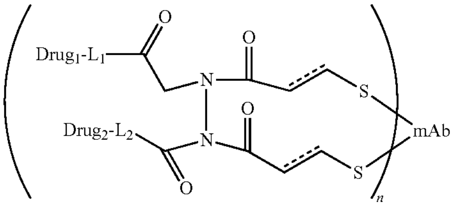

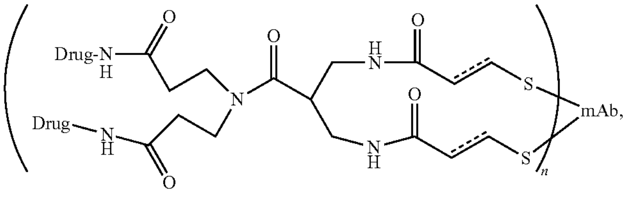

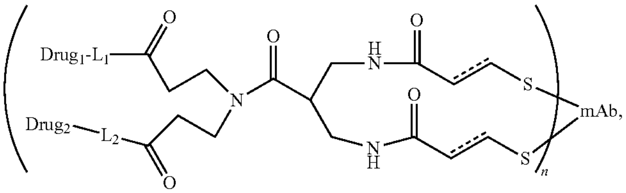

-continued
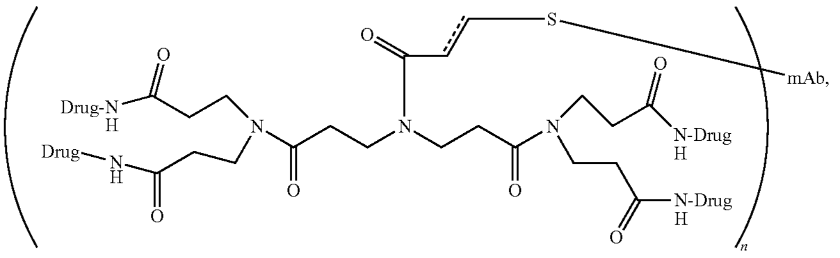
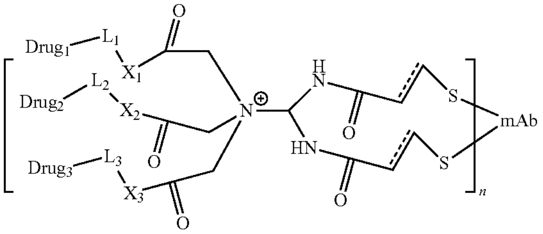
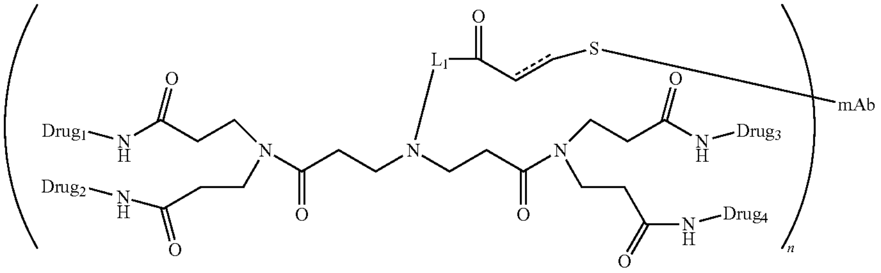
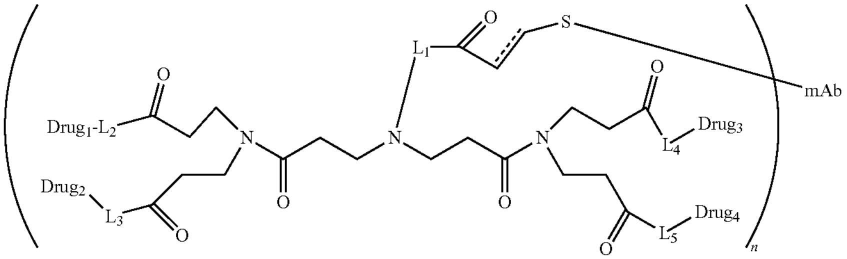
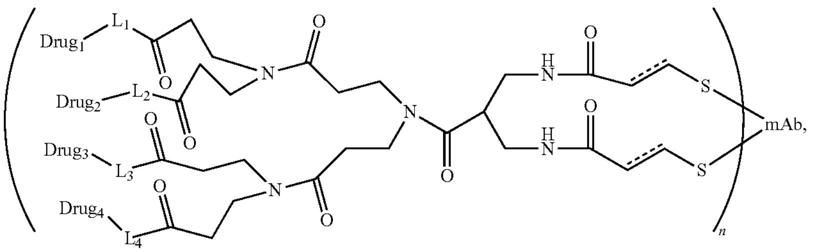
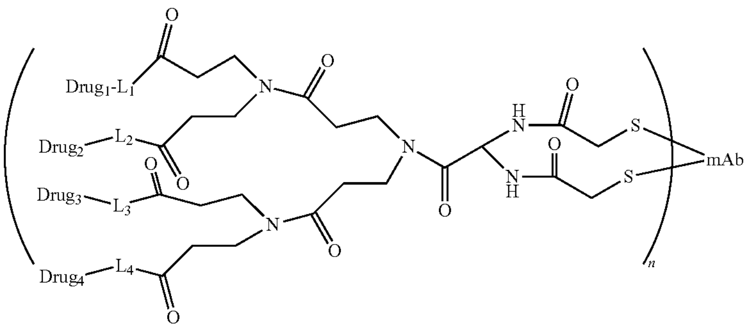

-continued
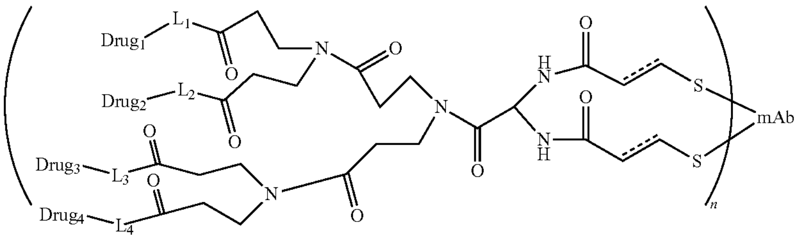
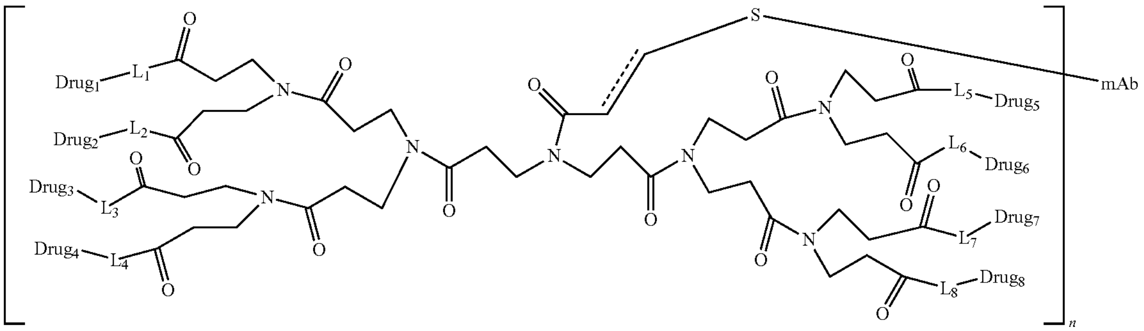
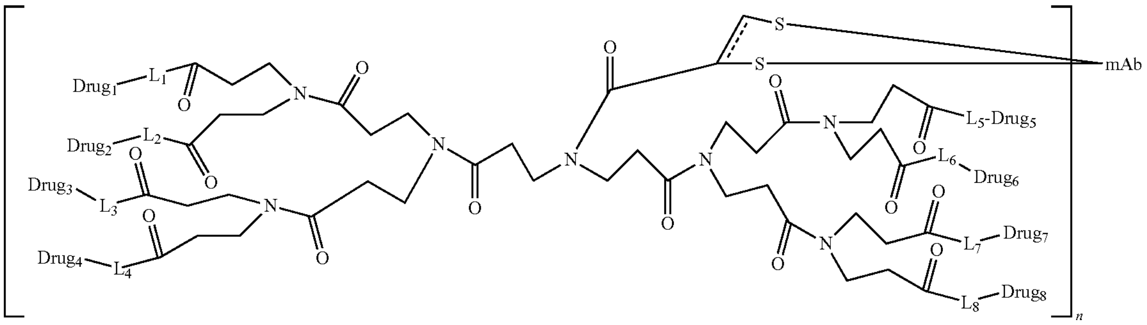
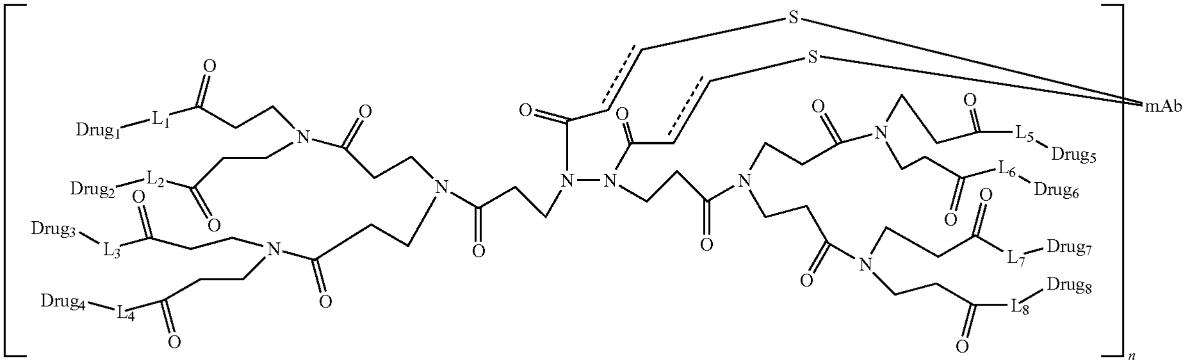
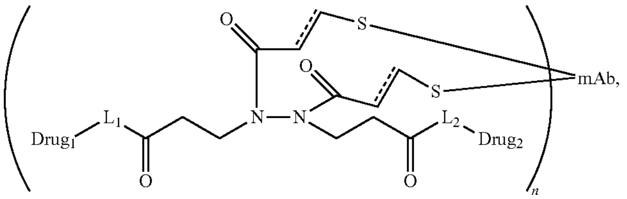
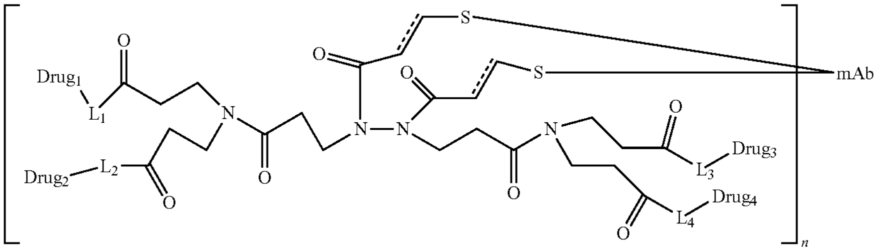

-continued
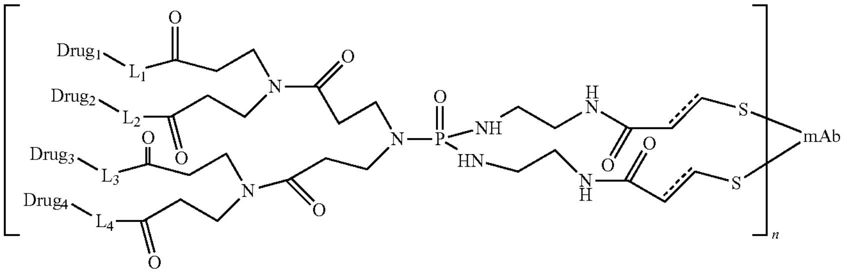
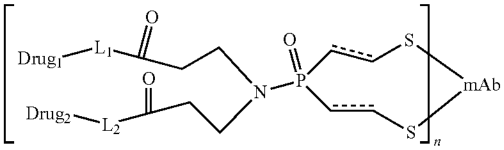
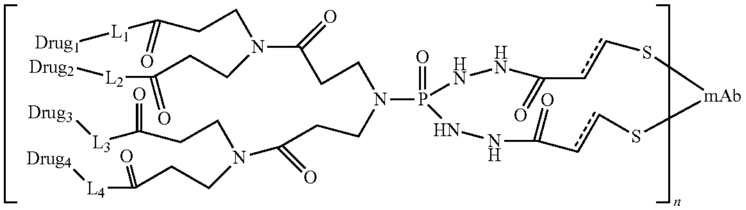
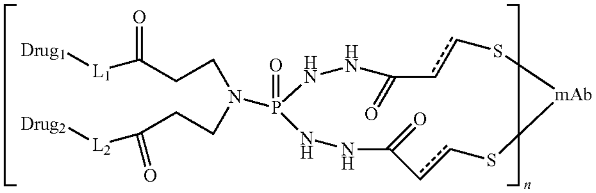
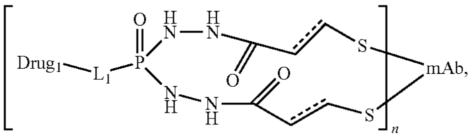
,
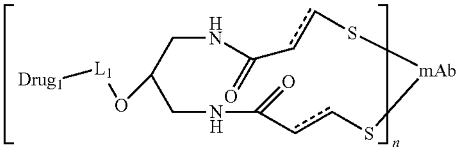
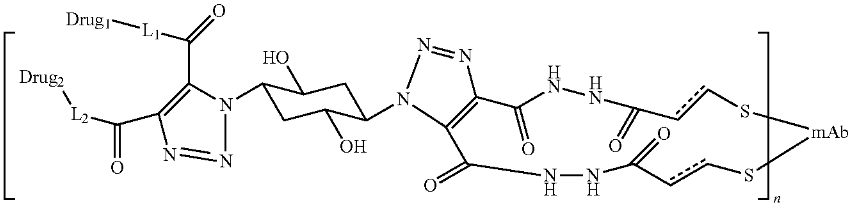
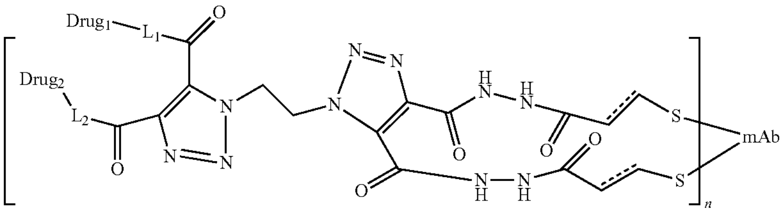
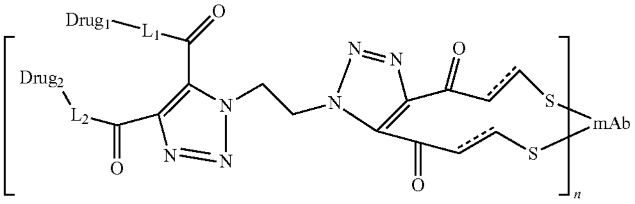

-continued

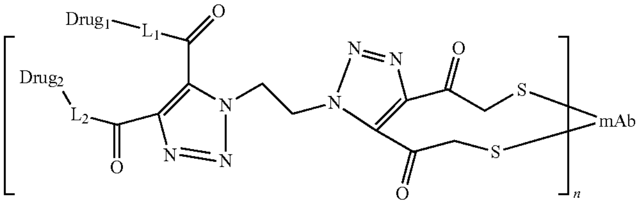

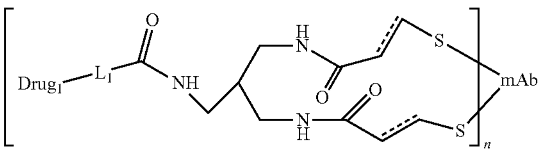

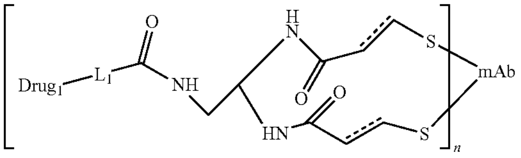

Modified Cell-Binding Agents/Molecules

The cell-binding agent modified by reaction with linkers of the present invention is preferably represented by the Formula (X), (XI), (XII), (XIII), (XIV), (XV), or (XVI):

(X)

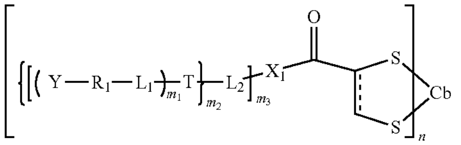

(XI)

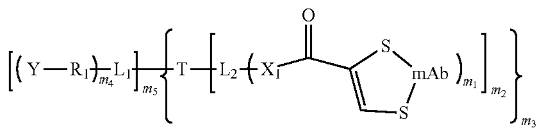

(XII)

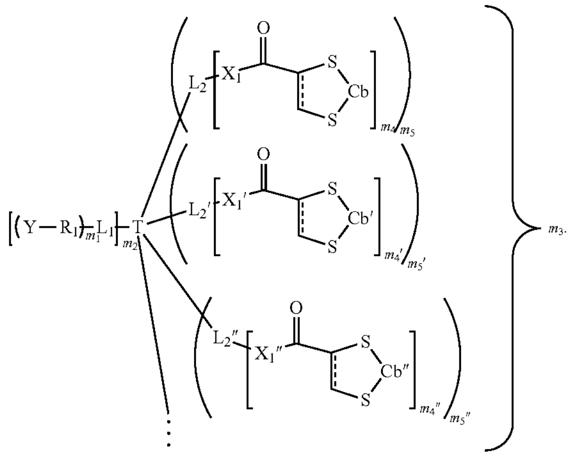

(XIII)

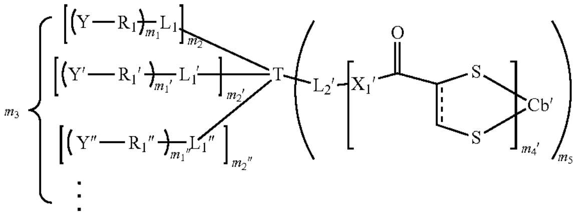

-continued (XIV)

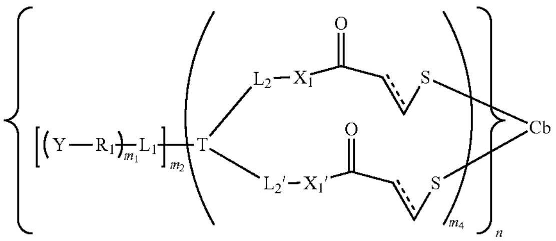

(XV)

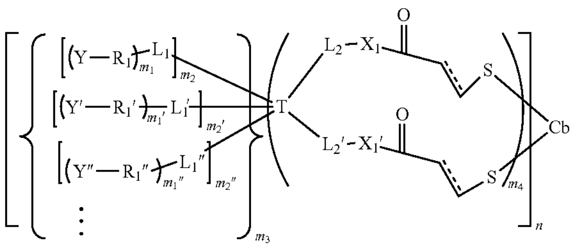

(XVI)

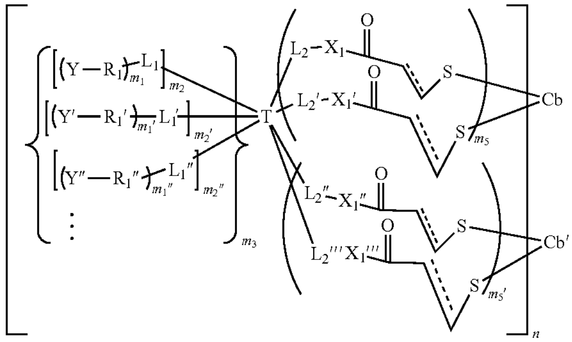

Wherein $R_1$, $R_{1'}$, $R_{1''}$, $R_2$, $X_1$, $X_{1'}$, $X_{1''}$, $L_1$, $L_{1'}$, $L_{1''}$, $L_2$, $L_{2'}$, $L_{2''}$, "⎓", Cb, $m_1$, $m_{1'}$, $m_{1''}$, $m_2$, $m_{2'}$, $m_{2''}$, $m_3$, $m_4$, $m_5$, $m_{4'}$, $m_{5'}$, $m_{4''}$, and $m_{5''}$ are defined the same as in Formula (III)—(IX).

Wherein ⎓ represents either a single bond, or a double bond.

Wherein Y, Y', and Y" are defined the same as Y in Formula (I) and (II).

In preferred embodiments, Y, Y', and Y" are independently a disulfide substituent, maleimido, haloacetyl, alkoxyamine, azido, ketone, aldehyde, hydrazine, alkyne, an N-hydroxysuccinimide ester, or a carboxyl ester formed with phenol;

dinitrophenol; pentafluorophenol; tetrafluoro-phenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate. Y, Y', and Y" can independently react with a cytotoxic agent through disulfide, thioether, hydrazone, amide, alkoxime, carbamate, ester, ether bond or hetero-aromatic ring. The modified cell-binding agent can be prepared via a reaction of the cell-binding agent with the linkers of Formula (I) or (II) as described in Formula (III) above.

In order to achieve a higher yield of conjugation reaction of the substituted acrylic group, or propiolic group of the Formula (I) or (II) with a pair of free thiols on the cell-binding molecule, preferably on an antibody, a small percentage of organic co-solvent may be required to add to the reaction mixture, as well in the solution after the reaction to maintain solubility of the Formula (III)~(IX) in aqueous solution. To modify the cell-binding agents, the cross-linking reagent (linker) of Formula (I) or (II) can be first dissolved in a polar organic solvent that is miscible with water, for example different alcohols, such as methanol, ethanol, and propanol, acetone, acetonitrile, tetrahydrofuran (THF), 1,4-dioxane, dimethyl formamide (DMF), dimethyl acetamide (DMA), or dimethylsulfoxide (DMSO) at a high concentration, for example 1-500 mM. Meanwhile, the cell-binding molecule, such as antibody dissolved in an aqueous buffer pH 4~9.5, preferably pH 6~8.5, at 1~35 mg/ml concentration was treated with 1~20 equivalent of TCEP or DTT for 20 min to 48 hour. After the reduction, DTT can be removed by SEC chromatographic purification. TCEP can be optionally removed by SEC chromatography too, or staying in the reaction mixture for the next step reaction without further purification. Furthermore, the reduction of antibodies or the other cell-binding agents with TCEP can be performed with a linker of Formula (I) or (II), for which the cross-linking conjugation for the cell-binding molecules can be achieved simultaneously along with the TCEP reduction. As described above, the formation of the modified cell-binding molecule of Formula (X), (XI), (XII) or (XIII), is conducted with assistance of a UV beam light at 340-380 nm. And the formation of the modified cell-binding molecule of Formula (XIV), (XV) or (XVI) is conducted without optionally assistance of UV lights.

The aqueous solutions for the modification of cell-binding agents are buffered between pH 4 and 9, preferably between 6.0 and 7.5 and can contain any non-nucleophilic buffer salts useful for these pH ranges. Typical buffers include phosphate, acetate, triethanolamine HCl, HEPES, and MOPS buffers, which can contain additional components, such as cyclodextrins, sucrose and salts, for examples, NaCl and KCl. After the addition of the bridge linker of Formula (I) or (II) into the solution containing the reduced cell-binding molecules, the reaction mixture is incubated at a temperature of from 4° C. to 45° C., preferably at 15° C.—ambient temperature. The progress of the reaction can be monitored by measuring the decrease in the absorption at a certain UV wavelength, such as at 254 nm, or increase in the absorption at a certain UV wavelength, such as 280 nm, or the other appropriate wavelength. After the reaction is complete, isolation of the modified cell-binding agent can be performed in a routine way, using for example gel filtration chromatography, or adsorptive chromatography.

The extent of modification can be assessed by measuring the absorbance of the nitropyridine thione, dinitropyridine dithione, pyridine thione, carboxylamidopyridine dithione and dicarboxyl-amidopyridine dithione group released via UV spectra. For the conjugation without a chromophore group, the modification or conjugation reaction can be monitored by LC-MS, preferably by UPLC-QTOF mass spectrometry, or Capillary electrophoresis-mass spectrometry (CE-MS). The bridge cross-linkers described herein have diverse functional groups that can react with any drugs, preferably cytotoxic agents that possess a suitable substituent. For examples, the modified cell-binding molecules bearing an amino or hydroxyl substituent can react with drugs bearing an N-hydroxysuccinimide (NHS) ester, the modified cell-binding molecules bearing a thiol substituent can react with drugs bearing a maleimido or haloacetyl group. Additionally, the modified cell-binding molecules bearing a carbonyl (ketone or aldehyde) substituent can react with drugs bearing a hydrazide or an alkoxyamine. One skilled in the art can readily determine which linker to use based on the known reactivity of the available functional group on the linkers.

Modified Cytotoxic Drugs

The cytotoxic drugs modified by reaction with cross-linkers of the present invention are preferably represented by the Formula (XVII) and (XVIII), in which the drug, "Drug", has reacted with the linker of Formula (I) and (II), which still have a thiol reactive group of substituted acrylic group, or propiolic group, capable of reacting with a pair of thiols of the cell-binding agent:

(XVII)

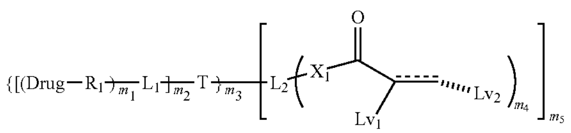

(XVIII)

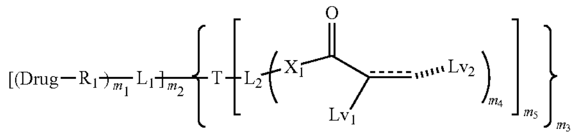

Wherein "⋯⋯", "=̶=̶", $L_1$, $L_2$, $R_1$, T, $m_1$, $m_2$, $m_3$, $m_4$, $m_5$, $X_1$, $L_{V1}$ and $L_{V2}$ are defined the same as in Formula (I). $Drug_1$ is defined the same as in Formula (II).

The modified drugs can be prepared via reaction of the drug with the linkers of the Formula (I) and (II) to give a modified drug of Formula (XVII) and (XVIII) bearing functionality of a substituted acrylic group, or propiolic group. But for drugs containing a thiol, or the drugs undergoing to conjugation of a cell-binding molecule via the bridge linkers through thioether, thioester or disulfide bond, it is therefore preferred that the $Drug_1$ may be synthesized to connect to $R_1$ in a piece of components via the linkage of thioether, thioester or disulfide bond first. Then the synthesized $R_1$-Drug component is assembled to a substituted acrylic group, or propiolic group, to form the bridge linker modified drugs of Formula (XVII) and (XVIII).

For examples of the synthesis, a thiol-containing drug can be reacted with the linker of components $R_1$ bearing a maleimido substituent at neutral pH in aqueous buffer to give a $R_1$-Drug compartment bearing thioether linkage, and following by condensation with substituted acrylic group, or propiolic group, to give a modified drug of Formula (XVII) or (XVIII) bearing thioether linkage. A drug bearing a hydroxyl group can be reacted with a linker component $R_1$ bearing a halogen, or a tosylate, or a mesylate, in the presence of a mild base, to give a $R_1$-Drug compartment bearing ether linkage, and following by condensation with acrylic group, or substituted propiolic group, to give a modified drug of Formula (XVII) or (XVIII) bearing thioether linkage. A hydroxyl group containing drug can be condensed with a linker of Formula (I) bearing a carboxyl group, in the presence of a dehydrating agent, such as EDC or dicyclohexylcarbodiimide (DCC), to give a modified drug of Formula (XVII) or (XVIII) via ester linkage. A drug bearing a thiol group can also react the linker of components $R_1$ bearing a maleimido or a vinylsulfonyl, or a haloacetyl group, to give a $R_1$-Drug compartment bearing thioether linkage, and following by condensation with a compartment of acrylic group, or substituted propiolic group, to give a modified drug of Formula (XVII) or (XVIII) bearing thioether linkage. An amino group containing drug can similarly undergo condensation with a carboxyl group on the bridge linker of Formula (I) or (II) to give a modified drug of Formula (XVII) or (XVIII) bearing amide bonds. The modified drug can be purified by standard methods such as column chromatography over silica gel or alumina, crystallization, preparatory thin layer chromatography, ion exchange chromatography, or HPLC.

In preferred embodiments, Formula (XVII) or (XVIII) having the following structures:

4-1

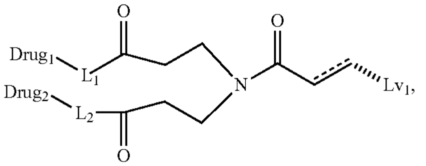

4-2

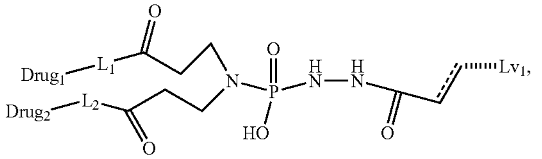

4-3

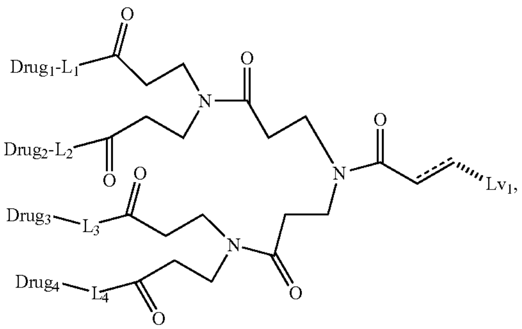

4-4

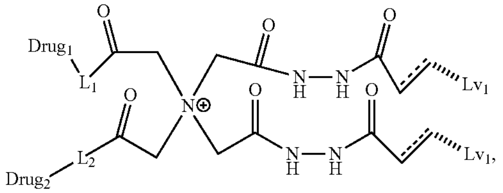

4-5

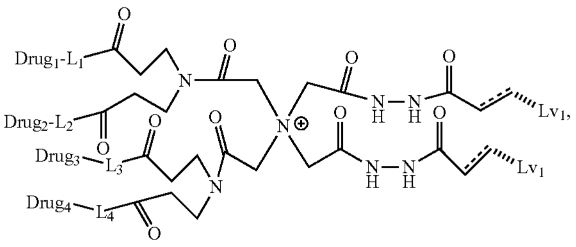

4-6

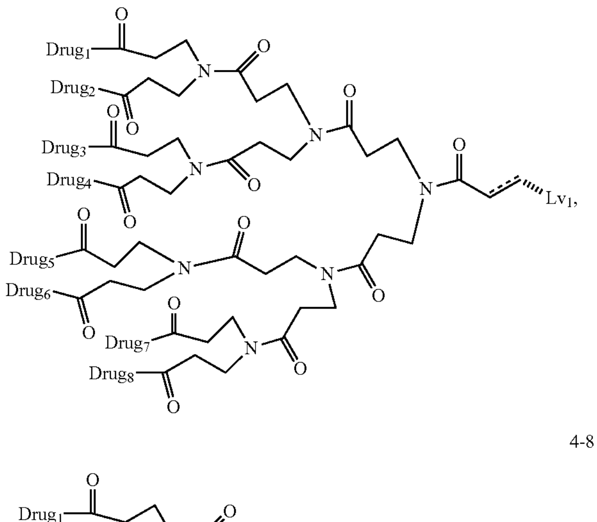

4-7

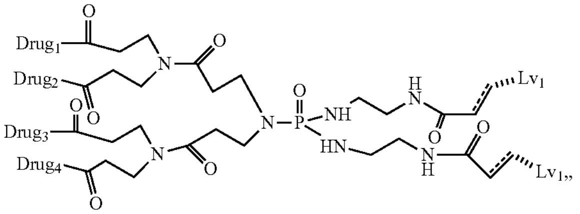

4-8

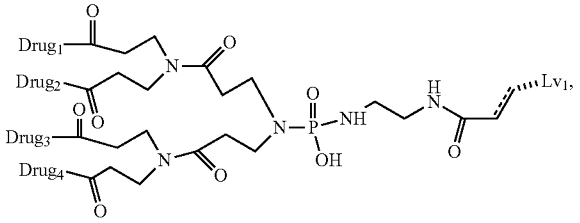

-continued 4-9

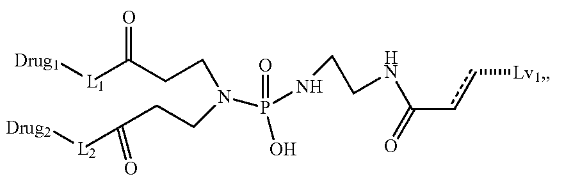

4-10

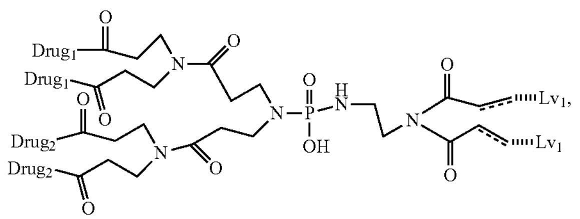

4-11

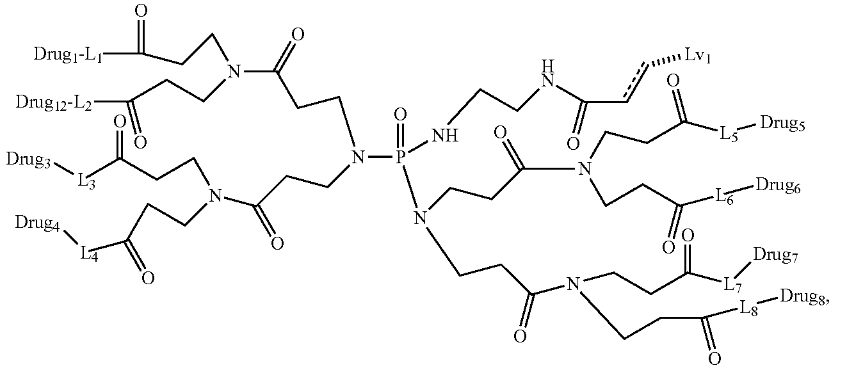

4-12

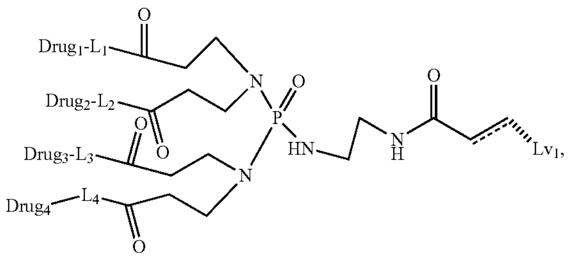

4-13

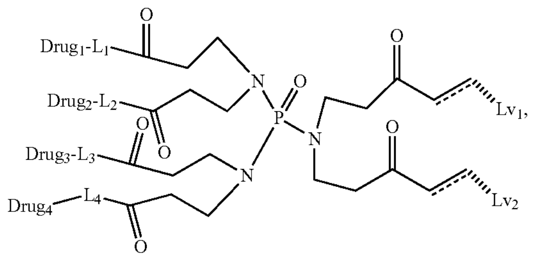

4-14

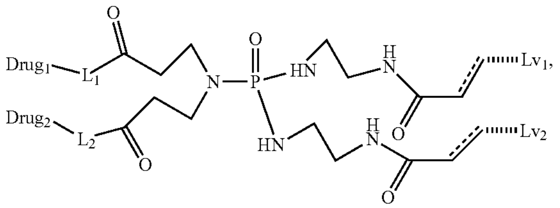

4-15

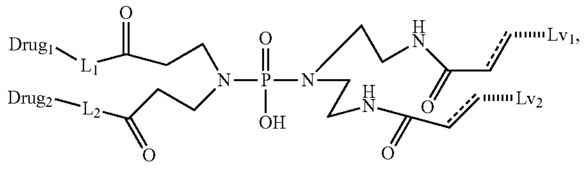

4-16

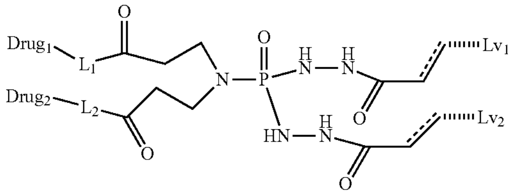

4-17

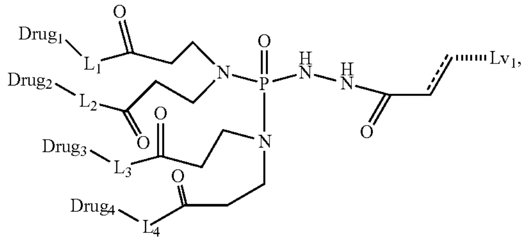

wherein ⎓, $L_{V1}$, and $L_{V2}$ are defined the same in Formula (I); $L_1$, $L_2$, $L_3$, $L_4$, $L_5$, $L_6$, $L_7$ and $L_8$ are the same or different, and are defined the same as $L_1$ in Formula (I); $Drug_1$, $Drug_2$, $Drug_3$, $Drug_4$, $Drug_5$, $Drug_6$, $Drug_7$, and $Drug_8$ are the same or different, and are defined the same as $Drug_1$ in Formula (II);

Cell-Binding Agents

The cell-binding molecule, Cb, that comprises the conjugates and the modified cell-binding agents of the present invention may be of any kind presently known, or that become known, molecule that binds to, complexes with, or reacts with a moiety of a cell population sought to be therapeutically or otherwise biologically modified.

The cell binding agents include, but are not limited to, large molecular weight proteins such as, for example, antibody, an antibody-like protein, full-length antibodies (polyclonal antibodies, monoclonal antibodies, dimers, multimers, multispecific antibodies (e.g., bispecific antibodies);

single chain antibodies; fragments of antibodies such as Fab, Fab', $F(ab')_2$, $F_v$, [Parham, J. Immunol. 131, 2895-902 (1983)], fragments produced by a Fab expression library, anti-idiotypic (anti-Id) antibodies, CDR's, diabody, triabody, tetrabody, miniantibody, small immune proteins (SIP), and epitope-binding fragments of any of the above which immuno-specifically bind to cancer cell antigens, viral antigens, microbial antigens or a protein generated by the immune system that is capable of recognizing, binding to a specific antigen or exhibiting the desired biological activity (Miller et al (2003) J. of Immunology 170: 4854-61); interferons (such as type I, II, III); peptides; lymphokines such as IL-2, IL-3, IL-4, IL-5, IL-6, IL-10, GM-CSF, interferon-gamma (IFN-γ); hormones such as insulin, TRH (thyrotropin releasing hormones), MSH (melanocyte-stimulating hormone), steroid hormones, such as androgens and estrogens, melanocyte-stimulating hormone (MSH); growth factors and colony-stimulating factors such as epidermal growth factors (EGF), granulocyte-macrophage colony-stimulating factor (GM-CSF), transforming growth factors (TGF), such as TGFα, TGFβ, insulin and insulin like growth factors (IGF-I, IGF-II) G-CSF, M-CSF and GM-CSF [Burgess, Immunology Today, 5, 155-8 (1984)]; vaccinia growth factors (VGF); fibroblast growth factors (FGFs); smaller molecular weight proteins, poly-peptide, peptides and peptide hormones, such as bombesin, gastrin, gastrin-releasing peptide; platelet-derived growth factors; interleukin and cytokines, such as interleukin-2 (IL-2), interleukin-6 (IL-6), leukemia inhibitory factors, granulocyte-macrophage colony-stimulating factor (GM-CSF); vitamins, such as folate; apoproteins and glycoproteins, such as transferrin [O'Keefe et al, 260 J. Biol. Chem. 932-7 (1985)]; sugar-binding proteins or lipoproteins, such as lectins; cell nutrient-transport molecules; and small molecular inhibitors, such as prostate-specific membrane antigen (PSMA) inhibitors and small molecular tyrosine kinase inhibitors (TKI), non-peptides or any other cell binding molecule or substance, such as bioactive polymers (Dhar, et al, Proc. Natl. Acad. Sci. 2008, 105, 17356-61); bioactive dendrimers (Lee, et al, Nat. Biotechnol. 2005, 23, 1517-26; Almutairi, et al; Proc. Natl. Acad. Sci. 2009, 106, 685-90); nanoparticles (Liong, et al, ACS Nano, 2008, 2, 1309-12; Medarova, et al, Nat. Med. 2007, 13, 372-7; Javier, et al, Bioconjugate Chem. 2008, 19, 1309-12); liposomes (Medinai, et al, Curr. Phar. Des. 2004, 10, 2981-9); viral capsides (Flenniken, et al, Viruses Nanotechnol. 2009, 327, 71-93).

In general, a monoclonal antibody is preferred as a cell-surface binding agent if an appropriate one is available. And the antibody may be murine, human, humanized, chimeric, or derived from other species.

Production of antibodies used in the present invention involves in vivo or in vitro procedures or combinations thereof. Methods for producing polyclonal anti-receptor peptide antibodies are well-known in the art, such as in U.S. Pat. No. 4,493,795 (to Nestor et al). A monoclonal antibody is typically made by fusing myeloma cells with the spleen cells from a mouse that has been immunized with the desired antigen (Köhler, G.; Milstein, C. (1975). Nature 256: 495-7). The detailed procedures are described in "Antibodies—A Laboratory Manual", Harlow and Lane, eds., Cold Spring Harbor Laboratory Press, New York (1988), which is incorporated herein by reference. Particularly monoclonal antibodies are produced by immunizing mice, rats, hamsters or any other mammal with the antigen of interest such as the intact target cell, antigens isolated from the target cell, whole virus, attenuated whole virus, and viral proteins. Splenocytes are typically fused with myeloma cells using polyethylene glycol (PEG) 6000. Fused hybrids are selected by their sensitivity to HAT (hypoxanthine-aminopterin-thymine). Hybridomas producing a monoclonal antibody useful in practicing this invention are identified by their ability to immunoreact specified receptors or inhibit receptor activity on target cells.

A monoclonal antibody used in the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques, such as using protein-A affinity chromatography; anion, cation, hydrophobic, or size exclusive chromatographies (particularly by affinity for the specific antigen after protein A, and sizing column chromatography); centrifugation, differential solubility, or by any other standard technique for the purification of proteins.

Media useful for the preparation of these compositions are both well-known in the art and commercially available and include synthetic culture media. An exemplary synthetic medium is Dulbecco's minimal essential medium (DMEM; Dulbecco et al., Virol. 8, 396 (1959)) supplemented with 4.5 g/l glucose, 0-20 mM glutamine, 0-20% fetal calf serum, several ppm amount of heavy metals, such as Cu, Mn, Fe, or Zn, etc, or/and the other heavy metals added in their salt forms, and with an anti-foaming agent, such as polyoxyethylene-polyoxypropylene block copolymer.

In addition, antibody-producing cell lines can also be created by techniques other than fusion, such as direct transformation of B lymphocytes with oncogenic DNA, or transfection with an oncovirus, such as Epstein-Barr virus (EBV, also called human herpesvirus 4 (HHV-4)) or Kaposi's sarcoma-associated herpesvirus (KSHV). See, U.S. Pat. Nos. 4,341,761; 4,399,121; 4,427,783; 4,444,887; 4,451,570; 4,466,917; 4,472,500; 4,491,632; 4,493,890. A monoclonal antibody may also be produced via an anti-receptor peptide or peptides containing the carboxyl terminal as described well-known in the art. See Niman et al., Proc. Natl. Acad. Sci. USA, 80: 4949-53 (1983); Geysen et al., Proc. Natl. Acad. Sci. USA, 82: 178-82 (1985); Lei et al. Biochemistry 34(20): 6675-88, (1995). Typically, the anti-receptor peptide or a peptide analog is used either alone or conjugated to an immunogenic carrier, as the immunogen for producing anti-receptor peptide monoclonal antibodies.

There are also a number of other well-known techniques for making monoclonal antibodies as binding molecules in this invention. Particularly useful are methods of making fully human antibodies. One method is phage display technology which can be used to select a range of human antibodies binding specifically to the antigen using methods of affinity enrichment.

Phage display has been thoroughly described in the literature and the construction and screening of phage display libraries are well known in the art, see, e.g., Dente et al, Gene. 148(1):7-13 (1994); Little et al, Biotechnol Adv. 12(3): 539-55 (1994); Clackson et al., Nature 352: 264-8 (1991); Huse et al., Science 246: 1275-81 (1989).

Monoclonal antibodies derived by hybridoma technique from another species than human, such as mouse, can be humanized to avoid human anti-mouse antibodies when infused into humans. Among the more common methods of humanization of antibodies are complementarity-determining region grafting and resurfacing. These methods have been extensively described, see e.g. U.S. Pat. Nos. 5,859, 205 and 6,797,492; Liu et al, Immunol Rev. 222: 9-27 (2008); Almagro et al, Front Biosci. 13: 1619-33 (2008); Lazar et al, Mol Immunol. 44(8): 1986-98 (2007); $L_1$ et al, Proc. Natl. Acad. Sci. USA. 103(10): 3557-62 (2006) each incorporated herein by reference. Fully human antibodies can also be prepared by immunizing transgenic mice, rabbits, monkeys, or other mammals, carrying large portions of the human immunoglobulin heavy and light chains, with an immunogen. Examples of such mice are: the Xenomouse (Abgenix/Amgen), the HuMAb-Mouse (Medarex/BMS), the VelociMouse (Regeneron), see also U.S. Pat. Nos. 6,596, 541, 6,207,418, 6,150,584, 6,111,166, 6,075,181, 5,922,545, 5,661,016, 5,545,806, 5,436,149 and 5,569,825. In human therapy, murine variable regions and human constant regions can also be fused to construct called "chimeric antibodies" that are considerably less immunogenic in man than murine mAbs (Kipriyanov et al, Mol Biotechnol. 26: 39-60 (2004); Houdebine, Curr Opin Biotechnol. 13: 625-9 (2002) each incorporated herein by reference). In addition, site-directed mutagenesis in the variable region of an antibody can result in an antibody with higher affinity and specificity for its antigen (Brannigan et al, Nat Rev Mol Cell Biol. 3: 964-70, (2002)); Adams et al, J Immunol Methods. 231: 249-60 (1999)) and exchanging constant regions of a mAb can improve its ability to mediate effector functions of binding and cytotoxicity.

Antibodies immunospecific for a malignant cell antigen can also be obtained commercially or produced by any method known to one of skill in the art such as, e.g., chemical synthesis or recombinant expression techniques. The nucleotide sequence encoding antibodies immune-specific for a malignant cell antigen can be obtained commercially, e.g., from the GenBank database or a database like it, the literature publications, or by routine cloning and sequencing.

Apart from an antibody, a peptide or protein that bind/block/target or in some other way interact with the epitopes or corresponding receptors on a targeted cell can be used as a binding molecule. These peptides or proteins could be any random peptide or proteins that have an affinity for the epitopes or corresponding receptors and they don't necessarily have to be of the immune-globulin family. These peptides can be isolated by similar techniques as for phage display antibodies (Szardenings, J Recept Signal Transduct Res. 2003, 23(4): 307-49). The use of peptides from such random peptide libraries can be similar to antibodies and antibody fragments. The binding molecules of peptides or proteins may be conjugated on or linked to a large molecules or materials, such as, but is not limited, an albumin, a polymer, a liposome, a nano particle, a dendrimer, as long as such attachment permits the peptide or protein to retain its antigen binding specificity.

Examples of antibodies used for conjugation of drugs via the linkers of this prevention for treating cancer, autoimmune disease, and/or infectious disease include, but are not limited to, 3F8 (anti-GD2), Abagovomab (anti CA-125), Abeiximab (anti CD41 (integrin alpha-IIb), Adalimumab (anti-TNF-α), Adecatumumab (anti-EpCAM, CD326), Afelimomab (anti-TNF-α); Afutuzumab (anti-CD20), Alacizumab pegol (anti-VEGFR2), ALD518 (anti-IL-6), Alemtuzumab (Campath, MabCampath, anti-CD52), Altumomab (anti-CEA), Anatumomab (anti-TAG-72), Anrukinzumab (IMA-638, anti-IL-13), Apolizumab (anti-HLA-DR), Arcitumomab (anti-CEA), Aselizumab (anti-L-selectin (CD62L), Atlizumab (tocilizumab, Actemra, RoActemra, anti-IL-6 receptor), Atorolimumab (anti-Rhesus factor), Bapineuzumab (anti-beta amyloid), Basiliximab (Simulect, antiCD25 (α chain of IL-2 receptor), Bavituximab (anti-phosphatidylserine), Bectumomab (LymphoScan, anti-CD22), Belimumab (Benlysta, LymphoStat-B, anti-BAFF), Benralizumab (anti-CD125), Bertilimumab (anti-CCL11 (eotaxin-1)), Besilesomab (Scintimun, anti-CEA-related antigen), Bevacizumab (Avastin, anti-VEGF-A), Biciromab (FibriScint, anti-fibrin II beta chain), Bivatuzumab (anti-CD44 v6), Blinatumomab (BiTE, anti-CD19), Brentuximab (cAC10, anti-CD30 TNFRSF8), Briakinumab (anti-IL-12, IL-23) Canakinumab (Ilaris, anti-IL-1), Cantuzumab ($C_{242}$, anti-CanAg), Capromab, Catumaxomab (Removab, anti-EpCAM, anti-CD3), CC49 (anti-TAG-72), Cedelizumab (anti-CD4), Certolizumab pegol (Cimzia anti-TNF-α), Cetuximab (Erbitux, IMC-$C_{225}$, anti-EGFR), Citatuzumab bogatox (anti-EpCAM), Cixutumumab (anti-IGF-1), Clenoliximab (anti-CD4), Clivatuzumab (anti-MUC1), Conatumumab (anti-TRAIL-R2), CR6261 (anti-Influenza A hemagglutinin), Dacetuzumab (anti-CD40), Daclizumab (Zenapax, anti-CD25 (a chain of IL-2 receptor)), Daratumumab (anti-CD38 (cyclic ADP ribose hydrolase), Denosumab (Prolia, anti-RANKL), Detumomab (anti-B-lymphoma cell), Dorlimomab, Dorlixizumab, Ecromeximab (anti-GD3 ganglioside), Eculizumab (Soliris, anti-$C_5$), Edobacomab (anti-endotoxin), Edrecolomab (Panorex, MAb17-1A, anti-EpCAM), Efalizumab (Raptiva, anti-LFA-1 (CD11a), Efungumab (Mycograb, anti-Hsp90), Elotuzumab (anti-SLAMF7), Elsilimomab (anti-IL-6), Enlimomab pegol (anti-ICAM-1 (CD54)), Epitumomab (anti-episialin), Epratuzumab (anti-CD22), Erlizumab (anti-ITGB2 (CD18)), Ertumaxomab (Rexomun, anti-HER2/neu, CD3), Etaracizumab (Abegrin, anti-integrin $\alpha_v\beta3$), Exbivirumab (anti-hepatitis B surface antigen), Fanolesomab (NeutroSpec, anti-CD15), Faralimomab (anti-interferon receptor), Farletuzumab (anti-folate receptor 1), Felvizumab (anti-respiratory syncytial virus), Fezakinumab (anti-IL-22), Figitumumab (anti-IGF-1 receptor), Fontolizumab (anti-IFN-γ), Foravirumab (anti-rabies virus glycoprotein), Fresolimumab (anti-TGF-β), Galiximab (anti-CD80), Gantenerumab (anti-beta amyloid), Gavilimomab (anti-CD147 (basigin)), Gemtuzumab (anti-CD33), Girentuximab (anti-carbonic anhydrase 9), Glembatumumab (CRO11, anti-GPNMB), Golimumab (Simponi, anti-TNF-α), Gomiliximab (anti-CD23 (IgE receptor)), Ibalizumab (anti-CD4), Ibritumomab (anti-CD20), Igovomab (Indimacis-125, anti-CA-125), Imciromab (Myoscint, anti-cardiac myosin), Infliximab (Remicade, anti-TNF-α), Intetumumab (anti-CD51), Inolimomab (anti-CD25 (a chain of IL-2 receptor)), Inotuzumab (anti-CD22), Ipilimumab (anti-CD152), Iratumumab (anti-CD30 (TNFRSF8)), Keliximab (anti-CD4), Labetuzumab (CEA-Cide, anti-CEA), Lebrikizumab (anti-IL-13), Lemalesomab (anti-NCA-90 (granulocyte antigen)), Lerdelimumab (anti-TGF beta 2), Lexatumumab (anti-TRAIL-R2), Libivirumab (anti-hepatitis B surface antigen), Lintuzumab (anti-CD33), Lucatumumab (anti-CD40), Lumiliximab (anti-CD23 (IgE receptor), Mapatumumab (anti-TRAIL-R1), Maslimomab (anti-T-cell receptor), Matuzumab (anti-EGFR), Mepolizumab (Bosatria, anti-IL-5), Metelimumab (anti-TGF beta 1), Milatuzumab (anti-CD74), Minretumomab (anti-TAG-72), Mitumomab (BEC-2, anti-GD3 ganglioside), Morolimumab (anti-Rhesus factor), Motavizumab (Numax, anti-respiratory syncytial virus), Muromonab-CD3 (Orthoclone OKT3, anti-CD3), Nacolomab (anti-$C_{242}$), Naptumomab (anti-5T4), Natalizumab (Tysabri, anti-integrin $\alpha_4$), Nebacumab (anti-endotoxin), Necitumumab (anti-EGFR), Nerelimomab (anti-TNF-α), Nimotuzumab (Theracim, Theraloc, anti-EGFR), Nofetumomab, Ocrelizumab (anti-CD20), Odulimomab (Afolimomab, anti-LFA-1 (CD11a)), Ofatumumab (Arzerra, anti-CD20), Olaratumab (anti-PDGF-R a), Omalizumab (Xolair, anti-IgE Fc region), Oportuzumab (anti-EpCAM), Oregovomab (OvaRex, anti-CA-125), Otelixizumab (anti-CD3), Pagibaximab (anti-lipoteichoic acid), Palivizumab (Synagis, Abbosynagis, anti-respiratory syncytial virus), Panitumumab (Vectibix, ABX-EGF, anti-EGFR), Panobacumab (anti-*Pseudomonas aeruginosa*), Pascolizumab (anti-IL-4), Pemtumomab (Theragyn, anti-MUC1), Pertuzumab (Omnitarg, $2C_4$, anti-HER2/neu), Pexelizumab (anti-$C_5$), Pintumomab (anti-adenocarcinoma antigen), Priliximab (anti-CD4), Pritumumab (anti-vimentin), PRO 140 (anti-CCR5), Racotumomab (1E10, anti-(N-glycolylneuraminic acid (NeuGe, NGNA)-gangliosides GM3)), Rafivirumab (anti-rabies virus glycoprotein), Ramucirumab (anti-VEGFR2), Ranibizumab (Lucentis, anti-VEGF-A), Raxibacumab (anti-anthrax toxin, protective antigen), Regavirumab (anti-cytomegalovirus glycoprotein B), Reslizumab (anti-IL-5), Rilotumumab (anti-HGF), Rituximab (MabThera, Rituxanmab, anti-CD20), Robatumumab (anti-IGF-1 receptor), Rontalizumab (anti-IFN-α), Rovelizumab (LeukArrest, anti-CD 11, CD18), Ruplizumab (Antova, anti-CD154 (CD40L)), Satumomab (anti-TAG-72), Sevirumab (anti-cytomegalovirus), Sibrotuzumab (anti-FAP), Sifalimumab (anti-IFN-α), Siltuximab (anti-IL-6), Siplizumab (anti-CD2), (Smart) M195 (anti-CD33), Solanezumab (anti-beta amyloid), Sonepcizumab (anti-sphingosine-1-phosphate), Sontuzumab (anti-episialin), Stamulumab (anti-myostatin), Sulesomab (LeukoScan, (anti-NCA-90 (granulocyte antigen), Tacatuzumab (anti-alpha-fetoprotein), Tadocizumab (anti-integrin $\alpha_{IIb}\beta_3$), Talizumab (anti-IgE), Tanezumab (anti-NGF), Taplitumomab (anti-CD19), Tefibazumab (Aurexis, (anti-clumping factor A), Telimomab, Tenatumomab (anti-tenascin C), Teneliximab (anti-CD40), Teplizumab (anti-CD3), TGN1412 (anti-CD28), Ticilimumab (Tremelimumab, (anti-CTLA-4), Tigatuzumab (anti-TRAIL-R2), TNX-650 (anti-IL-13), Tocilizumab (Atlizumab, Actemra, RoActemra, (anti-IL-6 receptor), Toralizumab (anti-CD154 (CD40L)), Tositumomab (anti-CD20), Trastuzumab (Herceptin, (anti-HER2/neu), Tremelimumab (anti-CTLA-4), Tucotuzumab celmoleukin (anti-EpCAM), Tuvirumab (anti-hepatitis B virus), Urtoxazumab (anti-*Escherichia coli*), Ustekinumab (Stelara, anti-IL-12, IL-23), Vapaliximab (anti-$AOC_3$ (VAP-1)), Vedolizumab, (anti-integrin $\alpha_4\beta_7$), Veltuzumab (anti-CD20), Vepalimomab (anti-$AOC_3$ (VAP-1), Visilizumab (Nuvion, anti-CD3), Vitaxin (anti-vascular integrin avb3), Volociximab (anti-integrin $\alpha_5\beta_1$), Votumumab (HumaSPECT, anti-tumor antigen CTAA16.88), Zalutumumab (HuMax-EGFr, (anti-EGFR), Zanolimumab (HuMax-CD4, anti-CD4), Ziralimumab (anti-CD147 (basigin)), Zolimomab (anti-CD5), Etanercept (Enbrel®), Alefacept (Amevive®), Abatacept (Orencia®), Rilonacept (Arcalyst), 14F7 [anti-IRP-2 (Iron Regulatory Protein 2)], 14G2a (anti-GD2 ganglioside, from Nat. Cancer Inst. for melanoma and solid tumors), J591 (anti-PSMA, Weill Cornell Medical School for prostate cancers), 225.28S [anti-HMW-MAA (High molecular weight-melanoma-associated antigen), Sorin Radiofarmaci S.R.L. (Milan, Italy) for melanoma], COL-1 (anti-CEACAM3, CGM1, from Nat. Cancer Inst. USA for colorectal and gastric cancers), CYT-356 (Oncoltad®, for prostate cancers), HNK20 (OraVax Inc. for respiratory syncytial virus), ImmuRAIT (from Immunomedics for NHL), Lym-1 (anti-HLA-DR10, Peregrine Pharm. for Cancers), MAK-195F [anti-TNF (tumor necrosis factor; TNFA, TNF-alpha; TNFSF2), from Abbott/Knoll for Sepsis toxic shock], MEDI-500 [T10B9, anti-CD3, TRαβ (T cell receptor alpha/beta), complex, from MedImmune Inc for Graft-versus-host disease], RING SCAN [anti-TAG 72 (tumour associated glycoprotein 72), from Neoprobe Corp. for Breast, Colon and Rectal cancers], Avicidin (anti-EPCAM (epithelial cell adhesion molecule), anti-TACSTD1 (Tumor-associated calcium signal transducer 1), anti-GA733-2 (gastrointestinal tumor-associated protein 2), anti-EGP-2 (epithelial glycoprotein 2); anti-KSA; KS1/4 antigen; M4S; tumor antigen 17-1A; CD326, from NeoRx Corp. for Colon, Ovarian, Prostate cancers and NHL]; LymphoCide (Immunomedics, NJ), Smart ID10 (Protein Design Labs), Oncolym (Techniclone Inc, CA), Allomune (BioTransplant, CA), anti-VEGF (Genentech, CA); CEAcide (Immunomedics, NJ), IMC-1C11 (ImClone, NJ) and Cetuximab (ImClone, NJ).

Other antibodies as cell binding molecules/ligands include, but are not limited to, are antibodies against the following antigens: Aminopeptidase N (CD13), Annexin A1, B7-H3 (CD276, various cancers), CA125 (ovarian), CA15-3 (carcinomas), CA19-9 (carcinomas), $L_6$ (carcinomas), Lewis Y (carcinomas), Lewis X (carcinomas), alpha fetoprotein (carcinomas), CA242 (colorectal), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (Metastatic melanoma, sarcoma), CD52 (leukemia), CD56 (small cell lung cancers, ovarian cancer, Merkel cell carcinoma, and the liquid tumor, multiple myeloma), CD66e (cancers), CD70 (metastatic renal cell carcinoma and non-Hodgkin lymphoma), CD74 (multiple myeloma), CD80 (lymphoma), CD98 (cancers), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (carcinoembryonic antigen; CEA, CD66e) (breast, colorectal and lung cancers), DLL3 or DLL4 (delta-like-3 or delta-like-4), EGFR (Epidermal Growth Factor Receptor, various cancers), CTLA4 (melanoma), CXCR4 (CD184, Heme-oncology, solid tumors), Endoglin (CD105, solid tumors), EPCAM (epithelial cell adhesion molecule, bladder, head, neck, colon, NHL prostate, and ovarian cancers), ERBB2 (Epidermal Growth Factor Receptor 2; lung, breast, prostate cancers), FCGR1 (autoimmune diseases), FOLR (folate receptor, ovarian cancers), GD2 ganglioside (cancers), G-28 (a cell surface antigen glyvolipid, melanoma), GD3 idiotype (cancers), Heat shock proteins (cancers), HER1 (lung, stomach cancers), HER2 (breast, lung and ovarian cancers), HLA-DR10 (NHL), HLA-DRB (NHL, B cell leukemia), human chorionic gonadotropin (carcinoma), IGF1R (insulin-like growth factor 1 receptor, solid tumors, blood cancers), IL-2 receptor (interleukin 2 receptor, T-cell leukemia and lymphomas), IL-6R (interleukin 6 receptor, multiple myeloma, RA, Castleman's disease, IL6 dependent tumors), Integrins (αvβ3, α5β1, α6β4, α11β3, α5β5, αvβ5, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 or MUC1-KLH (breast, ovarian, cervix, bronchus and gastrointestinal cancer), MUC16 (CA125) (Ovarian cancers), CEA (colorectal), gp100 (melanoma), MART1 (melanoma), MPG (melanoma), MS4A 1 (membrane-spanning 4-domains subfamily A, small cell lung cancers, NHL), Nucleolin, Neu oncogene product (carcinomas), P21 (carcinomas), Paratope of anti-(N-glycolylneuraminic acid, Breast, Melanoma cancers), PLAP-like testicular alkaline phosphatase (ovarian, testicular cancers), PSMA (prostate tumors), PSA (prostate), ROBO4, TAG 72 (tumour associated glycoprotein 72, AML, gastric, colorectal, ovarian cancers), T cell transmembrane protein (cancers), Tie (CD202b), TNFRSF10B (tumor necrosis factor receptor superfamily member 10B, cancers), TNFRSF13B (tumor necrosis factor receptor superfamily member 13B, multiple myeloma, NHL, other cancers, RA and SLE), TPBG (trophoblast glycoprotein, Renal cell carcinoma), TRAIL-R1 (Tumor necrosis apoprosis Inducing ligand Receptor 1, lymphoma, NHL, colorectal, lung cancers), VCAM-1 (CD106, Melanoma), VEGF, VEGF-A, VEGF-2 (CD309) (various cancers). Some other tumor associated antigens recognized by antibodies have been reviewed (Gerber, et al, mAbs 1:3, 247-53 (2009); Novellino et al, Cancer Immunol Immunother. 54(3), 187-207 (2005). Franke, et al, Cancer Biother Radiopharm. 2000, 15, 459-76).

The cell-binding agents, more preferred antibodies, can be any agents that are able to against tumor cells, virus infected cells, microorganism infected cells, parasite infected cells, autoimmune cells, activated cells, myeloid cells, activated T-cells, B cells, or melanocytes.

More specifically the cell binding agents can be any agent/molecule that is able to against any one of the following antigens or receptors: CD3, CD4, CD5, CD6, CD7, CD8, CD9, CD10, CD11a, CD11b, CD11c, CD12w, CD14, CD15, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49b, CD49c, CD51, CD52, CD53, CD54, CD55, CD56, CD58, CD59, CD61, CD62E, CD62L, CD62P, CD63, CD66, CD68, CD69, CD70, CD72, CD74, CD79, CD79a, CD79b, CD80, CD81, CD82, CD83, CD86, CD87, CD88, CD89, CD90, CD91, CD95, CD96, CD98, CD100, CD103, CD105, CD106, CD109, CD 117, CD120, CD125, CD126, CD127, CD133, CD134, CD135, CD137, CD138, CD141, CD142, CD143, CD144, CD147, CD151, CD147, CD152, CD154, CD156, CD158, CD163, CD166, CD168, CD174, CD180, CD184, CDw186, CD194, CD195, CD200, CD200a, CD200b, CD209, CD221, CD227, CD235a, CD240, CD262, CD271, CD274, CD276 (B7-H3), CD303, CD304, CD309, CD326, 4-1BB, 5AC, 5T4 (Trophoblast glycoprotein, TPBG, 5T4, Wnt-Activated Inhibitory Factor 1 or WAIF1), Adenocarcinomaantigen, AGS-5, AGS-22M6, Activin receptor-like kinase 1, AFP, AKAP-4, ALK, Alpha intergrin, Alpha v beta6, Amino-peptidase N, Amyloid beta, Androgen receptor, Angiopoietin 2, Angiopoietin 3, Annexin A1, Anthrax toxin-protective antigen, Anti-transferrin receptor, $AOC_3$ (VAP-1), B7-H3, *Bacillus* anthracisanthrax, BAFF (B-cell activating factor), B-lymphoma cell, bcr-abl, Bombesin, BORIS, $C_5$, $C_{242}$ antigen, CA125 (carbohydrate antigen 125, MUC16), CA-IX (or CAIX, carbonic anhydrase 9), CALLA, CanAg, *Canis lupus familiaris* IL31, Carbonic anhydrase IX, Cardiac myosin, CCL11 (C—C motif chemokine 11), CCR4 (C—C chemokine receptor type 4, CD194), CCR5, CD3E (epsilon), CEA (Carcinoembryonic antigen), CEACAM3, CEACAM5 (carcinoembryonic antigen), CFD (Factor D), Ch4D5, Cholecystokinin 2 (CCK2R), CLDN18 (Claudin-18), Clumping factor A, CRIPTO, FCSF1R (Colony stimulating factor 1 receptor, CD115), CSF2 (colony stimulating factor 2, Granulocyte-macrophage colony-stimulating factor (GM-CSF)), CTLA4 (cytotoxic T-lymphocyte associated protein 4), CTAA16.88 tumor antigen, CXCR4 (CD184), C—X—C chemokine receptor type 4, cyclic ADP ribose hydrolase, Cyclin B1, CYP1B1, Cytomegalovirus, Cytomegalovirus glycoprotein B, Dabigatran, DLL3 or DLL4 (delta-like-ligand 3 or delta-like-ligand 4), DPP4 (Dipeptidyl-peptidase 4), DR5 (Death receptor 5), *E. coli* shiga toxintype-1, *E. coli* shiga toxintype-2, ED-B, EGFL7 (EGF-like domain-containing protein 7), EGFR, EGFRII, EGFRvIII, Endoglin (CD105), Endothelin B receptor, Endotoxin, EpCAM (epithelial cell adhesion molecule), EphA2, Episialin, ERBB2 (Epidermal Growth Factor Receptor 2), ERBB3, ERG (TMPRSS2 ETS fusion gene), *Escherichia coli*, ETV6-AML, FAP (Fibroblast activation proteinalpha), FCGR1, alpha-Fetoprotein, Fibrin II, beta chain, Fibronectin extra domain-B, FOLR (folate receptor), Folate receptor alpha, Folate hydrolase, Fos-related antigen 1, F protein of respiratory syncytial virus, Frizzled receptor, Fucosyl GM1, GD2 ganglioside, G-28 (a cell surface antigen glyvolipid), GD3 idiotype, GloboH, Glypican 3, N-glycolylneuraminic acid, GM3, GMCSF receptor α-chain, Growth differentiation factor 8, GP100, GPNMB (Transmembrane glycoprotein NMB), GUCY2C (Guanylate cyclase 2C, guanylyl cyclase C (GC-C), intestinal Guanylate cyclase, Guanylate cyclase-C receptor, Heat-stable enterotoxin receptor (hSTAR)), Heat shock proteins, Hemagglutinin, Hepatitis B surface antigen, Hepatitis B virus, HER1 (human epidermal growth factor receptor 1), HER2, HER2/neu, HER3 (ERBB-3), IgG4, HGF/SF (Hepatocyte growth factor/scatter factor), HHGFR, HIV-1, Histone complex, HLA-DR (human leukocyte antigen), HLA-DR10, HLA-DRB, HMWMAA, Human chorionic gonadotropin, HNGF, Human scatter factor receptor kinase, HPV E6/E7, Hsp90, hTERT, ICAM-1 (Intercellular Adhesion Molecule 1), Idiotype, IGF1R (IGF-1, insulin-like growth factor 1 receptor), IGHE, IFN-γ, Influeza hemagglutinin, IgE, IgE Fc region, IGHE, IL-1, IL-2 receptor (interleukin 2 receptor), IL-4, IL-5, IL-6, IL-6R (interleukin 6 receptor), IL-9, IL-10, IL-12, IL-13, IL-17, IL-17A, IL-20, IL-22, IL-23, IL31RA, ILGF2 (Insulin-like growth factor 2), Integrins ($\alpha 4$, $\alpha_{IIb}\beta 3$, $\alpha v\beta 3$, $\beta_4\beta_7$, $\alpha 5\beta 1$, $\alpha 6\beta 4$, $\alpha 7\beta 7$, $\alpha 11\beta 3$, $\alpha 5\beta 5$, $\alpha v\beta 5$), Interferon gamma-induced protein, ITGA2, ITGB2, KIR2D, LCK, Le, Legumain, Lewis-Y antigen, LFA-1 (Lymphocyte function-associated antigen 1, CD11a), LHRH, LINGO-1, Lipoteichoic acid, LIVIA, LMP2, LTA, MAD-CT-1, MAD-CT-2, MAGE-1, MAGE-2, MAGE-3, MAGE A1, MAGE A3, MAGE 4, MART1, MCP-1, MIF (Macrophage migration inhibitory factor, or glycosylation-inhibiting factor (GIF)), MS4A1 (membrane-spanning 4-domains subfamily A member 1), MSLN (meso-thelin), MUC1 (Mucin 1, cell surface associated (MUC1) or polymorphic epithelial mucin (PEM)), MUC1-KLH, MUC16 (CA125), MCP1 (monocyte chemotactic protein 1), MelanA/MART1, ML-IAP, MPG, MS4A1 (membrane-spanning 4-domains subfamily A), MYCN, Myelin-associated glycoprotein, Myostatin, NA17, NARP-1, NCA-90 (granulocyte antigen), Nectin-4 (ASG-22ME), NGF, Neural apoptosis-regulated proteinase 1, NOGO-A, Notch receptor, Nucleolin, Neu oncogene product, NY—BR-1, NY-ESO-1, OX-40, OxLDL (Oxidized low-density lipoprotein), OY-TES1, P21, p53 nonmutant, P97, Page4, PAP, Paratope of anti-(N-glycolylneuraminic acid), PAX3, PAX5, PCSK9, PDCD1 (PD-1, Programmed cell death protein 1, CD279), PDGF-Ra (Alpha-type platelet-derived growth factor receptor), PDGFR-β, PDL-1, PLAC1, PLAP-like testicular alkaline phosphatase, Platelet-derived growth factor receptor beta, Phosphate-sodium co-transporter, PMEL 17, Polysialic acid, Proteinase3 (PR1), Prostatic carcinoma, PS (Phosphatidylserine), Prostatic carcinoma cells, *Pseudomonas aeruginosa*, PSMA, PSA, PSCA, Rabies virus glycoprotein, RHD (Rh polypeptide 1 (RhPI), CD240), Rhesus factor, RANKL, RhoC, Ras mutant, RGS5, ROBO4, Respiratory syncytial virus, RON, Sarcoma translocation breakpoints, SART3, Sclerostin, SLAMF7 (SLAM family member 7), Selectin P, SDC1 (Syndecan 1), sLe(a), Somatomedin C, SIP (Sphingosine-1-phosphate), Somatostatin, Sperm protein 17, SSX2, STEAP1 (six-transmembrane epithelial antigen of the prostate 1), STEAP2, STn, TAG-72 (tumor associated glycoprotein 72), Survivin, T-cell receptor, T cell transmembrane protein, TEM1 (Tumor endothelial marker 1), TENB2, Tenascin C (TN-C), TGF-α, TGF-β (Transforming growth factor beta), TGF-β1, TGF-β2 (Transforming growth factor-beta 2), Tie (CD202b), Tie2, TIM-1 (CDX-014), Tn, TNF, TNF-α, TNFRSF8, TNFRSF10B (tumor necrosis factor receptor superfamily member 10B), TNFRSF13B (tumor necrosis factor receptor superfamily member 13B), TPBG (trophoblast glycoprotein), TRAIL-R1 (Tumor necrosis apoprosis Inducing ligand Receptor 1), TRAILR2 (Death receptor 5 (DR5)), tumor-associated calcium signal transducer 2, tumor specific glycosylation of MUC1, TWEAK receptor, TYRP1 (glycoprotein 75), TROP-2, TRP-2, Tyrosinase, VCAM-1 (CD106), VEGF, VEGF-A, VEGF-2 (CD309), VEGFR-1, VEGFR2, or vimentin, WT1, XAGE 1, or cells expressing any insulin growth factor receptors, or any epidermal growth factor receptors.

In another specific embodiment, the cell-binding ligand-drug conjugates via the bridge linkers of this invention are used for the targeted treatment of cancers. The targeted cancers include, but are not limited, Adrenocortical Carcinoma, Anal Cancer, Bladder Cancer, Brain Tumor (Adult, Brain Stem Glioma, Childhood, Cerebellar Astrocytoma, Cerebral Astrocytoma, Ependymoma, Medulloblastoma, Supratentorial Primitive Neuroectodermal and Pineal Tumors, Visual Pathway and Hypothalamic Glioma), Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Eye Cancer, Intraocular Melanoma, Gallbladder Cancer, Gastric Cancer (Stomach), Germ Cell Tumor, Extragonadal, Gestational Trophoblastic Tumor, Head and Neck Cancer, Hypopharyngeal Cancer, Islet Cell Carcinoma, Kidney Cancer (renal cell cancer), Laryngeal Cancer, Leukemia (Acute Lymphoblastic, Acute Myeloid, Chronic Lymphocytic, Chronic Myelogenous, Hairy Cell), Lip and Oral Cavity Cancer, Liver Cancer, Lung Cancer (Non-Small Cell, Small Cell, Lymphoma (AIDS-Related, Central Nervous System, Cutaneous T-Cell, Hodgkin's Disease, Non-Hodgkin's Disease, Malignant Mesothelioma, Melanoma, Merkel Cell Carcinoma, Metastatic Squamous Neck Cancer with Occult Primary, Multiple Myeloma, and Other Plasma Cell Neoplasms, Mycosis Fungoides, Myelodysplastic Syndrome, Myeloproliferative Disorders, Nasopharyngeal Cancer, Neuroblastoma, Oral Cancer, Oropharyngeal Cancer, Osteosarcoma, Ovarian Cancer (Epithelial, Germ Cell Tumor, Low Malignant Potential Tumor), Pancreatic Cancer (Exocrine, Islet Cell Carcinoma), Paranasal Sinus and Nasal Cavity Cancer, Parathyroid Cancer, Penile Cancer, Pheochromocytoma Cancer, Pituitary Cancer, Plasma Cell Neoplasm, Prostate Cancer Rhabdomyosarcoma, Rectal Cancer, Renal Cell Cancer (kidney cancer), Renal Pelvis and Ureter (Transitional Cell), Salivary Gland Cancer, Sezary Syndrome, Skin Cancer, Skin Cancer (Cutaneous T-Cell Lymphoma, Kaposi's Sarcoma, Melanoma), Small Intestine Cancer, Soft Tissue Sarcoma, Stomach Cancer, Testicular Cancer, Thymoma (Malignant), Thyroid Cancer, Urethral Cancer, Uterine Cancer (Sarcoma), Unusual Cancer of Childhood, Vaginal Cancer, Vulvar Cancer, Wilms' Tumor.

In another specific embodiment, the cell-binding-drug conjugates via the bridge linkers of this invention are used in accordance with the compositions and methods for the treatment or prevention of an autoimmune disease. The autoimmune diseases include, but are not limited, Achlorhydra Autoimmune Active Chronic Hepatitis, Acute Disseminated Encephalomyelitis, Acute hemorrhagic leukoencephalitis, Addison's Disease, Agammaglobulinemia, Alopecia areata, Amyotrophic Lateral Sclerosis, Ankylosing Spondylitis, Anti-GBM/TBM Nephritis, Antiphospholipid syndrome, Antisynthetase syndrome, Arthritis, Atopic allergy, Atopic Dermatitis, Autoimmune Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaffs encephalitis, Blau syndrome, Bullous Pemphigoid, Castleman's disease, Chagas disease, Chronic Fatigue Immune Dysfunction Syndrome, Chronic inflammatory demyelinating polyneuropathy, Chronic recurrent multifocal ostomyelitis, Chronic lyme disease, Chronic obstructive pulmonary disease, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease (a type of idiopathic inflammatory bowel diseases), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Discoid lupus erythematosus, Eczema, Endometriosis, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyalgia, Fibromyositis, Fibrosing aveolitis, Gastritis, Gastrointestinal pemphigoid, Giant cell arteritis, Glomerulonephritis, Goodpasture's syndrome, Graves' disease, Guillain-Barré syndrome, Hashimoto's encephalitis, Hashimoto's thyroiditis, Haemolytic anaemia, Henoch-Schonlein purpura, Herpes gestationis, Hidradenitis suppurativa, Hughes syndrome (See Antiphospholipid syndrome), Hypogammaglobulinemia, Idiopathic Inflammatory Demyelinating Diseases, Idiopathic pulmonary fibrosis, Idiopathic thrombocytopenic purpura (See Autoimmune thrombocytopenic purpura), IgA nephropathy (Also Berger's disease), Inclusion body myositis, Inflammatory demyelinating polyneuropathy, Interstitial cystitis, Irritable Bowel Syndrome, Juvenile idiopathic arthritis, Juvenile rheumatoid arthritis, Kawasaki's Disease, Lambert-Eaton myasthenic syndrome, Leukocytoclastic vasculitis, Lichen planus, Lichen sclerosus, Linear IgA disease (LAD), Lou Gehrig's Disease (Also Amyotrophic lateral sclerosis), Lupoid hepatitis, Lupus erythematosus, Majeed syndrome, Ménière's disease, Microscopic polyangiitis, Miller-Fisher syndrome, Mixed Connective Tissue Disease, Morphea, Mucha-Habermann disease, Muckle-Wells syndrome, Multiple Myeloma, Multiple Sclerosis, Myasthenia gravis, Myositis, Narcolepsy, Neuromyelitis optica (Devic's Disease), Neuromyotonia, Occular cicatricial pemphigoid, Opsoclonus myoclonus syndrome, Ord thyroiditis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria, Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic Arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatoid fever, Sarcoidosis, Schizophrenia, Schmidt syndrome, Schnitzler syndrome, Scleritis, Scleroderma, Sjögren's syndrome, Spondyloarthropathy, Sticky blood syndrome, Still's Disease, Stiff person syndrome, Subacute bacterial endocarditis, Susac's syndrome, Sweet syndrome, Sydenham Chorea, Sympathetic ophthalmia, Takayasu's arteritis, Temporal arteritis (giant cell arteritis), Tolosa-Hunt syndrome, Transverse Myelitis, Ulcerative Colitis (a type of idiopathic inflammatory bowel diseases), Undifferentiated connective tissue disease, Undifferentiated spondyloarthropathy, Vasculitis, Vitiligo, Wegener's granulomatosis, Wilson's syndrome, Wiskott-Aldrich syndrome In another specific embodiment, a binding molecule used for the conjugate via the bridge linkers of this invention for the treatment or prevention of an autoimmune disease can be, but are not limited to, anti-elastin antibody; Abys against epithelial cells antibody; Anti-Basement Membrane Collagen Type IV Protein antibody; Anti-Nuclear Antibody; Anti ds DNA; Anti ss DNA, Anti Cardiolipin Antibody IgM, IgG; anti-celiac antibody; Anti Phospholipid Antibody IgK, IgG; Anti SM Antibody; Anti Mitochondrial Antibody; Thyroid Antibody; Microsomal Antibody, T-cells antibody; Thyroglobulin Antibody, Anti SCL-70; Anti-Jo; Anti-U.sub.1RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody, Anti-ganglioside antibody; Anti-Desmogein 3 antibody; Anti-p62 antibody; Anti-sp100 antibody; Anti-Mitochondrial (M2) antibody; Rheumatoid factor antibody; Anti-MCV antibody; Anti-topoisomerase antibody; Anti-neutrophil cytoplasmic (cANCA) antibody.

In certain preferred embodiments, the binding molecule for the conjugate in the present invention, can bind to both a receptor and a receptor complex expressed on an activated lymphocyte which is associated with an autoimmune disease. The receptor or receptor complex can comprise an immunoglobulin gene superfamily member (e.g. CD2, CD3, CD4, CD8, CD19, CD20, CD22, CD28, CD30, CD33, CD37, CD38, CD56, CD70, CD79, CD79b, CD90, CD125, CD137, CD138, CD147, CD152/CTLA-4, PD-1, or ICOS), a TNF receptor superfamily member (e.g. CD27, CD40, CD95/Fas, CD134/OX40, CD137/4-1BB, INF—R1, TNFR-2, RANK, TACI, BCMA, osteoprotegerin, Apo2/TRAIL-R1, TRAIL-R2, TRAIL-R3, TRAIL-R4, and APO-3), an integrin, a cytokine receptor, a chemokine receptor, a major histocompatibility protein, a lectin (C-type, S-type, or I-type), or a complement control protein.

In another specific embodiment, useful cell binding ligands that are immunospecific for a viral or a microbial antigen are humanized or human monoclonal antibodies. As used herein, the term "viral antigen" includes, but is not limited to, any viral peptide, polypeptide protein (e.g. HIV gp120, HIV nef, RSV F glycoprotein, influenza virus neuramimidase, influenza virus hemagglutinin, HTLV tax, herpes simplex virus glycoprotein (e.g. gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacteria, fungi, pathogenic protozoa, or yeast polypeptides including, e.g., LPS and capsular polysaccharide 5/8) that is capable of eliciting an immune response. Examples of antibodies available 1 for the viral or microbial infection include, but are not limited to, Palivizumab which is a humanized anti-respiratory syncytial virus monoclonal antibody for the treatment of RSV infection; PR0542 which is a CD4 fusion antibody for the treatment of HIV infection; Ostavir which is a human antibody for the treatment of hepatitis B virus; PROTVIR which is a humanized IgG.sub.1 antibody for the treatment of cytomegalovirus; and anti-LPS antibodies.

The cell binding molecules-drug conjugates via the bridge linkers of this invention can be used in the treatment of infectious diseases. These infectious diseases include, but are not limited to, *Acinetobacter* infections, Actinomycosis, African sleeping sickness (African trypanosomiasis), AIDS (Acquired immune deficiency syndrome), Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis, *Bacteroides* infection, Balantidiasis, *Baylisascaris* infection, BK virus infection, Black *piedra, Blastocystis hominis* infection, Blastomycosis, Bolivian hemorrhagic fever, *Borrelia* infection, Botulism (and Infant botulism), Brazilian hemorrhagic fever, Brucellosis, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, *Chlamydia, Chlamydophila pneumoniae* infection, Cholera, Chromoblastomycosis, Clonorchiasis, *Clostridium difficile* infection, Coccidioido-mycosis, Colorado tick fever, Common cold (Acute viral rhinopharyngitis; Acute coryza), Creutzfeldt-Jakob disease, Crimean-Congo hemorrhagic fever, Cryptococcosis, Cryptosporidiosis, Cutaneous larva migrans, Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum, Fasciolopsiasis, Fasciolosis, Fatal familial insomnia, Filariasis, Food poisoning by *Clostridium perfringens*, Free-living amebic infection, *Fusobacterium* infection, Gas gangrene (Clostridial myonecrosis), Geotrichosis, Gerstmann-Striussler-Scheinker syndrome, Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome, *Helicobacter pylori* infection, Hemolytic-uremic syndrome, Hemorrhagic fever with renal syndrome, Hepatitis A, Hepatitis B, Hepatitis C, Hepatitis D, Hepatitis E, Herpes simplex, Histoplasmosis, Hookworm infection, Human bocavirus infection, Human *ewingii* ehrlichiosis, Human granulocytic anaplasmosis, Human metapneumovirus infection, Human monocytic ehrlichiosis, Human papillomavirus infection, Human parainfluenza virus infection, Hymenolepiasis, Epstein-Barr Virus Infectious Mononucleosis (Mono), Influenza, Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever, Measles, Melioidosis (Whitmore's disease), Meningitis, Meningococcal disease, Metagonimiasis, Microsporidiosis, *Molluscum contagiosum*, Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease, Pertussis (Whooping cough), Plague, Pneumococcal infection, *Pneumocystis* pneumonia, Pneumonia, Poliomyelitis, *Prevotella* infection, Primary amoebic meningoencephalitis, Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsial-pox, Rift Valley fever, Rocky mountain spotted fever, Rotavirus infection, Rubella, *Salmonellosis*, SARS (Severe Acute Respiratory Syndrome), Scabies, Schistosomiasis, Sepsis, Shigellosis (Bacillary dysentery), Shingles (Herpes zoster), Smallpox (*Variola*), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea *versicolor* (*Pityriasis versicolor*), Toxocariasis (Ocular Larva Migrans), Toxocariasis (Visceral Larva Migrans), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, Viral pneumonia, West Nile Fever, White *piedra* (Tinea blanca), *Yersinia* pseudotuberculosis infection, Yersiniosis, Yellow fever, Zygomycosis.

The cell binding molecule, which is more preferred to be an antibody described in this patent that are against pathogenic strains include, but are not limit, *Acinetobacter baumannii, Actinomyces israelii, Actinomyces gerencseriae* and *Propionibacterium propionicus, Trypanosoma brucei*, HIV (Human immunodeficiency virus), *Entamoeba histolytica, Anaplasma genus, Bacillus anthracis, Arcanobacterium haemolyticum, Junin virus, Ascaris lumbricoides, Aspergillus* genus, Astroviridae family, *Babesia* genus, *Bacillus cereus*, multiple bacteria, *Bacteroides* genus, *Balantidium coli, Baylisascaris* genus, BK virus, *Piedraia hortae, Blastocystis hominis, Blastomyces dermatitides*, Machupo virus, *Borrelia* genus, *Clostridium botulinum, Sabia, Brucella* genus, usually *Burkholderia cepacia* and other *Burkholderia* species, *Mycobacterium ulcerans, Caliciviridae family, Campylobacter* genus, usually *Candida albicans* and other *Candida* species, *Bartonella henselae*, Group A *Streptococcus* and *Staphylococcus, Trypanosoma cruzi, Haemophilus ducreyi*, Varicella zoster virus (VZV), *Chlamydia trachomatis, Chlamydophila pneumoniae, Vibrio cholerae, Fonsecaea pedrosoi, Clonorchis sinensis, Clostridium difficile, Coccidioides immitis* and *Coccidioides* posadasii, Colorado tick fever virus, rhinoviruses, coronaviruses, CJD prion, Crimean-Congo hemorrhagic fever virus, *Cryptococcus neoformans, Cryptosporidium genus, Ancylostoma braziliense*; multiple parasites, *Cyclospora cayetanensis, Taenia solium*, Cytomegalovirus, Dengue viruses (DEN-1, DEN-2, DEN-3 and DEN-4)—Flaviviruses, *Dientamoeba fragilis, Corynebacterium diphtheriae, Diphyllobothrium, Dracunculus medinensis*, Ebolavirus, *Echinococcus* genus, *Ehrlichia* genus, *Enterobius vermicularis, Enterococcus* genus, Enterovirus genus, *Rickettsia prowazekii*, Parvovirus B19, Human herpesvirus 6 and Human herpesvirus 7, *Fasciolopsis buski, Fasciola hepatica* and *Fasciola gigantica*, FFI prion, Filarioidea superfamily, *Clostridium perfringens, Fusobacterium genus, Clostridium perfringens*; other *Clostridium* species, *Geotrichum candidum*, GSS prion, *Giardia intestinalis, Burkholderia mallei, Gnathostoma spinigerum* and *Gnathostoma hispidum, Neisseria gonorrhoeae, Klebsiella granulomatis, Streptococcus pyogenes, Streptococcus agalactiae, Haemophilus influenzae*, Enteroviruses, mainly Coxsackie A virus and Enterovirus 71, Sin Nombre virus, *Helicobacter pylori, Escherichia coli* O157:H7, Bunyaviridae family, Hepatitis A Virus, Hepatitis B Virus, Hepatitis C Virus, Hepatitis D Virus, Hepatitis E Virus, Herpes simplex virus 1, Herpes simplex virus 2, *Histoplasma capsulatum, Ancylostoma duodenale* and *Necator americanus, Hemophilus influenzae*, Human bocavirus, *Ehrlichia ewingii, Anaplasma phagocytophilum*, Human metapneumovirus, *Ehrlichia chaffeensis*, Human papillomavirus, Human parainfluenza viruses, *Hymenolepis nana* and *Hymenolepis diminuta*, Epstein-Barr Virus, Orthomyxoviridae family, *Isospora belli, Kingella kingae, Klebsiella pneumoniae, Klebsiella ozaenas, Klebsiella* rhinoscleromotis, Kuru prion, Lassa virus, *Legionella pneumophila, Legionella pneumophila, Leishmania genus, Mycobacterium leprae* and *Mycobacterium* lepromatosis, *Leptospira* genus, *Listeria monocytogenes, Borrelia burgdorferi* and other *Borrelia* species, *Wuchereria bancrofti* and *Brugia malayi*, Lymphocytic choriomeningitis virus (LCMV), *Plasmodium* genus, Marburg virus, Measles virus, *Burkholderia pseudomallei, Neisseria meningitides, Metagonimus yokagawai, Microsporidia phylum, Molluscum contagiosum* virus (MCV), Mumps virus, *Rickettsia typhi, Mycoplasma pneumoniae*, numerous species of bacteria (Actinomycetoma) and fungi (Eumycetoma), parasitic dipterous fly larvae, *Chlamydia trachomatis* and *Neisseria gonorrhoeae*, vCJD prion, *Nocardia asteroides* and other *Nocardia* species, *Onchocerca volvulus, Paracoccidioides brasiliensis, Paragonimus westermani* and other *Paragonimus* species, *Pasteurella* genus, *Pediculus humanus capitis, Pediculus humanus corporis, Phthirus pubis, Bordetella pertussis, Yersinia pestis, Streptococcus pneumoniae, Pneumocystis jirovecii*, Poliovirus, *Prevotella* genus, *Naegleria fowleri*, JC virus, *Chlamydophila psittaci, Coxiella burnetii*, Rabies virus, *Streptobacillus moniliformis* and *Spirillum minus*, Respiratory syncytial virus, *Rhinosporidium seeberi*, Rhinovirus, *Rickettsia* genus, *Rickettsia akari*, Rift Valley fever virus, *Rickettsia rickettsii*, Rotavirus, Rubella virus, *Salmonella* genus, SARS coronavirus, *Sarcoptes scabiei, Schistosoma genus, Shigella* genus, Varicella zoster virus, *Variola major* or *Variola minor, Sporothrix schenckii, Staphylococcus genus, Staphylococcus genus, Staphylococcus aureus, Streptococcus pyogenes, Strongyloides stercoralis, Treponema pallidum, Taenia genus, Clostridium tetani, Trichophyton genus, Trichophyton tonsurans, Trichophyton genus, Epidermophyton floccosum, Trichophyton rubrum*, and *Trichophyton mentagrophytes, Trichophyton rubrum, Hortaea werneckii, Trichophyton genus, Malassezia genus, Toxocara canis* or *Toxocara cati, Toxoplasma gondii, Trichinella spiralis, Trichomonas vaginalis, Trichuris trichiura, Mycobacterium tuberculosis, Francisella tularensis, Ureaplasma urealyticum*, Venezuelan equine encephalitis virus, *Vibrio colerae*, Guanarito virus, West Nile virus, *Trichosporon beigelii, Yersinia pseudotuberculosis, Yersinia enterocolitica*, Yellow fever virus, Mucorales order (Mucormycosis) and Entomophthorales order (*Entomophthora*-mycosis), *Pseudomonas aeruginosa, Campylobacter* (*Vibrio*) fetus, *Aeromonas hydrophila, Edwardsiella tarda, Yersinia pestis, Shigella dysenteriae, Shigella flexneri, Shigella sonnei, Salmonella typhimurium, Treponema pertenue, Treponema carateneum, Borrelia vincentii, Borrelia burgdorferi, Leptospira icterohemorrhagiae, Pneumocystis carinii, Brucella abortus, Brucella suis, Brucella melitensis, Mycoplasma* spp., *Rickettsia* prowazeki, *Rickettsia* tsutsugumushi, Clamydia spp.; pathogenic fungi (*Aspergillus fumigatus, Candida albicans, Histoplasma capsulatum*); protozoa (Entomoeba *histolytica, Trichomonas tenas, Trichomonas hominis, Tryoanosoma gambiense, Trypanosoma rhodesiense, Leishmania donovani, Leishmania tropica, Leishmania braziliensis, Pneumocystis pneumonia, Plasmodium vivax, Plasmodium falciparum, Plasmodium* malaria); or Helminiths (*Schistosoma japonicum, Schistosoma mansoni, Schistosoma haematobium*, and hookworms).

Other antibodies as cell binding ligands used in this invention for treatment of viral disease include, but are not limited to, antibodies against antigens of pathogenic viruses, including as examples and not by limitation: Poxyiridae, Herpesviridae, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Non-A/Non-B Hepatitis virus, Rhinoviridae, Coronaviridae, Rotoviridae, Oncovirus [such as, HBV (Hepatocellular carcinoma), HPV (Cervical cancer, Anal cancer), Kaposi's sarcoma-associated herpesvirus (Kaposi's sarcoma), Epstein-Barr virus (Nasopharyngeal carcinoma, Burkitt's lymphoma, Primary central nervous system lymphoma), MCPyV (Merkel cell cancer), SV40 (Simian virus 40), HCV (Hepatocellular carcinoma), HTLV-I (Adult T-cell leukemia/lymphoma)], Immune disorders caused virus: [such as Human Immunodeficiency Virus (AIDS)]; Central nervous system virus: [such as, JCV (Progressive multifocal leukoencephalopathy), MeV (Subacute sclerosing panencephalitis), LCV (Lymphocytic choriomeningitis), Arbovirus encephalitis, Orthomyxoviridae (probable) (Encephalitis lethargica), RV (Rabies), Chandipura virus, Herpesviral meningitis, Ramsay Hunt syndrome type II; Poliovirus (Poliomyelitis, Post-polio syndrome), HTLV-I (Tropical spastic paraparesis)]; Cytomegalovirus (Cytomegalovirus retinitis, HSV (Herpetic keratitis)); Cardiovascular virus [such as CBV (Pericarditis, Myocarditis)]; Respiratory system/acute viral nasopharyngitis/viral pneumonia: [Epstein-Barr virus (EBV infection/Infectious mononucleosis), Cytomegalovirus; SARS coronavirus (Severe acute respiratory syndrome) Orthomyxoviridae: Influenzavirus A/B/C (Influenza/Avian influenza), Paramyxovirus: Human parainfluenza viruses (Parainfluenza), RSV (Human respiratory syncytialvirus), hMPV]; Digestive system virus [MuV (Mumps), Cytomegalovirus (Cytomegalovirus esophagitis); Adenovirus (Adenovirus infection); Rotavirus, Norovirus, Astrovirus, Coronavirus; HBV (Hepatitis B virus), CBV, HAV (Hepatitis A virus), HCV (Hepatitis C virus), HDV (Hepatitis D virus), HEV (Hepatitis E virus), HGV (Hepatitis G virus)]; Urogenital virus [such as, BK virus, MuV (Mumps)].

According to a further object, the present invention also concerns pharmaceutical compositions comprising the conjugate via the bridge linkers of the invention together with a pharmaceutically acceptable carrier, diluent, or excipient for treatment of cancers, infections or autoimmune disorders. The method for treatment of cancers, infections and autoimmune disorders can be practiced in vitro, in vivo, or ex vivo. Examples of in vitro uses include treatments of cell cultures in order to kill all cells except for desired variants that do not express the target antigen; or to kill variants that express undesired antigen. Examples of ex vivo uses include treatments of hematopoietic stem cells (HSC) prior to the performance of the transplantation (HSCT) into the same patient in order to kill diseased or malignant cells. For instance, clinical ex vivo treatment to remove tumour cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent graft-versus-host disease, can be carried out as follows.

Bone marrow is harvested from the patient or other individual and then incubated in medium containing serum to which is added the conjugate of the invention, concentrations range from about 1 pM to 0.1 mM, for about 30 minutes to about 48 hours at about 37° C. The exact conditions of concentration and time of incubation (=dose) are readily determined by the skilled clinicians. After incubation, the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the conjugate via the linkers of the invention will be supplied as solutions or as a lyophilized solid that can be redissolved in sterile water for injection.

Examples of suitable protocols of conjugate administration are as follows. Conjugates are given weekly for 8-20 weeks as an i.v. bolus. Bolus doses are given in 50 to 500 $m_1$ of normal saline to which human serum albumin (e.g. 0.5 to 1 mL of a concentrated solution of human serum albumin, 100 mg/mL) can be added. Dosages will be about 50 μg to 20 mg/kg of body weight per week, i.v. (range of 10 μg to 200 mg/kg per injection). 4-20 weeks after treatment, the patient may receive a second course of treatment. Specific clinical protocols with regard to route of administration, excipients, diluents, dosages, times, etc., can be determined by the skilled clinicians.

Examples of medical conditions that can be treated according to the in vivo or ex vivo methods of killing selected cell populations include malignancy of any types of cancer, autoimmune diseases, graft rejections, and infections (viral, bacterial or parasite).

The amount of a conjugate which is required to achieve the desired biological effect, will vary depending upon a number of factors, including the chemical characteristics, the potency, and the bioavailability of the conjugates, the type of disease, the species to which the patient belongs, the diseased state of the patient, the route of administration, all factors which dictate the required dose amounts, delivery and regimen to be administered.

In general terms, the conjugates via the linkers of this invention may be provided in an aqueous physiological buffer solution containing 0.1 to 10% w/v conjugates for parenteral administration. Typical dose ranges are from 1 μg/kg to 0.1 g/kg of body weight per day; a preferred dose range is from 0.01 mg/kg to 20 mg/kg of body weight per day, or per week, or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the conjugates by the chosen delivery route, and the speed (bolus or continuous infusion) and schedule of administrations (number of repetitions in a given period of time).

The conjugates via the linkers of the present invention are also capable of being administered in unit dose forms, wherein the term "unit dose" means a single dose which is capable of being administered to a patient, and which can be readily handled and packaged, remaining as a physically and chemically stable unit dose comprising either the active conjugate itself, or as a pharmaceutically acceptable composition, as described hereinafter. As such, typical total daily/weekly/biweekly/monthly dose ranges are from 0.01 to 100 mg/kg of body weight. By way of general guidance, unit doses for humans range from 1 mg to 3000 mg per day, or per week, per two weeks (biweekly) or per month. Preferably the unit dose range is from 1 to 500 mg administered one to four times a week and even more preferably from 1 mg to 100 mg, once a week, or once a biweekly, or once a triweekly or monthly. Conjugates provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasal, particularly in the form of powders, nasal drops, or aerosols; or dermally, for example, topically in ointments, creams, lotions, gels or sprays, or via transdermal patches.

Drugs/Cytotoxic Agents

Drugs that can be conjugated to a cell-binding molecule in the present invention are small molecule drugs including cytotoxic agents, which can be linked to or after they are modified for linkage to the cell-binding agent. A "small molecule drug" is broadly used herein to refer to an organic, inorganic, or organometallic compound that may have a molecular weight of, for example, 100 to 2500, more suitably from 120 to 1500. Small molecule drugs are well characterized in the art, such as in WO05058367A2, and in U.S. Pat. No. 4,956,303, among others and are incorporated in their entirety by reference. The drugs include known drugs and those that may become known drugs.

Drugs that are known include, but not limited to,

1). Chemotherapeutic agents: a). Alkylating agents: such as Nitrogen mustards: chlorambucil, chlornaphazine, cyclophosphamide, dacarbazine, estramustine, ifosfamide, mechlorethamine, mechlorethamine oxide hydrochloride, mannomustine, mitobronitol, melphalan, mitolactol, pipobroman, novembichin, phenesterine, prednimustine, thiotepa, trofosfamide, uracil mustard; CC-1065 (including its adozelesin, carzelesin and bizelesin synthetic analogues); Duocarmycin (including the synthetic analogues, KW-2189 and CBI-TMI); Benzodiazepine dimers (e.g., dimmers of pyrrolobenzodiazepine (PBD) or tomaymycin, indolinobenzodiazepines, imidazobenzothiadiazepines, or oxazolidinobenzodiazepines); Nitrosoureas: (carmustine, lomustine, chlorozotocin, fotemustine, nimustine, ranimustine); Alkylsulphonates: (busulfan, treosulfan, improsulfan and piposulfan); Triazenes: (dacarbazine); Platinum containing compounds: (carboplatin, cisplatin, oxaliplatin); aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamine]; b). Plant Alkaloids: such as *Vinca* alkaloids: (vincristine, vinblastine, vindesine, vinorelbine, navelbin); Taxoids: (paclitaxel, docetaxol) and their analogs, Maytansinoids (DM1, DM2, DM3, DM4, maytansine and ansamitocins) and their analogs, cryptophycins (particularly cryptophycin 1 and cryptophycin 8); epothilones, eleutherobin, discodermolide, bryostatins, dolostatins, auristatins, tubulysins, cephalostatins; pancratistatin; a sarcodictyin; spongistatin; c). DNA Topoisomerase Inhibitors: such as [Epipodophyllins: (9-aminocamptothecin, camptothecin, crisnatol, daunomycin, etoposide, etoposide phosphate, irinotecan, mitoxantrone, novantrone, retinoic acids (retinols), teniposide, topotecan, 9-nitrocamptothecin (RFS 2000)); mitomycins: (mitomycin C)]; d). Anti-metabolites: such as {[Anti-folate: DHFR inhibitors: (methotrexate, trimetrexate, denopterin, pteropterin, aminopterin (4-aminopteroic acid) or the other folic acid analogues); IMP dehydrogenase Inhibitors: (mycophenolic acid, tiazofurin, ribavirin, EICAR); Ribonucleotide reductase Inhibitors: (hydroxyurea, deferoxamine)]; [Pyrimidine analogs: Uracil analogs: (ancitabine, azacitidine, 6-azauridine, capecitabine (Xeloda), carmofur, cytarabine, dideoxyuridine, doxifluridine, enocitabine, 5-Fluorouracil, floxuridine, ratitrexed (Tomudex)); Cytosine analogs: (cytarabine, cytosine arabinoside, fludarabine); Purine analogs: (azathioprine, fludarabine, mercaptopurine, thiamiprine, thioguanine)]; folic acid replenisher, such as frolinic acid}; e). Hormonal therapies: such as {Receptor antagonists: [Anti-estrogen: (megestrol, raloxifene, tamoxifen); LHRH agonists: (goscrclin, leuprolide acetate); Anti-androgens: (bicalutamide, flutamide, calusterone, dromostanolone propionate, epitiostanol, goserelin, leuprolide, mepitiostane, nilutamide, testolactone, trilostane and other androgens inhibitors)]; Retinoids/Deltoids: [Vitamin D3 analogs: (CB 1093, EB 1089 KH 1060, cholecalciferol, ergocalciferol); Photodynamic therapies: (verteporfin, phthalocyanine, photosensitizer Pc4, demethoxyhypocrellin A); Cytokines: (Interferon-alpha, Interferon-gamma, tumor necrosis factor (TNFs), human proteins containing a TNF domain)]}; f). Kinase inhibitors, such as BIBW 2992 (anti-EGFR/Erb2), imatinib, gefitinib, pegaptanib, sorafenib, dasatinib, sunitinib, erlotinib, nilotinib, lapatinib, axitinib, pazopanib. vandetanib, E7080 (anti-VEGFR2), mubritinib, ponatinib (AP24534), bafetinib (INNO-406), bosutinib (SKI-606), cabozantinib, vismodegib, iniparib, ruxolitinib, CYT387, axitinib, tivozanib, sorafenib, bevacizumab, cetuximab, Trastuzumab, Ranibizumab, Panitumumab, ispinesib; g). A poly (ADP-ribose) polymerase (PARP) inhibitors, such as olaparib, niraparib, iniparib, talazoparib, veliparib, veliparib, CEP 9722 (Cephalon's), E7016 (Eisai's), BGB-290 (BeiGene's), 3-aminobenzamide.

h). antibiotics, such as the enediyne antibiotics (e.g. calicheamicins, especially calicheamicin yl, 61, al and p01, see, e.g., J. Med. Chem., 39 (11), 2103-2117 (1996), Angew Chem Intl. Ed. Engl. 33:183-186 (1994); dynemicin, including dynemicin A and deoxydynemicin; esperamicin, kedarcidin, C-1027, maduropeptin, as well as neocarzinostatin chromophore and related chromoprotein enediyne antibiotic chromomophores), aclacinomycin, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin and deoxydoxorubicin, epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; i). Others: such as Polyketides (acetogenins), especially bullatacin and bullatacinone; gemcitabine, epoxomicins (e. g. carfilzomib), bortezomib, thalidomide, lenalidomide, pomalidomide, tosedostat, zybrestat, $PLX_{4032}$, STA-9090, Stimuvax, allovectin-7, Xegeva, Provenge, Yervoy, Isoprenylation inhibitors (such as Lovastatin), Dopaminergic neurotoxins (such as 1-methyl-4-phenylpyridinium ion), Cell cycle inhibitors (such as staurosporine), Actinomycins (such as Actinomycin D, dactinomycin), Bleomycins (such as bleomycin A2, bleomycin B2, peplomycin), Anthracyclines (such as daunorubicin, doxorubicin (adriamycin), idarubicin, epirubicin, pirarubicin, zorubicin, mtoxantrone, MDR inhibitors (such as verapamil), $Ca^{2+}$ ATPase inhibitors (such as thapsigargin), Histone deacetylase inhibitors (Vorinostat, Romidepsin, Panobinostat, Valproic acid, Mocetinostat (MGCD0103), Belinostat, PCI-24781, Entinostat, SB939, Resminostat, Givinostat, AR-42, CUDC-101, sulforaphane, Trichostatin A); Thapsigargin, Celecoxib, glitazones, epigallocatechin gallate, Disulfiram, Salinosporamide A.; Anti-adrenals, such as aminoglutethimide, mitotane, trilostane; aceglatone; aldophosphamide glycoside; aminolevulinic acid; amsacrine; arabinoside, bestrabucil; bisantrene; edatraxate; defofamine; demecolcine; diaziquone; eflornithine (DFMO), elfomithine; elliptinium acetate, etoglucid; gallium nitrate; gacytosine, hydroxyurea; ibandronate, lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verrucarin A, roridin A and anguidine); urethane, siRNA, antisense drugs, and a nucleolytic enzyme.

2). An anti-autoimmune disease agent includes, but is not limited to, cyclosporine, cyclosporine A, aminocaproic acid, azathioprine, bromocriptine, chlorambucil, chloroquine, cyclophosphamide, corticosteroids (e.g. amcinonide, betamethasone, budesonide, hydrocortisone, flunisolide, fluticasone propionate, fluocortolone danazol, dexamethasone, Triamcinolone acetonide, beclometasone dipropionate), DHEA, enanercept, hydroxychloroquine, infliximab, meloxicam, methotrexate, mofetil, mycophenylate, prednisone, sirolimus, tacrolimus.

3). An anti-infectious disease agent includes, but is not limited to, a). Aminoglycosides: amikacin, astromicin, gentamicin (netilmicin, sisomicin, isepamicin), hygromycin B, kanamycin (amikacin, arbekacin, bekanamycin, dibekacin, tobramycin), neomycin (framycetin, paromomycin, ribostamycin), netilmicin, spectinomycin, streptomycin, tobramycin, verdamicin; b). Amphenicols: azidamfenicol, chloramphenicol, florfenicol, thiamphenicol; c). Ansamycins: geldanamycin, herbimycin; d). Carbapenems: biapenem, doripenem, ertapenem, imipenem/cilastatin, meropenem, panipenem; e). Cephems: carbacephem (loracarbef), cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cefbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpimizole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cephamycin (cefoxitin, cefotetan, cefmetazole), oxacephem (flomoxef, latamoxef); f). Glycopeptides: bleomycin, vancomycin (oritavancin, telavancin), teicoplanin (dalbavancin), ramoplanin; g). Glycylcyclines: e. g. tigecycline; g). β-Lactamase inhibitors: penam (sulbactam, tazobactam), clavam (clavulanic acid); i). Lincosamides: clindamycin, lincomycin; j). Lipopeptides: daptomycin, A54145, calcium-dependent antibiotics (CDA); k). Macrolides: azithromycin, cethromycin, clarithromycin, dirithromycin, erythromycin, flurithromycin, josamycin, ketolide (telithromycin, cethromycin), midecamycin, miocamycin, oleandomycin, rifamycins (rifampicin, rifampin, rifabutin, rifapentine), rokitamycin, roxithromycin, spectinomycin, spiramycin, tacrolimus (FK506), troleandomycin, telithromycin; 1). Monobactams: aztreonam, tigemonam; m). Oxazolidinones: linezolid; n). Penicillins: amoxicillin, ampicillin (pivampicillin, hetacillin, bacampicillin, metampicillin, talampicillin), azidocillin, azlocillin, benzylpenicillin, benzathine benzylpenicillin, benzathine phenoxymethyl-penicillin, clometocillin, procaine benzylpenicillin, carbenicillin (carindacillin), cloxacillin, dicloxacillin, epicillin, flucloxacillin, mecillinam (pivmecillinam), mezlocillin, meticillin, nafcillin, oxacillin, penamecillin, penicillin, pheneticillin, phenoxymethylpenicillin, piperacillin, propicillin, sulbenicillin, temocillin, ticarcillin; o). Polypeptides: bacitracin, colistin, polymyxin B; p). Quinolones: alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacin, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, trovafloxacin; q). Streptogramins: pristinamycin, quinupristin/dalfopristin); r). Sulfonamides: mafenide, prontosil, sulfacetamide, sulfamethizole, sulfanilimide, sulfasalazine, sulfisoxazole, trimethoprim, trimethoprim-sulfamethoxazole (co-trimoxazole); s). Steroid antibacterials: e.g. fusidic acid; t). Tetracyclines: doxycycline, chlortetracycline, clomocycline, demeclocycline, lymecycline, meclocycline, metacycline, minocycline, oxytetracycline, penimepicycline, rolitetracycline, tetracycline, glycylcyclines (e.g. tigecycline); u). Other types of antibiotics: annonacin, arsphenamine, bactoprenol inhibitors (Bacitracin), DADAL/AR inhibitors (cycloserine), dictyostatin, discodermolide, eleutherobin, epothilone, ethambutol, etoposide, faropenem, fusidic acid, furazolidone, isoniazid, laulimalide, metronidazole, mupirocin, mycolactone, NAM synthesis inhibitors (e. g. fosfomycin), nitrofurantoin, paclitaxel, platensimycin, pyrazinamide, quinupristin/dalfopristin, rifampicin (rifampin), tazobactam tinidazole, uvaricin;

4). Anti-viral drugs: a). Entry/fusion inhibitors: aplaviroc, maraviroc, vicriviroc, gp41 (enfuvirtide), PRO 140, CD4 (ibalizumab); b). Integrase inhibitors: raltegravir, elvitegravir, globoidnan A; c). Maturation inhibitors: bevirimat, vivecon; d). Neuraminidase inhibitors: oseltamivir, zanamivir, peramivir; e). Nucleosides & nucleotides: abacavir, aciclovir, adefovir, amdoxovir, apricitabine, brivudine, cidofovir, clevudine, dexelvucitabine, didanosine (ddI), elvucitabine, emtricitabine (FTC), entecavir, famciclovir, fluorouracil (5-FU), 3'-fluoro-substituted 2', 3'-dideoxynucleoside analogues (e.g. 3'-fluoro-2',3'-dideoxythymidine (FLT) and 3'-fluoro-2',3'-dideoxyguanosine (FLG), fomivirsen, ganciclovir, idoxuridine, lamivudine (3TC), 1-nucleosides (e.g. β-1-thymidine and β-1-2'-deoxycytidine), penciclovir, racivir, ribavirin, stampidine, stavudine (d4T), taribavirin (viramidine), telbivudine, tenofovir, trifluridine valaciclovir, valganciclovir, zalcitabine (ddC), zidovudine (AZT); f). Non-nucleosides: amantadine, ateviridine, capravirine, diarylpyrimidines (etravirine, rilpivirine), delavirdine, docosanol, emivirine, efavirenz, foscarnet (phosphonoformic acid), imiquimod, interferon alfa, loviride, lodenosine, methisazone, nevirapine, NOV-205, peginterferon alfa, podophyllotoxin, rifampicin, rimantadine, resiquimod (R-848), tromantadine; g). Protease inhibitors: amprenavir, atazanavir, boceprevir, darunavir, fosamprenavir, indinavir, lopinavir, nelfinavir, pleconaril, ritonavir, saquinavir, telaprevir (VX-950), tipranavir; h). Other types of anti-virus drugs: abzyme, arbidol, calanolide a, ceragenin, cyanovirin-n, diarylpyrimidines, epigallocatechin gallate (EGCG), foscarnet, griffithsin, taribavirin (viramidine), hydroxyurea, KP-1461, miltefosine, pleconaril, portmanteau inhibitors, ribavirin, seliciclib.

5). The drugs used for conjugates via a bridge linker of the present invention also include radioisotopes. Examples of radioisotopes (radionuclides) are $^{3}H$, $^{11}C$, $^{14}C$, $^{18}F$, $^{32}P$, $^{35}S$, $^{64}Cu$, $^{68}Ga$, $^{86}Y$ $^{99}Tc$, $^{111}In$, $^{123}I$, $^{124}I$, $^{125}I$, $^{131}I$, $^{133}Xe$, $^{177}Lu$, $^{211}At$, or $^{213}Bi$. Radioisotope labeled antibodies are useful in receptor targeted imaging experiments or can be for targeted treatment such as with the antibody-drug conjugates of the invention (Wu et al (2005) Nature Biotechnology 23(9): 1137-46). The cell binding molecules, e.g. an antibody can be labeled with ligand reagents through the bridge linkers of the present patent that bind, chelate or otherwise complex a radioisotope metal, using the techniques described in Current Protocols in Immunology, Volumes 1 and 2, Coligen et al, Ed. Wiley-Interscience, New York, Pubs. (1991). Chelating ligands which may complex a metal ion include DOTA, DOTP, DOTMA, DTPA and TETA (Macrocyclics, Dallas, Tex. USA).

6). The pharmaceutically acceptable salts, acids or derivatives of any of the above drugs.

In another embodiment, the drug in the Formula (II) and/or (IV) can be a chromophore molecule, for which the conjugate can be used for detection, monitoring, or study the interaction of the cell binding molecule with a target cell. Chromophore molecules are a compound that have the ability to absorb a kind of light, such as UV light, florescent light, IR light, near IR light, visual light; A chromatophore molecule includes a class or subclass of xanthophores, erythrophores, iridophores, leucophores, melanophores, and cyanophores; a class or subclass of fluorophore molecules which are fluorescent chemical compounds re-emitting light upon light; a class or subclass of visual phototransduction molecules; a class or subclass of photophore molecules; a class or subclass of luminescence molecules; and a class or subclass of luciferin compounds.

The chromophore molecule can be selected from, but not limited, non-protein organic fluorophores, such as: Xanthene derivatives (fluorescein, rhodamine, Oregon green, eosin, and Texas red); Cyanine derivatives: (cyanine, indocarbocyanine, oxacarbocyanine, thiacarbocyanine, and merocyanine); Squaraine derivatives and ring-substituted squaraines, including Seta, SeTau, and Square dyes; Naphthalene derivatives (dansyl and prodan derivatives); Coumarin derivatives; Oxadiazole derivatives (pyridyloxazole, nitrobenzoxadiazole and benzoxadiazole); Anthracene derivatives (anthraquinones, including DRAQ5, DRAQ7 and CyTRAK Orange); Pyrene derivatives (cascade blue, etc); Oxazine derivatives (Nile red, Nile blue, cresyl violet, oxazine 170 etc). Acridine derivatives (proflavin, acridine orange, acridine yellow etc). Arylmethine derivatives (auramine, crystal violet, malachite green). Tetrapyrrole derivatives (porphin, phthalocyanine, bilirubin).

Or a chromophore molecule can be selected from any analogs and derivatives of the following fluorophore compounds: CF dye (Biotium), DRAQ and CyTRAK probes (BioStatus), BODIPY (Invitrogen), Alexa Fluor (Invitrogen), DyLight Fluor (Thermo Scientific, Pierce), Atto and Tracy (Sigma Aldrich), FluoProbes (Interchim), Abberior Dyes (Abberior), DY and MegaStokes Dyes (Dyomics), Sulfo Cy dyes (Cyandye), HiLyte Fluor (AnaSpec), Seta, SeTau and Square Dyes (SETA BioMedicals), Quasar and Cal Fluor dyes (Biosearch Technologies), SureLight Dyes (APC, RPEPerCP, Phycobilisomes)(Columbia Biosciences), APC, APCXL, RPE, BPE (Phyco-Biotech).

Examples of the widely used fluorophore compounds which are reactive or conjugatable with the linkers of the invention are: Allophycocyanin (APC), Aminocoumarin, APC-Cy7 conjugates, BODIPY-FL, Cascade Blue, Cy2, Cy3, Cy3.5, Cy3B, Cy5, Cy5.5, Cy7, Fluorescein, FluorX, Hydroxycoumarin, IR-783, Lissamine Rhodamine B, Lucifer yellow, Methoxycoumarin, NBD, Pacific Blue, Pacific Orange, PE-Cy5 conjugates, PE-Cy7 conjugates, PerCP, R-Phycoerythrin (PE), Red 613, Seta-555-Azide, Seta-555-DBCO, Seta-555-NHS, Seta-580-NHS, Seta-680-NHS, Seta-780-NHS, Seta-APC-780, Seta-PerCP-680, Seta-R-PE-670, SeTau-380-NHS, SeTau-405-Maleimide, SeTau-405-NHS, SeTau-425-NHS, SeTau-647-NHS, Texas Red, TRITC, TruRed, X-Rhodamine.

The fluorophore compounds that can be linked to the linkers of the invention for study of nucleic acids or proteins are selected from the following compounds or their derivatives: 7-AAD (7-aminoactinomycin D, CG-selective), Acridine Orange, Chromomycin A3, CyTRAK Orange (Biostatus, red excitation dark), DAPI, DRAQ5, DRAQ7, Ethidium Bromide, Hoechst33258, Hoechst33342, LDS 751, Mithramycin, PropidiumIodide (PI), SYTOX Blue, SYTOX Green, SYTOX Orange, Thiazole Orange, TO-PRO: Cyanine Monomer, TOTO-1, TO-PRO-1, TOTO-3, TO-PRO-3, YOSeta-1, YOYO-1. The fluorophore compounds that can be linked to the linkers of the invention for study cells are selected from the following compounds or their derivatives: DCFH (2'7'Dichorodihydro-fluorescein, oxidized form), DHR (Dihydrorhodamine 123, oxidized form, light catalyzes oxidation), Fluo-3 (AM ester. pH >6), Fluo-4 (AM ester. pH 7.2), Indo-1 (AM ester, low/high calcium (Ca2+)), and SNARF (pH 6/9). The preferred fluorophore compounds that can be linked to the linkers of the invention for study proteins/antibodies are selected from the following compounds or their derivatives: Allophycocyanin (APC), AmCyanl (tetramer, Clontech), AsRed2 (tetramer, Clontech), Azami Green (monomer, MBL), Azurite, B-phycoerythrin (BPE), Cerulean, CyPet, DsRed monomer (Clontech), DsRed2 ("RFP", Clontech), EBFP, EBFP2, ECFP, EGFP (weak dimer, Clontech), Emerald (weak dimer, Invitrogen), EYFP (weak dimer, Clontech), GFP (S65A mutation), GFP (S65C mutation), GFP (S65L mutation), GFP (S65T mutation), GFP (Y66F mutation), GFP (Y66H mutation), GFP (Y66W mutation), GFPuv, HcRedl, J-Red, Katusha, Kusabira Orange (monomer, MBL), mCFP, mCherry, mCitrine, Midoriishi Cyan (dimer, MBL), mKate (TagFP635, monomer, Evrogen), mKeima-Red (monomer, MBL), mKO, mOrange, mPlum, mRaspberry, mRFP1 (monomer, Tsien lab), mStrawberry, mTFP1, mTurquoise2, P3 (phycobilisome complex), Peridinin Chlorophyll (PerCP), R-phycoerythrin (RPE), T-Sapphire, TagCFP (dimer, Evrogen), TagGFP (dimer, Evrogen), TagRFP (dimer, Evrogen), TagYFP (dimer, Evrogen), tdTomato (tandem dimer), Topaz, TurboFP602 (dimer, Evrogen), TurboFP635 (dimer, Evrogen), TurboGFP (dimer, Evrogen), TurboRFP (dimer, Evrogen), TurboYFP (dimer, Evrogen), Venus, Wild Type GFP, YPet, ZsGreen1 (tetramer, Clontech), ZsYellowl (tetramer, Clontech).

The examples of the structure of the conjugates of the antibody-chromophore molecules via the bridge linker are as following Ac01, Ac02, Ac03, Ac04, Ac05, Ac06, Ac07, Ac08 and Ac09:

Ac01

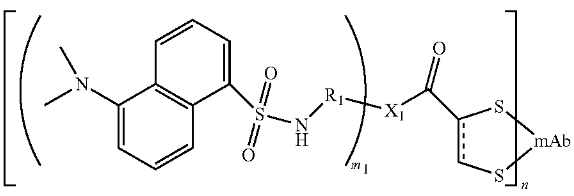

Ac02

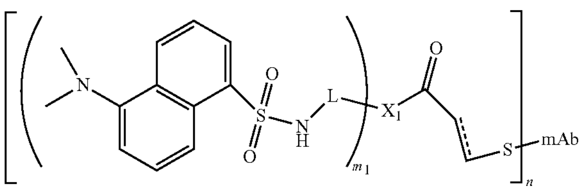

Ac03

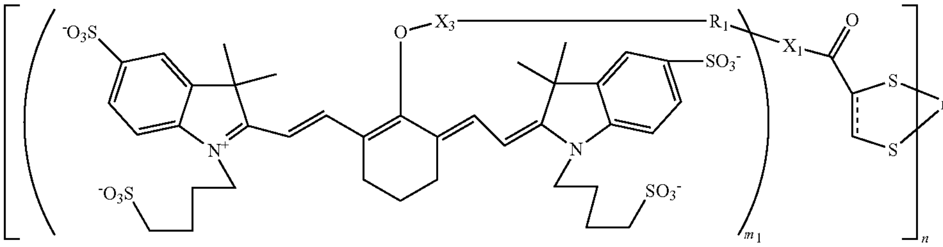

Ac04

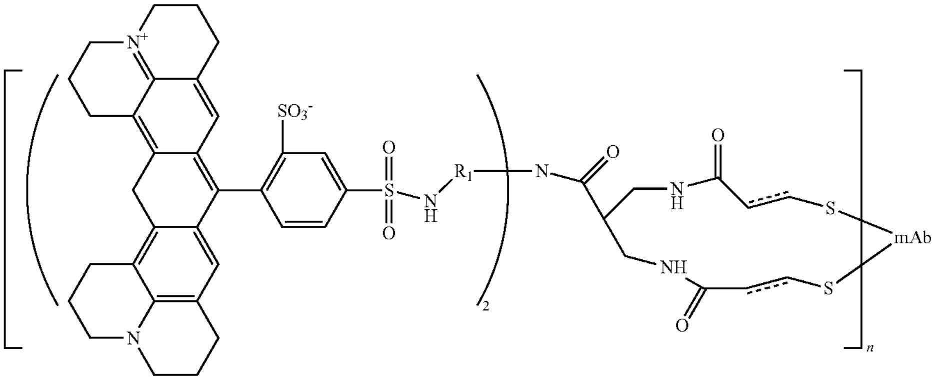

-continued
Ac05
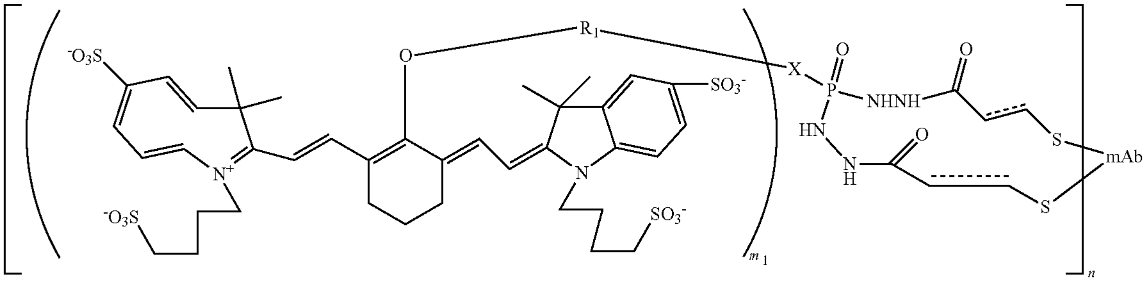
(FNIR-774 conjugate)
Ac06
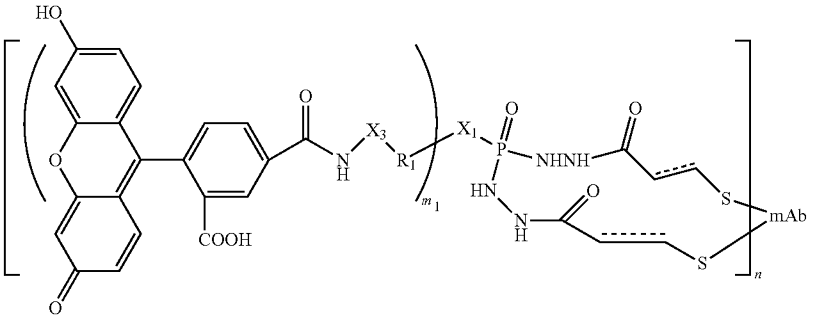
Ac07
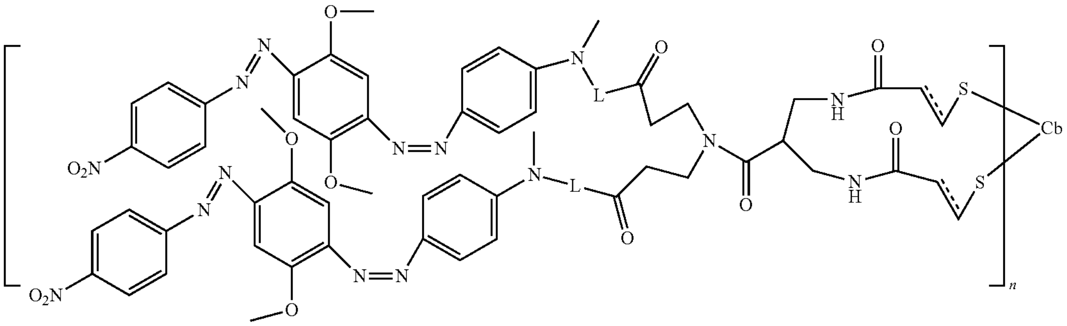
Ac08
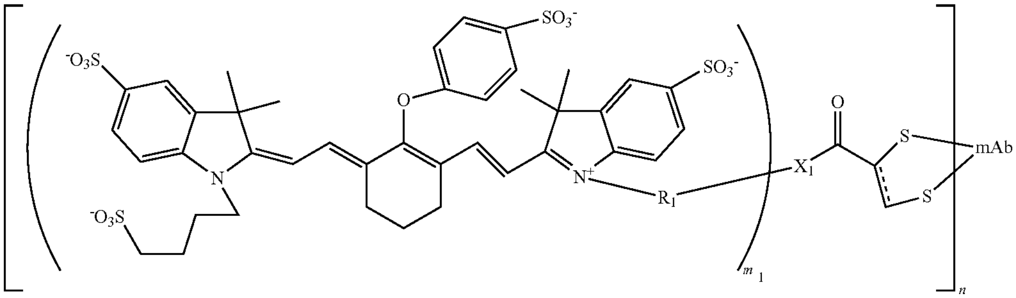
(IR800CW conjugate)

-continued

Ac09

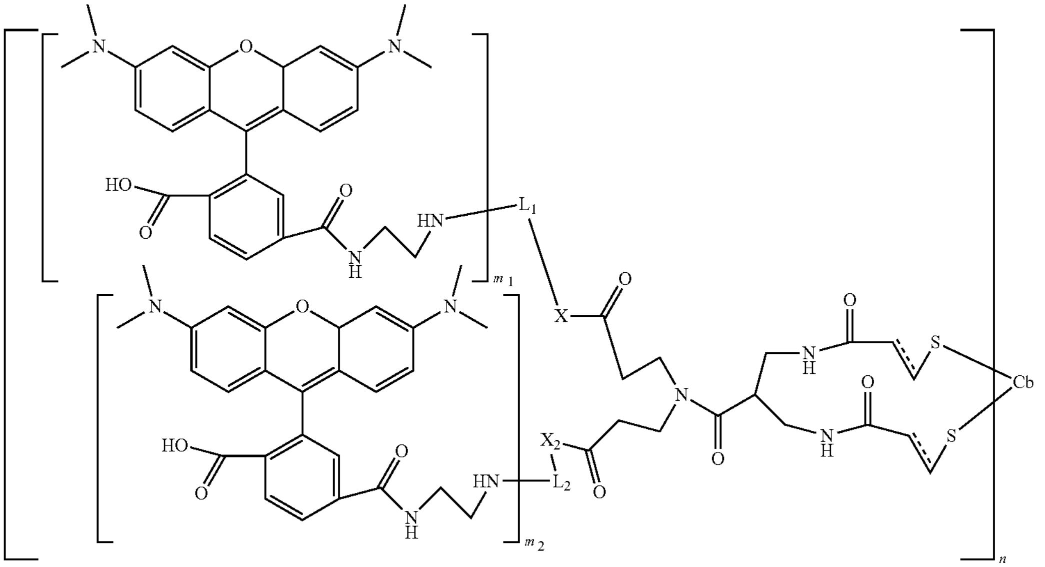

Wherein "═" represents either single bond or double bond; mAb is antibody, preferably monoclonal antibody; n, $m_1$, $m_2$, $X_1$, $X_2$, $X_3$, $R_1$, $R_2$ $R_3$, $L_1$, $L_2$, and L are the same defined in Formula (I) and (II).

In another embodiment, the drug in the Formula (II) and (IV) can be polyalkylene glycols that are used for extending the half-life of the cell-binding molecule when administered to a mammal. Polyalkcylene glycols include, but are not limited to, poly(ethylene glycols) (PEGs), poly(propylene glycol) and copolymers of ethylene oxide and propylene oxide; particularly preferred are PEGs, and more particularly preferred are monofunctionally activated hydroxyPEGs (e.g., hydroxyl PEGs activated at a single terminus, including reactive esters of hydroxyPEG-monocarboxylic acids, hydroxyPEG-monoaldehydes, hydroxyPEG-monoamines, hydroxyPEG-monohydrazides, hydroxyPEG-monocarbazates, hydroxyl PEG-monoiodoacetamides, hydroxyl PEG-monomaleimides, hydroxyl PEG-monoorthopyridyl disulfides, hydroxyPEG-monooximes, hydroxyPEG-monophenyl carbonates, hydroxyl PEG-monophenyl glyoxals, hydroxyl PEG-monothiazolidine-2-thiones, hydroxyl PEG-monothioesters, hydroxyl PEG-monothiols, hydroxyl PEG-monotriazines and hydroxyl PEG-monovinylsulfones).

In certain such embodiments, the polyalkylene glycol has a molecular weight of from about 10 Daltons to about 200 kDa, preferably about 88 Da to about 40 kDa; two branches each with a molecular weight of about 88 Da to about 40 kDa; and more preferably two branches, each of about 88 Da to about 20 kDa. In one particular embodiment, the polyalkylene glycol is poly(ethylene) glycol and has a molecular weight of about 10 kDa; about 20 kDa, or about 40 kDa. In specific embodiments, the PEG is a PEG 10 kDa (linear or branched), a PEG 20 kDa (linear or branched), or a PEG 40 kDa (linear or branched). A number of US patents have disclosed the preparation of linear or branched "non-antigenic" PEG polymers and derivatives or conjugates thereof, e.g., U.S. Pat. Nos. 5,428,128; 5,621,039; 5,622,986; 5,643,575; 5,728,560; 5,730,990; 5,738,846; 5,811,076; 5,824,701; 5,840,900; 5,880,131; 5,900,402; 5,902,588; 5,919,455; 5,951,974; 5,965,119; 5,965,566; 5,969,040; 5,981,709; 6,011,042; 6,042,822; 6,113,906; 6,127,355; 6,132,713; 6,177,087, and 6,180,095. The structure of the conjugates of the antibody-polyalkylene glycols via the bridge linker is as following Pg01, Pg02, Pg03, Pg04, Pg05, Pg06, and Pg07:

Pg01

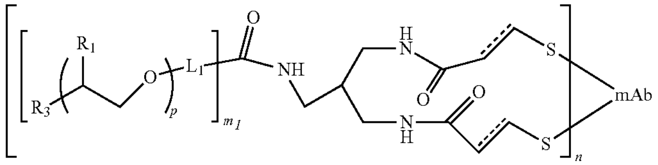

Pg02

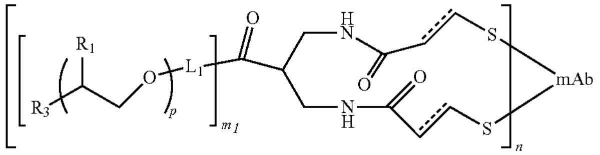

-continued

Pg03

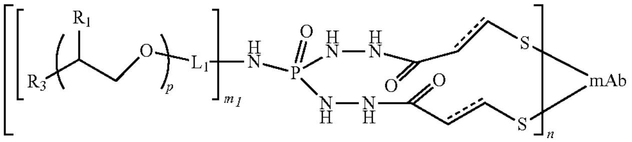

Pg04

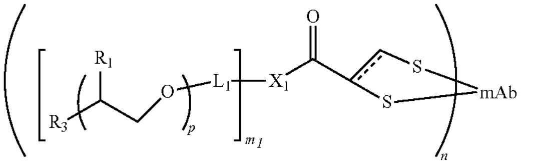

Pg05

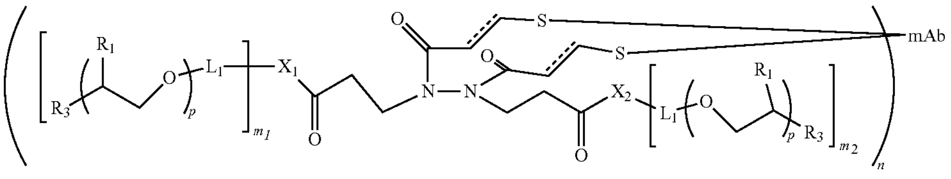

Pg06

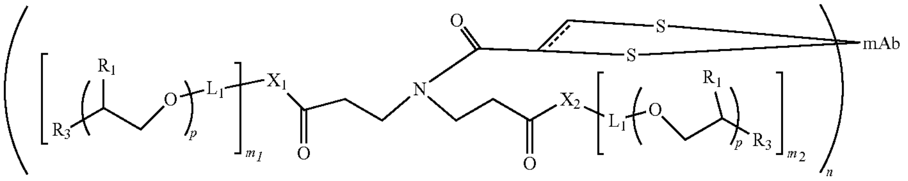

Pg07

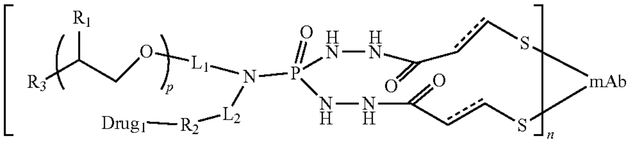

wherein mAb is an antibody; R' is H or $CH_3$; $m_3$ is an integer from ito 5000; $R_3$ is OH, H, or $R_1$; "⎓" represents either single bond or double bond; $m_1$, $m_2$, n, $L_1$, $L_2$, $X_1$, $X_2$, $R_1$, $R_2$, and $R_3$ are the same defined in Formula (I) and (II). In addition, $R_1$ and $R_3$ can be H, OH, $OCH_3$ or $OC_2H_5$ independently; p is 1-2000; Drug1 is defined the same in Formula (III).

In yet another embodiment, the preferred cytotoxic agents that conjugated to a cell-binding molecule via a bridge linker of this patent are tubulysins, maytansinoids, taxanoids (taxanes), CC-1065 analogs, daunorubicin and doxorubicin compounds, amatoxins, benzodiazepine dimers (e.g., dimers of pyrrolobenzodiazepine (PBD), tomaymycin, anthramycin, indolinobenzodiazepines, imidazobenzothiadiazepines, or oxazolidinobenzodiazepines), calicheamicins and the enediyne antibiotics, actinomycin, azaserines, bleomycins, epirubicin, tamoxifen, idarubicin, dolastatins, auristatins (e.g. monomethyl auristatin E, MMAE, MMAF, auristatin PYE, auristatin TP, Auristatins 2-AQ, 6-AQ, EB (AEB), and EFP (AEFP)), duocarmycins, geldanamycins, methotrexates, thiotepa, vindesines, vincristines, hemiasterlins, nazumamides, microginins, radiosumins, alterobactins, microsclerodermins, theonellamides, esperamicins, PNU-159682, and their analogues and derivatives above thereof.

Tubulysins that are preferred for conjugation in the present invention are well known in the art and can be isolated from natural sources according to known methods or prepared synthetically according to known methods (e. g. Balasubramanian, R., et al. J. Med. Chem., 2009, 52, 238-40; Wipf, P., et al. Org. Lett., 2004, 6, 4057-60; Pando, O., et al. J. Am. Chem. Soc., 2011, 133, 7692-5; Reddy, J. A., et al. Mol. Pharmaceutics, 2009, 6, 1518-25; Raghavan, B., et al. J. Med. Chem., 2008, 51, 1530-33; Patterson, A. W., et al. J. Org. Chem., 2008, 73, 4362-9; Pando, O., et al. Org. Lett., 2009, 11 (24), 5567-9; Wipf, P., et al. Org. Lett., 2007, 9 (8), 1605-7; Friestad, G. K., Org. Lett., 2004, 6, 3249-52; Peltier, H. M., et al. J. Am. Chem. Soc., 2006, 128, 16018-9; Chandrasekhar, S., et al J. Org. Chem., 2009, 74, 9531-4; Liu, Y., et al. Mol. Pharmaceutics, 2012, 9, 168-75; Friestad, G. K., et al. Org. Lett., 2009, 11, 1095-8; Kubicek, K., et al., Angew Chem Int Ed Engl, 2010.49: 4809-12; Chai, Y., et al., Chem Biol, 2010, 17: 296-309; Ullrich, A., et al., Angew Chem Int Ed Engl, 2009, 48, 4422-5; Sani, M., et al. Angew Chem Int Ed Engl, 2007, 46, 3526-9; Domling, A., et al., Angew Chem Int Ed Engl, 2006, 45, 7235-9; Patent applications: Zanda, M., et al, Can. Pat. Appl. CA 2710693 (2011); Chai, Y., et al. Eur. Pat. Appl. 2174947 (2010), WO 2010034724; Leamon, C. et al, WO2010033733, WO 2009002993; Ellman, J., et al, PCT WO2009134279; WO 2009012958, US appl. 20110263650, 20110021568; Matschiner, G., et al, WO2009095447; Vlahov, I., et al, WO2009055562, WO 2008112873; Low, P., et al, WO2009026177; Richter, W., WO2008138561; Kjems, J., et al, WO 2008125116; Davis, M.; et al, WO2008076333; Diener, J.; et al, U.S. Pat. Appl. 20070041901, WO2006096754; Matschiner, G., et al, WO2006056464; Vaghefi, F., et al, WO2006033913; Doemling, A., Ger. Offen. DE102004030227, WO2004005327, WO2004005326, WO2004005269; Stanton, M., et al, U.S. Pat. Appl. Publ. 20040249130; Hoefle, G., et al, Ger. Offen. DE10254439, DE10241152, DE10008089; Leung, D., et al, WO2002077036; Reichenbach, H., et al, Ger. Offen. DE19638870; Wolfgang, R., US20120129779; Chen, H., US appl. 20110027274. The preferred structures of tubulysins for conjugation of cell binding molecules are described in the patent application of PCT/IB2012/053554.

Examples of the structures of the conjugates of the antibody-tubulysin analogs via the linker of the patent are TO1, T02, T03, T04, T05, T06 T07, T08, T09, T10, and T11 as following:

T01

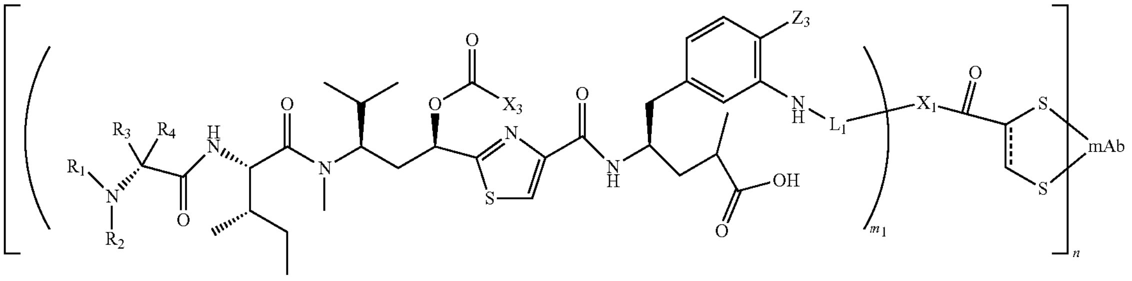

T02

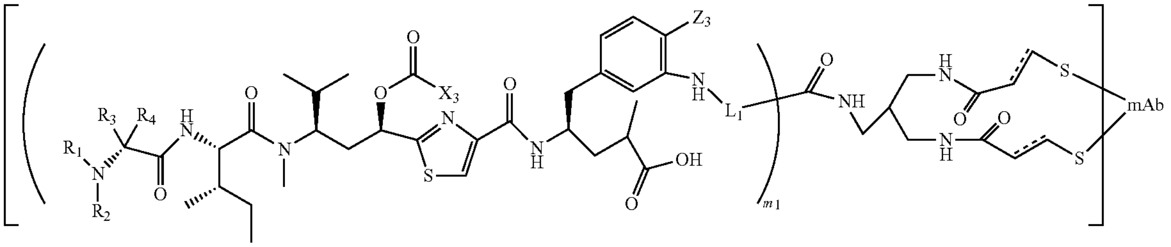

T03

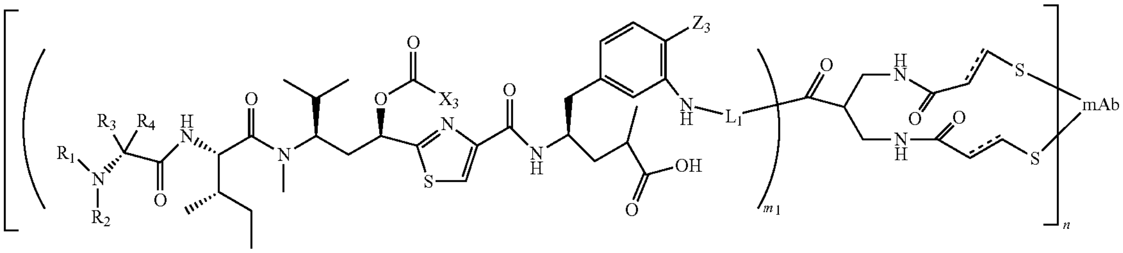

T04

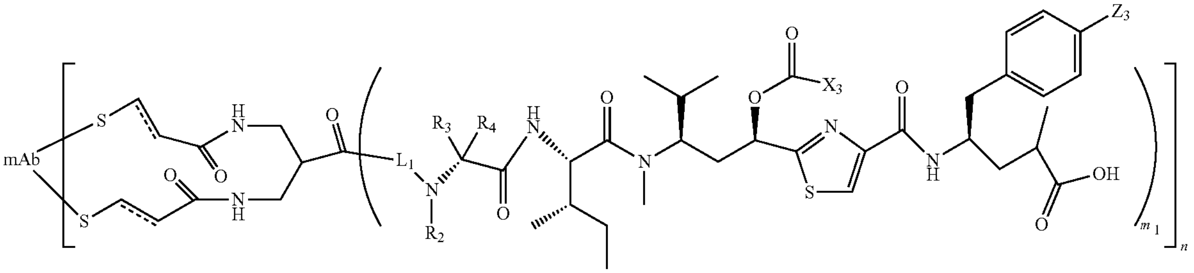

T05

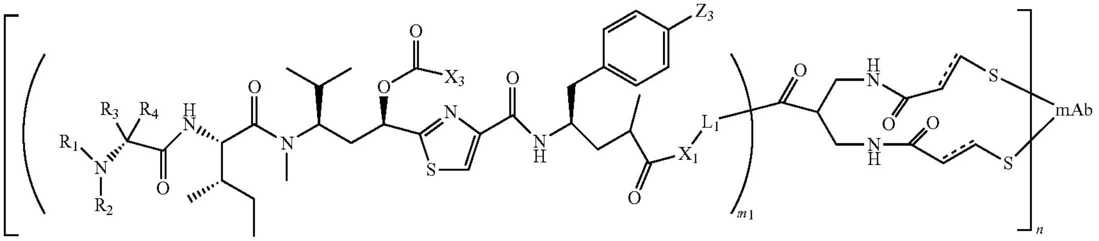

-continued
T06
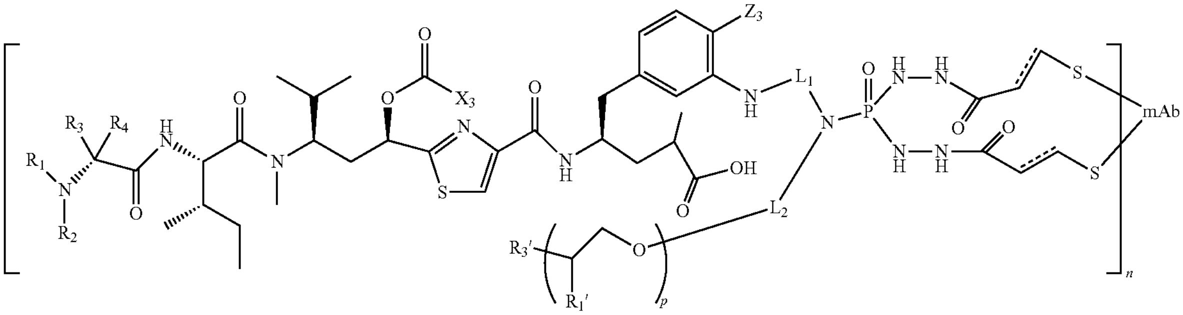
T07
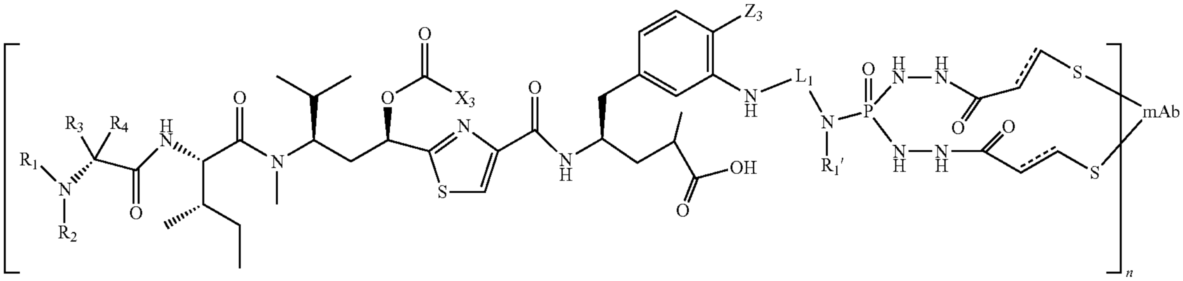
T08
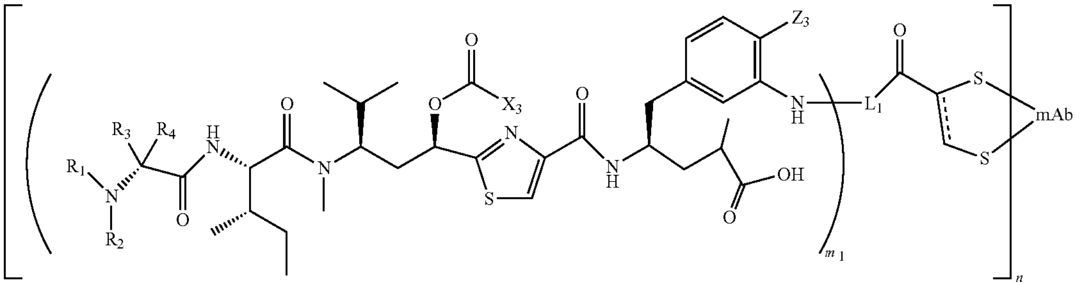
T09
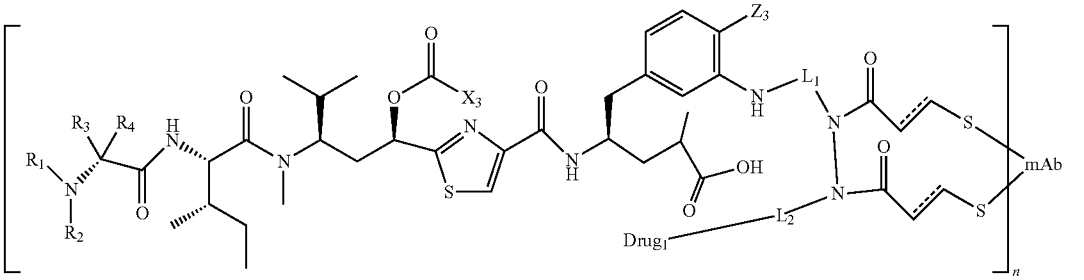
T10
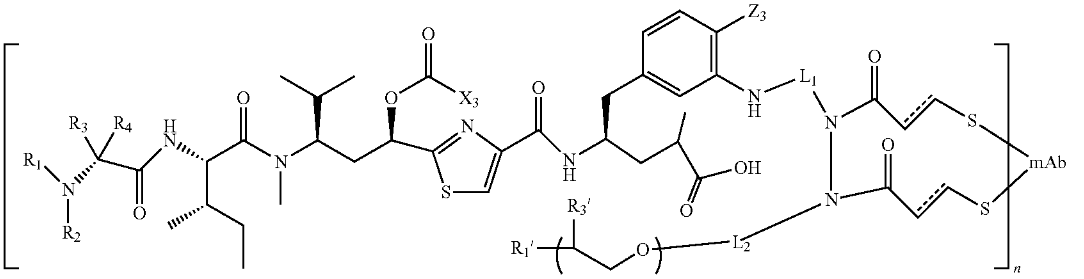

-continued
T11
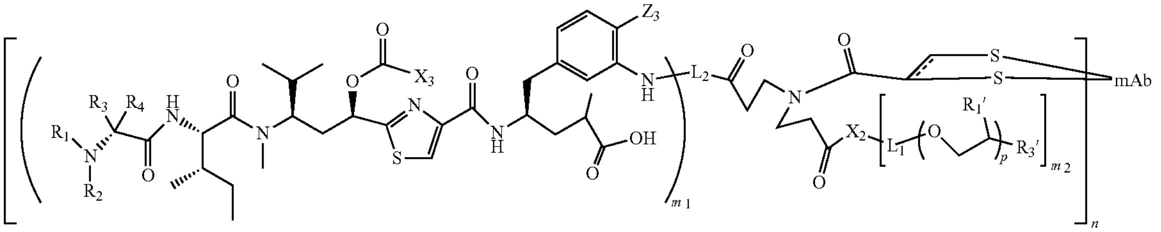
T12
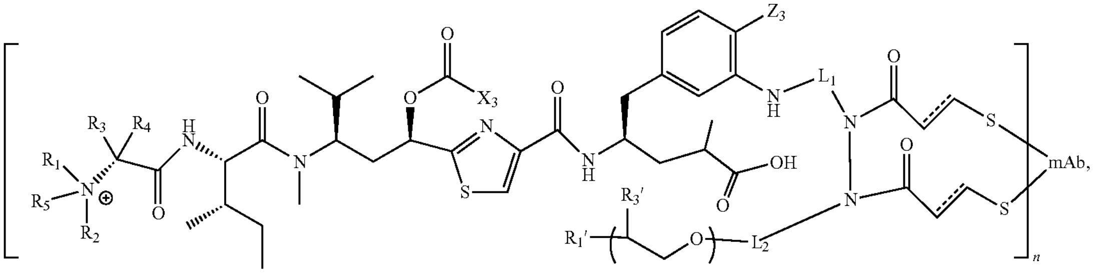
T13
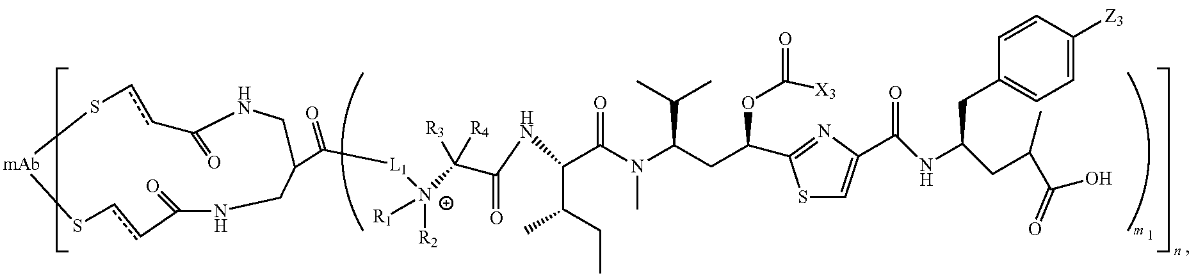
T14
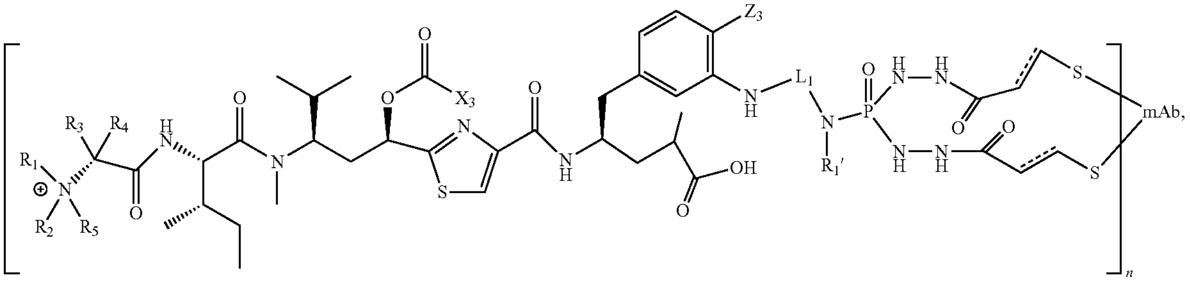
T15
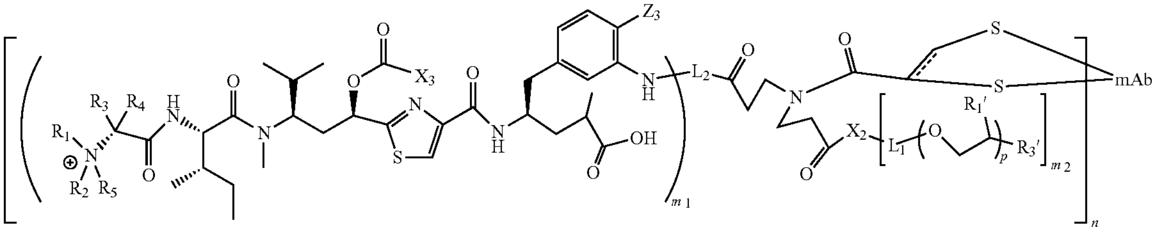
T16
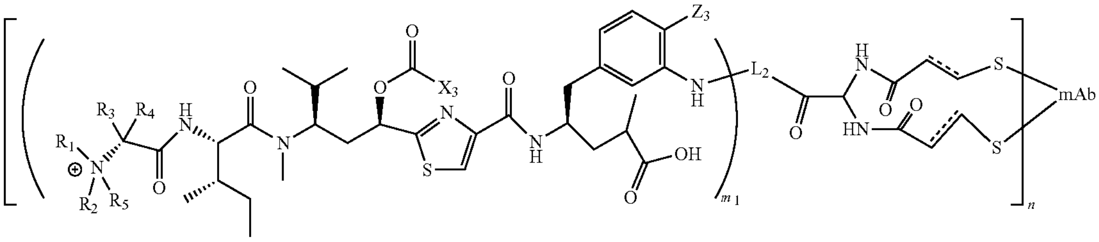

-continued

T17

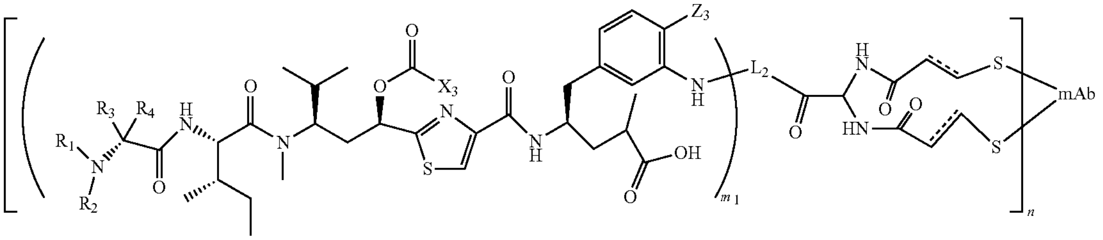

T18

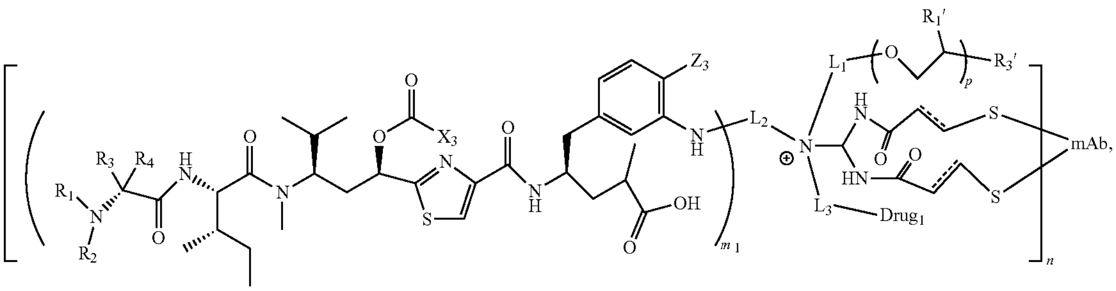

wherein mAb is an antibody, or a cell-binding molecule; n, $m_1$, $m_2$, $Drug_1$, $X_1$, $X_2$, $L_1$, $L_2$, $L_3$, $R_1$, $R_2$, $R_3$, $R_4$, and $R_5$ are the same defined in Formula (I) and (II); preferably, $R_1$, $R_2$, $R_3$, and $R_4$ are independently H, $C_1$-$C_8$ of lineal or branched alkyl, aryl, heteroaryl, heteroalkyl, alkylcycloalkyl, ester, ether, amide, amines, heterocycloalkyl, or acyloxylamines; or peptides containing 1-8 aminoacids, or polyethyleneoxy unit of formula $(OCH_2CH_2)_p$ or $(OCH_2CH(CH_3))_p$, wherein p is an integer from 1 to about 2000. The two Rs: R1$R_2$, R2$R_3$, $R_1R_3$ or R3$R_4$ can form 3-8 member cyclic ring of alkyl, aryl, heteroaryl, heteroalkyl, or alkylcycloalkyl group; $X_3$ is H, $CH_3$ or $X_1$'$R_1$', wherein $X_{1'}$ is NH, $N(CH_3)$, NHNH, O, or S, and $R_{1'}$ is H or $C_1$-$C_8$ lineal or branched alkyl, aryl, heteroaryl, heteroalkyl, alkylcycloalkyl, acyloxylamines; $R_{3'}$ is H or $C_1$-$C_6$ lineal or branched alkyl; p is 0-2000; Z3 is H, OH, $OP(O)(OM_1)(OM_2)$, $OCH_2OP(O)(OM_1)(OM_2)$, $OSO_3M_1$, $R_1$, or O-glycoside (glucoside, galactoside, mannoside, glucuronoside/glucuronide, alloside, fructoside, etc), NH-glycoside, S-glycoside or $CH_2$-glycoside; "$\overset{\cdots}{=}$" represents either single bond or double bond; $M_1$ and $M_2$ are independently H, Na, K, Ca, Mg, $NH_4$, $NR_1R_2R_3$; In addition, $R_{1'}$ can be a cytotoxic agent, which is described through the patent.

Calicheamicins and their related enediyne antibiotics that are preferred for cell-binding molecule-drug conjugates of this patent are described in: Nicolaou, K. C. et al, Science 1992, 256, 1172-1178; Proc. Natl. Acad. Sci USA. 1993, 90, 5881-8), U.S. Pat. Nos. 4,970,198; 5,053,394; 5,108,912; 5,264,586; 5,384,412; 5,606,040; 5,712,374; 5,714,586; 5,739,116; 5,770,701; 5,770,710; 5,773,001; 5,877,296; 6,015,562; 6,124,310; 8,153,768. Examples of the structure of the conjugate of the antibody-Calicheamicin analog via the bridge linker are C01 and C02 as the following:

C01

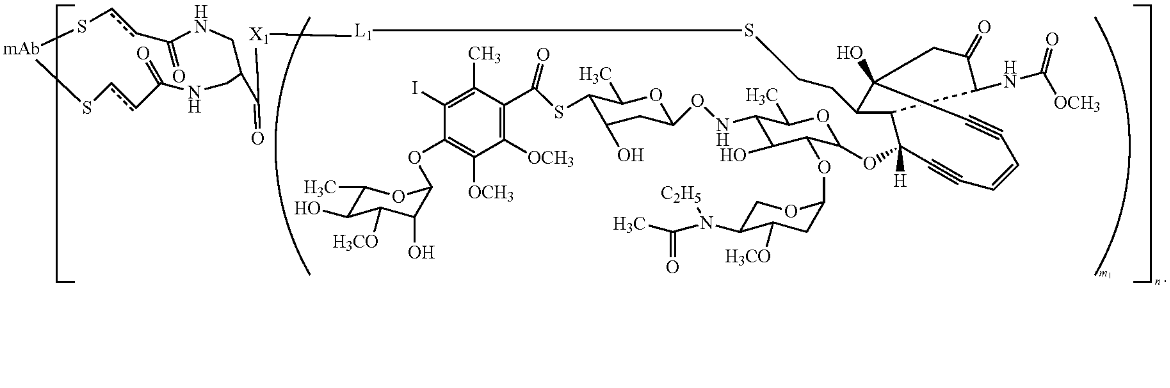

-continued

C02

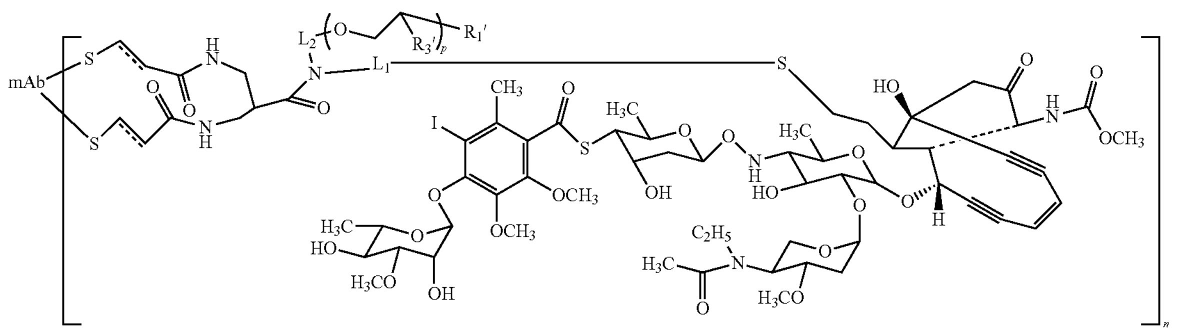

wherein mAb is an antibody or a cell-binding molecule; “$\overset{\cdots}{=}$”, n, $m_1$, $X_1$, $L_1$, $L_2$, and $R_1$ are defined the same in Formula (I) and (II); $R_{1'}$ and $R_{3'}$ are independently H or $C_1$-$C_6$ of lineal or branched alkyl; p is 0-2000. In addition, $R_{1'}$ can be a cytotoxic agent, Drug, which is described through the patent.

Maytansinoids that are preferred to be used in the present invention including maytansinol and its analogues are described in U.S. Pat. Nos. 4,256,746, 4,361,650, 4,307,016, 4,294,757, 4,294,757, 4,371,533, 4,424,219, 4,331,598, 4,450,254, 4,364,866, 4,313,946, 4,315,929 4,362,663, 4,322,348, 4,371,533, 4,424,219, 5,208,020, 5,416,064, 5,208,020; 5,416,064; 6,333,410; 6,441,163; 6,716,821, 7,276,497, 7,301,019, 7,303,749, 7,368,565, 7,411,063, 7,851,432, and 8,163,888. An example of the structure of the conjugate of the antibody-Maytansinoids via the linker of the patent is as the following My01, My02 and My03:

My01

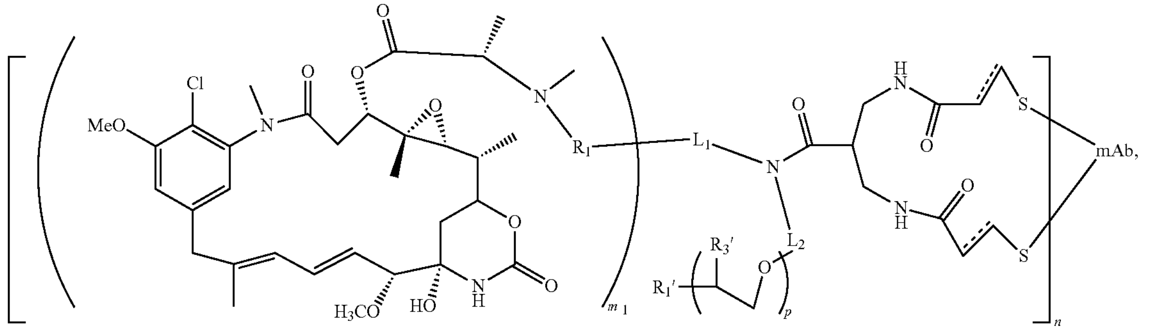

My02

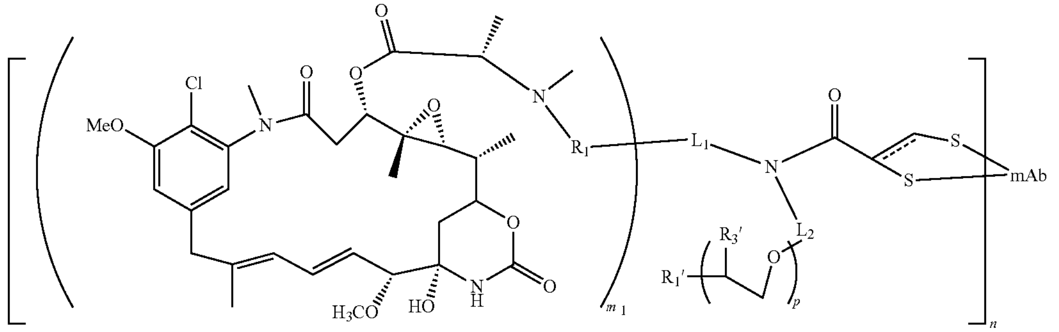

-continued

My03

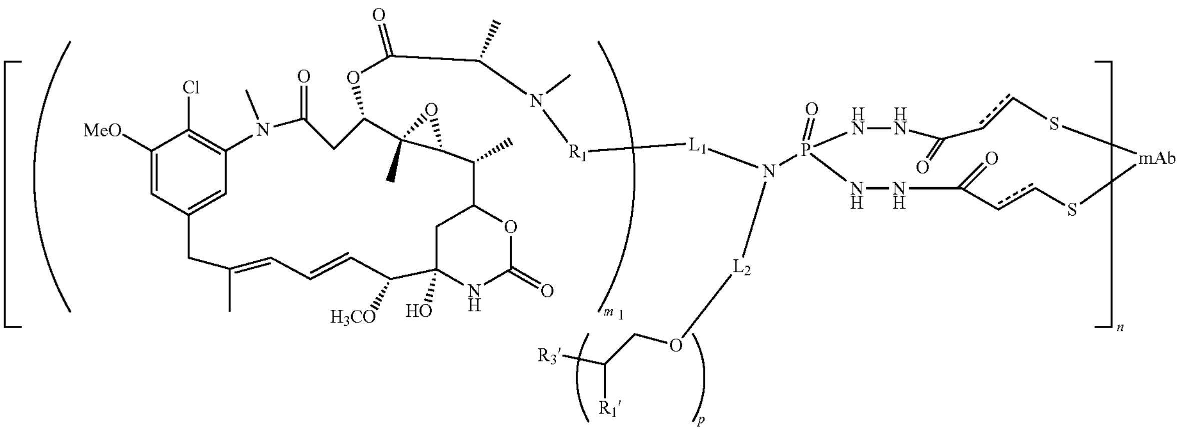

Wherein mAb is an antibody or a cell-binding molecule; "═", n, $m_1$, $X_1$, $L_1$, $L_2$, and $R_1$ are the same defined in Formula (I) and (II); $R_{1'}$ and $R_{3'}$ are independently H or $C_1$-$C_6$ lineal or branched alkyl; p is 0-2000. In addition, $R_{1'}$ can be a cytotoxic agent, $Drug_1$, which is described through the patent.

Taxanes, which include Paclitaxel (Taxol), a cytotoxic natural product, and docetaxel (Taxotere), a semi-synthetic derivative, and their analogs which are preferred for conjugation via the bridge linkers of the present patent are exampled in: K C. Nicolaou et al., J. Am. Chem. Soc. 117, 2409-20, (1995); Ojima et al, J. Med. Chem. 39:3889-3896 (1996); 40:267-78 (1997); 45, 5620-3 (2002); Ojima et al., Proc. Natl. Acad. Sci., 96:4256-61 (1999); Kim et al., Bull. Korean Chem. Soc., 20, 1389-90 (1999); Miller, et al. J. Med. Chem., 47, 4802-5(2004); U.S. Pat. No. 5,475,011 5,728,849, 5,811,452; 6,340,701; 6,372,738; 6,391,913, 6,436,931; 6,589,979; 6,596,757; 6,706,708; 7,008,942; 7,186,851; 7,217,819; 7,276,499; 7,598,290; and 7,667,054.

Examples of the structures of the conjugate of the antibody-taxanes via the linker of the patent are as the following Tx01, Tx02 and Tx03.

Tx01

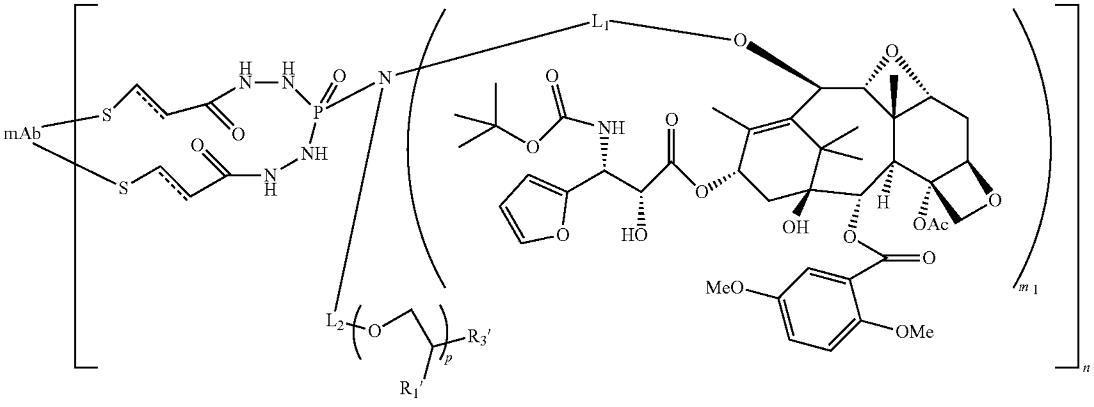

Tx02

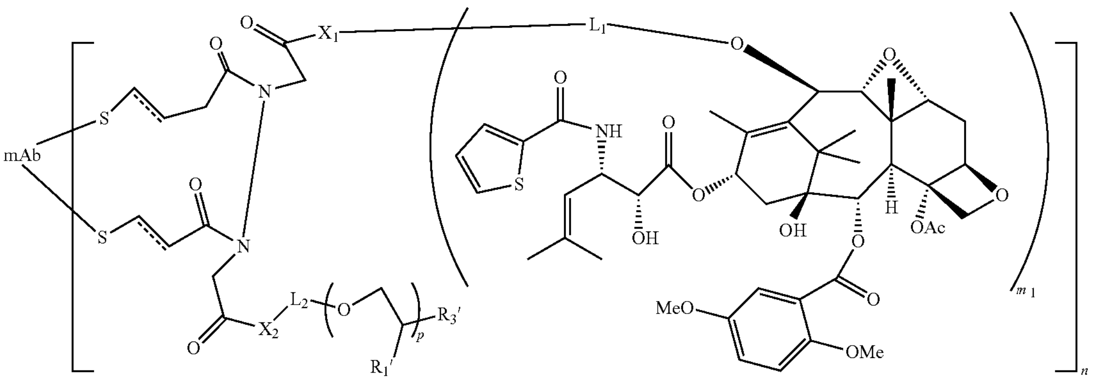

-continued

Tx03

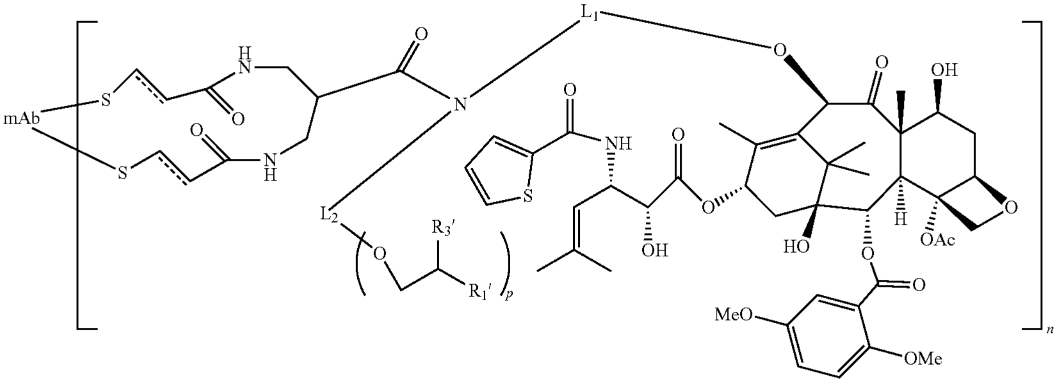

Wherein mAb is an antibody or a cell-binding molecule; "$\equiv$" represents either single bond or double bond; n, $m_1$, $X_1$, $L_1$, $L_2$, and $R_1$ are the same defined in Formula (I) and (II); $R_{1'}$ and $R_{3'}$ are independently H or $C_1$-$C_6$ lineal or branched alkyl; p is 0-2000; In addition, $R_{1'}$ can be a cytotoxic agent, $Drug_1$, which is described through the patent.

CC-1065 analogues and duocarmycin analogs are also preferred to be used for a conjugate with the bridge linkers of the present patent. The examples of the CC-1065 analogues and duocarmycin analogs as well as their synthesis are described in: e.g. Warpehoski, et al, J. Med. Chem. 31:590-603 (1988); D. Boger et al., J. Org. Chem; 66; 6654-61, 2001; U.S. Pat. Nos. 4,169,888, 4,391,904, 4,671, 958, 4,816,567, 4,912,227, 4,923,990, 4,952,394, 4,975,278, 4,978,757, 4,994,578, 5,037,993, 5,070,092, 5,084,468, 5,101,038, 5,117,006, 5,137,877, 5,138,059, 5,147,786, 5,187,186, 5,223,409, 5,225,539, 5,288,514, 5,324,483, 5,332,740, 5,332,837, 5,334,528, 5,403,484, 5,427,908, 5,475,092, 5,495,009, 5,530,101, 5,545,806, 5,547,667, 5,569,825, 5,571,698, 5,573,922, 5,580,717, 5,585,089, 5,585,499, 5,587,161, 5,595,499, 5,606,017, 5,622,929, 5,625,126, 5,629,430, 5,633,425, 5,641,780, 5,660,829, 5,661,016, 5,686,237, 5,693,762, 5,703,080, 5,712,374, 5,714,586, 5,739,116, 5,739,350, 5,770,429, 5,773,001, 5,773,435, 5,786,377 5,786,486, 5,789,650, 5,814,318, 5,846,545, 5,874,299, 5,877,296, 5,877,397, 5,885,793, 5,939,598, 5,962,216, 5,969,108, 5,985,908, 6,060,608, 6,066,742, 6,075,181, 6,103,236, 6,114,598, 6,130,237, 6,132,722, 6,143,901, 6,150,584, 6,162,963, 6,172,197, 6,180,370, 6,194,612, 6,214,345, 6,262,271, 6,281,354, 6,310,209, 6,329,497, 6,342,480, 6,486,326, 6,512,101, 6,521,404, 6,534,660, 6,544,731, 6,548,530, 6,555,313, 6,555,693, 6,566,336, 6,586,618, 6,593,081, 6,630,579, 6,756,397, 6,759,509, 6,762,179, 6,884,869, 6,897,034, 6,946,455, 7,049,316, 7,087,600, 7,091,186, 7,115,573, 7,129,261, 7,214,663, 7,223,837, 7,304,032, 7,329,507, 7,329,760, 7,388,026, 7,655,660, 7,655,661, 7,906,545, and 8,012,978. Examples of the structures of the conjugate of the antibody-CC-1065 analogs via the linker of the patent are as the following CC01, CC02, and CC03.

CC01

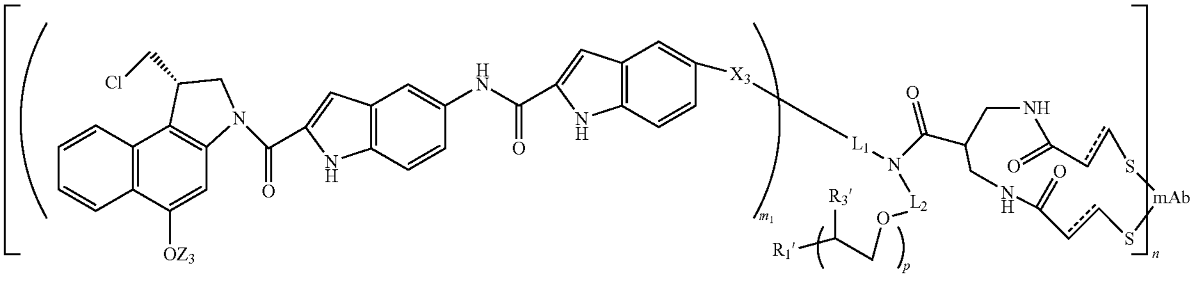

-continued

CC02

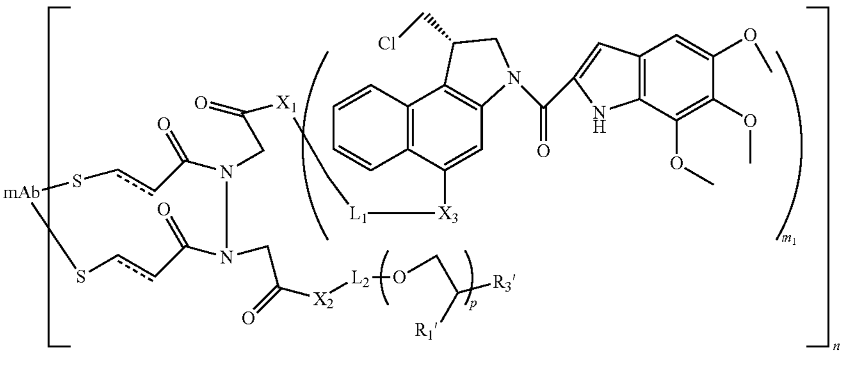

CC03

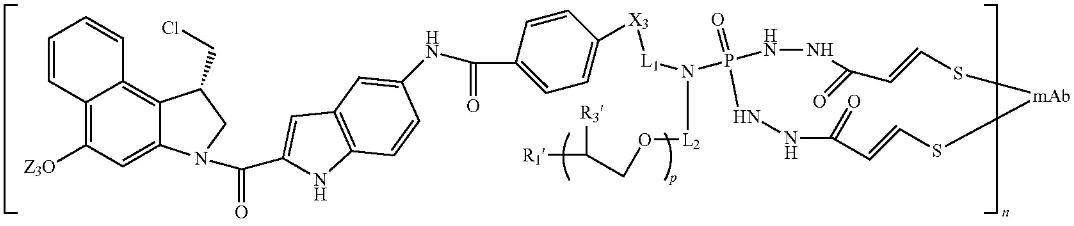

Wherein mAb is an antibody; $Z_3$ is H, $PO(OM_1)(OM_2)$, $SO_3M_1$, $CH_2PO(OM_1)(OM_2)$, $CH_3N(CH_2CH_2)_2NC(O)$—, $O(CH_2CH_2)_2NC(O)$—, $R_1$, or glycoside; $X_3$ is O, NH, NHC(O), OC(O), —C(O)O, $R_1$, or absent; "⎓" represents either single bond or double bond; n, $m_1$, $m_2$, "—", $X_1$, $X_2$, $R_1$, $R_2$, are the same defined in Formula (I) and (II); $R_{1'}$ and $R_{3'}$ are independently H or $C_1$-$C_6$ lineal or branched alkyl; p is 0-2000. In addition, $R_{1'}$ can be a cytotoxic agent, $Drug_1$, which is described through the patent.

Daunorubicin/Doxorubicin Analogues are also preferred for conjugation via the bridge linkers of the present patent. The preferred structures and their synthesis are exampled in: Hurwitz, E., et al., Cancer Res. 35, 1175-81 (1975). Yang, H. M., and Reisfeld, R. A., Proc. Natl. Acad. Sci. 85, 1189-93 (1988); Pietersz, C. A., E., et al., E., et al., "Cancer Res. 48, 926-311 (1988); Trouet, et al., 79, 626-29 (1982); Z. Brich et al., J. Controlled Release, 19, 245-58 (1992); Chen et al., Syn. Comm., 33, 2377-90, 2003; King et al., Bioconj. Chem., 10, 279-88, 1999; King et al., J. Med. Chem., 45, 4336-43, 2002; Kratz et al., J Med Chem. 45, 5523-33, 2002; Kratz et al., Biol Pharm Bull. January 21, 56-61, 1998; Lau et al., Bioorg. Med. Chem. 3, 1305-12, 1995; Scott et al., Bioorg. Med. Chem. Lett. 6, 1491-6, 1996; Watanabe et al., Tokai J. Experimental Clin. Med. 15, 327-34, 1990; Zhou et al., J. Am. Chem. Soc. 126, 15656-7, 2004; WO 01/38318; U.S. Pat. Nos. 5,106,951; 5,122,368; 5,146,064; 5,177,016; 5,208,323; 5,824,805; 6,146,658; 6,214,345; 7,569,358; 7,803,903; 8,084,586; 8,053,205. Examples of the structures of the conjugate of the antibody-CC-1065 analogs via the linker of the patent are as the following Da01, Da02, Da03 and Da04.

Da01

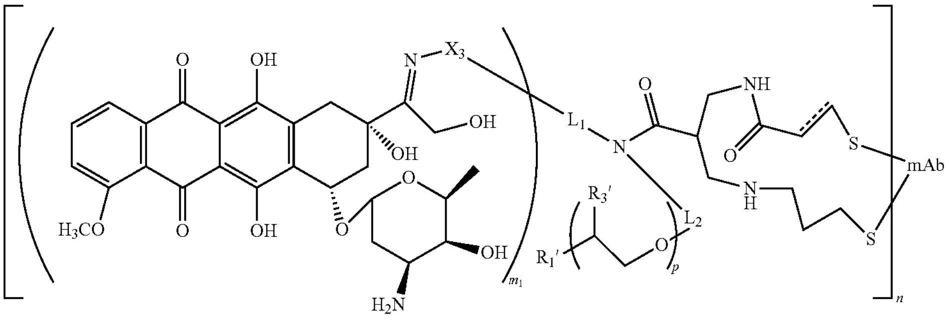

-continued

Da02

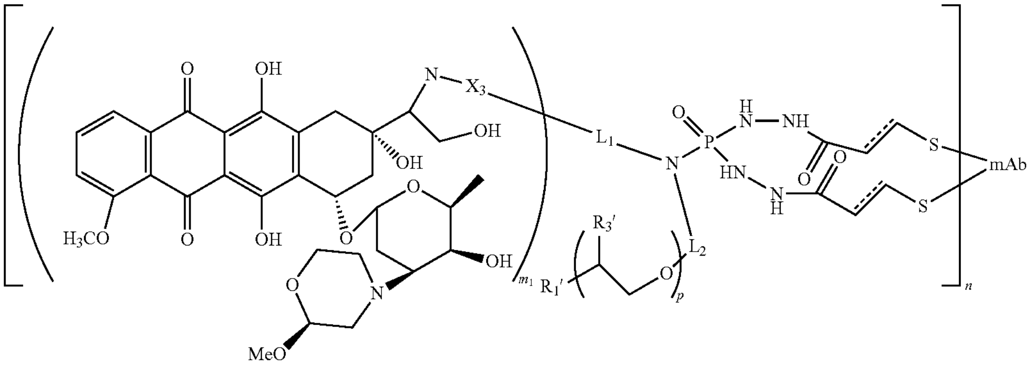

Da03

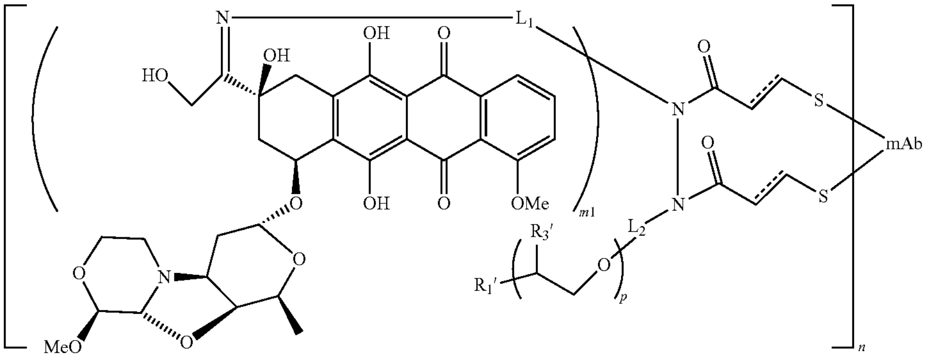

Da04

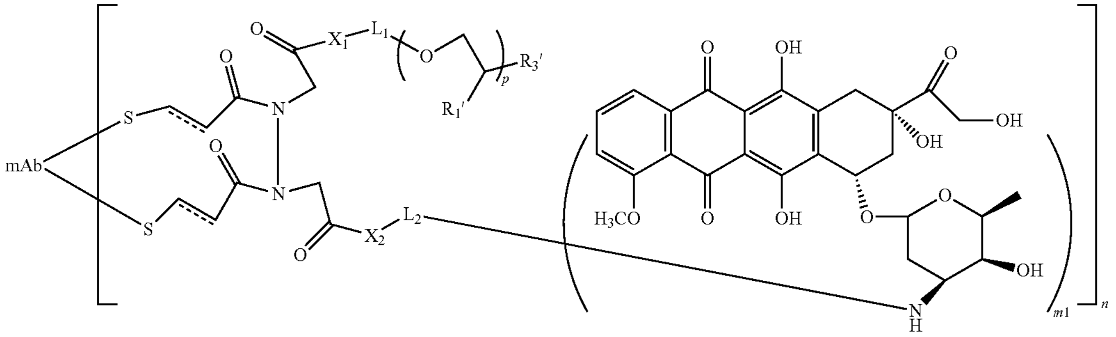

wherein mAb is an antibody or a cell-binding molecule; "⎓" represents either single bond or double bond; n, $m_1$, $X_1$, $X_2$, $L_1$, $L_2$, and $R_1$ are the same defined in Formula (I) and (II); $R_{1'}$ and $R_{3'}$ are independently H or $C_1$-$C_6$ lineal or branched alkyl; p is 0-2000. In addition, $R_{1'}$ can be a cytotoxic agent, $Drug_1$, which is described through the patent.

Auristatins and dolastatins are preferred in conjugation via the bridge linkers of this patent. The auristatins (e.g. auristatin E (AE) auristatin EB (AEB), auristatin EFP (AEFP), monomethyl auristatin E (MMAE), Monomethyl-auristatin (MMAF), Auristatin F phenylene diamine (AFP) and a phenylalanine variant of MMAE) which are synthetic analogs of dolastatins, are described in Int. J. Oncol. 15: 367-72 (1999); Molecular Cancer Therapeutics, vol. 3, No. 8, pp. 921-32 (2004); U.S. Application Nos. 11134826, 20060074008, 2006022925. U.S. Pat. Nos. 4,414,205, 4,753,894, 4,764,368, 4,816,444, 4,879,278, 4,943,628, 4,978,744, 5,122,368, 5,165,923, 5,169,774, 5,286,637, 5,410,024, 5,521,284, 5,530,097, 5,554,725, 5,585,089, 5,599,902, 5,629,197, 5,635,483, 5,654,399, 5,663,149, 5,665,860, 5,708,146, 5,714,586, 5,741,892, 5,767,236, 5,767,237, 5,780,588, 5,821,337, 5,840,699, 5,965,537, 6,004,934, 6,033,876, 6,034,065, 6,048,720, 6,054,297, 6,054,561, 6,124,431, 6,143,721, 6,162,930, 6,214,345, 6,239,104, 6,323,315, 6,342,219, 6,342,221, 6,407,213, 6,569,834, 6,620,911, 6,639,055, 6,884,869, 6,913,748, 7,090,843, 7,091,186, 7,097,840, 7,098,305, 7,098,308, 7,498,298, 7,375,078, 7,462,352, 7,553,816, 7,659,241, 7,662,387, 7,745,394, 7,754,681, 7,829,531, 7,837,980, 7,837,995, 7,902,338, 7,964,566, 7,964,567, 7,851,437, 7,994,135. Examples of the structures of the conjugate of the antibody-auristatins via the linker of the patent are as the following Au01, Au02, Au03, Au04, Au05, Au06, Au07, Au08, Au09, Au10, Aul 1, Au12 and Au13

Au01
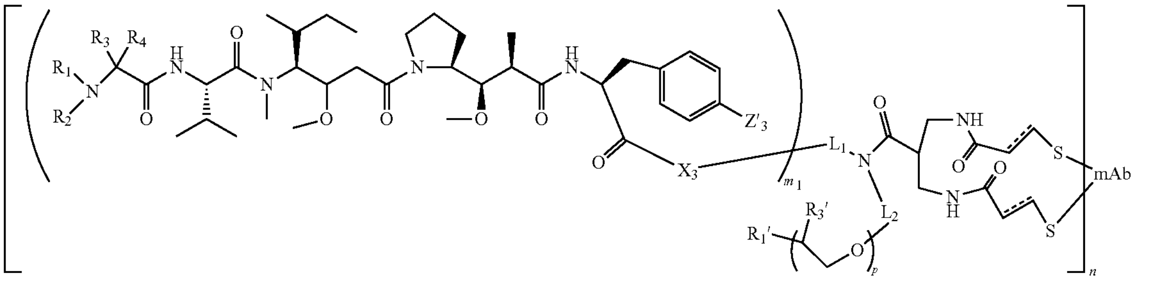
Au02
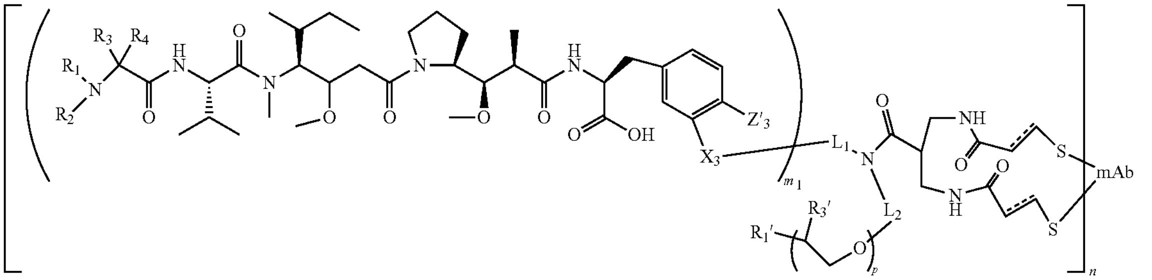
Au03
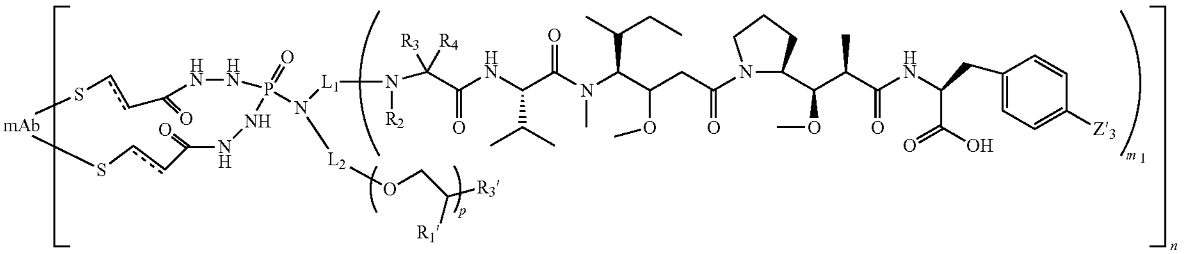
Au04
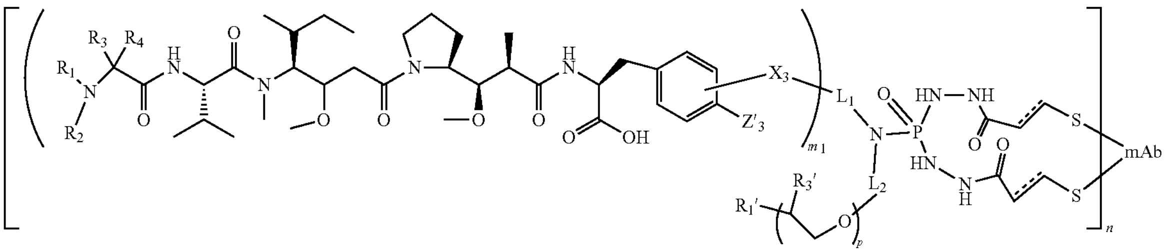
Au05
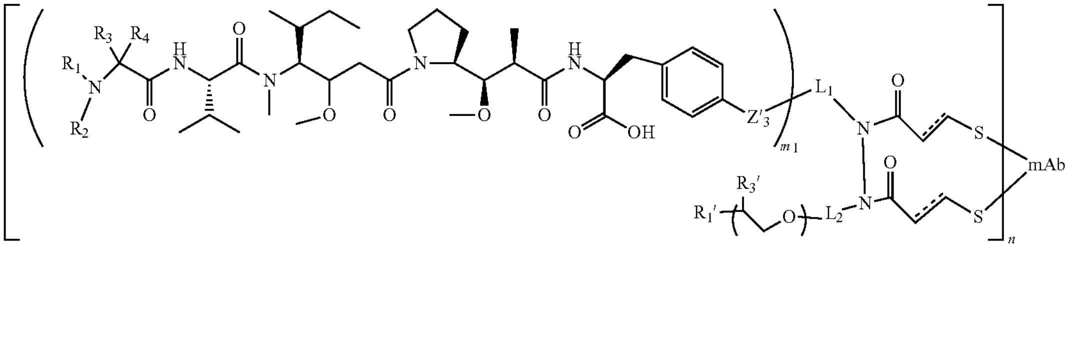

-continued
Au06
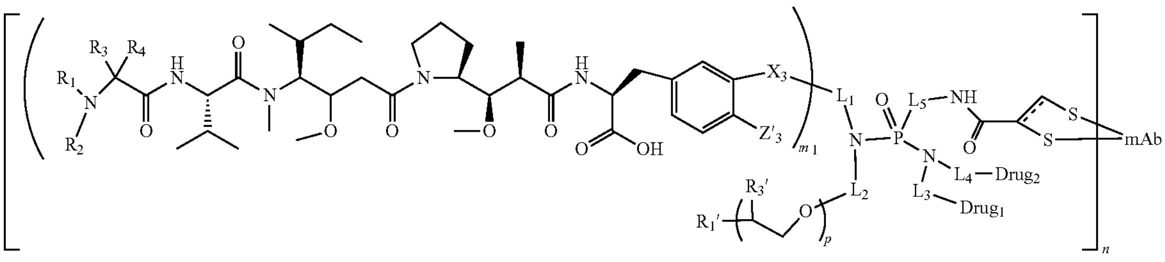
Au07
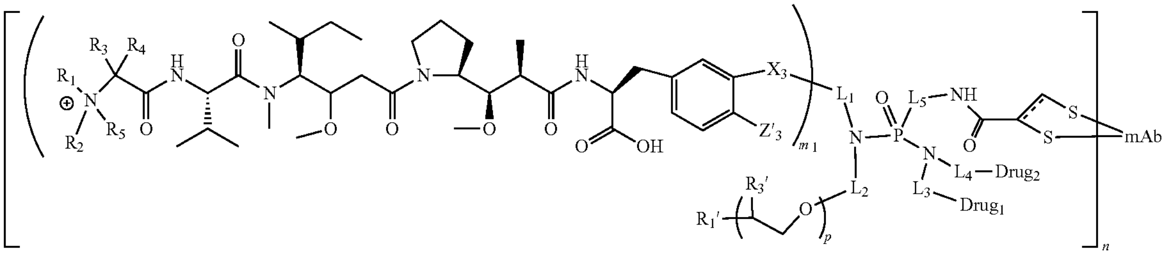
Au08
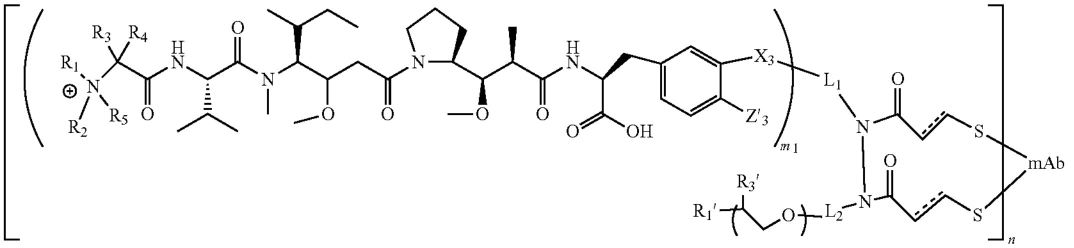
Au09
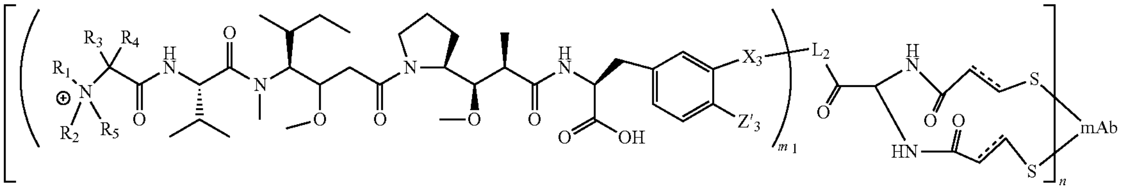
Au10
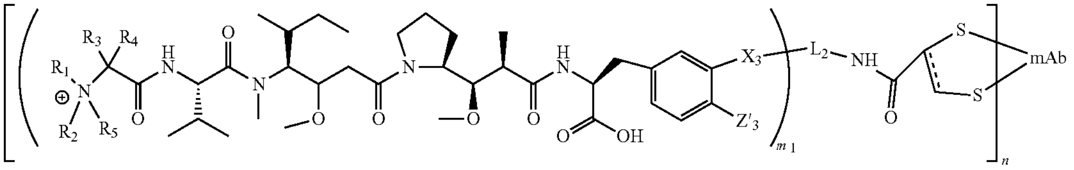
Au11
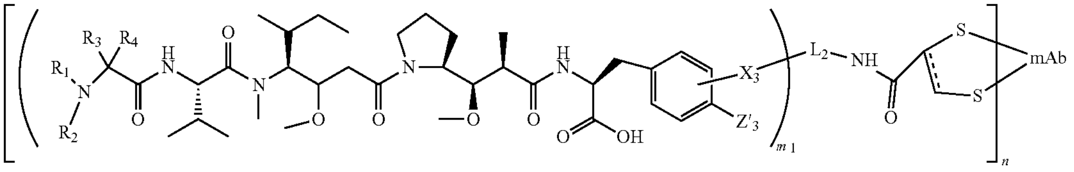
Au12
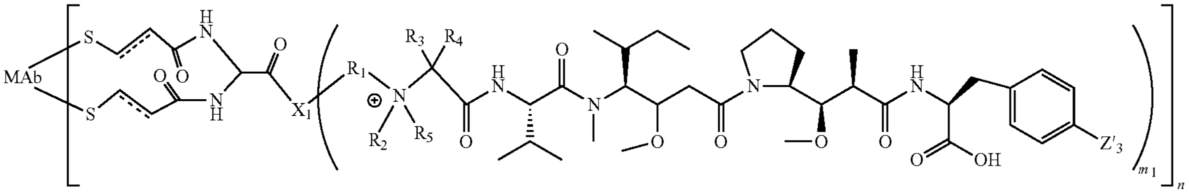

-continued

Au13

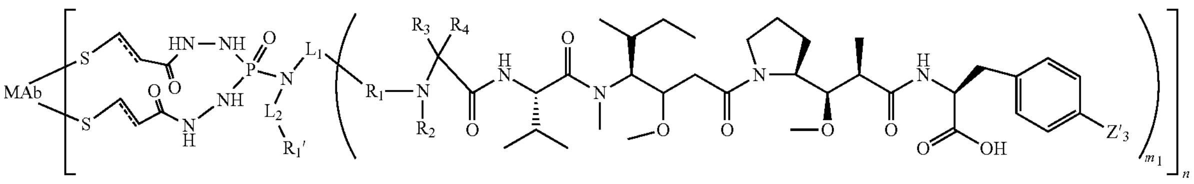

wherein "⎓", n, $m_1$, $m_2$, $X_1$, $X_2$, $R_1$, $R_2$, $R_3$, $R_4$ and $R_5$ are the same defined in Formula (I) or (II), or (III); mAb is an antibody, or a cell-binding molecule; $L_1$, $L_2$, $L_3$, $L_4$, and $L_5$ are independently defined as $L_1$ in Formula (I); Z3' is H, $OP(O)(OM_1)(OM_2)$, $OOCCH_3$, $OCH_2OP(O)(OM_1)(OM_2)$, $OSO_3M_1$, $R_1$, or O-glycoside (glucoside, galactoside, mannoside, glucuronoside, alloside, fructoside, etc), NH-glycoside, S-glycoside or $CH_2$-glycoside; In addition, the two Rs: $R_1R_2$, $R2R_3$, $R_1R_3$ or $R3R_4$ can form 3-8 member cyclic ring of alkyl, aryl, heteroaryl, heteroalkyl, or alkylcycloalkyl group; $X_3$ is H, $CH_3$, or $X_1$'$R_1$', wherein $X_{1'}$ is NH, $N(CH_3)$, NHNH, O, or S, and $R_{1'}$ is H or $C_1$-$C_8$ of lineal or branched alkyl, aryl, heteroaryl, heteroalkyl, alkylcycloalkyl, acyloxylamines; $R_{3'}$ is H or $C_1$-$C_6$ of lineal or branched alkyl; p is 0-2000; $M_1$ and $M_2$ are independently H, Na, K, Ca, Mg, $NH_4$, $NR_1R_2R_3$; In addition, $R_1$', $Drug_1$ and Drug2 can be a cytotoxic agent, $Drug_1$, which is described through the patent.

The benzodiazepine dimers (e. g. dimmers of pyrrolobenzodiazepine (PBD) or (tomaymycin), indolinobenzodiazepines, imidazobenzothiadiazepines, or oxazolidinobenzodiazepines) which are preferred cytotoxic agents according to the present invention are exampled in the art: U.S. Pat. Nos. 8,163,736; 8,153,627; 8,034,808; 7,834,005; 7,741,319; 7,704,924; 7,691,848; 7,678,787; 7,612,062; 7,608,615; 7,557,099; 7,528,128; 7,528,126; 7,511,032; 7,429,658; 7,407,951; 7,326,700; 7,312,210; 7,265,105; 7,202,239; 7,189,710; 7,173,026; 7,109,193; 7,067,511; 7,064,120; 7,056,913; 7,049,311; 7,022,699; 7,015,215; 6,979,684; 6,951,853; 6,884,799; 6,800,622; 6,747,144; 6,660,856; 6,608,192; 6,562,806; 6,977,254; 6,951,853; 6,909,006; 6,344,451; 5,880,122; 4,935,362; 4,764,616; 4,761,412; 4,723,007; 4,723,003; 4,683,230; 4,663,453; 4,508,647; 4,464,467; 4,427,587; 4,000,304; US patent appl. 20100203007, 20100316656, 20030195196. Examples of the structures of the conjugate of the antibody-benzodiazepine dimers via the bridge linker are as the following PB01, PB02, PB03, PB04, PB05, PB06, PB07, PB08, PB09, PB10 and PB11.

PB01

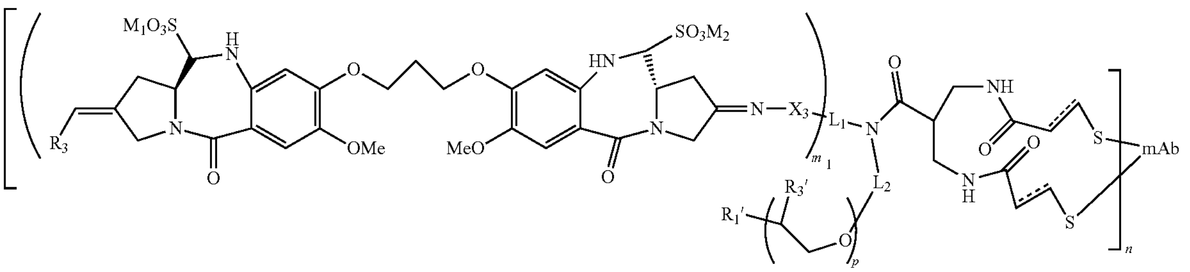

PB02

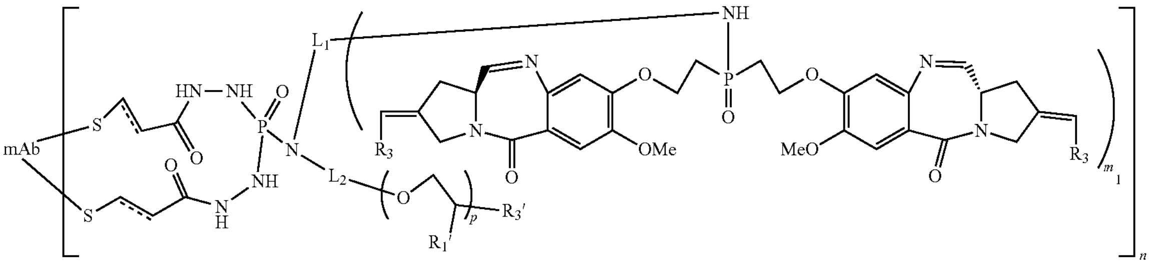

-continued
PB03
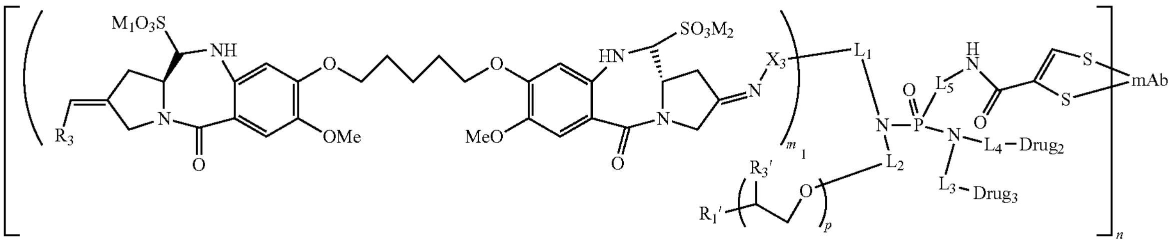
PB04
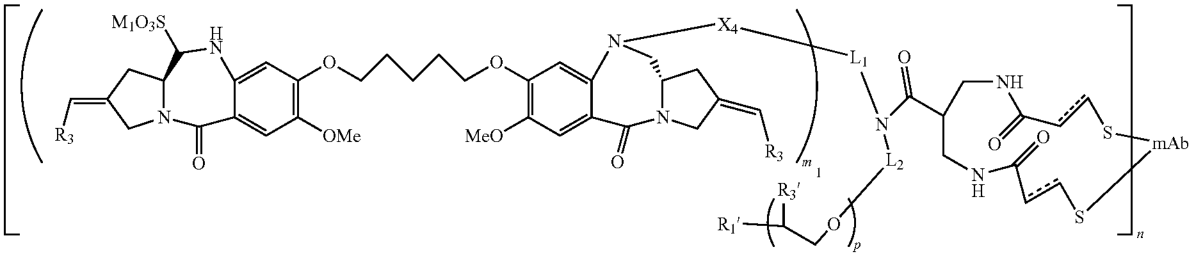
PB05
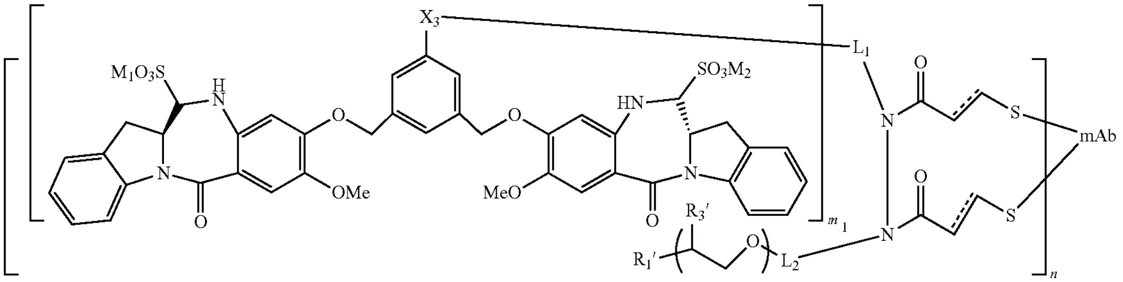
PB06
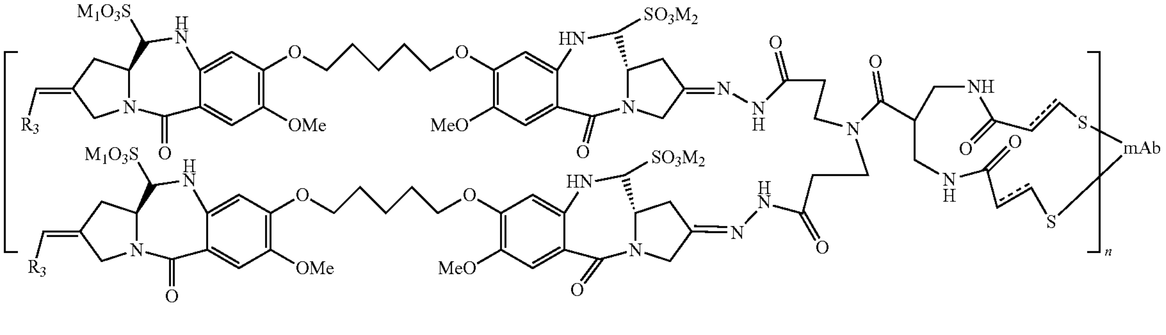
PB07
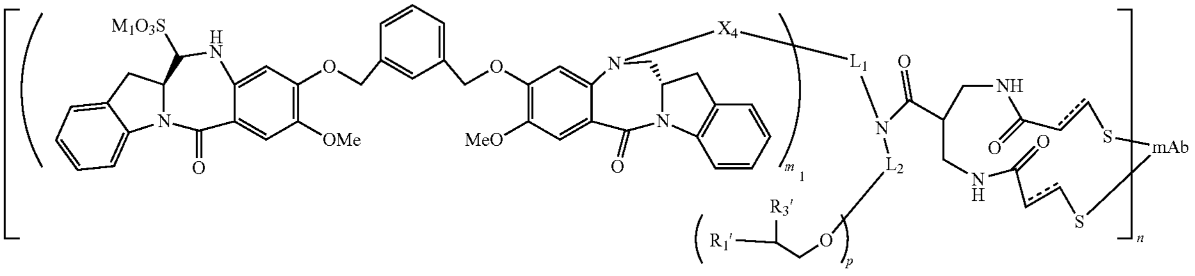

-continued

PB08

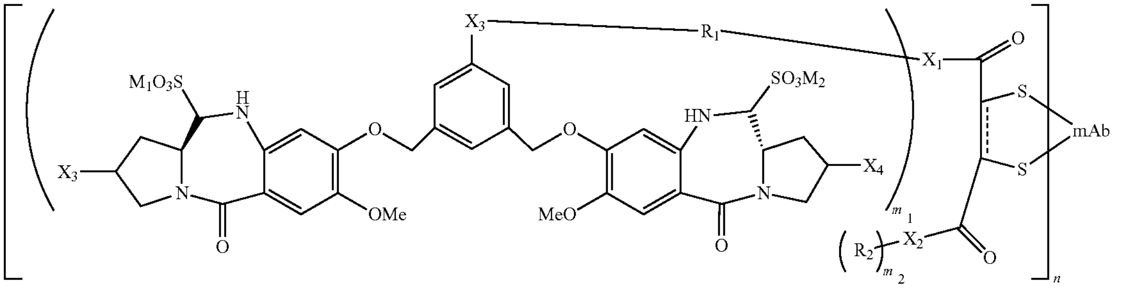

PB09

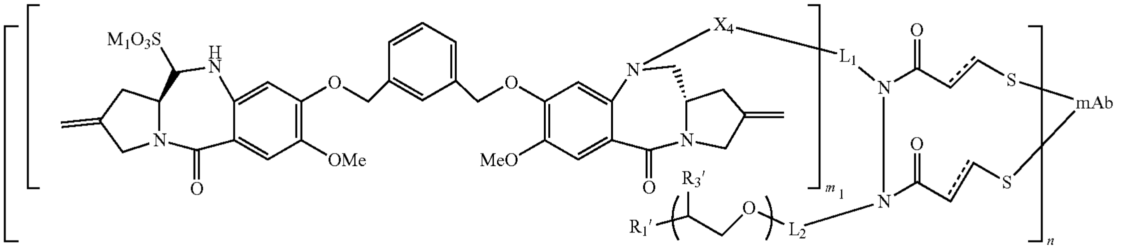

PB10

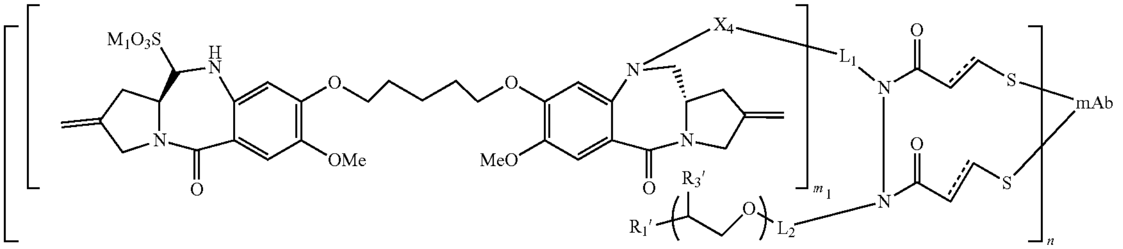

PB11

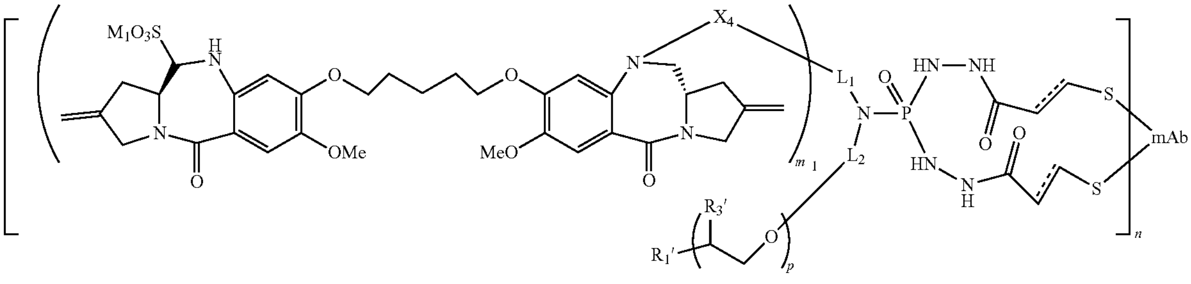

wherein mAb is an antibody; $X_3$ is $CH_2$, O, NH, NHC(O), NHC(O)NH, C(O), OC(O), $OC(O)(NR_3)$, $R_1$, $NHR_1$, $NR_1$, $C(O)R_1$ or absent; $X_4$ is $CH_2$, C(O), C(O)NH, $C(O)N(R_1)$, $R_1$, $NHR_1$, $NR_1$, $C(O)R_1$ or C(O)O; $M_1$ and $M_2$ are independently H, Na, K, Ca, Mg, $NH_4$, $NR_1R_2R_3$; "$\equiv$" represents either single bond or double bond; n, $m_1$, $m_2$, $X_1$, $X_2$, $L_1$, $L_2$, $R_1$, $R_2$ and $R_3$ are the same defined in Formula (I) and (II). $R_{1'}$ and $R_{3'}$ are independently H or $C_1$-$C_6$ lineal or branched alkyl; p is 0-2000. In addition, $R_{1'}$ can be a cytotoxic agent, $Drug_1$, which is described through the patent.

Amatoxins which are a subgroup of at least ten toxic compounds originally found in several genera of poisonous mushrooms, most notably *Amanita phalloides* and several other mushroom species, are also preferred for conjugation via the bridge linkers of the present patent. These ten amatoxins, named α-Amanitin, β-Amanitin, γ-Amanitin, ε-Amanitin, Amanullin, Amanullinic acid, Amaninamide, Amanin, Proamanullin, are rigid bicyclic peptides that are synthesized as 35-amino-acid proproteins, from which the final eight amino acids are cleaved by a prolyl oligopeptidase (Litten, W. 1975 Scientific American 232 (3): 90-101; H. E. Hallen, et al 2007 Proc. Nat. Aca. Sci. USA 104, 19097-101; K. Baumann, et al, 1993 Biochemistry 32 (15): 4043-50; Karlson-Stiber C, Persson H. 2003, Toxicon 42 (4): 339-49; Horgen, P. A. et al. 1978 Arch. Microbio. 118 (3): 317-9). Amatoxins kill cells by inhibiting RNA polymerase II (Pol II), shutting down gene transcription and protein biosynthesis (Brodner, 0. G. and Wieland, T. 1976 Biochemistry, 15(16): 3480-4; Fiume, L., Curr Probl Clin Biochem, 1977, 7: 23-8; Karlson-Stiber C, Persson H. 2003, Toxicon 42(4): 339-49; Chafin, D. R., Guo, H. & Price, D. H. 1995 J. Biol. Chem. 270 (32): 19114-19; Wieland (1983) Int. J. Pept. Protein Res. 22(3): 257-76.). Amatoxins can be produced from collected *Amanita phalloides* mushrooms (Yocum, R. R. 1978 Biochemistry 17(18): 3786-9; Zhang, P. et al, 2005, FEMS Microbiol. Lett. 252(2), 223-8), or from fermentation using a basidiomycete (Muraoka, S. and Shinozawa T., 2000 J. Biosci. Bioeng. 89(1): 73-6) or from fermentation using *A. fissa* (Guo, X. W., et al, 2006 Wei Sheng Wu Xue Bao 46(3): 373-8), or from culturing *Galerina fasciculata* or *Galerina helvoliceps*, a strain belonging to the genus (WO/1990/009799, JP11137291). However the yields from these isolation and fermentation were quite low (less than 5 mg/L culture). Several preparations of amatoxins and their analogs have been reported in the past three decades (W. E. Savige, A. Fontana, Chem. Commun. 1976, 600-1; Zanotti, G., et al, Int J Pept Protein Res, 1981. 18(2): 162-8; Wieland, T., et al, Eur. J. Biochem. 1981, 117, 161-4; P. A. Bartlett, et al, Tetrahedron Lett. 1982, 23, 619-22; Zanotti, G., et al., Biochim Biophys Acta, 1986. 870(3): 454-62; Zanotti, G. et al., Int. J. Peptide Protein Res. 1987, 30, 323-9; Zanotti, G. et al., Int. J. Peptide Protein Res. 1987, 30, 450-9; Zanotti, G., et al., Int J Pept Protein Res, 1988. 32(1): 9-20; G. Zanotti, T. et al, Int. J. Peptide Protein Res. 1989, 34, 222-8; Zanotti, G., et al., Int J Pept Protein Res, 1990. 35(3): 263-70; Mullersman, J. E. and J. F. Preston, 3rd, Int J Pept Protein Res, 1991. 37(6): 544-51; Mullersman, J. E., et al, Int J Pept Protein Res, 1991. 38(5): 409-16; Zanotti, G., et al, Int J Pept Protein Res, 1992. 40(6): 551-8; Schmitt, W. et al, J. Am. Chem. Soc. 1996, 118, 4380-7; Anderson, M. O., et al, J. Org. Chem., 2005, 70(12): 4578-84; J. P. May, et al, J. Org. Chem. 2005, 70, 8424-30; F. Brueckner, P. Cramer, Nat. Struct. Mol. Biol. 2008, 15, 811-8; J. P. May, D. M. Perrin, Chem. Eur. J. 2008, 14, 3404-9; J. P. May, et al, Chem. Eur. J. 2008, 14, 3410-17; Q. Wang, et al, Eur. J. Org. Chem. 2002, 834-9; May, J. P. and D. M. Perrin, Biopolymers, 2007. 88(5): 714-24; May, J. P., et al., Chemistry, 2008. 14(11): 3410-7; S. De Lamo Marin, et al, Eur. J. Org. Chem. 2010, 3985-9; Pousse, G., et al., Org Lett, 2010. 12(16): 3582-5; Luo, H., et al., Chem Biol, 2014. 21(12): 1610-7; Zhao, L., et al., Chembiochem, 2015. 16(10): 1420-5) and most of these preparations were by partial synthesis. Because of their extreme potency and unique mechanism of cytotoxicity, amatoxins have been used as payloads for conjugations (Fiume, L., Lancet, 1969. 2 (7625): 853-4; Barbanti-Brodano, G. and L. Fiume, Nat New Biol, 1973. 243(130): 281-3; Bonetti, E., M. et al, Arch Toxicol, 1976. 35(1): p. 69-73; Davis, M. T., Preston, J. F. Science 1981, 213, 1385-1388; Preston, J. F., et al, Arch Biochem Biophys, 1981. 209(1): 63-71; H. Faulstich, et al, Biochemistry 1981, 20, 6498-504; Barak, L. S., et al., Proc Natl Acad Sci USA, 1981. 78(5): 3034-8; Faulstich, H. and L. Fiume, Methods Enzymol, 1985. 112: 225-37; Zhelev, Z., A. et al, Toxicon, 1987. 25(9): 981-7; Khalacheva, K., et al, Eksp Med Morfol, 1990. 29(3): 26-30; U. Bermbach, H. Faulstich, Biochemistry 1990, 29, 6839-45; Mullersman, J. E. and J. F. Preston, Int. J. Peptide Protein Res. 1991, 37, 544-51; Mullersman, J. E. and J. F. Preston, Biochem Cell Biol, 1991. 69(7): 418-27; J. Anderl, H. Echner, H. Faulstich, Beilstein J. Org. Chem. 2012, 8, 2072-84; Moldenhauer, G., et al, J. Natl. Cancer Inst. 2012, 104, 622-34; A. Moshnikova, et al; Biochemistry 2013, 52, 1171-8; Zhao, L., et al., Chembiochem, 2015. 16(10): 1420-5; Zhou, B., et al., Biosens Bioelectron, 2015. 68: 189-96; WO2014/043403, US20150218220, EP 1661584). We have been working on the conjugation of amatoxins for a while. Examples of the structures of the conjugate of the antibody-amatoxins via the bridge linker are preferred as the following structures of Am01, Am02, Am03, and Am04.

Am01

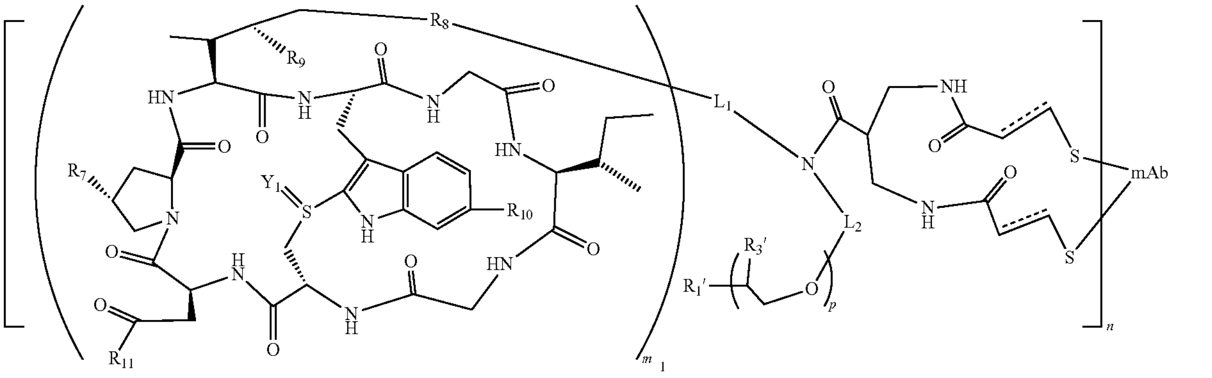

Am02

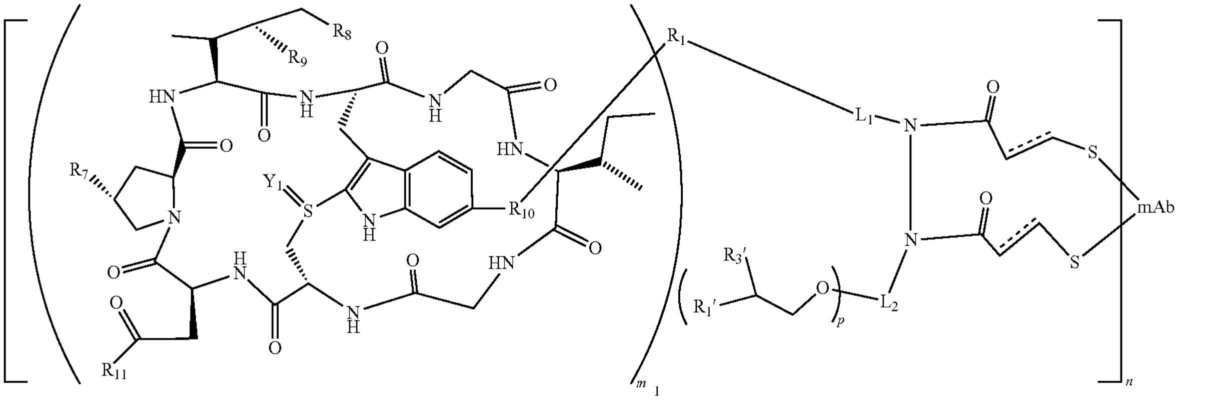

-continued

Am03

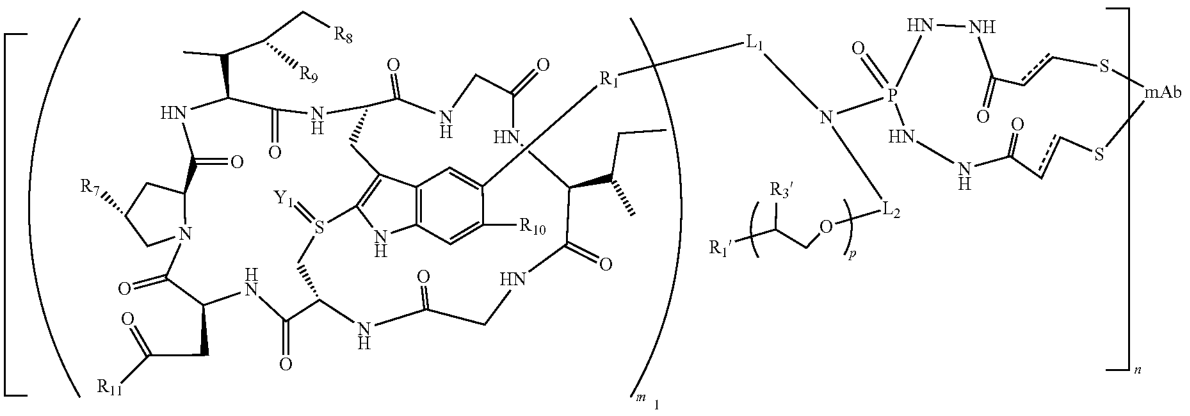

Am04

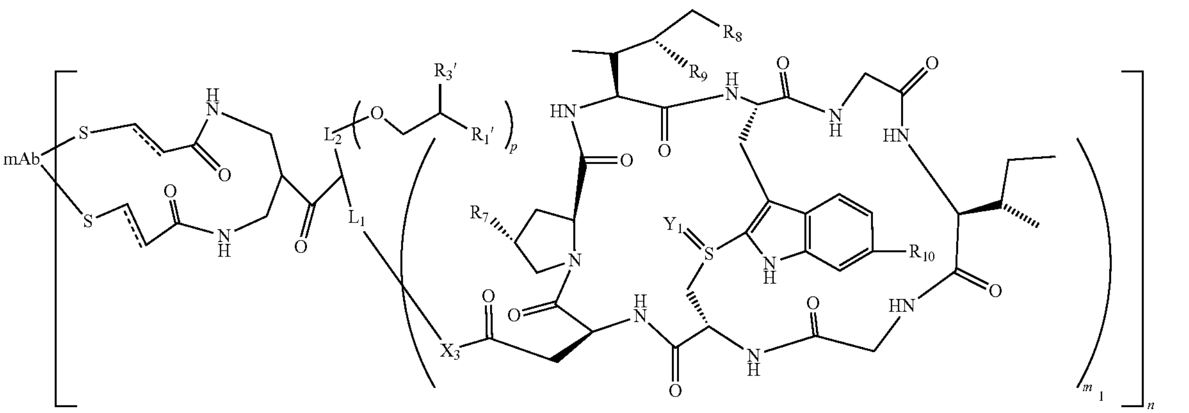

wherein mAb is an antibody; $X_3$ is $CH_2$, O, NH, NHC(O), NHC(O)NH, C(O), OC(O), $OC(O)(NR_3)$, $R_1$, $NHR_1$, $NR_1$, $C(O)R_1$ or absent; $R_7$, $R_8$, $R_9$, $R_{10}$ and $R_{11}$ are independently H, OH, $OR_1$, $NH_2$, $NHR_1$, $C_1$-$C_6$ alkyl, or absent; $Y_1$ is O, $O_2$, S, NH, or absent; "$\equiv$" represents either single bond or double bond; n, $m_1$, $m_2$, $X_1$, $X_2$, $L_1$, $L_2$, $R_1$, $R_2$ and $R_3$ are the same defined in Formula (I) and (II). $R_{1'}$ and $R_{3'}$ are independently H or $C_1$-$C_6$ lineal or branched alkyl; p is 0-2000. In addition, $R_{1'}$ can be a cytotoxic agent, $Drug_1$, which is described through the patent.

In yet another embodiment, two or more different cytotoxic agents are preferred conjugated to a cell-binding molecule via a bridge linker of this patent. The two or more different cytotoxic agents can be selected from any combinations of tubulysins, maytansinoids, taxanoids (taxanes), CC-1065 analogs, daunorubicin and doxorubicin compounds, benzodiazepine dimers (e.g., dimers of pyrrolobenzodiazepine (PBD), tomaymycin, anthramycin, indolinobenzodiazepines, imidazobenzothiadiazepines, or oxazolidinobenzodiazepines), calicheamicins and the enediyne antibiotics, actinomycins, amanitins, azaserines, bleomycins, epirubicin, tamoxifen, idarubicin, dolastatins, auristatins (e.g. monomethyl auristatin E, MMAE, MMAF, auristatin PYE, auristatin TP, Auristatins 2-AQ, 6-AQ, EB (AEB), and EFP (AEFP)), duocarmycins, thiotepa, vincristines, hemiasterlins, nazumamides, microginins, radiosumins, alterobactins, microsclerodermins, theonellamides, esperamicins, PNU-159682, and their analogues and derivatives above thereof. Examples of the structures of the conjugates containing two or more different cytotoxic agents via the bridge linker are as the following Z01, Z02, Z02, Z04, Z05, Z06, Z07, Z08, Z09, Z10, Z12, Z13, Z14, Z15, Z16, Z17 and Z18:

Z01
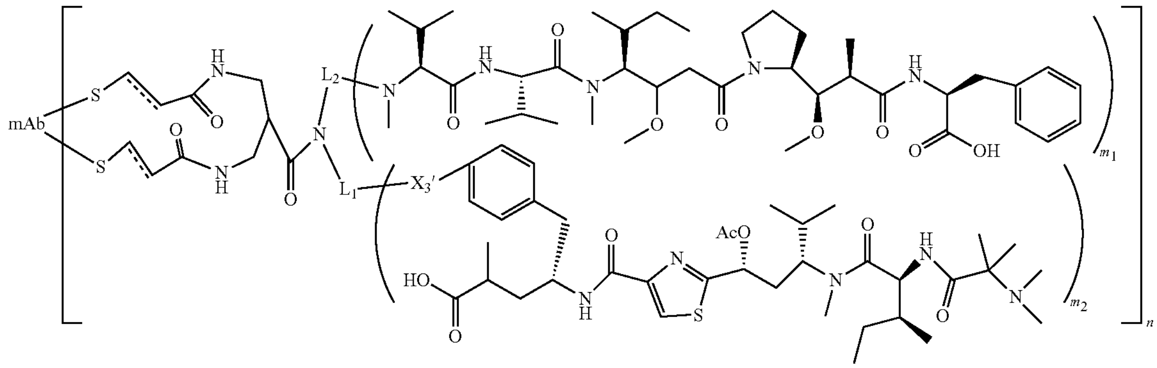
Z02
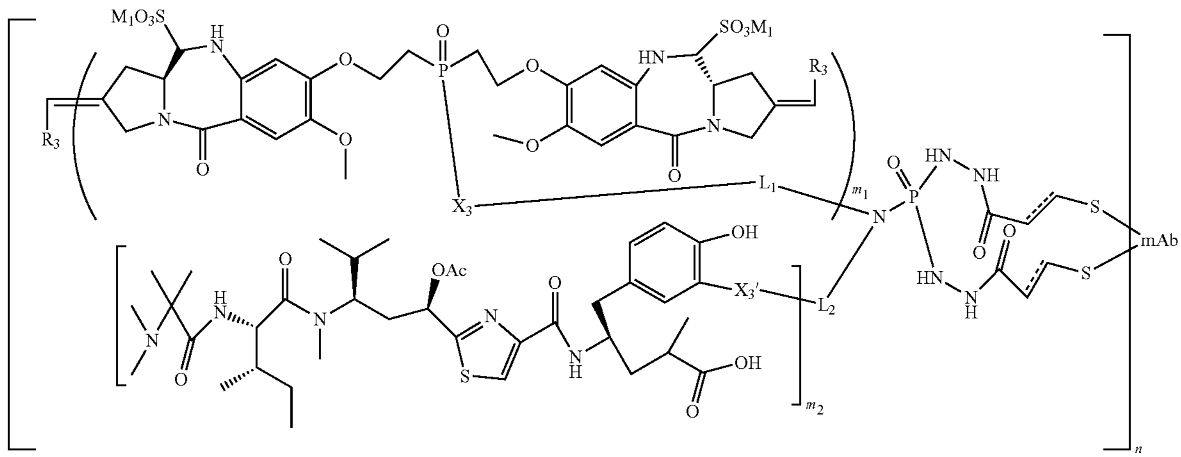
Z03
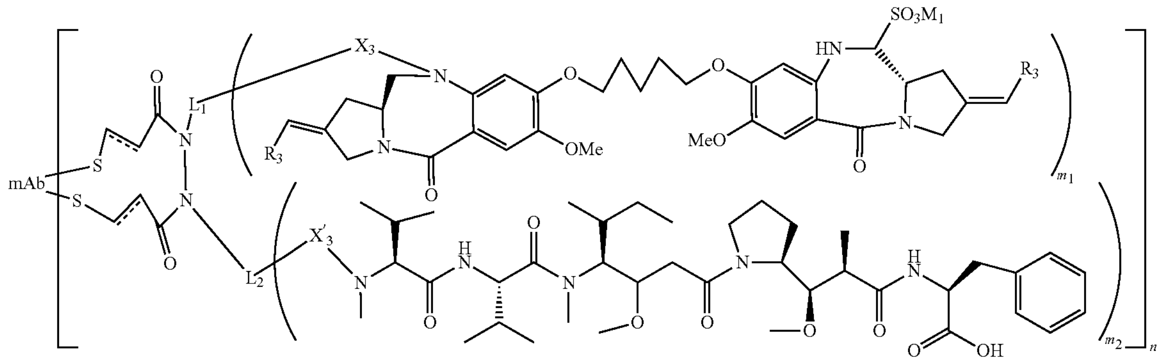
Z04
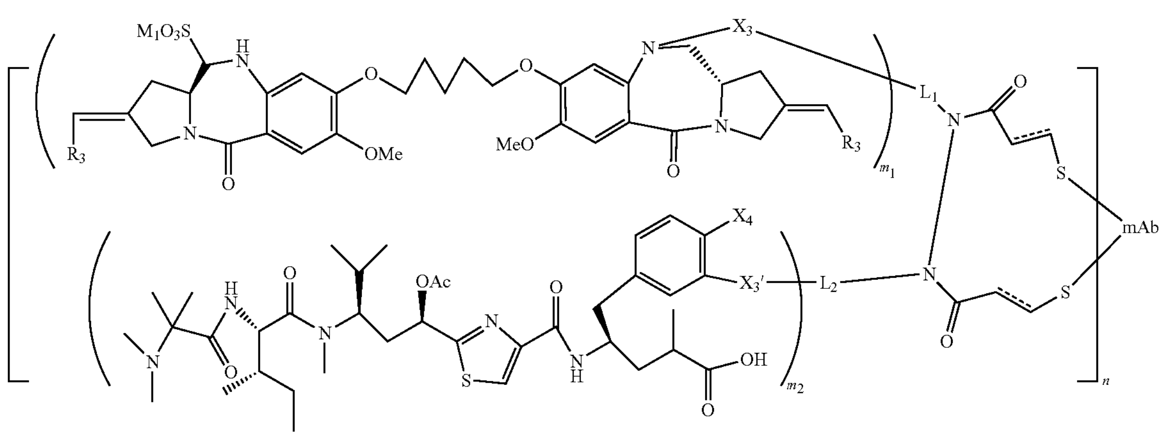

-continued
Z05
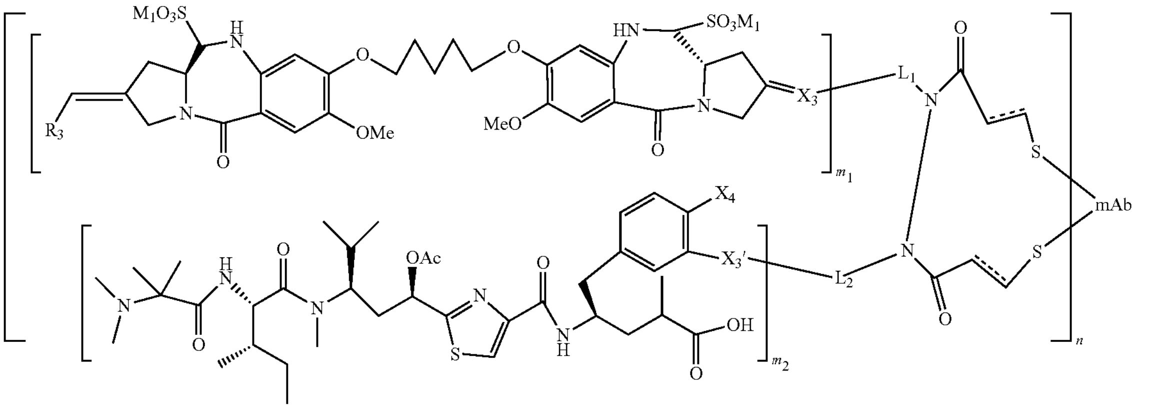
Z06
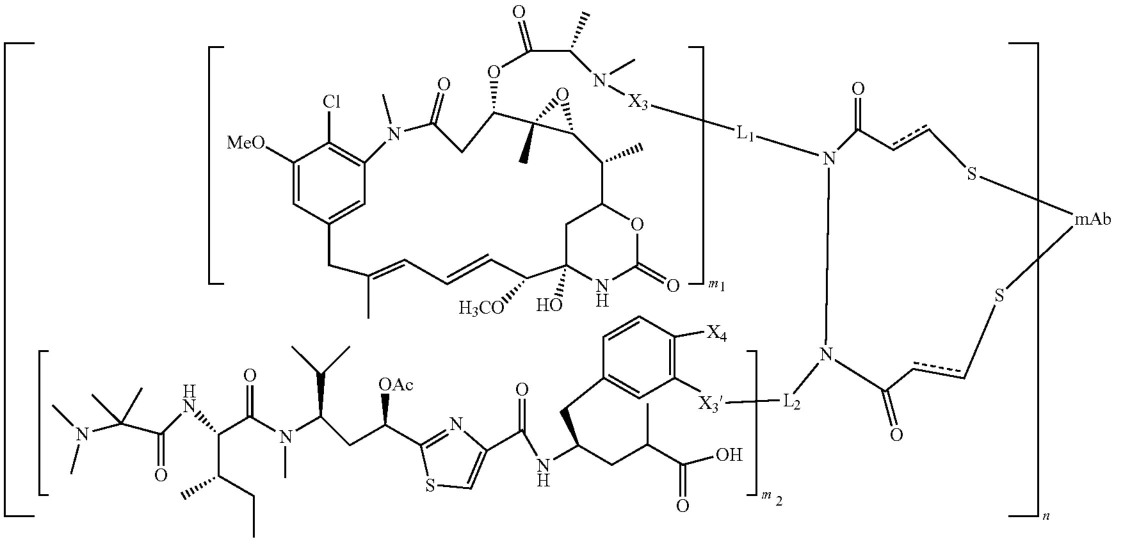
Z07
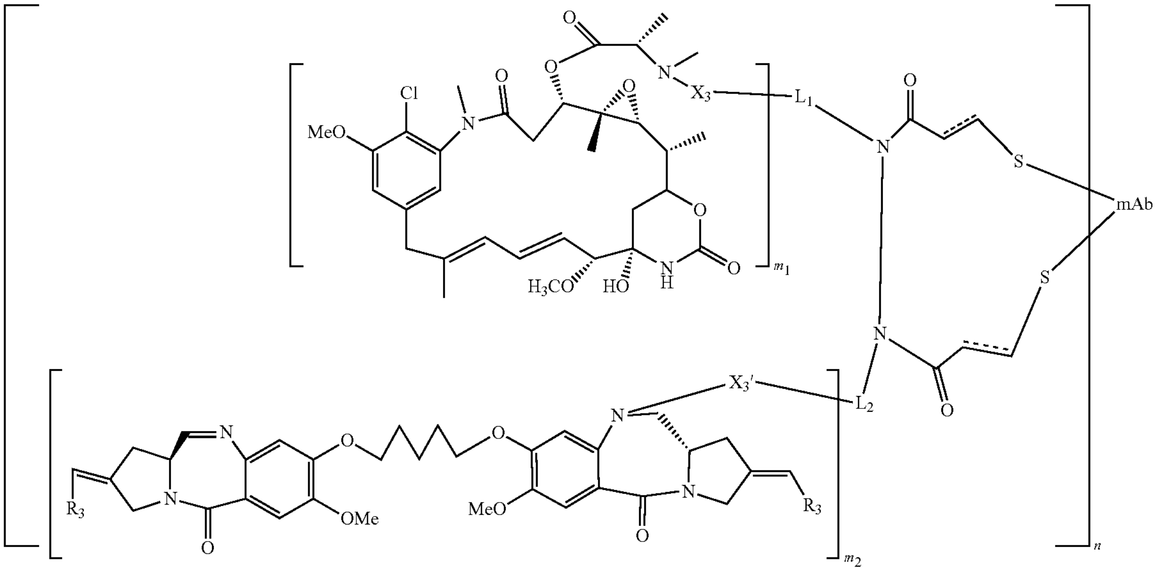

-continued
Z08
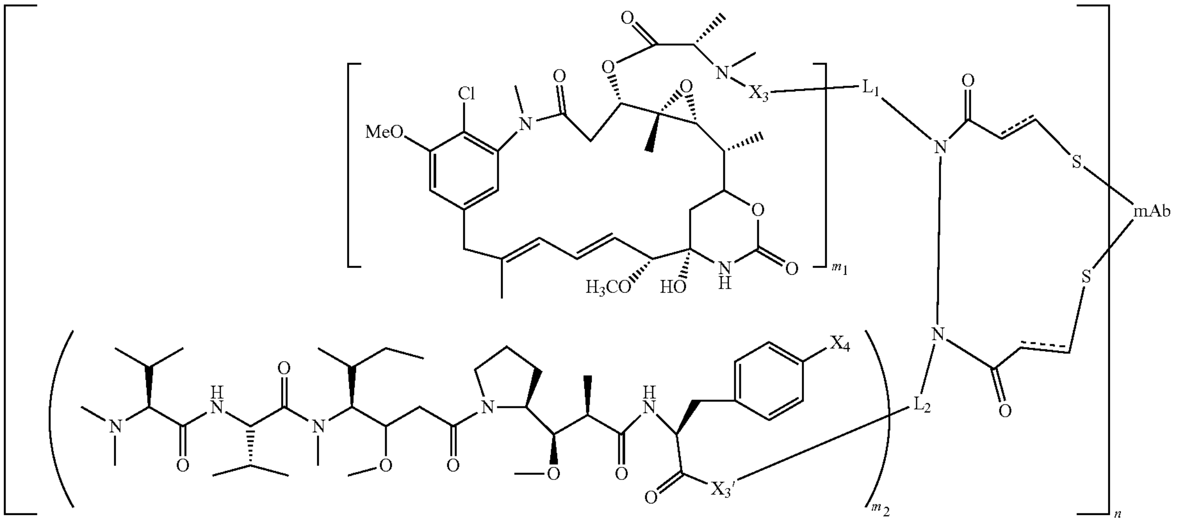
Z09
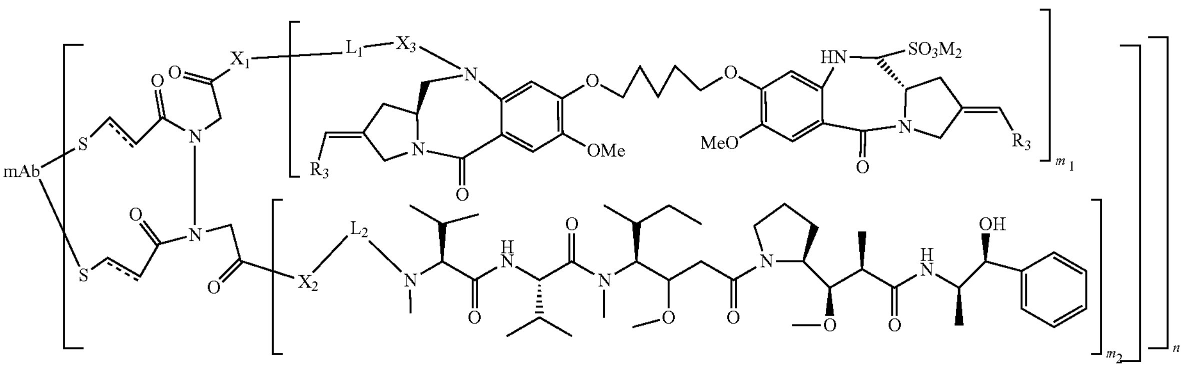
Z10
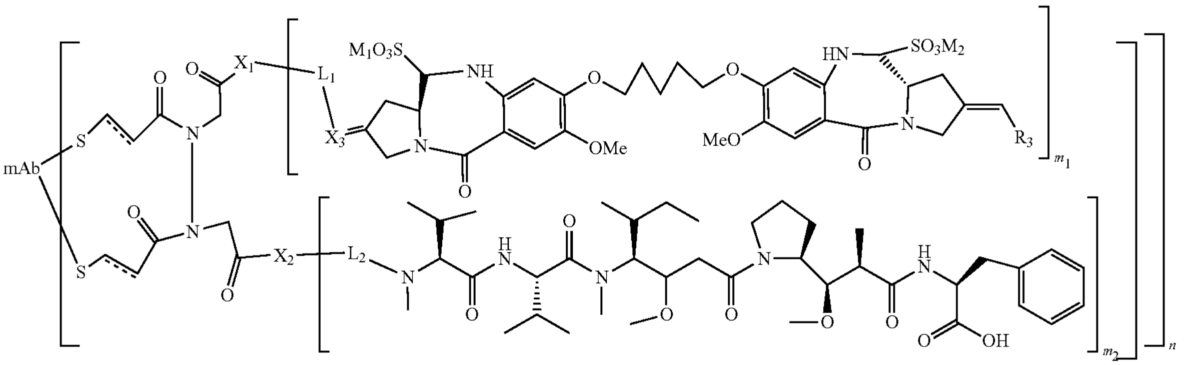

-continued
Z11
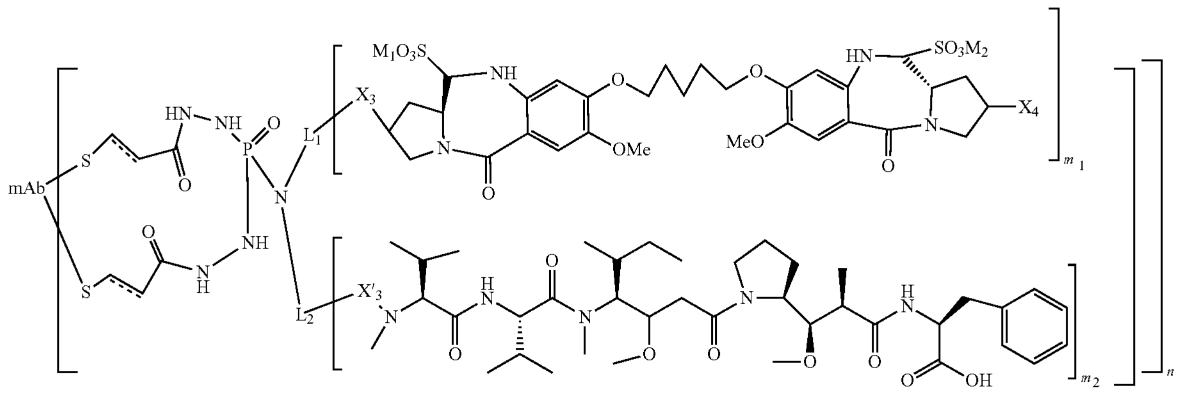
Z12
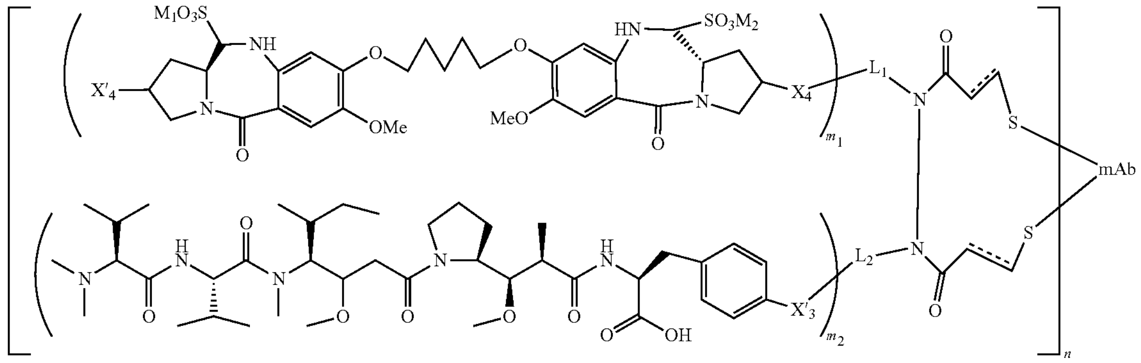
Z13
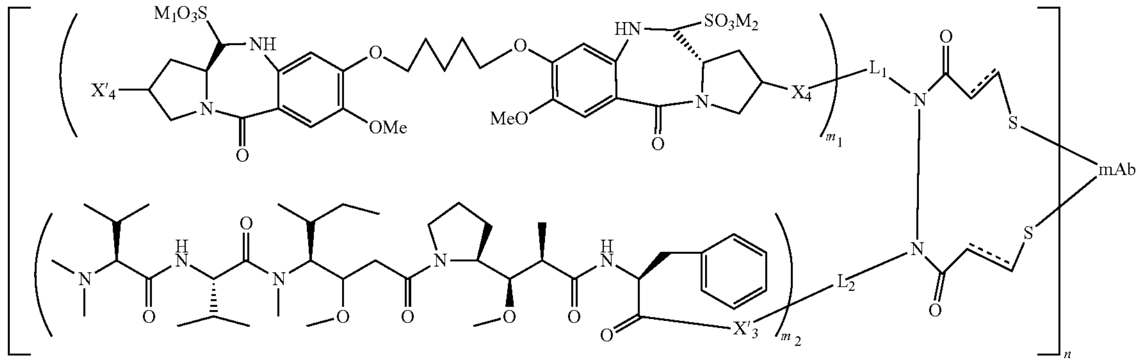
Z14
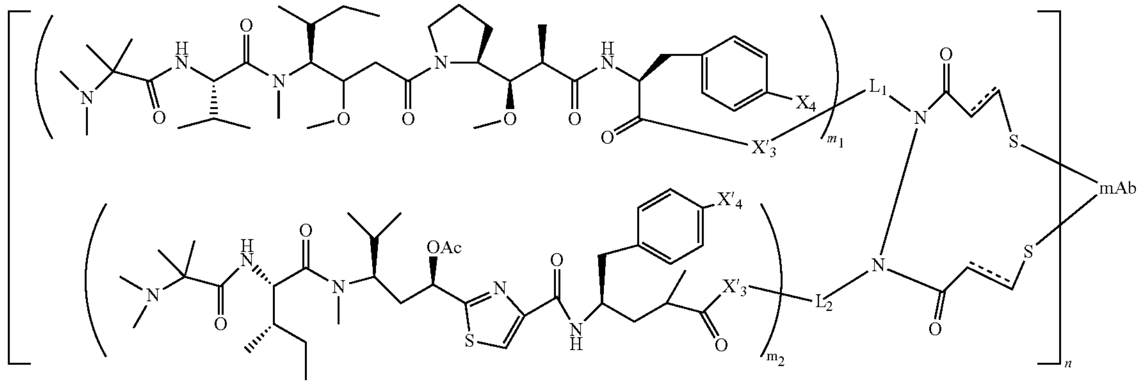

-continued
Z15
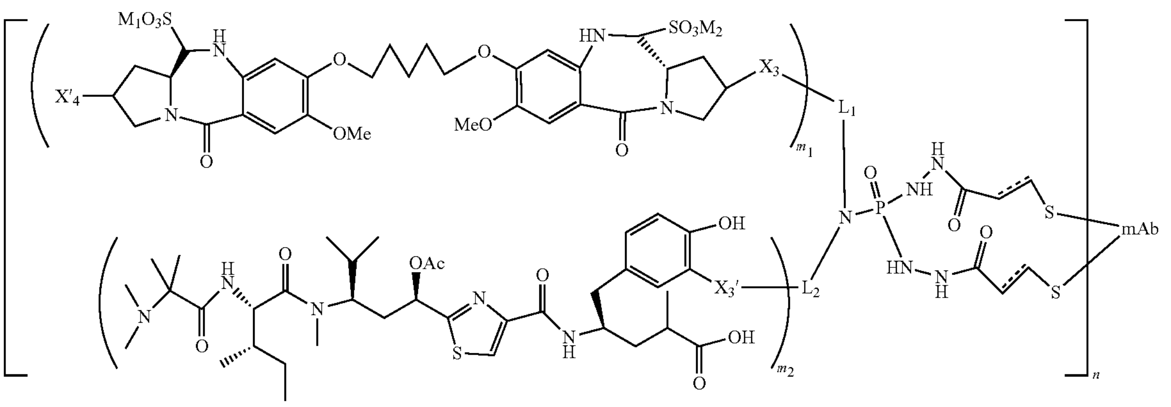
Z16
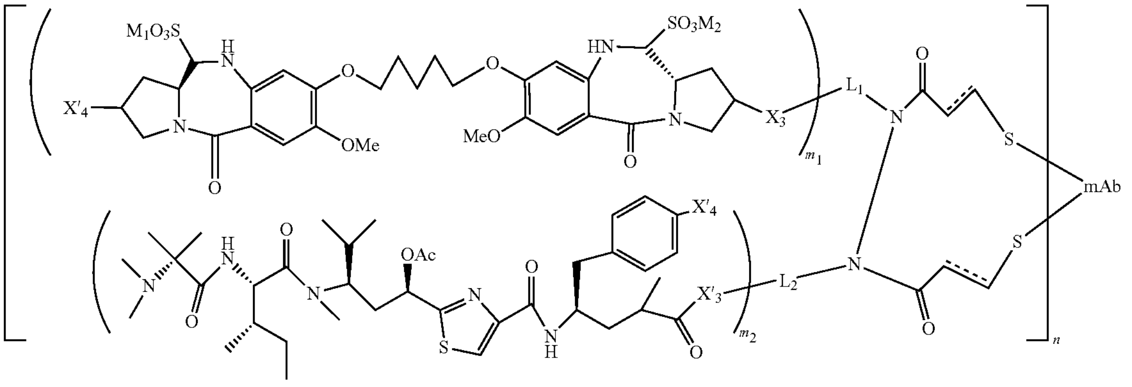
Z17
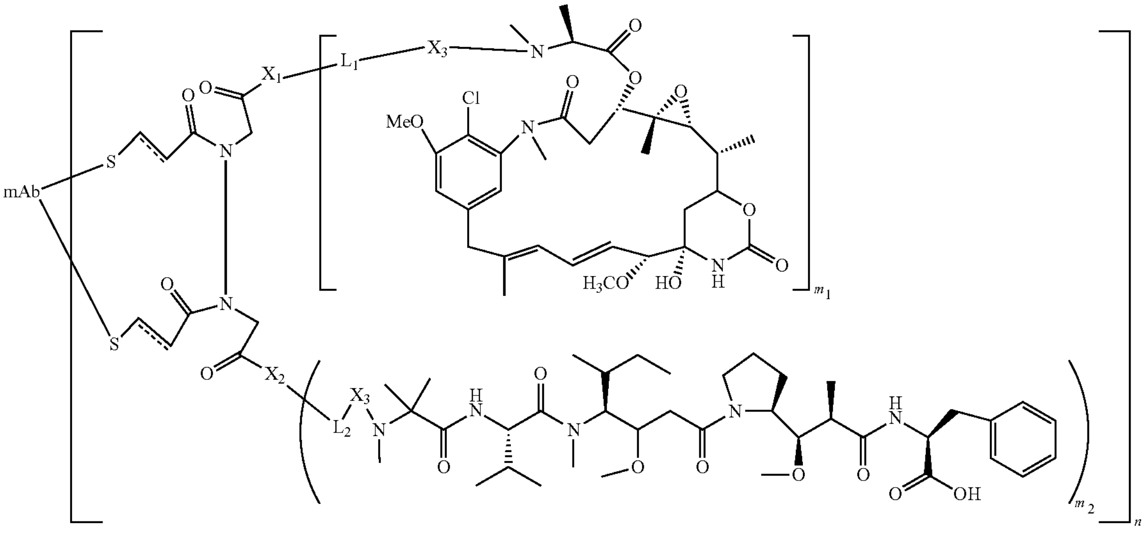

-continued

Z18

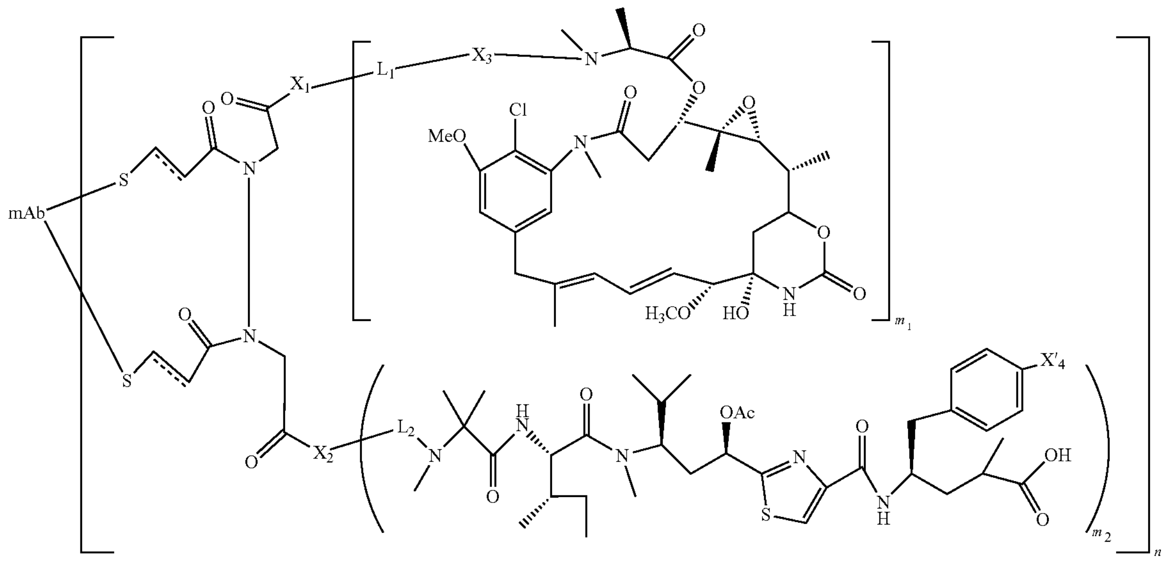

Wherein mAb is an antibody; $X_3$ and $X'_3$ are independently $CH_2$, O, NH, NHC(O), NHC(O)NH, C(O), OC(O), OC(O)($NR_3$), $R_1$, $NHR_1$, $NR_1$, $C(O)R_1$ or absent; $X_4$ and $X'_4$ are independently H, $CH_2$, OH, O, C(O), C(O)NH, C(O)N($R_1$), $R_1$, $NHR_1$, $NR_1$, $C(O)R_1$ or C(O)O; $M_1$ and $M_2$ are independently H, Na, K, Ca, Mg, $NH_4$, $NR_1R_2R_3$; n, $m_1$, $m_2$, "—", "⎓", $X_1$, $X_2$, $R_1$, $R_2$ and $R_3$ are the same defined in Formula (I) and (II). In addition, $R_1$ and/or $R_2$ can be absent independently.

In yet another embodiment, an immunotoxin can be conjugated to a cell-binding molecule via a linker of this patent. An immunotoxin herein is a macromolecular drug which is usually a cytotoxic protein derived from a bacterial or plant protein, such as Diphtheria toxin (DT), Cholera toxin (CT), Trichosanthin (TCS), Dianthin, *Pseudomonas* exotoxin A (ETA'), Erythrogenic toxins, Diphtheria toxin, AB toxins, Type III exotoxins, etc. It also can be a highly toxic bacterial pore-forming protoxin that requires proteolytic processing for activation. An example of this protoxin is proaerolysin and its genetically modified form, topsalysin. Topsalysin is a modified recombinant protein that has been engineered to be selectively activated by an enzyme in the prostate, leading to localized cell death and tissue disruption without damaging neighboring tissue and nerves.

In yet another embodiment, cell-binding ligands or cell receptor agonists can be conjugated to a cell-binding molecule via a linker of this patent. These conjugated cell-binding ligands or cell receptor agonists, in particular, antibody-receptor conjugates, can be not only to work as a targeting conductor/director to deliver the conjugate to malignant cells, but also be used to modulate or co-stimulate a desired immune response or altering signaling pathways.

In the immunotherapy, the cell-binding ligands or receptor agonists are preferred to conjugate to an antibody of TCR (T cell receptors) T cell, or of CARs (chimeric antigen receptors) T cells, or of B cell receptor (BCR), Natural killer (NK) cells, or the cytotoxic cells. Such antibody is preferably anti-CD3, CD4, CD8, CD16 (FcγRIII), CD27, CD40, CD40L, CD45RA, CD45RO, CD56, CD57, $CD57^{bright}$, TNFβ, Fas ligand, MHC class I molecules (HLA-A, B, C), or NKR—P1. The cell-binding ligands or receptor agonists are selected, but not limited, from: Folate derivatives (binding to the folate receptor, a protein over-expressed in ovarian cancer and in other malignancies) (Low, P. S. et al 2008, Acc. Chem. Res. 41, 120-9); Glutamic acid urea derivatives (binding to the prostate specific membrane antigen, a surface marker of prostate cancer cells) (Hillier, S. M. et al, 2009, Cancer Res. 69, 6932-40); Somatostatin (also known as growth hormone-inhibiting hormone (GHIH) or somatotropin release-inhibiting factor (SRIF)) or somatotropin release-inhibiting hormone) and its analogues such as octreotide (Sandostatin) and lanreotide (Somatuline) (particularly for neuroendocrine tumors, GH-producing pituitary adenoma, paraganglioma, nonfunctioning pituitary adenoma, pheochromocytomas) (Ginj, M., et al, 2006, Proc. Natl. Acad. Sci. U.S.A. 103, 16436-41). In general, Somatostatin and its receptor subtypes (sstl, sst2, sst3, sst4, and sst5) have been found in many types of tumors, such as neuroendocrine tumors, in particular in GH-secreting pituitary adenomas (Reubi J. C., Landolt, A. M. 1984 J. Clin. Endocrinol Metab 59: 1148-51; Reubi J. C., Landolt A. M. 1987 J Clin Endocrinol Metab 65: 65-73; Moyse E, et al, J Clin Endocrinol Metab 61: 98-103) and gastroenteropancreatic tumors (Reubi J. C., et al, 1987 J Clin Endocrinol Metab 65: 1127-34; Reubi, J. C, et al, 1990 Cancer Res 50: 5969-77), pheochromocytomas (Epel-baum J, et al 1995 J Clin Endocrinol Metab 80:1837-44; Reubi J. C., et al, 1992 J Clin Endocrinol Metab 74: 1082-9), neuroblastomas (Prevost G, 1996 Neuroendocrinology 63:188-197; Moertel, C. L, et al 1994 Am J Clin Path 102:752-756), medullary thyroid cancers (Reubi, J. C, et al 1991 Lab Invest 64:567-573) small cell lung cancers (Sagman U, et al, 1990 Cancer 66:2129-2133), nonneuroendocrine tumors including brain tumors such as meningiomas, medulloblastomas, or gliomas (Reubi J. C., et al 1986 J Clin Endocrinol Metab 63: 433-8; Reubi J. C., et al 1987 Cancer Res 47: 5758-64; Fruhwald, M. C, et al 1999 Pediatr Res 45: 697-708), breast carcinomas (Reubi J. C., et al 1990 Int J Cancer 46: 416-20; Srkalovic G, et al 1990 J Clin Endocrinol Metab 70: 661-669), lymphomas (Reubi J. C., et al 1992, Int J Cancer 50: 895-900), renal cell cancers (Reubi J. C., et al 1992, Cancer Res 52: 6074-6078), mesenchymal tumors (Reubi J. C., et al 1996 Cancer Res 56: 1922-31), prostatic (Reubi J. C., et al 1995, J. Clin. Endocrinol Metab 80: 2806-14; et al 1989, Prostate 14:191-208; Halmos G, et al J. Clin. Endocrinol Metab 85: 2564-71), ovarian (Halmos, G, et al, 2000 J Clin Endocrinol Metab 85: 3509-12; Reubi J. C., et al 1991 Am J Pathol 138:1267-72), gastric (Reubi J. C., et al 1999, Int J Cancer 81: 376-86; Miller, G. V, 1992 Br J Cancer 66: 391-95), hepatocellular (Kouroumalis E, et al 1998 Gut 42: 442-7; Reubi J. C., et al 1999 Gut 45: 66-774) and naso-pharyngeal carcinomas (Loh K. S, et al, 2002 Virchows Arch 441: 444-8); certain Aromatic sulfonamides, specific to carbonic anhydrase IX (a marker of hypoxia and of renal cell carcinoma) (Neri, D., et al, Nat. Rev. Drug Discov. 2011, 10, 767-7); Pituitary adenylate cyclase activating peptides (PACAP) (PACi) for pheochromocytomas and paraganglio-mas; Vasoactive intestinal peptides (VIP) and their receptor subtypes (VPAC1, VPAC2) for cancers of lung, stomach, colon, rectum, breast, prostate, pancreatic ducts, liver, urinary bladder and epithelial tumors; α-Melanocyte-stimulating hormone (α-MSH) receptors for various tumors; Cholecystokinin (CCK)/gastrin receptors and their receptor subtypes (CCK1 (formerly CCK-A) and CCK2 for small cell lung cancers, medullary thyroid carcinomas, astrocytomas, insulinomas and ovarian cancers; Bombesin(Pyr-Gln-Arg-Leu-Gly-Asn-Gln-Trp-Ala-Val-Gly-His-Leu-Met-$NH_2$)/gastrin-releasing peptide (GRP) and their receptor subtypes (BB1, GRP receptor subtype (BB2), the BB3 and BB4) for renal cell, breast, lung, gastric and prostate carcinomas, and neuroblastoma (and neuroblastoma (Ohlsson, B., et al, 1999, Scand. J. Gastroenterology 34 (12): 1224-9; Weber, H. C., 2009, Cur. Opin. Endocri. Diab. Obesity 16(1): 66-71, Gonzalez N, et al, 2008, Cur. Opin. Endocri. Diab. Obesity 15(1), 58-64); Neurotensin receptors and its receptor subtypes (NTR1, NTR2, NTR3) for small cell lung cancer, neuroblastoma, pancreatic, colonic cancer and Ewing sarcoma; Substance P receptors and their receptor subtypes (such as NK1 receptor for Glial tumors, Hennig I. M., et al 1995 Int. J. Cancer 61, 786-792); Neuropeptide Y (NPY) receptors and its receptor subtypes (Y1-Y6) for breast carcinomas; Homing Peptides include RGD (Arg-Gly-Asp), NGR (Asn-Gly-Arg), the dimeric and multimeric cyclic RGD peptides (e.g. cRGDfV) that recognize receptors (integrins) on tumor surfaces (Laakkonen P, Vuorinen K. 2010, Integr Biol (Camb). 2(7-8): 326-337; Chen K, Chen X. 2011, Theranostics. 1:189-200; Garanger E, et al, Anti-Cancer Agents Med Chem. 7 (5): 552-558; Kerr, J. S. et al, Anticancer Research, 19(2A), 959-968; Thumshirn, G, et al, 2003 Chem. Eur. J. 9, 2717-2725), and TAASGVRSMH or LTLRWVGLMS (chondroitin sulfate proteoglycan NG2 receptor) and F3 peptides (31 amino acid peptide that binds to cell surface-expressed nucleolin receptor) (Zitzmann, S., 2002 Cancer Res., 62, 18, pp. 5139-5143, Temminga, K., 2005, Drug Resistance Updates, 8, 381-402; P. Laakkonen and K. Vuorinen, 2010 Integrative Biol, 2(7-8), 326-337; M. A. Burg, 1999 Cancer Res., 59(12), 2869-2874; K. Porkka, et al 2002, Proc. Nat. Acad. Sci. USA 99(11), 7444-9); Cell Penetrating Peptides (CPPs) (Nakase I, et al, 2012, J. Control Release. 159(2), 181-188); Peptide Hormones, such as luteinizing hormone-releasing hormone (LHRH) agonists and antagonists, and gonadotropin-releasing hormone (GnRH) agonist, acts by targeting follicle stimulating hormone (FSH) and luteinising hormone (LH), as well as testosterone production, e.g. buserelin (Pyr-His-Trp-Ser-Tyr-D-Ser(OtBu)-Leu-Arg-Pro-NHEt), Gonadorelin (Pyr-His-Trp-Ser-Tyr-Gly-Leu-Arg-Pro-Gly-$NH_2$), Goserelin (Pyr-His-Trp-Ser-Tyr-D-Ser(OtBu)-Leu-Arg-Pro-AzGly-$NH_2$), Histrelin (Pyr-His-Trp-Ser-Tyr-D-His(N-benzyl)-Leu-Arg-Pro-NHEt), leuprolide (Pyr-His-Trp-Ser-Tyr-D-Leu-Leu-Arg-Pro-NHEt), Nafarelin (Pyr-His-Trp-Ser-Tyr-2Nal-Leu-Arg-Pro-Gly-$NH_2$), Triptorelin (Pyr-His-Trp-Ser-Tyr-D-Trp-Leu-Arg-Pro-Gly-$NH_2$), Nafarelin, Deslorelin, Abarelix (Ac-D-2Nal-D-4-chloroPhe-D-3-(3-pyridyl)Ala-Ser-(N-Me)Tyr-D-Asn-Leu-isopropylLys-Pro-DAla-$NH_2$), Cetrorelix (Ac-D-2Nal-D-4-chloro-Phe-D-3-(3-pyridyl) Ala-Ser-Tyr-D-Cit-Leu-Arg-Pro-D-Ala-$NH_2$), Degarelix (Ac-D-2Nal-D-4-chloroPhe-D-3-(3-pyridyl)Ala-Ser-4-aminoPhe(L-hydroorotyl)-D-4-aminoPhe(carba-moyl)-Leu-isopropylLys-Pro-D-Ala-$NH_2$), and Ganirelix (Ac-D-2Nal-D-4-chloroPhe-D-3-(3-pyridyl)Ala-Ser-Tyr-D-(N9, N10-diethyl)-homoArg-Leu-(N9, N10-diethyl)-homoArg-Pro-D-Ala-$NH_2$) (Thundimadathil, J., J. Amino Acids, 2012, 967347, doi:10.1155/2012/967347; Boccon-Gibod, L.; et al, 2011, Therapeutic Advances in Urology 3(3): 127-140; Debruyne, F., 2006, Future Oncology, 2(6), 677-696; Schally A. V; Nagy, A. 1999 Eur J Endocrinol 141:1-14; Koppan M, et al 1999 Prostate 38:151-158); and Pattern Recognition Receptors (PRRs), such as Toll-like receptors (TLRs), C-type lectins and Nodlike Receptors (NLRs) (Fukata, M., et al, 2009, Semin. Immunol. 21, 242-253; Maisonneuve, C., et al, 2014, Proc. Natl. Acad. Sci. U.S.A 111, 1-6; Botos, I., et al, 2011, Structure 19, 447-459; Means, T. K., et al, 2000, Life Sci. 68, 241-258) that range in size from small molecules (imiquimod, guanisine and adenosine analogs) tolarge and complex biomacromolecules such as lipopolysaccharide (LPS), nucleic acids (CpG DNA, polyl:C) and lipopeptides ($Pam_3$CSK4) (Kasturi, S. P., et al, 2011, Nature 470, 543-547; Lane, T., 2001, J. R. Soc. Med. 94, 316; Hotz, C., and Bourquin, C., 2012, Oncoimmunology 1, 227-228; Dudek, A. Z., et al, 2007, Clin. Cancer Res. 13, 7119-25); Calcitonin receptors which is a 32-amino-acid neuropeptide involved in the regulation of calcium levels largely through its effects on osteoclasts and on the kidney (Zaidi M, et al, 1990 Crit Rev Clin Lab Sci 28, 109-174; Gorn, A. H., et al 1995 J Clin Invest 95:2680-91); And integrin receptors and their receptor subtypes (such as $\alpha_b\beta_1$, $\alpha_v\beta_3$, $\alpha_v\beta_5$, $\alpha_v\beta_6$, $\alpha_6\beta_4$, $\alpha_7\beta_1$, $\alpha_L\beta_2$, $\alpha_{11b}\beta_3$, etc) which generally play important roles in angiogenesis are expressed on the surfaces of a variety of cells, in particular, of osteoclasts, endothelial cells and tumor cells (Ruoslahti, E. et al, 1994 Cell 77, 477-8; Albelda, S. M. et al, 1990, Cancer Res., 50, 6757-64). Short peptides, GRGDSPK and Cyclic RGD pentapeptides, such as cyclo(RGDfV) (L1) and its derives [cyclo(-N(Me)R-GDfV), cyclo(R-Sar-DfV), cyclo-(RG-N(Me)D-fV), cyclo(RGD-N(Me)f-V), cyclo(RGDf-N (Me)V-)(Cilengitide)] have shown high binding affinities of the intergrin receptors (Dechantsreiter, M. A. et al, 1999 J. Med. Chem. 42, 3033-40, Goodman, S. L., et al, 2002 J. Med. Chem. 45, 1045-51).

The cell-binding ligands or cell receptor agonists can be Ig-based and non-Ig-based protein scaffold molecules. The Ig-Based scaffolds can be selected, but not limited, from Nanobody (a derivative of VHH (camelid Ig)) (Muyldermans S., 2013 Annu Rev Biochem. 82, 775-97); Domain antibodies (dAb, a derivative of VH or VL domain) (Holt, L. J, et al, 2003, Trends Biotechnol. 21, 484-90); Bispecific T cell Engager (BiTE, a bispecific diabody) (Baeuerle, P. A, et al, 2009, Curr. Opin. Mol. Ther. 11, 22-30); Dual Affinity ReTargeting (DART, a bispecific diabody) (Moore P. A. P, et al. 2011, Blood 117(17), 4542-51); Tetravalent tandem antibodies (TandAb, a dimerized bispecific diabody) (Cochlovius, B, et al. 2000, Cancer Res. 60(16):4336-4341). The Non-Ig scaffolds can be selected, but not limited, from Anticalin (a derivative of Lipocalins) (Skerra A. 2008, FEBS J., 275(11): 2677-83; Beste G, et al, 1999 Proc. Nat. Acad.

USA. 96(5):1898-903; Skerra, A. 2000 Biochim Biophys Acta, 1482(1-2): 337-50; Skerra, A. 2007, Curr Opin Biotechnol. 18(4): 295-304; Skerra, A. 2008, FEBS J. 275(11): 2677-83); Adnectins (10th FN3 (Fibronectin)) (Koide, A, et al, 1998 J. Mol. Biol., 284(4):1141-51; Batori V, 2002, Protein Eng. 15(12): 1015-20; Tolcher, A. W, 2011, Clin. Cancer Res. 17(2): 363-71; Hackel, B. J, 2010, Protein Eng. Des. Sel. 23(4): 211-19); Designed Ankyrin Repeat Proteins (DARPins) (a derivative of ankrin repeat (AR) proteins) (Boersma, Y. L, et al, 2011 Curr Opin Biotechnol. 22(6): 849-57), e.g. DARPin $C_9$, DARPin Ec4 and DARPin E69_LZ3_E01 (Winkler J, et al, 2009 Mol Cancer Ther. 8(9), 2674-83; Patricia M-K. M., et al, Clin Cancer Res. 2011; 17(1):100-10; Boersma Y. L, et al, 2011 J. Biol. Chem. 286(48), 41273-85); Avimers (a domain A/low-density lipoprotein (LDL) receptor) (Boersma Y. L, 2011 J. Biol. Chem. 286(48): 41273-41285; Silverman J, et al, 2005 Nat. Biotechnol., 23(12):1556-61).

Examples of the structures of the conjugate of the antibody-cell-binding ligands or cell receptor agonists via the linker of the patent application are the followings: LBO1 (Folate conjugate conjugate), LB02 (PMSA ligand conjugate), LB03 (PMSA ligand conjugate), LB04 (Somatostatin conjugate), LB05 (Octreotide, a Somatostatin analog conjugate), LB06 (Lanreotide, a Somatostatin analog conjugate), LB07 (Vapreotide (Sanvar), a Somatostatin analog conjugate), LB08 (CAIX ligand conjugate), LB09 (CAIX ligand conjugate), LB10 (Gastrin releasing peptide receptor (GRPr), MBA conjugate), LB 11 (luteinizing hormone-releasing hormone (LH-RH) ligand and GnRH conjugate), LB12 (luteinizing hormone-releasing hormone (LH-RH) and GnRH ligand conjugate), LB13 (GnRH antagonist, Abarelix conjugate), LB14 (cobalamin, vitamin B12 analog conjugate), LB15 (cobalamin, vitamin B12 analog conjugate), LB16 (for $\alpha_v\beta_3$ integrin receptor, cyclic RGD pentapeptide conjugate), LB17 (hetero-bivalent peptide ligand conjugate for VEGF receptor), LB18 (Neuromedin B conjugate), LB19 (bombesin conjugate for a G-protein coupled receptor), LB20 ($TLR_2$ conjugate for a Toll-like receptor), LB21 (for an androgen receptor), LB22 (Cilengitide/cyclo (-RGDfV-) conjugate for an av intergrin receptor, LB23 (Fludrocortisone conjugate), LB24 (Dexamethasone conjugate), LB25 (fluticasone propionate conjugate), LB26 (Beclometasone dipropionate), LB27 (Triamcinolone acetonide conjugate), LB28 (Prednisone conjugate), LB29 (Prednisolone conjugate), LB30 (Methylprednisolone conjugate), LB31 (Betamethasone conjugate), LB32 (Irinotecan analog), LB33 (Crizotinib analog), LB34 (Bortezomib analog), LB35 (Carfilzomib analog), LB36 (Carfilzomib analog), LB37 (Leuprolide analog), LB38 (Triptorelin analog), LB39 (Liraglutide analog), LB40 (Semaglutide analog), and LB41 (Lixisenatide analog), which are shown in the following structures:

LB01

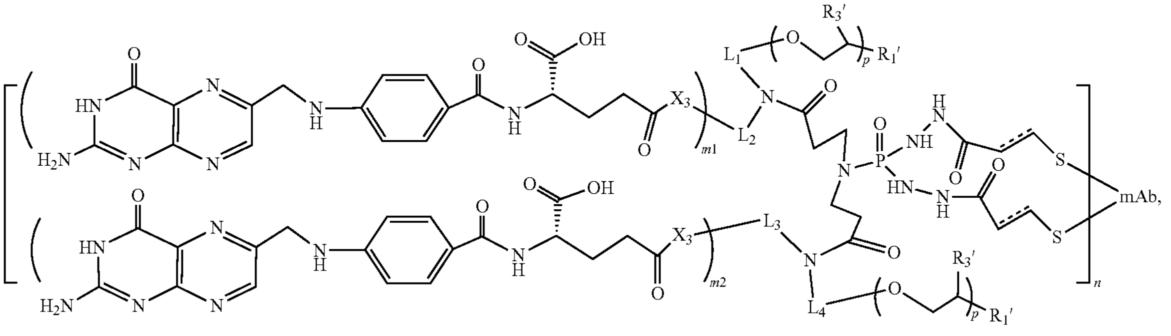

(Folate conjugate)

LB02

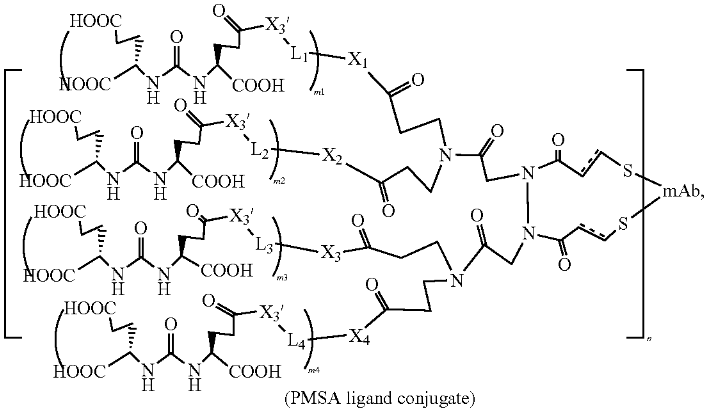

(PMSA ligand conjugate)

-continued
LB03
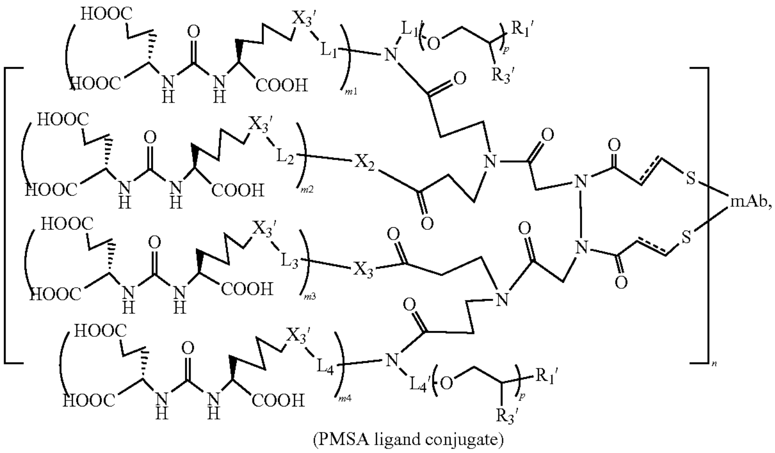
(PMSA ligand conjugate)
LB04
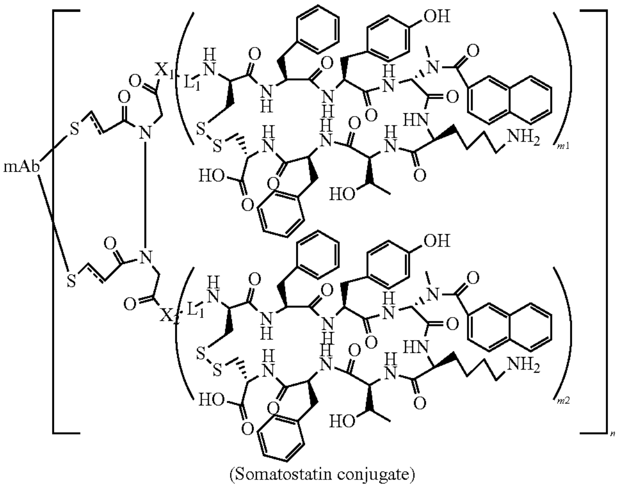
(Somatostatin conjugate)
LB05
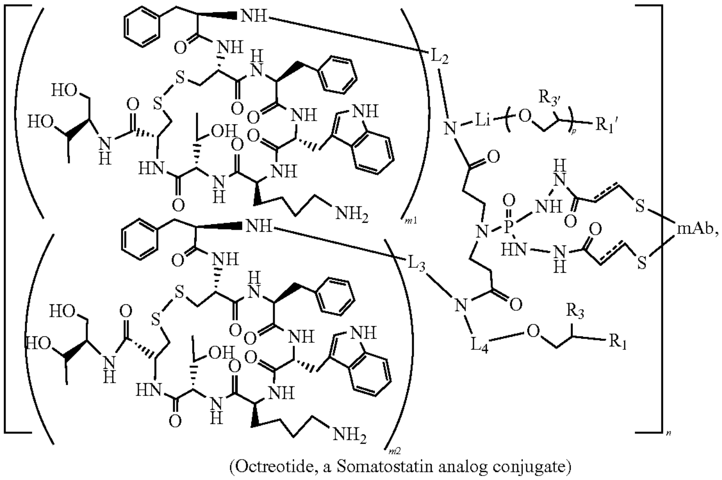
(Octreotide, a Somatostatin analog conjugate)

-continued
LB06
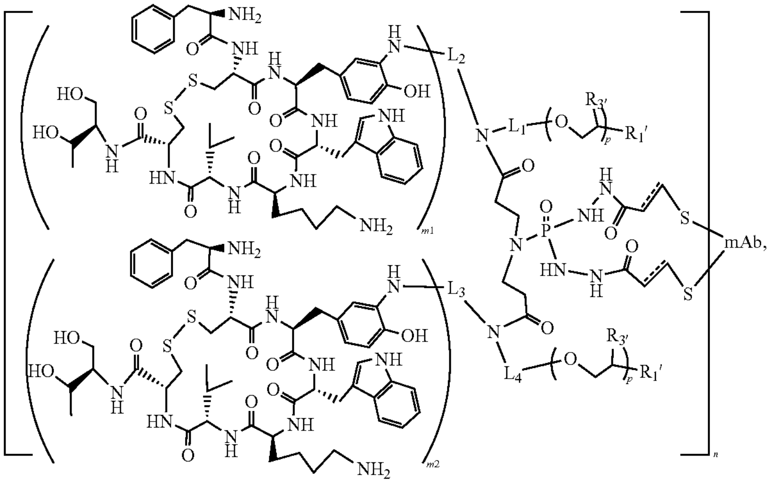
(Lanreotide, a Somatostatin analog conjugate)
LB07
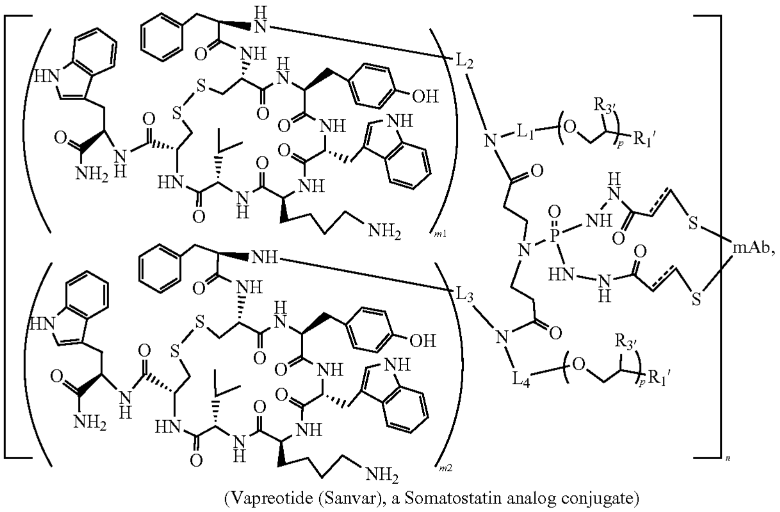
(Vapreotide (Sanvar), a Somatostatin analog conjugate)
LB08
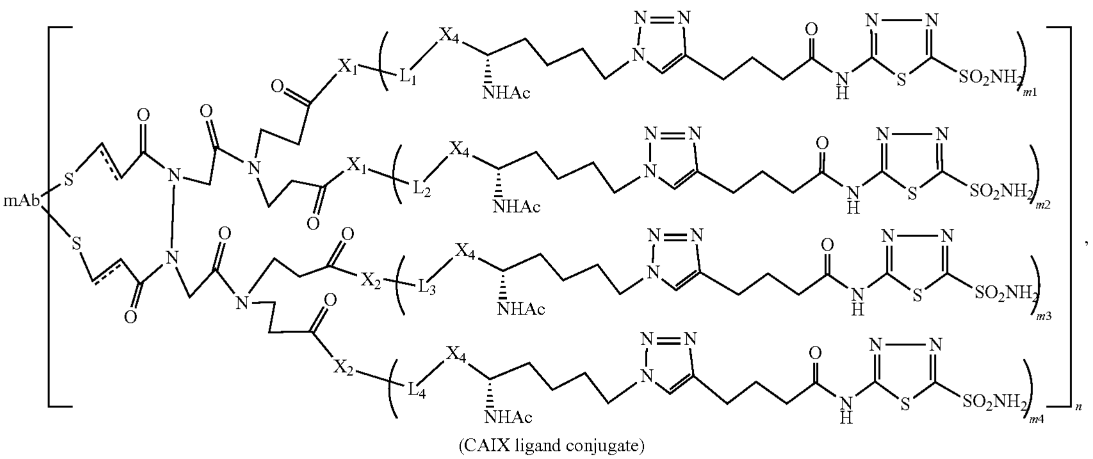
(CAIX ligand conjugate)

-continued
LB09
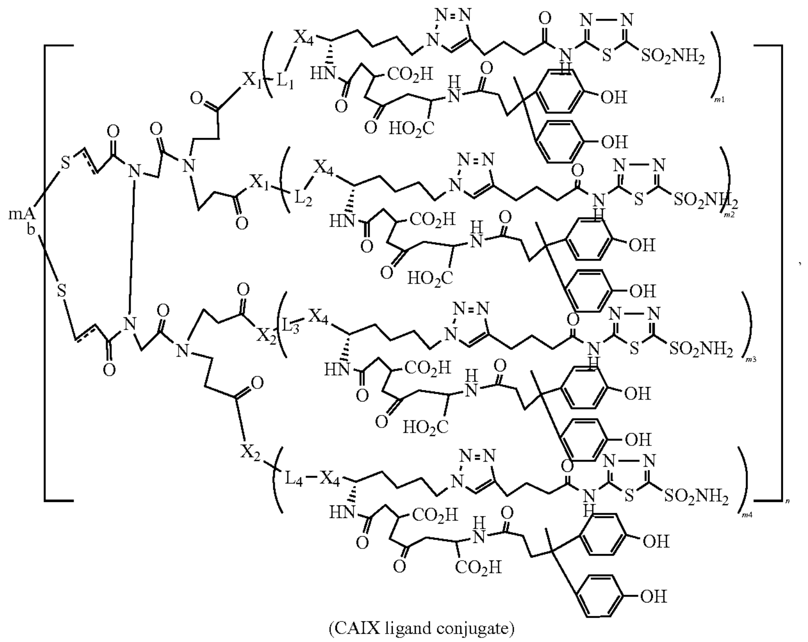
(CAIX ligand conjugate)
LB10
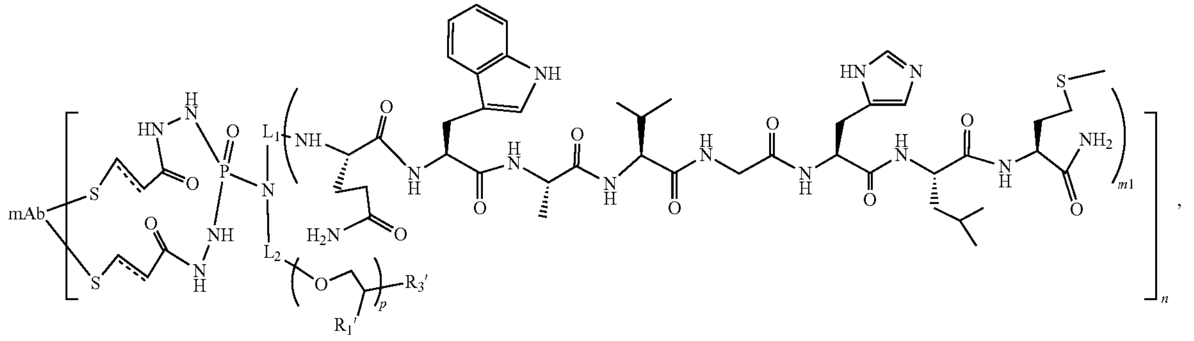
(Gastrin releasing peptide receptor (GRPr), MBA conjugate)

-continued
LB11
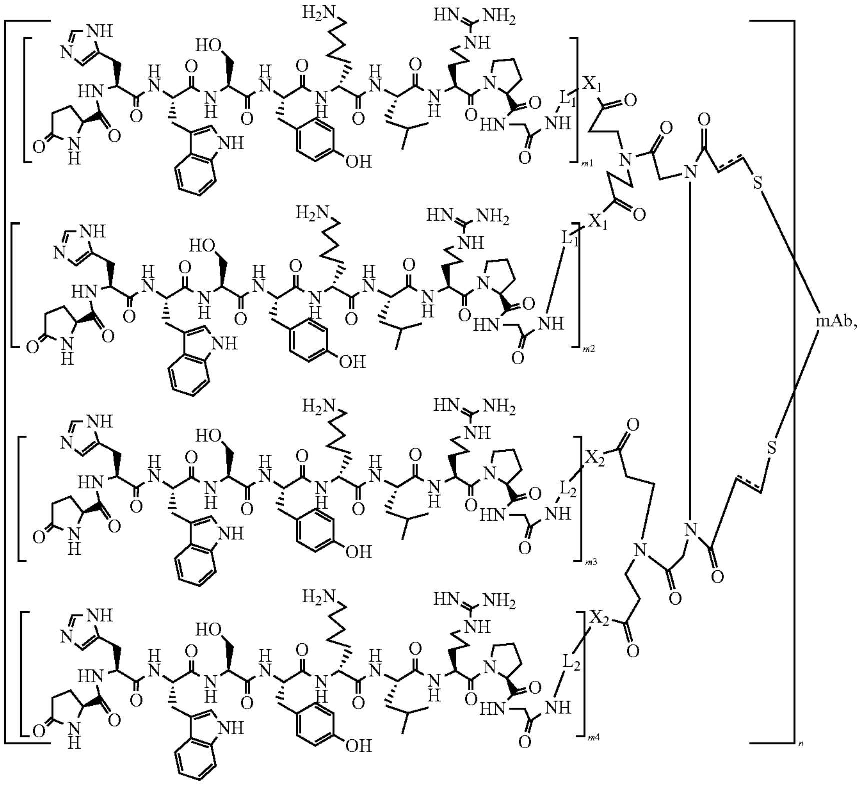
(luteinizing hormone-releasing hormone (LH—RH) ligand and GnRH conjugate)
LB12
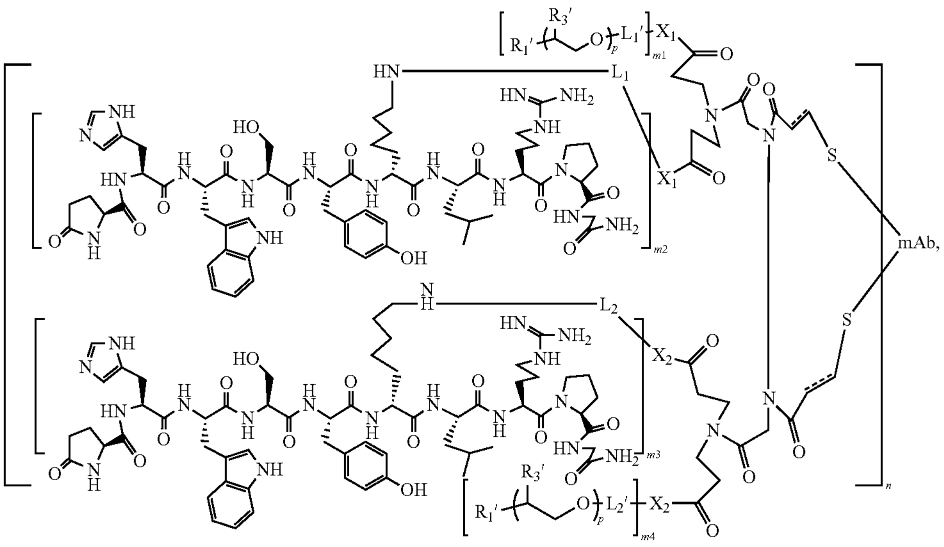
(luteinizing hormone-releasing hormone (LH—RH) ligand and GnRH ligand conjugate)

-continued
LB13
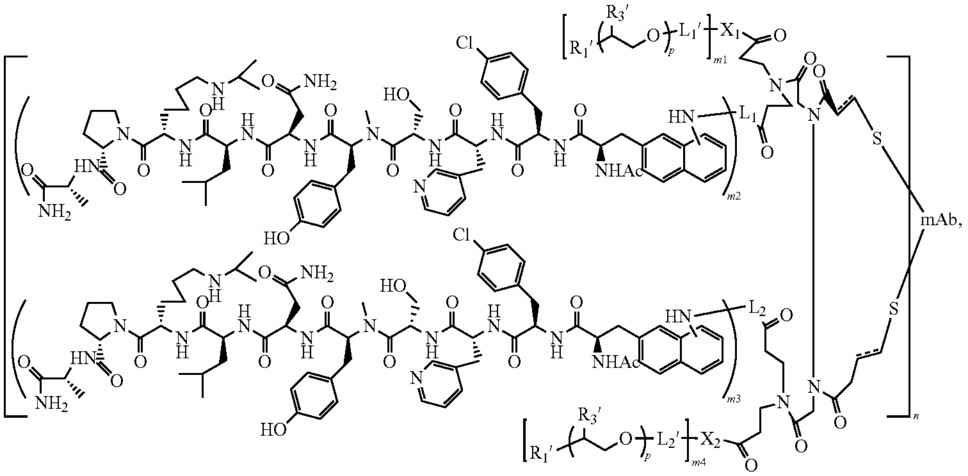
(GnRH antagonist, Abarelix conjugate)
LB14
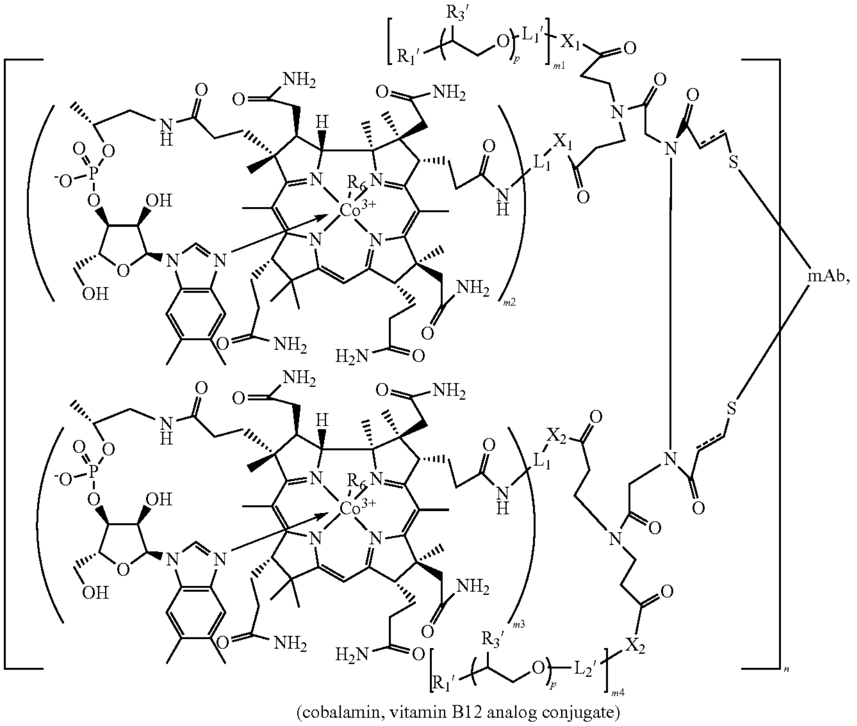
(cobalamin, vitamin B12 analog conjugate)

-continued
LB15
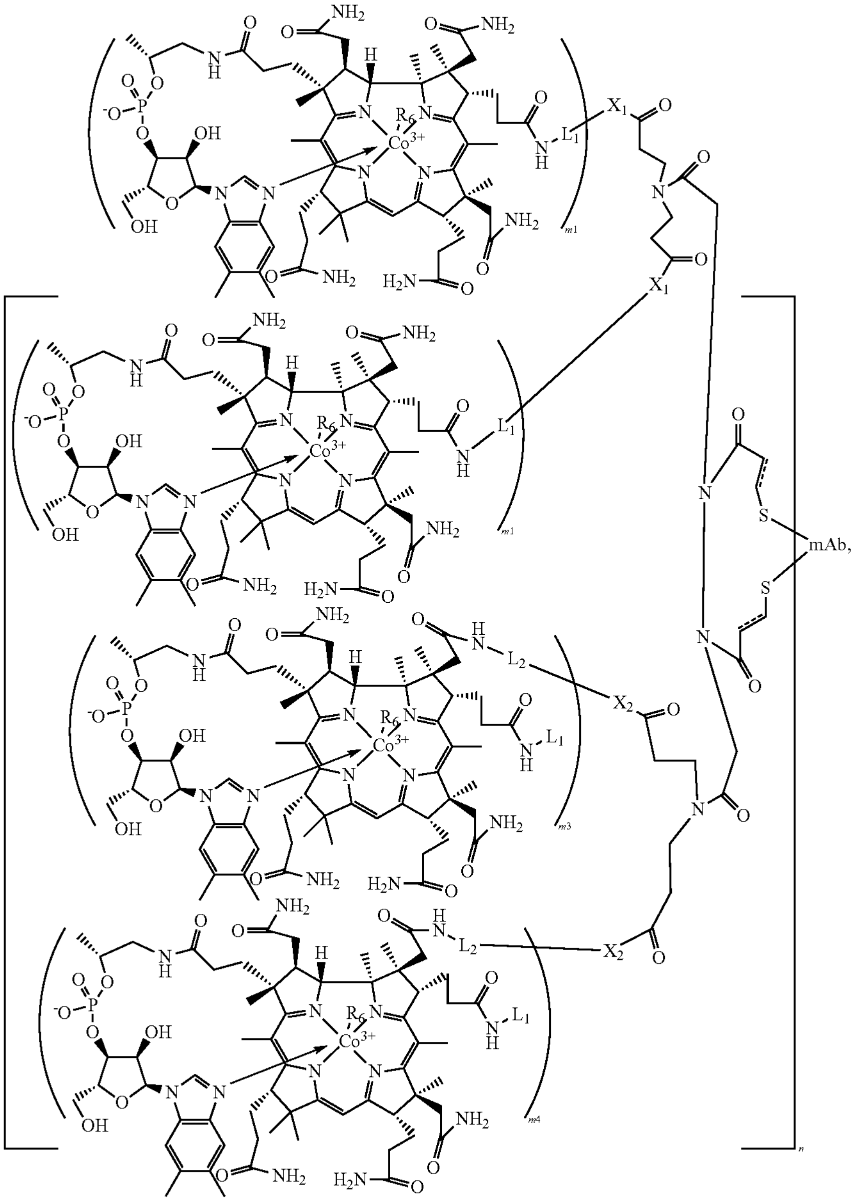
(cobalamin, vitamin B12 analog conjugate)
LB16
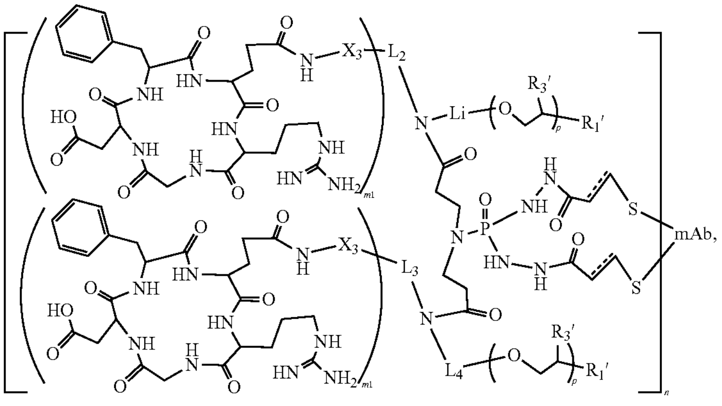
(for $\alpha_v\beta_3$ integrin receptor, cyclic RGD pentapeptide conjugate)

-continued
LB17
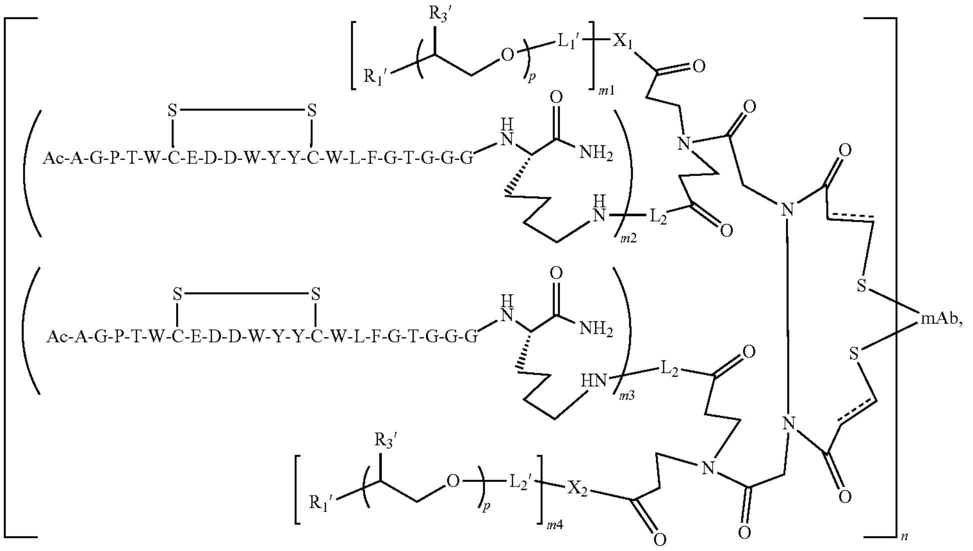
(hetero-bivalent peptide ligand conjugate for VEGF receptor)
LB18
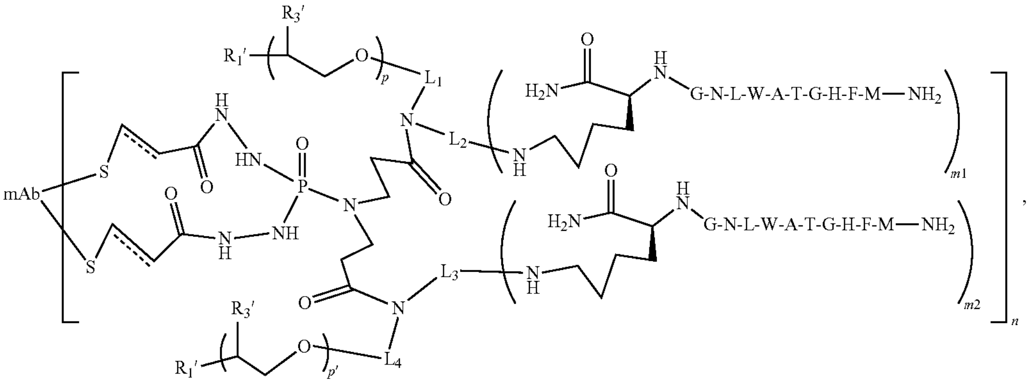
(Neuromedin B conjugate)
LB19
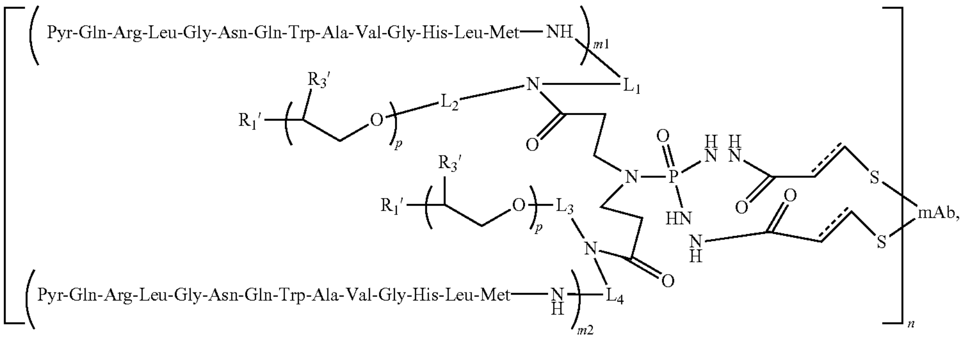
(bombesin conjugate for a G-protein coupled receptor)

-continued
LB20
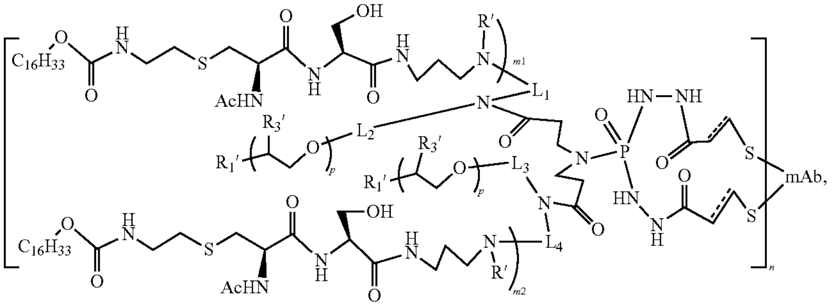
(TLR$_2$ conjugate for a Toll-like receptor,)
LB21
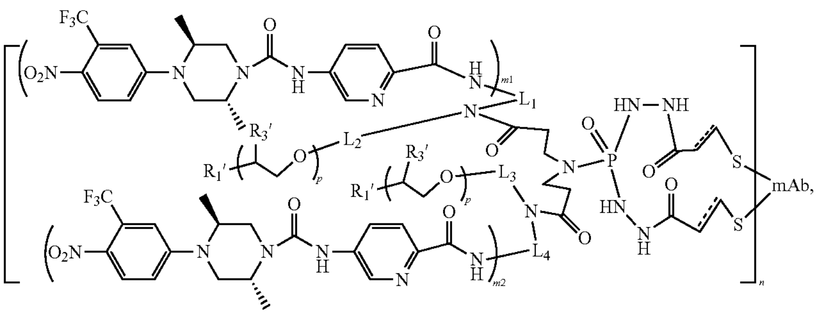
(an androgen receptor)
LB22
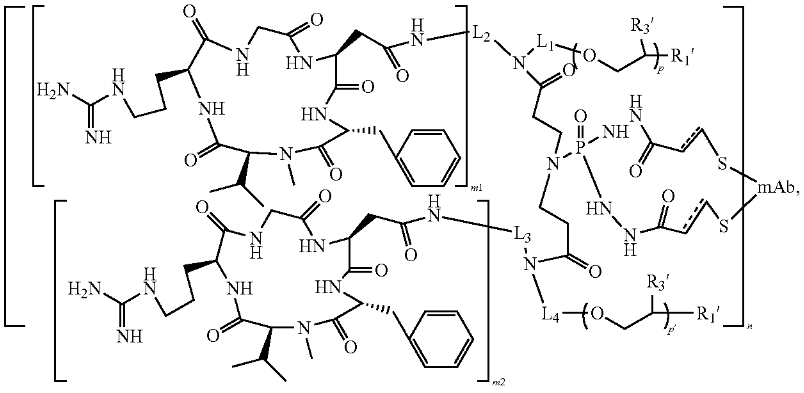
(Cilengitide/cyclo(-RGDfV-) conjugate for an $\alpha_v$ intergrin receptor)
LB23
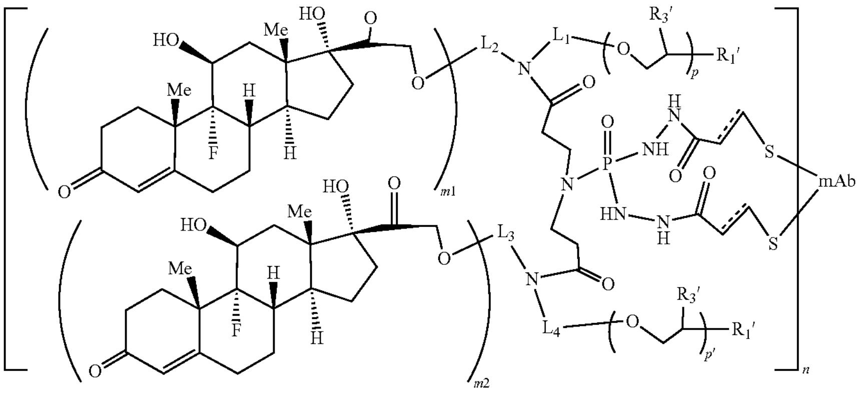
(Fludrocortisone conjugate)

-continued
LB24
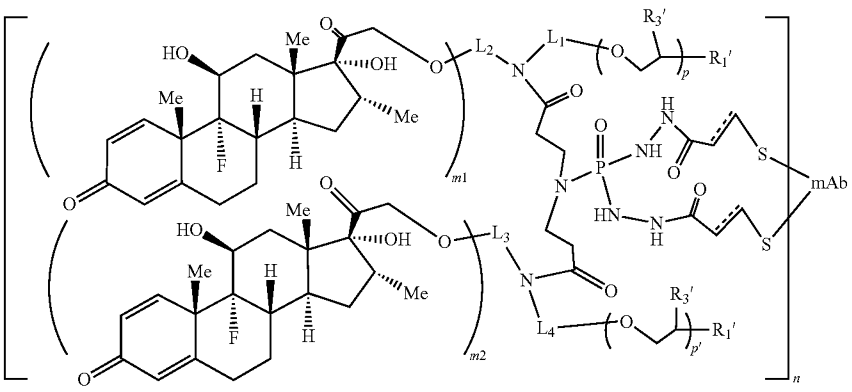
(Dexamethasone conjugate)
LB25
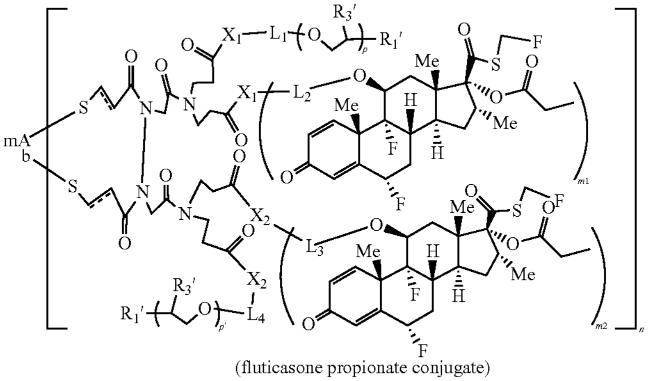
(fluticasone propionate conjugate)
LB26
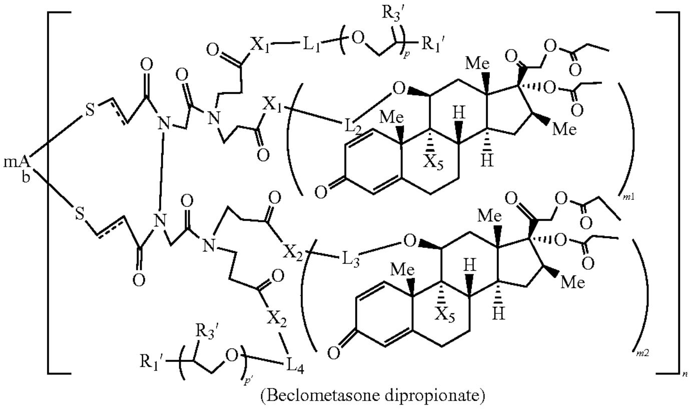
(Beclometasone dipropionate)
LB27
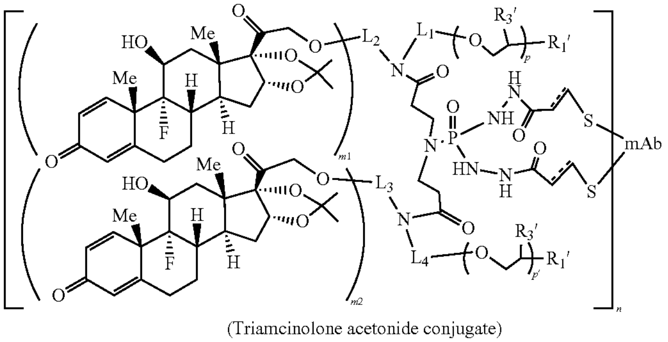
(Triamcinolone acetonide conjugate)

-continued
LB28
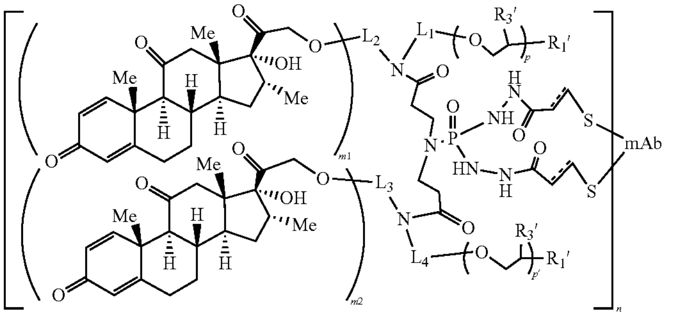
(Prednisone conjugate)
LB29
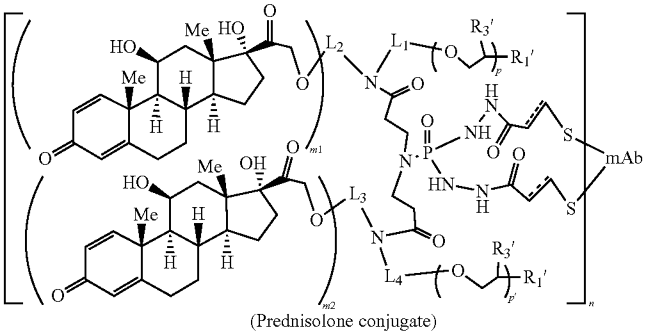
(Prednisolone conjugate)
LB30
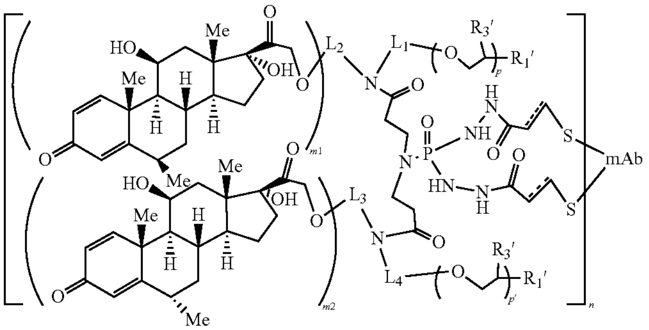
(Methylprednisolone conjugate)
LB31
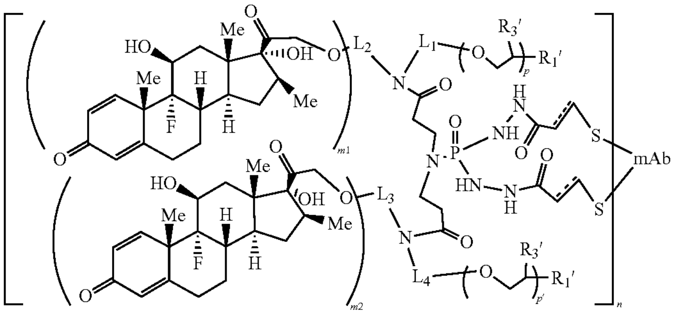
(Betamethasone conjugate)

-continued
LB32
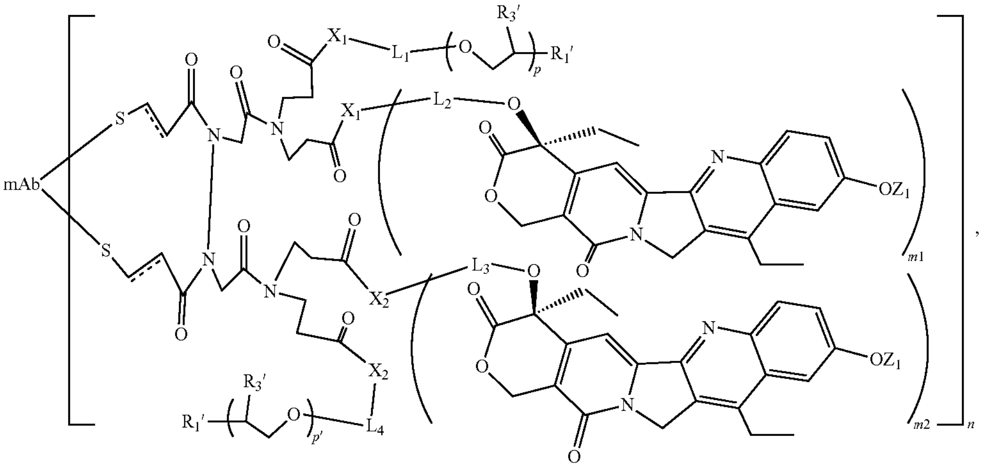
(Irinotecan analog)
LB33
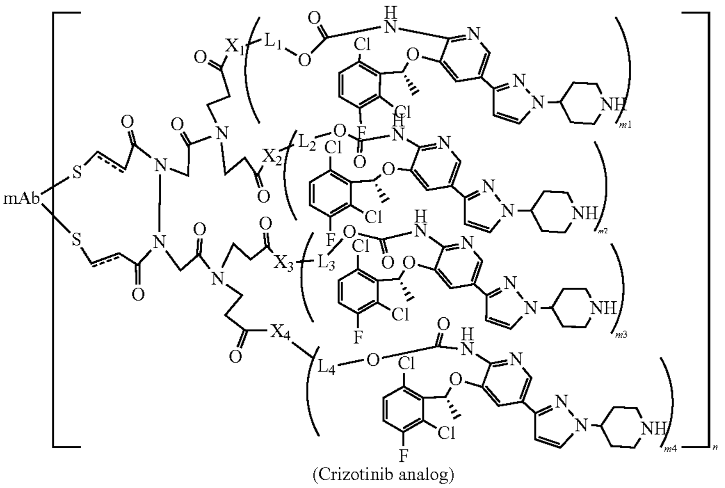
(Crizotinib analog)
LB34
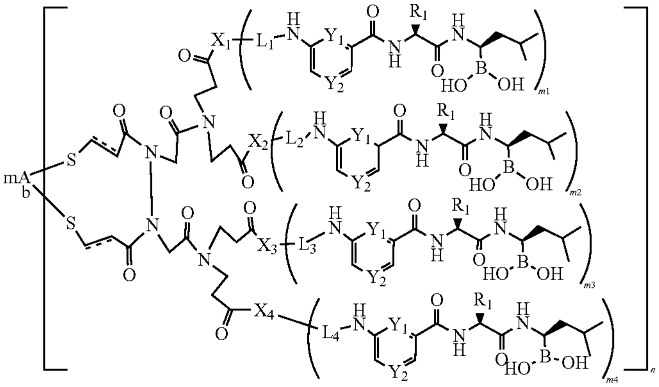
(Bortexomib analog), wherein $Y_1$, $Y_2$ is N, CH, C(Cl), C($CH_3$), C($COOR_1$) independently, $R_1$ is H, $C_1$-$C_6$ of Alkyl, $C_3$-$C_8$ of Ar.

-continued
LB35
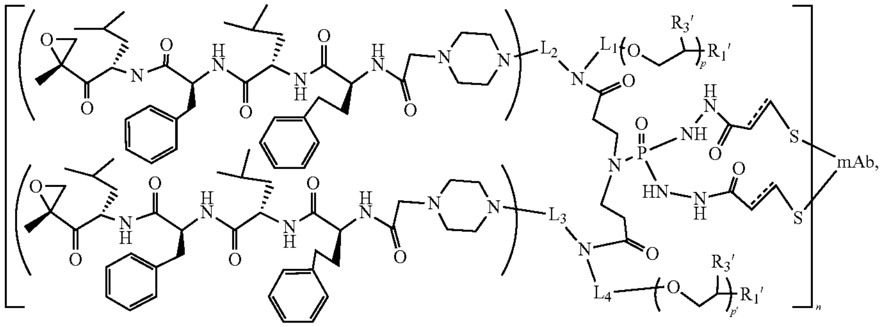
(Carfilaomib analog)
LB36
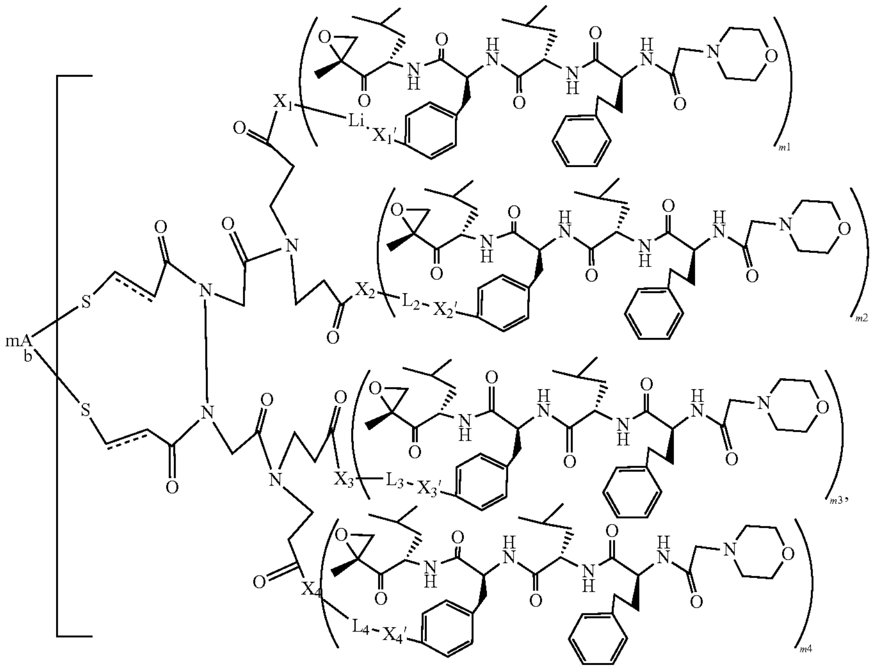
(Carfilzomib analog)
LB37
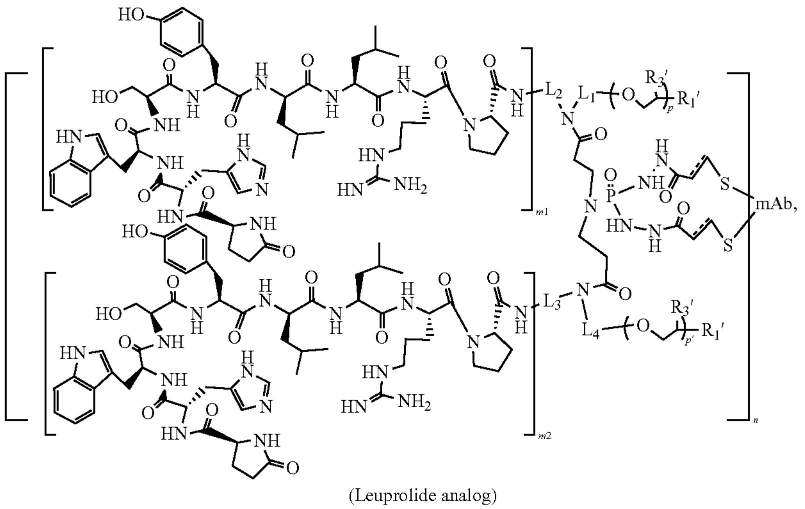
(Leuprolide analog)

-continued
LB38
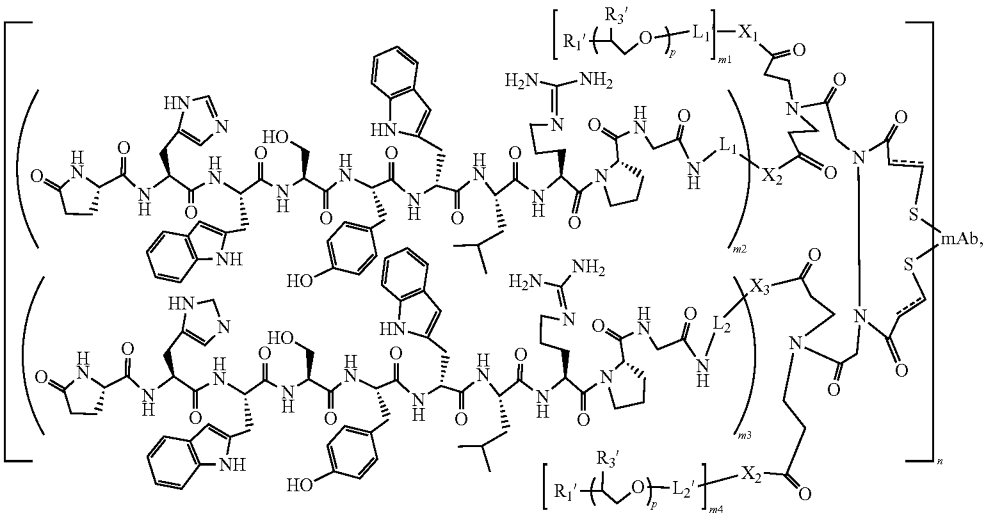
(Triptorelin analog)
LB39
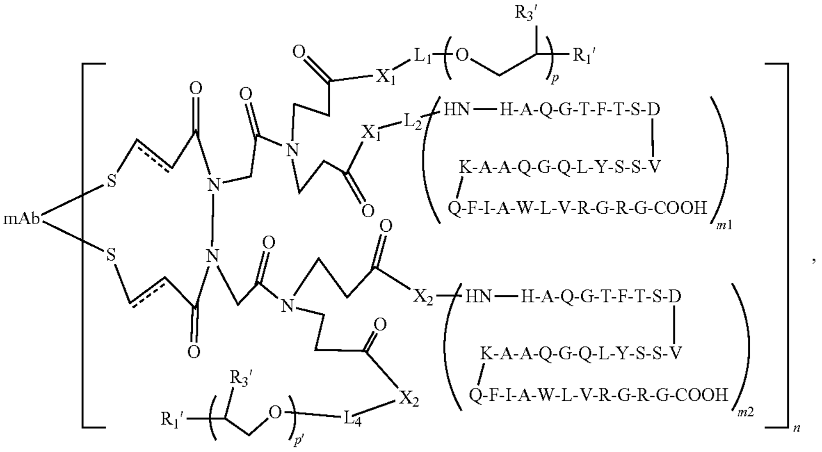
(Liraglutide analog)
LB40
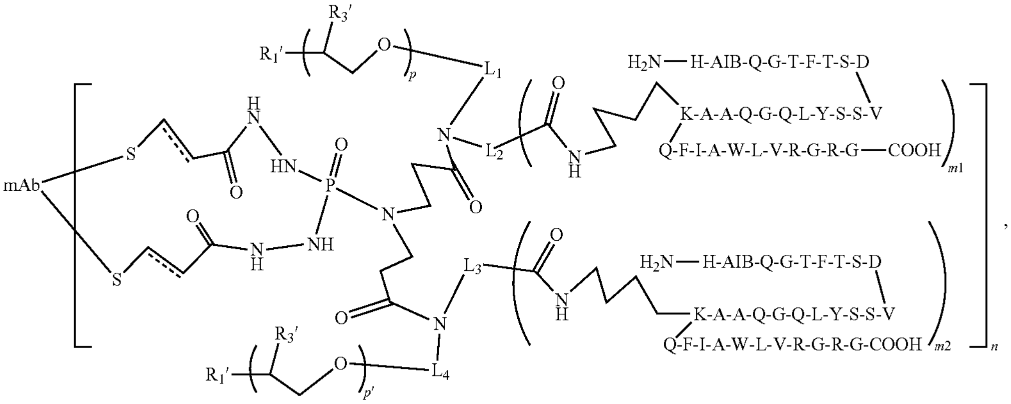
(Semaglutide analog)

-continued

LB41

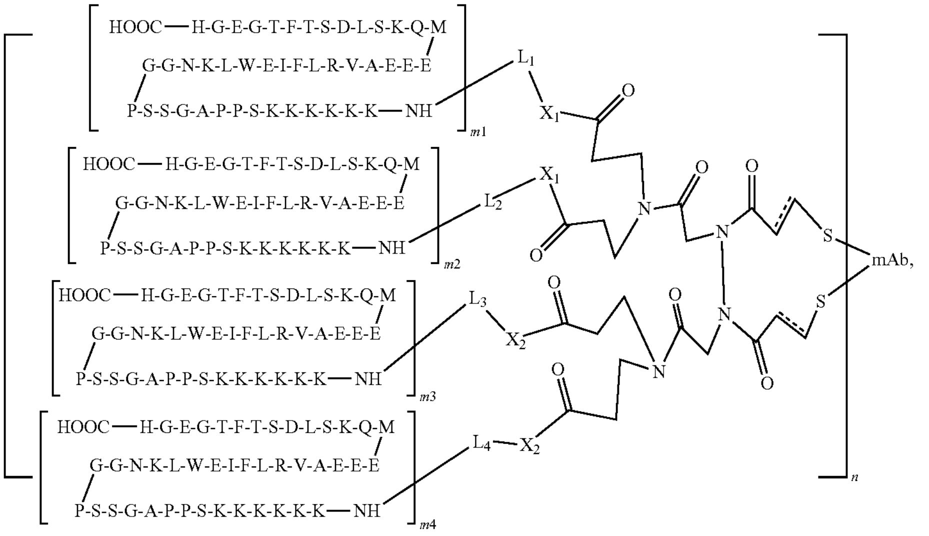

(Lixisenatide analog)

wherein mAb is an antibody; $X_3$ is $CH_2$, O, NH, NHC(O), NHC(O)NH, C(O), OC(O), OC(O)($NR_3$), $R_1$, $NHR_1$, $NR_1$, C(O)$R_1$ or absent; $X_4$ is H, $CH_2$, OH, 0, C(O), C(O)NH, C(O)N($R_1$), $R_1$, $NHR_1$, $NR_1$, C(O)$R_1$ or C(O)O; $X_5$ is H, $CH_3$, F, or Cl; $M_1$ and $M_2$ are independently H, Na, K, Ca, Mg, $NH_4$, $NR_1R_2R_3$; $R_6$ is 5'-deoxyadenosyl, Me, OH, or CN; “ ” represents either single bond or double bond; $m_1$, $m_2$, n, “ ”, $X_1$, $X_2$, $R_1$, and $R_2$ are the same defined in Formula (I). In addition, $R_1$ can be absent and $R_2$ can be H.

In yet another embodiment, one, two or more DNA, RNA, mRNA, small interfering RNA (siRNA), microRNA (miRNA), and PIWI interacting RNAs (piRNA) are preferred conjugated to a cell-binding molecule via a linker of this patent. Small RNAs (siRNA, miRNA, piRNA) and long non-coding antisense RNAs are known responsible for epigenetic changes within cells (Goodchild, J (2011), Methods in molecular biology (Clifton, N.J.). 764: 1-15). DNA, RNA, mRNA, siRNA, miRNA or piRNA herein can be single or double strands with nucleotide units from 3 to 1 million and some of their nucleotide can be none natural (synthetic) forms, such as oligonucleotide with phosphorothioate linkage as example of Fomivirsen, or the nucleotides are linked with phosphorothioate linkages rather than the phosphodiester linkages of natural RNA and DNA, and the sugar parts are deoxyribose in the middle part of the molecule and 2'-O-methoxyethyl-modified ribose at the two ends as example Mipomersen, or oligonucleotide made with peptide nucleic acid (PNA), Morpholino, Phosphorothioate, Thiophosphoramidate, or with 2'-O-Methoxyethyl (MOE), 2'-O-Methyl, 2'-Fluoro, Locked Nucleic Acid (LNA), or Bicyclic Nucleic Acid (BNA) of ribose sugar, or nucleic acids are modified to remove the 2'-3' carbon bond in the sugar ring (Whitehead, K. A.; et al (2011), *Annual Review of Chemical and Biomolecular Engineering* 2: 77-96; Bennett, C. F.; Swayze, E. E. (2010), *Annu. Rev. Pharmacol. Toxicol.* 50: 259-29). Preferably, oligonucleotide range in length is from approximately 8 to over 100 nucleotides. Examples of the structure of the conjugates are displayed below:

SI-1

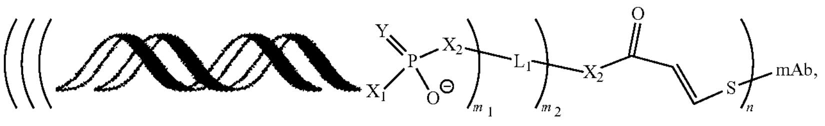

-continued
SI-2
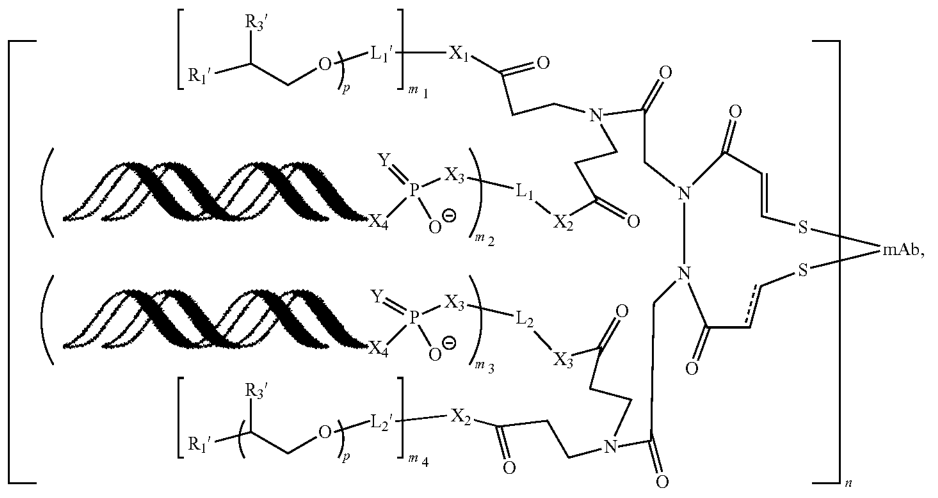
SI-3
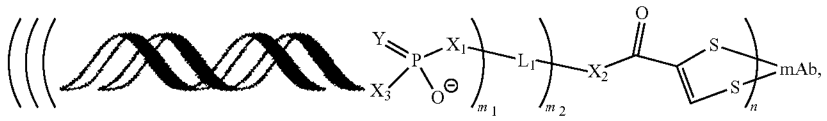
SI-4
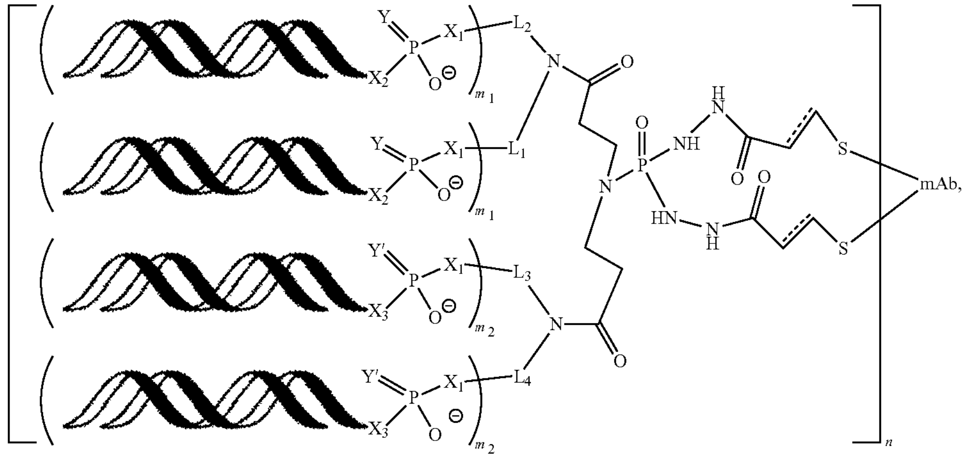
SI-5
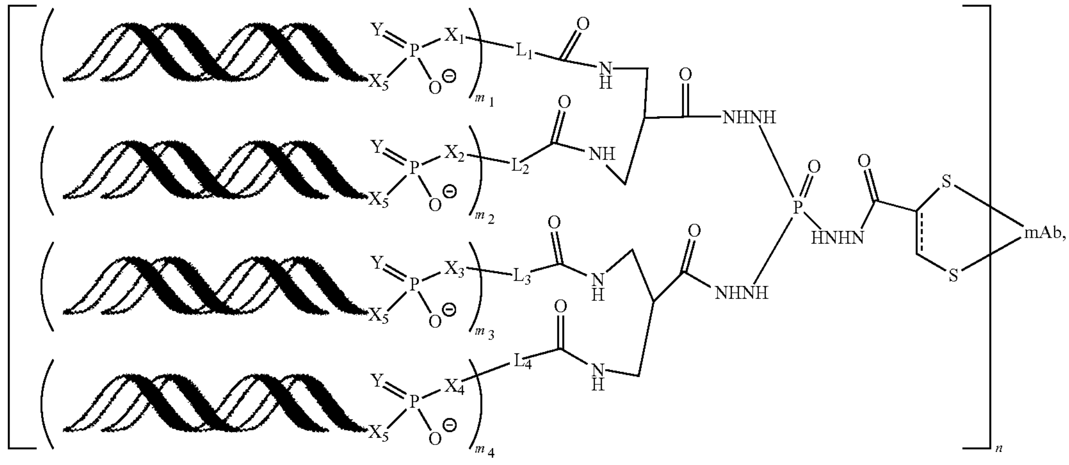

-continued

SI-6

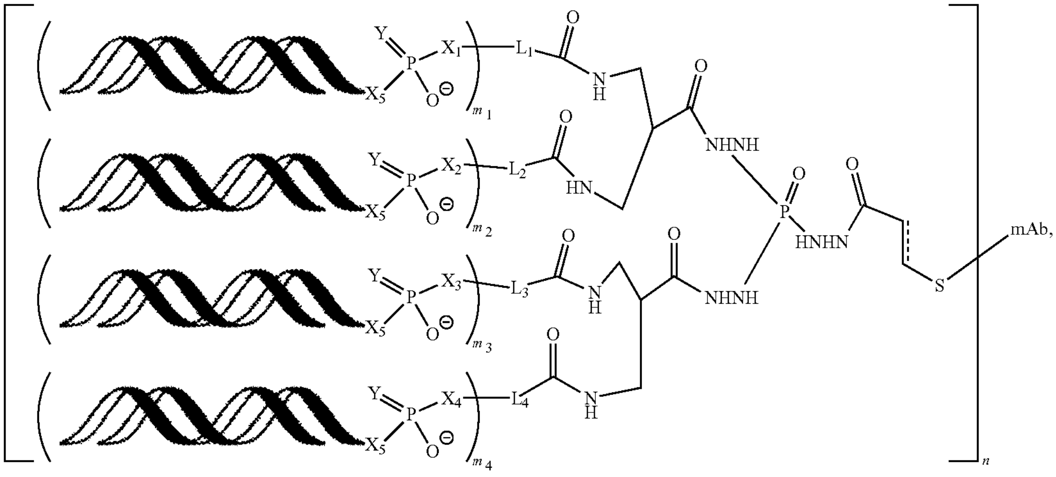

wherein mAb, $m_1$, $m_2$, n, $X_1$, $X_2$, $X_3$, $X_4$, Rr, R2% $L_1$, $L_2$, $L_3$, $L_4$, “====” “____”, are the same defined in Formula (I) or above; 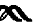 is single or double strands of DNA, RNA, mRNA, siRNA, miRNA, or piRNA; $X_5$ is defined the same as $X_1$; and Y and Y' are O, S, NH or $CH_2$.

Figure 46A:
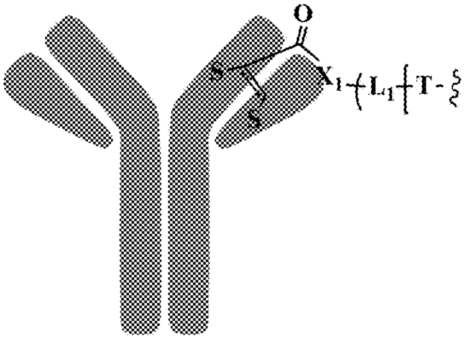
FIGS. 46*a* and 46*b* show the structures of IgG antibody conjugates ST1 to ST14.
Figure 46A:
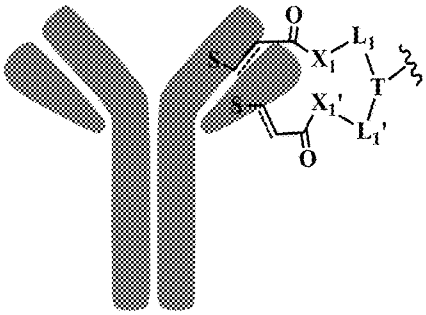
Figure 46A:
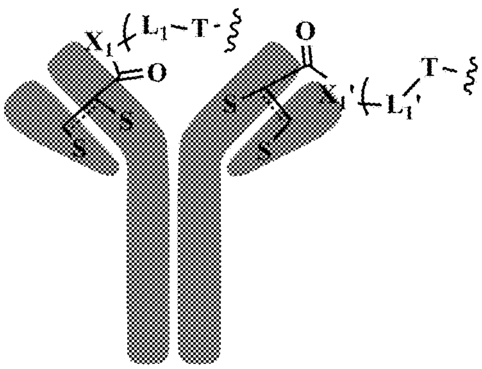
Figure 46A:
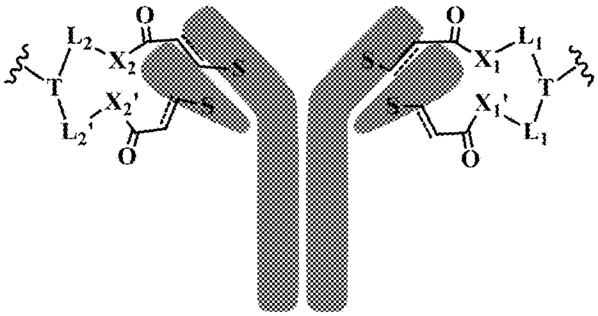
Figure 46A:
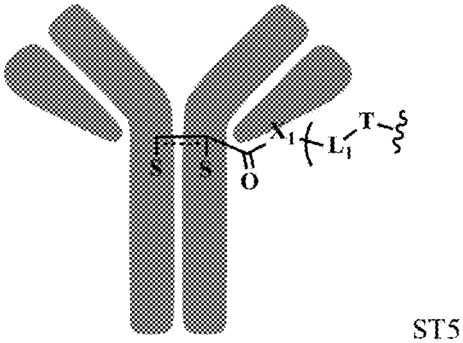
Figure 46A:
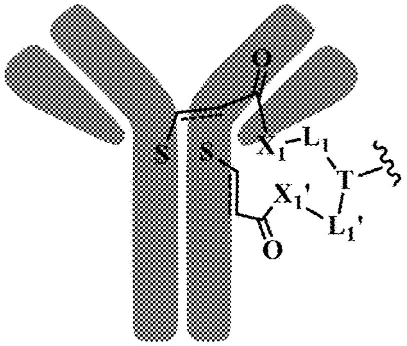
Figure 46A:
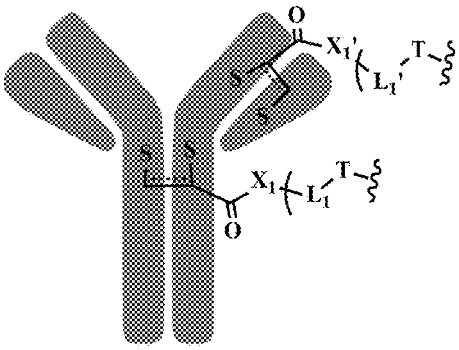
Figure 46A:
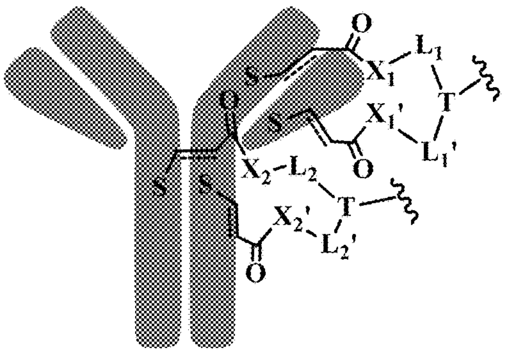
Figure 46B:
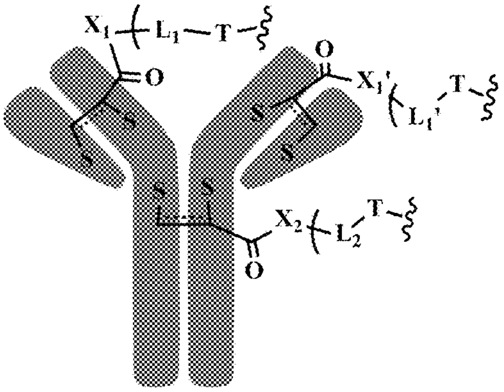
Figure 46B:
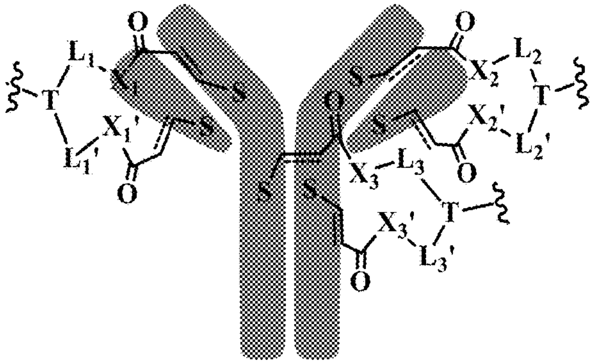
Figure 46B:
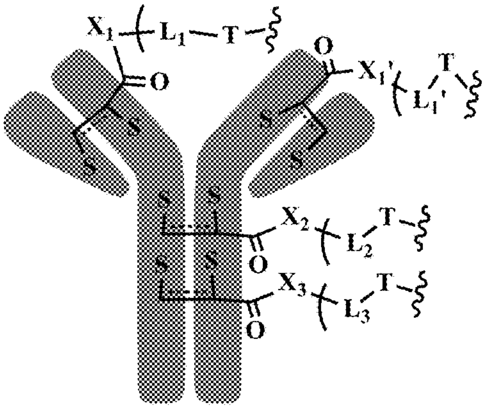
Figure 46B:
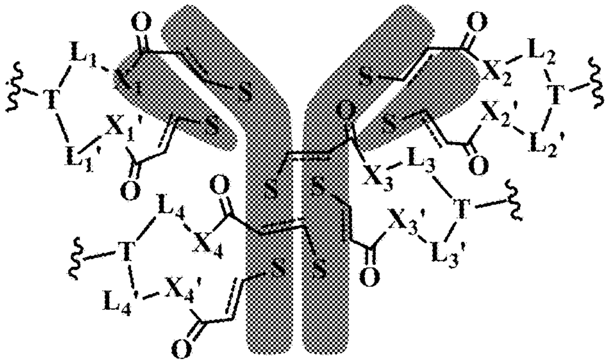
Figure 46B:
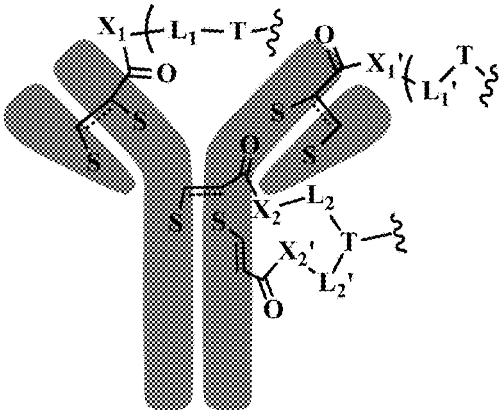
Figure 46B:
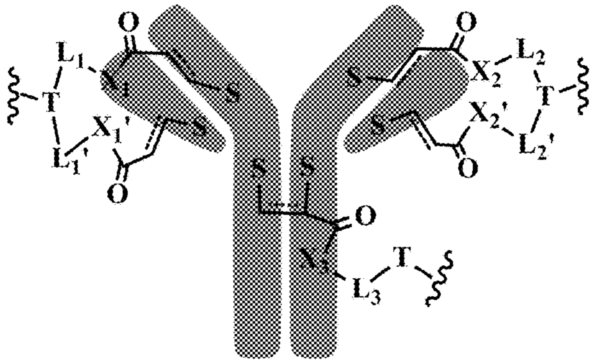

In yet another embodiment, IgG antibody conjugates conjugated with one, or two, or more differently function molecules or drugs are preferred to be conjugated specifically to a pair of thiols (through reduction of the disulfide bonds) between the light chain and heavy chain, the upper disulfide bonds between the two heavy chains, and the lower disulfide bonds between the two heavy chains as shown in structure, ST1, ST2, ST3, ST4, ST5, ST6, ST7 or ST8 shown in FIGS. 46*a* and 46*b*.

In yet another embodiment, a pharmaceutical composition comprising a therapeutically effective amount of the conjugate of Formula (II) or any conjugates described through the present patent can be administered concurrently with the other therapeutic agents such as the chemotherapeutic agent, the radiation therapy, immunotherapy agents, autoimmune disorder agents, anti-infectious agents or the other conjugates for synergistically effective treatment or prevention of a cancer, or an autoimmune disease, or an infectious disease. The synergistic agents are preferably selected from one or several of the following drugs: Abatacept (Orencia), Abiraterone acetate (Zytiga®), Acetaminophen/hydrocodone, Adalimumab, afatinib dimaleate (Gilotrif®), Alectinib (Alecensa), alemtuzumab (Campath®), Alitretinoin (Panretin®), ado-trastuzumab emtansine (Kadcyla™), Amphetamine mixed salts (Amphetamine/dextroamphetamine, or Adderall XR), anastrozole (Arimidex®), Aripiprazole, Atazanavir, Atezolizumab (Tecentriq, MPDL3280A), Atorvastatin, axitinib (Inlyta®), AZD9291, belinostat (Beleodaq™), Bevacizumab (Avastin®), Bortezomib (PS-341; Velcade, Neomib, Bortecad), Cabazitaxel (Jevtana®), Cabozantinib (Cometriq™), bexarotene (Targrtin®), Blinatumomab (Blincyto™), Bortezomib (Velcade®), bosutinib (Bosulif®), brentuximab vedotin (Adcetris®), Budesonide, Budesonide/formoterol, Buprenorphine, Capecitabine, carfilzomib (Kyprolis®), Celecoxib, ceritinib (LDK378/Zykadia), Cetuximab (Erbitux®), Ciclosporin, Cinacalcet, crizotinib (Xalkori®), Cobimetinib (Cotellic), Dabigatran, dabrafenib (Tafinlar®), Daratumumab (Darzalex), Darbepoetin alfa, Darunavir, imatinib mesylate (Gleevec®), dasatinib (Sprycel®), denileukin diftitox (Ontak®), Denosumab (Xgeva®), Depakote, Dexamethasone, Dexlansoprazole, Dexmethylphenidate, Dinutuximab (Unituxin™), Doxycycline, Duloxetine, Durvalumab (MEDI4736), Elotuzumab (Empliciti), Emtricitabine/Rilpivirine/Tenofovir disoproxil fumarate, Emtricitbine/tenofovir/efavirenz, Enoxaparin, Enzalutamide (Xtandi®), Epoetin alfa, erlotinib (Tarceva®), Esomeprazole, Eszopiclone, Etanercept, Everolimus (Afinitor®), exemestane (Aromasin®), everolimus (Afinitor®), Ezetimibe, Ezetimibe/simvastatin, Fenofibrate, Filgrastim, fingolimod, Fluticasone propionate, Fluticasone/salmeterol, fulvestrant (Faslodex®), gefitinib (Iressa®), Glatiramer, Goserelin acetate (Zoladex), Icotinib, Imatinib (Gleevec), Ibritumomab tiuxetan (Zevalin®), ibrutinib (Imbruvica™), idelalisib (Zydelig®), Infliximab, iniparib, Insulin aspart, Insulin detemir, Insulin glargine, Insulin lispro, Interferon beta 1a, Interferon beta 1b, lapatinib (Tykerb®), Ipilimumab (Yervoy®), Ipratropium bromide/salbutamol, Ixazomib (Ninlaro), Lanreotide acetate (Somatuline® Depot), Lenaliomide (Revlimid®), Lenvatinib (Lenvima™), letrozole (Femara®), Levothyroxine, Levothyroxine, Lidocaine, Linezolid, Liraglutide, Lisdexamfetamine, MEDI4736 (AstraZeneca, Celgene), Memantine, Methylphenidate, Metoprolol, Modafinil, Mometasone, Necitumumab (Portrazza), Nilotinib (Tasigna®), niraparib, Nivolumab (Opdivo®), ofatumumab (Arzerra®), obinutuzumab (Gazyva™), Olaparib (Lynparza™), Olmesartan, Olmesartan/hydrochlorothiazide, Omalizumab, Omega-3 fatty acid ethyl esters, Oseltamivir, Osimertinib (or mereletinib, Tagrisso), Oxycodone, Palbociclib (Ibrance®), Palivizumab, panitumumab (Vectibix®), panobinostat (Farydak®), pazopanib (Votrient®), Pembrolizumab (Keytruda®), Pemetrexed (Alimta), pertuzumab (Perjeta™), Pneumococcal conjugate vaccine, pomalidomide (Pomalyst®), Pregabalin, Propranolol, Quetiapine, Rabeprazole, radium 223 chloride (Xofigo®), Raloxifene, Raltegravir, ramucirumab (Cyramza®), Ranibizumab, regorafenib (Stivarga®), Rituximab (Rituxan®), Rivaroxaban, romidepsin (Istodax®), Rosuvastatin, ruxolitinib phosphate (JakafiT$^{M}$), Salbutamol, Sevelamer, Sildenafil, siltuximab (Sylvant™), Sitagliptin, Sitagliptin/metformin, Solifenacin, Sonidegib (LDE225, Odomzo), Sorafenib (Nexavar®), Sunitinib (Sutent®), Tadalafil, tamoxifen, Telaprevir, talazoparib, temsirolimus (Torisel®), Tenofovir/emtricitabine, Testosterone gel, Thalidomide (Immunoprin, Talidex), Tiotropium bromide, toremifene (Fareston®), trametinib (Mekinist®), Trastuzumab, Trabectedin (ecteinascidin 743, Yondelis), Trifluridine/tipiracil (Lonsurf, TAS-102), Tretinoin (Vesanoid®), Ustekinumab, Valsartan, veliparib, vandetanib (Caprelsa®), Vemurafenib (Zelboraf®), Venetoclax (Venclexta), vorinostat (Zolinza®), ziv-aflibercept (Zaltrap®), Zostavax., and their analogs, derivatives, pharmaceutically acceptable salts, carriers, diluents, or excipients thereof, or a combination above thereof.

The drugs/cytotoxic agents used for conjugation via a bridge linker of the present patent can be any analogues and/or derivatives of drugs/molecules described in the present patent. One skilled in the art of drugs/cytotoxic agents will readily understand that each of the drugs/cytotoxic agents described herein can be modified in such a manner that the resulting compound still retains the specificity and/or activity of the starting compound. The skilled artisan will also understand that many of these compounds can be used in place of the drugs/cytotoxic agents described herein. Thus, the drugs/cytotoxic agents of the present invention include analogues and derivatives of the compounds described herein.

All references cited herein and in the examples that follow are expressly incorporated by reference in their entireties.

EXAMPLES

The invention is further described in the following examples, which are not intended to limit the scope of the invention. Cell lines described in the following examples were maintained in culture according to the conditions specified by the American Type Culture Collection (ATCC) or Deutsche Sammlung von Mikroorganismen und Zellkulturen GmbH, Braunschweig, Germany (DMSZ), or The Shanghai Cell Culture Institute of Chinese Acadmy of Science, unless otherwise specified. Cell culture reagents were obtained from Invitrogen Corp., unless otherwise specified. All anhydrous solvents were commercially obtained and stored in Sure-seal bottles under nitrogen. All other reagents and solvents were purchased as the highest grade available and used without further purification. The preparative HPLC separations were performed with Varain PreStar HPLC. NMR spectra were recorded on Varian Mercury 400 MHz Instrument. Chemical shifts (.delta.) are reported in parts per million (ppm) referenced to tetramethylsilane at 0.00 and coupling constants (J) are reported in Hz. The mass spectral data were acquired on a Waters Xevo QTOF mass spectrum equipped with Waters Acquity UPLC separations module and Acquity TUV detector.

Example 1. Synthesis of di-tert-butyl 1,2-bis(2-(tert-butoxy)-2-oxoethyl)hydrazine-1,2-dicarboxylate (38)

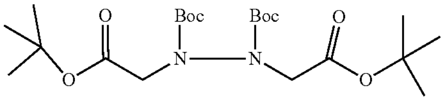 [SMILES: CC(C)(C)OC(=O)CN(C(=O)OC(C)(C)C)N(CC(=O)OC(C)(C)C)C(=O)OC(C)(C)C]

To di-tert-butyl hydrazine-1,2-dicarboxylate (37) (8.01 g, 34.4 mmol) in DMF (150 ml) was added NaH (60% in oil, 2.76 g, 68.8 mmol). After stirred at RT for 30 min, tert-butyl 2-bromoacetate (14.01 g, 72.1 mmol) was added. The mixture was stirred overnight, quenched with addition of methanol (3 ml), concentrated, diluted with EtOAc (100 ml) and water (100 $m_l$), separated, and the aqueous layer was extracted with EtOAc (2×50 ml). The organic layers were combined, dried over $MgSO_4$, filtered, evaporated, and purified by $SiO_2$ column chromatography (EtOAc/Hexane 1:5 to 1:3) to afford the title compound (12.98 g, 82% yield) as colorless oil. MS ESI m/z calcd for $C_{22}H_{41}N_2O_8$ $[M+H]^+$ 461.28, found 461.40.

Example 2. Synthesis of 2,2'-(hydrazine-1,2-diyl)diacetic acid (39)

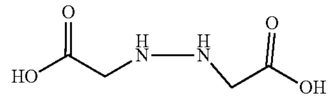

Di-tert-butyl 1,2-bis(2-(tert-butoxy)-2-oxoethyl)hydrazine-1,2-dicarboxylate (6.51 g, 14.14 mmol) in 1,4-dioxane (40 ml) was added HCl (12 M, 10 ml). The mixture was stirred for 30 min, diluted with dioxane (20 ml) and toluene (40 ml), evaporated and co-evaporated with dioxane (20 ml) and toluene (40 ml) to dryness to afford the crude title product for the next step without further production (2.15 g, 103% yield, ~93% pure). MS ESI m/z calcd for $C_4H_9N_2O_4$ $[M+H]^+$ 149.05, found 149.40.

Example 3. Synthesis of 2,2'-(1,2-bis((E)-3-bromoacryloyl)hydrazine-1,2-diyl)diacetic acid (36)

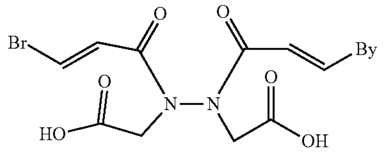

To a solution of 2,2'-(hydrazine-1,2-diyl)diacetic acid (1.10 g, 7.43 mmol) in the mixture of THF (50 ml) and $NaH_2PO_4$ (0.1 M, 80 ml, pH 6.0) was added (E)-3-bromoacryloyl bromide (5.01 g, 23.60 mmol). The mixture was stirred for 6 h, concentrated and purified on $SiO_2$ column eluted with $H_2O/CH_3CN$ (1:9) containing 3% formic acid to afford the title compound (2.35 g, 77% yield, ~93% pure). MS ESI m/z calcd for $C_{10}H_{11}Br_2N_2O_6$ $[M+H]^+$ 412.89, found 413.50.

Example 4. Synthesis of 2,2'-(1,2-bis((E)-3-bromoacryloyl)hydrazine-1,2-diyl)diacetyl chloride (41)

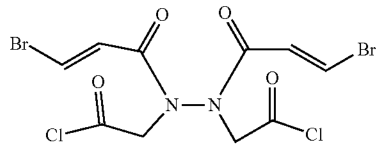 [SMILES: O=C(Cl)CN(C(=O)/C=C/Br)N(CC(=O)Cl)C(=O)/C=C/Br]

2,2'-(1,2-Bis((E)-3-bromoacryloyl)hydrazine-1,2-diyl)diacetic acid (210 mg, 0.509 mmol) in dichloroethane (15 ml) was added $(COCl)_2$ (505 mg, 4.01 mmol), followed by addition of 0.040 $m_l$ of DMF. After stirred at RT for 2 h, the mixture was concentrated and co-evaporated with dichloroethane (2x20 ml) and toluene (2x15 ml) to dryness to afford the title crude product (which is not stable) for the next step without further purification (245 mg, 107% yield). MS ESI m/z calcd for $C_{10}H_9Br_2Cl_2N_2O_4$ $[M+H]^+$ 448.82, 450.82, 452.82, 454.82, found 448.60, 450.60, 452.60, 454.60.

Example 5. Synthesis of tert-butyl 2,8-dioxo-1,5-oxazocane-5-carboxylate (47)

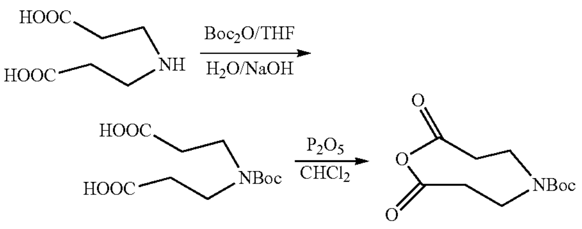

To a solution of 3,3'-azanediyldipropanoic acid (42) (10.00 g, 62.08 mmol) in 1.0 M NaOH (300 ml) at 4° C. was added di-tert-butyl dicarbonate (22.10 g, 101.3 mmol) in 200 $m_l$ THF in 1 h. After addition, the mixture was kept to stirring for 2 h at 4° C. The mixture was carefully acidified to pH ~4 with 0.2 M $H_3PO_4$, concentrated in vacuo, extracted with CH2C12, dried over Na2SO4, evaporated and purified with flash $SiO_2$ chromatography eluted with AcOH/MeOH/$CH_2Cl_2$ (0.01:1:5) to afford 3,3'-((tert-butoxycarbonyl)azanediyl)dipropanoic acid (46) (13.62 g, 84% yield). ESI MS m/z $C_{11}H_{19}NO_6$ $[M+H]^+$, cacld. 262.27, found 262.40.

To a solution of 3,3'-((tert-butoxycarbonyl)azanediyl) dipropanoic acid (8.0 g, 30.6 mmol) in $CH_2Cl_2$ (500 ml) at 0° C. was added phosphorus pentoxide (8.70 g, 61.30 mmol). The mixture was stirred at 0° C. for 2 h and then r.t. for 1 h, filtered through short $SiO_2$ column, and rinsed the column with EtOAc/$CH_2Cl_2$ (1:6). The filtrate was concentrated and triturated with EtOAc/hexane to afford the title compound (47) (5.64 g, 74% yield). ESI MS m/z $C_{11}H_{17}NO_5$ $[M+H]^+$, cacld. 244.11, found 244.30.

Example 6. Synthesis of 2,5-dioxopyrrolidin-1-yl propiolate (61)

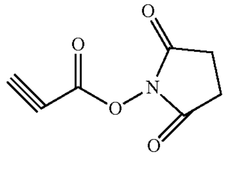

Propiolic acid (5.00 g, 71.4 mmol), NHS (9.01 g, 78.3 mmol) and EDC (20.0 g, 104.1 mmol) in $CH_2Cl_2$ (150 ml) and DIPEA (5 ml, 28.7 mmol) was stirred for overnight, evaporated and purified by $SiO_2$ column chromatography (EtOAc/Hexane 1:4) to afforded the title compound (9.30 g, 79% yield) as a colorless oil. $^1H$ NMR (500 MHz, $CDCl_3$) δ 2.68 (s, 1H), 2.61 (s, 4H). MS ESI m/z calcd for $C_7H_5NaNO_4$ $[M+Na]^+$190.02, found 190.20.

Example 7. Synthesis of tert-butyl 2-propioloylhydrazinecarboxylate (88)

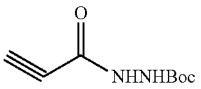

Propiolic acid (5.00 g, 71.4 mmol), tert-butyl hydrazinecarboxylate (9.45 g, 71.5 mmol) and EDC (20.0 g, 104.1 mmol) in $CH_2Cl_2$ (150 ml) and DIPEA (5 ml, 28.7 mmol) was stirred for overnight, evaporated and purified by $SiO_2$ column chromatography (EtOAc/Hexane 1:5) to afforded the title compound (7.92 g, 84% yield) as a colorless oil. $^1H$ NMR (500 MHz, $CDCl_3$) δ 8.76 (m, 2H), 2.68 (s, 1H), 1.39 (s, 9H). MS ESI m/z calcd for $C_5H_{12}NaN_2O_2$ $[M+Na]^+$ 155.09, found 155.26.

Example 8. Synthesis of propiolohydrazide, HCl salt (89)

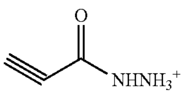

Tert-butyl 2-propioloylhydrazinecarboxylate (4.01 g, 30.35 mmol) dissolved in 1,4-dioxane (12 mL) was treated with 4 $m_l$ of HCl (conc.) at 4° C. The mixture was stirred for 30 min, diluted with Dioxane (30 ml) and toluene (30 ml) and concentrated under vacuum. The crude mixture was purified on silica gel using a mixture of methanol (from 5% to 10%) and 1% formic acid in methylene chloride as the eluant to give title compound (2.11 g, 83% yield), ESI MS m/z $C_3H_5N_2O$ $[M+H]^+$, cacld. 85.03, found 85.30.

Example 9. Synthesis of (S, E)-2-methyl-N-(3-methylbutan-2-ylidene)propane-2-sulfonamide (186)

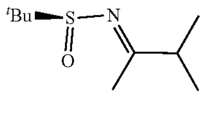

To a solution of (S)-2-methylpropane-2-sulfinamide (100 g, 0.825 mol, 1.0 eq.) in 1 L THF was added $Ti(OEt)_4$ (345 mL, 1.82 mol, 2.2 eq.) and 3-methyl-2-butanone (81 mL, 0.825 mol, 1.0 eq.) under $N_2$ at r.t. The reaction mixture was refluxed for 16 h, then cooled to r.t. and poured onto iced water. The mixture was filtered and the filter cake was washed with EtOAc. The organic layer was separated, dried over anhydrous $Na_2SO_4$ and concentrated to give a residue which was purified by vacuum distillation (15-20 torr, 95° C.) to afford the title product (141 g, 90% yield) as a yellow oil. $^1H$ NMR (500 MHz, $CDCl_3$) δ 2.54-2.44 (m, 1H), 2.25 (s, 3H), 1.17 (s, 9H), 1.06 (dd, J=6.9, 5.1 Hz, 6H). MS ESI m/z calcd for $C_9H_{19}NaNOS$ $[M+Na]^+$ 212.12; found 212.11.

Example 10. Synthesis of (2S,3S)-2-azido-3-methylpentanoic acid (177)

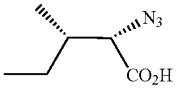

To a solution of $NaN_3$ (20.0 g, 308 mmol) in a mixture of water (50 mL) and dichloromethane (80 mL), cooled at 0° C., $Tf_2O$ (10 mL, 59.2 mmol, 2.0 eq.) was added slowly. After addition, the reaction was stirred at 0° C. for 2 h, then the organic phase was separated and the aqueous phase was extracted with dichloromethane (2×40 mL). The combined organic phases were washed with saturated $NaHCO_3$ solution and used as is. The dichloromethane solution of triflyl azide was added to a mixture of (L)-isoleucine (4.04 g, 30.8 mmol, 1.0 eq.), $K_2CO_3$ (6.39 g, 46.2 mmol, 1.5 eq.), $CuSO_4 \cdot 5H_2O$ (77.4 mg, 0.31 mmol, 0.01 eq.) in water (100 $m_l$) and methanol (200 ml). The mixture was stirred at r.t. for 16 h. The organic solvents were removed under reduced pressure and the aqueous phase was diluted with water (250 mL) and acidified to pH 6 with concentrated HCl and diluted with phosphate buffer (0.25 M, pH 6.2, 250 mL). The aqueous layer was washed with EtOAc (5×100 mL) to remove the sulfonamide by-product, and then acidified to pH 2 with concentrated HCl, extracted with EtOAc (3×150 mL). The combined organic layers were dried over anhydrous $Na_2SO_4$, filtered and concentrated to give the title product (4.90 g, 99% yield) as colorless oil. $^1H$ NMR (500 MHz, $CDCl_3$) δ 12.01 (s, 1H), 3.82 (d, J=5.9 Hz, 1H), 2.00 (ddd, J=10.6, 8.6, 5.5 Hz, 1H), 1.54 (dqd, J=14.8, 7.5, 4.4 Hz, 1H), 1.36-1.24 (m, 1H), 1.08-0.99 (m, 3H), 0.97-0.87 (m, 3H).

Example 11. Synthesis of D-N-methyl pipecolinic acid

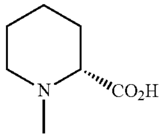

To a solution of D-pipecolinic acid (10.0 g, 77.4 mmol, 1.0 eq.) in methanol (100 mL) was added formaldehyde (37% aqueous solution, 30.8 mL, 154.8 mmol, 2.0 eq.), followed by Pd/C (10 wt %, 1.0 g). The reaction mixture was stirred under H2 (1 atm) overnight, and then filtered through Celite, with washing of the filter pad with methanol. The filtrate was concentrated under reduced pressure to afford the title compound (10.0 g, 90% yield) as a white solid.

Example 12. Synthesis of (R)-perfluorophenyl 1-methylpiperidine-2-carboxylate

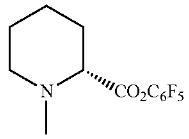

To a solution of D-N-methyl pipecolinic acid (2.65 g, 18.5 mmol) in EtOAc (50 mL) were added pentafluorophenol (3.75 g, 20.4 mmol) and DCC (4.21 g, 20.4 mmol). The reaction mixture was stirred at r.t. for 16 h, and then filtered over Celite. The filter pad was washed with 10 mL of EtOAc. The filtrate was used immediately without further purification or concentration.

Example 13. Synthesis of 2,2-diethoxyethanethioamide (180)

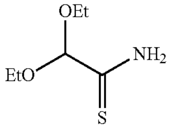

2,2-diethoxyacetonitrile (100 g, 0.774 mol, 1.0 eq.) was mixed with $(NH_4)_2S$ aqueous solution (48%, 143 mL, 1.05 mol, 1.36 eq.) in methanol (1.5 L) at room temperature. After stirring for 16 h, the reaction mixture was concentrated and the residue was taken up in dichloromethane, washed with saturated $NaHCO_3$ solution and brine, dried over anhydrous $Na_2SO_4$ and concentrated. The residue was triturated with a solvent mixture of petroleum ether and dichloromethane. After filtration, the desired title product as a white solid was collected (100 g, 79% yield). $^1H$ NMR (500 MHz, $CDCl_3$) δ 7.81 (d, J=71.1 Hz, 2H), 5.03 (s, 1H), 3.73 (dq, J=9.4, 7.1 Hz, 2H), 3.64 (dq, J=9.4, 7.0 Hz, 2H), 1.25 (t, J=7.1 Hz, 6H).

Example 14. Synthesis of ethyl 2-(diethoxymethyl)thiazole-4-carboxylate (182)

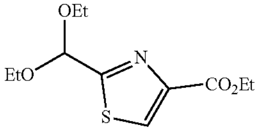 [SMILES: CCOC(=O)c1csc(C(OCC)OCC)n1]

90 g of molecular sieves (3A) was added to a mixture of 2,2-diethoxyethanethioamide (100 g, 0.61 mol, 1.0 eq.) and ethyl bromopyruvate (142 mL, 1.1 mol, 1.8 eq.) in 1 L EtOH. The mixture was refluxed (internal temperature about 60° C.) for 1 h, then ethanol was removed on rotovap and the residue was taken up in dichloromethane. The solid was filtered off and the filtrate was concentrated and purified by column chromatography (PE/EtOAc 5:1-3:1) to give the title (thiazole carboxylate) compound (130 g, 82% yield) as a yellow oil.

Example 15. Synthesis of ethyl 2-formylthiazole-4-carboxylate (183)

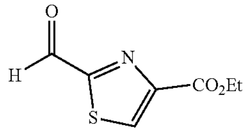 [SMILES: CCOC(=O)c1csc(C=O)n1]

To a solution of 2-(diethoxymethyl)thiazole-4-carboxylate (130 g, 0.50 mol) in acetone (1.3 L) was added 2 N HCl (85 mL, 0.165 mol, 0.33 eq.). The reaction mixture was refluxed (internal temperature about 60° C.), monitored by TLC analysis until starting material was completely consumed (about 1-2 h). Acetone was removed under reduced pressure and the residue was taken up in dichloromethane (1.3 L), washed with saturated $NaHCO_3$ solution, water and brine, and then dried over anhydrous $Na_2SO_4$. The solution was filtered and concentrated under reduced pressure. The crude product was purified by recrystallization from petroleum ether and diethyl ether to afford the title compound as a white solid (40 g, 43% yield). $^1H$ NMR (500 MHz, $CDCl_3$) δ 10.08-10.06 (m, I H), 8.53-8.50 (m, 1H), 4.49 (q, J=7.1 Hz, 2H), 1.44 (t, J=7.1 Hz, 3H). MS ESI m/z calcd for $C_7H_8NO_3S$ $[M+H]^+$ 186.01; found 186.01.

Example 16. Synthesis of ethyl 2-((R,E)-3-(((S)-tert-butylsulfinyl)imino)-1-hydroxy-4-methylpentyl) thiazole-4-carboxylate (187)

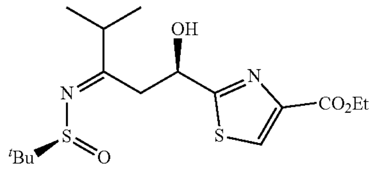 [SMILES: CCOC(=O)c1csc([C@H](O)C/C(=N\[S@@](=O)C(C)(C)C)C(C)C)n1]

To a solution of diisopropylamine (121 mL, 0.86 mol, 4.0 eq.) in dry THF (300 mL) was added n-butyllithium (2.5 M, 302 mL, 0.76 mol 3.5 eq.) at −78° C. under $N_2$. The reaction mixture was warmed to 0° C. over 30 min and then cooled back to −78°. (S, E)-2-methyl-N-(3-methylbutan-2-ylidene) propane-2-sulfonamide (57 g, 0.3 mol, 1.4 eq.) in THF (200 mL) was added. The reaction mixture was stirred for 1 h before $ClTi(OPr)_3$ (168.5 g, 0.645 mol, 3.0 eq.) in THF (350 mL) was added dropwise. After stirring for 1 h, ethyl 2-formylthiazole-4-carboxylate (40 g, 0.215 mol, 1.0 eq.) dissolved in THF (175 mL) was added dropwise and the resulting reaction mixture was stirred for 2 h. The completion of the reaction was indicated by TLC analysis. The reaction was quenched by a mixture of acetic acid and THF (v/v 1:4, 200 mL), then poured onto iced water, extracted with EtOAc (4×500 mL). The organic phase was washed with water and brine, dried over anhydrous $Na_2SO_4$, filtered and concentrated. The residue was purified by column chromatography (DCM/EtOAc/PE 2:1:2) to afford the title compound (60 g, 74% yield) as a colorless oil. $^1H$ NMR (500 MHz, $CDCl_3$) δ 8.13 (s, 1H), 6.63 (d, J=8.2 Hz, 1H), 5.20-5.11 (m, 11H), 4.43 (q, J=7.0 Hz, 2H), 3.42-3.28 (m, 2H), 2.89 (dt, J=13.1, 6.5 Hz, 1H), 1.42 (t, J=7.1 Hz, 3H), 1.33 (s, 9H), 1.25-1.22 (m, 6H). MS ESI m/z calcd for $C_{16}H_{26}NaN_2O_4S_2$ $[M+Na]^+$397.13, found 397.11.

Example 17. Synthesis of ethyl 2-((1R,3R)-3-((S)-1,1-dimethylethylsulfinamido)-1-hydroxy-4-methylpentyl)thiazole-4-carboxylate (188)

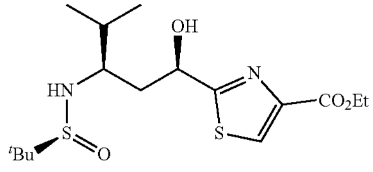 [SMILES: CCOC(=O)c1csc([C@H](O)C[C@@H](N[S@@](=O)C(C)(C)C)C(C)C)n1]

A solution of ethyl 2-((R,E)-3-(((S)-tert-butylsulfinyl) imino)-1-hydroxy-4-methylpentyl) thiazole-4-carboxylate (23.5 g, 62.7 mmol) dissolved in THF (200 mL) was cooled to −45° C. $Ti(OEt)_4$ (42.9 mL, 188 mmol, 3.0 eq.) was added slowly. After the completion of addition, the mixture was stirred for 1 h, before $NaBH_4$ (4.75 g, 126 mmol, 2.0 eq.) was added in portions. The reaction mixture was stirred at −45° C. for 3 h. TLC analysis showed some starting material still remained. The reaction was quenched with HOAc/THF (v/v 1:4, 25 mL), followed by EtOH (25 mL). The reaction mixture was poured onto ice (100 g) and warmed to r.t. After filtration over Celite, the organic phase was separated and washed with water and brine, dried over anhydrous $Na_2SO_4$, filtered, and concentrated. The residue was purified by column chromatography (EtOAc/PE 1:1) to deliver the title product (16.7 g, 71% yield) as a white solid. $^1H$ NMR (500 MHz, $CDCl_3$) δ 8.10 (s, 1H), 5.51 (d, J=5.8 Hz, 1H), 5.23-5.15 (m, 1H), 4.41 (q, J=7.0 Hz, 2H), 3.48-3.40 (m, 1H), 3.37 (d, J=8.3 Hz, 1H), 2.29 (t, J=13.0 Hz, 1H), 1.95-1.87 (m, 1H), 1.73-1.67 (m, 1H), 1.40 (t, J=7.1 Hz, 3H), 1.29 (s, 9H), 0.93 (d, J=7.3 Hz, 3H), 0.90 (d, J=7.2 Hz, 3H). MS ESI m/z calcd for $C_{16}H_{28}NaN_2O_4S_2$ $[M+Na]^+$ 399.15, found 399.14.

Example 18. Synthesis of ethyl 2-((1R,3R)-3-amino-1-hydroxy-4-methylpentyl)thiazole-4-carboxylate hydrochloride (189)

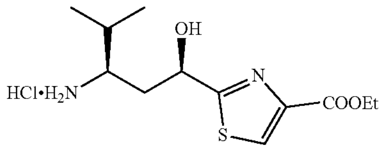

To a solution of ethyl 2-((1R,3R)-3-((S)-1,1-dimethylethylsulfinamido)-1-hydroxy-4-methylpentyl)thiazole-4-carboxylate (6.00 g, 16.0 mmol, 1.0 eq.) in ethanol (40 mL) was added 4 N HCl in dioxane (40 mL) slowly at 0° C. The reaction was allowed to warm to r.t. and stirred for 2.5 h then concentrated and triturated with petroleum ether. A white solid title compound (4.54 g, 92% yield) was collected and used in the next step.

Example 19. Synthesis of ethyl 2-((1R,3R)-3-((2S,3S)-2-azido-3-methylpentanamido)-1-hydroxy-4-methylpentyl)thiazole-4-carboxylate (190)

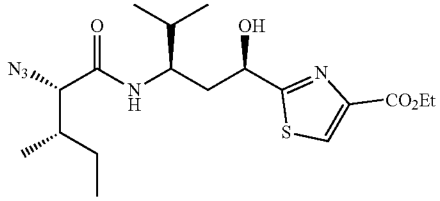 [SMILES: CCOC(=O)c1csc([C@H](O)C[C@@H](NC(=O)[C@@H](N=[N+]=[N-])[C@@H](C)CC)C(C)C)n1]

(2S,3S)-2-azido-3-methylpentanoic (5.03 g, 28.8 mmol, 2.0 eq.) was dissolved in THF (120 mL) and cooled to 0° C., to which NMM (6.2 mL, 56.0 mmol, 4.0 eq.) and isobutylchloroformate (3.7 mL, 28.8 mmol, 2.0 eq.) were added in sequence. The reaction was stirred at 0° C. for 30 min and r.t. 1.0 h, and then cooled back to 0° C. Ethyl 2-((1R,3R)-

3-amino-1-hydroxy-4-methylpentyl)thiazole-4-carboxylate hydrochloride (4.54 g, 14.7 mmol, 1.0 eq.) was added in portions. After stirring at 0° C. for 30 min, the reaction was warmed to r.t. and stirred for 2 h. Water was added at 0° C. to quench the reaction and the resulting mixture was extracted with ethyl acetate for three times. The combined organic layers were washed with 1N HCl, saturated $NaHCO_3$ and brine, dried over anhydrous $Na_2SO_4$, filtered and concentrated. The residue was purified by column chromatography (0-30% EtOAc/PE) to give a white solid title compound (4.55 g, 74% yield).

Example 20. Synthesis of ethyl 2-((1R,3R)-3-((2S,3S)-2-azido-3-methylpentanamido)-4-methyl-1-((triethylsilyl)oxy)pentyl)thiazole-4-carboxylate (191)

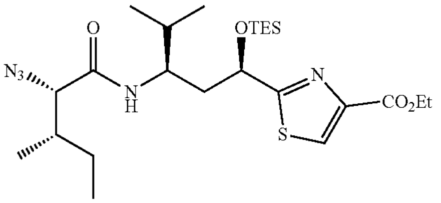

To a solution of ethyl 2-((1R,3R)-3-((2S,3S)-2-azido-3-methylpentanamido)-1-hydroxy-4-methylpentyl)thiazole-4-carboxylate (5.30 g, 12.8 mmol, 1.0 eq.) in $CH_2Cl_2$ (50 mL) was added imidazole (1.75 g, 25.6 mmol, 2.0 eq.), followed by chlorotriethylsilane (4.3 mL, 25.6 mmol, 2.0 eq.) at 0° C. The reaction mixture was allowed to warm to r.t. over 1 hour and stirred for an additional hour. Brine was added to the reaction mixture, the organic layer was separated and the aqueous layer was extracted with EtOAc. The combined organic phases were dried, filtered, concentrated under reduced pressure, and purified by column chromatography with a gradient of 15-35% EtOAc in petroleum ether to afford the title product (6.70 g, 99% yield) as a white solid. $^1H$ NMR (500 MHz, $CDCl_3$) δ 8.12 (s, 1H), 6.75 (d, J=8.0 Hz, 1H), 5.20-5.12 (m, 1H), 4.44 (q, J=7.0 Hz, 2H), 4.06-3.97 (m, 1H), 3.87 (d, J=3.8 Hz, 11H), 2.14 (d, J=3.8 Hz, 1H), 2.01-1.91 (m, 3H), 1.42 (t, J=7.1 Hz, 3H), 1.34-1.25 (m, 2H), 1.06 (d, J=6.8 Hz, 3H), 1.00-0.93 (m, 18H), 0.88 (dd, J=19.1, 6.8 Hz, 6H). MS ESI m/z calcd for $C_{24}H_{44}N_5O_4SSi$ $[M+H]^+$ 526.28, found 526.28.

Example 21. Synthesis of ethyl 2-((1R,3R)-3-((2S,3S)-2-azido-N,3-dimethyl pentanamido)-4-methyl-1-((triethylsilyl)oxy)pentyl)thiazole-4-carboxylate (192)

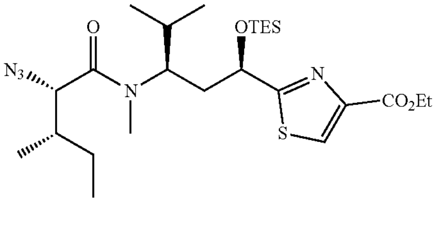

A solution of ethyl 2-((1R,3R)-3-((2S,3S)-2-azido-3-methylpentanamido)-4-methyl-1-((triethylsilyl)oxy)pentyl) thiazole-4-carboxylate (5.20 g, 9.9 mmol, 1.0 eq.) in THF (50 mL) was cooled to −45° C. and KHMDS (1M in toluene, 23.8 mL, 23.8 mmol, 2.4 eq.) was added. The resulting mixture was stirred at −45° C. for 20 min. Methyl iodide (1.85 mL, 29.7 mmol, 3.0 eq.) was then added, and the reaction mixture was allowed to warm to r.t. over 4.5 h, at which time the reaction was quenched with EtOH (10 mL). The crude product was diluted with EtOAc (250 mL) and washed with brine (100 mL). The aqueous layer was extracted with EtOAc (3×50 ml). The organic layers were dried, filtered, concentrated and purified by column chromatography with a gradient of 15-35% EtOAc in petroleum ether to afford the title product (3.33 g, 63% yield) as a light yellow oil. $^1H$ NMR (500 MHz, $CDCl_3$) δ 8.09 (s, 1H), 4.95 (d, J=6.6 Hz, 1H), 4.41 (q, J=7.1 Hz, 2H), 3.56 (d, J=9.5 Hz, 1H), 2.98 (s, 3H), 2.27-2.06 (m, 4H), 1.83-1.70 (m, 2H), 1.41 (t, J=7.2 Hz, 3H), 1.29 (ddd, J=8.9, 6.8, 1.6 Hz, 3H), 1.01 (d, J=6.6 Hz, 3H), 0.96 (dt, J=8.0, 2.9 Hz, 15H), 0.92 (d, J=6.6 Hz, 3H), 0.90 (d, J=6.7 Hz, 3H). MS ESI m/z calcd for $C_{25}H_{46}N_5O_4SSi$ $[M+H]^+$ 540.30, found 540.30.

Example 22. Synthesis of ethyl 2-((3S,6R,8R)-3-((S)-sec-butyl)-10,10-diethyl-6-isopropyl-5-methyl-1-((R)-1-methylpiperidin-2-yl)-1,4-dioxo-9-oxa-2,5-diaza-10-siladodecan-8-yl)thiazole-4-carboxylate

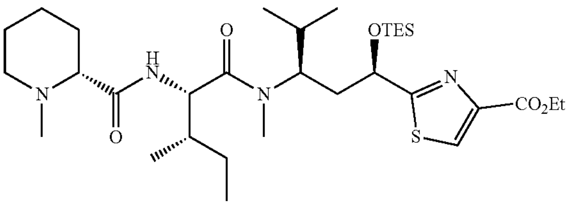

Dry Pd/C (10 wt %, 300 mg) and ethyl 2-((1R,3R)-3-((2S,3S)-2-azido-N,3-dimethyl pentanamido)-4-methyl-1-((triethylsilyl)oxy)pentyl)thiazole-4-carboxylate (3.33 g, 6.61 mmol) were added to (R)-perfluorophenyl 1-methylpiperidine-2-carboxylate in EtOAc. The reaction mixture was stirred under hydrogen atmosphere for 27 h, and then filtered through a plug of Celite, with washing of the filter pad with EtOAc. The combined organic portions were concentrated and purified by column chromatography with a gradient of 0-5% methanol in EtOAc to deliver the title product (3.90 g, 86% yield). MS ESI m/z calcd for $C_{32}H_{59}N_4O_5SSi$ $[M+H]^+$ 639.39, found 639.39.

Example 23. Synthesis of ethyl 2-((1R,3R)-3-((2S,3S)—N,3-dimethyl-2-((R)-1-methyl piperidine-2-carboxamido)pentanamido)-1-hydroxy-4-methylpentyl)thiazole-4-carboxylate

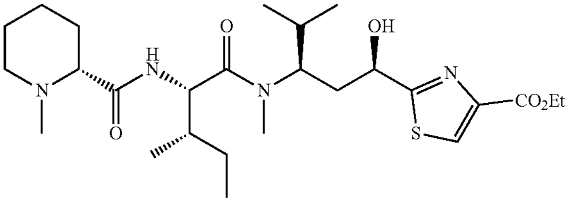 [SMILES: CCOC(=O)c1csc([C@H](O)C[C@H](C(C)C)N(C)C(=O)[C@@H](NC(=O)[C@H]2CCCCN2C)[C@@H](C)CC)n1]

Ethyl 2-((3S,6R,8R)-3-((S)-sec-butyl)-10,10-diethyl-6-isopropyl-5-methyl-1-((R)-1-methylpiperidin-2-yl)-1,4-dioxo-9-oxa-2,5-diaza-10-siladodecan-8-yl)thiazole-4-carboxylate (3.90 g, 6.1 mmol) was dissolved in deoxygenated AcOH/water/THF (v/v/v 3:1:1, 100 mL), and stirred at r.t. for 48 h. The reaction was then concentrated and purified by column chromatography (2:98 to 15:85 MeOH/EtOAc) to afford the title compound (2.50 g, 72% yield over 2 steps). MS ESI m/z calcd for $C_{26}H_{45}N_4O_5S$ $[M+H]^+$ 525.30, found 525.33.

Example 24. Synthesis of 2-((1R,3R)-3-((2S,3S)—N,3-dimethyl-2-((R)-1-methylpiperidine-2-carboxamido)pentanamido)-1-hydroxy-4-methylpentyl) thiazole-4-carboxylic acid

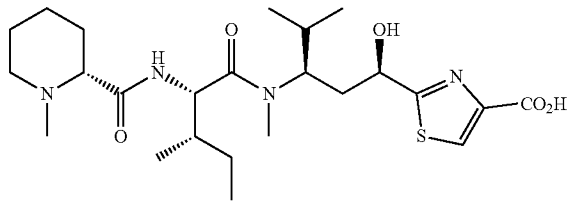 [SMILES: CC[C@H](C)[C@H](NC(=O)[C@H]1CCCCN1C)C(=O)N(C)[C@H](C[C@@H](O)c1nc(C(=O)O)cs1)C(C)C]

An aqueous solution of LiOH (0.4 N, 47.7 mL, 19.1 mmol, 4.0 eq.) was added to a solution of ethyl 2-((1R,3R)-3-((2S,3S)—N,3-dimethyl-2-((R)-1-methyl piperidine-2-carboxamido)-pentanamido)-1-hydroxy-4-methylpentyl) thiazole-4-carboxylate (2.50 g, 4.76 mmol, 1.0 eq.) in dioxane (47.7 mL) at 0° C. The reaction mixture was stirred at r.t. for 2 h and then concentrated. Column chromatography (100% $CH_2Cl_2$ then $CH_2Cl_2$/MeOH/$NH_{40}H$ 80:20:1) afforded the title compound (2.36 g, 99% yield) as an amorphous solid. MS ESI m/z calcd for $C_{24}H_{41}N_4O_5S$ $[M+H]^+$ 497.27, found 497.28.

Example 25. Synthesis of 2-((1R,3R)-1-acetoxy-3-((2S,3S)—N,3-dimethyl-2-((R)-1-methylpiperidine-2-carboxamido)pentanamido)-4-methylpentyl)thiazole-4-carboxylic acid

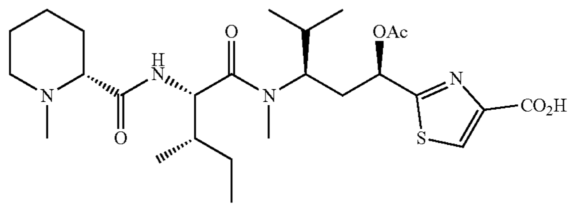 [SMILES: CC[C@H](C)[C@H](NC(=O)[C@H]1CCCCN1C)C(=O)N(C)[C@H](C[C@@H](OC(C)=O)c1nc(C(=O)O)cs1)C(C)C]

To a solution of 2-((1R,3R)-3-((2S,3S)—N,3-dimethyl-2-((R)-1-methylpiperidine-2-carboxamido)pentanamido)-1-hydroxy-4-methylpentyl)thiazole-4-carboxylic acid (2.36 g, 4.75 mmol) in pyridine (50 mL) at 0° C., acetic anhydride (2.25 mL, 24 mmol) was added slowly. The reaction mixture was allowed to warm to r.t. over 2 h and stirred at r.t. for 24 h. The reaction was concentrated and the residue was purified by reverse phase HPLC ($C_{18}$ column, 10-90% acetonitrile/water) to afford the title compound (2.25 g, 88% yield) as an amorphous white solid. MS ESI m/z calcd for $C_{26}H_{43}N_4O_6S$ $[M+H]^+$ 539.28, found 539.28.

Example 26. Synthesis of (1R,3R)-3-((2S,3S)—N,3-dimethyl-2-((R)-1-methylpiperidine-2-carboxamido)pentanamido)-4-methyl-1-(4-(perfluorobenzoyl)thiazol-2-yl)pentyl acetate (294)

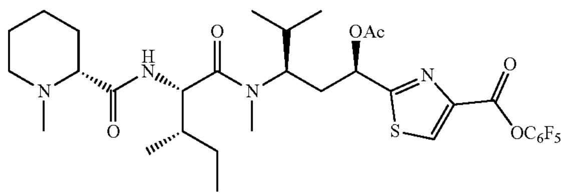

To a solution of 2-((1R,3R)-1-acetoxy-3-((2S,3S)—N,3-dimethyl-2-((R)-1-methyl-piperidine-2-carboxamido)pentanamido)-4-methylpentyl)thiazole-4-carboxylic acid (86 mg, 0.16 mmol, 1.0 eq.) in dichloromethane (2 mL) was added pentafluorophenol (44 mg, 0.24 mmol, 1.5 eq.) and N,N'-diisopropylcarbodiimide (22 mg, 0.175 mmol, 1.1 eq.) at 0° C. The reaction mixture was warmed to room temperature and stirred overnight. After the solvent was removed under reduced pressure, the reaction mixture was diluted with EtOAc (2 mL) then filtered over Celite. The filtrate was concentrated to afford the title compound, which was used directly without further purification.

Example 27. Synthesis of tert-butyl 3-(2-(2-(2-hydroxyethoxy)ethoxy)ethoxy) propanoate

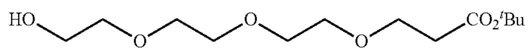 [SMILES: CC(C)(C)OC(=O)CCOCCOCCOCCO]

To a solution of 2,2'-(ethane-1,2-diylbis(oxy))diethanol (55.0 mL, 410.75 mmol, 3.0 eq.) in anhydrous THF (200 mL) was added sodium (0.1 g). The mixture was stirred until Na disappeared and then tert-butyl acrylate (20.0 mL, 137.79 mmol, 1.0 eq.) was added dropwise. The mixture was stirred overnight and then quenched by HCl solution (20.0 mL, 1N) at 0° C. THF was removed by rotary evaporation, brine (300 mL) was added and the resulting mixture was extracted with EtOAc (3×100 mL). The organic layers were washed with brine (3×300 mL), dried over anhydrous $Na_2SO_4$, filtered and concentrated to afford a colourless oil (30.20 g, 79.0% yield), which was used without further purification. MS ESI m/z calcd for $C_{13}H_{27}O_6$ $[M+H]^+$ 278.1729, found 278.1730.

Example 28. Synthesis of tert-butyl 3-(2-(2-(2-(tosyloxy)ethoxy)ethoxy)ethoxy) propanoate

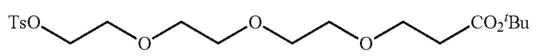

To a solution of tert-butyl 3-(2-(2-(2-hydroxyethoxy) ethoxy)ethoxy) propanoate (30.20 g, 108.5 mmol, 1.0 eq.) and TsCl (41.37 g, 217.0 mmol, 2.0 eq.) in anhydrous DCM (220 mL) at 0° C. was added TEA (30.0 mL, 217.0 mmol, 2.0 eq.). The mixture was stirred at room temperature overnight, and then washed with water (3×300 mL) and brine (300 mL), dried over anhydrous $Na_2SO_4$, filtered, concentrated and purified by $SiO_2$ column chromatography (3:1 hexanes/EtOAc) to give a colorless oil (39.4 g, 84.0% yield). MS ESI m/z calcd for $C_{20}H_{33}O_8S$ $[M+H]^+$ 433.1818, found 433.2838.

Example 29. Synthesis of tert-butyl 3-(2-(2-(2-azidoethoxy)ethoxy)ethoxy) propanoate

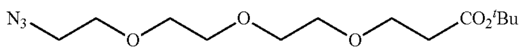 [SMILES: CC(C)(C)OC(=O)CCOCCOCCOCCN=[N+]=[N-]]

To a solution of tert-butyl 3-(2-(2-(2-(tosyloxy)ethoxy) ethoxy)ethoxy) propanoate (39.4 g, 91.1 mmol, 1.0 eq.) in anhydrous DMF (100 mL) was added $NaN_3$ (20.67 g, 316.6 mmol, 3.5 eq.). The mixture was stirred at room temperature overnight. Water (500 mL) was added and extracted with EtOAc (3×300 mL). The combined organic layers were washed with water (3×900 mL) and brine (900 mL), dried over anhydrous $Na_2SO_4$, filtered, concentrated and purified by $SiO_2$ column chromatography (5:1 hexanes/EtOAc) to give a light yellow oil (23.8 g, 85.53% yield). MS ESI m/z calcd for $C_{13}H_{25}O_3N_5Na$ $[M+Na]^+$ 326.2, found 326.2.

Example 30. Synthesis of tert-butyl 3-(2-(2-(2-aminoethoxy)ethoxy)ethoxy) propanoate

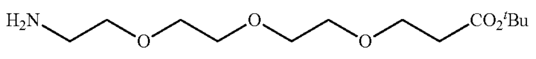 [SMILES: CC(C)(C)OC(=O)CCOCCOCCOCCN]

Raney-Ni (7.5 g, suspended in water) was washed with water (three times) and isopropyl alcohol (three times) and mixed with compound 147 (5.0 g, 16.5 mmol) in isopropyl alcohol. The mixture was stirred under a H2 balloon at r.t. for 16 h and then filtered over a Celite pad, with washing of the pad with isopropyl alcohol. The filtrate was concentrated and purified by column chromatography (5-25% MeOH/DCM) to give a light yellow oil (2.60 g, 57% yield). MS ESI m/z calcd for $C_{13}H_{28}NO_5$ $[M+H]^+$ 279.19; found 279.19.

Example 31. Synthesis of 2-(2-(dibenzylamino)ethoxy)ethanol (298)

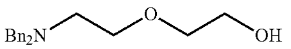

2-(2-aminoethoxy)ethanol (21.00 g, 200 mmol, 1.0 eq.) and $K_2CO_3$ (83.00 g, 600 mmol, 3.0 eq.) in acetonitrile (350 mL) was added BnBr (57.0 mL, 480 mmol, 2.4 eq.). The mixture was refluxed overnight. Water (1 L) was added and extracted with EtOAc (3×300 mL). The combined organic layers were washed with brine (1000 mL), dried over anhydrous $Na_2SO_4$, filtered, concentrated and purified by $SiO_2$ column chromatography (4:1 hexanes/EtOAc) to give a colorless oil (50.97 g, 89.2% yield). MS ESI m/z calcd for $C_{18}H_{23}NO_2Na$ [M+Na]309.1729, found 309.1967.

Example 32. Synthesis of tert-butyl 3-(2-(2-(dibenzylamino)ethoxy)ethoxy) propanoate (300)

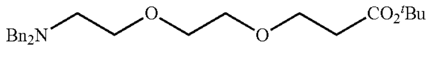

To a mixture of 2-(2-(dibenzylamino)ethoxy)ethanol (47.17 g, 165.3 mmol, 1.0 eq.), tert-butyl acrylate (72.0 mL, 495.9 mmol, 3.0 eq.) and n-$Bu_4NI$ (6.10 g, 16.53 mmol, 0.1 eq.) in DCM (560 mL) was added sodium hydroxide solution (300 mL, 50%). The mixture was stirred overnight. The organic layer was separated and the water layer was extracted with EtOAc (3×100 mL). The organic layers were washed with water (3×300 mL) and brine (300 mL), dried over anhydrous $Na_2SO_4$, filtered, concentrated and purified by $SiO_2$ column chromatography (7:1 hexanes/EtOAc) to give a colorless oil (61.08 g, 89.4% yield). MS ESI m/z calcd for $C_{25}H_{36}NO_4$ $[M+H]^+$ 414.2566, found 414.2384.

Example 33. Synthesis of tert-butyl 3-(2-(2-aminoethoxy)ethoxy)propanoate (301)

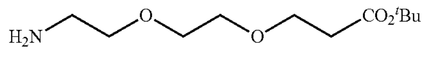

To a solution of tert-butyl 3-(2-(2-(dibenzylamino) ethoxy)ethoxy) propanoate (20.00 g, 48.36 mmol, 1.0 eq.) in THF (30 mL) and MeOH (60 mL) was added Pd/C (2.00 g, 10 wt %, 50% wet) in a hydrogenation bottle. The mixture was shaken overnight, filtered through Celite (filter aid), and the filtrate was concentrated to afford a colorless oil (10.58 g, 93.8% yield). MS ESI m/z calcd for $C_{11}H_{24}NO_4$ $[M+H]^+$ 234.1627, found 234.1810.

Example 34. Synthesis of tert-butyl 3-(2-(2-hydroxyethoxy)ethoxy)propanoate

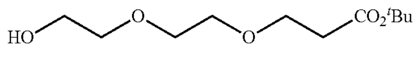 [SMILES: CC(C)(C)OC(=O)CCOCCOCCO]

To a solution of 2,2'-oxydiethanol (19.7 mL, 206.7 mmol, 3.0 eq.) in anhydrous THF (100 mL) was added sodium (0.1 g). The mixture was stirred until Na disappeared and then tert-butyl acrylate (10.0 mL, 68.9 mmol, 1.0 eq.) was added dropwise. The mixture was stirred overnight, and brine (200 mL) was added and extracted with EtOAc (3×100 mL). The organic layers were washed with brine (3×300 mL), dried over anhydrous $Na_2SO_4$, filtered, concentrated and purified by $SiO_2$ column chromatography (1:1 hexanes/EtOAc) to give to a colorless oil (8.10 g, 49.4% yield). MS ESI m/z calcd for $C_{11}H_{23}O_5[M+H]^+$ 235.1467, found 235.1667.

Example 35. Synthesis of tert-butyl 3-(2-(2-(tosyloxy)ethoxy)ethoxy)propanoate

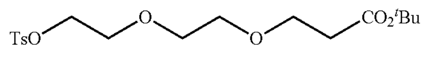 [SMILES: Cc1ccc(S(=O)(=O)OCCOCCOCCC(=O)OC(C)(C)C)cc1]

To a solution of tert-butyl 3-(2-(2-hydroxyethoxy)ethoxy) propanoate (6.24 g, 26.63 mmol, 1.0 eq.) and TsCl (10.15 g, 53.27 mmol, 2.0 eq.) in anhydrous DCM (50 mL) at 0° C. was added pyridine (4.3 mL, 53.27 mmol, 2.0 eq.). The mixture was stirred at room temperature overnight, and then washed with water (100 mL) and the water layer was extracted with DCM (3×50 mL). The combined organic layers were washed with brine (300 mL), dried over anhydrous $Na_2SO_4$, filtered, concentrated and purified by $SiO_2$ column chromatography (5:1 hexanes/EtOAc) to give a colorless oil (6.33 g, 61.3% yield). MS ESI m/z calcd for $C_{18}H_{27}O_7S$ $[M+H]^+$ 389.1556, found 389.2809.

Example 36. Synthesis of tert-butyl 3-(2-(2-azidoethoxy)ethoxy)propanoate

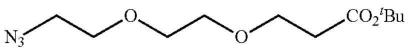 [SMILES: CC(C)(C)OC(=O)CCOCCOCCN=[N+]=[N-]]

To a solution of tert-butyl 3-(2-(2-(tosyloxy)ethoxy)ethoxy)propanoate (5.80 g, 14.93 mmol, 1.0 eq.) in anhydrous DMF (20 mL) was added $NaN_3$ (5.02 g, 77.22 mmol, 5.0 eq.). The mixture was stirred at room temperature overnight. Water (120 mL) was added and extracted with EtOAc (3×50 mL). The combined organic layers were washed with water (3×150 mL) and brine (150 mL), dried over anhydrous $Na_2SO_4$, filtered, concentrated and purified by $SiO_2$ column chromatography (5:1 hexanes/EtOAc) to give a colorless oil (3.73 g, 69.6% yield). MS ESI m/z calcd for $C_{11}H_{22}O_3N_4Na$ $[M+H]^+$ 260.1532, found 260.2259.

Example 37. Synthesis of tert-butyl 3-(2-(2-aminoethoxy)ethoxy)propanoate

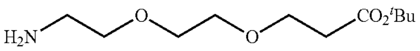

Tert-Butyl 3-(2-(2-azidoethoxy)ethoxy)propanoate (0.18 g, 0.69 mmol) was dissolved in MeOH (3.0 mL, with 60 μL concentrated HCl) and hydrogenated with Pd/C (10 wt %, 20 mg) under a H2 balloon for 30 min. The catalyst was filtered through a Celite pad, with washing of the pad with MeOH. The filtrate was concentrated to give colorless oil (0.15 g, 93% yield). MS ESI m/z calcd for $C_{11}H_{24}NO_4$ $[M+H]^+$ 234.16; found 234.14.

Example 38. 3-(2-(2-azidoethoxy)ethoxy)propanoic acid

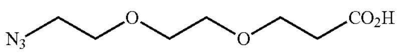

Tert-Butyl 3-(2-(2-azidoethoxy)ethoxy)propanoate (2.51 g, 9.68 mmol) dissolved in 1,4-dioxane (30 mL) was treated with 10 $m_l$ of HCl (conc.) at r.t. The mixture was stirred for 35 min, diluted with EtOH (30 ml) and toluene (30 ml) and concentrated under vacuum. The crude mixture was purified on silica gel using a mixture of methanol (from 5% to 10%) and 1% formic acid in methylene chloride as the eluant to give title compound (1.63 g, 83% yield), ESI MS m/z $C_7H_{12}N_3O_4$ $[M-H]^-$, cacld. 202.06, found 202.30.

Example 39. 2,5-dioxopyrrolidin-1-yl 3-(2-(2-azidoethoxy)ethoxy)propanoate

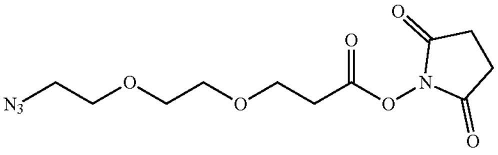 [SMILES: [N-]=[N+]=NCCOCCOCCC(=O)ON1C(=O)CCC1=O]

To 3-(2-(2-azidoethoxy)ethoxy)propanoic acid (1.60 g, 7.87 mmol) in 30 mL of dichloromethane was added NHS (1.08 g, 9.39 mmol) and EDC (3.60 g, 18.75 mmol) with stirring. After 8 h TLC analysis revealed that the reaction was complete, the reaction mixture was concentrated and purified on silica gel using a mixture of ethyl acetate (from 5% to 10%) in methylene chloride as the eluant to give title compound (1.93 g, 82% yield). ESI MS m/z $C_{11}H_{17}N_4O_6$ $[M+H]^+$, cacld. 301.11, found 301.20.

Example 40. Synthesis of (S)-15-azido-5-isopropyl-4,7-dioxo-10,13-dioxa-3,6-diazapentadecan-1-oic acid

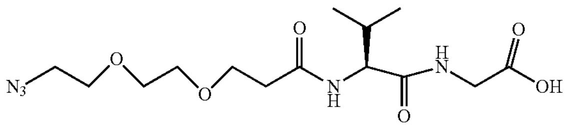 [SMILES: CC(C)[C@H](NC(=O)CCOCCOCCN=[N+]=[N-])C(=O)NCC(=O)O]

To a solution of (S)-2-(2-amino-3-methylbutanamido) acetic acid (Val-Gly) (1.01 g, 5.80 mmol) in the mixture of DMA (50 ml) and 0.1 M $NaH_2PO_4$ (50 ml, pH 7.5) was added 2,5-dioxopyrrolidin-1-yl 3-(2-(2-azidoethoxy)ethoxy)propanoate (1.90 g, 6.33). The mixture was stirred for 4 h, evaporated in vacuo, purified on silica gel using a mixture of methanol (from 5% to 15%) in methylene chloride containing 0.5% acetic acid as the eluant to give title compound (1.52 g, 73% yield). ESI MS m/z $C_{14}H_{26}N_5O_6$ $[M+H]^+$, cacld. 360.18, found 360.40.

Example 41. Synthesis of (S)-2,5-dioxopyrrolidin-1-yl 15-azido-5-isopropyl-4,7-dioxo-10,13-dioxa-3,6-diazapentadecan-1-oate

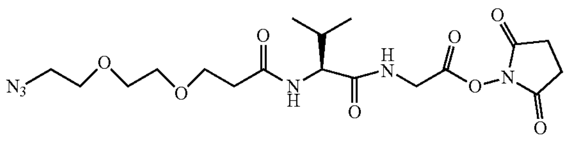 [SMILES: CC(C)[C@H](NC(=O)CCOCCOCCN=[N+]=[N-])C(=O)NCC(=O)ON1C(=O)CCC1=O]

To a solution of(S)-15-azido-5-isopropyl-4,7-dioxo-10,13-dioxa-3,6-diazapentadecan-1-oic acid (1.50 g, 4.17 mmol) in 40 mL of dichloromethane was added NHS (0.88 g, 7.65 mmol) and EDC (2.60 g, 13.54 mmol) with stirring. After 8 h TLC analysis revealed that the reaction was complete, the reaction mixture was concentrated and purified on silica gel using a mixture of ethyl acetate (from 5% to 20%) in methylene chloride as the eluant to give title compound (1.48 g, 78% yield). ESI MS m/z $C_{18}H_{29}N_6O_8$ $[M+H]^+$, cacld. 457.20, found 457.50.

Example 42. Synthesis of 4-(((benzyloxy)carbonyl)amino)butanoic acid

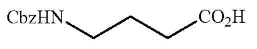

A solution of 4-aminobutyric acid (7.5 g, 75 mmol) and NaOH (6 g, 150 mmol) in $H_2O$ (40 mL) was cooled to 0° C. and treated with a solution of CbzCl (16.1 g, 95 mmol) in THF (32 $m_l$) dropwise. After 1 h, the reaction was allowed to warm to r.t. and stirred for 3 h. THF was removed under vacuum, the pH of the aqueous solution was adjusted to 1.5 by addition of 6 N HCl. Extracted with ethyl acetate, and the organic layer was washed with brine, dried and concentrated to give the title compound (16.4 g, 92% yield). MS ESI m/z calcd for $C_{12}H_{16}NO_5$ $[M+H]^+$ 238.10, found 238.08.

Example 43. Synthesis of tert-butyl 4-(((benzyloxy)carbonyl)amino)butanoate

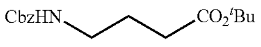

DMAP (0.8 g, 6.56 mmol) and DCC (17.1 g, 83 mmol) were added to a solution of 4-(((benzyloxy)carbonyl)amino) butanoic acid (16.4 g, 69.2 mmol) and t-BuOH (15.4 g, 208 mmol) in DCM (100 mL). After stirring at r.t. overnight, the reaction was filtered and filtrate concentrated. The residue was dissolved in ethyl acetate and then washed with 1N HCl, brine and dried over $Na_2SO_4$. Concentration and purification by column chromatography (10 to 50% EtOAc/hexanes) yielded the title compound (7.5 g, 37% yield). MS ESI m/z calcd for $C_{16}H_{23}NO_4Na$ $[M+Na]^+$316.16, found 316.13.

Example 44. Synthesis of tert-butyl 4-aminobutanoate

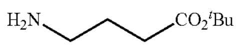

Tert-Butyl 4-(((benzyloxy)carbonyl)amino)butanoate (560 mg, 1.91 mmol) was dissolved in MeOH (50 mL), and mixed with Pd/C catalyst (10 wt %, 100 mg) then hydrogenated (1 atm) at room temperature for 3 h. The catalyst was filtered off and all volatiles were removed under vacuum to afford the title compound (272 mg, 90% yield). MS ESI m/z calcd for $C_8H_{18}NO_2$ $[M+H]^+$ 160.13, found 160.13.

Example 45. Synthesis of tert-butyl 2-(triphenylphosphoranylidene)propanoate (206)

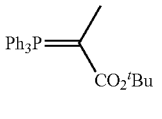

A mixture of tert-butyl-2-bromopropanoate (15.5 g, 74.1 mmol, 1.0 eq.) and triphenyl phosphine (19.4 g, 74.1 mmol, 1.0 eq.) in dry acetonitrile (45 mL) was stirred at room temperature for 18 h. Acetonitrile was removed under reduced pressure and toluene was added to crash out a white precipitate. Toluene was then decanted off and the white solid was dissolved in dichloromethane (100 mL) and transferred to a separatory funnel. 10% NaOH (100 mL) was added to the funnel, and the organic layer immediately turned yellow after shaking. The organic layer was separated and the aqueous layer was extracted with dichloromethane (30 mL) once. The dichloromethane layers were combined and washed with brine (50 mL) once, then dried over $Na_2SO_4$, filtered and concentrated, giving the ylide as a yellow solid (16.8 g, 58%).

Example 46. Synthesis of (S)-methyl 3-(4-(benzyloxy)phenyl)-2-((tert-butoxy carbonyl)amino)propanoate (203)

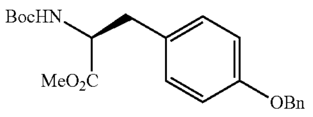 [SMILES: COC(=O)[C@H](Cc1ccc(OCc2ccccc2)cc1)NC(=O)OC(C)(C)C]

To a mixture of Boc-L-Tyr-OMe (20.0 g, 67.7 mmol, 1.0 eq.), $K_2CO_3$ (14.0 g, 101.6 mmol, 1.5 eq.) and KI (1.12 g, 6.77 mmol, 0.1 eq.) in acetone (100 mL) was added BnBr (10.5 mL, 81.3 mmol, 1.2 eq.) slowly. The mixture was then refluxed overnight. Water (250 mL) was added and the reaction mixture was extracted with EtOAc (3×100 mL). The combined organic layers were washed with brine (300 mL), dried over anhydrous $Na_2SO_4$, filtered, concentrated and purified by $SiO_2$ column chromatography (4:1 hexanes/EtOAc) to give a white solid title compound (26.12 g, 99% yield). $^1H$ NMR (500 MHz, $CDCl_3$) δ 7.44-7.41 (m, 2H), 7.41-7.36 (m, 2H), 7.35-7.30 (m, 1H), 7.04 (d, J=8.5 Hz, 2H), 6.93-6.89 (m, 2H), 5.04 (s, 2H), 4.97 (d, J=7.7 Hz, 1H), 4.55 (d, J=6.9 Hz, 1H), 3.71 (s, 3H), 3.03 (dd, J=14.4, 5.7 Hz, 2H), 1.44 (d, J=18.6 Hz, 10H). MS ESI m/z calcd for $C_{22}H_{27}NO_5Na$ $[M+Na]^+$408.18, found 408.11.

Example 47. Synthesis of (S)-tert-butyl (1-(4-(benzyloxy)phenyl)-3-oxopropan-2-yl)carbamate (204)

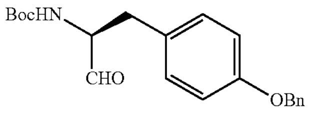 [SMILES: CC(C)(C)OC(=O)N[C@H](C=O)Cc1ccc(OCc2ccccc2)cc1]

To a solution of (S)-methyl 3-(4-(benzyloxy)phenyl)-2-((tert-butoxy carbonyl)amino)-propanoate (26.1 g, 67.8 mmol, 1.0 eq.) in anhydrous dichloromethane (450 mL) at −78° C. was added DIBAL (1.0 M in hexanes, 163 mL, 2.2 eq.) in 1 h. The mixture was stirred at −78° C. for 3 h and then quenched with 50 mL of ethanol. 1N HCl was added dropwise until pH 4 was reached. The resulting mixture was allowed to warm to 0° C. Layers were separated and the aqueous layer was further extracted with EtOAc (3×100 mL). The combined organic solution was washed with brine, dried over anhydrous $Na_2SO_4$, and concentrated. Trituration with PE/EtOAc and filtration gave a white solid title compound (18.3 g, 76% yield). MS ESI m/z calcd for $C_{22}H_{27}NO_5Na$ $[M+Na]^+$378.11, found 378.11.

Example 48. Synthesis of (S,Z)-tert-butyl 5-(4-(benzyloxy)phenyl)-4-((tert-butoxycarbonyl)amino)-2-methylpent-2-enoate (207)

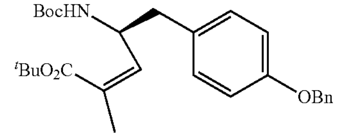 [SMILES: C/C(=C/[C@H](Cc1ccc(OCc2ccccc2)cc1)NC(=O)OC(C)(C)C)C(=O)OC(C)(C)C]

(S)-tert-Butyl (1-(4-(benzyloxy)phenyl)-3-oxopropan-2-yl)carbamate (0.84 g, 2 mmol, 1.0 eq.) was dissolved in dry dichloromethane (50 mL), to which tert-butyl 2-(triphenylphosphoranylidene)propanoate (1.6 g, 4 mmol, 2.0 eq.) was added and the solution was stirred at r.t. for 1.5 h as determined complete by TLC. Purification by column chromatography (10-50% EtOAc/hexanes) afforded the title compound (1.16 g, 98% yield).

Example 49. Synthesis of (4R)-tert-butyl 4-((tert-butoxycarbonyl)amino)-5-(4-hydroxyphenyl)-2-methylpentanoate

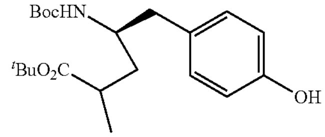 [SMILES: CC(C[C@H](Cc1ccc(O)cc1)NC(=O)OC(C)(C)C)C(=O)OC(C)(C)C]

(S,Z)-Tert-Butyl 5-(4-(benzyloxy)phenyl)-4-((tert-butoxycarbonyl)amino)-2-methylpent-2-enoate (467 mg, 1 mmol) was dissolved in methanol (30 mL) and hydrogenated (1 atm) with Pd/C catalyst (10 wt %, 250 mg) at r.t. overnight. The catalyst was filtered off and the filtrate was concentrated under reduced pressure to afford the title compound (379 mg, 99% yield).

Example 50. Synthesis of (4R)-tert-butyl 4-((tert-butoxycarbonyl)amino)-5-(4-hydroxy-3-nitrophenyl)-2-methylpentanoate

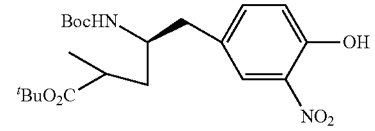 [SMILES: CC(C[C@H](Cc1ccc(O)c([N+](=O)[O-])c1)NC(=O)OC(C)(C)C)C(=O)OC(C)(C)C]

(4R)-tert-Butyl 4-((tert-butoxycarbonyl)amino)-5-(4-hydroxyphenyl)-2-methylpentanoate (379 mg, 1 mmol, 1.0 eq.) was dissolved in THF (20 mL), to which a solution of tert-butyl nitrite (315 mg, 3 mmol, 3.0 eq.) in THF (2 mL) was added. The reaction was stirred at r.t. for 3 h and then poured onto water, extracted with EtOAc (2×50 mL) and the combined organic phases were washed with brine (50 mL), dried over anhydrous $Na_2SO_4$, filtered and concentrated. Purification by column chromatography (10-50% EtOAc/hexanes) afforded the title compound (300 mg, 71% yield).

Example 51. Synthesis of (4R)-tert-butyl 5-(3-amino-4-hydroxyphenyl)-4-((tert-butoxycarbonyl)amino)-2-methylpentanoate (210)

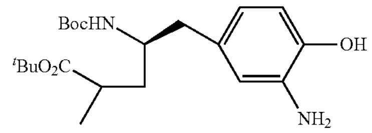 [SMILES: CC(C[C@H](Cc1ccc(O)c(N)c1)NC(=O)OC(C)(C)C)C(=O)OC(C)(C)C]

(4R)-Tert-butyl 4-((tert-butoxycarbonyl)amino)-5-(4-hydroxy-3-nitrophenyl)-2-methylpentanoate (200 mg, 0.47 mmol) was dissolved in EtOAc (30 mL) and mixed with palladium catalyst (10% on carbon, 100 mg), then hydrogenated (1 atm) at r.t. for 2 h. The catalyst was filtered off and all volatiles were removed under vacuum, which afforded the title compound (185 mg, 99%).

Alternatively, (4R)-tert-butyl 4-((tert-butoxycarbonyl)amino)-5-(4-hydroxy-3-nitrophenyl)-2-methylpentanoate (56 mg, 0.132 mmol) was dissolved in EtOAc (20 mL) and mixed with Pd/C catalyst (10 wt %, 50 mg) and hydrogenated (1 atm) at r.t. for 3 h. The catalyst was filtered off and all volatiles were removed under vacuum to afford the title compound (52 mg, 99% yield). MS ESI m/z calcd for $C_{21}H_{35}N_2O_5$ $[M+H]^+$ 395.25, found 395.26.

Example 52. Synthesis of (4R)-tert-butyl 4-((tert-butoxycarbonyl)amino)-5-(4-((tert-butyldimethylsilyl)oxy)-3-nitrophenyl)-2-methylpentanoate

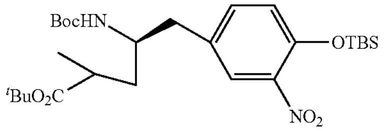 [SMILES: CC(C[C@H](Cc1ccc(O[Si](C)(C)C(C)(C)C)c([N+](=O)[O-])c1)NC(=O)OC(C)(C)C)C(=O)OC(C)(C)C]

To a solution of (4R)-tert-butyl 4-((tert-butoxycarbonyl)amino)-5-(4-hydroxy-3-nitrophenyl)-2-methylpentanoate (424 mg, 1 mmol) in DCM (20 mL), imidazole (408 mg, 6 mmol) and tert-butylchlorodimethylsilane (602 mg, 4 mmol) were added. The resulting solution was stirred at r.t. for 3 h. Afterwards, the reaction mixture was washed with brine (50 mL), dried over anhydrous $Na_2SO_4$, concentrated and purified by column chromatography (10% to 30% EtOAc/hexanes) to yield the title compound (344 mg, 64% yield).

Example 53. Synthesis of (4R)-tert-butyl 5-(3-amino-4-((tert-butyldimethylsilyl) oxy)phenyl)-4-((tert-butoxycarbonyl)amino)-2-methylpentanoaten (215)

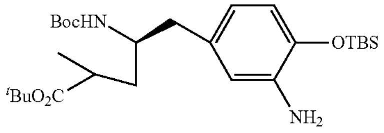

(4R)-tert-Butyl 4-((tert-butoxycarbonyl)amino)-5-(4-((tert-butyldimethylsilyl)oxy)-3-nitrophenyl)-2-methylpentanoate (200 mg, 0.37 mmol) was dissolved in EtOAc (30 mL), mixed with palladium catalyst (10 wt % on carbon, 100 mg) and hydrogenated (1 atm) at r.t. for 2 h. The catalyst was filtered off and all volatiles were removed under vacuum to afford the title compound (187 mg, 99% yield).

Example 54. Synthesis of (S)-tert-butyl 2-(hydroxymethyl)pyrrolidine-1-carboxylate

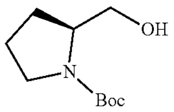 [SMILES: CC(C)(C)OC(=O)N1CCC[C@H]1CO]

Boc-L-proline (10.0 g, 46.4 mmol) dissolved in 50 mL THE was cooled to 0° C., to which $BH_3$ in THF (1.0 M, 46.4 mL) was added carefully. The mixture was stirred at 0° C. for 1.5 h then poured onto ice water and extracted with ethyl acetate. The organic layer was washed with brine (50 mL), dried over anhydrous $Na_2SO_4$, and concentrated under reduced pressure to give the title compound (8.50 g, 91% yield) as a white solid. $^1H$ NMR (500 MHz, $CDCl_3$) δ 3.94 (dd, J=4.9, 2.7 Hz, 2H), 3.60 (ddd, J=18.7, 11.9, 9.3 Hz, 2H), 3.49-3.37 (m, 1H), 3.34-3.23 (m, 1H), 2.06-1.91 (m, 1H), 1.89-1.69 (m, 2H), 1.65-1.51 (m, 1H), 1.49-0.40 (m, 9H).

Example 55. Synthesis of (S)-tert-butyl 2-formylpyrrolidine-1-carboxylate

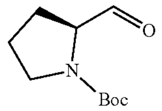 [SMILES: CC(C)(C)OC(=O)N1CCC[C@H]1C=O]

To a solution of (S)-tert-butyl 2-(hydroxymethyl)pyrrolidine-1-carboxylate (13.0 g, 64.6 mmol) in dimethyl sulfoxide (90 mL) was added triethylamine (40 mL) and the stirring was continued for 15 min. The mixture was cooled over ice bath and sulfur trioxide-pyridine complex (35.98 g, 226 mmol) was added in portions over a 40 min period. The reaction was warmed to r.t. and stirred for 2.5 h. After addition of ice (250 g), the mixture was extracted with dichloromethane (150 $m_{1\times3}$). The organic phase was washed with 50% citric acid solution (150 mL), water (150 mL), saturated sodium bicarbonate solution (150 mL), and brine (150 mL), dried over anhydrous $Na_2SO_4$. Removal of solvent in vacuo yielded the title aldehyde (10.4 g, 81% yield) as dense oil which was used without further purification. $^1H$ NMR (500 MHz, $CDCl_3$) δ 9.45 (s, 1H), 4.04 (s, 1H), 3.53 (dd, J=14.4, 8.0 Hz, 2H), 2.00-1.82 (m, 4H), 1.44 (d, J=22.6 Hz, 9H).

Example 56. Synthesis of (4R,5S)-4-methyl-5-phenyl-3-propionyloxazolidin-2-one

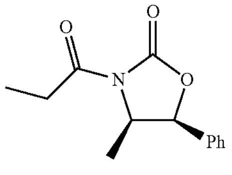 [SMILES: CCC(=O)N1C(=O)O[C@@H](c2ccccc2)[C@H]1C]

n-Butyllithium in hexane (21.6 mL, 2.2 M, 47.43 mmol) was added dropwise at −78° C. to a stirred solution of 4-methyl-5-phenyloxazolidin-2-one (8.0 g, 45.17 mmol) in THF (100 mL) under $N_2$. The solution was maintained at −78° C. for 1 h then propionyl chloride (4.4 mL, 50.59 mmol) was added slowly. The reaction mixture was warmed to −50° C., stirred for 2 h then quenched by addition of a saturated solution of ammonium chloride (100 mL). The organic solvent was removed in vacuo and the resultant solution was extracted with ethyl acetate (3×100 mL). The organic layer was washed with saturated sodium bicarbonate solution (100 mL) and brine (100 mL), dried over $Na_2SO_4$, filtered and concentrated in vacuo. The residue was purified by column chromatography (20% ethyl acetate/hexanes) to afford the title compound as dense oil (10.5 g, 98% yield). $^1H$ NMR (500 MHz, $CDCl_3$) S 7.45-7.34 (m, 3H), 7.30 (d, J=7.0 Hz, 2H), 5.67 (d, J=7.3 Hz, 11H), 4.82-4.70 (m, 11H), 2.97 (dd, J=19.0, 7.4 Hz, 2H), 1.19 (t, J=7.4 Hz, 3H), 0.90 (d, J=6.6 Hz, 3H).

Example 57. Synthesis of (S)-tert-butyl 2-((1R,2R)-1-hydroxy-2-methyl-3-((4R,5S)-4-methyl-2-oxo-5-phenyloxazolidin-3-yl)-3-oxopropyl)pyrrolidine-1-carboxylate

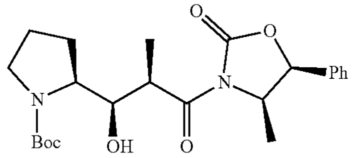 [SMILES: C[C@@H]1[C@H](c2ccccc2)OC(=O)N1C(=O)[C@H](C)[C@@H](O)[C@@H]1CCCN1C(=O)OC(C)(C)C]

To a solution of (4R,5S)-4-methyl-5-phenyl-3-propionyloxazolidin-2-one (9.40 g, 40.4 mmol) in dichloromethane (60 mL) was added $Et_3N$ (6.45 mL, 46.64 mmol) at 0° C., followed by 1M dibutylboron triflate in dichloromethane (42 mL, 42 mmol). The mixture was stirred at 0° C. for 45 min, cooled to −70° C., (S)-tert-butyl 2-formylpyrrolidine-1-carboxylate (4.58 g, 22.97 mmol) in dichloromethane (40 mL) was then added slowly over a 30 min period. The reaction was stirred at −70° C. for 2 h, 0° C. 1 h, and r.t. 15 min, and then quenched with phosphate buffer solution (pH 7, 38 mL). After the addition of MeOH-30% $H_2O_2$ (2:1, 100 mL) at below 10° C. and stirring for 20 min, water (100 mL) was added and the mixture was concentrated in vacuo. More water (200 mL) was added to the residue and the mixture was extracted with ethyl acetate (3×100 mL). The organic layer was washed with 1N $KHSO_4$ (100 mL), sodium bicarbonate solution (100 mL) and brine (100 mL), dried over anhydrous $Na_2SO_4$ and concentrated in vacuo. The residue was purified by flash column chromatography (10%-50% ethyl acetate/hexanes) to afford the title compound as a white solid (7.10 g, 71% yield). $^1H$ NMR (500 MHz, $CDCl_3$) δ 7.39 (dt, J=23.4, 7.1 Hz, 3H), 7.30 (d, J=7.5 Hz, 2H), 5.67 (d, J=7.1 Hz, I H), 4.84-4.67 (m, 1H), 4.08-3.93 (m, 3H), 3.92-3.84 (m, 11H), 3.50 (d, J=9.0 Hz, 11H), 3.24 (d, J=6.7 Hz, 1H), 2.15 (s, 11H), 1.89 (dd, J=22.4, 14.8 Hz, 3H), 1.48 (d, J=21.5 Hz, 9H), 1.33 (d, J=6.9 Hz, 3H), 0.88 (d, J=6.4 Hz, 3H).

Example 58. Synthesis of (S)-tert-butyl 2-((1R,2R)-1-methoxy-2-methyl-3-((4R,5S)-4-methyl-2-oxo-5-phenyloxazolidin-3-yl)-3-oxopropyl)pyrrolidine-1-carboxylate

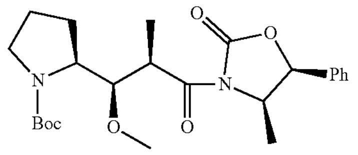 [SMILES: CO[C@H]([C@@H](C)C(=O)N1C(=O)O[C@@H](c2ccccc2)[C@H]1C)[C@@H]1CCCN1C(=O)OC(C)(C)C]

To a mixture of (S)-tert-butyl 2-((1R,2R)-1-hydroxy-2-methyl-3-((4R,5S)-4-methyl-2-oxo-5-phenyloxazolidin-3-yl)-3-oxopropyl)pyrrolidine-1-carboxylate (5.1 g 11.9 mmol) and molecular sieves (4 Å, 5 g) was added anhydrous dichloroethane (30 mL) under $N_2$. The mixture was stirred at room temperature for 20 min and cooled to 0° C. Proton sponge (6.62 g, 30.9 mmol) was added, followed by trimethyloxonium tetrafluoroborate (4.40 g, 29.7 mmol). Stirring was continued for 2 h at 0° C. and 48 h at r.t. The reaction mixture was filtrated and the filtrate was concentrated and purified by column chromatography (20-70% ethyl acetate/hexanes) to afford the title compound as a white solid (1.80 g, 35% yield). $^1$H NMR (500 MHz, $CDCl_3$) δ 7.46-7.27 (m, 5H), 5.65 (s, 1H), 4.69 (s, 1H), 3.92 (s, 1H), 3.83 (s, 1H), 3.48 (s, 3H), 3.17 (s, 2H), 2.02-1.68 (m, 5H), 1.48 (d, J=22.3 Hz, 9H), 1.32 (t, J=6.0 Hz, 3H), 0.91-0.84 (m, 3H).

Example 59. Synthesis of (2R,3R)-3-((S)-1-(tert-butoxycarbonyl)pyrrolidin-2-yl)-3-methoxy-2-methylpropanoic acid

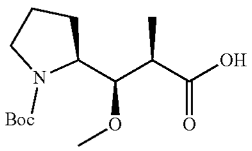 [SMILES: CO[C@H]([C@@H](C)C(=O)O)[C@@H]1CCCN1C(=O)OC(C)(C)C]

To a solution of (S)-tert-butyl 2-((1R,2R)-1-methoxy-2-methyl-3-((4R,5S)-4-methyl-2-oxo-5-phenyloxazolidin-3-yl)-3-oxopropyl)pyrrolidine-1-carboxylate (1.80 g, 4.03 mmol) in THF (30 mL) and $H_2O$ (7.5 mL), 30% $H_2O_2$ (1.44 mL, 14.4 mmol) was added over a 5 min period at 0° C., followed by a solution of LiOH (0.27 g, 6.45 mmol) in water (5 mL). After stirring at 0° C. for 3 h, 1 N sodium sulfite (15.7 mL) was added and the mixture was allowed to warm to r.t. and stirred overnight. THF was removed in vacuo and the aqueous phase was washed with dichloromethane (3×50 mL) to remove the oxazolidinone auxiliary. The aqueous phase was acidified to pH 3 with 1N HCl and extracted with ethyl acetate (3×50 mL). The organic layer was washed with brine (50 mL), dried over $Na_2SO_4$, filtered and concentrated in vacuo to afford the title compound as colorless oil (1.15 g, 98% yield). $^1$H NMR (500 MHz, $CDCl_3$) δ 3.99-3.74 (m, 2H), 3.44 (d, J=2.6 Hz, 3H), 3.23 (s, 1H), 2.60-2.45 (m, 1H), 1.92 (tt, J=56.0, 31.5 Hz, 3H), 1.79-1.69 (m, 1H), 1.58-1.39 (m, 9H), 1.30-1.24 (m, 3H).

Example 60. Synthesis of (4S,5S)-ethyl 4-((tert-butoxycarbonyl)amino)-5-methyl-3-oxo heptanoate

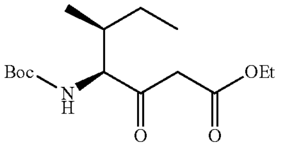 [SMILES: CCOC(=O)CC(=O)[C@@H](NC(=O)OC(C)(C)C)[C@@H](C)CC]

To an ice-cooled solution of N-Boc-L-isoleucine (4.55 g, 19.67 mmol) in THF (20 mL) was added 1,1'-carbonyldiimidazole (3.51 g, 21.63 mmol). After evolution of gas ceased, the resultant mixture was stirred at r.t. for 3.5 h.

A solution of freshly prepared isopropylmagnesium bromide in THF (123 mmol, 30 mL) was added dropwise to a pre-cooled (0° C.) solution of ethyl hydrogen malonate (6.50 g, 49.2 mmol) at such a rate to keep the internal temperature below 5° C. The mixture was stirred at r.t. for 1.5 h. This solution of the magnesium enolate was then cooled over an ice-water bath, followed by the gradual addition of the imidazolide solution over a 1 h period via a double-ended needle at 0° C. The resultant mixture was stirred at 0° C. for 30 min then r.t. 64 h. The reaction mixture was quenched by addition of 10% aqueous citric acid (5 mL), and acidified to pH 3 with an additional 10% aqueous citric acid (110 mL). The mixture was extracted with ethyl acetate (3×150 mL). The organic extracts were washed with water (50 mL), saturated aqueous sodium hydrogen carbonate (50 mL), and saturated aqueous sodium chloride (50 mL), dried over $Na_2SO_4$, and concentrated in vacuo. The residue was purified by column chromatography on silica gel using ethyl acetate/hexane (1:4) as an eluent to give the title compound (5.50 g, 93% yield). $^1$H NMR (500 MHz, $CDCl_3$) δ 5.04 (d, J=7.8 Hz, 1H), 4.20 (p, J=7.0 Hz, 3H), 3.52 (t, J=10.7 Hz, 2H), 1.96 (d, J=3.7 Hz, 1H), 1.69 (s, 2H), 1.44 (s, 9H), 1.28 (dd, J=7.1, 2.9 Hz, 3H), 0.98 (t, J=6.9 Hz, 3H), 0.92-0.86 (m, 3H).

Example 61. Synthesis of (3R,4S,5S)-ethyl 4-((tert-butoxycarbonyl)amino)-3-hydroxy-5-methylheptanoate

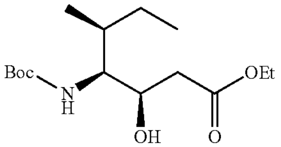 [SMILES: CCOC(=O)C[C@@H](O)[C@@H](NC(=O)OC(C)(C)C)[C@@H](C)CC]

To a solution of (4S,5S)-ethyl 4-((tert-butoxycarbonyl)amino)-5-methyl-3-oxo heptanoate (5.90 g, 19.83 mmol) in ethanol (6 mL) at −60° C. was added sodium borohydride (3.77 g, 99.2 mmol) in one portion. The reaction mixture was stirred for 5.5 h below −55° C. then quenched with 10% aqueous citric acid (100 mL). The resultant solution was acidified to pH 2 with an additional 10% aqueous citric acid, followed by extraction with ethyl acetate (3×100 mL). The organic extracts were washed with saturated aqueous sodium chloride (100 mL), dried over $Na_2SO_4$, and concentrated in vacuo. The residue was purified by column chromatography (10-50% ethyl acetate/hexane) to give pure the title compound as diastereomer (2.20 g, 37% yield) and a mixture of two diastereomers (2.0 g, 34% yield, about 9:1 ratio). $^1$H NMR (500 MHz, $CDCl_3$) δ 4.41 (d, J=9.3 Hz, 1H), 4.17 (tt, J=7.1, 3.6 Hz, 2H), 4.00 (t, J=6.9 Hz, 1H), 3.55 (dd, J=11.7, 9.3 Hz, 1H), 2.56-2.51 (m, 2H), 2.44 (dd, J=16.4, 9.0 Hz, 1H), 1.79 (d, J=3.8 Hz, 1H), 1.60-1.53 (m, 1H), 1.43 (s, 9H), 1.27 (dd, J=9.3, 5.0 Hz, 3H), 1.03-0.91 (m, 7H).

Example 62. Synthesis of (3R,4S,5S)-4-((tert-butoxycarbonyl)amino)-3-hydroxy-5-methyl heptanoic acid

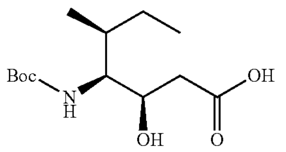 [SMILES: CC[C@H](C)[C@H](NC(=O)OC(C)(C)C)[C@H](O)CC(=O)O]

To a solution of (3R,4S,5S)-ethyl 4-((tert-butoxycarbonyl)amino)-3-hydroxy-5-methylheptanoate (2.20 g, 7.20 mmol) in ethanol (22 mL) was added 1 N aqueous sodium hydroxide (7.57 mL, 7.57 mmol). The mixture was stirred at 0° C. for 30 min then r.t. 2 h. The resultant solution was acidified to pH 4 by addition of 1 N aqueous hydrochloric acid, which was then extracted with ethyl acetate (3×50 mL). The organic extracts were washed with 1 N aqueous potassium hydrogen sulfate (50 mL), and saturated aqueous sodium chloride (50 mL), dried over $Na_2SO_4$, and concentrated in vacuo to give the compound (1.90 g, 95% yield). $^1$H NMR (500 MHz, $CDCl_3$) δ 4.50 (d, J=8.7 Hz, 1H), 4.07 (d, J=5.5 Hz, 1H), 3.59 (d, J=8.3 Hz, 1H), 2.56-2.45 (m, 2H), 1.76-1.65 (m, 1H), 1.56 (d, J=7.1 Hz, 1H), 1.45 (s, 9H), 1.26 (t, J=7.1 Hz, 3H), 0.93 (dd, J=14.4, 7.1 Hz, 6H).

Example 63. Synthesis of (3R,4S,5S)-4-((tert-butoxycarbonyl)(methyl)amino)-3-methoxy-5-methylheptanoic acid

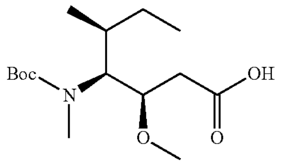 [SMILES: CC[C@H](C)[C@@H]([C@@H](CC(=O)O)OC)N(C)C(=O)OC(C)(C)C]

To a solution of (3R,4S,5S)-4-((tert-butoxycarbonyl) amino)-3-hydroxy-5-methyl heptanoic acid (1.90 g, 6.9 mmol) in THF (40 mL) was added sodium hydride (60% oil suspension, 1.93 g, 48.3 mmol) at 0° C. After stirring for 1 h, methyl iodide (6.6 mL, 103.5 mmol) was added. The stirring was continued at 0° C. for 40 h before saturated aqueous sodium hydrogen carbonate (50 mL) was added, followed by water (100 mL). The mixture was washed with diethyl ether (2×50 mL) and the aqueous layer was acidified to pH 3 by 1 N aqueous potassium hydrogen sulfate, then extracted with ethyl acetate (3×50 mL). The combined organic extracts were washed with 5% aqueous sodium thiosulfate (50 mL) and saturated aqueous sodium chloride (50 mL), dried over $Na_2SO_4$, and concentrated in vacuo to give the title compound (1.00 g, 48% yield). $^1$H NMR (500 MHz, $CDCl_3$) δ 3.95 (d, J=75.4 Hz, 2H), 3.42 (d, J=4.4 Hz, 3H), 2.71 (s, 3H), 2.62 (s, 1H), 2.56-2.47 (m, 2H), 1.79 (s, 1H), 1.47 (s, 1H), 1.45 (d, J=3.3 Hz, 9H), 1.13-1.05 (m, 1H), 0.96 (d, J=6.7 Hz, 3H), 0.89 (td, J=7.2, 2.5 Hz, 3H).

Example 64. Synthesis of Boc-N-Me-L-Val-OH

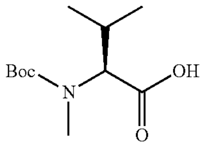 [SMILES: CC(C)[C@@H](C(=O)O)N(C)C(=O)OC(C)(C)C]

To a solution of Boc-L-Val-OH (2.00 g, 9.2 mmol) and methyl iodide (5.74 mL, 92 mmol) in anhydrous THF (40 mL) was added sodium hydride (3.68 g, 92 mmol) at 0° C. The reaction mixture was stirred at 0° C. for 1.5 h, then warmed to r.t. and stirred for 24 h. The reaction was quenched by ice water (50 mL). After addition of water (100 mL), the reaction mixture was washed with ethyl acetate (3×50 mL) and the aqueous solution was acidified to pH 3 then extracted with ethyl acetate (3×50 mL). The combined organic phase was dried over $Na_2SO_4$ and concentrated to afford Boc-N-Me-Val-OH (2.00 g, 94% yield) as a white solid. $^1$H NMR (500 MHz, $CDCl_3$) δ 4.10 (d, J=10.0 Hz, 1H), 2.87 (s, 3H), 2.37-2.13 (m, 1H), 1.44 (d, J=26.7 Hz, 9H), 1.02 (d, J=6.5 Hz, 3H), 0.90 (t, J=8.6 Hz, 3H).

Example 65. Synthesis of (S)-tert-butyl 2-((1R,2R)-1-methoxy-3-(((S)-1-methoxy-1-oxo-3-phenylpropan-2-yl)amino)-2-methyl-3-oxopropyl)pyrrolidine-1-carboxylate

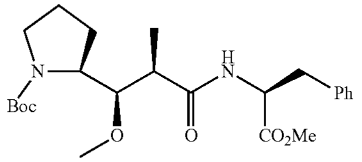 [SMILES: COC(=O)[C@H](Cc1ccccc1)NC(=O)[C@H](C)[C@@H](OC)[C@@H]1CCCN1C(=O)OC(C)(C)C]

To a solution of (2R,3R)-3-((S)-1-(tert-butoxycarbonyl) pyrrolidin-2-yl)-3-methoxy-2-methylpropanoic acid (100 mg, 0.347 mmol) and L-phenylalanine methyl ester hydrochloride (107.8 mg, 0.500 mmol) in DMF (5 mL) at 0° C. was added diethyl cyanophosphonate (75.6 μL, 0.451 mmol), followed by $Et_3N$ (131 μL, 0.94 mmol). The reaction mixture was stirred at 0° C. for 2 h, then warmed to r.t. and stirred overnight. The reaction mixture was then diluted with ethyl acetate (80 mL), washed with 1 N aqueous potassium hydrogen sulfate (40 mL), water (40 mL), saturated aqueous sodium hydrogen carbonate (40 mL), and saturated aqueous sodium chloride (40 mL), dried over $Na_2SO_4$, and concentrated in vacuo. The residue was purified by column chromatography (15-75% ethyl acetate/hexanes) to afford the title compound (130 mg, 83% yield) as a white solid. $^1$H NMR (500 MHz, $CDCl_3$) δ 7.28 (dd, J=7.9, 6.5 Hz, 2H), 7.23 (t, J=7.3 Hz, 1H), 7.16 (s, 2H), 4.81 (s, 1H), 3.98-3.56 (m, 5H), 3.50 (s, 1H), 3.37 (d, J=2.9 Hz, 3H), 3.17 (dd, J=13.9, 5.4 Hz, 2H), 3.04 (dd, J=14.0, 7.7 Hz, 1H), 2.34 (s, 1H), 1.81-1.69 (m, 2H), 1.65 (s, 3H), 1.51-1.40 (m, 9H), 1.16 (d, J=7.0 Hz, 3H).

Example 66. General Procedure for the Removal of the Boc Functions with Trifluoroacetic Acid To a solution of the N-Boc amino acid (1.0 mmol) in methylene chloride (2.5 mL) was added trifluoroacetic acid (1.0 mL). After being stirred at room temperature for 1-3 h, the reaction mixture was concentrated in vacuo. Co-evaporation with toluene gave the deprotected product, which was used without any further purification.

Example 67. Synthesis of (S)-methyl 2-((2R,3R)-3-((S)-1-((3R,4S,5S)-4-((tert-butoxycarbonyl)(methyl)amino)-3-methoxy-5-methylheptanoyl)pyrrolidin-2-yl)-3-methoxy-2-methylpropanamido)-3-phenylpropanoate

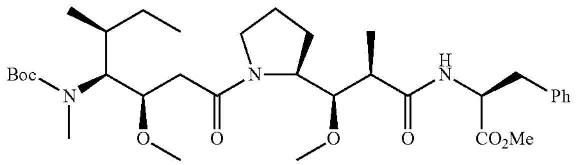 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)OC(C)(C)C]

To a solution of the Boc-deprotected product of (S)-tert-butyl 2-((1R,2R)-1-methoxy-3-(((S)-1-methoxy-1-oxo-3-phenylpropan-2-yl)amino)-2-methyl-3-oxopropyl)pyrrolidine-1-carboxylate (0.29 mmol) and (3R,4S,5S)-4-((tert-butoxycarbonyl)(methyl)amino)-3-methoxy-5-methylheptanoic acid (96.6 mg, 0.318 mmol) in DMF (5 mL) at 0° C. was added diethyl cyanophosphonate (58 μL, 0.347 mmol), followed by $Et_3N$ (109 μL, 0.78 mmol). The reaction mixture was stirred at 0° C. for 2 h, then warmed to r.t. and stirred overnight. The reaction mixture was diluted with ethyl acetate (80 mL), washed with 1 N aqueous potassium hydrogen sulfate (40 mL), water (40 mL), saturated aqueous sodium hydrogen carbonate (40 mL), and saturated aqueous sodium chloride (40 mL), dried over $Na_2SO_4$ and concentrated in vacuo. The residue was purified by column chromatography (15-75% ethyl acetate/hexanes) to afford the title compound (150 mg, 81% yield) as a white solid. LC-MS (ESI) m/z calcd. for $C_{34}H_{55}N_3O_8$ $[M+H]^+$: 634.40, found: 634.40.

Example 68. Synthesis of (S)-methyl 2-((2R,3R)-3-((S)-1-((3R,4S,5S)-4-((S)-2-((tert-butoxycarbonyl)amino)-N,3-dimethylbutanamido)-3-methoxy-5-methylheptanoyl)pyrrolidin-2-yl)-3-methoxy-2-methylpropanamido)-3-phenylpropanoate

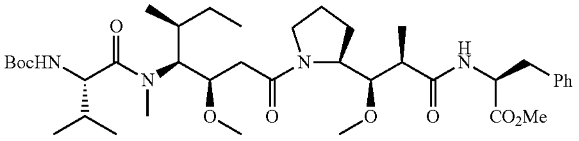 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)OC(C)(C)C)C(C)C]

To a solution of the Boc-deprotected product of (S)-methyl 2-((2R,3R)-3-((S)-1-((3R,4S,5S)-4-((tert-butoxycarbonyl)(methyl)amino)-3-methoxy-5-methylheptanoyl)-pyrrolidin-2-yl)-3-methoxy-2-methylpropanamido)-3-phenylpropanoate (0.118 mmol) and Boc-Val-OH (51.8 mg, 0.236 mmol) in DCM (5 mL) at 0° C. was added BroP (70.1 mg, 0.184 mmol), followed by diisopropylethylamine (70 μL, 0.425 mmol). The mixture was shielded from light and stirred at 0° C. for 30 min then at r.t. for 2 days. The reaction mixture was diluted with ethyl acetate (80 mL), washed with 1 N aqueous potassium hydrogen sulfate (40 mL), water (40 mL), saturated aqueous sodium hydrogen carbonate (40 mL), and saturated aqueous sodium chloride (40 mL), dried over $Na_2SO_4$ and concentrated in vacuo. The residue was purified by column chromatography (20-100% ethyl acetate/hexanes) to afford the title compound (67 mg, 77% yield) as a white solid. LC-MS (ESI) m/z calcd. for $C_{39}H_{64}N_4O_9$ $[M+H]^+$: 733.47, found: 733.46.

Example 69. Synthesis of (S)-methyl 2-((2R,3R)-3-((S)-1-((6S,9S,12S,13R)-12-((S)-sec-butyl)-6,9-diisopropyl-13-methoxy-2,2,5,11-tetramethyl-4,7,10-trioxo-3-oxa-5,8,11-triazapentadecan-15-oyl)pyrrolidin-2-yl)-3-methoxy-2-methylpropanamido)-3-phenylpropanoate (221)

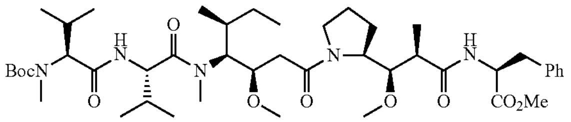 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)C(=O)OC(C)(C)C)C(C)C]

To a solution of the Boc-deprotected product of (S)-methyl 2-((2R,3R)-3-((S)-1-((3R,4S,5S)-4-((S)-2-((tert-butoxycarbonyl)amino)-N,3-dimethylbutanamido)-3-methoxy-5-methylheptanoyl)pyrrolidin-2-yl)-3-methoxy-2-methylpropanamido)-3-phenylpropanoate (0.091 mmol) and Boc-N-Me-Val-OH (127 mg, 0.548 mmol) in DMF (5 mL) at 0° C. was added diethyl cyanophosphonate (18.2 μL, 0.114 mmol), followed by N-methylmorpholine (59 μL, 0.548 mmol). The reaction mixture was stirred at 0° C. for 2 h, then warmed to r.t. and stirred overnight. The reaction mixture was diluted with ethyl acetate (80 mL), washed with 1 N aqueous potassium hydrogen sulfate (40 mL), water (40 mL), saturated aqueous sodium hydrogen carbonate (40 mL), and saturated aqueous sodium chloride (40 mL), dried over sodium sulfate, and concentrated in vacuo. The residue was purified by column chromatography (20-100% ethyl acetate/hexanes) to afford the title compound (30 mg, 39% yield) as a white solid. LC-MS (ESI) m/z calcd. for $C_{45}H_{75}N_5O_{10}$ $[M+H]^+$: 846.55, found: 846.56.

Example 70. Synthesis of (S)-methyl 2-((2R,3R)-3-((S)-1-((3R,4S,5S)-4-((S)—N,3-dimethyl-2-((S)-3-methyl-2-(methylamino)butanamido)butanamido)-3-methoxy-5-methyl-heptanoyl)pyrrolidin-2-yl)-3-methoxy-2-methylpropanamido)-3-phenylpropanoate (222)

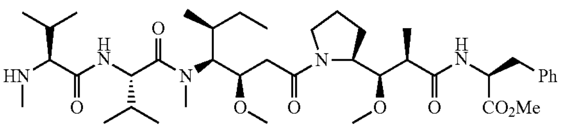 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@@H](NC)C(C)C)C(C)C]

To a solution of (S)-methyl 2-((2R,3R)-3-((S)-1-((6S,9S,12S,13R)-12-((S)-sec-butyl)-6,9-diisopropyl-13-methoxy-2,2,5,11-tetramethyl-4,7,10-trioxo-3-oxa-5,8,11-triazapentadecan-15-oyl)pyrrolidin-2-yl)-3-methoxy-2-methylpropanamido)-3-phenylpropanoate (75.0 mg, 0.0886 mmol) in methylene chloride (5 mL) was added trifluoroacetic acid (2 mL) at room temperature. After being stirred at room temperature for 1 h, the reaction mixture was concentrated in vacuo. Co-evaporation with toluene gave the deprotected title product, which was used without further purification.

Example 71. Synthesis of di-tert-butyl 3,3'-(benzylazanediyl)dipropanoate (227)

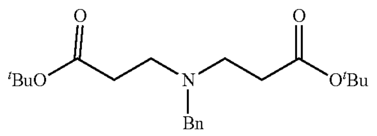 [SMILES: CC(C)(C)OC(=O)CCN(CCC(=O)OC(C)(C)C)Cc1ccccc1]

A mixture of phenylmethanamine (2.0 mL, 18.29 mmol, 1.0 eq) and tert-butyl acrylate (13.3 mL, 91.46 mmol, 5.0 eq) was refluxed at 80° C. overnight and then concentrated. The crude product was purified by $SiO_2$ column chromatography (20:1 hexanes/EtOAc) to give the title compound as colorless oil (5.10 g, 77% yield). ESI MS m/z: calcd for $C_{21}H_{34}NO_4$ $[M+H]^+$ 364.2, found 364.2. $^1H$ NMR (400 MHz, $CDCl_3$) δ 7.38-7.21 (m, 5H), 3.58 (s, 2H), 2.76 (t, J=7.0 Hz, 4H), 2.38 (t, J=7.0 Hz, 4H), 1.43 (s, 17H).

Example 72. Synthesis of di-tert-butyl 3,3'-azanediyldipropanoate (228)

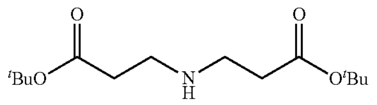 [SMILES: CC(C)(C)OC(=O)CCNCCC(=O)OC(C)(C)C]

To a solution of di-tert-butyl 3,3'-(benzylazanediyl)dipropanoate (1.37 g, 3.77 mmol, 1.0 equiv) in MeOH (10 mL) was added Pd/C (0.20 g, 10% Pd/C, 50% wet) in a hydrogenation bottle. The mixture was shaken overnight under H2 atmosphere and then filtered through a Celite pad. The filtrate was concentrated to give the title compound as colorless oil (1.22 g, 89% yield). ESI MS m/z: calcd for $C_{14}H_{28}NO_4$ $[M+H]^+$ 274.19, found 274.20.

Example 73. Synthesis of di-tert-butyl 3,3'-(propioloylazanediyl)dipropanoate (229)

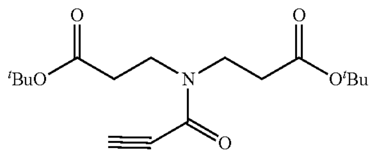 [SMILES: C#CC(=O)N(CCC(=O)OC(C)(C)C)CCC(=O)OC(C)(C)C]

To a solution of di-tert-butyl 3,3'-azanediyldipropanoate (1.22 g, 4.45 mmol, 1.0 eq.) and propiolic acid (0.468 g, 6.68 mmol, 1.5 eq.) in anhydrous DMF (100 mL) at 0° C. was added PyBrop (2.49 g, 5.34 mmol, 1.2 eq.) and DIPEA (2.32 mL, 13.4 mmol, 3.0 eq.). The reaction was stirred at 0° C. for 10 minutes and then warmed to room temperature and stirred for 1.5 h.

Water (500 mL) was added and the mixture was extracted with EtOAc (6×200 mL). The combined organic layers were washed with water (4×600 mL) and brine (600 mL), dried with $Na_2SO_4$, filtered, concentrated and purified by $SiO_2$ column chromatography (4:1 petroleum ether/ethyl acetate) to give the title compound as a light yellow oil (1.00 g, 82% yield). ESI MS m/z: calcd for $C_{17}H_{28}NO_5$ $[M+H]^+$ 326.18, found 326.208.

Example 74. Synthesis of 3,3'-(propioloylazanediyl)dipropanoic acid (230)

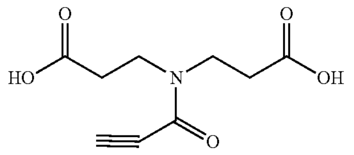

To a solution of di-tert-butyl 3,3'-(propioloylazanediyl) dipropanoate (0.078 g, 0.240 mmol, 1.0 eq) in DCM (3 mL) at room temperature was added TFA (1 mL) and the reaction was stirred for 30 minutes then diluted with anhydrous toluene and concentrated, this operation was repeated for three times to give the title compound as a light yellow oil (0.051 g, theoretical yield). ESI MS m/z: calcd for $C_9H_{12}NO_5$ $[M+H]^+$ 214.06, found 214.06.

Example 75. Synthesis of (3R,4S,7S,10S,13S)-4-((S)-sec-butyl)-7,10-diisopropyl-3-(2-((S)-2-((1R, 2R)-1-methoxy-3-(((S)-1-methoxy-1-oxo-3-phenyl-propan-2-yl)amino)-2-methyl-3-oxopropyl) pyrrolidin-1-yl)-2-oxoethyl)-5,11,13-trimethyl-6,9, 12,15-tetraoxo-18-propioloyl-2-oxa-5,8,11,14,18-pentaazahenicosan-21-oic acid (231)

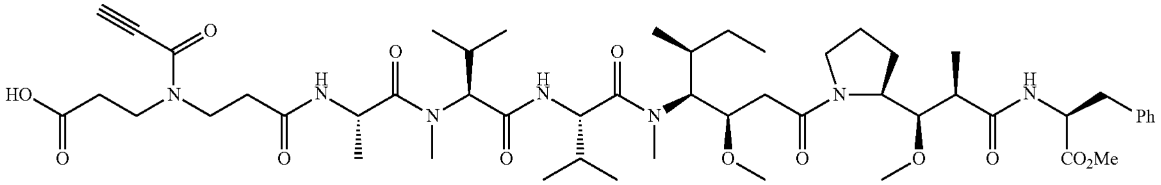 [SMILES: C#CC(=O)N(CCC(=O)O)CCC(=O)N[C@@H](C)C(=O)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)OC)OC)C(C)C)C(C)C]

To a solution of 3,3'-(propioloylazanediyl)dipropanoic acid (0.051 g, 0.240 mmol, 6.5 eq.) and (S)-methyl 2-((2R, 3R)-3-((S)-1-((3R,4S,5S)-4-((S)-2-((S)-2-((S)-2-amino-N-methyl-propanamido)-3-methylbutanamido)-N,3-dimethylbutanamido)-3-methoxy-5-methyl-heptanoyl)pyrrolidin-2-yl)-3-methoxy-2-methylpropanamido)-3-phenylpropanoate (0.030 g, 0.0368 mmol, 1.0 eq.) in anhydrous DMF (3 mL) at 0° C. were added PyBrop (0.021 g, 0.0442 mmol, 1.2 eq.) and DIPEA (0.019 mL, 0.110 mmol, 3.0 eq.). The reaction was stirred for 10 minutes at 0° C., then warmed to room temperature and stirred for 1.0 h. Two drops of water was added and the mixture was concentrated and purified on prep-HPLC ($C_{18}$ column, mobile phase A: water, mobile phase B: acetonitrile, from 20% of B to 80% of B in 50 min.). The fractions were pooled and lyophilized to give the title compound as colorless oil (21 mg, 57% yield). ESI MS m/z: calcd for $C_{52}H_{82}N_7O_{13}$ $[M+H]^+$ 1012.58, found 1012.59.

Example 76. Synthesis of (S)-methyl 2-((2R,3R)-3-((S)-1-((14S,17S,20S,23S,24R)-23-((S)-sec-butyl)-17,20-diisopropyl-24-methoxy-14,16,22-trimethyl-6,12,15,18,21-pentaoxo-9-propioloyl-2-oxa-5,9,13,16,19,22-hexaazahexacosan-26-oyl)pyrrolidin-2-yl)-3-methoxy-2-methylpropanamido)-3-phenylpropanoate (233)

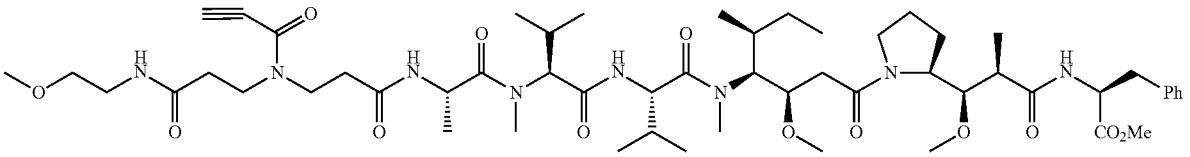 [SMILES: C#CC(=O)N(CCC(=O)NCCOC)CCC(=O)N[C@@H](C)C(=O)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)OC)OC)C(C)C)C(C)C]

To a solution of (3R,4S,7S,10S,13S)-4-((S)-sec-butyl)-7,10-diisopropyl-3-(2-((S)-2-((1R,2R)-1-methoxy-3-(((S)-1-methoxy-1-oxo-3-phenylpropan-2-yl)amino)-2-methyl-3-oxopropyl)pyrrolidin-1-yl)-2-oxoethyl)-5,11,13-trimethyl-6,9,12,15-tetraoxo-18-propioloyl-2-oxa-5,8,11,14,18-pentaazahenicosan-21-oic acid (0.008 g, 0.00791 mmol, 1.0 eq.) and 2-methoxyethanamine (0.006 g, 0.0791 mmol, 10.0 eq.) in anhydrous DMF (2 mL) at 0° C. were added PyBrop (0.004 g, 0.00870 mmol, 1.1 eq.) and DIPEA (0.004 mL, 0.00267 mmol, 3.0 eq.). The reaction was stirred for 10 minutes at 0° C., then warmed to room temperature and stirred for 1.0 h. Two drops of water was added and the mixture was concentrated and purified on prep-HPLC ($C_{18}$ column, mobile phase A: water, mobile phase B: acetonitrile, from 20% of B to 80% of B in 50 min.). The fractions were pooled and lyophilized to give the title compound as colorless oil (7.0 mg, 83% yield). ESI MS m/z: calcd for $C_{55}H_{89}N_8O_{13}$ $[M+H]^+$ 1069.64, found 1069.66.

Example 77. Synthesis of (S)-methyl 2-((2R,3R)-3-((S)-1-((81S,84S,87S,90S,91R)-90-((S)-sec-butyl)-1-hydroxy-84,87-diisopropyl-91-methoxy-81,83,89-trimethyl-73,79,82,85,88-pentaoxo-76-propioloyl-3,6,9,12,15,18,21,24,27,30,33,36,39,42,45,48,51,54,57,60,63,66,69-tricosaoxa-72,76,80,83,86,89-hexaazatrinonacontan-93-oyl)pyrrolidin-2-yl)-3-methoxy-2-methylpropanamido)-3-phenylpropanoate (237)

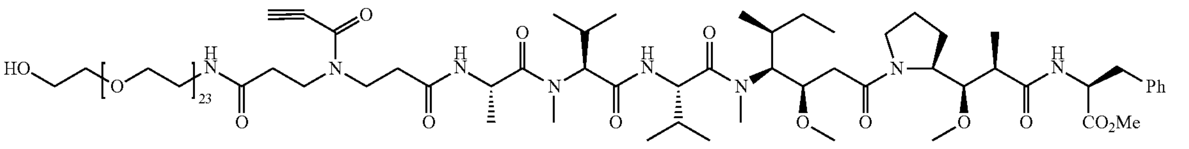

To a solution of (3R,4S,7S,10S,13S)-4-((S)-sec-butyl)-7,10-diisopropyl-3-(2-((S)-2-((1R,2R)-1-methoxy-3-(((S)-1-methoxy-1-oxo-3-phenylpropan-2-yl)amino)-2-methyl-3-oxopropyl)pyrrolidin-1-yl)-2-oxoethyl)-5,11,13-trimethyl-6,9,12,15-tetraoxo-18-propioloyl-2-oxa-5,8,11,14,18-pentaazahenicosan-21-oic acid (0.021 g, 0.0208 mmol, 1.0 eq.) and HO-$PEG_{24}$-$NH_2$ (0.027 g, 0.0250 mmol, 1.2 eq.) in anhydrous DMF (3 mL) at 0° C. were added PyBrop (0.010 g, 0.0218 mmol, 1.05 eq.) and DIPEA (0.011 mL, 0.0624 mmol, 3.0 eq.). The reaction was stirred for 10 minutes at 0° C., then warmed to room temperature and stirred for 1.0 h. Two drops of water was added and the mixture was concentrated and purified on prep-HPLC ($C_{18}$ column, mobile phase A: water, mobile phase B: acetonitrile, from 20% of B to 80% of B in 50 min.). The fractions were pooled and lyophilized to give the title compound as a colorless oil (35 mg, 81% yield), ESI MS m/z: calcd for $C_{100}H_{179}N_8O_{36}$ $[M+H]^+$ 2068.23, found 2068.25.

Example 78. Synthesis of tert-butyl 4-(2-(((benzyloxy)carbonyl)amino)propan amido)-butanoate (251)

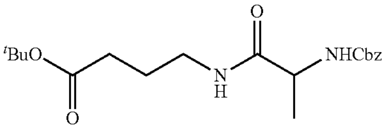 [SMILES: CC(NC(=O)OCc1ccccc1)C(=O)NCCCC(=O)OC(C)(C)C]

To a solution of tert-butyl 4-aminobutanoate (1.00 g, 6.28 mmol, 1.0 eq.) and Z-L-alaine (2.10 g, 9.42 mmol, 1.5 eq.) in anhydrous DCM (50 mL) at 0° C. were added HATU (3.10 g, 8.164 mmol, 1.3 eq.) and TEA (2.6 mL, 18.8 mmol, 3.0 eq.). The reaction was stirred at 0° C. for 10 min., then warmed to room temperature and stirred overnight. The mixture was diluted with DCM and washed with water and brine, dried over anhydrous $Na_2SO_4$, concentrated and purified by $SiO_2$ column chromatography (10:3 petroleum ether/ethyl acetate) to give the title compound as a colorless oil (1.39 g, 61% yield). ESI MS m/z: calcd for $C_{19}H_{29}N_2O_5Na$ $[M+H]^+$ 387.2, found 387.2.

Example 79. Synthesis of tert-butyl 4-(2-aminopropanamido)butanoate (252)

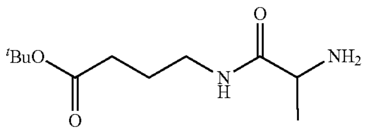 [SMILES: CC(N)C(=O)NCCCC(=O)OC(C)(C)C]

To a solution of tert-butyl 4-(2-(((benzyloxy)carbonyl) amino)propanamido) butanoate (1.39 g, 3.808 mmol, 1.0 eq.) in MeOH (12 mL) was added Pd/C (0.20 g, 10 wt %, 10% wet) in a hydrogenation bottle. The mixture was shaken for 2 h and then filtered through Celite (filter aid), concentrated to give the title compound as a light yellow oil (0.838 g, 95% yield). ESI MS m/z: calcd. for $C_{11}H_{23}N_2O_3$ $[M+H]^+$ 231.16, found 231.15.

Example 80. Synthesis of 3-(2-(2-(dibenzylamino) ethoxy)ethoxy)propanoic acid (254)

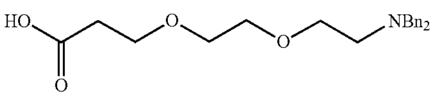

To a solution of tert-butyl 3-(2-(2-(dibenzylamino) ethoxy)ethoxy)propanoate (2.3 g, 5.59 mmol, 1.0 eq) in DCM (10 mL) at room temperature was added TFA (5 mL). After stirring for 90 min., the reaction mixture was diluted with anhydrous toluene and concentrated, this operation was repeated for three times to give the title compound as a light yellow oil (2.0 g, theoretical yield), which was directly used in the next step. ESI MS m/z calcd. for $C_{21}H_{28}NO_4$ $[M+H]^+$ 358.19, found 358.19.

Example 81. Synthesis of perfluorophenyl 3-(2-(2-(dibenzylamino)ethoxy) ethoxy)-propanoate (255)

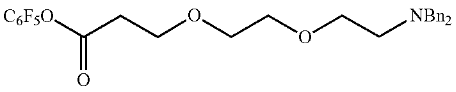

To a solution of 3-(2-(2-(dibenzylamino)ethoxy)ethoxy) propanoic acid (2.00 g, 5.59 mmol, 1.0 eq.) in anhydrous DCM (30 mL) at 0° C. was added DIPEA until pH was neutral, and then PFP (1.54 g, 8.38 mmol, 1.5 eq.) and DIC (1.04 mL, 6.70 mmol, 1.2 eq.) were added. After 10 min. the reaction was warmed to room temperature and stirred overnight. The mixture was filtered, concentrated and purified by $SiO_2$ column chromatography (15:1 petroleum ether/ethyl acetate) to give the title compound as a colorless oil (2.10 g, 72% yield). ESI MS m/z: calcd. for $C_{27}H_{27}F_5NO_4$ $[M+H]^+$ 524.2, found 524.2.

Example 82. Synthesis of tert-butyl 2-benzyl-13-methyl-11,14-dioxo-1-phenyl-5,8-dioxa-2,12,15-triazanonadecan-19-oate (256)

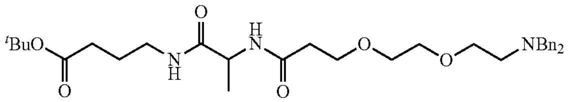

To a solution of tert-butyl 4-(2-aminopropanamido)butanoate (0.736 g, 3.2 mmol, 1.0 eq.) and perfluorophenyl 3-(2-(2-(dibenzylamino)ethoxy) ethoxy)propanoate (2.01 g, 3.84 mmol, 1.2 eq.) in anhydrous DMA (20 mL) at 0° C. was added DIPEA (1.7 mL, 9.6 mmol, 3.0 eq.). After stirring at 0° C. for 10 min. the reaction was warmed to room temperature and stirred overnight.

Water (100 mL) was added and the mixture was extracted with EtOAc (3×100 mL). The combined organic layers were washed with water (3×200 mL) and brine (200 mL), dried over $Na_2SO_4$, filtered, concentrated and purified by $SiO_2$ column chromatography (25:2 DCM/MeOH) to give the title compound as a colorless oil (1.46 g, 80% yield). ESI MS m/z: calcd. for $C_{32}H_{48}N_3O_6$ $[M+H]^+$ 570.34, found 570.33.

Example 83. Synthesis of 2-benzyl-13-methyl-11,14-dioxo-1-phenyl-5,8-dioxa-2,12,15-triazanonadecan-19-oic acid (257)

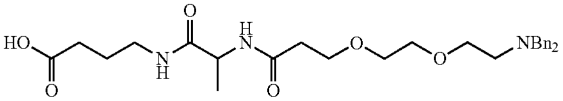

To a solution of tert-butyl 2-benzyl-13-methyl-11,14-dioxo-1-phenyl-5,8-dioxa-2,12,15-triazanonadecan-19-oate (0.057 g, 0.101 mmol, 1.0 eq) in DCM (3 mL) at room temperature was added TFA (1 mL) and stirred for 40 min. The reaction was diluted with anhydrous toluene and then concentrated. This operation was repeated three times to give the title compound as a colorless oil (0.052 g, theoretical yield), which was used directly in the next step. ESI MS m/z: calcd for $C_{28}H_{40}N_3O_6$ $[M+H]^+$ 514.28, found 514.28.

Example 84. Synthesis of (2S)-methyl 2-((2R,3R)-3-((2S)-1-((21S,24S,27S,28R)-2-benzyl-27-((S)-sec-butyl)-21,24-diisopropyl-28-methoxy-13,20,26-trimethyl-11,14,19,22,25-pentaoxo-1-phenyl-5,8-dioxa-2,12,15,20,23,26-hexaazatriacontan-30-oyl) pyrrolidin-2-yl)-3-methoxy-2-methylpropanamido)-3-phenylpropanoate (258)

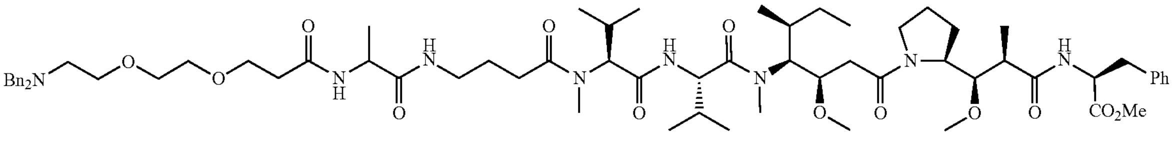

To a solution of 2-benzyl-13-methyl-11,14-dioxo-1-phenyl-5,8-dioxa-2,12,15-triazanonadecan-19-oic acid (0.052 g, 0.101 mmol, 1.5 eq.) and Synthesis of (S)-methyl 2-((2R,3R)-3-((S)-1-((3R,4S,5S)-4-((S)—N,3-dimethyl-2-((S)-3-methyl-2-(methylamino)-butanamido)butanamido)-3-methoxy-5-methyl-heptanoyl)pyrrolidin-2-yl)-3-methoxy-2-methylpropanamido)-3-phenylpropanoate (0.050 g, 0.0671 mmol, 1.0 eq.) in anhydrous DCM (5 mL) at 0° C. were added BrOP (0.034 g, 0.0872 mmol, 1.3 eq.) and DIPEA (0.035 mL, 0.201 mmol, 3.0 eq.). After stirring for 10 min. at 0° C., the reaction was warmed to room temperature and stirred overnight. Two drops of water was added and the mixture was concentrated and purified on HPLC ($C_{18}$ column, mobile phase A: water, mobile phase B: acetonitrile, from 20% of B to 80% of B in 50 min). The fractions were pooled and lyophilized to give the title compound as a colorless oil (60 mg, 72% yield). ESI MS m/z: calcd for $C_{68}H_{105}N_8O_{13}$ $[M+H]^+$ 1241.77, found 1241.77.

Example 85. Synthesis of (2S)-methyl 2-((2R,3R)-3-((2S)-1-((19S,22S,25S,26R)-1-amino-25-((S)-sec-butyl)-19,22-diisopropyl-26-methoxy-11,18,24-trimethyl-9,12,17,20,23-pentaoxo-3,6-dioxa-10,13,18,21,24-pentaazaoctacosan-28-oyl)pyrrolidin-2-yl)-3-methoxy-2-methylpropanamido)-3-phenylpropanoate (259)

$SiO_2$ column chromatography (15:1 DCM/MeOH) to give the title compound as a yellow oil (0.489 g, 74% yield). ESI MS m/z: calcd for $C_{11}H_{18}NO_3Na$ $[M+H]^+$ 234.1, found 234.1.

Example 87. Synthesis of 4-propiolamidobutanoic acid

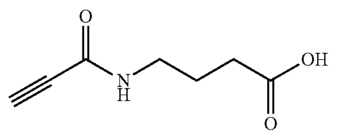

To a solution of tert-butyl 4-propiolamidobutanoate (0.498 g, 2.32 mmol, 1.0 eq) in DCM (3 mL) at room temperature was added TFA (1 mL) and the reaction was stirred for 2 h and then diluted with anhydrous toluene and concentrated. This operation was repeated three times to give the title compound as a light yellow oil (0.051 g, theoretical yield), which was used directly in the next step. ESI MS m/z: calcd for $C_7H_{10}NO_3$ $[M+H]^+$ 156.1, found 156.1.

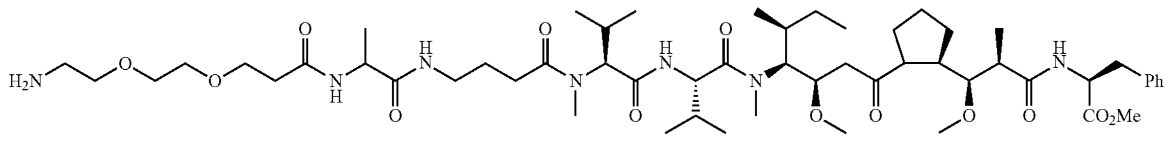

To a solution of (2S)-methyl 2-((2R,3R)-3-((2S)-1-((21S,24S,27S,28R)-2-benzyl-27-((S)-sec-butyl)-21,24-diisopropyl-28-methoxy-13,20,26-trimethyl-11,14,19,22,25-pentaoxo-1-phenyl-5,8-dioxa-2,12,15,20,23,26-hexaazatriacontan-30-oyl)pyrrolidin-2-yl)-3-methoxy-2-methylpropanamido)-3-phenylpropanoate (0.030 g, 0.0288 mmol, 1.0 equiv) in MeOH (3 mL) was added a drop of 6 N HCl and Pd/C (0.050 g, 10 wt %, 10% wet) in a hydrogenation bottle. The mixture was shaken for 2 h and then filtered through Celite (filter aid), concentrated to give the title compound as a light yellow oil (0.030 g, theoretical yield). ESI MS m/z: calcd for $C_{54}H_{93}N_8O_{13}$ $[M+1]^+$ 1061.67, found 1061.69.

Example 86. Synthesis of tert-butyl 4-propiolamidobutanoate

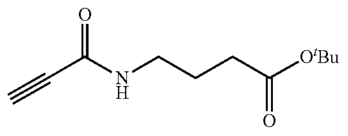

To a solution of tert-butyl 4-aminobutanoate (0.500 g, 3.14 mmol, 1.0 eq.) and propiolic acid (0.330 g, 4.71 mmol, 1.5 eq.) in anhydrous DCM (60 mL) at room temperature was added DCC (0.972 g, 4.71 mmol, 1.5 eq.). The reaction was stirred for 3 h, then filtered, concentrated and purified by Example 88. Synthesis of di-tert-butyl 3,3'-((4-propiolamidobutanoyl)azanediyl) dipropanoate

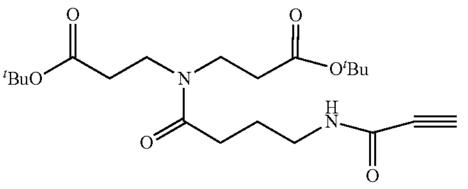 [SMILES: C#CC(=O)NCCCC(=O)N(CCC(=O)OC(C)(C)C)CCC(=O)OC(C)(C)C]

To a solution of 4-propiolamidobutanoic acid (0.360 g, 2.32 mmol, 1.2 eq.) and di-tert-butyl 3,3'-azanediyldipropanoate (0.528 g, 1.93 mmol, 1.0 eq.) in anhydrous DCM (15 mL) at 0° C. was added PyBrop (0.990 g, 2.22 mmol, 1.1 eq.) and DIPEA (1.0 mL, 5.80 mmol, 3.0 eq.). After 10 min. the reaction was warmed to room temperature and stirred overnight. The mixture was then diluted with DCM and washed with water and brine, dried over anhydrous $Na_2SO_4$, concentrated and purified by $SiO_2$ column chromatography (5:2 petroleum ether/ethyl acetate) to give the title compound as a yellow oil (0.367 g, 46% yield). ESI MS m/z: calcd for $C_{21}H_{35}N_2O_6$ $[M+H]^+$ 411.2, found 411.3.

Example 89. Synthesis of 3,3'-((4-propiolamidobutanoyl)azanediyl)dipropanoic acid

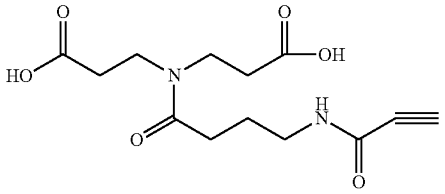 [SMILES: C#CC(=O)NCCCC(=O)N(CCC(=O)O)CCC(=O)O]

To a solution of di-tert-butyl 3,3'-((4-propiolamidobutanoyl)azanediyl) dipropanoate (0.367 g, 0.895 mmol, 1.0 eq) in DCM (3 mL) at room temperature was added TFA (1 mL) and the reaction was stirred for 3 h then diluted with anhydrous toluene and concentrated. This operation was repeated three times to give the title compound as a light yellow oil (0.266 g, theoretical yield), which was used directly in the next step. ESI MS m/z: calcd for $C_{13}H_{19}N_2O_6$ $[M+H]^+$ 299.1, found 299.1.

Example 90. Synthesis of (3R,4S,7S,10S)-4-((S)-sec-butyl)-7,10-diisopropyl-3-(2-((S)-2-((1R,2R)-1-methoxy-3-(((S)-1-methoxy-1-oxo-3-phenylpropan-2-yl)amino)-2-methyl-3-oxopropyl)pyrrolidin-1-yl)-2-oxoethyl)-5,11,18-trimethyl-6,9,12,17,20,30-hexaoxo-33-(4-propiolamidobutanoyl)-2,23,26-trioxa-5,8,11,16,19,29,33-heptaazahexatriacontan-36-oic acid (260)

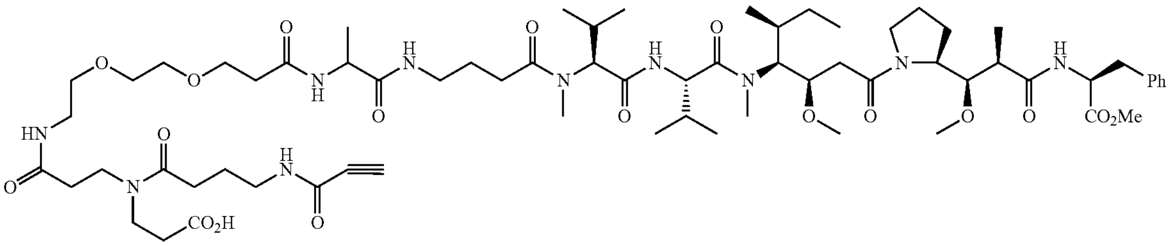 [SMILES: C#CC(=O)NCCCC(=O)N(CCC(=O)O)CCC(=O)NCCOCCOCCC(=O)NC(C)C(=O)NCCCC(=O)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)OC)OC)C(C)C)C(C)C]

To a solution of (2S)-methyl 2-((2R,3R)-3-((2S)-1-((19S,22S,25S,26R)-1-amino-25-((S)-sec-butyl)-19,22-diisopropyl-26-methoxy-11,18,24-trimethyl-9,12,17,20,23-pentaoxo-3,6-dioxa-10,13,18,21,24-pentaazaoctacosan-28-oyl) pyrrolidin-2-yl)-3-methoxy-2-methylpropanamido)-3-phenylpropanoate (0.030 g, 0.0288 mmol, 1.0 eq.) and 3,3'-((4-propiolamidobutanoyl)azanediyl)dipropanoic acid (0.026 g, 0.0865 mmol, 3.0 eq.) in anhydrous DMF (3 mL) at 0° C. was added PyBrop (0.017 g, 0.0374 mmol, 1.3 eq.) and DIPEA (0.035 mL, 0.064 mmol, 3.0 eq.). After stirring at 0° C. for 10 min. the reaction was warmed to room temperature and stirred for 1h. Two drop of water was added and the mixture was concentrated and purified on HPLC ($C_{18}$ column, mobile phase A: water, mobile phase B: acetonitrile, from 20% of B to 80% of B in 50 min). The fractions were pooled and lyophilized to give the title compound as a colorless oil (18.1 mg, 47% yield). ESI MS m/z: calcd for $C_{67}H_{109}N_{10}O_{18}$ $[M+H]^+$ 1341.784, found 1341.81.

Example 91. Synthesis of (S)-methyl 2-((2R,3R)-3-((S)-1-((5S,8S,11S,14S,15R)-14-((S)-sec-butyl)-8,11-diisopropyl-15-methoxy-5,7,13-trimethyl-3,6,9,12-tetraoxo-1-phenyl-2-oxa-4,7,10,13-tetraazaheptadecan-17-oyl)pyrrolidin-2-yl)-3-methoxy-2-methylpropanamido)-3-phenylpropanoate (263)

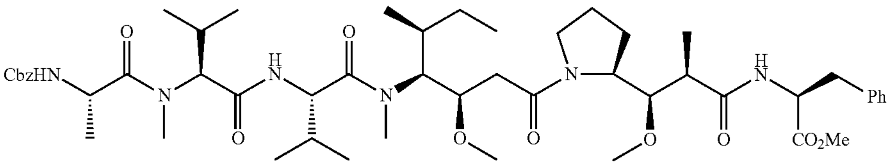 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)C(=O)[C@H](C)NC(=O)OCc1ccccc1)C(C)C]

To a solution of MMAF-OMe (0.132 g, 0.178 mmol, 1.0 eq.) and Z-L-Alanine (0.119 g, 0.533 mmol, 3.0 eq.) in anhydrous DCM (10 mL) at 0° C. were added HATU (0.135 g, 0.356 mmol, 2.0 eq.) and NMM (0.12 mL, 1.07 mmol, 6.0 eq.) in sequence. The reaction was stirred at 0° C. for 10 minutes, then warmed to room temperature and stirred overnight. The mixture was diluted with DCM and washed with water and brine, dried over anhydrous $Na_2SO_4$, concentrated and purified by $SiO_2$ column chromatography (20:1 DCM/MeOH) to give the title compound as a white foamy solid (0.148 g, 88% yield). ESI MS m/z: calcd for $C_{51}H_{79}N_6O_1$i $[M+H]^+$ 951.6, found 951.6.

Example 92. Synthesis of (S)-methyl 2-((2R,3R)-3-((S)-1-((3R,4S,5S)-4-((S)-2-((S)-2-((S)-2-amino-N-methylpropanamido)-3-methylbutanamido)-N,3-dimethylbutanamido)-3-methoxy-5-methylheptanoyl)pyrrolidin-2-yl)-3-methoxy-2-methylpropanamido)-3-phenylpropanoate (264)

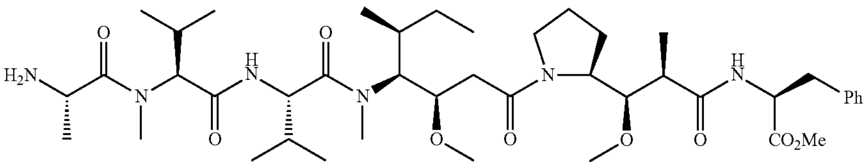 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)C(=O)[C@H](C)N)C(C)C]

To a solution of (S)-methyl 2-((2R,3R)-3-((S)-1-((5S,8S,11S,14S,15R)-14-((S)-sec-butyl)-8,11-diisopropyl-15-methoxy-5,7,13-trimethyl-3,6,9,12-tetraoxo-1-phenyl-2-oxa-4,7,10,13-tetraazaheptadecan-$1^7$-oyl)pyrrolidin-2-yl)-3-methoxy-2-methylpropanamido)-3-phenylpropanoate (0.148 g, 0.156 mmol, 1.0 equiv) in MeOH (5 mL) was added Pd/C (0.100 g, 10% Pd/C, 50% wet) in a hydrogenation bottle. The mixture was shaken for 5 h then filtered through a Celite pad. The filtrate was concentrated to give the title compound as a white foamy solid (0.122 g, 96% yield). ESI MS m/z: calcd for $C_{43}H_{73}N_6O_9$ $[M+H]^+$ 817.5, found 817.5.

Example 93. Synthesis of (E)-tert-butyl 3-(2-(2-(3-bromoacrylamido)ethoxy) ethoxy)propanoate (302)

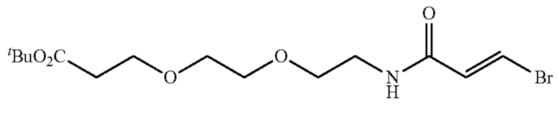 [SMILES: CC(C)(C)OC(=O)CCOCCOCCNC(=O)/C=C/Br]

To a solution of (E)-3-bromoacrylic acid (0.15 g, 1 mmol), DMAP (0.15 g, 1.2 mmol) and DCC (0.21 g, 1 mmol) in DCM (10 ml), tert-butyl 3-(2-(2-aminoethoxy) ethoxy)propanoate (0.23 g, 1 mmol) were added at 0° C. The reaction mixture was allowed to warm to r.t. and stirred overnight. The crude product was concentrated and purified by $SiO_2$ column chromatography with a gradient of EA/DCM to give the title product (0.31 g, 85% yield). ESI MS m/z: calcd for $C_{14}H_{25}BrNO_5$ $[M+H]^+$: 366.08, found 366.08.

Example 94. Synthesis of (E)-3-(2-(2-(3-bromo-acrylamido)ethoxy)ethoxy) propanoic acid (303)

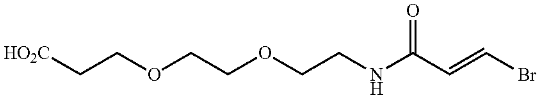 [SMILES: O=C(O)CCOCCOCCNC(=O)/C=C/Br]

(E)-Tert-butyl 3-(2-(2-(3-bromoacrylamido)ethoxy) ethoxy)propanoate (0.31 g, 0.84 mmol) was dissolved in formic acid (4 mL) at 0° C. then $H_2O$ (2 mL) was added. The reaction mixture was allowed to warm to r.t. and stirred overnight. The crude product was concentrated and used for the next step without further purification. ESI MS m/z: calcd for $C_{10}H_{17}BrNO_5$ $[M+H]^+$: 310.02, found 310.03.

Example 95. Synthesis of (E)-2,5-dioxopyrrolidin-1-yl 3-(2-(2-(3-bromoacrylamido)ethoxy)ethoxy) propanoate (304)

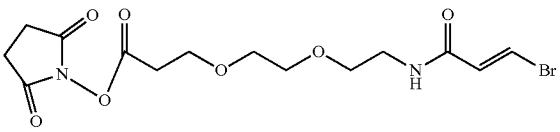 [SMILES: O=C(/C=C/Br)NCCOCCOCCC(=O)ON1C(=O)CCC1=O]

(E)-3-(2-(2-(3-bromoacrylamido)ethoxy)ethoxy) propanoic acid (0.12 g, 0.39 mmol), NHS (0.067 g, 0.58 mmol) and EDC (0.11 g, 0.58 mmol) were dissolved in DCM (10 mL) and the mixture was stirred at r.t. overnight, concentrated and purified by $SiO_2$ column chromatography to give the title product (0.13 g, 82% yield). ESI MS m/z: calcd for $C_{14}H_{20}BrN_2O_7$ $[M+H]^+$: 407.04, found 407.04.

Example 96. Synthesis of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-(3-(2-(2-((E)-3-bromoacrylamido)ethoxy)ethoxy)propanamido)-4-hydroxyphenyl)-2-methylpentanoic acid (306)

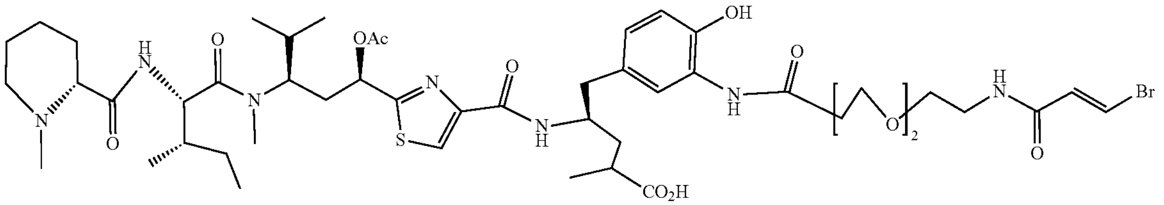

To a solution of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-amino-4-hydroxyphenyl)-2-methylpentanoic acid (305) (Huang Y. et al, Med Chem. #44, $249^{th}$ ACS National Meeting, Denver, CO, Mar. 22-26, 2015; WO2014009774) (50 mg, 0.066 mmol), (E)-2,5-dioxopyrrolidin-1-yl 3-(2-(2-(3-bromoacryl amido)ethoxy)ethoxy) propanoate (60 mg, 0.148 mmol) in DMA (3 ml) was added $NaH_2PO_4$ (17.8 mg, 0.15 mmol). The mixture was stirred at r.t. overnight, concentrated and purified by reverse phase HPLC with a gradient of $MeCN/H_2O$ to give the title product (22.6 mg, 33% yield). ESI MS m/z: calcd for $C_{48}H_{73}BrN_7O_{12}S$ $[M+H]^+$: 1052.41, found 1052.40.

Example 97. Synthesis of tert-butyl 3-(2-(2-propiolamidoethoxy)ethoxy) propanoate (320)

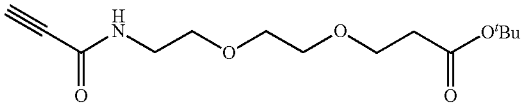 [SMILES: C#CC(=O)NCCOCCOCCC(=O)OC(C)(C)C]

Tert-butyl 3-(2-(2-aminoethoxy)ethoxy)propanoate (466 mg, 2 mmol) and propiolic acid (210 mg, 3 mmol) were dissolved in DCM (50 mL), to which DCC (618 mg, 3 mmol) was added. The resulting solution was stirred at r.t. for 3 h and then concentrated. Purification by column chromatography (10% to 100% EtOAc/hexanes) yielded the title compound (400 mg, 70%). ESI MS m/z 286.17 ($[M+H]^+$).

Example 98. Synthesis of 3-(2-(2-propiolamidoethoxy)ethoxy)propanoic acid (321)

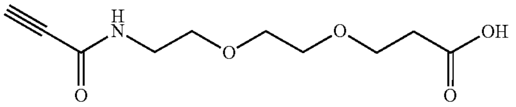 [SMILES: C#CC(=O)NCCOCCOCCC(=O)O]

Tert-Butyl 3-(2-(2-propiolamidoethoxy)ethoxy) propanoate (200 mg, 0.7 mmol) was dissolved in DCM (5 mL), to which formic acid (7 mL) was added. The resulting solution was stirred at 38° C. overnight. All volatiles were removed under vacuum to afford the title compound (160 mg, theoretical yield). ESI MS m/z 230.11 ($[M+H]^+$).

Example 99. Synthesis of 2,5-dioxopyrrolidin-1-yl 3-(2-(2-propiolamido ethoxy)-ethoxy)propanoate (322)

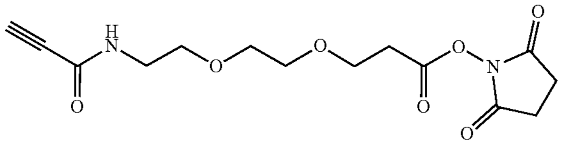 [SMILES: C#CC(=O)NCCOCCOCCC(=O)ON1C(=O)CCC1=O]

NHS (115 mg, 1 mmol) and EDC (192 mg, 1 mmol) were added to a solution of 3-(2-(2-propiolamidoethoxy)ethoxy) propanoic acid (149 mg, 0.65 mmol) in DCM (15 mL). After stirring at r.t. overnight, the reaction was concentrated and purified by column chromatography (0% to 10% MeOH/DCM) to yield the title compound (180 mg, 85%). ESI MS m/z 327.11 ($[M+H]^+$).

Example 100. Synthesis of (4R)-tert-butyl 4-((tert-butoxycarbonyl) amino)-5-(4-hydroxy-3-(3-(2-(2-propiolamidoethoxy)ethoxy)propanamido)phenyl)-2-methylpentanoate (323)

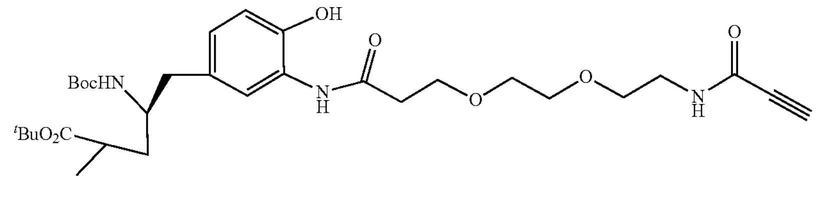 [SMILES: C#CC(=O)NCCOCCOCCC(=O)Nc1cc(C[C@@H](CC(C)C(=O)OC(C)(C)C)NC(=O)OC(C)(C)C)ccc1O]

$NaH_2PO_4$ (0.1M, 1.5 mL) was added to a solution of 2,5-dioxopyrrolidin-1-yl 3-(2-(2-propiolamido ethoxy) ethoxy)propanoate (90 mg, 0.276 mmol) and (4R)-tert-butyl 5-(3-amino-4-hydroxyphenyl)-4-((tert-butoxycarbonyl) amino)-2-methylpentanoate (109 mg, 0.276 mmol) in EtOH (7.5 mL). The resulting solution was stirred at r.t. for 24 h. All volatiles were removed under vacuum, and the residue was purification by column chromatography (30% to 100% EtOAc/hexanes) to yield the title compound (160 mg, 96%). ESI MS m/z 606.34 ($[M+H]^+$).

Example 101. Synthesis of (4R)-4-amino-5-(4-hydroxy-3-(3-(2-(2-propiolamido ethoxy)-ethoxy)propanamido)phenyl)-2-methylpentanoic acid (324)

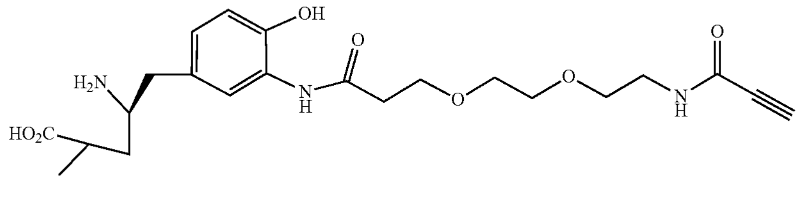 [SMILES: C#CC(=O)NCCOCCOCCC(=O)Nc1cc(C[C@H](N)CC(C)C(=O)O)ccc1O]

(4R)-tert-butyl 4-((tert-butoxycarbonyl) amino)-5-(4-hydroxy-3-(3-(2-(2-propiolamido-ethoxy)ethoxy)propanamido)phenyl)-2-methylpentanoate (40 mg, 0.066 mmol) was dissolved in DCM (3 mL) and treated with TFA (3 mL) at r.t. for 2 h. All volatiles were removed in vacuum, which afforded the title compound (29 mg, 99%). ESI MS m/z 450.23 ($[M+H]^+$).

Example 102. Synthesis of (4R)-4-(2-((6S,9R,11R)-6-((S)-sec-butyl)-9-isopropyl-2,3,3,8-tetramethyl-4,7,13-trioxo-12-oxa-2,5,8-triazatetradecan-11-yl)thiazole-4-carboxamido)-5-(4-hydroxy-3-(3-(2-(2-propiolamidoethoxy)ethoxy)propanamido)phenyl)-2-methylpentanoic acid (325)

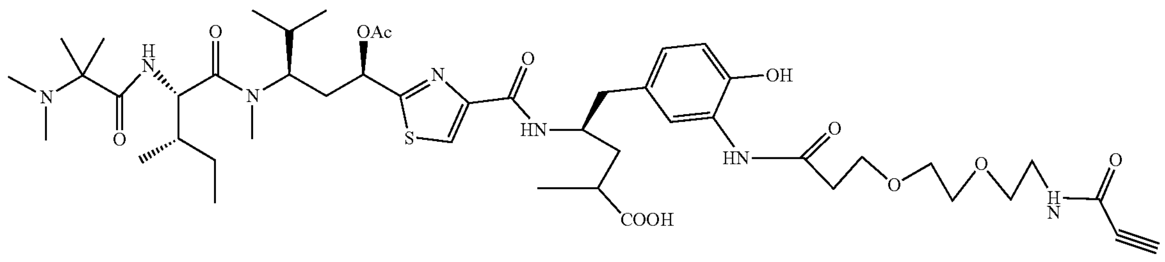 [SMILES: C#CC(=O)NCCOCCOCCC(=O)Nc1cc(C[C@@H](CC(C)C(=O)O)NC(=O)c2csc([C@@H](C[C@H](C(C)C)N(C)C(=O)[C@@H](NC(=O)C(C)(C)N(C)C)[C@@H](C)CC)OC(C)=O)n2)ccc1O]

(4R)-4-amino-5-(4-hydroxy-3-(3-(2-(2-propiolamido ethoxy)-ethoxy)propanamido)-phenyl)-2-methylpentanoic acid (30 mg, 0.066 mmol) and perfluorophenyl 2-((6S,9R,11R)-6-((S)-sec-butyl)-9-isopropyl-2,3,3,8-tetramethyl-4,7,13-trioxo-12-oxa-2,5,8-triazatetradecan-11-yl)thiazole-4-carboxylate (46 mg, 0.066 mmol) were dissolved in DMA (3 mL). DIPEA (10 mg, 0.078 mmol) was then added and stirred at r.t. for 1.5 h. The solvent was removed under vacuum, and the residue was purified on preparative HPLC ($C_{18}$ column, 10-90% MeCN/$H_2O$) to afford the title compound (15 mg, 24%). ESI MS m/z 958.47 ($[M+H]^+$).

Example 103. Synthesis of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-(3-(2-(2-azidoethoxy)ethoxy)propanamido)-4-hydroxyphenyl)-2-methylpentanoic acid (335)

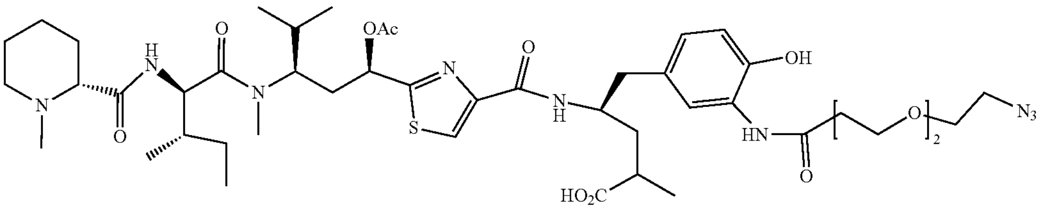

To a solution of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-amino-4-hydroxyphenyl)-2-methylpentanoic acid (Huang Y. et al, Med Chem. #44, $_{249}$th ACS National Meeting, Denver, CO, Mar. 22-26, 2015; WO2014009774) (100 mg, 0.131 mmol) in the mixture of DMA (10 ml) and $NaH_2PO_4$ buffer solution (pH 7.5, 1.0 M, 0.7 ml) was added 2,5-dioxopyrrolidin-1-yl 3-(2-(2-azidoethoxy)ethoxy)propanoate (80.0 mg, 0.266 mmol) in four portions in 2 h. The mixture was stirred overnight, concentrated and purified on CIs preparative HPLC (3.0×25 cm, 25 ml/min), eluted with from 80% water/methanol to 10% water/methanol in 45 min to afford the title compound (101.5 mg, 82% yield). LC-MS (ESI) m/z calcd. for $C_{45}H_{70}N_9O_{11}S$ $[M+H]^+$: 944.48, found: 944.70.

Example 104. Synthesis of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-(3-(2-(2-aminoethoxy)ethoxy)propanamido)-4-hydroxyphenyl)-2-methylpentanoic acid (336)

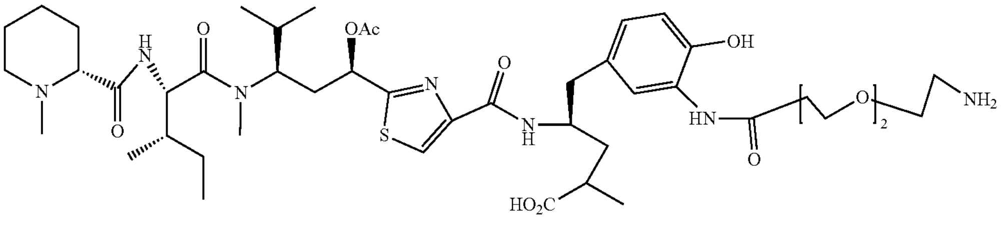

To a solution of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-(3-(2-(2-azidoethoxy)ethoxy)propanamido)-4-hydroxyphenyl)-2-methylpentanoic acid (100.0 mg, 0.106 mmol) in methanol (25 ml) containing 0.1% HCl in a hydrogenation bottle was added Pd/C (25 mg, 10% Pd, 50% wet). After air was vacuumed out in the vessel and 35 psi H2 was conducted in, the mixture was shaken for 4 h, filtered through celite. The filtrate was concentrated and purified on $C_{18}$ preparative HPLC (3.0×25 cm, 25 ml/min), eluted with from 85% water/methanol to 15% water/methanol in 45 min to afford the title compound (77.5 mg, 79% yield). LC-MS (ESI) m/z calcd. for $C_{45}H_{72}N_7O_{11}S$ $[M+H]^+$: 918.49, found: 918.60.

Example 105. Synthesis of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-((3R,4S,7S,10S)-4-((S)-sec-butyl)-7,10-diisopropyl-3-(2-((S)-2-((1R,2R)-1-methoxy-3-(((S)-1-methoxy-1-oxo-3-phenylpropan-2-yl)amino)-2-methyl-3-oxopropyl)pyrrolidin-1-yl)-2-oxoethyl)-5,11,18-trimethyl-6,9,12,17,20,30,36-heptaoxo-33-(5-oxohept-6-ynoyl)-2,23,26,40,43-pentaoxa-5,8,11,16,19,29,33,37-octaazahexatetracontanamido)-4-hydroxyphenyl)-2-methylpentanoic acid (338)

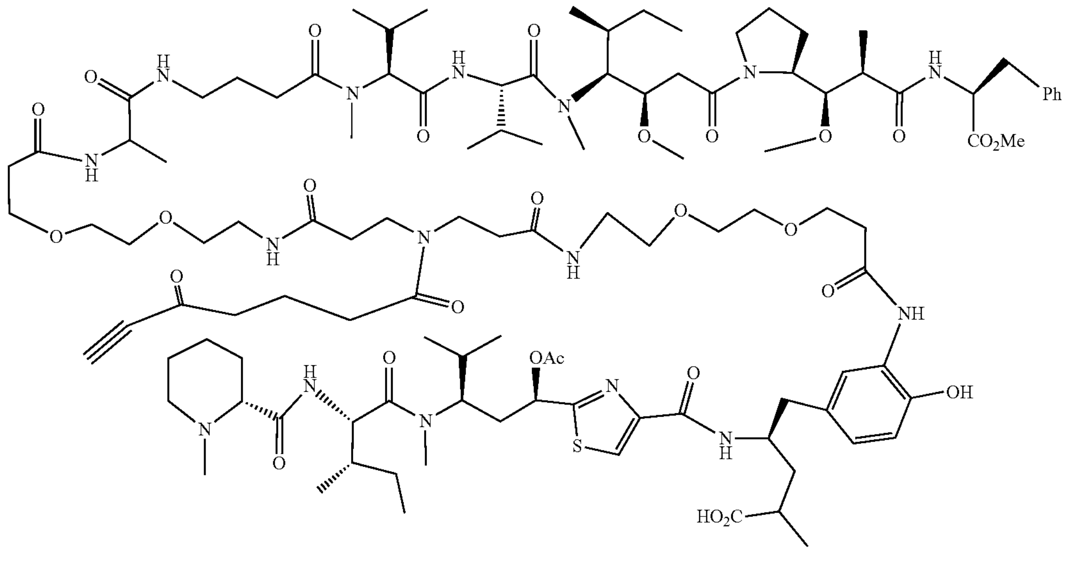 [SMILES: C#CC(=O)CCCC(=O)N(CCC(=O)NCCOCCOCCC(=O)Nc1cc(C[C@@H](CC(C)C(=O)O)NC(=O)c2csc([C@@H](C[C@H](C(C)C)N(C)C(=O)[C@@H](NC(=O)[C@H]3CCCCN3C)[C@@H](C)CC)OC(C)=O)n2)ccc1O)CCC(=O)NCCOCCOCCC(=O)NC(C)C(=O)NCCCC(=O)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)OC)OC)C(C)C)C(C)C]

To a suspension of (3R,4S,7S,10S)-4-((S)-sec-butyl)-7,10-diisopropyl-3-(2-((S)-2-((1R,2R)-1-methoxy-3-(((S)-1-methoxy-1-oxo-3-phenylpropan-2-yl)amino)-2-methyl-3-oxopropyl)pyrrolidin-1-yl)-2-oxoethyl)-5,11,18-trimethyl-6,9,12,17,20,30-hexaoxo-33-(4-propiolamidobutanoyl)-2,23,26-trioxa-5,8,11,16,19,29,33-heptaazahexatriacontan-36-oic acid (0.018 g, 0.0134 mmol) in dichloromethane (5 mL) was added pentafluorophenol (3.7 mg, 0.0201 mmol) and DIC (2.0 mg, 0.0161 mmol). The reaction was stirred at r.t. for 4 h and filtered over celite. The filtrate was concentrated and dissolved in DMF (1 mL), to which (4R)-4-(2-((1R,3R)-1-acetoxy-3-((2S,3S)—N,3-dimethyl-2-((R)-1-methyl-piperidine-2-carboxamido)pentanamido)-4-methylpentyl)thiazole-4-carboxamido)-5-(3-(3-(2-(2-aminoethoxy)ethoxy)propanamido)-4-hydroxyphenyl)-2-methylpentanoic acid (13.5 mg, 0.0147 mmol) in anhydrous DMF (2 mL) was added. After stirring at 0° C. for 2 h, the mixture was concentrated and purified on HPLC ($C_{18}$ column, mobile phase A: water, mobile phase B: acetonitrile, from 20% of B to 80% of B in 50 min). The fractions were pooled and lyophilized to give the title compound as colorless oil (8.9 mg, 30% yield). ESI MS m/z: calcd for $C_{112}H_{176}N_{16}O_{28}S$ $[M+H]^+$ 2226.26, found 2226.48.

Example 106. Synthesis of (2S,4R)-methyl 4-hydroxypyrrolidine-2-carboxylate hydrochloric

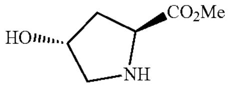

To a solution of trans-4-hydroxy-L-proline (15.0 g, 114.3 mmol) in dry methanol (250 mL) was added thionyl chloride (17 mL, 231 mmol) dropwise at 0 to 4° C. The resulting mixture was stirred for at r.t. overnight, concentrated, crystallized with EtOH/hexane to provide the title compound (18.0 g, 87% yield). ESI MS m/z 168.2 ($[M+Na]^+$).

Example 107. Synthesis of (2S,4R)-1-tert-butyl 2-methyl 4-hydroxypyrrolidine-1,2-dicarboxylate

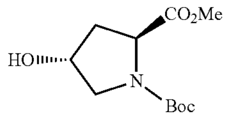 [SMILES: COC(=O)[C@@H]1C[C@@H](O)CN1C(=O)OC(C)(C)C]

To a solution of trans-4-hydroxy-L-proline methyl ester (18.0 g, 107.0 mmol) in the mixture of MeOH (150 ml) and sodium bicarbonate solution (2.0 M, 350 ml) was added $Boc_2O$ (30.0 g, 137.6 mmol) in three portions in 4 h. After stirring for an additional 4 h, the reaction was concentrated to ~350 $m_l$ and extracted with EtOAc (4×80 mL). The combined organic layers were washed with brine (100 mL), dried ($MgSO_4$), filtered, concentrated and purified by $SiO_2$ column chromatography (1:1 hexanes/EtOAc) to give the title compound (22.54 g, 86% yield). ESI MS m/z 268.2 ($[M+Na]^+$).

Example 108. Synthesis of (S)-1-tert-butyl 2-methyl 4-oxopyrrolidine-1,2-dicarboxylate

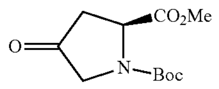 [SMILES: COC(=O)[C@@H]1CC(=O)CN1C(=O)OC(C)(C)C]

The title compound prepared through Dess-Martin oxidation was described in: Franco Manfre et al. J. Org. Chem. 1992, 57, 2060-2065. Alternatively Swern oxidation procedure is as following: To a solution of $(COCl)_2$ (13.0 ml, 74.38 mmol) in $CH_2Cl_2$ (350 ml) cooled to −78° C. was added dry DMSO (26.0 mL). The solution was stirred at −78° C. for 15 min and then (2S,4R)-1-tert-butyl 2-methyl 4-hydroxypyrrolidine-1,2-dicarboxylate (8.0 g, 32.63 mmol) in $CH_2Cl_2$ (100 ml) was added. After stirring at −78° C. for 2 h, triethylamine (50 ml, 180.3 mmol) was added dropwise, and the reaction solution was warmed to room temperature. The mixture was diluted with aq. $NaH_2PO_4$ solution (1.0 M, 400 ml) and phases separated. The aqueous layer was extracted with $CH_2Cl_2$ (2×60 ml). The organic layers were combined, dried over $MgSO_4$, filtered, concentrated and purified by $SiO_2$ column chromatography (7:3 hexanes/EtOAc) to give the title compound (6.73 g, 85% yield). ESI MS m/z 266.2 ($[M+Na]^+$).

Example 109. Synthesis of (S)-1-tert-butyl 2-methyl 4-methylenepyrrolidine-1,2-dicarboxylate

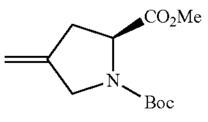 [SMILES: C=C1C[C@@H](C(=O)OC)N(C(=O)OC(C)(C)C)C1]

To a suspension of methyltriphenylphosphonium bromide (19.62 g, 55.11 mmol) in THF (150 mL) at 0° C. was added potassium-t-butoxide (6.20 g, 55.30 mmol) in anhydrous THF (80 mL). After stirring at 0° C. for 2 h, the resulting yellow ylide was added to a solution of (S)-1-tert-butyl 2-methyl 4-oxopyrrolidine-1,2-dicarboxylate (6.70 g, 27.55 mmol) in THF (40 mL). After stirring at r.t. for 1 h, the reaction mixture was concentrated, diluted with EtOAc (200 mL), washed with $H_2O$ (150 mL), brine (150 mL), dried over $MgSO_4$, concentrated and purified on $SiO_2$ column chromatography (9:1 hexanes/EtOAc) to yield the title compound (5.77 g, 87% yield). EI MS m/z 264 ($[M+Na]^+$).

Example 110. Synthesis of (S)-methyl 4-methylenepyrrolidine-2-carboxylate hydrochloride

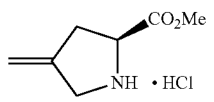

To a solution of (S)-1-tert-butyl 2-methyl 4-methylenepyrrolidine-1,2-dicarboxylate (5.70 g, 23.63 mmol) in EtOAc (40 ml) at 4° C. was added HCl (12 M, 10 ml). The mixture was stirred for 1 h, diluted with toluene (50 ml), concentrated, and crystallized with EtOH/hexane to yield the title compound as HCl salt (3.85 g, 92% yield). EI MS m/z 142.2 ($[M+H]^+$).

Example 111. Synthesis of 4-(benzyloxy)-3-methoxybenzoic acid

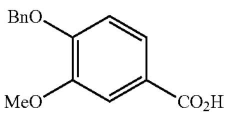 [SMILES: COc1cc(C(=O)O)ccc1OCc1ccccc1]

To a mixture of 4-hydroxy-3-methoxybenzoic acid (50.0 g, 297.5 mmol) in ethanol (350 $m_l$) and aq. NaOH solution (2.0 M, 350 ml) was added BnBr (140.0 g, 823.5 mmol). The mixture was stirred at 65° C. for 8 h, concentrated, co-evaporated with water (2×400 ml) and concentrated to ~400 ml, acidified to pH 3.0 with 6 N HCl. The solid was collected by filtration, crystallized with EtOH, dried at 45° C. under vacuum to afford the title compound (63.6 g, 83% yield). ESI MS m/z 281.2 ($[M+Na]^+$).

Example 112. Synthesis of 4-(benzyloxy)-5-methoxy-2-nitrobenzoic acid

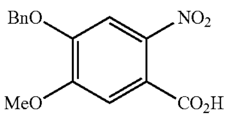 [SMILES: COc1cc(C(=O)O)c([N+](=O)[O-])cc1OCc1ccccc1]

To a solution of 4-(benzyloxy)-3-methoxybenzoic acid (63.5 g, 246.0 mmol) in $CH_2Cl_2$ (400 ml) and HOAc (100 ml) was added $HNO_3$ (fuming, 25.0 ml, 528.5 mmol). The mixture was stirred for 6 h, concentrated, crystallized with EtOH, dried at 40° C. under vacuum to afford the title compound (63.3 g, 85% yield). ESI MS m/z 326.1 ($[M+Na]^+$).

Example 113. Synthesis of (S)-methyl 1-(4-(benzyloxy)-5-methoxy-2-nitrobenzoyl)-4-methylenepyrrolidine-2-carboxylate

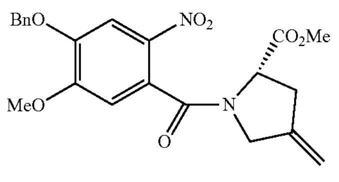 [SMILES: C=C1C[C@@H](C(=O)OC)N(C(=O)c2cc(OC)c(OCc3ccccc3)cc2[N+](=O)[O-])C1]

A catalytic amount of DMF (30 μl) was added to a solution of 4-(benzyloxy)-5-methoxy-2-nitrobenzoic acid (2.70 g, 8.91 mmol) and oxalyl chloride (2.0 mL, 22.50 mmol) in anhydrous $CH_2Cl_2$ (70 mL) and the resulting mixture was stirred at room temperature for 2 h. Excess $CH_2Cl_2$ and oxalyl chloride was removed with rotavap. The acetyl chloride was re-suspended in fresh $CH_2Cl_2$ (70 mL) and was added slowly to a pre-mixed solution of (S)-methyl 4-methylenepyrrolidine-2-carboxylate hydrochloride (1.58 g, 8.91 mmol) and $Et_3N$ (6 mL) in $CH_2Cl_2$ at 0° C. under $N_2$ atmosphere. The reaction mixture was allowed to warm to r.t. and stirring was continued for 8 h. After removal of $CH_2Cl_2$ and $Et_3N$, the residue was partitioned between $H_2O$ and EtOAc (70/70 mL). The aqueous layer was further extracted with EtOAc (2×60 mL). The combined organic layers were washed with brine (40 mL), dried ($MgSO_4$) and concentrated. Purification of the residue with flash chromatography (silica gel, 2:8 hexanes/EtOAc) yielded the title compound (2.88 g, 76% yield). EI MS m/z 449.1 ([M+Na]$^+$).

Example 114. Synthesis of (S)-1-(4-(benzyloxy)-5-methoxy-2-nitrobenzoyl)-4-methylenepyrrolidine-2-carbaldehyde

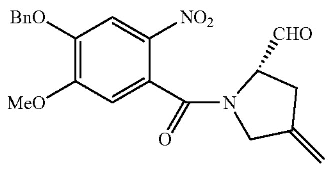 [SMILES: C=C1C[C@@H](C=O)N(C(=O)c2cc(OC)c(OCc3ccccc3)cc2[N+](=O)[O-])C1]

To a vigorously stirred solution of (S)-methyl 1-(4-(benzyloxy)-5-methoxy-2-nitro benzoyl)-4-methylenepyrrolidine-2-carboxylate (2.80 g, 6.57 mmol) in anhydrous $CH_2Cl_2$ (60 mL) was added DIBAL-H (1N in $CH_2Cl_2$, 10 mL) dropwise at −78° C. under $N_2$ atmosphere. After the mixture was stirred for an additional 90 min, excess reagent was decomposed by addition of 2 $m_l$ of methanol, followed by 5% HCl (10 mL). The resulting mixture was allowed to warm to 0° C. Layers were separated and the aqueous layer was further extracted with $CH_2Cl_2$ (3×50 mL). Combined organic layers were washed with brine, dried ($MgSO_4$) and concentrated. Purification of the residue with flash chromatography (silica gel, 95:5 $CHCl_3$/MeOH) yielded the title compound (2.19 g, 84% yield). EI MS m/z 419.1 ([M+Na]$^+$).

Example 115. Synthesis of (S)-8-(benzyloxy)-7-methoxy-2-methylene-2,3-dihydro-1H-benzo[e]-pyrrolo[1,2-a]azepin-5(11aH)-one

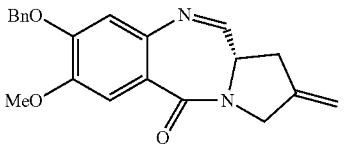 [SMILES: C=C1C[C@H]2C=Nc3cc(OCc4ccccc4)c(OC)cc3C(=O)N2C1]

A mixture of (S)-1-(4-(benzyloxy)-5-methoxy-2-nitrobenzoyl)-4-methylenepyrrolidine-2-carbaldehyde (2.18 g, 5.50 mmol) and $Na_2S_2O_4$ (8.0 g, 45.97 mmol) in THF (60 ml) and $H_2O$ (40 ml) was stirred at room temperature for 20 h. Solvents were removed under high vacuum. The residue was re-suspended in MeOH (60 mL), and HCl (6M) was added dropwise until pH ~2 was reached. The resulting mixture was stirred at r.t. for 1 h. The reaction was worked-up by removing most of MeOH, then diluted with EtOAc (100 mL). The EtOAc solution was washed with sat. $NaHCO_3$, brine, dried ($MgSO_4$), and concentrated. Purification of the residue with flash chromatography (silica gel, 97:3 $CHCl_3$/MeOH) yielded the title compound (1.52 g, 80%). EI MS m/z 372.1 ([M+Na]$^+$).

Example 116. Synthesis of (S)-8-hydroxy-7-methoxy-2-methylene-2,3-dihydro-1H-benzo[e]-pyrrolo[1,2-a]azepin-5(11aH)-one

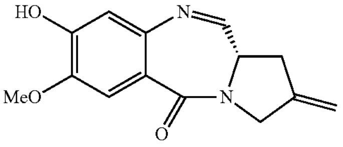 [SMILES: C=C1C[C@H]2C=Nc3cc(O)c(OC)cc3C(=O)N2C1]

To a solution of (S)-8-(benzyloxy)-7-methoxy-2-methylene-2,3-dihydro-1H-benzo[e]-pyrrolo[1,2-a]azepin-5 (11aH)-one (1.50 g, 4.32 mmol) in 70 $m_l$ of $CH_2C_2$ was added 25 $m_l$ of $CH_3SO_3H$ at 0° C. The mixture was stirred at 0° C. for 10 min then r.t. for 2 h, diluted with $CH_2Cl_2$, pH adjusted with cold 1.0 N $NaHCO_3$ to 4 and filtered. The aqueous layer was extracted with $CH_2Cl_2$ (3×60 ml). The organic layers were combined, dried over $Na_2SO_4$, filtered, evaporated and purified on $SiO_2$ column chromatography ($CH_{30}H/CH_2Cl_2$ 1:15) to afford 811 mg (73% yield) of the title product. EI MS m/z 281.1 ([M+Na]$^+$).

Example 117. Synthesis of (11aS,11a'S)-8,8'-(pentane-1,5-diylbis(oxy))bis(7-methoxy-2-methylene-2,3-dihydro-1H-benzo[e]pyrrolo[1,2-a][1,4]diazepin-5(11aH)-one)

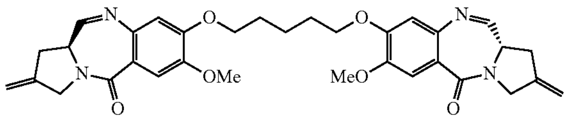

To a stirred suspended solution of $Cs_2CO_3$ (0.761 g, 2.33 mmol) in butanone (8 ml) were added (S)-8-hydroxy-7-methoxy-2-methylene-2,3-dihydro-1H-benzo[e]-pyrrolo[1,2-a]azepin-5(11aH)-one (401 mg, 1.55 mmol) and 1,5-diiodopentane (240 mg, 0.740 mmol). The mixture was stirred at r.t. overnight, concentrated, and purified on $SiO_2$ chromatography (EtOAc/$CH_2Cl_2$ 1:10) to afford 337 mg (78% yield) of the title product. EI MS m/z 607.2 ([M+Na]$^+$).

Example 118. Synthesis of (S)-7-methoxy-8-((5-(((S)-7-methoxy-2-methylene-5-oxo-2,3,5,10,11,11a-hexahydro-1H-benzo[e]pyrrolo[1,2-a][1,4]diazepin-8-yl)oxy)pentyl)oxy)-2-methylene-2,3-dihydro-1H-benzo[e]pyrrolo[1,2-a][1,4]diazepin-5(11aH)-one (340)

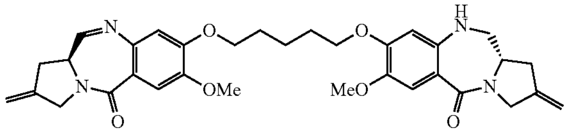

To a solution of (11aS,11a'S)-8,8'-(pentane-1,5-diylbis(oxy))bis(7-methoxy-2-methylene-2,3-dihydro-1H-benzo[e]pyrrolo[1,2-a][1,4]diazepin-5(11aH)-one) (150 mg, 0.256 mmol) in anhydrous dichloromethane (1 mL) and absolute ethanol (1.5 mL) was added sodium borohydride in methoxyethyl ether (85 μl, 0.5 M, 0.042 mmol) at 0° C. The ice bath was removed after 5 minutes and the mixture was stirred at room temperature for 3 hours, then cooled to 0° C., quenched with saturated ammonium chloride, diluted with dichloromethane, and phases separated. The organic layer was washed with brine, dried over anhydrous $Na_2SO_4$, filtered through Celite and concentrated. The residue was purified by reverse phase HPLC (C 18 column, acetonitrile/water). The corresponding fractions were extracted with dichloromethane and concentrated to afford the title compound (64.7 mg, 43%), MS m/z 609.2 ([M+Na]$^+$), 625.3 ([M+K]$^+$) and 627.2 ([M+Na+$H_2O$]$^+$); the fully reduced compound was obtained (16.5 mg, 11%), MS m/z 611.2 ([M+Na]$^+$), 627.2 ([M+K]$^+$), 629.2 ([M+Na+$H_2O$]$^+$); and the unreacted starting material was also recovered (10.2 mg, 7%), MS m/z 607.2 ([M+Na]$^+$), 625.2 ([M+Na+$H_2O$]$^+$).

Example 119. Synthesis of (S)-8-((5-(((S)-10-(3-(2-(2-azidoethoxy)ethoxy) propanoyl)-7-methoxy-2-methylene-5-oxo-2,3,5,10,11,11a-hexahydro-1H-benzo[e]pyrrolo[1,2-a][1,4]diazepin-8-yl)oxy) pentyl)oxy)-7-methoxy-2-methylene-2,3-dihydro-1H-benzo[e]pyrrolo[1,2-a][1,4]diazepin-5(11aH)-one (341)

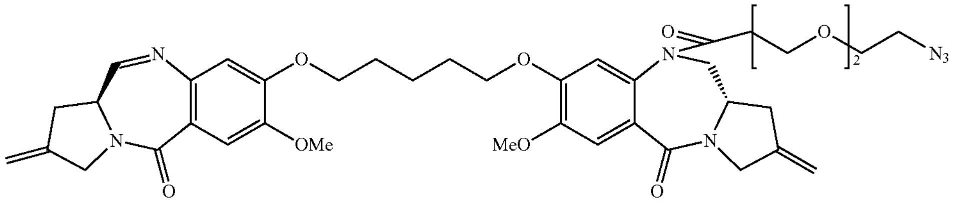

To the mixture of (S)-7-methoxy-8-((5-(((S)-7-methoxy-2-methylene-5-oxo-2,3,5,10,11,11a-hexahydro-1H-benzo[e]pyrrolo[1,2-a][1,4]diazepin-8-yl)oxy)pentyl)oxy)-2-methylene-2,3-dihydro-1H-benzo[e]pyrrolo[1,2-a][1,4]diazepin-5(11aH)-one (60.0 mg, 0.102 mmol) and 2,5-dioxopyrrolidin-1-yl 3-(2-(2-azidoethoxy)ethoxy) propanoate (40.5 mg, 0.134 mmol) in dichloromethane (5 ml) was added EDC (100.5 mg, 0.520 mmol). The mixture was stirred at r.t. overnight, concentrated and purified on $SiO_2$ column chromatography (EtOAc/$CH_2Cl_2$, 1:6) to afford 63.1 mg (81% yield) of the title product. ESI MS m/z $C_{40}H_{50}N_7O_9$[M+H]$^+$, cacld. 772.36, found 772.30.

Example 120. Synthesis of (S)-8-((5-(((S)-10-(3-(2-(2-aminoethoxy)ethoxy) propanoyl)-7-methoxy-2-methylene-5-oxo-2,3,5,10,11,11a-hexahydro-1H-benzo[e]pyrrolo[1,2-a][1,4]diazepin-8-yl)oxy) pentyl)oxy)-7-methoxy-2-methylene-2,3-dihydro-1H-benzo[e]pyrrolo[1,2-a][1,4]diazepin-5(11aH)-one (342)

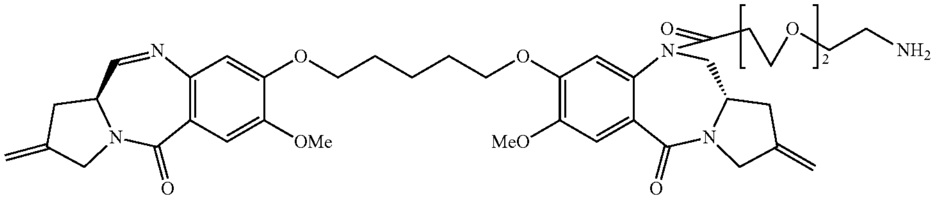

To a solution of (S)-8-((5-(((S)-10-(3-(2-(2-azidoethoxy)ethoxy) propanoyl)-7-methoxy-2-methylene-5-oxo-2,3,5,10,11,11a-hexahydro-1H-benzo[e]pyrrolo[1,2-a][1,4]diazepin-8-yl)oxy)pentyl)oxy)-7-methoxy-2-methylene-2,3-dihydro-1H-benzo[e]pyrrolo[1,2-a][1,4]diazepin-5(11aH)-one (60 mg, 0.078 mmol) in the mixture of THF (5 ml) and $NaH_2PO_4$ buffer solution (pH 7.5, 1.0 M, 0.7 ml) was added $PPh_3$ (70 mg, 0.267 mmol). The mixture was stirred at r.t. overnight, concentrated and purified on $C_{18}$ preparative HPLC, eluted with water/$CH_3CN$ (from 90% water to 35% water in 35 min) to afford 45.1 mg (79% yield) of the title product after drying under high vacuum. ESI MS m/z $C_{40}H_{52}N_5O_9$ $[M+H]^+$, cacld. 746.37, found 746.50.

-

Example 121. Synthesis of (2S)-methyl 2-((2R,3R)-3-((2S)-1-((37S,40S,43S,44R)-43-((S)-sec-butyl)-37,40-diisopropyl-44-methoxy-1-((S)-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepin-10(5H)-yl)-29,36,42-trimethyl-1,11,17,27,30,35,38,41-octaoxo-14-(4-propiolamidobutanoyl)-4,7,21,24-tetraoxa-10,14,18,28,31,36,39,42-octaazahexatetracontan-46-oyl)pyrrolidin-2-yl)-3-methoxy-2-methylpropanamido)-3-phenylpropanoate (343)

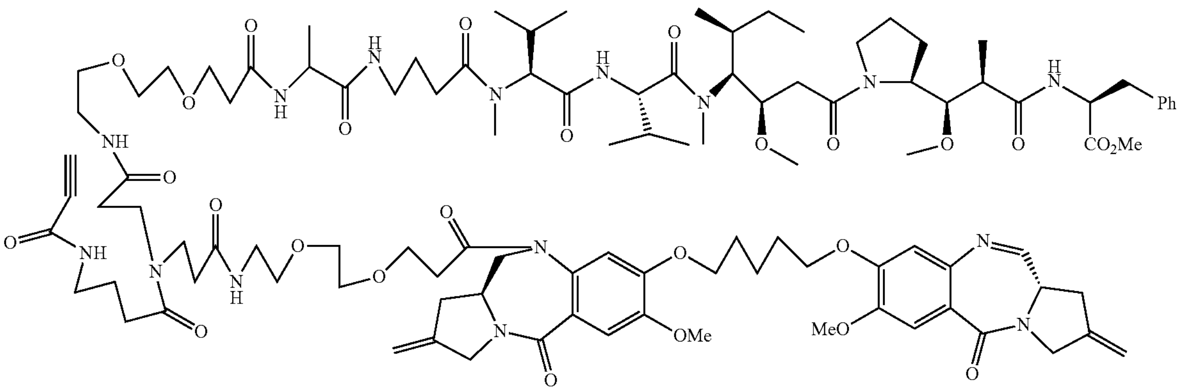 [SMILES: C#CC(=O)NCCCC(=O)N(CCC(=O)NCCOCCOCCC(=O)NC(C)C(=O)NCCCC(=O)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)OC)OC)C(C)C)C(C)C)CCC(=O)NCCOCCOCCC(=O)N1C[C@@H]2CC(=C)CN2C(=O)c2cc(OC)c(OCCCCCOc3cc4c(cc3OC)C(=O)N3CC(=C)C[C@H]3C=N4)cc21]

To a solution of (3R,4S,7S,10S)-4-((S)-sec-butyl)-7,10-diisopropyl-3-(2-((S)-2-((1R,2R)-1-methoxy-3-(((S)-1-methoxy-1-oxo-3-phenylpropan-2-yl)amino)-2-methyl-3-oxopropyl)pyrrolidin-1-yl)-2-oxoethyl)-5,11,18-trimethyl-6,9,12,17,20,30-hexaoxo-33-(4-propiolamidobutanoyl)-2,23,26-trioxa-5,8,11,16,19,29,33-heptaazahexatriacontan-36-oic acid (0.018 g, 0.0134 mmol) and (S)-8-((5-(((S)-10-(3-(2-(2-aminoethoxy)ethoxy) propanoyl)-7-methoxy-2-methylene-5-oxo-2,3,5,10,11,11a-hexahydro-1H-benzo[e]pyrrolo[1,2-a][1,4]diazepin-8-yl)oxy)pentyl)oxy)-7-methoxy-2-methylene-2,3-dihydro-1H-benzo[e]pyrrolo[1,2-a][1,4]diazepin-5(11aH)-one (11.0 mg, 0.0145 mmol) in anhydrous DMF (3 mL) was added EDC (0.020 g, 0.104 mmol). After stirring at room temperature for 4 h, the mixture was concentrated and purified on HPLC ($C_{18}$ column, mobile phase A: water, mobile phase B: acetonitrile, from 20% of B to 80% of B in 50 min). The fractions were pooled and lyophilized to give the title compound as a colorless oil (15.2 mg, 55% yield). ESI MS m/z: calcd for $C_{107}H_{157}N_{15}O_{26}$ $[M+H]^+$ 2069.14, found 2069.42.

Example 122. Synthesis of(S)-2-(3-(2-(2-azidoethoxy)ethoxy)propanamido)-N-(2-((S)-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepin-10(5H)-yl)-2-oxoethyl)-3-methylbutanamide (351)

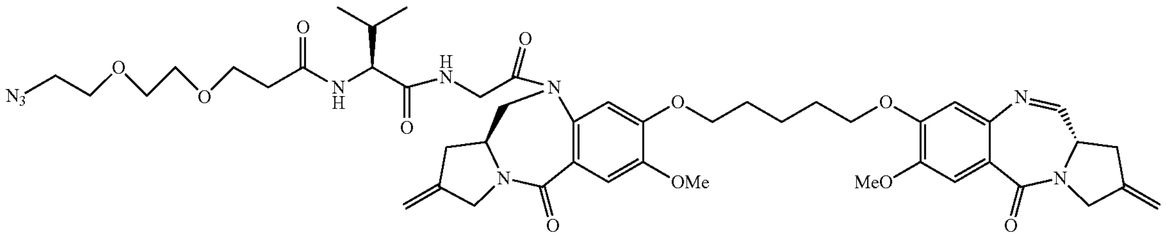 [SMILES: C=C1C[C@H]2CN(C(=O)CNC(=O)[C@@H](NC(=O)CCOCCOCCN=[N+]=[N-])C(C)C)c3cc(OCCCCCOc4cc5c(cc4OC)C(=O)N4CC(=C)C[C@H]4C=N5)c(OC)cc3C(=O)N2C1]

To the mixture of (S)-7-methoxy-8-((5-(((S)-7-methoxy-2-methylene-5-oxo-2,3,5,10,11,11a-hexahydro-1H-benzo[e]pyrrolo[1,2-a][1,4]diazepin-8-yl)oxy)pentyl)oxy)-2-methylene-2,3-dihydro-1H-benzo[e]pyrrolo[1,2-a][1,4]diazepin-5(11aH)-one (60.0 mg, 0.102 mmol) and (S)-15-azido-5-isopropyl-4,7-dioxo-10,13-dioxa-3,6-diazapentadecan-1-oic acid (45.1 mg, 0.125 mmol) in dichloromethane (7 ml) was added BrOP (120.1 mg, 0.309 mmol). The mixture was stirred at r.t. overnight, concentrated and purified on $SiO_2$ column chromatography ($EtOAc/CH_2Cl_2$, 1:6) to afford 71.4 mg (77% yield) of the title product. ESI MS m/z $C_{47}H_{62}N_9O_{11}$ $[M+H]^+$, cacld. 928.45, found 928.60.

Example 123. Synthesis of(S)-2-(3-(2-(2-aminoethoxy)ethoxy)propanamido)-N-(2-((S)-7-methoxy-8-((5-(((S)-7-methoxy-2-methylene-5-oxo-2,3,5,11a-tetrahydro-1H-benzo[e]pyrrolo-[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepin-10(5H)-yl)-2-oxoethyl)-3-methylbutanamide (352)

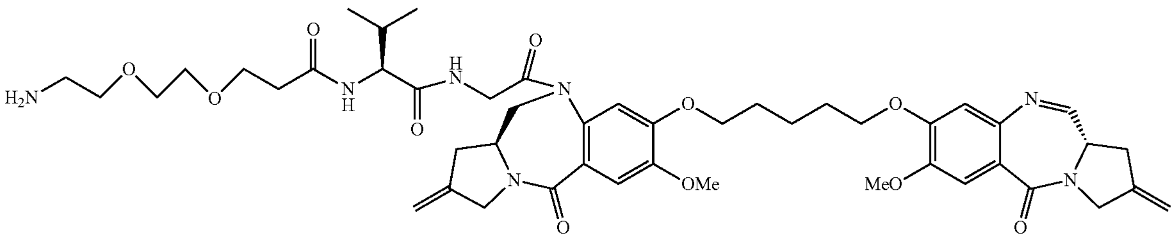 [SMILES: C=C1C[C@H]2CN(C(=O)CNC(=O)[C@@H](NC(=O)CCOCCOCCN)C(C)C)c3cc(OCCCCCOc4cc5c(cc4OC)C(=O)N4CC(=C)C[C@H]4C=N5)c(OC)cc3C(=O)N2C1]

To a solution of(S)-2-(3-(2-(2-azidoethoxy)ethoxy)propanamido)-N-(2-((S)-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepin-10(5H)-yl)-2-oxoethyl)-3-methylbutanamide (63 mg, 0.068 mmol) in the mixture of THF (5 ml) and $NaH_2PO_4$ buffer solution (pH 7.5, 1.0 M, 0.7 $m_1$) was added $PPh_3$ (70 mg, 0.267 mmol). The mixture was stirred at r.t. overnight, concentrated and purified on Cis preparative HPLC, eluted with water/$CH_3CN$ (from 90% water to 35% water in 35 min) to afford 46.5 mg (76% yield) of the title product after drying under high vacuum. ESI MS m/z $C_{47}H_{64}N_7O_{11}$ $[M+H]^+$, cacld. 902.46, found 902.60.

Example 124. Synthesis of (2S)-methyl 2-((2R,3R)-3-((2S)-1-((5S,43S,46S,49S,50R)-49-((S)-sec-butyl)-5,43,46-triisopropyl-50-methoxy-1-((S)-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)-pentyl)oxy)-2-methylene-5-oxo-2,3,11,11a-tetrahydro-1H-benzo[e]pyrrolo[1,2-a][1,4]diazepin-10(5H)-yl)-35,42,48-trimethyl-1,4,7,17,23,33,36,41,44,47-decaoxo-20-(4-propiolamido-butanoyl)-10,13,27,30-tetraoxa-3,6,16,20,24,34,37,42,45,48-decaazadopentacontan-52-oyl)pyrrolidin-2-yl)-3-methoxy-2-methylpropanamido)-3-phenylpropanoate (353)

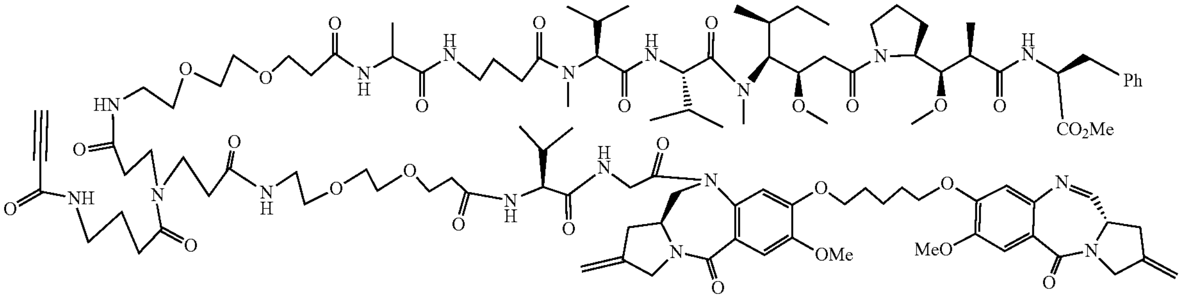

To a solution of (3R,4S,7S,10S)-4-((S)-sec-butyl)-7,10-diisopropyl-3-(2-((S)-2-((1R,2R)-1-methoxy-3-(((S)-1-methoxy-1-oxo-3-phenylpropan-2-yl)amino)-2-methyl-3-oxopropyl)-pyrrolidin-1-yl)-2-oxoethyl)-5,11,18-trimethyl-6,9,12,17,20,30-hexaoxo-33-(4-propiolamido-butanoyl)-2,23,26-trioxa-5,8,11,16,19,29,33-heptaazahexatriacontan-36-oic acid (18.0 mg, 0.0134 mmol) and (S)-2-(3-(2-(2-amino ethoxy)ethoxy)propanamido)-N-(2-((S)-7-methoxy-8-((5-(((S)-7-methoxy-2-methylene-5-oxo-2,3,5,11a-tetrahydro-1H-benzo[e]pyrrolo-[1,2-a][1,4]-diazepin-8-yl)oxy)pentyl)oxy)-2-methylene-5-oxo-2,3,11,11a-tetrahydro-1H-benzo[e]pyrrolo-[1,2-a][1,4]diazepin-10(5H)-yl)-2-oxoethyl)-3-methylbutanamide (13.0 mg, 0.0144 mmol) in anhydrous DMF (3 mL) was added EDC (0.020 g, 0.104 mmol). After stirring at room temperature for 4 h, the mixture was concentrated and purified on HPLC ($C_{18}$ column, mobile phase A: water, mobile phase B: acetonitrile, from 20% of B to 80% of B in 50 min). The fractions were pooled and lyophilized to give the title compound as colorless oil (18.1 mg, 47% yield). ESI MS m/z: calcd for $C_{114}H_{170}N_{17}O_{28}$ $[M+H]^+$ 2225.23, found 2226.22.

Example 125. Antibody conjugate of (2S)-methyl 2-((2R,3R)-3-((2S)-1-((5S,37S,40S,43S,44R)-43-((S)-sec-butyl)-5,37,40-triisopropyl-44-methoxy-1-((S)-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepin-10(5H)-yl)-29,36,42-trimethyl-1,4,7,14,20,27,30,35,38,41-decaoxo-17-(4-propiolamidobutanoyl)-10,24-dioxa-3,6,13,17,21,28,31,36,39,42-decaazahexatetracontan-46-oyl) pyrrolidin-2-yl)-3-methoxy-2-methylpropanamido)-3-phenylpropanoate (354)

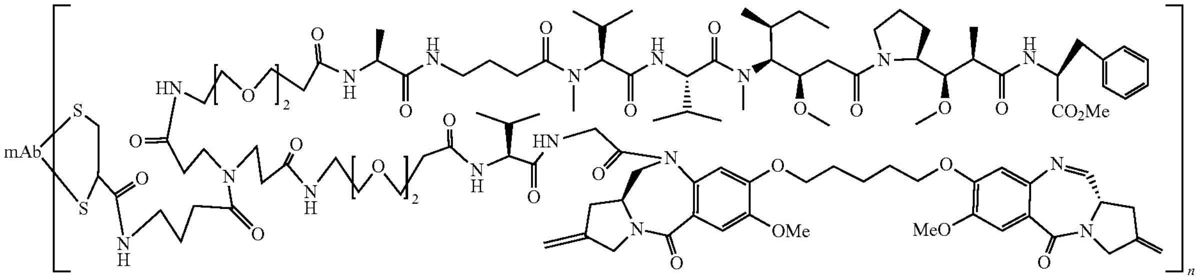

To a mixture of 1.0 mL of 20 mg/$m_l$ Herceptin in pH 7.5, were added of 1.0 mL PBS buffer of 100 mM $NaH_2PO_4$, pH 7.5 buffers, TCEP (25 μL, 20 mM in water) in a Quartz tube. After incubated with stirring at 25° C. for 30 min (2S)-methyl 2-((2R,3R)-3-((2S)-1-((5S,37S,40S,43S,44R)-43-((S)-sec-butyl)-5,37,40-triisopropyl-44-methoxy-1-((S)-7-methoxy-8-((5-(((S)-7-methoxy-2-methylene-5-oxo-2,3,5,11a-tetrahydro-1H-benzo[e]pyrrolo[1,2-a][1,4]-diazepin-8-yl)oxy)pentyl)oxy)-2-methylene-5-oxo-2,3,11,11a-tetrahydro-1H-benzo[e]pyrrolo-[1,2-a][1,4]diazepin-10(5H)-yl)-29,36,42-trimethyl-1,4,7,14,20,27,30,35,38,41-decaoxo-17-(4-propiolamidobutanoyl)-10,24-dioxa-3,6,13,17,21,28,31,36,39,42-decaazahexatetracontan-46-oyl)pyrrolidin-2-yl)-3-methoxy-2-methylpropanamido)-3-phenylpropanoate 353 (27 μL, 20 mM in DMA). The mixture was cooled at 15° C. and a UV light at 365 nm (100 W, light flux of ~20 $W/m^2$ (measured with o-Nitrobenzaldehyde, Willett, K. and Hites, R., *J. Chem. Educ.*, 2000, 77, 900) for 4~6 h, then DHAA (135 μL, 50 mM) was added in. After the quartz tube was taken out from cooler, the mixture was continuously incubated at RT overnight, then purified on G-25 column eluted with 100 mM $NaH_2PO_4$, 50 mM NaCl pH 6.0~7.5 buffer to afford 14.8 mg of the conjugate compound (74% yield) accordingly in 2.73 $m_l$ buffer. The drug/antibody ratio (DAR) was 2.60 (dual drugs) or 5.18 (when MMAF and PBD were individually accounted), which was determined via UPLC-QTOF mass spectrum. It was 94~99% monomer analyzed by SEC HPLC (Tosoh Bioscience, Tskgel G3000SW, 7.8 mm ID×30 cm, 0.5 ml/min, 100 min) and a single band measured by SDS-PAGE gel.

Example 126. Synthesis of (S)-2-((2R,3R)-3-((S)-1-((3R,4S,5S)-4-((S)—N,3-dimethyl-2-((S)-3-methyl-2-(methylamino)butanamido)butanamido)-3-methoxy-5-methylheptanoyl)-pyrrolidin-2-yl)-3-methoxy-2-methylpropanamido)-3-phenylpropanoic acid (356)

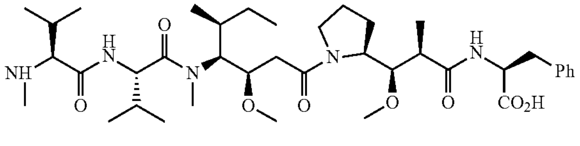 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NC)C(C)C)C(C)C]

(S)-Methyl 2-((2R,3R)-3-((S)-1-((3R,4S,5S)-4-((S)—N,3-dimethyl-2-((S)-3-methyl-2-(methylamino)butanamido)butanamido)-3-methoxy-5-methylheptanoyl)pyrrolidin-2-yl)-3-methoxy-2-methylpropanamido)-3-phenylpropanoate (25 mg, 0.030 mmol) in the mixture of conc. HCl (0.3 ml) and 1,4-dioxane (0.9 ml) was stirred at r.t. for 35 min. The mixture was diluted with EtOH (1.0 ml) and toluene (1.0 ml), concentrated and co-evaporated with EtOH/toluene (2:1) to afford the title compound as a white solid (22 mg, ~100% yield), which was used in the next step without further purification. LC-MS (ESI) m/z calcd. for $C_{39}H_{66}N_5O_8$ $[M+H]^+$: 732.48, found: 732.60.

Example 127. Synthesis of (2S)-2-((2R,3R)-3-((2S)-1-((11S,14S,17S)-1-azido-17-((R)-sec-butyl)-11,14-diisopropyl-18-methoxy-10,16-dimethyl-9,12,15-trioxo-3,6-dioxa-10,13,16-triazaicosan-20-oyl)pyrrolidin-2-yl)-3-methoxy-2-methylpropanamido)-3-phenylpropanoic acid (357)

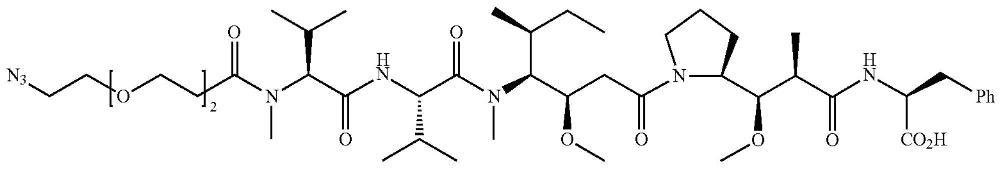

To the crude (S)-2-((2R,3R)-3-((S)-1-((3R,4S,5S)-4-((S)—N,3-dimethyl-2-((S)-3-methyl-2-(methylamino)butanamido)butanamido)-3-methoxy-5-methylheptanoyl)-pyrrolidin-2-yl)-3-methoxy-2-methylpropanamido)-3-phenylpropanoic acid (22 mg, 0.030 mmol) in a mixture of DMA (0.8 ml) and $NaH_2PO_4$ buffer solution (pH 7.5, 1.0 M, 0.7 ml) was added 2,5-dioxopyrrolidin-1-yl 3-(2-(2-azidoethoxy)ethoxy)propanoate (18.0 mg, 0.060 mmol) in four portions in 2 h. The mixture was stirred overnight, concentrated and purified on $SiO_2$ column chromatography ($CH_{30}H/CH_2Cl_2$/HOAc 1:8:0.01) to afford the title compound (22.5 mg, 82% yield). LC-MS (ESI) m/z calcd. for $C_{46}H_{77}N_8O_{11}$ $[M+H]^+$: 917.56, found: 917.60.

Example 128. Synthesis of (2S)-2-((2R,3R)-3-((2S)-1-((11S,14S,17S)-1-amino-17-((R)-sec-butyl)-11,14-diisopropyl-18-methoxy-10,16-dimethyl-9,12,15-trioxo-3,6-dioxa-10,13,16-triazaicosan-20-oyl)pyrrolidin-2-yl)-3-methoxy-2-methylpropanamido)-3-phenylpropanoic acid (358)

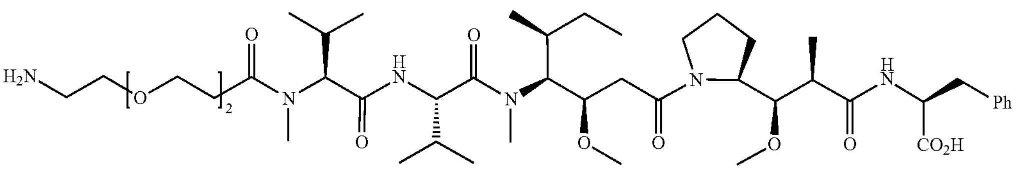

To (2S)-2-((2R,3R)-3-((2S)-1-((11S,14S,17S)-1-azido-17-((R)-sec-butyl)-11,14-diisopropyl-18-methoxy-10,16-dimethyl-9,12,15-trioxo-3,6-dioxa-10,13,16-triazaicosan-20-oyl)pyrrolidin-2-yl)-3-methoxy-2-methylpropanamido)-3-phenylpropanoic acid (22.0 mg, 0.024 mmol) in methanol (5 ml) in a hydrogenation bottle was added Pd/C (5 mg, 10% Pd, 50% wet). After air was vacuumed out and 25 psi H2 was conducted in, the mixture was shaken for 4 h, filtered through celite. The filtrate was concentrated to afford the crude title product (~20 mg, 92% yield), which was used in the next step without further purification. ESI MS m/z+ $C_{46}H_{79}N_6O_{11}$ (M+H), cacld. 891.57, found 891.60.

Example 129. Synthesis of (2S)-2-((2R,3R)-3-((2S)-1-((3R,4S,7S,10S,48S,51S,54S,55R)-4,54-di((S)-sec-butyl)-7,10,48,51-tetraisopropyl-55-methoxy-3-(2-((S)-2-((1R,2R)-1-methoxy-3-(((S)-1-methoxy-1-oxo-3-phenylpropan-2-yl)amino)-2-methyl-3-oxopropyl)pyrrolidin-1-yl)-2-oxoethyl)-5,11,18,47,53-pentamethyl-6,9,12,17,20,30,36,46,49,52-decaoxo-33-(4-propiolamidobutanoyl)-2,23,26,40,43-pentaoxa-5,8,11,16,19,29,33,37,47,50,53-undecaazaheptapentacontan-57-oyl)pyrrolidin-2-yl)-3-methoxy-2-methylpropanamido)-3-phenylpropanoic acid (359)

Example 130. Synthesis of (S)-2-((2R,3R)-3-((S)-1-((6S,9S,12S,13R)-12-((S)-sec-butyl)-6,9-diisopropyl-13-methoxy-2,2,5,11-tetramethyl-4,7,10-trioxo-3-oxa-5,8,11-triazapenta-decan-15-oyl)pyrrolidin-2-yl)-3-methoxy-2-methylpropanamido)-3-phenylpropanoic acid

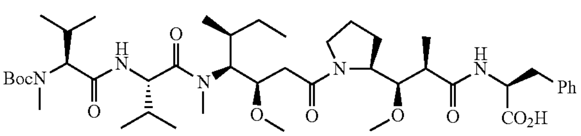

To a solution of (S)-methyl 2-((2R,3R)-3-((S)-1-((6S,9S,12S,13R)-12-((S)-sec-butyl)-6,9-diisopropyl-13-methoxy-2,2,5,11-tetramethyl-4,7,10-trioxo-3-oxa-5,8,11-triazapentadecan-15-oyl)pyrrolidin-2-yl)-3-methoxy-2-methylpropanamido)-3-phenylpropanoate (30 mg, 0.035 mmol) in THF (1.0 ml) was added LiOH in water (1.0M, 0.8 ml). The mixture was stirred at r.t. for 35 min, neutralized with 0.5 M H3$PO_4$ to pH 6, concentrated and purified on $SiO_2$ column chromatography ($CH_{30}H/CH_2Cl_2$/HOAc 1:10:

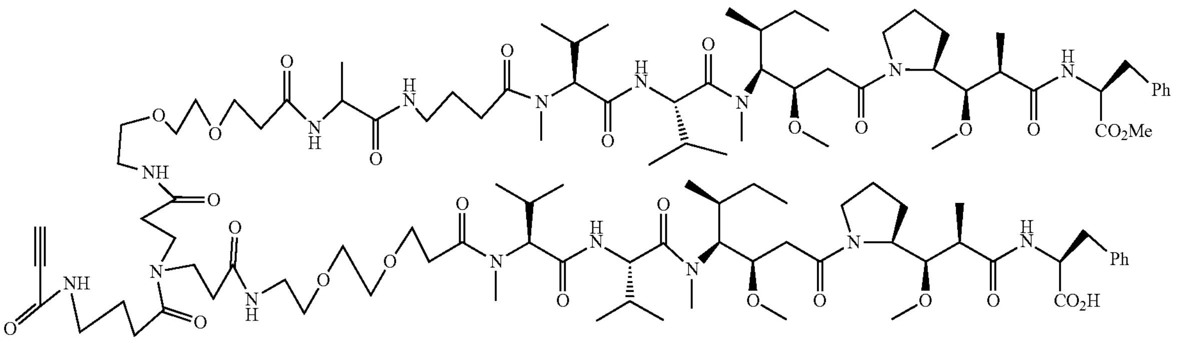 [SMILES: C#CC(=O)NCCCC(=O)N(CCC(=O)NCCOCCOCCC(=O)NC(C)C(=O)NCCCC(=O)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)OC)OC)C(C)C)C(C)C)CCC(=O)NCCOCCOCCC(=O)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

To a suspension of (3R,4S,7S,10S)-4-((S)-sec-butyl)-7,10-diisopropyl-3-(2-((S)-2-((1R,2R)-1-methoxy-3-(((S)-1-methoxy-1-oxo-3-phenylpropan-2-yl)amino)-2-methyl-3-oxopropyl)pyrrolidin-1-yl)-2-oxoethyl)-5,11,18-trimethyl-6,9,12,17,20,30-hexaoxo-33-(4-propiolamidobutanoyl)-2,23,26-trioxa-5,8,11,16,19,29,33-heptaazahexatriacontan-36-oic acid (0.018 g, 0.0134 mmol) in dichloromethane (5 mL) was added pentafluorophenol (3.7 mg, 0.0201 mmol) and DIC (2.0 mg, 0.0161 mmol). The reaction was stirred at r.t. for 4 h and filtered over celite. The filtrate was concentrated and dissolved in DMF (1 mL), to which (2S)-2-((2R,3R)-3-((2S)-1-((11S,14S,17S)-1-amino-17-((R)-sec-butyl)-11,14-diisopropyl-18-methoxy-10,16-dimethyl-9,12,15-trioxo-3,6-dioxa-10,13,16-triazaicosan-20-oyl)pyrrolidin-2-yl)-3-methoxy-2-methylpropanamido)-3-phenylpropanoic acid (13.1 mg, 0.0147 mmol) in anhydrous DMF (2 mL) was added. After stirring at r.t. for 2 h, the mixture was concentrated and purified on HPLC ($C_{18}$ column, mobile phase A: water, mobile phase B: acetonitrile, from 20% of B to 80% of B in 50 min). The fractions were pooled and lyophilized to give the title compound as colorless oil (17.8 mg, 60% yield). ESI MS m/z: calcd for $C_{13}H_{184}N_{16}O_{28}$ $[M+H]^+$ 2214.35, found 2214.36.

0.01) to afford the title compound (25.0 mg, 85% yield). LC-MS (ESI) m/z calcd. for $C_{44}H_{74}N_5O_{10}$ $[M+H]^+$: 832.54, found: 832.60.

Example 131. Synthesis of(S)-2-((2R,3R)-3-((S)-1-((3R,4S,5S)-4-((S)—N,3-dimethyl-2-((S)-3-methyl-2-(methylamino)butanamido)butanamido)-3-methoxy-5-methylheptanoyl)-pyrrolidin-2-yl)-3-methoxy-2-methylpropanamido)-3-phenylpropanoic acid (356)

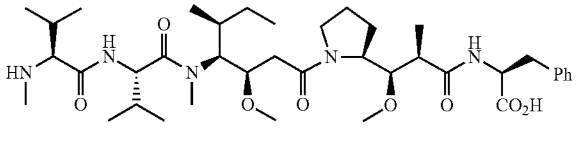 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NC)C(C)C)C(C)C]

To a solution of(S)-2-((2R,3R)-3-((S)-1-((6S,9S,12S,13R)-12-((S)-sec-butyl)-6,9-diisopropyl-13-methoxy-2,2,5,11-tetramethyl-4,7,10-trioxo-3-oxa-5,8,11-triazapenta-decan-15-oyl)pyrrolidin-2-yl)-3-methoxy-2-methylpropanamido)-3-phenylpropanoic acid (25 mg, 0.030 mmol) in dioxane (2.0 ml) was added HCl (12.0M, 0.6 ml). The mixture was stirred at r.t. for 30 min, diluted with dioxane (4 ml) and toluene (4 ml), concentrated and purified on C-18 HPLC column chromatography eluted with MeOH and water ($L_{200}$ mm×Φ 20 mm, v=9 $m_l$/min, from 5% methanol to 40% methanol in 40 min) to afford the title compound (20.0 mg, 90% yield). LC-MS (ESI) m/z calcd. for $C_{39}H_{66}N_5O_8$ $[M+H]^+$: 732.48, found: 732.90.

Example 132. Synthesis of 4-(((benzyloxy)carbonyl)amino)butanoic acid

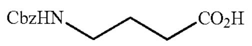

A solution of 4-aminobutyric acid (7.5 g, 75 mmol) and NaOH (6 g, 150 mmol) in $H_2O$ (40 mL) was cooled to 0° C. and treated with a solution of CbzCl (16.1 g, 95 mmol) in THF (32 ml) dropwise. After 1 h, the reaction was allowed to warm to r.t. and stirred for 3 h. THF was removed under vacuum, the pH of the aqueous solution was adjusted to 1.5 by addition of 6 N HCl. Extracted with ethyl acetate, and the organic layer was washed with brine, dried and concentrated to give the title compound (16.4 g, 92% yield). MS ESI m/z calcd for $C_{12}H_{16}NO_5$ $[M+H]^+$ 238.10, found 238.08.

Example 133. Synthesis of tert-butyl 4-(((benzyloxy)carbonyl)amino)butanoate

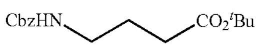

DMAP (0.8 g, 6.56 mmol) and DCC (17.1 g, 83 mmol) were added to a solution of 4-(((benzyloxy)carbonyl)amino) butanoic acid (16.4 g, 69.2 mmol) and t-BuOH (15.4 g, 208 mmol) in DCM (100 mL). After stirring at r.t. overnight, the reaction was filtered and filtrate concentrated. The residue was dissolved in ethyl acetate and then washed with 1N HCl, brine and dried over $Na_2SO_4$. Concentration and purification by column chromatography (10 to 50% EtOAc/hexanes) yielded the title compound (7.5 g, 37% yield). MS ESI m/z calcd for $C_{16}H_{23}NO_4Na$ $[M+Na]^+$316.16, found 316.13.

Example 134. Synthesis of tert-butyl 4-aminobutanoate

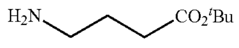

tert-Butyl 4-(((benzyloxy)carbonyl)amino)butanoate (560 mg, 1.91 mmol) was dissolved in MeOH (50 mL), and mixed with Pd/C catalyst (10 wt %, 100 mg) then hydrogenated (1 atm) at room temperature for 3 h. The catalyst was filtered off and all volatiles were removed under vacuum to afford the title compound (272 mg, 90% yield). MS ESI m/z calcd for $C_8H_{18}NO_2$ $[M+H]^+$ 160.13, found 160.13.

Example 135. Synthesis of 2,2-dipropiolamidoacetic acid (373)

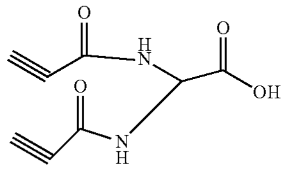

2,2-diaminoacetic acid (2.0 g, 22.2 mmol) in the mixture of EtOH (15 ml) and 50 mM $NaH_2PO_4$ pH 7.5 buffer (25 ml) was added 2,5-dioxopyrrolidin-1-yl propiolate (9.0 g. 53.8 mmol). The mixture was stirred for 8 h, concentrated, acidified to pH 3.0 with 0.1 M HCl, extracted with EtOAc (3x30 ml). The organic layers were combined, dried over $Na_2SO_4$, filtered, concentrated and purified on $SiO_2$ column eluted with $MeOH/CH_2Cl_2$ (1:10 to 1:6) to afford the title compound (3.27 g, 76% yield). 1H NMR ($CDCl_3$) 11.8 (br, 1H), 8.12 (d, 2H), 6.66 (m, 1H), 2.66 (s, 2H). ESI MS m/z: calcd for $C_8H_6N_2O_4$ $[M+H]^+$ 195.03, found 195.20.

Example 136. Synthesis of perfluorophenyl 2,2-dipropiolamidoacetate (421)

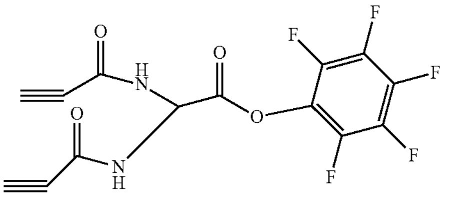 [SMILES: C#CC(=O)NCC(NC(=O)C#C)C(=O)Oc1c(F)c(F)c(F)c(F)c1F]

2,2-Dipropiolamidoacetic acid (2.01 g, 10.31 mmol), pentafluorophenol (2.08 g, 11.30 mmol), DIPEA (1.00 ml, 5.73 mmol) and EDC (4.01 g, 20.88 mmol) in $CH_2Cl_2$ (100 ml) were stirred at RT overnight, concentrated and purified on $SiO_2$ column eluted with $EtOAc/CH_2Cl_2$ (1:15 to 1:8) to afford the title compound (3.08 g, 83% yield). 1H NMR ($CDCl_3$) 8.10 (d, 2H), 6.61 (m, 1H), 2.67 (s, 2H). ESI MS m/z: calcd for $C_{14}H_6F_5N_2O_4$ $[M+H]^+$ 361.02, found 361.20.

Example 137. Synthesis of (S)-2-((S)-2-(2,2-dipropiolamidoacetamido)propanamido)-propanoic acid (423)

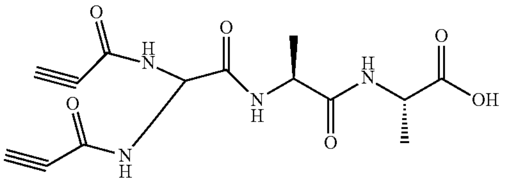 [SMILES: C#CC(=O)NCC(NC(=O)C#C)C(=O)N[C@@H](C)C(=O)N[C@@H](C)C(=O)O]

(S)-2-((S)-2-Aminopropanamido)propanoic acid (422) (1.10 g, 6.87 mmol) in the mixture of DMA (18 ml) and 50 mM $NaH_2PO_4$ pH 7.5 buffer (30 ml) was added perfluorophenyl 2,2-dipropiolamidoacetate (3.00 g. 8.33 mmol). The mixture was stirred for 14 h, concentrated, acidified to pH 3.0 with 0.1 M HCl, extracted with EtOAc (3×40 ml). The organic layers were combined, dried over $Na_2SO_4$, filtered, concentrated and purified on $SiO_2$ column eluted with $MeOH/CH_2Cl_2$ (1:10 to 1:5) to afford the title compound (1.80 g, 78% yield). ESI MS m/z: calcd for $C_{14}H_{17}N_4O_6$ $[M+H]^+$ 337.11, found 337.30.

Example 138. Synthesis of (S)-2,5-dioxopyrrolidin-1-yl 2-((S)-2-(2,2-dipropiolamido-acetamido)propanamido)propanoate (424)

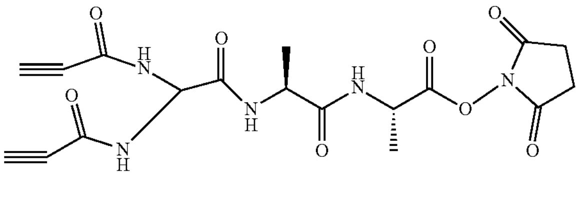 [SMILES: C#CC(=O)NCC(NC(=O)C#C)C(=O)N[C@@H](C)C(=O)N[C@@H](C)C(=O)ON1C(=O)CCC1=O]

(S)-2-((S)-2-(2,2-dipropiolamidoacetamido)propanamido)-propanoic acid (1.01 g, 3.00 mmol), NHS (0.41 g, 3.56 mmol), DIPEA (0.40 ml, 2.29 mmol) and EDC (1.51 g, 7.86 mmol) in $CH_2Cl_2$ (50 ml) were stirred at RT overnight, concentrated and purified on $SiO_2$ column eluted with $EtOAc/CH_2Cl_2$ (1:15 to 1:7) to afford the title compound (1.05 g, 81% yield). ESI MS m/z: calcd for $C_{18}H_{20}N_5O_8$ $[M+H]^+$ 434.12, found 434.40.

Example 139. Synthesis of (4R)-tert-butyl 5-(4-acetoxy-3-nitrophenyl)-4-((tert-butoxycarbonyl)amino)-2-methylpentanoate

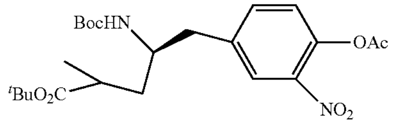 [SMILES: CC(=O)Oc1ccc(C[C@@H](CC(C)C(=O)OC(C)(C)C)NC(=O)OC(C)(C)C)cc1[N+](=O)[O-]]

To a solution of compound 190 (107.1 mg, 0.252 mmol) in dichloromethane (4.0 mL) at 0° C. was added acetic anhydride (0.11 mL, 1.17 mmol) and triethylamine (0.16 mL) in sequence. The reaction was then warmed to r.t. and stirred for 1 h, diluted with dichloromethane and washed with water and brine, dried over anhydrous $Na_2SO_4$, filtered and concentrated. The residue was purified by column chromatography (0-15% EA/PE) to give colorless oil (120.3 mg, theoretical yield). MS ESI m/z calcd for $C_{23}H_{35}N_2O_8$ $[M+H]^+$ 467.23, found 467.23.

Example 140. Synthesis of (4R)-tert-butyl 5-(4-acetoxy-3-aminophenyl)-4-((tert-butoxycarbonyl)amino)-2-methylpentanoate

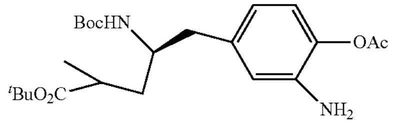 [SMILES: CC(=O)Oc1ccc(C[C@@H](CC(C)C(=O)OC(C)(C)C)NC(=O)OC(C)(C)C)cc1N]

Phenyl nitrile 348 (120.3 mg, 0.258 mmol) was dissolved in ethyl acetate (5 mL) and acetic acid (0.5 mL). To which Pd/C (10 wt %, 10 mg) was added and the mixture was stirred under H2 balloon at r.t. for 30 min before filtration through a celite pad with washing of the pad with ethyl acetate. The filtrate was concentrated and purified by column chromatography (0-25% EA/PE) to give yellow oil (120.9 mg, theoretical yield). MS ESI m/z calcd for $C_{23}H_{37}N_2O_6$ $[M+H]^+$ 437.26, found 437.28.

Example 141. Synthesis of (4R)-ethyl 5-(3-(4-(((benzyloxy)carbonyl)amino) butanamido)-4-((tert-butyldimethylsilyl)oxy)phenyl)-4-((tert-butoxycarbonyl)amino)-2-methylpentanoate

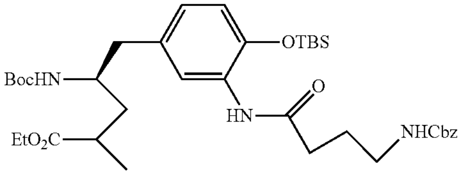 [SMILES: CCOC(=O)C(C)C[C@H](Cc1ccc(O[Si](C)(C)C(C)(C)C)c(NC(=O)CCCNC(=O)OCc2ccccc2)c1)NC(=O)OC(C)(C)C]

2,5-dioxopyrrolidin-1-yl 4-(((benzyloxy)carbonyl)amino) butanoate (0.396 g, 1.2 mmol) and (4R)-ethyl 5-(3-amino-4-hydroxyphenyl)-4-((tert-butoxycarbonyl) amino)-2-methylpentanoate (0.44 g, 1.2 mmol) were dissolved in EtOH (10 mL), and phosphate buffer solution (pH=7.5, 0.1M, 2 ml) was added. The reaction mixture was stirred at r.t. overnight and then the solvent was removed under reduced pressure and the residue purified by $SiO_2$ column chromatography to give the title product (0.485 g, 70%). ESI: m/z: calcd for $C_{31}H_{44}N_3O_8$ $[M+H]^+$: 586.31, found 586.31.

Example 142. Synthesis of (4R)-ethyl 5-(3-(4-aminobutanamido)-4-((tert-butyl dimethylsilyl)oxy) phenyl)-4-((tert-butoxycarbonyl)amino)-2-methylpentanoate

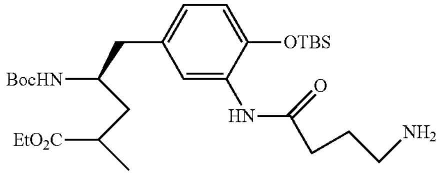 [SMILES: CCOC(=O)C(C)C[C@H](Cc1ccc(O[Si](C)(C)C(C)(C)C)c(NC(=O)CCCN)c1)NC(=O)OC(C)(C)C]

(4R)-ethyl 5-(3-(4-(((benzyloxy)carbonyl)amino) butanamido)-4-((tert-butyldimethyl-silyl)oxy)phenyl)-4-((tert-butoxycarbonyl)amino)-2-methylpentanoate (0.35 g, 0.5 mmol) was dissolved in MeOH (5 ml), and Pd/C (10 wt %, 35 mg) was then added. The reaction mixture was stirred at r.t. under H2 balloon overnight, then filtered through celite and the filtrate was concentrated under reduced pressure to give the title product (0.22 g, 79% yield). ESI MS m/z: calcd for $C_{29}H_{52}N_3O_6Si$ $[M+H]^+$: 566.35, found 566.35.

Example 143. Synthesis of 2-((6S,9S,12R,14R)-9-((S)-sec-butyl)-14-hydroxy-6,12-diisopropyl-2,2,5,11-tetramethyl-4,7,10-trioxo-3-oxa-5,8,11-triazatetradecan-14-yl)thiazole-4-carboxylic acid (381)

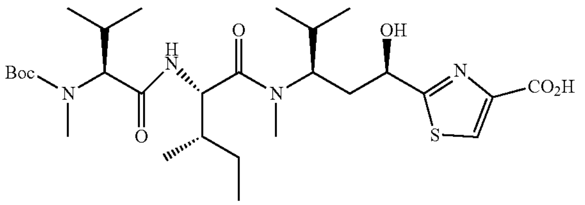 [SMILES: CC[C@H](C)[C@H](NC(=O)[C@H](C(C)C)N(C)C(=O)OC(C)(C)C)C(=O)N(C)[C@H](C[C@@H](O)c1nc(C(=O)O)cs1)C(C)C]

To a solution of Boc-N-Me-L-Val-OH (33 mg, 0.14 mmol) in EtOAc was added pentafluorophenol (39 mg, 0.21 mmol) and DCC (32 mg, 0.154 mmol). The reaction mixture was stirred at r.t. for 16 h and then filtered over a celite pad, with washing of the pad with EtOAc. The filtrate was concentrated and re-dissolved in DMA (2 mL), and then 2-((1R,3R)-3-((2S,3S)-2-amino-N,3-dimethylpentanamido)-1-hydroxy-4-methylpentyl)thiazole-4-carboxylic acid (52 mg, 0.14 mmol) and DIPEA (48.5 μL, 0.28 mmol) were added. The reaction mixture was stirred at r.t. for 24 h and then concentrated and purified by reverse phase HPLC ($C_{18}$ column, 10-100% acetonitrile/water) to afford the title compound (40.2 mg, 49% yield). ESI MS m/z: calcd for $C_{28}H_{49}N_4O_7S$ $[M+H]^+$: 585.32, found 585.32.

Example 144. Synthesis of 2-((6S,9S,12R,14R)-9-((S)-sec-butyl)-6,12-di-isopropyl-2,2,5,11-tetramethyl-4,7,10,16-tetraoxo-3,15-dioxa-5,8,11-triazaheptadecan-14-yl)thiazole-4-carboxylic acid

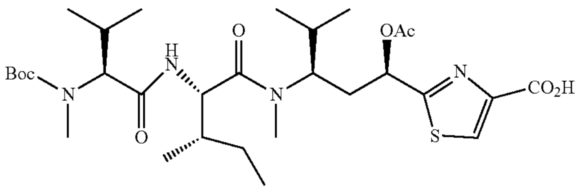 [SMILES: CC[C@H](C)[C@H](NC(=O)[C@H](C(C)C)N(C)C(=O)OC(C)(C)C)C(=O)N(C)[C@H](C[C@@H](OC(C)=O)c1nc(C(=O)O)cs1)C(C)C]

2-((6S,9S,12R,14R)-9-((S)-sec-butyl)-14-hydroxy-6,12-diisopropyl-2,2,5,11-tetramethyl-4,7,10-trioxo-3-oxa-5,8,11-triazatetradecan-14-yl)thiazole-4-carboxylic acid (40 mg, 0.069 mmol) was dissolved in pyridine (8 mL), to which acetic anhydride (20.4 mg, 0.2 mmol) was added at 0° C. and the reaction was allowed to warm to r.t. and stirred overnight. The mixture was concentrated and the residue purified by $SiO_2$ column chromatography with a gradient of DCM/MeOH to give the title product (48.1 mg, ~100% yield). ESI MS m/z: calcd for $C_{30}H_{51}N_4O_8S$ $[M+H]^+$ 627.33, found 627.33.

Example 145. Synthesis of (4R)-4-(2-((6S,9S,12R,14R)-9-((S)-sec-butyl)-6,12-diisopropyl-2,2,5,11-tetramethyl-4,7,10,16-tetraoxo-3,15-dioxa-5,8,11-triazaheptadecan-14-yl)thiazole-4-carboxamido)-2-methyl-5-phenylpentanoic acid

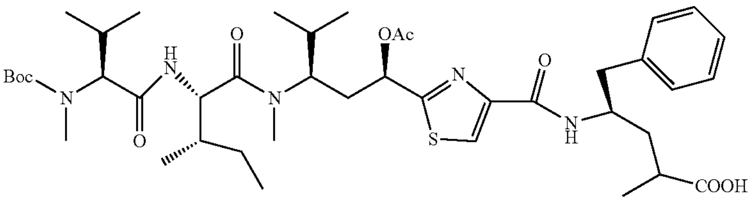 [SMILES: CC[C@H](C)[C@H](NC(=O)[C@H](C(C)C)N(C)C(=O)OC(C)(C)C)C(=O)N(C)[C@H](C[C@@H](OC(C)=O)c1nc(C(=O)N[C@@H](Cc2ccccc2)CC(C)C(=O)O)cs1)C(C)C]

To a solution of 2-((6S,9S,12R,14R)-9-((S)-sec-butyl)-6,12-di-isopropyl-2,2,5,11-tetramethyl-4,7,10,16-tetraoxo-3,15-dioxa-5,8,11-triazaheptadecan-14-yl)thiazole-4-carboxylic acid (48.1 mg, 0.077 mmol) in EtOAc was added pentafluorophenol (21.2 mg, 0.115 mmol) and DCC (17.4 mg, 0.085 mmol). The reaction mixture was stirred at r.t. for 16 h and then filtered over a celite pad, with washing of the pad with EtOAc. The filtrate was concentrated and re-dissolved in DMA (4 mL), and then (4R)-4-amino-2-methyl-5-phenylpentanoic acid (20.7 mg, 0.1 mmol) and DIPEA (26.8 μL, 0.154 mmol) were added. The reaction mixture was stirred at r.t. for 24 h and then concentrated and purified by reverse phase HPLC ($C_{18}$ column, 10-100% acetonitrile/water) to afford the title compound (63 mg, ~100% yield). ESI MS m/z: calcd for $C_{42}H_{66}N_5O_9S$ $[M+H]^+$ 816.45, found 816.45.

Example 146. Synthesis of (4R)-4-(2-((3S,6S,9R,11R)-6-((S)-sec-butyl)-3,9-diisopropyl-8-methyl-4,7,13-trioxo-12-oxa-2,5,8-triazatetradecan-11-yl)thiazole-4-carboxamido)-2-methyl-5-phenylpentanoic acid hydrochloride salt (474)

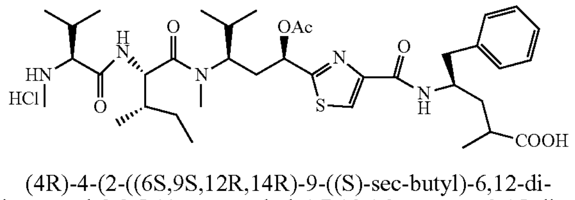

(4R)-4-(2-((6S,9S,12R,14R)-9-((S)-sec-butyl)-6,12-di-isopropyl-2,2,5,11-tetramethyl-4,7,10,16-tetraoxo-3,15-dioxa-5,8,11-triazaheptadecan-14-yl)thiazole-4-carboxamido)-2-methyl-5-phenylpentanoic acid (60 mg, 0.073 mmol) in ethyl acetate (3 ml) and hydrogen chloride (0.8 ml, 12 M). The mixture was stirred for 30 min and diluted with toluene (5 ml) and dioxane (5 ml). The mixture was evaporated and co-evaporated with dioxane (5 ml) and toluene (5 ml) to dryness. The yielded crude title product (57.1 mg, 103% yield) was used for the next step without further purification. ESI MS m/z: calcd for $C_{37}H_{58}N_5O_7S$ $[M+H]^+$ 716.40, found 716.60.

Example 147. Synthesis of (4R)-4-(2-((4R,6R,9S,12S,15S,18S)-9-((S)-sec-butyl)-6,12-diisopropyl-7,13,15,18-tetramethyl-2,8,11,14,17,20,23-heptaoxo-21-propiolamido-3-oxa-7,10,13,16,19,22-hexaazapentacos-24-yn-4-yl)thiazole-4-carboxamido)-2-methyl-5-phenylpentanoic acid (475)

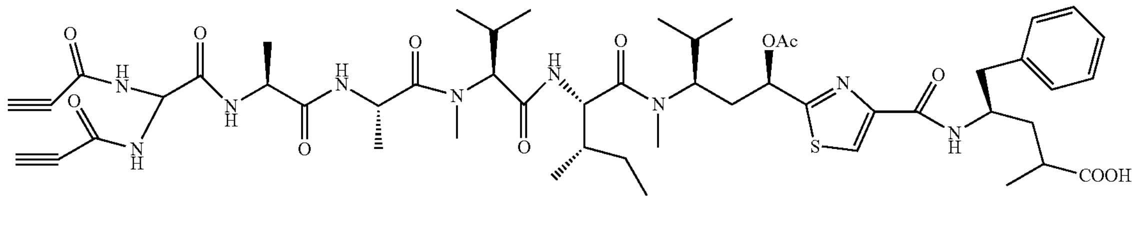 [SMILES: C#CC(=O)NC(NC(=O)C#C)C(=O)N[C@@H](C)C(=O)N[C@@H](C)C(=O)N(C)[C@H](C(=O)N[C@H](C(=O)N(C)[C@H](C[C@@H](OC(C)=O)c1nc(C(=O)N[C@@H](Cc2ccccc2)CC(C)C(=O)O)cs1)C(C)C)[C@@H](C)CC)C(C)C]

To Compound 474 (25 mg, 0.034 mmol) in the mixture of DMA (2 ml) and 0.1 M $Na_2HPO_4$, pH 8.0 (1 ml) was added compound 424 (23.1 mg, 0.053 mmol) in three portions in 3 h and the mixture was then stirred for another 12 hr. The mixture was concentrated, and purified by reverse phase HPLC (200 (L) mm×10 (d) mm, $C_{18}$ column, 10-100% acetonitrile/water in 40 min, v=8 ml/min) to afford the title compound (30.0 mg, 85% yield). ESI MS m/z: calcd for $C_{51}H_{71}N_9O_{12}S$ $[M+H]^+$ 1034.49, found 1034.90.

Example 148. Synthesis of(S)-2-((2R,3R)-3-((S)-1-((8S,11S,14S,17S,20S,21R)-20-((S)-sec-butyl)-14,17-diisopropyl-21-methoxy-8,11,13,19-tetramethyl-3,6,9,12,15,18-hexaoxo-5-propiolamido-4,7,10,13,16,19-hexaazatricos-1-yn-23-oyl)pyrrolidin-2-yl)-3-methoxy-2-methylpropanamido)-3-phenylpropanoic acid (477)

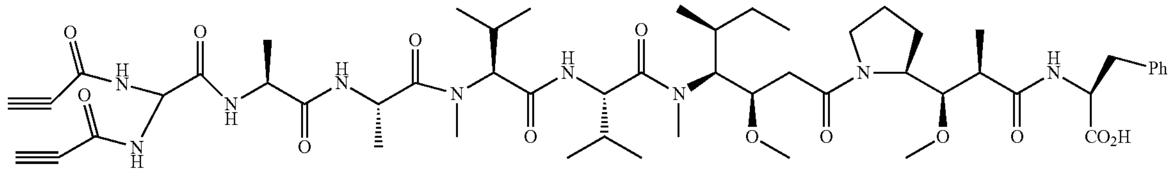 [SMILES: C#CC(=O)NC(NC(=O)C#C)C(=O)N[C@@H](C)C(=O)N[C@@H](C)C(=O)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

To Compound 356 (20 mg, 0.027 mmol) in the mixture of DMA (2 ml) and 0.1 M $Na_2HPO_4$, pH 8.0 (1 ml) was added compound 424 (20.1 mg, 0.046 mmol) in three portions in 3 h and the mixture was then stirred for another 12 hr. The mixture was concentrated, and purified by reverse phase HPLC (200 (L) mm×10 (d) mm, $C_{18}$ column, 10-100% acetonitrile/water in 40 min, v=8 ml/min) to afford the title compound (22.1 mg, 78% yield). ESI MS m/z: calcd for $C_{53}H_{80}N_9O_{13}$ $[M+H]^+$ 1050.58, found 1050.96.

Example 149. Synthesis of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(4-hydroxy-3-(3-(2-(2-((bis(2-propioloylhydrazinyl)phosphoryl)amino)ethoxy)ethoxy)-propanamido)phenyl)-2-methylpentanoic acid (480)

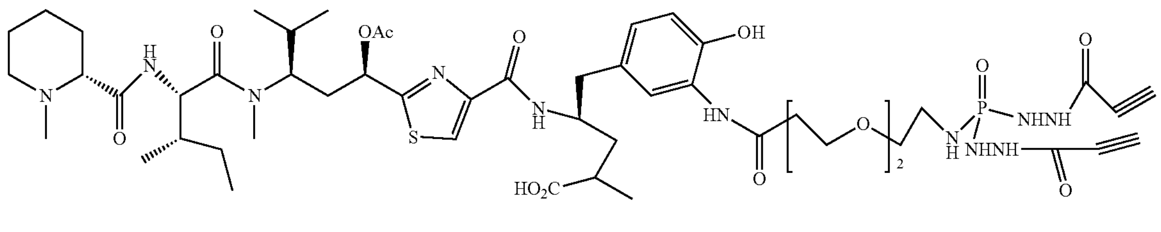

To compound 89 HCl salt (16.1 mg, 0.132 mmol) in the mixture of THF (5 ml) and DIPEA (10 μl, 0.057 mmol) at 0° C. was added $POCl_3$ (10.1 mg, 0.0665 mmol). After stirred at 0° C. for 20 min, the mixture was warmed to room temperature and kept to stirring for another 4 h. Then to the mixture was added compound 336 (60 mg, 0.065 mmol) and DIPEA (20 μl, 0.114 mmol). The mixture was stirred at 50° C. for overnight, concentrated, and purified by reverse phase HPLC (200 (L) mm×10 (d) mm, $C_{18}$ column, 10-100% acetonitrile/water in 40 min, v=8 ml/min) to afford the title compound (23.1 mg, 32% yield). ESI MS m/z: calcd for $C_{51}H_{76}N_{11}O_{14}PS$ $[M+H]^+$ 1130.50, found 1131.20.

Example 150. Synthesis of (2S)-2-((2R,3R)-3-((2S)-1-((11S,14S,17S,18R)-17-((S)-sec-butyl)-11,14-diisopropyl-18-methoxy-10,16-dimethyl-9,12,15-trioxo-1-((bis(2-propioloylhydrazinyl)phosphoryl)amino)-3,6-dioxa-10,13,16-triazaicosan-20-oyl)pyrrolidin-2-yl)-3-methoxy-2-methylpropanamido)-3-phenylpropanoic acid (482)

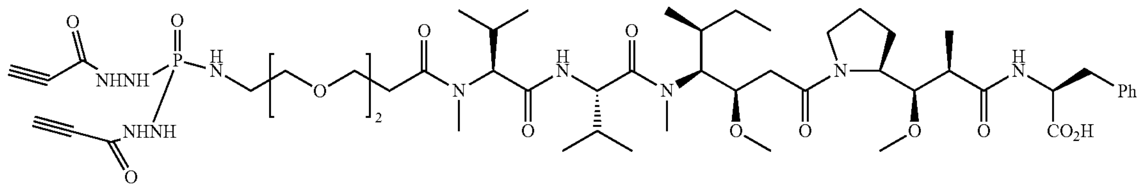

To compound 89 HCl salt (16.1 mg, 0.132 mmol) in the mixture of THF (5 ml) and DIPEA (10 μl, 0.057 mmol) at 0° C. was added $POCl_3$ (10.1 mg, 0.0665 mmol). After stirred at 0° C. for 20 min, the mixture was warmed to room temperature and kept to stirring for another 4 h. Then to the mixture was added compound 358 (60 mg, 0.067 mmol) and DIPEA (20 μl, 0.114 mmol). The mixture was stirred at 50° C. for overnight, concentrated, and purified by reverse phase HPLC (200 (L) mm×10 (d) mm, $C_{18}$ column, 10-100% acetonitrile/water in 40 min, v=8 ml/min) to afford the title compound (25.6 mg, 34% yield). ESI MS m/z: calcd for $C_{52}H_{84}N_{10}O_{14}P$ $[M+H]^+$ 1103.58, found 1104.10.

Example 151. Synthesis of (2S,2'S)-2,2'-((13,14-bis((E)-3-bromoacryloyl)-11,16-dioxo-4,7,20,23-tetraoxa-10,13,14,17-tetraazahexacosane-1,26-dioyl)bis(azanediyl))bis(N-(2-((S)-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepin-10(5H)-yl)-2-oxoethyl)-3-methylbutanamide) (497)

Example 153. Preparation of Conjugate 232, 234, 238, 261, 307, 326, 339, 344 or 360

The preparation of Conjugate 232, 234, 238, 261, 308, 327, 339, 344 or 360 from compound 231, 233, 237, 260, 306, 325, 338, 343 or 359 respectively is similar to the preparation of Conjugate 354 from compound 353 as described in Example 125.

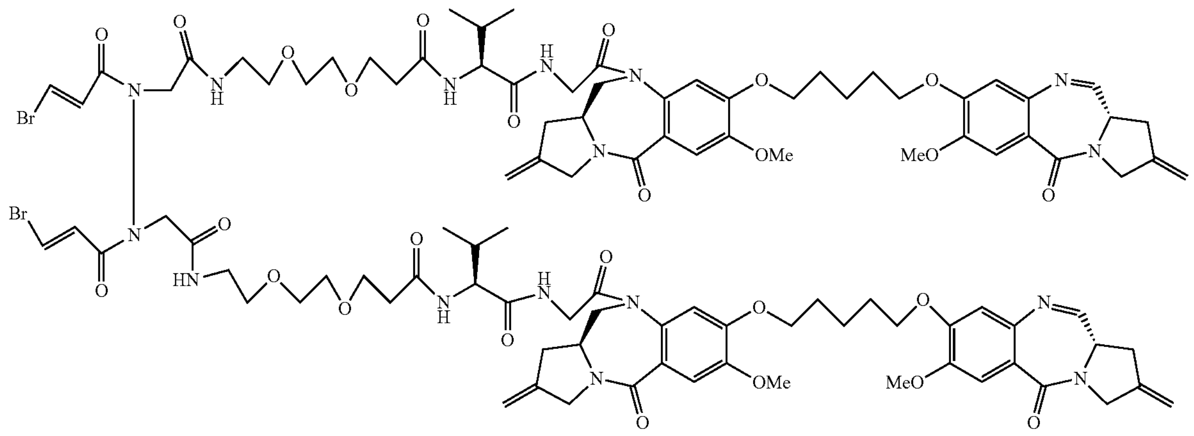 [SMILES: C=C1C[C@H]2CN(C(=O)CNC(=O)[C@@H](NC(=O)CCOCCOCCNC(=O)CN(C(=O)/C=C/Br)N(CC(=O)NCCOCCOCCC(=O)N[C@H](C(=O)NCC(=O)N3C[C@@H]4CC(=C)CN4C(=O)c4cc(OC)c(OCCCCCOc5cc6c(cc5OC)C(=O)N5CC(=C)C[C@H]5C=N6)cc43)C(C)C)C(=O)/C=C/Br)C(C)C)c3cc(OCCCCCOc4cc5c(cc4OC)C(=O)N4CC(=C)C[C@H]4C=N5)c(OC)cc3C(=O)N2C1]

Compound 352 (25.1 mg, 0.0278 mmol), compound 36 (11.50 mg, 0.0279 mmol) and EDC (15 mg, 0.078 mmol) in DMA (2 ml) was stirred for overnight, concentrated, and purified by reverse phase HPLC (200 (L) mm×10 (d) mm, $C_{18}$ column, 10-100% acetonitrile/water in 40 min, v=8 ml/min) to afford the title compound (23.8 mg, 39% yield). QTOF ESI MS m/z: calcd for $C_{104}H_{133}Br_2N_{16}O_{26}$ $[M+H]^+$ 2179.79, found 2180.50 $[M+H]^+$, 219780 $[M+H_2O+H]^+$, 2215.81 $[M+2H_2O+H]^+$.

Example 152. Synthesis of Compound 499

Example 154. General method of Preparation of Conjugate 235, 239, 307, 327, 339, 345, 355, 361, 476, 478, 481, 483, 498, or 500

To a mixture of 2.0 mL of 10 mg/ml Herceptin in pH 6.0-8.0, were added of 0.70 ~2.0 mL PBS buffer of 100 m-M $NaH_2PO_4$, pH 6.5~8.5 buffers, TCEP (14-35 μL, 20 mM in water) and the compound 231, 233, 237, 306, 325, 343, 353, 359, 475, 477, 480, 482, 497 or 499 (14-28 μL, 20 mM in DMA, (compounds 497 and 498 were added 14~18 μL)) independently. The mixture was incubated at RT for 4-18 h, then DHAA (135 μL, 50 mM) was added in. After continu-

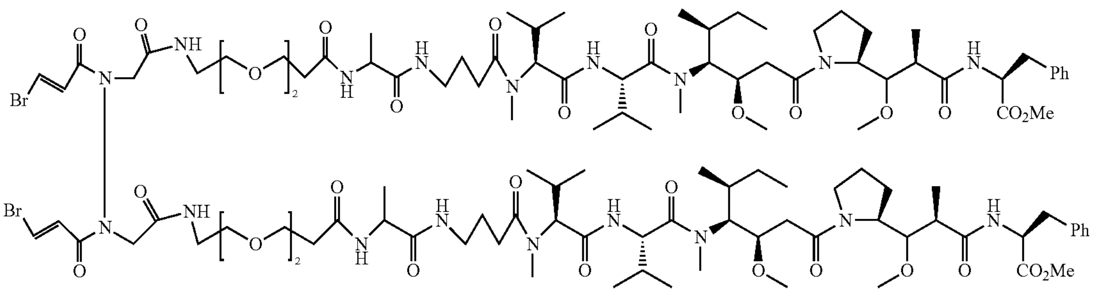

Compound 259 (26.1 mg, 0.0246 mmol), compound 36 (10.20 mg, 0.0247 mmol) and EDC (15 mg, 0.078 mmol) in DMA (2 ml) was stirred for overnight, concentrated, and purified by reverse phase HPLC (200 (L) mm×10 (d) mm, $C_{18}$ column, 10-100% acetonitrile/water in 40 min, v=8 ml/min) to afford the title compound (27.6 mg, 45% yield). QTOF ESI MS m/z: calcd for $C_{118}H_{190}Br_2N_{18}O_{30}$ $[M+H]^+$ 2498.23, found 2499.50 $[M+H]^+$.

ous incubation at RT overnight, the mixture was purified on G-25 column eluted with 100 mM $NaH_2PO_4$, 50 mM NaCl pH 6.0~7.5 buffer to afford 12.8~18.1 mg of the conjugate compound 235, 239, 307, 327, 339, 345, 355, 361, 476, 478, 481, 483, 498, or 500 (60%~91% yield) accordingly in 13.4~15.8 $m_l$ buffer. The drug/antibody ratio (DAR) was 2.1~4.2 for conjugate 235, 239, 307, 327, 339, 345, 355, 361, 476, 478, 481, or 483, or DAR is 2.6~5.3 for conjugate 498, or 500, wherein DAR was determined via UPLC-QTOF mass spectrum. It was 94~99% monomer analyzed by SEC HPLC (Tosoh Bioscience, Tskgel G3000SW, 7.8 mm ID×30 cm, 0.5 m/min, 100 min) and a single band measured by SDS-PAGE gel.

Example 155. In Vitro Cytotoxicity Evaluation of Conjugate 232, 234, 235, 238, 239, 261, 307, 308, 326, 327, 339, 344, 345, 354, 355, 360, 361, 476, 478, 481, 483, 498, or 500 in Comparison with T-DM 1

The cell line used in the cytotoxicity assays was NCI-N87, a human gastric carcinoma cell line; The cells were grown in RPMI-1640 with 10% FBS. To run the assay, the cells (180 Ail, 6000 cells) were added to each well in a 96-well plate and incubated for 24 hours at 37° C. with 5% $CO_2$. Next, the cells were treated with test compounds (20 µl) at various concentrations in appropriate cell culture medium (total volume, 0.2 mL). The control wells contain cells and the medium but lack the test compounds. The plates were incubated for 120 hours at 37° C. with 5% $C_{O2}$. MTT (5 mg/ml) was then added to the wells (20 µl) and the plates were incubated for 1.5 hr at 37° C. The medium was carefully removed and DMSO (180 µl) was added afterward. After it was shaken for 15 min, the absorbance was measured at 490 nm and 570 nm with a reference filter of 620 nm. The inhibition % was calculated according to the following equation:

inhibition %=[1−(assay-blank)/(control-blank)]×100.

The Cytotoxicity Results of $IC_{50}$:

| | DAR (drug ratio) | N87 cell (Ag+) $IC_{50}$ (nM) |
|---|---|---|
| Conjugate 232 | 3.1 | 0.112 nM |
| Conjugate 234 | 2.3 | 0.17 nM |
| Conjugate 235 | 4.1 | 0.014 nM |
| Conjugate 238 | 2.2 | 33.83 nM |
| Conjugate 239 | 3.8 | 2.31 nM |
| Conjugate 261 | 2.6 | 1.36 nM |
| Conjugate 307 | 3.8 | 0.83 nM |
| Conjugate 308 | 3.8 | 0.31 nM |
| Conjugate 326 | 3.6 | 0.16 nM |
| Conjugate 327 | 3.2 | 0.65 nM |
| Conjugate 339 | 5.2 | 0.0013 nM |
| Conjugate 344 | 4.8 | 0.0012 nM |
| Conjugate 345 | 5.9 | 0.0013 nM |
| Conjugate 354 | 5.2 | 0.00082 nM |
| Conjugate 355 | 6.2 | 0.00012 nM |
| Conjugate 360 | 4.8 | 0.0016 nM |
| Conjugate 361 | 6.1 | 0.00041 nM |
| Conjugate 476 | 3.9 | 0.0123 nM |
| Conjugate 478 | 3.8 | 0.0081 nM |
| Conjugate 481 | 3.8 | 0.0132 nM |
| Conjugate 483 | 3.8 | 0.043 nM |
| Conjugate 498 | 5.6 | 0.00012 nM |
| Conjugate 500 | 5.6 | 0.00036 nM |
| T-DM1 | 3.5 | 0.152 nM |

Example 156. Antitumor Activity In Vivo (BALB/c Nude Mice Bearing NCI-N87 Xenograft Tumor)

The in vivo efficacy of conjugates 232, 308, 327, 339, 476, 483, and 500 along with T-DM1 were evaluated in a human gastric carcinoma N-87 cell line tumor xenograft models. Five-week-old female BALB/c Nude mice (54 animals) were inoculated subcutaneously in the area under the right shoulder with N-87 carcinoma cells ($5\times10^6$ cells/mouse) in 0.1 $m_1$ of serum-free medium. The tumors were grown for 8 days to an average size of 135 $mm^3$. The animals were then randomly divided into 9 groups (6 animals per group). The first group of mice served as the control group and was treated with the phosphate-buffered saline (PBS) vehicle. 6 groups were treated with conjugates 232, 308, 327, 476, 483, and T-DM 1 respectively at dose of 5 mg/Kg administered intravenously. The remaining 2 groups were treated with conjugate 339 and 500 respectively at dose of 4 mg/Kg administered intravenously. Three dimensions of the tumor were measured every 4 days and the tumor volumes were calculated using the formula tumor volume=½ (length×width×height). The weight of the animals was also measured at the same time. A mouse was sacrificed when any one of the following criteria was met: (1) loss of body weight of more than 20% from pretreatment weight, (2) tumor volume larger than 2000 $mm^3$, (3) too sick to reach food and water, or (4) skin necrosis. A mouse was considered to be tumor-free if no tumor was palpable.

Figure 45:
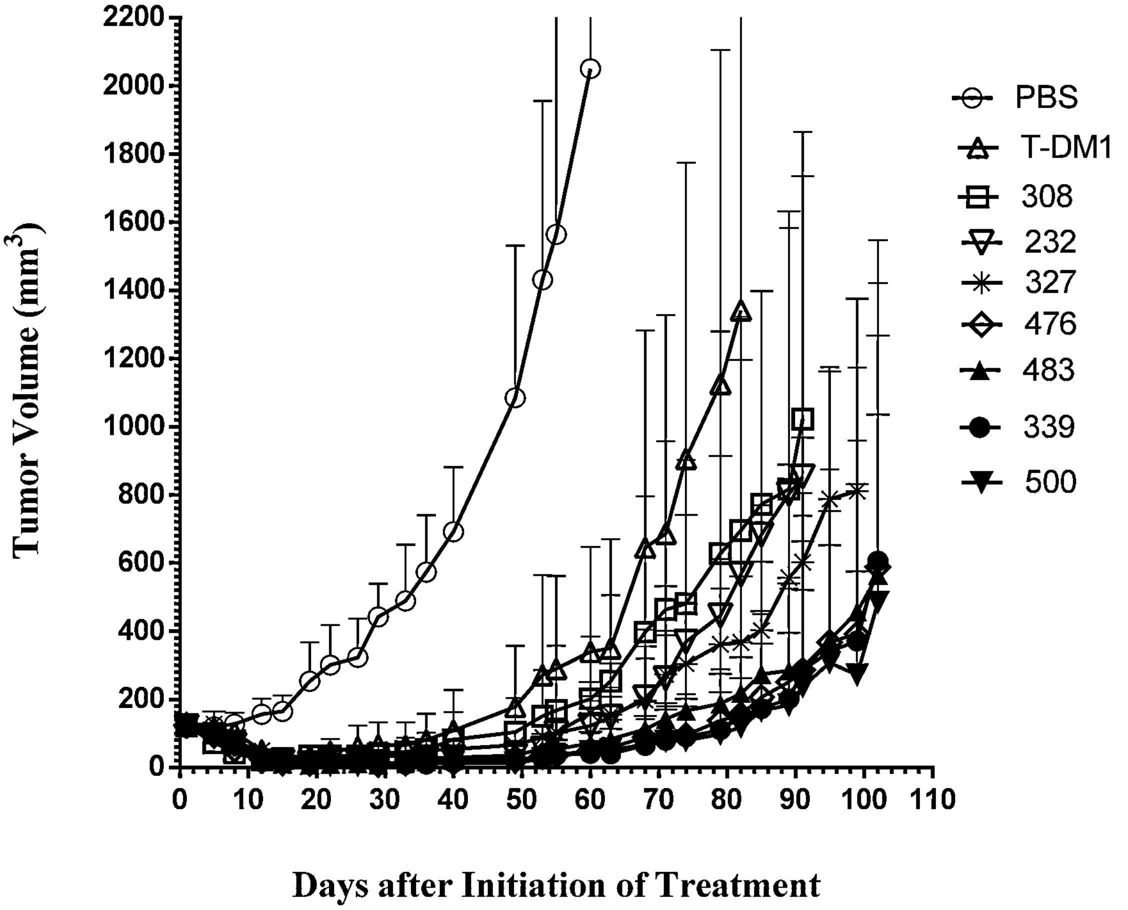
FIG. 45 shows the comparison of the anti-tumor effect of conjugate compounds 232, 308, 327, 339, 476, 485 and 500 with T-DM1 using human gastric tumor N87 cell model, i.v., one injection at dosing of 5 mg/kg for conjugates 232, 308, 327, 339, 476 and 485, and at dosing of 4 mg/kg for conjugates 339 and 500. Seven conjugates tested here demonstrated better anti-tumor activity than T-DM1. All 6/6 animals at the groups of compounds 476, 483, 339 and 500 had completely no tumor measurable at day 14 till day 52. In contrast T-DM1 at dose of 5 mg/Kg was not able to eliminate the tumors and it only inhibited the tumor growth for 31 days. Conjugate compounds 232, 308, and 327 did not eradicate the tumor at dose of 5 mg/Kg completely.

The results were plotted in FIG. 45. All the 8 conjugates did not cause the animal body weight loss. And the animals at control group were sacrificed at day 56 due to the tumor volume larger than 2200 $mm^3$ and they were too sick. Here 7 conjugates tested demonstrated better anti-tumor activity than T-DM1. All 6/6 animals at the groups of compounds 476, 483, 339 and 500 had completely no tumor measurable at day 14 till day 52. In contrast T-DM1 at dose of 5 mg/Kg was not able to eliminate the tumors and it only inhibited the tumor growth for 31 days. Conjugate compounds 232, 308, and 327 did not eradicate the tumor at dose of 5 mg/Kg completely. The inhibition of the tumor growth is:

| conjugate | Tumor growth delay |
|---|---|
| T-DM1 | 31 days |
| 308 | 39 days |
| 327 | 46 days |
| 232 | 52 days |
| 476 | 65 days |
| 483 | 66 days |
| 339 | 66 days |
| 500 | 67 days |

The invention claimed is:

1. A linker compound of Formula (I) or (II):

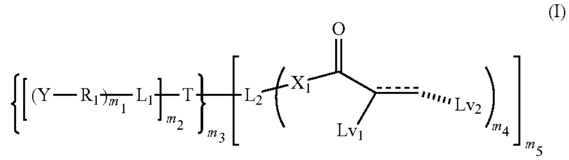

(I)

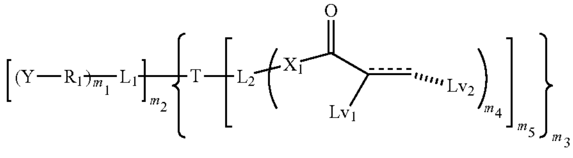

(II)

wherein

“ —— ” and “ ıııııı ” represent a single bond, and “ ıııııı ” can be an enantiomer or stereoisomer bond when linked to a single or a double bond;

≡ represents either a single bond, or a double bond, or a triple bond;

provided that when ≡ represents a single bond, both $L_{V1}$ and $L_{V2}$ are not H; when ≡ represents a double bond, either $L_{V1}$ or $L_{V2}$ can be H, but they are not H at the same time; when ≡ represents a triple bond, $L_{V1}$ is absent and $L_{V2}$ can optionally be H;

$L_{V1}$ and $L_{V2}$, represent H or a same or different leaving group that is optionally substituted by a thiol, and the leaving group is selected from the group consisting of a halide selected from fluoride, chloride, bromide, and iodide, methanesulfonyl (mesyl), toluenesulfonyl (tosyl), trifluoromethyl-sulfonyl (triflate), trifluoromethylsulfonate, nitrophenoxyl, N-succinimidyloxyl (NHS), phenoxyl; dinitrophenoxyl; pentafluorophenoxyl, tetrafluorophenoxyl, trifluorophenoxyl, difluorophenoxyl, monofluorophenoxyl, pentachlorophenoxyl, 1H-imidazole-1-yl, chlorophenoxyl, dichlorophenoxyl, trichlorophenoxyl, tetrachlorophenoxyl, N-(benzotriazol-yl)oxyl, 2-ethyl-5-phenylisoxazolium-3'-sulfonyl, phenyloxadiazole-sulfonyl (-sulfone-ODA), 2-ethyl-5-phenylisoxazolium-yl, phenyloxadiazol-yl (ODA), and oxadiazol-yl;

Y is a functional group that selected from the group consisting of following structures:

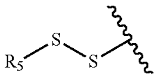

disulfide;

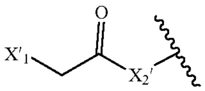

haloacetyl;

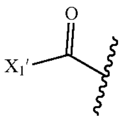

acyl halide (acid halide);

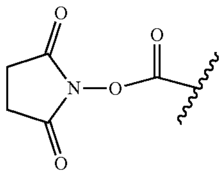 [SMILES: *C(=O)ON1C(=O)CCC1=O]

N-hydroxysuccinimide ester;

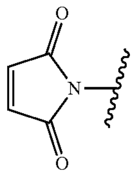 [SMILES: *N1C(=O)C=CC1=O]

maleimide;

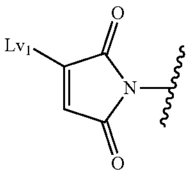

monosubstituted maleimide;

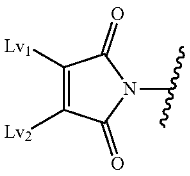

disubstituted maleimide;

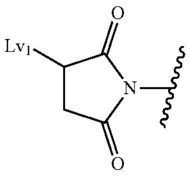

monosubstituted succinimide;

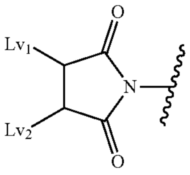

disubstituted succinimide; —CHO aldehyde;

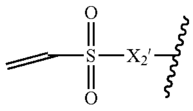

ethenesulfonyl;

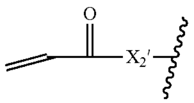
acryl (acryloyl);
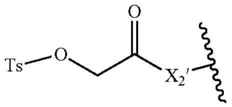
2-(tosyloxy)acetyl;
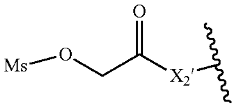
2-(mesyloxy)acetyl;
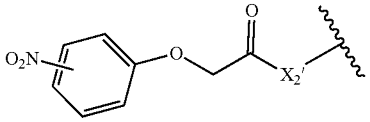
2-(nitrophenoxy)acetyl;
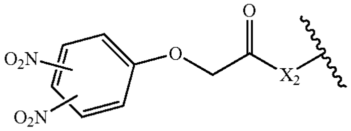
(dinitrophenoxy)acetyl;
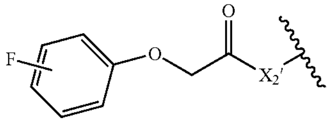
2-(fluorophenoxy)-acetyl;
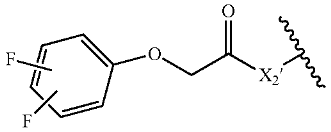
2-(difluorophenoxy)-acetyl;
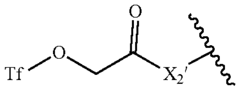
2-(((trifluoromethyl)-sulfonyl)oxy)acetyl;
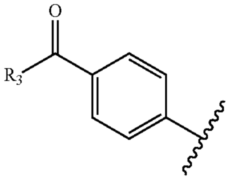
ketone, or aldehyde,
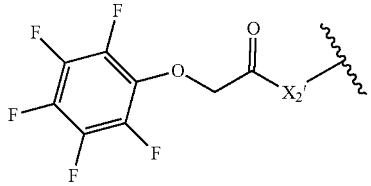
2-(pentafluorophenoxy)acetyl;
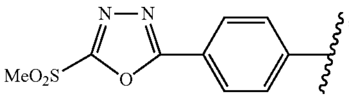,
methylsulfonephenyloxadiazole (ODA);
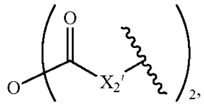, 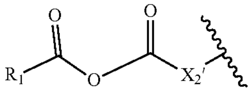
acid anhydride,
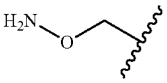 [SMILES: *CON]
alkyloxyamino;
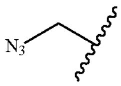 [SMILES: *CN=[N+]=[N-]]
azido,

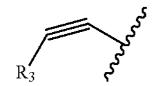

alkynyl and

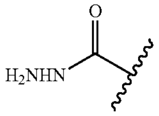

hydrazide, wherein $X_{1'}$ is F, Cl, Br, I or $L_{V3}$; $X_2'$ is O, NH, N(Ria), or $CH_2$; $R_3$ and $R_5$ are independently H, $R_{1a}$, aromatic, heteroaromatic, or aromatic group wherein one or several H atoms are replaced independently by —$R_{1a}$, -halogen, —$OR_{1a}$, —$SR_{1a}$, —$NR_{1a}R_2$, —$NO_2$, —$S(O)R_{1a}$, —$S(O)_2R_{1a}$, or —$COOR_{1a}$; $L_{V3}$ is a leaving group selected from the group consisting of nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, and anhydrides formed its self, or formed with acetyl anhydride, or formyl anhydride; $R_{1a}$ is selected from the group consisting of H, $C_1$-$C_8$ alkyl; $C_2$-$C_8$ heteroalkyl, alkylcycloalkyl, heterocycloalkyl; $C_3$-$C_8$ aryl, Aralkyl, heterocyclic, carbocyclic, cycloalkyl, heteroalkylcycloalkyl, alkylcarbonyl, heteroaryl; $C_2$-$C_8$ ester, ether, amide, amine, imine, polyamine, hydrazine, hydrazone, urea, semicarbazide, carbazide, alkoxyamine, alkoxylamine, urethane, amino acid, acyloxylamine, glycoside, or hydroxamic acid: peptide containing 1-8 amino acids, or polyethyleneoxy unit of formula $(OCH_2CH_2)_p$ or $(OCH_2CH(CH_3))_p$, wherein p is an integer from 1 to about 1000, and a combination thereof;

$R_1$ is absent;

T is

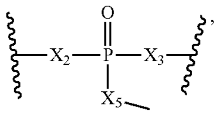

wherein  is the site of linkage, $X_2$, $X_3$, and $X_5$ each are NHNH;

m, $m_1$, $m_2$, $m_3$, $m_4$ and $m_5$ are independently an integer from 1 to 10, $L_1$ is alkylcarbonyl;

$L_2$, and $X_1$ are absent.

2. The linker compound of claim 1, wherein ═ represents a triple bond.

3. The linker compound of claim 1, wherein ═ represents a triple bond, and $L_{V2}$ is H.

4. The linker compound of claim 1, wherein Y is

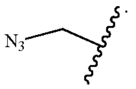

5. The linker compound of claim 1, wherein ═ represents a triple bond, $L_{V2}$ is H, and Y is

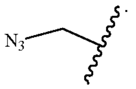

6. The linker compound of claim 1, wherein ═ represents a single bond, and $L_{V1}$ and $L_{V2}$ represent Br or I.

7. The linker compound of claim 1, wherein ═ represents a double bond, and $L_{V1}$ and $L_{V2}$ represent H or Br.

8. The linker compound of claim 1, wherein $m_1$ is 2.

9. The linker compound of claim 1, wherein $m_5$ is 2.

* * * * *